US012624096B2

(12) United States Patent
Harrington et al.

(10) Patent No.: US 12,624,096 B2
(45) Date of Patent: May 12, 2026

(54) ANTI-TAU ANTIBODIES AND METHODS OF USE THEREOF

(71) Applicant: GTInvent Limited, Aberdeen (GB)

(72) Inventors: Charles Robert Harrington, Aberdeen (GB); Soumya Palliyil Soman, Aberdeen (GB); Andrew Justin Radcliffe Porter, Aberdeen (GB); Claude Michel Wischik, Aberdeen (GB); Mohammad Arastoo, Aberdeen (GB); Lewis Kirk Penny, Aberdeen (GB); Richard Lofthouse, Aberdeen (GB)

(73) Assignee: GTInvent Limited, Aberdeen (GB)

( * ) Notice: Subject to any disclaimer, the term of this patent is extended or adjusted under 35 U.S.C. 154(b) by 643 days.

(21) Appl. No.: 18/004,772

(22) PCT Filed: Jul. 9, 2021

(86) PCT No.: PCT/EP2021/069160
§ 371 (c)(1),
(2) Date: Jan. 9, 2023

(87) PCT Pub. No.: WO2022/008719
PCT Pub. Date: Jan. 13, 2022

(65) Prior Publication Data
US 2023/0257452 A1    Aug. 17, 2023

(30) Foreign Application Priority Data
Jul. 10, 2020    (GB) ...................................... 2010652

(51) Int. Cl.
| | |
|---|---|
| C07K 16/00 | (2006.01) |
| A61K 39/00 | (2006.01) |
| A61K 39/395 | (2006.01) |
| A61K 49/00 | (2006.01) |
| A61P 25/28 | (2006.01) |
| C07K 16/18 | (2006.01) |
| G01N 33/53 | (2006.01) |
| G01N 33/68 | (2006.01) |

(52) U.S. Cl.
CPC .............. C07K 16/18 (2013.01); A61P 25/28 (2018.01); G01N 33/6896 (2013.01); A61K 2039/505 (2013.01)

(58) Field of Classification Search
CPC ................ C07K 16/18; C07K 2317/34; C07K 237/565; C07K 2317/24; C07K 2317/16; C07K 14/4711; A61P 25/28; A61P 25/00; A61K 38/17; A61K 39/00; A61K 2039/505; G01N 33/6896; G01N 2333/46; G01N 33/53; G01N 2800/2821; G01N 2800/2814
See application file for complete search history.

(56) References Cited

U.S. PATENT DOCUMENTS

| | | | |
|---|---|---|---|
| 8,609,097 | B2 | 12/2013 | Bohrmann et al. |
| 2016/0289309 | A1 | 10/2016 | Griswold-Prenner et al. |
| 2025/0147051 | A1* | 5/2025 | Lofthouse ........ G01N 33/57488 |

FOREIGN PATENT DOCUMENTS

| | | | |
|---|---|---|---|
| CA | 3046857 A1 | 6/2018 |
| KR | 101231777 B1 | 2/2013 |
| WO | 2015004163 A1 | 1/2015 |
| WO | 2016201434 A2 | 12/2016 |
| WO | 2018031361 A2 | 2/2018 |
| WO | 2018106781 A1 | 6/2018 |
| WO | 2018183175 A1 | 10/2018 |

OTHER PUBLICATIONS

Burgess et al. J of Cell Bio. 1990, 111:2129-2138.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Anger. Neurotoxicology 1991. 12: 403-13.*
Tayebati. Mech. Ageing Dev. 2006. 127: 100-8.*
Sarter. Neurosci. and Biobehav. Rev. 2004. 28: 645-650.*
Falkenburger et al., J. Neural. Transm, 2006; 70:261-268.*
Swerdlow, Clin. Interv. Ageing 2007; 2:347-359.*
Atwood et al., J. Alzheimer's Disease; 2015; 47:33-47.*
Henstridge et al., Nat. Rev. Neurosci. 2019; 20: 94-107.*
Sigurdsson. Immunotherapy Targeting Pathological Tau Protein in Alzheimer's Disease and Related Tauopathies, J Alzheimers Dis., 2008, 15(2), 157-168.
Harrington et al. Cellular Models of Aggregation-dependent Template-directed Proteolysis to Characterize Tau Aggregation Inhibitors for Treatment of Alzheimer Disease, Journal of Biological Chemistry. 2015, 290(17), 10862-10875.
Al-Hilaly et al. Alzheimer's Disease-like Paired Helical Filament Assembly from Truncated Tau Protein Is Independent of Disulfide Crosslinking, Journal of Molecular Biology, 2017, 429(23), 3650-3665.
Al-Hilaly et al. Tau (297-391) forms filaments that structurally mimic the core of paired helical filaments in Alzheimer's disease brain, FEBS letters, 2019, 594(5), 944-950.
Pollack et al. Paired Helical Filament-Forming Region of Tau (297-391) Influences Endogenous Tau Protein and Accumulates in Acidic Compartments in Human Neuronal Cells, Journal of Molecular Biology, 2020, 432(17), 4891-4907.

* cited by examiner

*Primary Examiner* — Chang-Yu Wang
(74) *Attorney, Agent, or Firm* — Arrigo, Lee, Guttman & Mouta-Bellum LLP

(57) ABSTRACT

The invention relates to specific binding molecules, such as antibodies, directed to key epitopes of tau. The specific binding molecules of the invention find applications in diagnostics and therapeutics of tauopathies including Alzheimer's disease.

Figure 5:
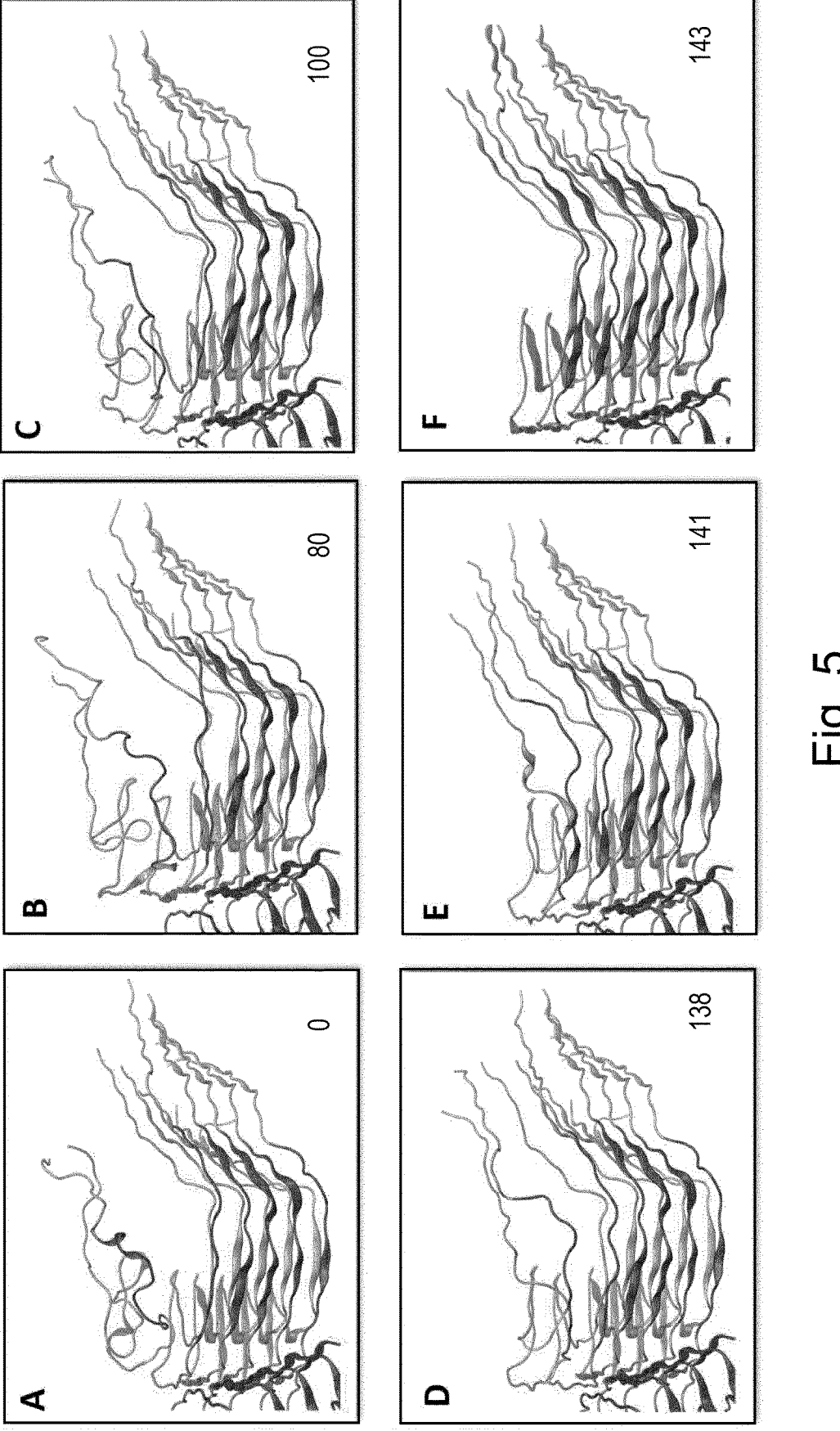

16 Claims, 64 Drawing Sheets
Specification includes a Sequence Listing.

Antibody Variable Heavy Chain (SEQ ID NO: 62)

QVQLQESGPSLVKPSQTLSLTCTVSGFSLNNNAVGWVRQAPGKVPESLVGCSSDGTCYYNSALKSRLDITRDTSKNQISLSLSSVTTDDAAVYYCTRGHYSIYGYDYLGTIDYWGPGLLLVTVSS

Kabat numbering and CDRs

Chothia numbering and CDRs

Martin numbering and CDRs

HCDR1   HCDR2   HCDR3

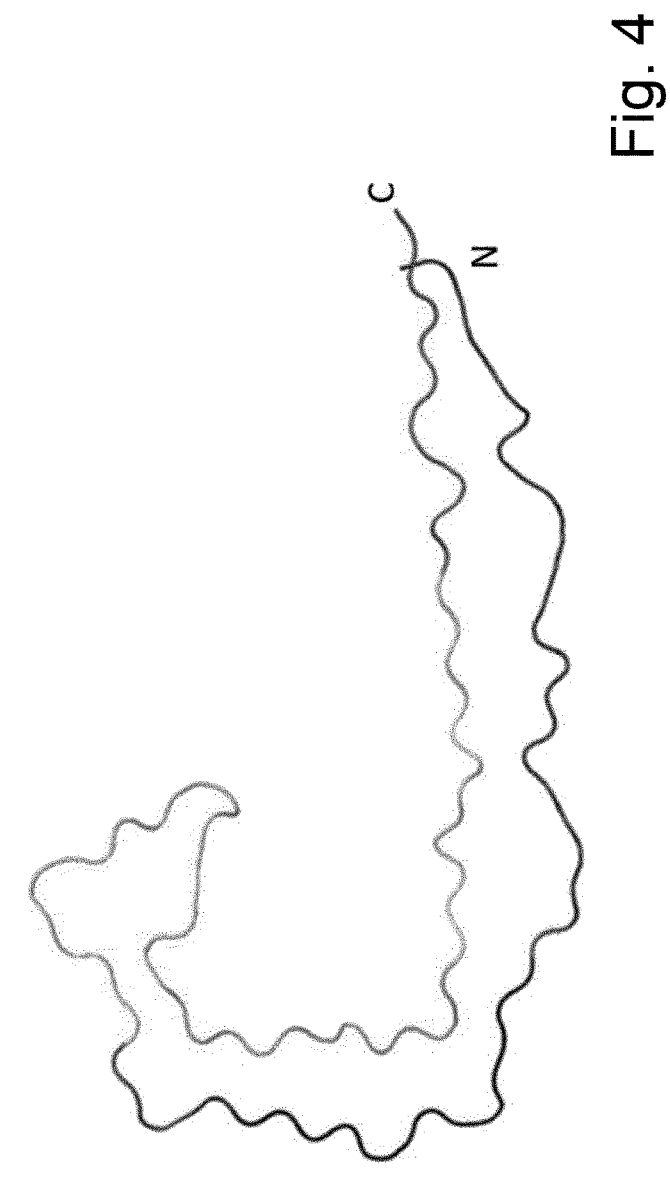
Fig. 4

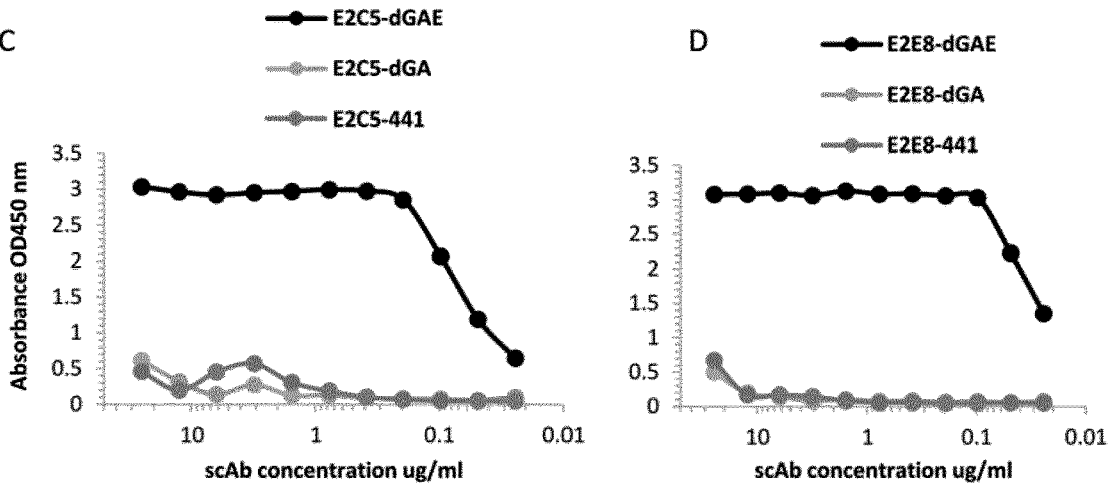
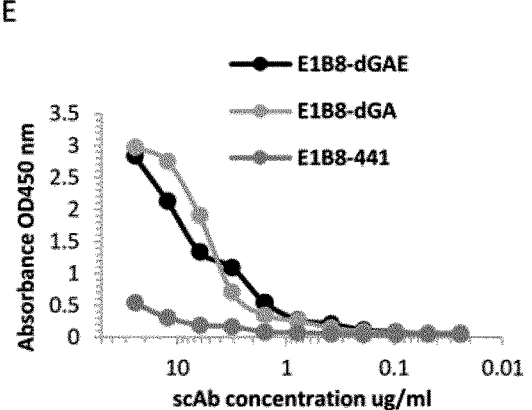
Fig. 8

A
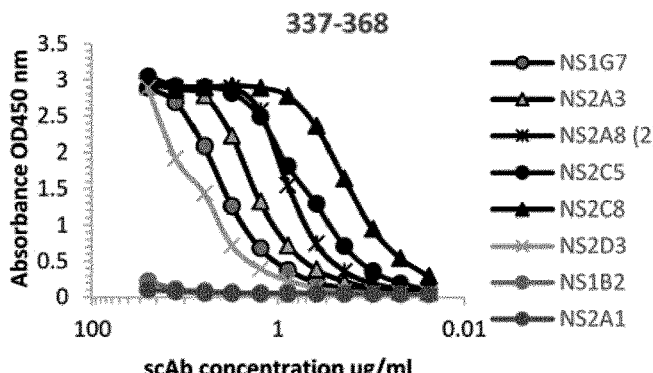
B
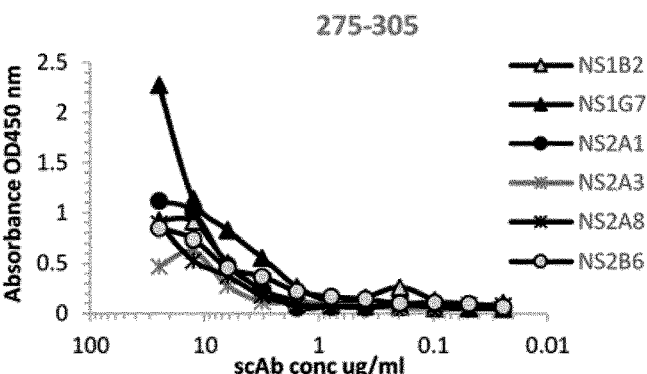
C
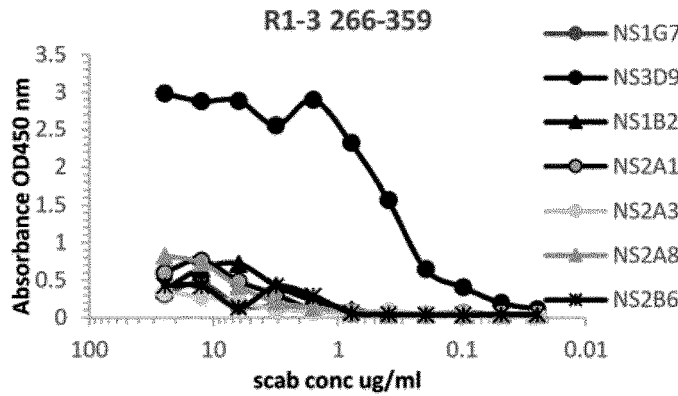
Fig. 10

D
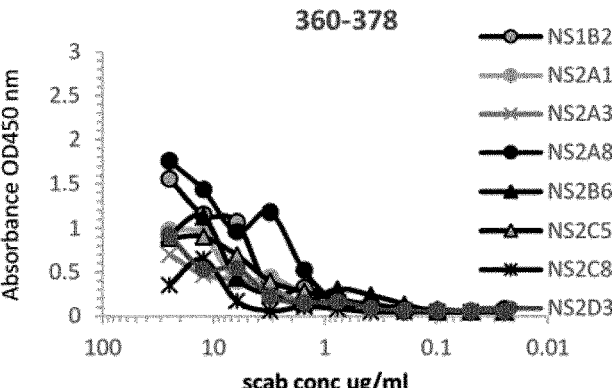
E
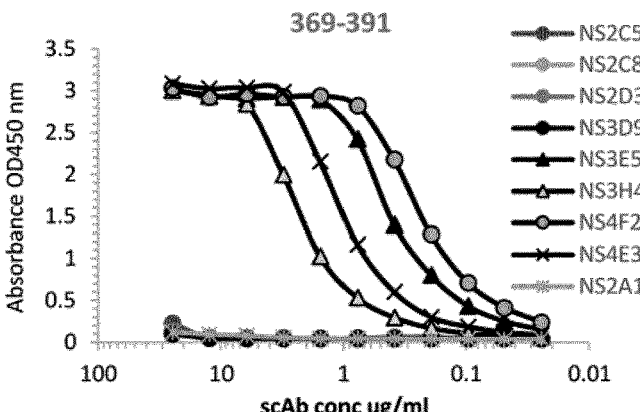
F
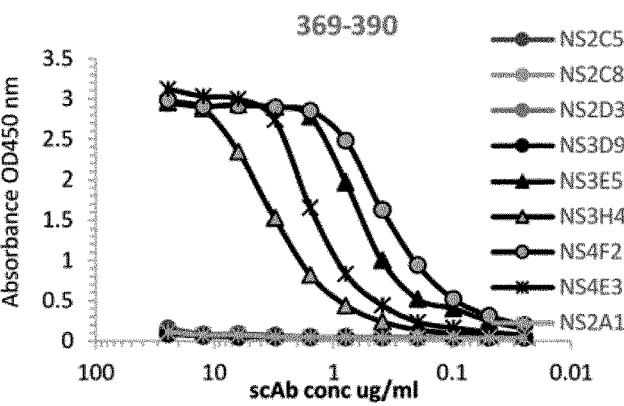
Fig. 10 (cont)

Fig. 11

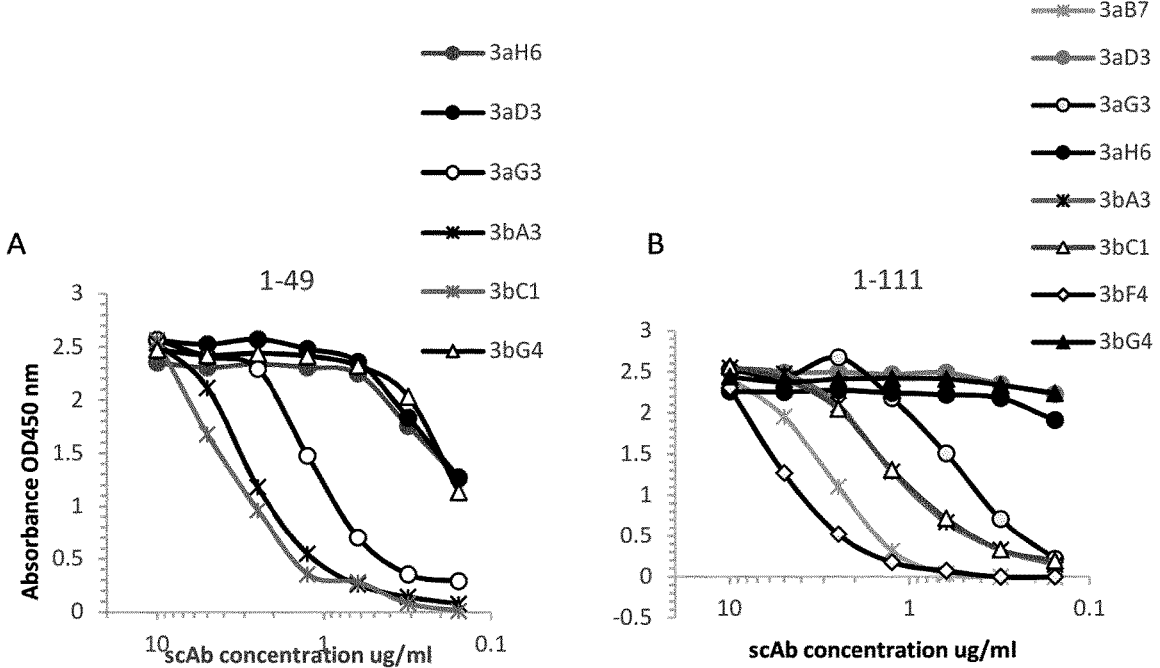
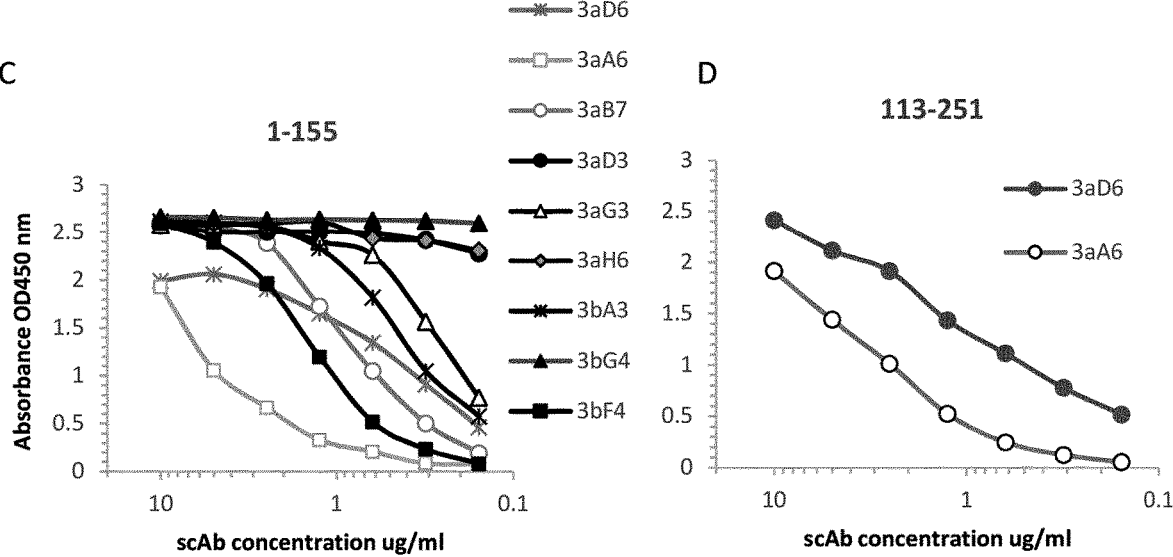
Fig. 14

A
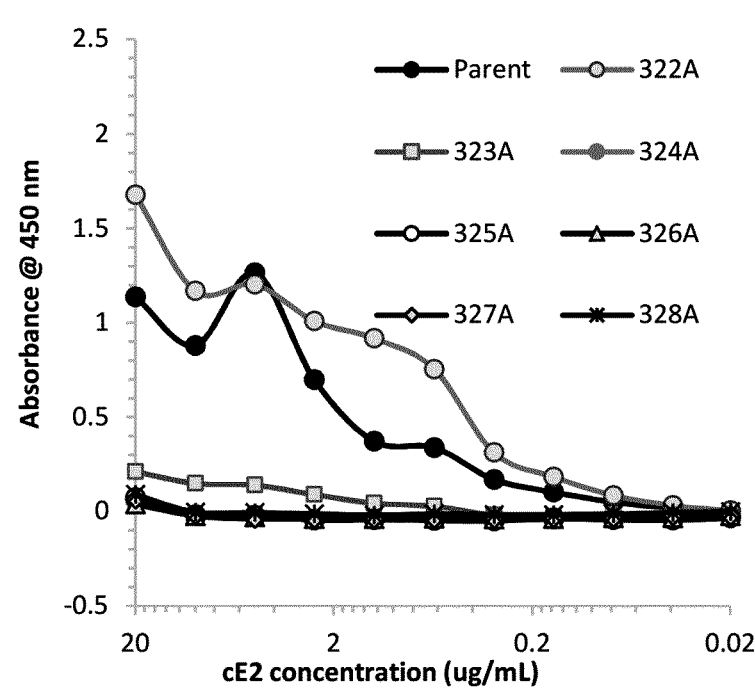
B
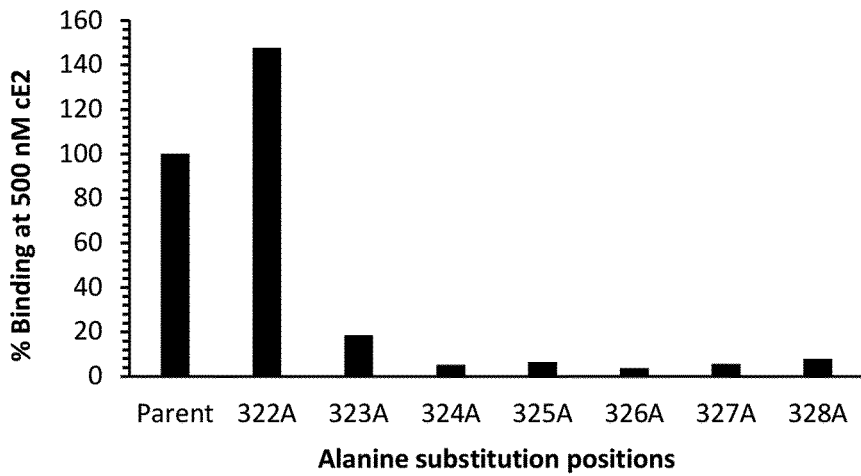
Fig. 15

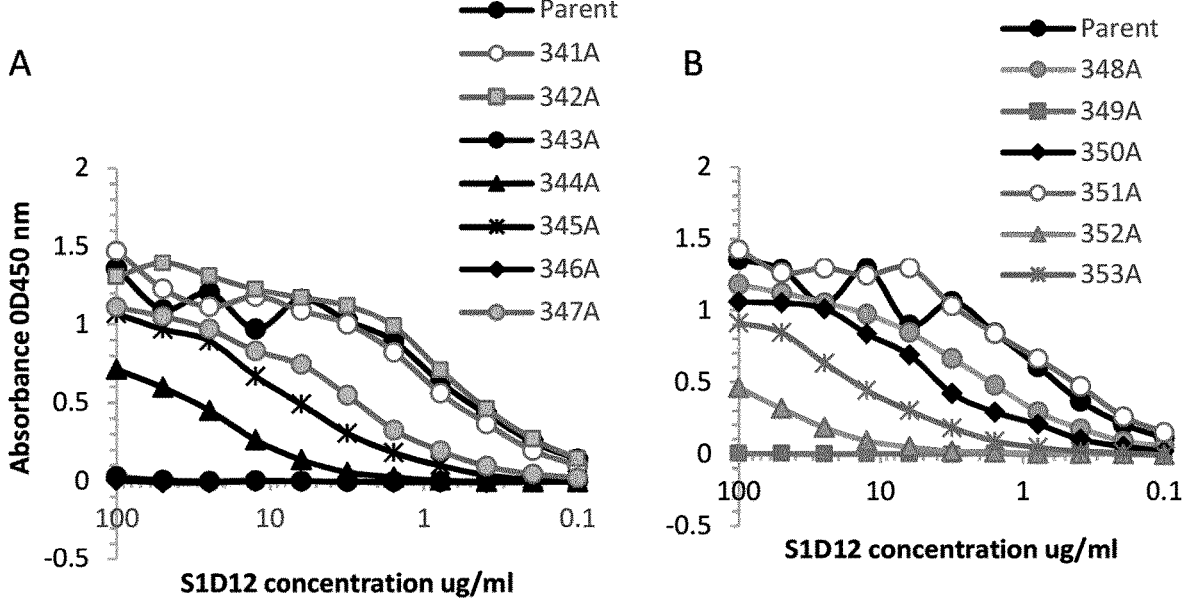
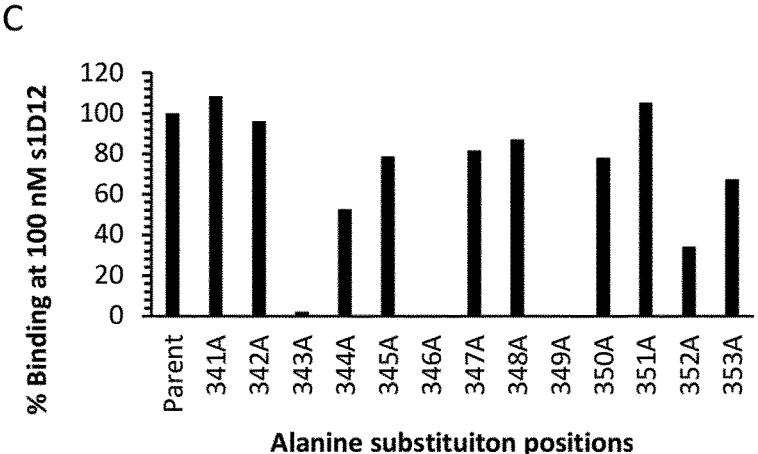
Fig. 16

A
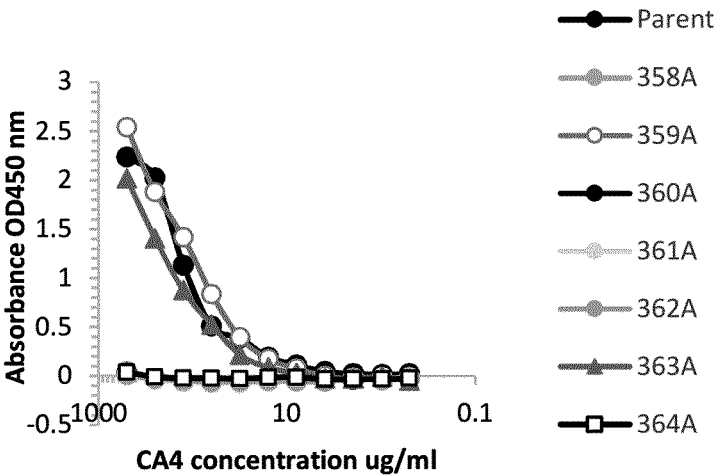
B
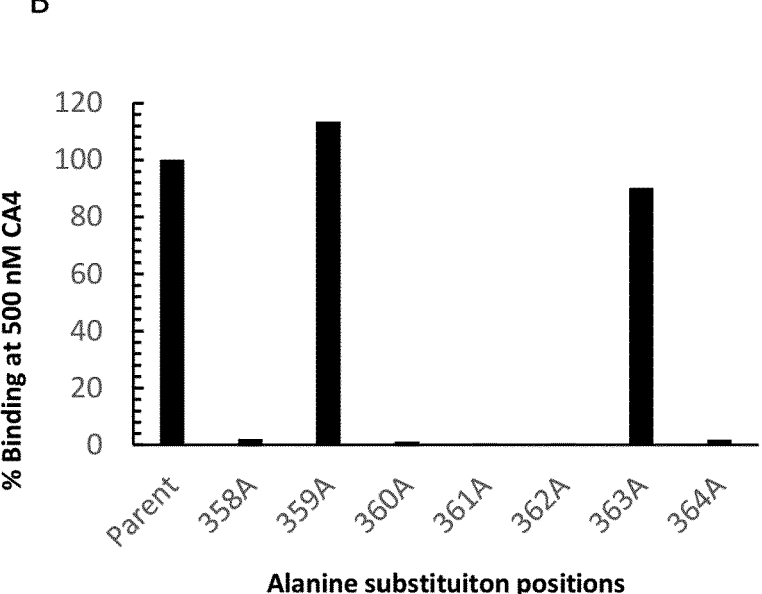
Fig. 18

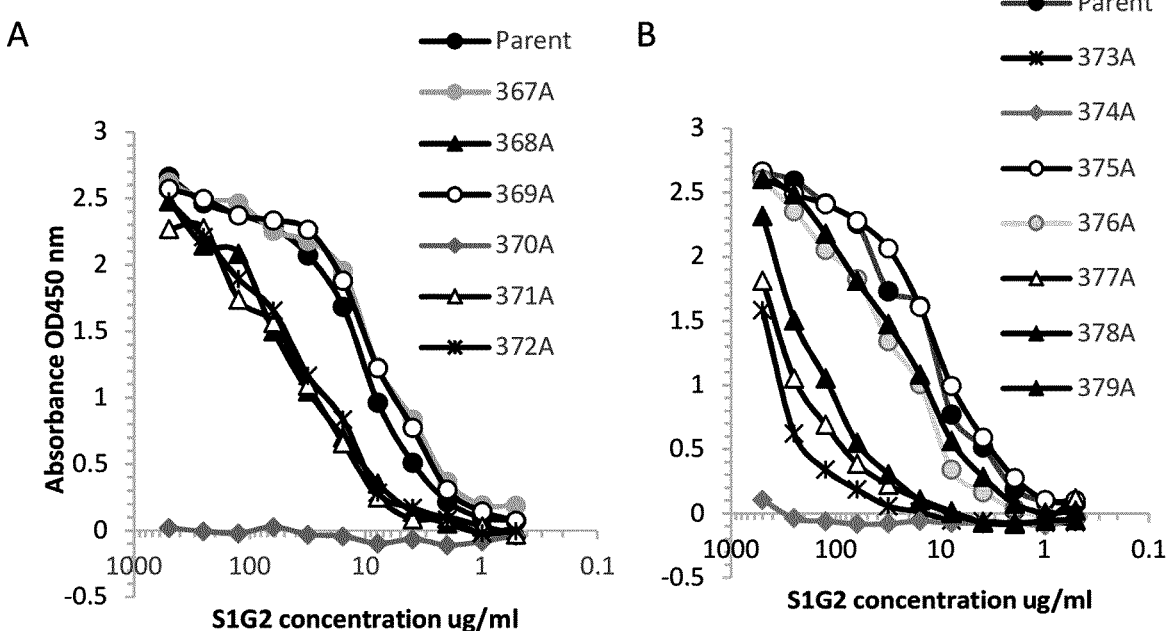
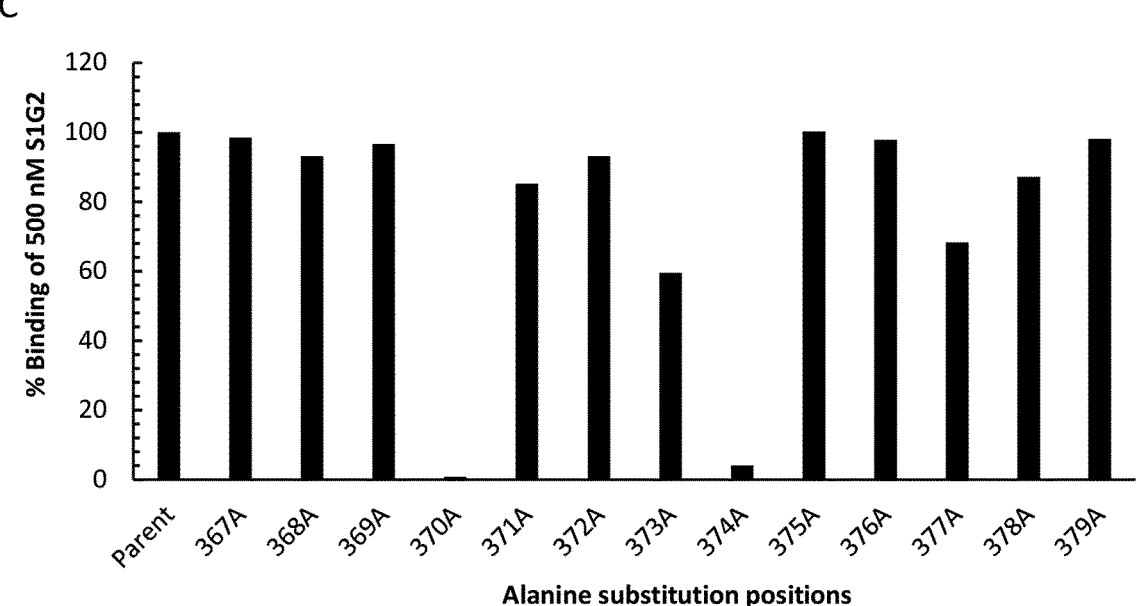
Fig. 19

A
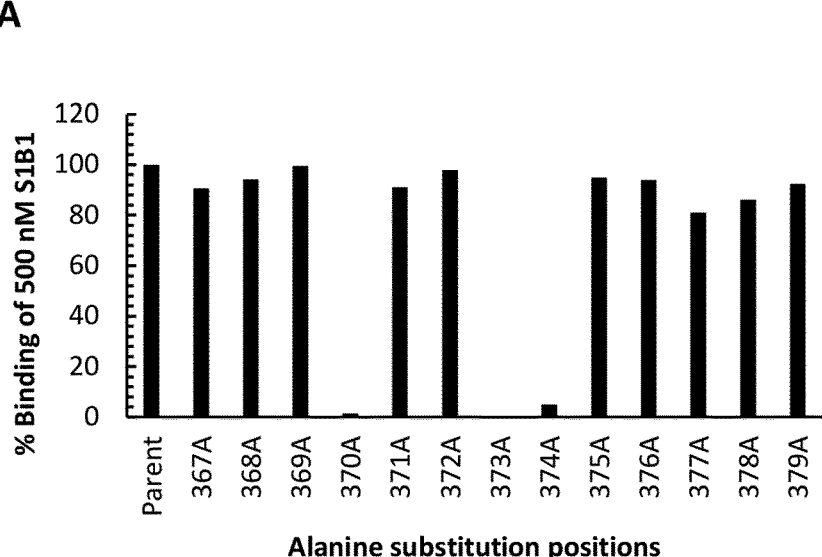
B
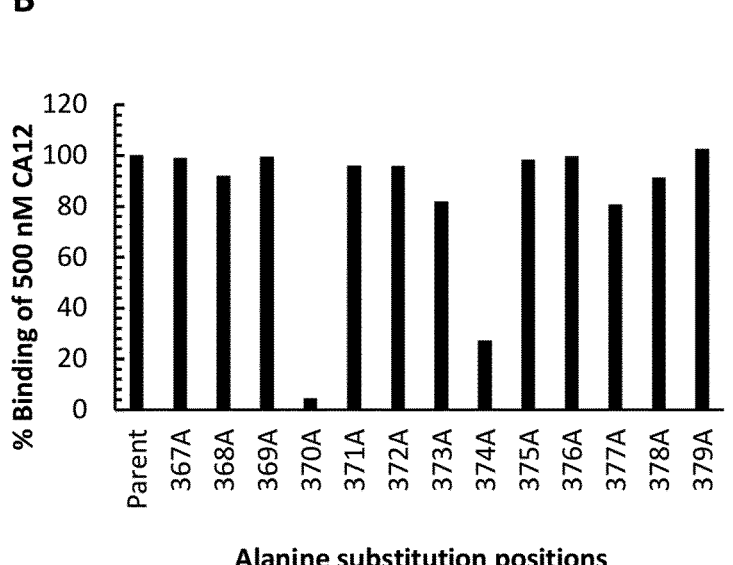
Fig. 20

C
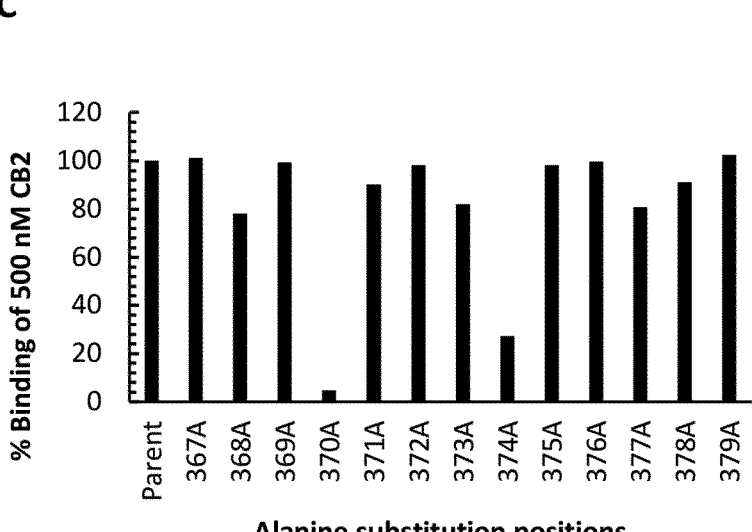
D
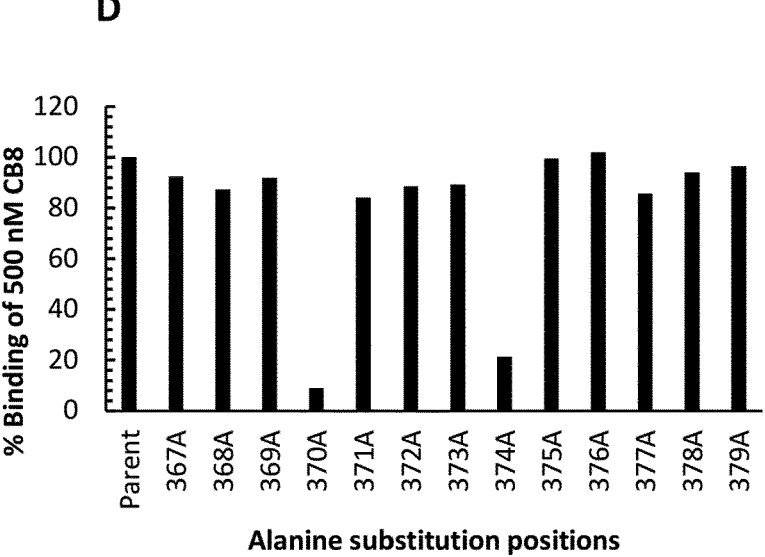
Fig. 20 (cont)

E
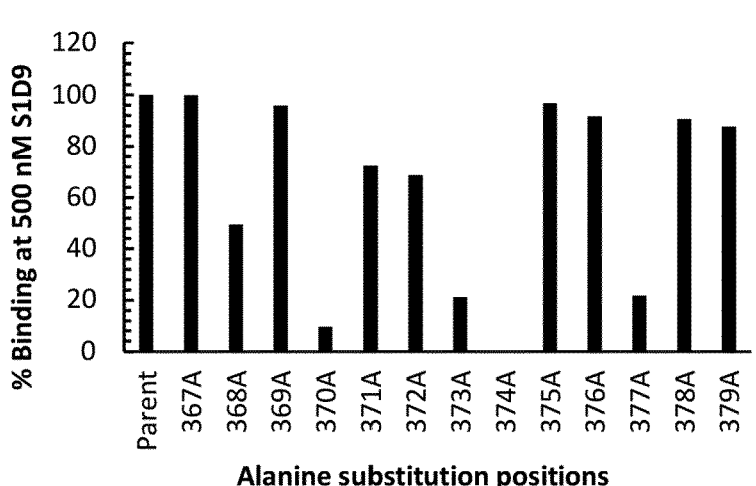
F
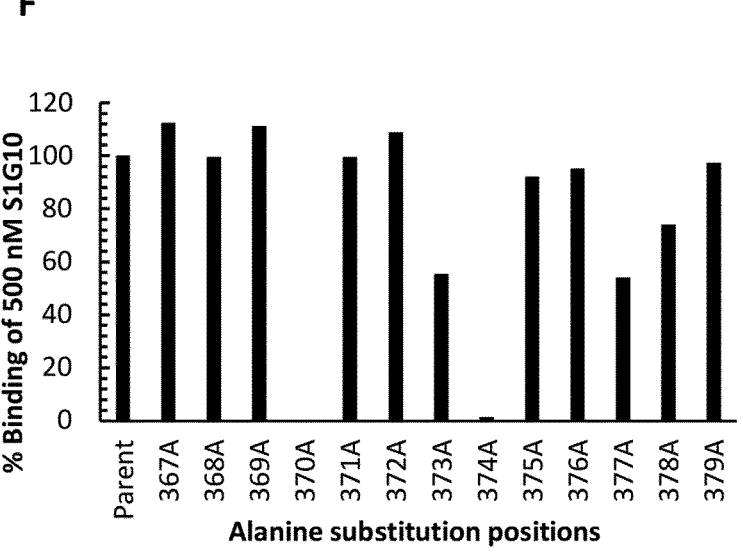
Fig. 20 (cont)

G
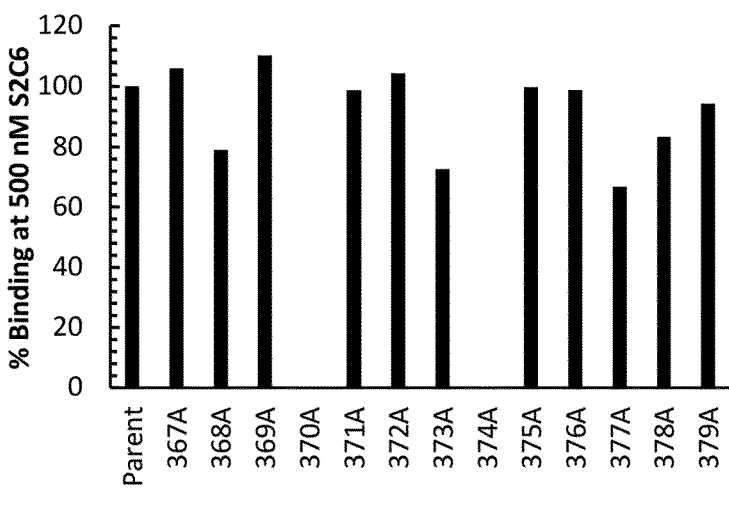
H
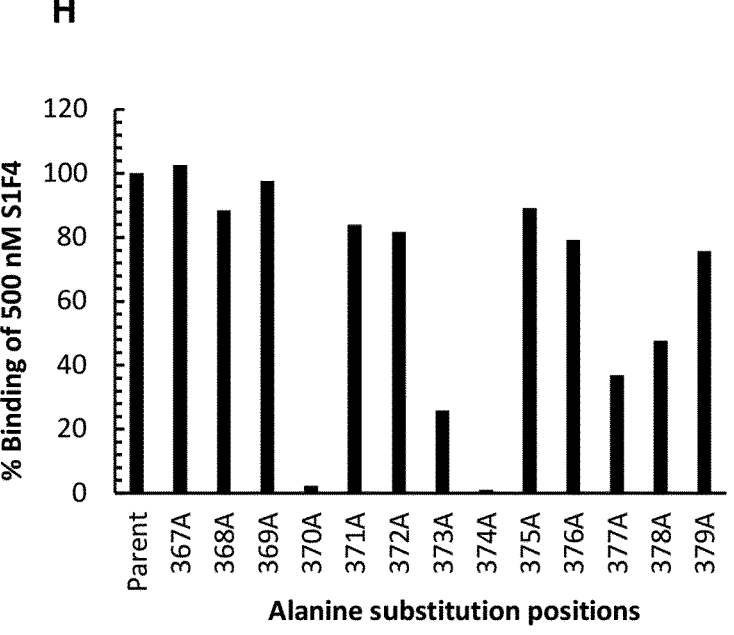
Fig. 20 (cont)

I
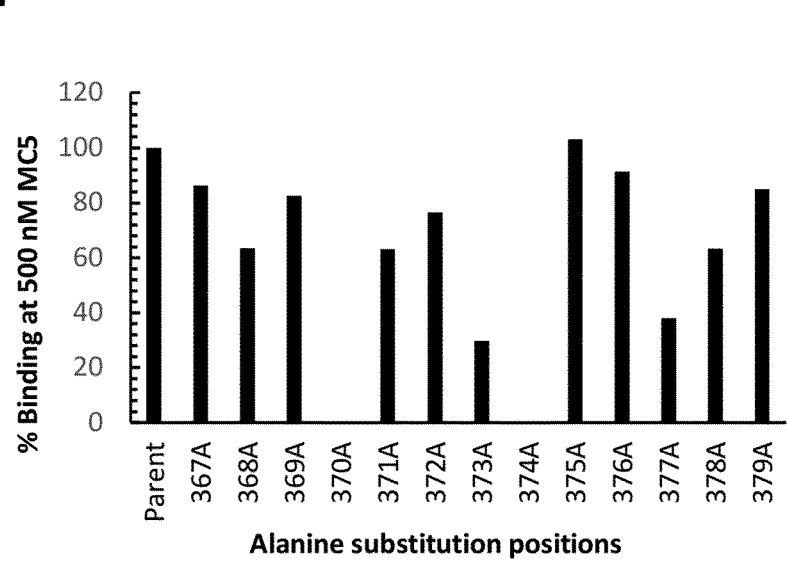
J
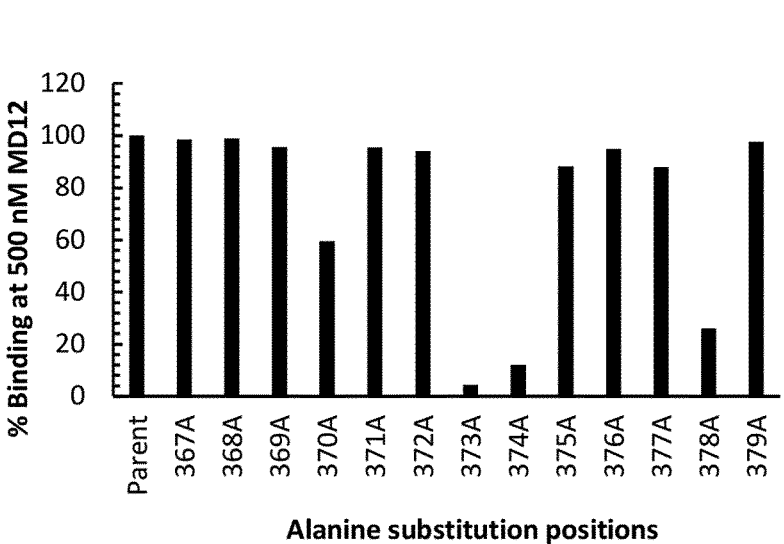
Fig. 20 (cont)

A
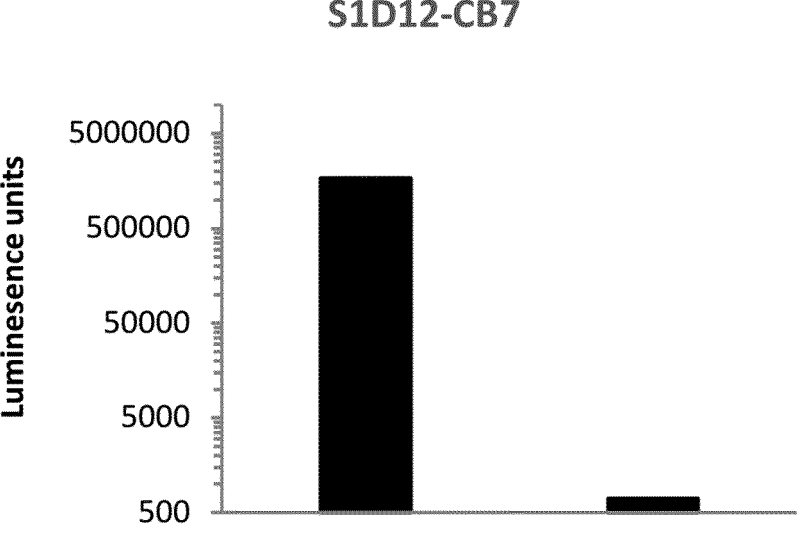
B
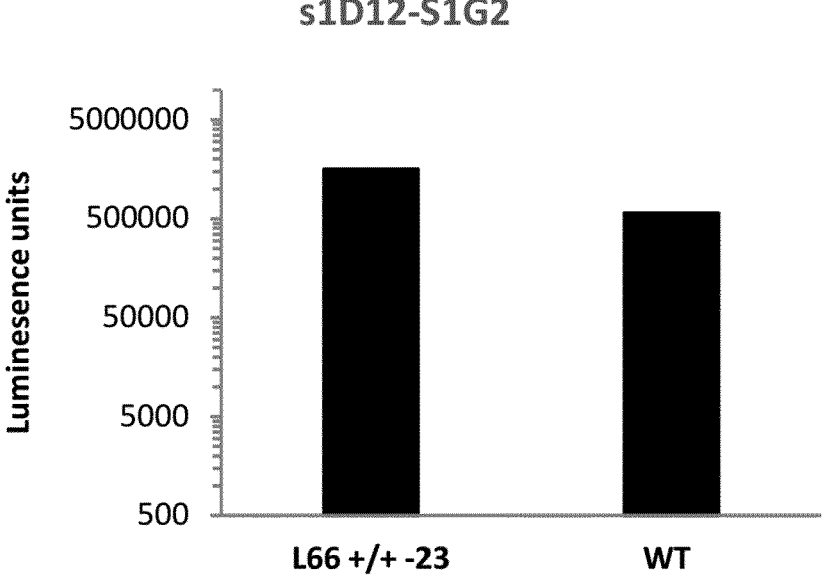
Fig. 32

| scAb | $B_{50}$ (nM) |
| --- | --- |
| S2C6 | 51 |
| CA12 | 59 |
| NS2A1 | 62 |
| S1G2 | 65 |
| S1D12 | 80 |
| S1E12 | 92 |
| CB2 | 93 |
| S1B1 | 101 |
| S1D9 | 107 |
| S1G10 | 207 |
| CE3 | 209 |
| CE2 | 211 |
| CA4 | 221 |
| CB7 (-ve) | >10000 |
| 3aD6 (-ve) | >10000 |

Sequence alignment of human and mouse tau

```
                         CB7 (13-25)
P10636-8|TAU_HUMAN  MAEPRQEFEVMEDHAGTYGLGDRKDQGGYTMHQDQEGDTDAGLKESPLQTPTEDGSEEPG  60
P10637-2|TAU_MOUSE  MADPRQEFDTMEDHAGDY----------TLLQDQEGDMDHGLKESPPQPPADDGAEEPG   49
                    **:*****:.*******  *  *:****:**** *::*:.:**:*.**

P10636-8|TAU_HUMAN  SETSDAKSTPTAEDVTAPLVDEGAPGKQAAAQPHTEIPEGTTAEEAGIGDTPSLEDEAAG  120
P10637-2|TAU_MOUSE  SETSDAKSTPTAEDVTAPLVDERAPDKQAAAQPHTEIPEGTTAEEAGIGDTPNQEDQAAG  109
                    **********************.**:***********************.  **:***

CC7 (145-157)
P10636-8|TAU_HUMAN  HVTQARMVSKSKDGTGSDDKKAKGADGK--TKIATPRGAAPPGQKGQANATRIPAKTPPA  178
P10637-2|TAU_MOUSE  HVTQARVASKD--RTGNDEKKAKGADGKTGAKIATPRGAASPAQKGTSNATRIPAKTTPS  167
                    ******:.***  *.:** **:*:************ :.****  :.  *********  *:

P10636-8|TAU_HUMAN  PKTPPSSGEPPKSGDRSGYSSPGSPGTPGSRSRTPSLPTPPTREPKKVAVVRTPPKSPSS  238
P10637-2|TAU_MOUSE  PKTPPGSGEPPKSGERSGYSSPGSPGTPGSRSRTPSLPTPPTREPKKVAVVRTPPKSPSA  227
                    *****.********:*****************************************  .

P10636-8|TAU_HUMAN  AKSRLQTAPVPMPDLKNVKSKIGSTENLKHQPGGGKVQIINKKLDLSNVQSKCGSKDNIK  298
P10637-2|TAU_MOUSE  SKSRLQTAPVPMPDLKNVRSKIGSTENLKHQPGGGKVQIINKKLDLSNVQSKCGSKDNIK  287
                    :*****************  *:*

S-1D12 (337-355)
P10636-8|TAU_HUMAN  HVPGGGSVQIVYKPVDLSKVTSKCGSLGNIHHKPGGGQVEVKSEKLDFKDRVQSKIGSLD  358
P10637-2|TAU_MOUSE  HVPGGGSVQIVYKPVDLSKVTSKCGSLGNIHHKPGGGQVEVKSEKLDFKDRVQSKIGSLD  347
          S-1G2 (367-379)          ************************************************************

P10636-8|TAU_HUMAN  NITHVPGGGNKKIETHKLTFRENAKAKTDHGAEIVYKSPVVSGDTSPRHLSNVSSTGSID  418
P10637-2|TAU_MOUSE  NITHVPGGGNKKIETHKLTFRENAKAKTDHGAEIVYKSPVVSGDTSPRHLSNVSSTGSID  407
                    ************************************************************

P10636-8|TAU_HUMAN  MVDSPQLATLADEVSASLAKQGL  441
P10637-2|TAU_MOUSE  MVDSPQLATLADEVSASLAKQGL  430
```

Fig. 45

A
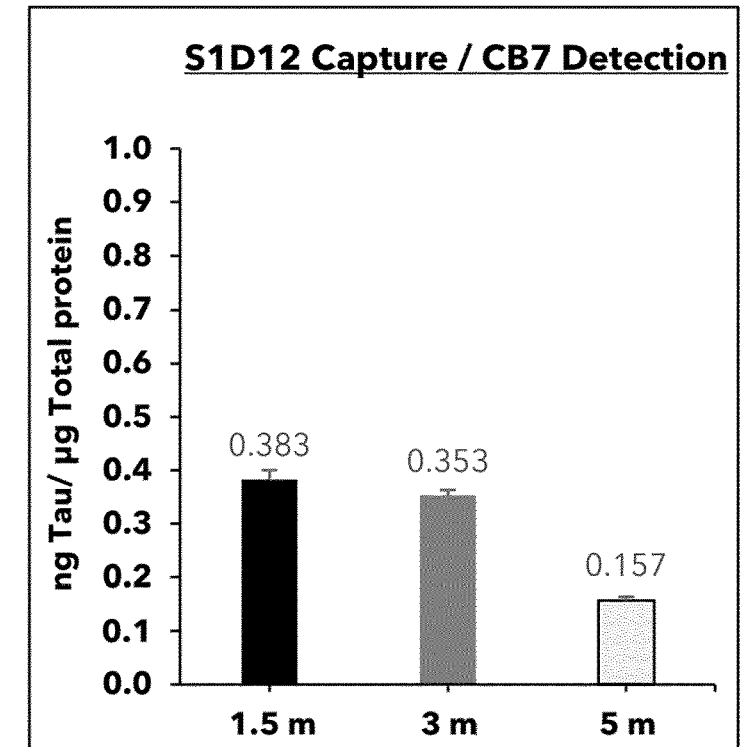
B
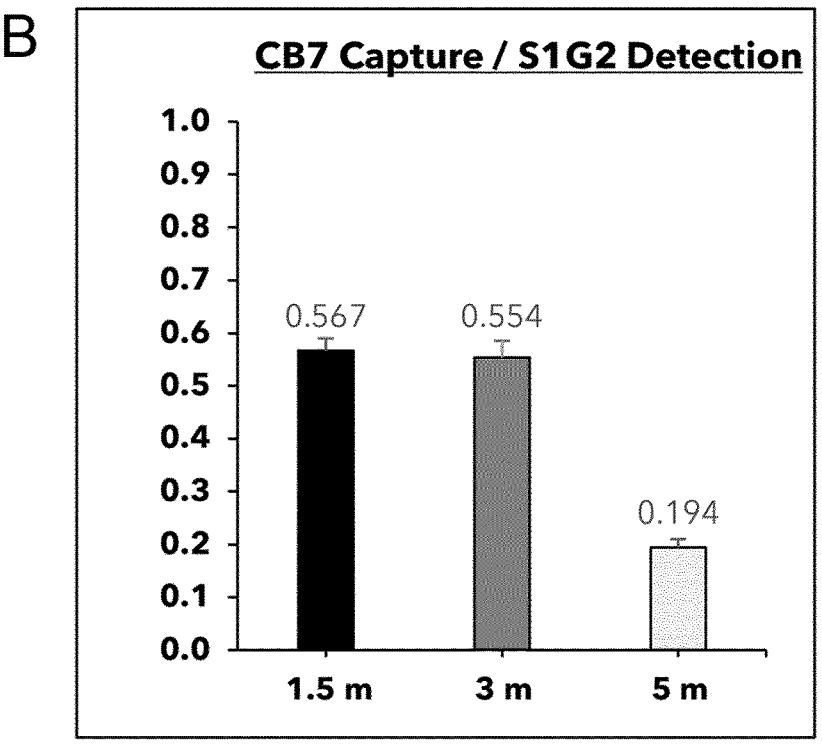
Fig. 46

ANTI-TAU ANTIBODIES AND METHODS OF USE THEREOF

The invention relates to specific binding molecules, such as antibodies, directed to key epitopes of tau. The specific binding molecules of the invention find applications in diagnostics and therapeutics of tauopathies including Alzheimer's disease.

Disorders related to tau are collectively referred to as neurodegenerative tauopathies. Alzheimer's disease (AD) is part of this group of neurodegenerative diseases. Conditions of dementia such as Alzheimer's disease (AD) are frequently characterised by a progressive accumulation of intracellular and/or extracellular deposits of proteinaceous structures such as β-amyloid plaques and neurofibrillary tangles (NFTs) composed of tau, in the brains of affected patients. The appearance of tau aggregation lesions largely correlates with pathological neurofibrillary degeneration and brain atrophy, as well as with cognitive impairment. In AD, tau protein self-assembles to form paired helical filaments (PHFs) and straight filaments that constitute the neurofibrillary tangles within neurons and dystrophic neurites in the brain. Protein misfolding to form amyloid fibrils is a hallmark of many different diseases collectively known as the amyloidoses, each of which is characterised by a specific precursor protein.

The long history of research into the causes of AD and other protein conformational disorders has not led to the hoped-for major advances in diagnostics or therapeutics. One reason for the limited progress is thought to be a lack of high-affinity specific binding molecules targeted to key epitopes of tau. The present inventors address this shortcoming by the creation of the specific binding molecules disclosed herein. The disclosed specific binding molecules are derived from antibodies isolated from sheep immunised with full length tau protein and a truncated tau fragment from the core of the PHF. The use of sheep as a source of specific binding molecules is thought to have contributed to the high affinity of the specific binding molecules of the invention.

SUMMARY OF THE INVENTION

According to a first aspect, the invention provides a specific binding molecule that binds to an epitope within SEQ ID NO: 1 with a binding affinity greater than the binding affinity with which antibody mAb423 binds to an epitope within SEQ ID NO: 1.

According to a second aspect, the invention provides a composition comprising a specific binding molecule according to the first aspect of the invention, wherein at least 90% of the specific binding molecules in the composition that bind an epitope within SEQ ID NO: 1 bind with a $K_D$ of less than 25 nM.

According to a third aspect, the invention provides a nucleic acid molecule comprising a nucleic acid sequence encoding a specific binding molecule according to the first aspect of the invention.

According to a fourth aspect, the invention provides a construct comprising a nucleic acid molecule of the third aspect of the invention.

According to a fifth aspect, the invention provides a vector comprising a nucleic acid molecule of the third aspect of the invention or a construct of the fourth aspect of the invention.

According to a sixth aspect, the invention provides a host cell comprising a nucleic acid molecule of the third aspect of the invention, a construct of the fourth aspect of the invention or a vector of the fifth aspect of the invention.

According to a seventh aspect, the invention provides a method of preparing a specific binding molecule according to the first aspect of the invention comprising:
  i) introducing into a host cell a nucleic acid molecule of the third aspect of the invention, a construct of the fourth aspect of the invention or a vector of the fifth aspect of the invention;
  ii) expressing the nucleic acid molecule such that the specific binding molecule is produced; and
  iii) collecting the specific binding molecule, preferably by purification.

According to an eighth aspect, the invention provides a specific binding molecule obtainable by a method according to the seventh aspect of the invention.

According to a ninth aspect, the invention provides a pharmaceutical composition comprising a specific binding molecule according to the first aspect of the invention or a composition according to a second aspect of the invention and one or more pharmaceutically acceptable diluents, carriers or excipients.

According to a tenth aspect, the invention provides a specific binding molecule according to the first aspect of the invention, a composition according to the second aspect of the invention or a pharmaceutical composition according to the ninth aspect of the invention for use in therapy.

According to an eleventh aspect, the invention provides a specific binding molecule according to the first aspect of the invention, a composition according to the second aspect of the invention or a pharmaceutical composition according to the ninth aspect of the invention for use in treatment of a tauopathy.

According to a twelfth aspect, the invention provides a method of treating a tauopathy, comprising administering to a subject in need thereof a specific binding molecule according to the first aspect of the invention, a composition according to the second aspect of the invention or a pharmaceutical composition according to the ninth aspect of the invention.

According to a thirteenth aspect, the invention provides an in vitro method of inhibiting aggregation of a tau protein or a fragment thereof comprising contacting the tau protein or a fragment thereof with a specific binding molecule according to the first aspect of the invention.

According to a fourteenth aspect, the invention provides an in vitro method for detecting a tau protein or a fragment thereof in a sample comprising contacting the sample with a specific binding molecule of the first aspect of the invention.

According to a fifteenth aspect, the invention provides a diagnostic method comprising contacting a sample with a specific binding molecule of the first aspect of the invention.

According to a sixteenth aspect, the invention provides a diagnostic device for use in a method according to the fifteenth aspect of the invention.

According to a seventeenth aspect, the invention provides a kit comprising a specific binding molecule according to the first aspect of the invention and reagents for detecting a tau protein or a fragment thereof in a sample.

Reference is made to a number of Figures as follows:

Figure 1:
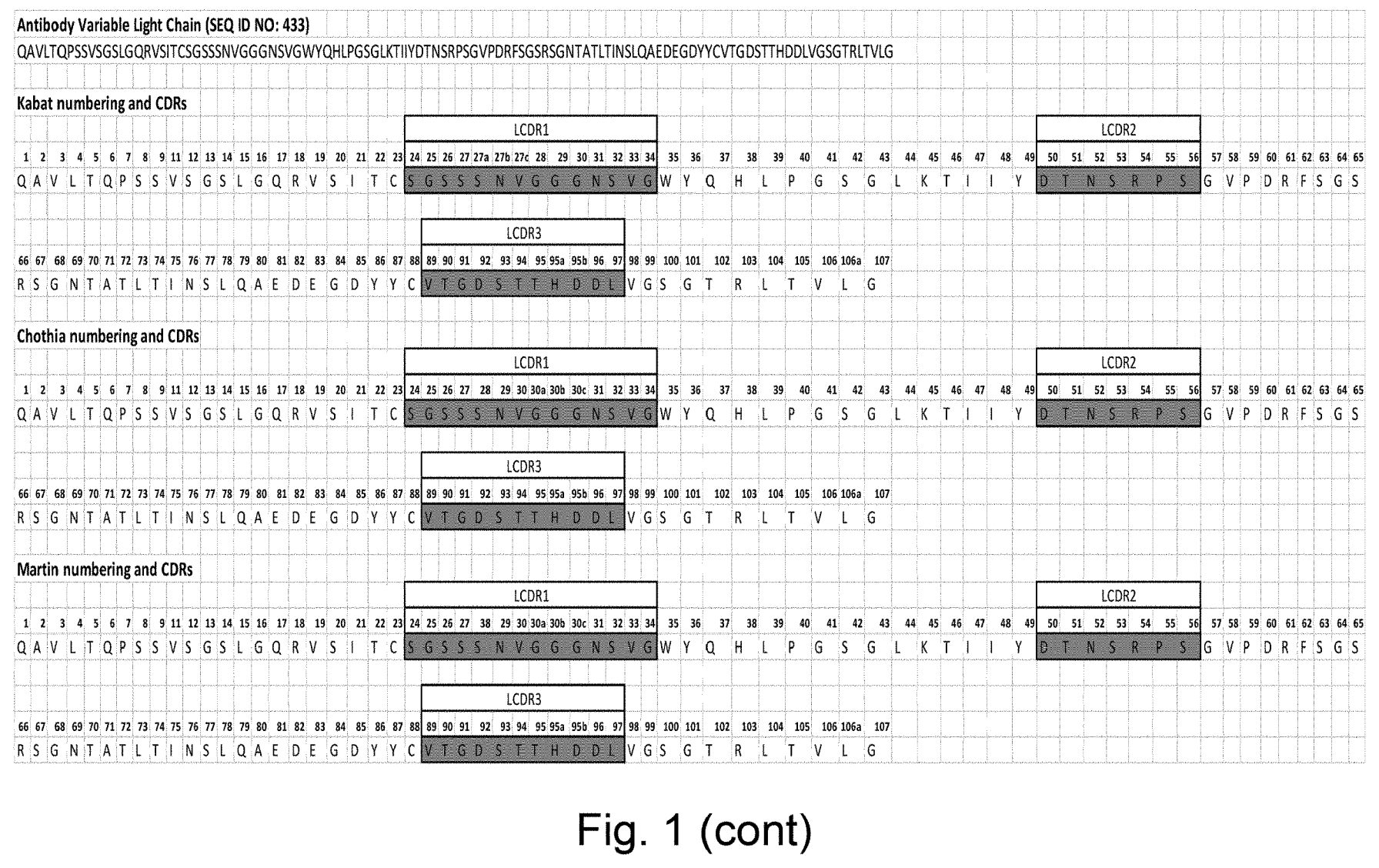

FIG. 1. Alternative CDR definitions for S1D12 according to Kabat, Chothia and Martin.

Figures 2, 3:
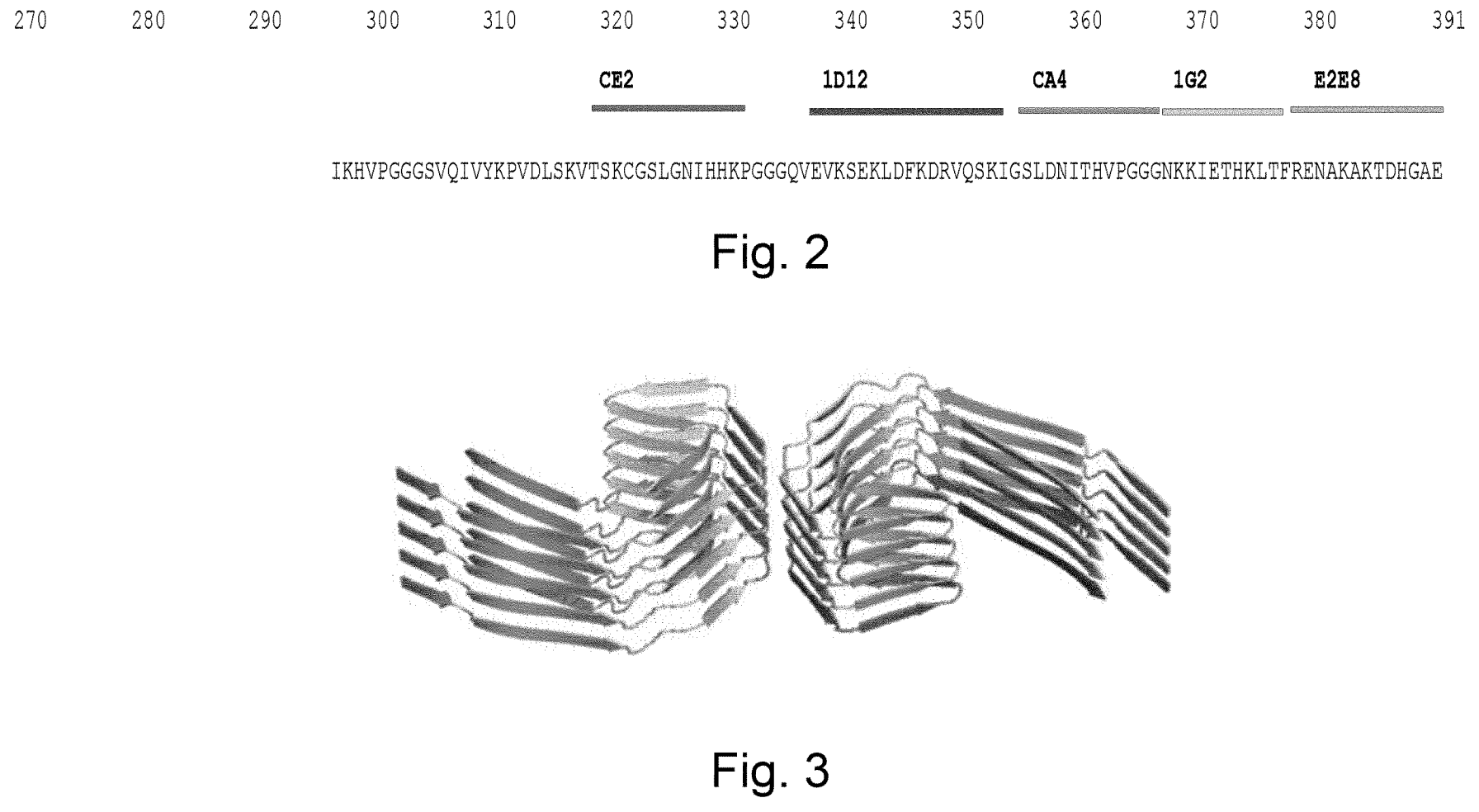

FIG. 2. The sequence (SEQ ID NO:4) of the predominant fragment isolated from the proteolytically stable core of the paired helical filament (PHF; Wischik et al., 1988). This fragment (referred to 'dGAE') comprises residues 296-391 of full-length tau and encompasses the fragment identified by cryo-electron-microscopy (residues 308-378) as constituting the PHF core (Fitzpatrick et al., 2017) and shown in FIG. 3. The locations of the epitopes of the selected antibodies/scAbs are also shown FIG. 3. The PHF core shown in the context of a PHF.

FIG. 4. The same core sequence (SEQ ID NO:4) and locations of corresponding epitopes in relation to the fundamental C-shaped subunit structure of the core. The 1D12 epitope forms the critical fold or "hairpin" of the C-shaped subunit.

FIG. 5. Molecular modelling showing how a new dGAE unit progressively unfolds and becomes aligned with the structure of the existing oligomer.

Figure 6:
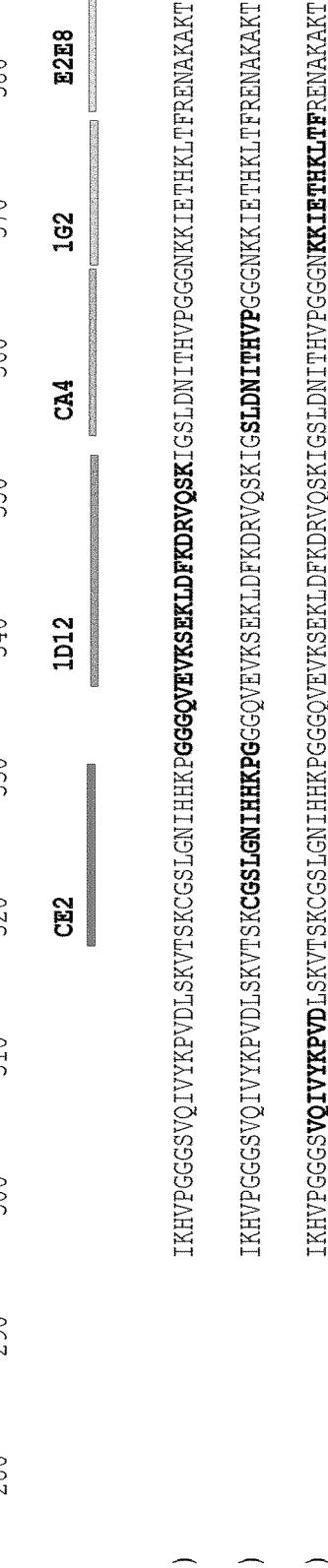

FIG. 6. The attachment sequence (SEQ ID NO:4) shown in terms of 3 stages corresponding to progressive binding of key segments of dGAE and their epitopes into the oligomer. As can be seen, the hinge region recognised by 1D12 is the primary site of attachment, followed by progressive symmetrical binding of the other domains.

Figure 7:
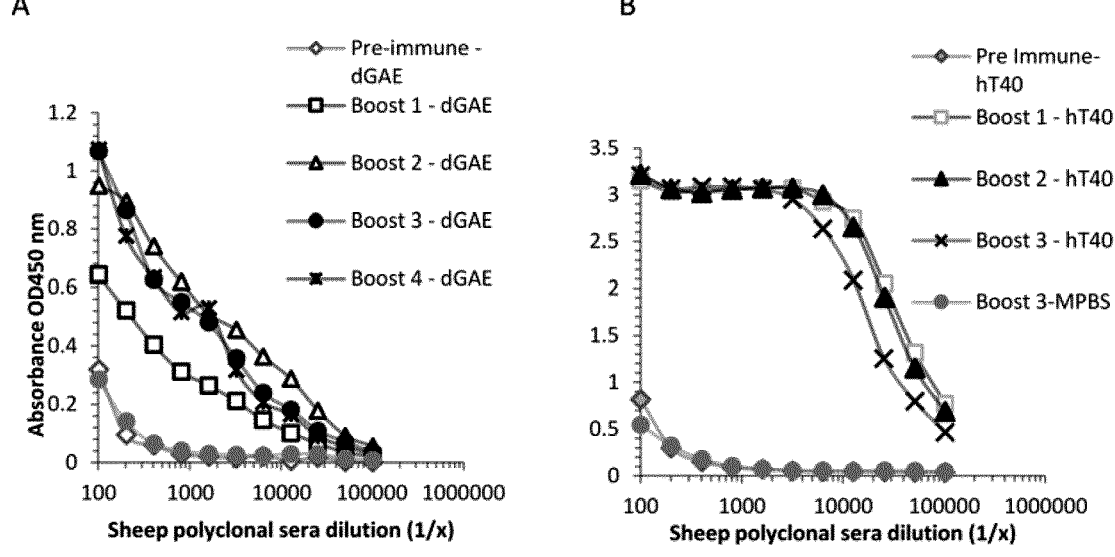

FIG. 7. (A) dGAE antigen specific immune response of sheep polyclonal sera after various rounds of immunisation. (B) hT40 antigen specific immune response of sheep polyclonal sera after various rounds of immunisation. MPBS coated wells included as negative control.

FIG. 8. ELISA based characterisation of the cross-reactivity of 'E' group scAbs using hT40, dGA and dGAE antigens (A) E1E8 scAb, (B) E2B7 scAb, (C) E2C5 scAb, (D) E2E8 scAb, (E) E1B8 scAb. All these scAbs except E1B8 showing specific dGAE binding and therefore requires C terminally accessible '391E' epitope for immnunoreactivity. E1B8 cross-reacts with dGA and a detailed mapping of its binding region is shown in FIG. 9

Figure 9:
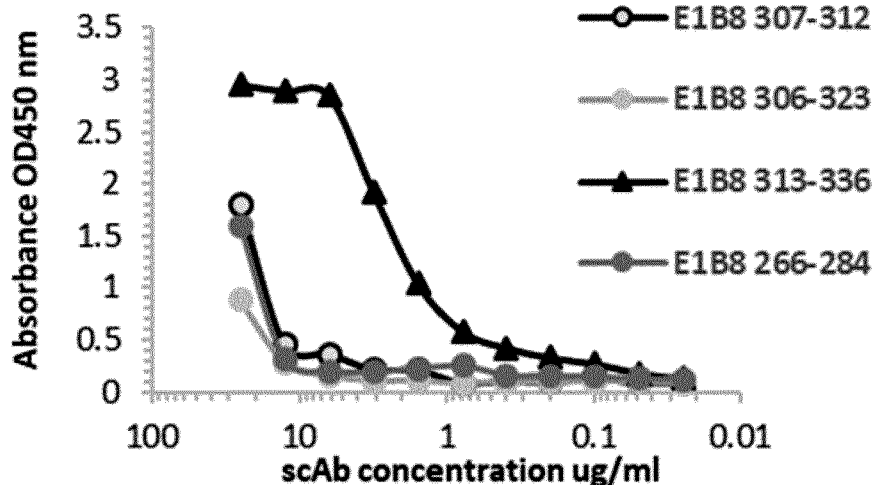

FIG. 9. Detailed mapping of E1B8 scAb which shows specific binding to the tau peptide representing amino acids from 313-336 on hT40 protein.

FIG. 10. ELISA based characterisation of the cross-reactivity of 'NS' group scAbs using various short tau fragments with numbers corresponding to hT40 amino acid residues. (A) 337-368, (B) 275-305 (C) 266-359 (R1-3) (D) 360-378 (E) 369-391, (F) 369-390. A summary of specific NS scAb binding to these shorter antigens are shown in Table 16

Figure 11:
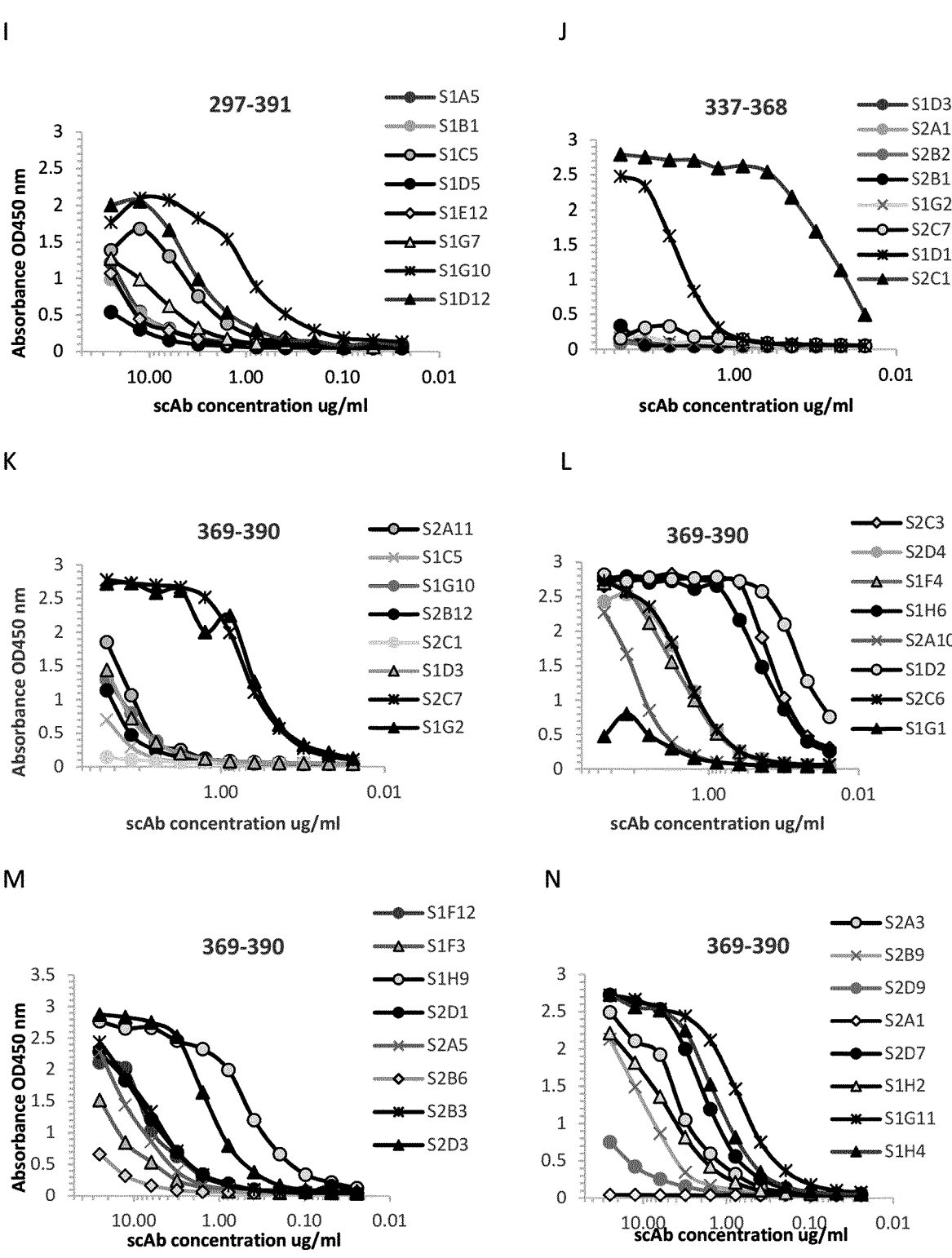
Figure 11:
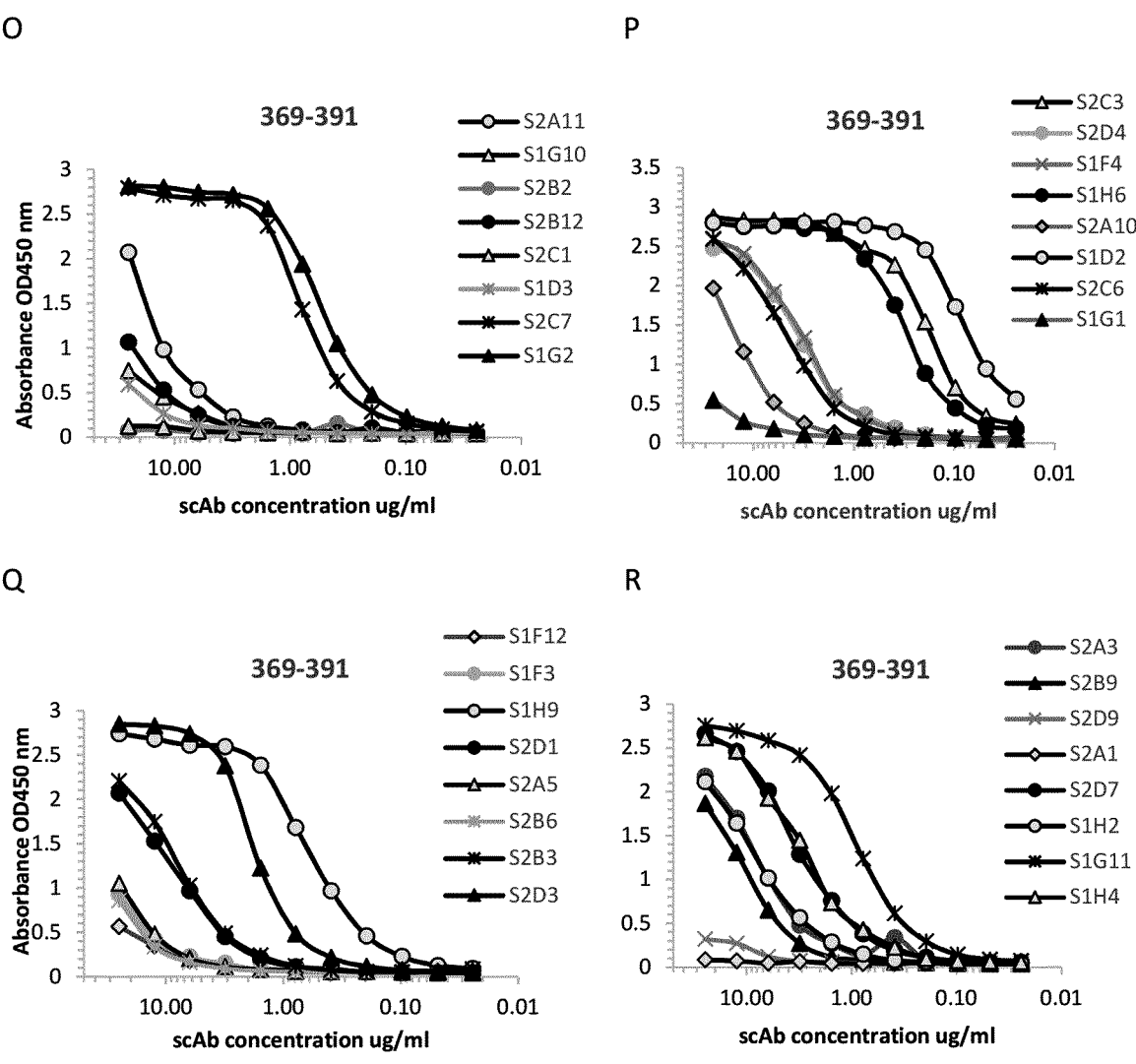

FIG. 11. ELISA based characterisation of the cross-reactivity of 'S' group scAbs using various short tau fragments numbered according to their corresponding amino acid residues on hT40 molecule. (A) 186-350, (B) 275-305 (C-D) 266-359 (R1-3), (E-I) 297-391, (J) 360-378 (K-N) 369-391, (O-R) 369-390. A summary of specific 'S' scAb binding to these shorter antigens are shown in Table 16

Figure 12:
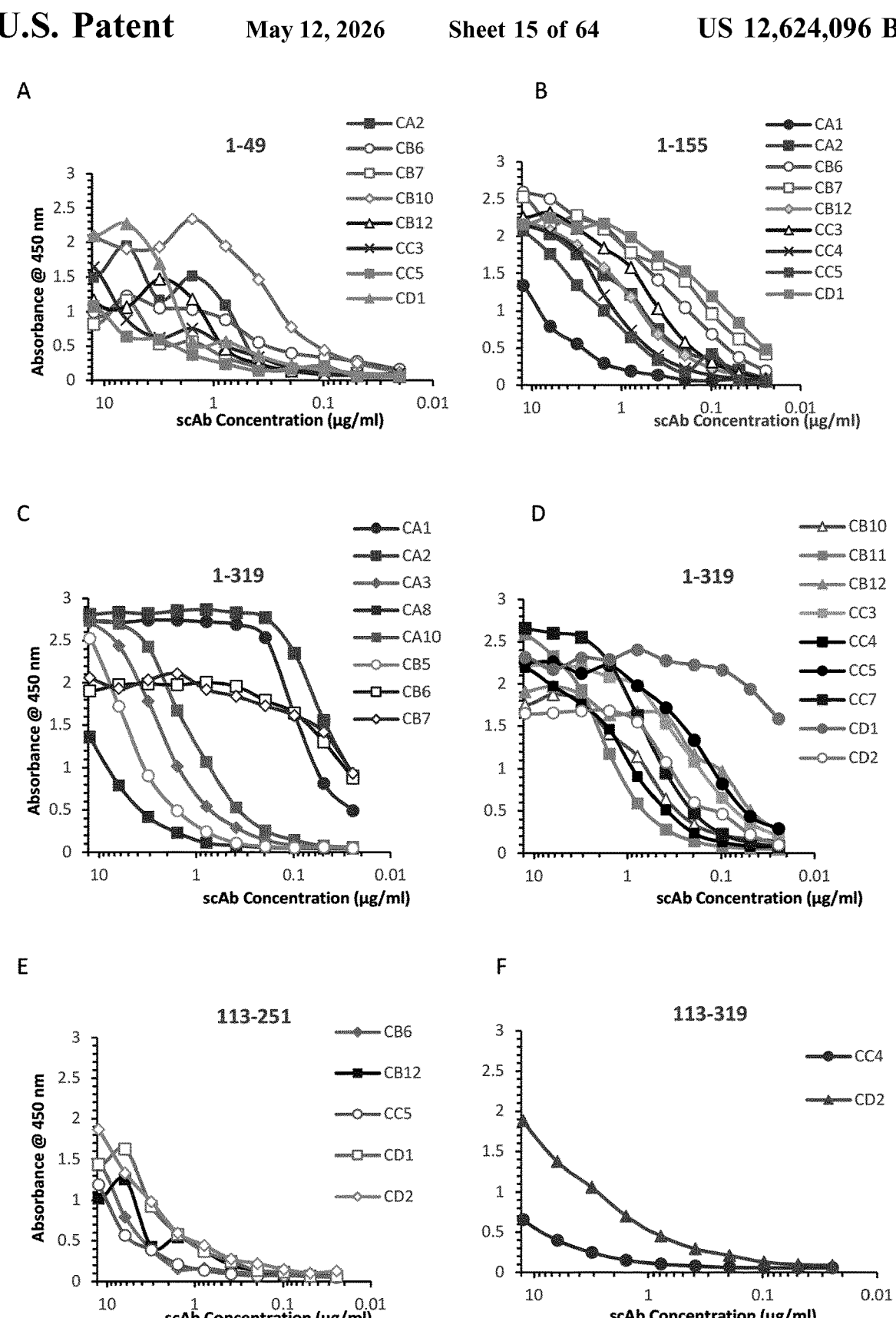
Figure 12:
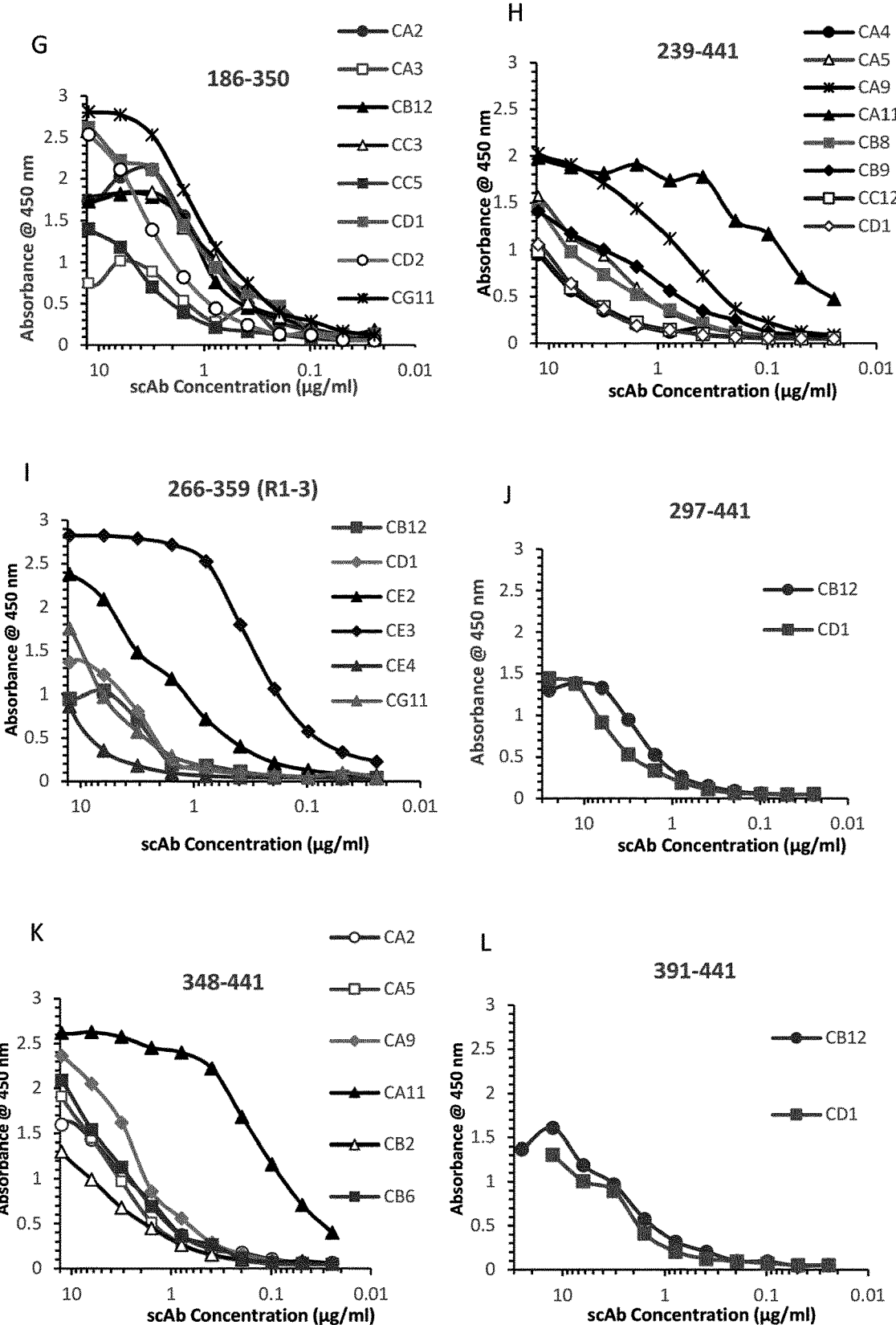

FIG. 12. ELISA based characterisation of the cross-reactivity of 'C' group scAbs using various short tau fragments numbered according to their corresponding amino acid residues on hT40 molecule. (A) 1-49, (B) 1-155 (C-D) 1-319, (E) 113-251 (F) 113-319, (G) 186-350 (H) 239-441 (I) 266-359 (R1-3), (J) 297-441. (K) 348-441, (L) 391-441. A summary of specific 'C' scAb binding to these shorter antigens are shown in Table 17

Figure 13:
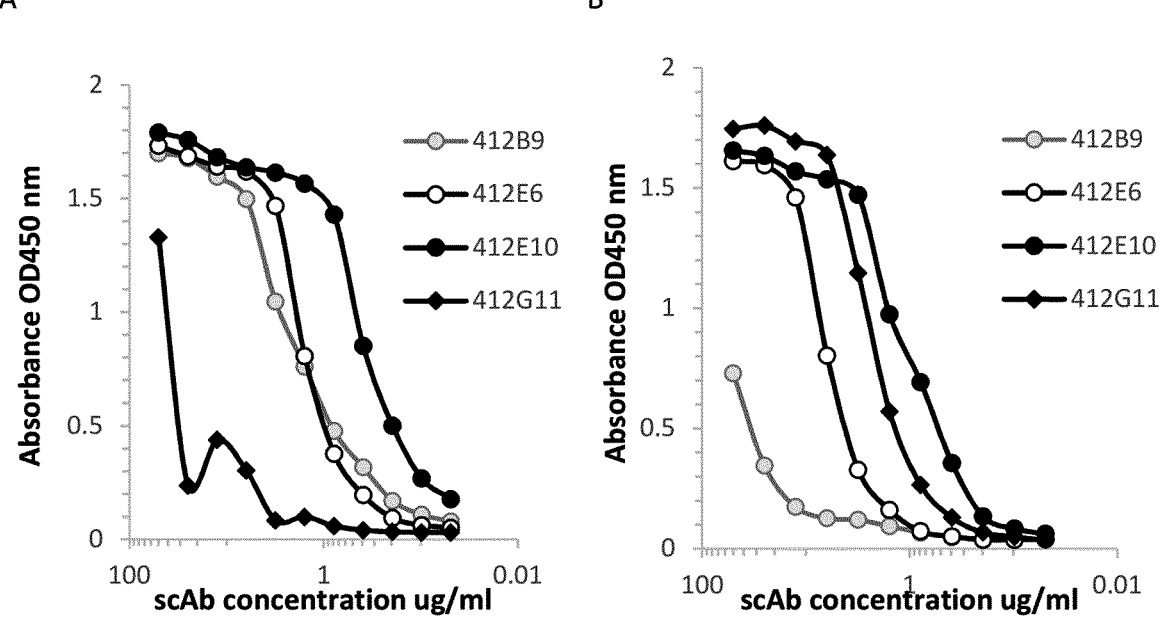

FIG. 13. Cross-reactivity of '412' group scAbs to hT40. (A) showing binding of scAbs to biotinylated 412-441 peptide which was used as the antigen for the selection of C terminal binders. (B) binding profiles of four scAbs which were shown to be cross-reactive in hT40 binding ELISA.

FIG. 14. ELISA based characterisation of the cross-reactivity of '3a' & '3b' group scAbs using various short tau fragments numbered according to their corresponding amino acid residues on hT40 molecule. (A) 1-49, (B) 1-111 (C-D)

1-155, (E) 113-251. A summary of specific '3a' & '3b' group scAbs binding to these shorter antigens are shown in Table 18

FIG. 15. (A) Immunoreactivity of CE2 scAb to the parent peptide and a series of alanine substituted residues at positions indicated in table 19. (B) Percentage binding of 500 nM scAb to each of these ASM peptides with respect to the parent peptide.

FIG. 16. (A-B) Immunoreactivity of S1D12 scAb to the parent peptide and a series of alanine substituted residues at positions indicated in table 20. (C) Percentage binding of 500 nM scAb to each of these ASM peptides with respect to the parent peptide.

Figure 17:
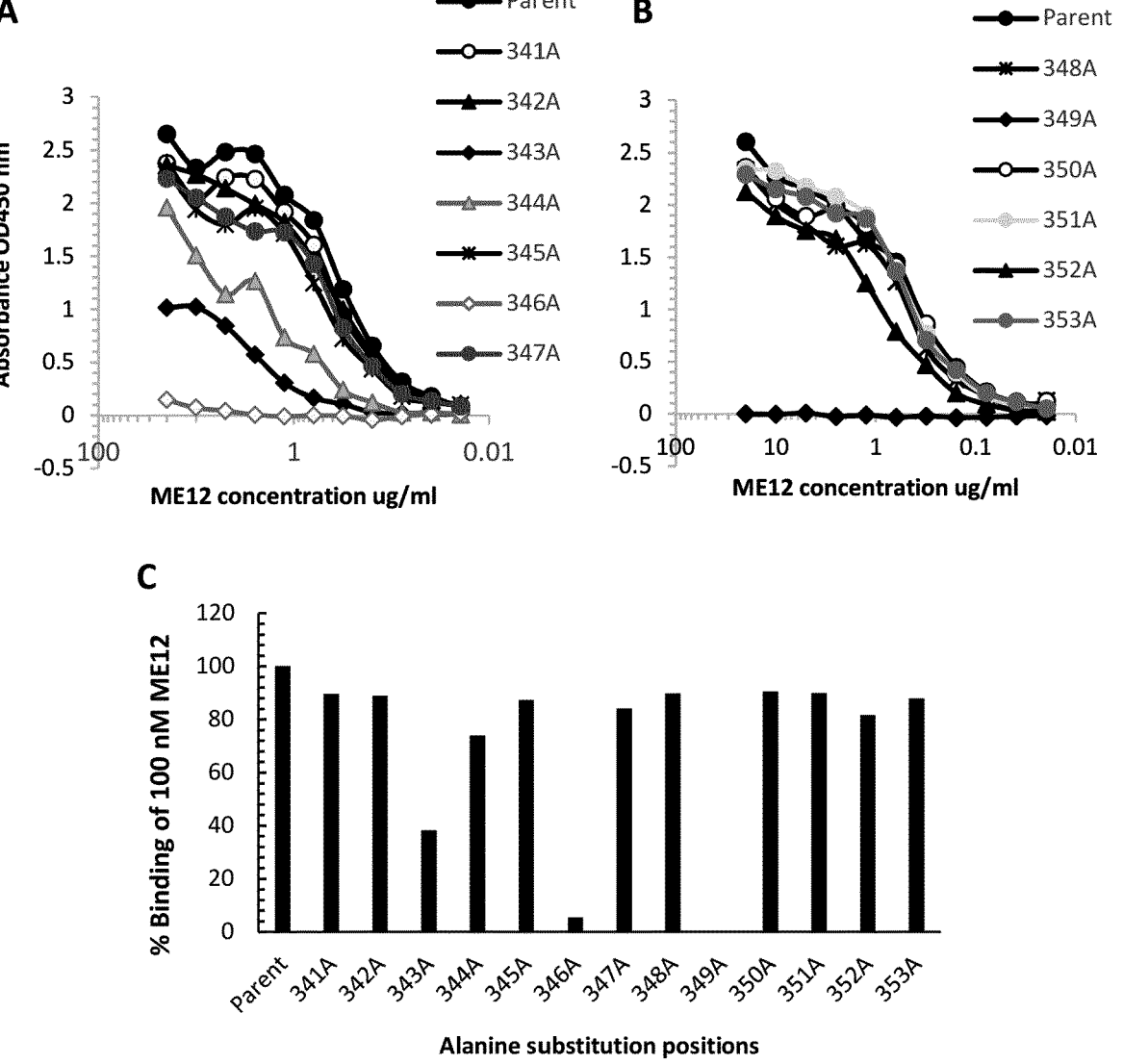

FIG. 17. (A-B) Immunoreactivity of ME12 scAb to the parent peptide and a series of alanine substituted residues at positions indicated in table 20. (C) Percentage binding of 100 nM scAb to each of these ASM peptides with respect to the parent peptide.

FIG. 18. (A) Immunoreactivity of CA4 scAb to the parent peptide and a series of alanine substituted residues at positions indicated in table 21. (B) Percentage binding of 500 nM scAb to each of these ASM peptides with respect to the parent peptide.

FIG. 19. (A-B) Immunoreactivity of S1G2 scAb to the parent peptide and a series of alanine substituted residues at positions indicated in table 22. (C) Percentage binding of 500 nM scAb to each of these ASM peptides with respect to the parent peptide.

FIG. 20. Percentage binding of various 367-379 region scAbs to ASM peptides with respect to the parent peptide. The scAbs tested included (A) S1B1, (B) CA12, (C) CB2, (D) CB8, (E) S1D9, (F) S1G10, (G) S2C6, (H) S1F4, (I) MC5, (J) MD12. The critical binding residues of these scAbs are similar to the representative clone S1G2, where alanine substitution in positions 370, 373, 374, 377 or 378 resulted in reduction in antibody binding.

Figure 21:
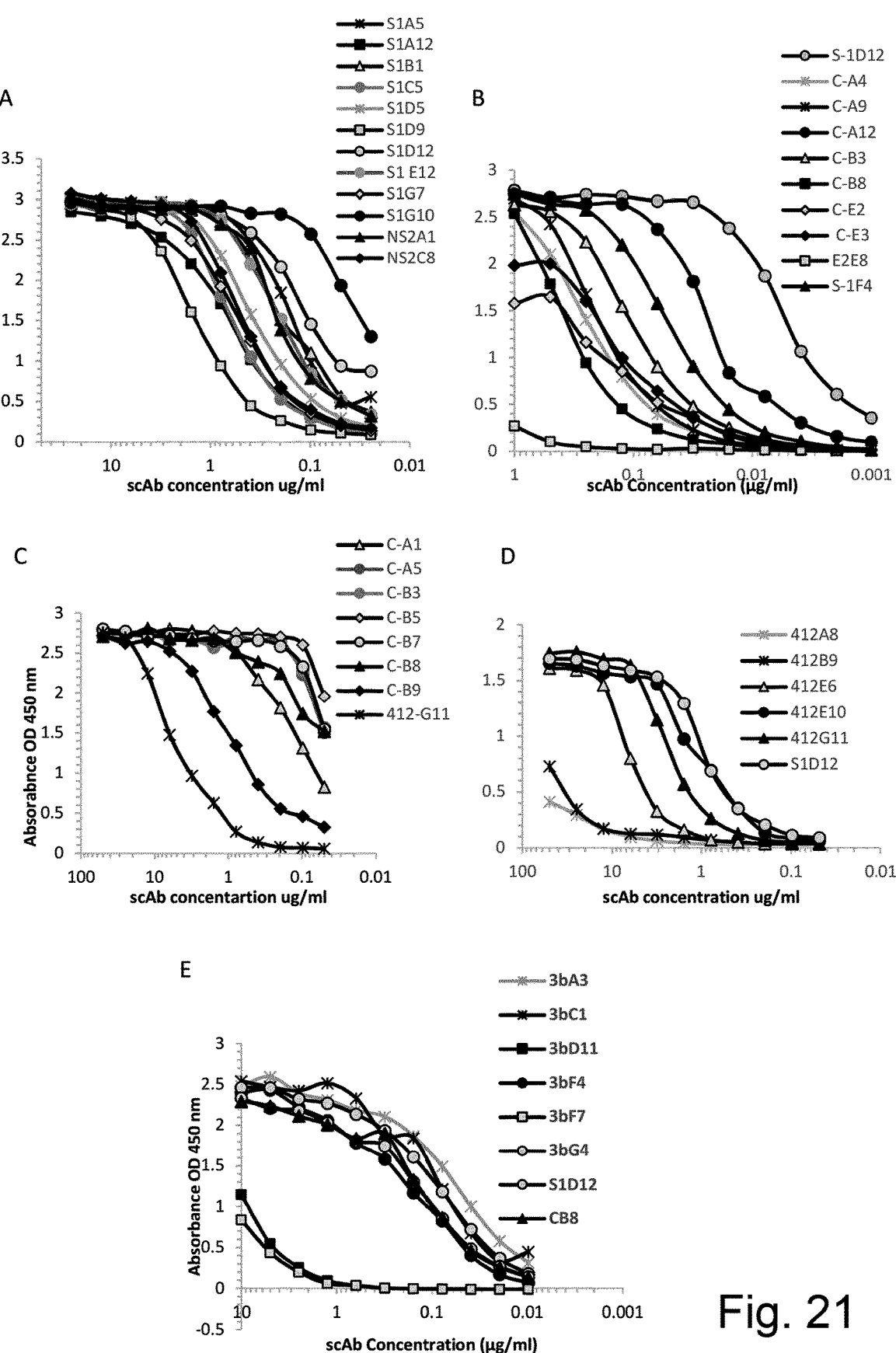

FIG. 21. Ranking of the binding affinities of anti-Tau scAbs using hT40, scAbs with known kD values such as NS2A1 and S1D12 were used to rank the relative binding affinities of test scAbs and those with similar binding profiles were shortlisted and selected for Biacore analysis (A) 'S' group clones, (B-C) 'C' clones, (D) '412' clones (E) '3a' clones FIG. 22. Schematic representation of the sandwich ELISA format for calculating the LoDs of various antibody pairs.

Figure 23:
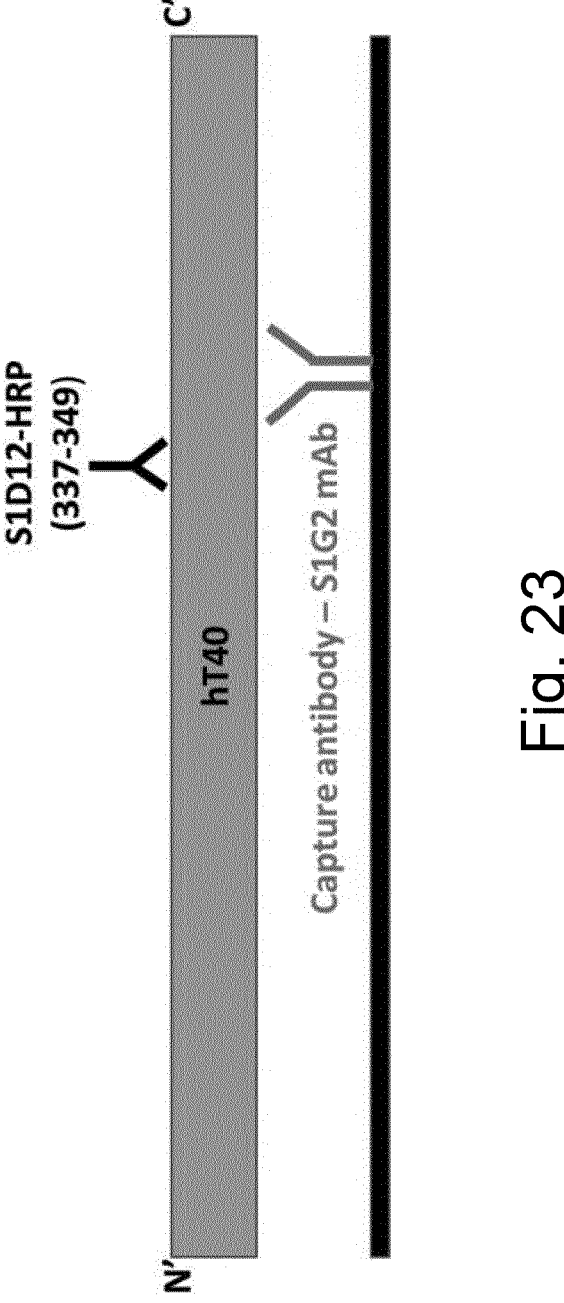

FIG. 23. Schematic representation of the sandwich ELISA format for calculating the LoDs using S1G2 mAb as the capture antibody and HRP conjugated S1D12 mAb for detection FIG. 24. Sandwich ELISA graph showing the LoD achieved using S1G2 mAb as the capture antibody and HRP labelled S1D12 mAb detection. Antibody binding was measured using chemiluminescence and the LOD for hT40 is ~1 ng/ml for this assay set up.

Figure 25:
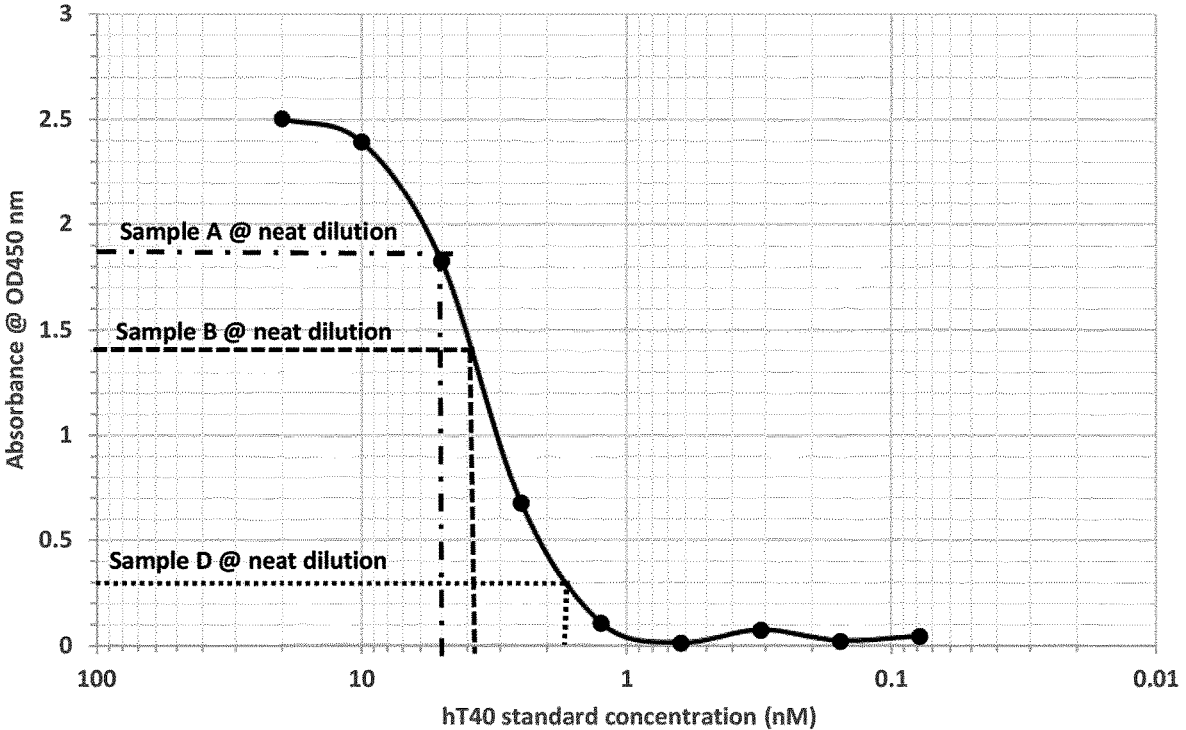

FIG. 25. ELISA #1 hT40 standard curve generated using S1D12 mAb capture and CB7 scAb detection. Concentrations of the four spiked samples—Sample A, B, C and D were determined by plotting their respective absorbance values on this standard curve. Sample C did not generate a binding signal and therefore confirmed the absence of any tau species with N terminal region in this mix. Concentrations and types of tau species deduced from this assay is given in table 29.

Figure 26:
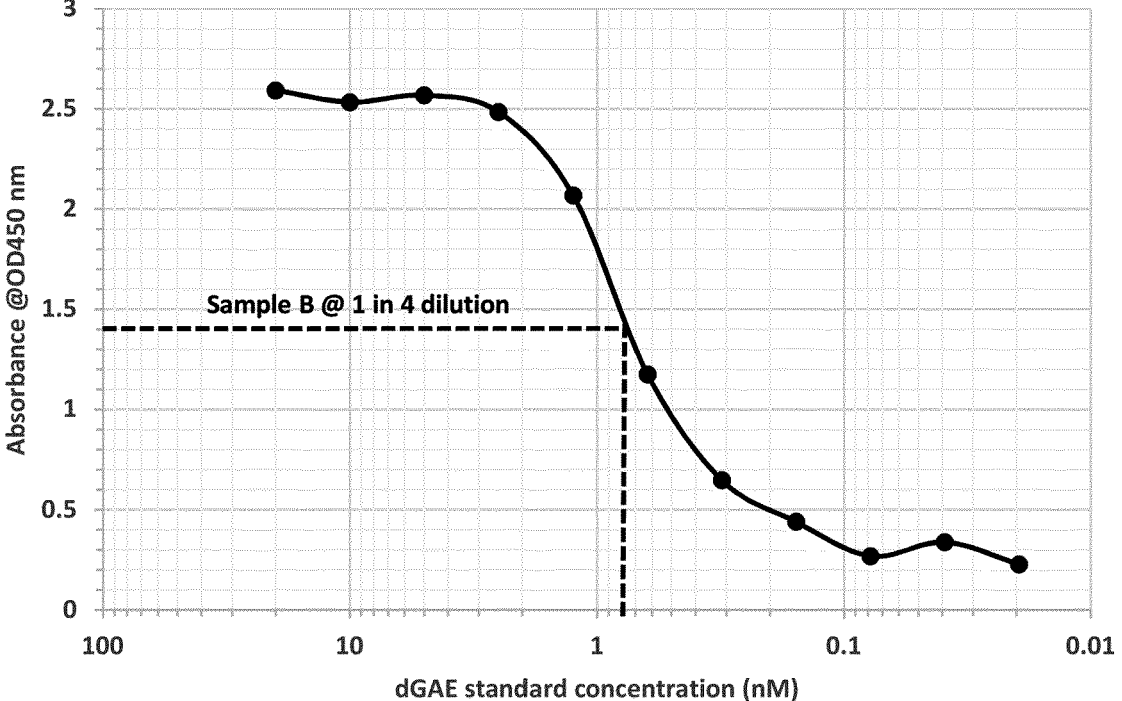

FIG. 26. ELISA #2 dGAE standard curve generated using S1D12 mAb capture and E2E8 scAb detection. Concentrations of the four spiked samples—Sample A, B, C and D were determined by plotting their respective absorbance values on this standard curve. Samples A, C and D did not generate any binding signals and therefore confirmed the absence of dGAE species within these mixes. Concentrations and types of tau species deduced from this assay is given in table 29.

Figure 27:
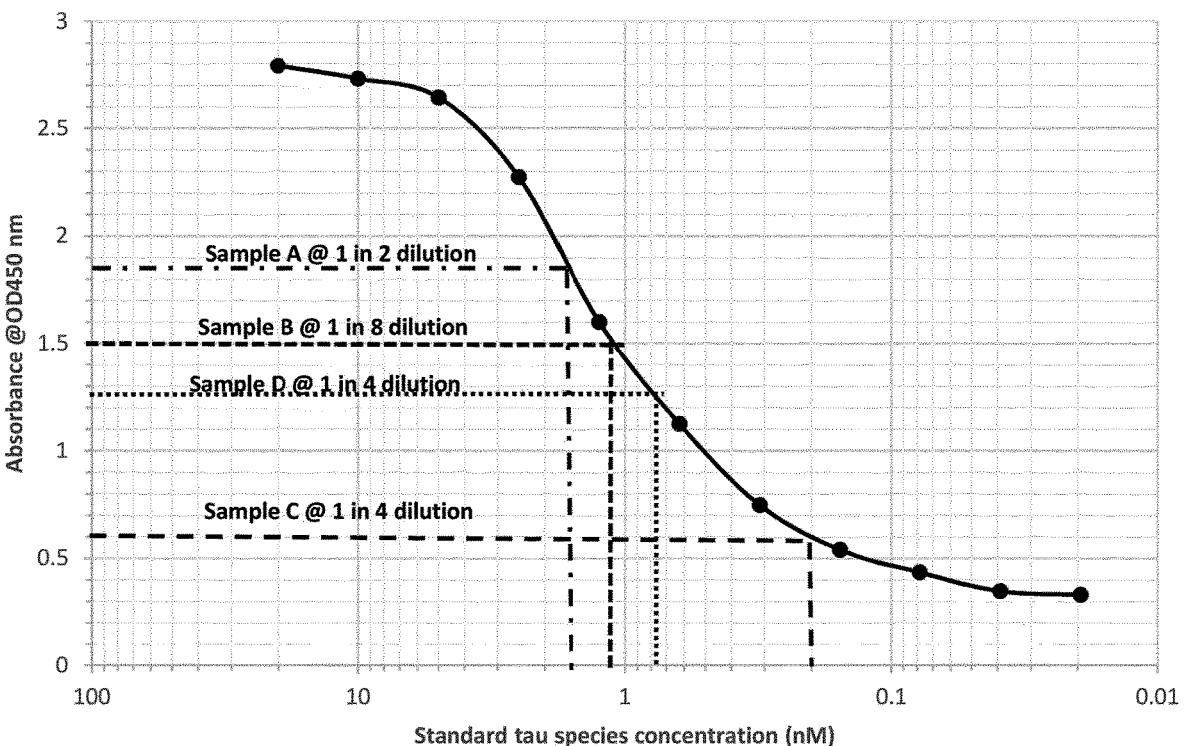

FIG. 27. ELISA #3 Average standard curve generated using S1D12 mAb capture and S1G2 scAb detection. Concentrations of the four spiked samples—Sample A, B, C and D were determined by plotting their respective absorbance values on this standard curve. Concentrations and types of tau species deduced from this assay is given in table 29.

Figure 28:
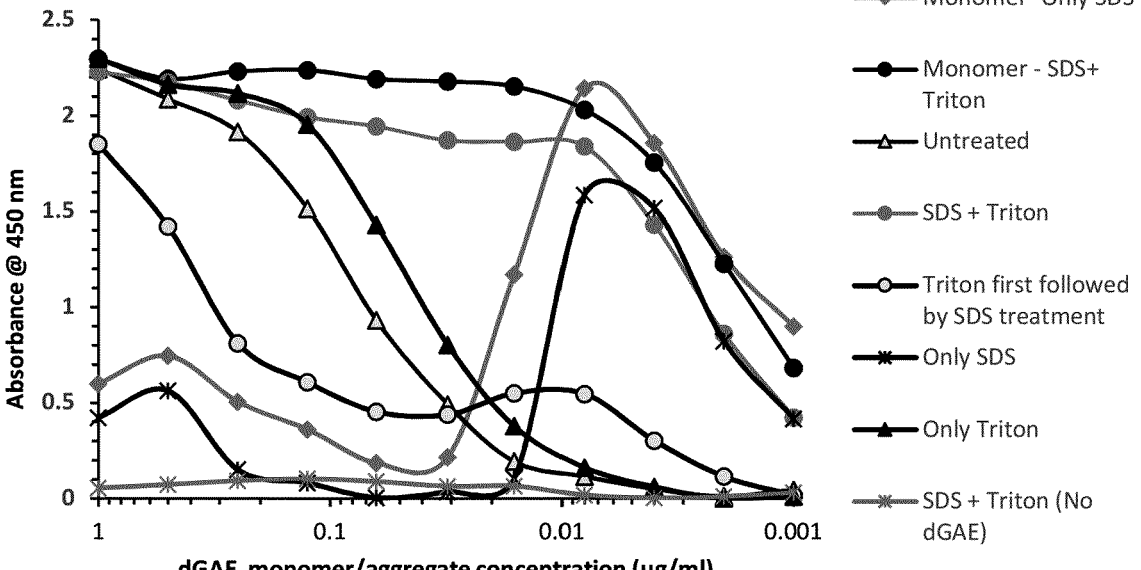

FIG. 28. Comparison of the binding profiles of various SDS (+/− Triton X-100) treated dGAE monomer or aggregates in a sandwich ELISA system. S1D12 mAb was used as the capture antibody and S1G2 as the detection scAb. Here the effect of SDS+Triton X-100 in restoring the immunoreactivity of is noticed. This mAb-scAb pairing can detect approximately 2 ng/ml dGAE aggregates in a simple sandwich ELISA.

Figure 29:
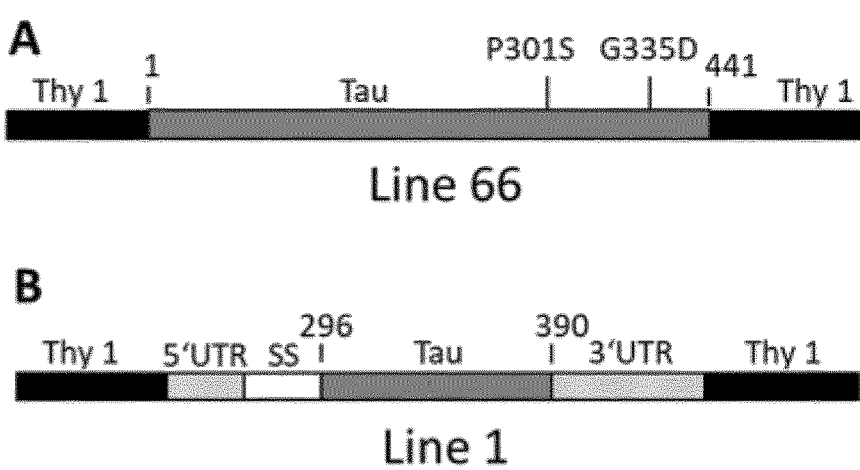

FIG. 29. A) L66 cDNA containing human tau (hT40) and the point mutations P301S and G335D (2N4R Tau, 441 amino acids) B) L1 cDNA codes for human tau amino acid residues 296-390 with a signal sequence and murine Thy1 expression sequences as described in Melis et al., 2015

Figure 30:
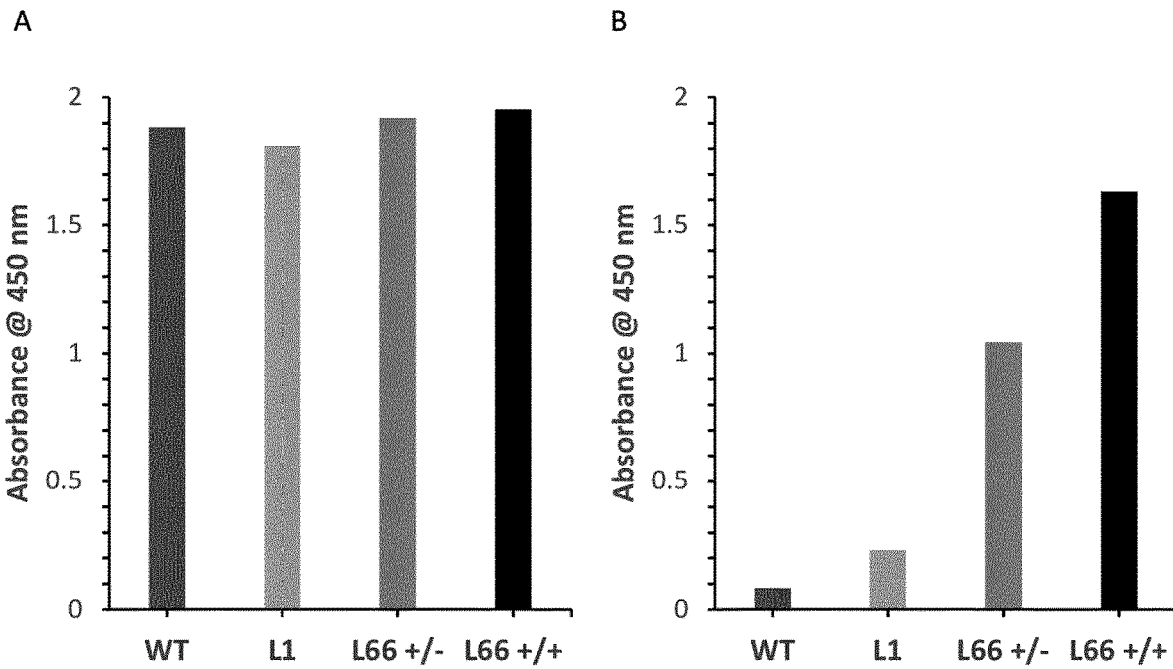

FIG. 30. (A) Detection of tau protein in 50 μg brain homogenate isolated from WT, L1. L66+/− and L66+/+ mice using S1D12mAb capture and S-1G2 scAb detection. All four samples have similar tau levels when detected using a core region specific antibody pairing (B) Detection of tau protein in 50 μg brain homogenate isolated from WT, L1, L66+/− and L66+/+ mice using S1D12mAb capture and CB7 scAb detection. N' terminally directed CB7 scAb can specifically detect human tau in Line66 homozygous and heterozygous samples and able to differentiate levels of expression between the two groups.

Figure 31:
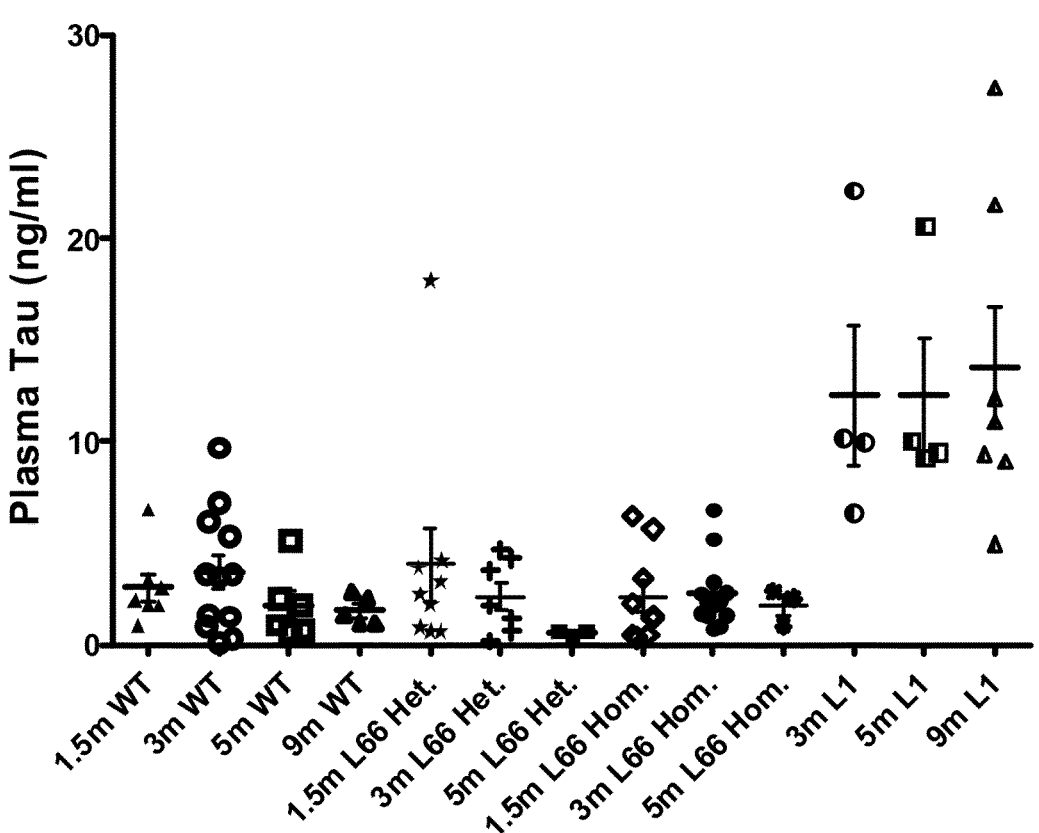

FIG. 31. Plasma tau levels in WT (5 month: 1.947 ng/ml), (9 month: 2.177 ng/ml); L66 (Both 5 month) (+/−: 0.567 ng/ml), (+/+: 1.937 ng/ml); and L1 (5 month: 12.355 ng/ml) (9 month 13.661 ng/ml). Data collected using S1D12 mAb capture and S1G2 scAb detection. Tau species concentrations were determined using standard curves of hT40 for WT and L66 and dGA (296-390) for L1.

FIG. 32. Detection of plasma tau levels in Line66+/+ mouse sample no: 23 at 1.5 months and comparison with age matched wild type mouse plasma using two different sandwich ELISA pairing. (A) Shows the chemiluminescent signal readings for Line66+/+ and wildtype mice using S1D12 mAb capture and CB7 scAb detection. (b) the signal readings for the same samples using S1D12 mAb capture and S1G2 scAb detection. Line66+/+ mouse shows at least 1000-fold increase in signal intensity compared to the wild type when using S1D12 mAb-CB7 scAb pairing which specifically detects N terminal hT40 in this sample.

Figure 33:
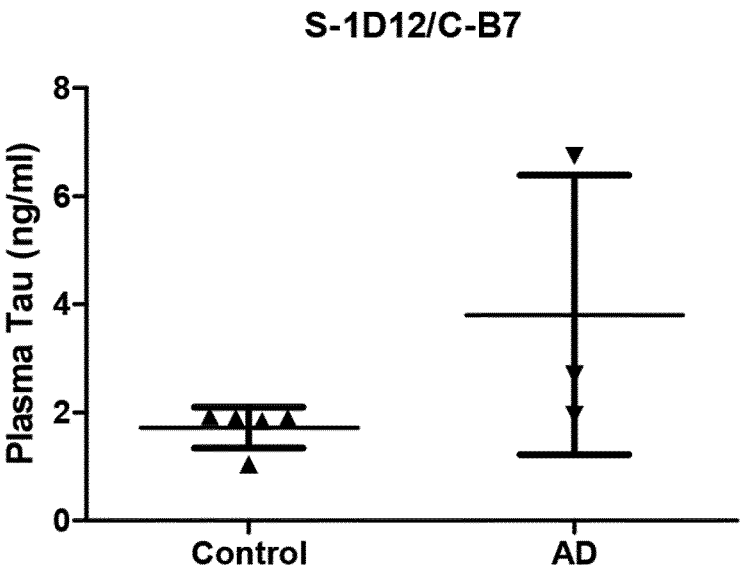

FIG. 33. Plasma tau levels in AD samples vs age matched controls using S1D12-S1G12 (core region) and S1D12-CB7 (N terminal) detection pairs.

Figure 34:
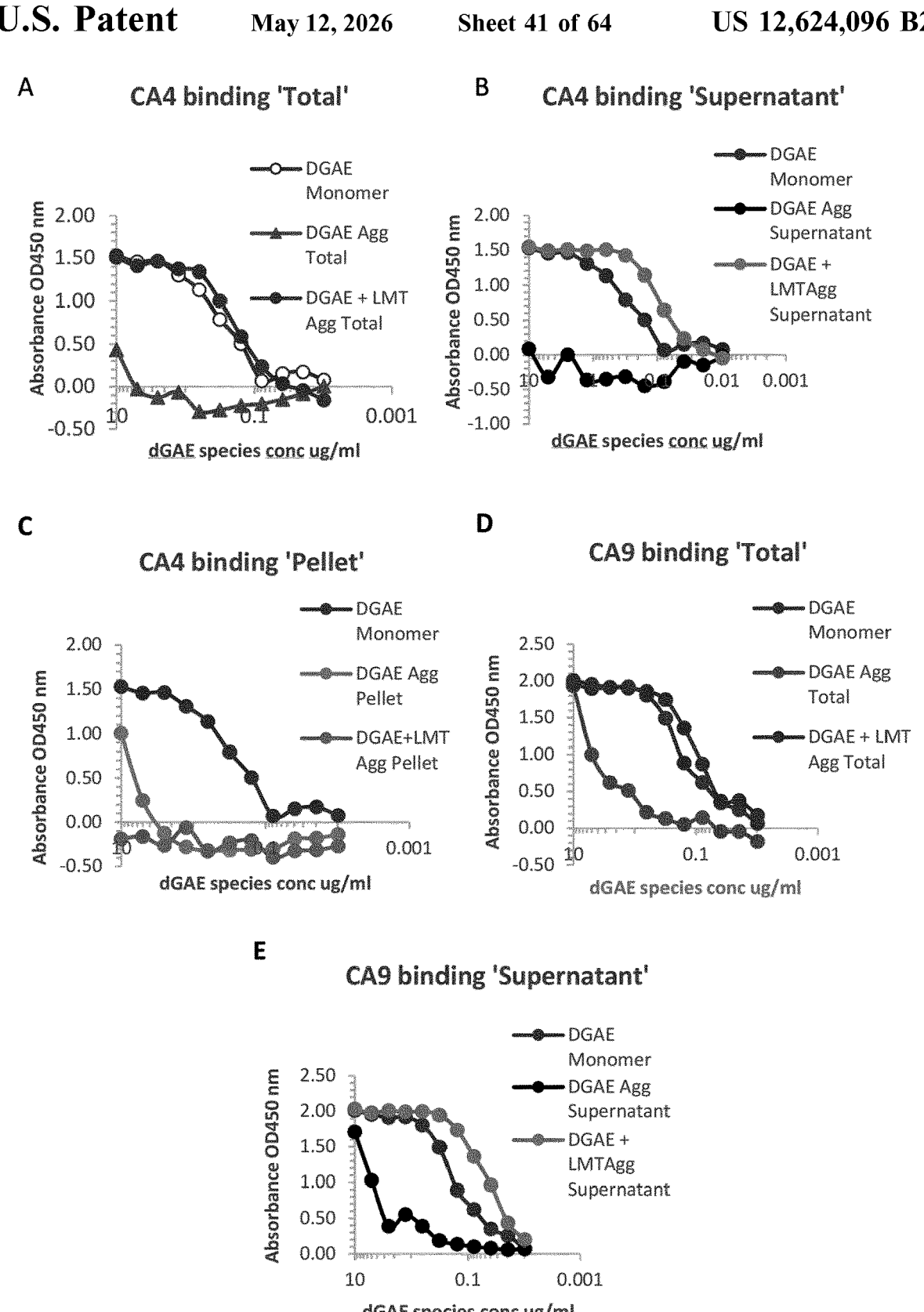
Figure 34:
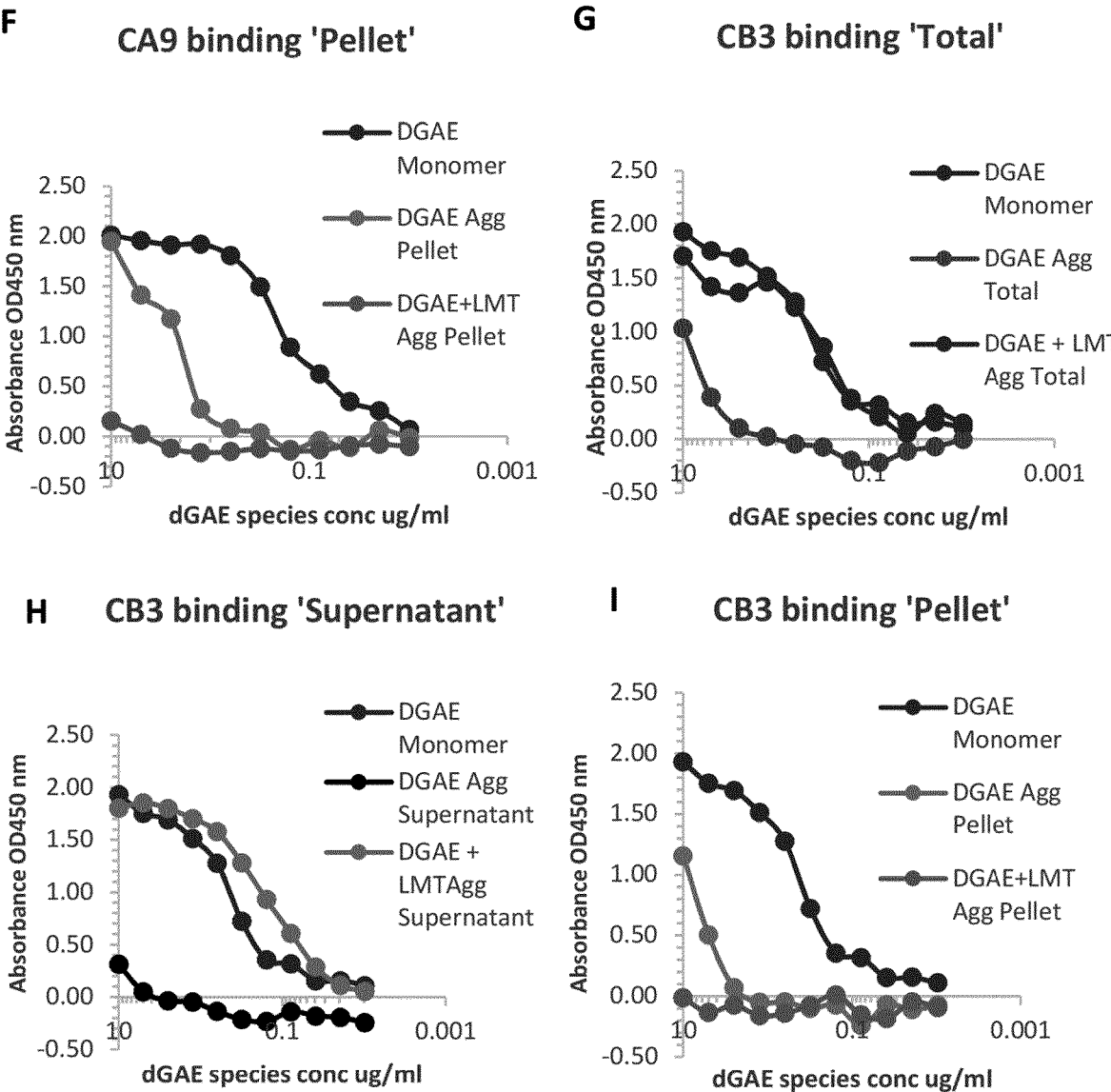
Figure 34:
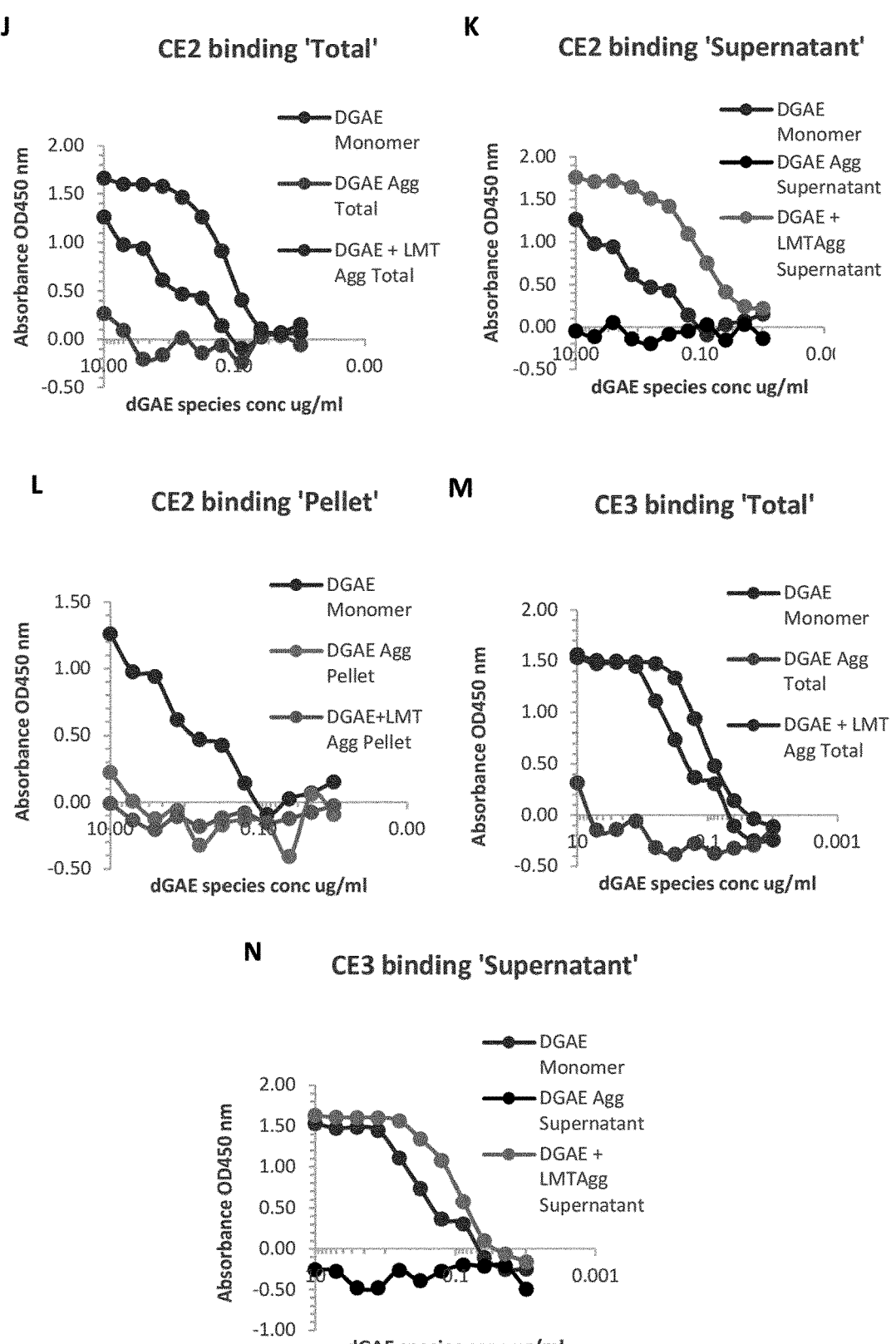
Figure 34:
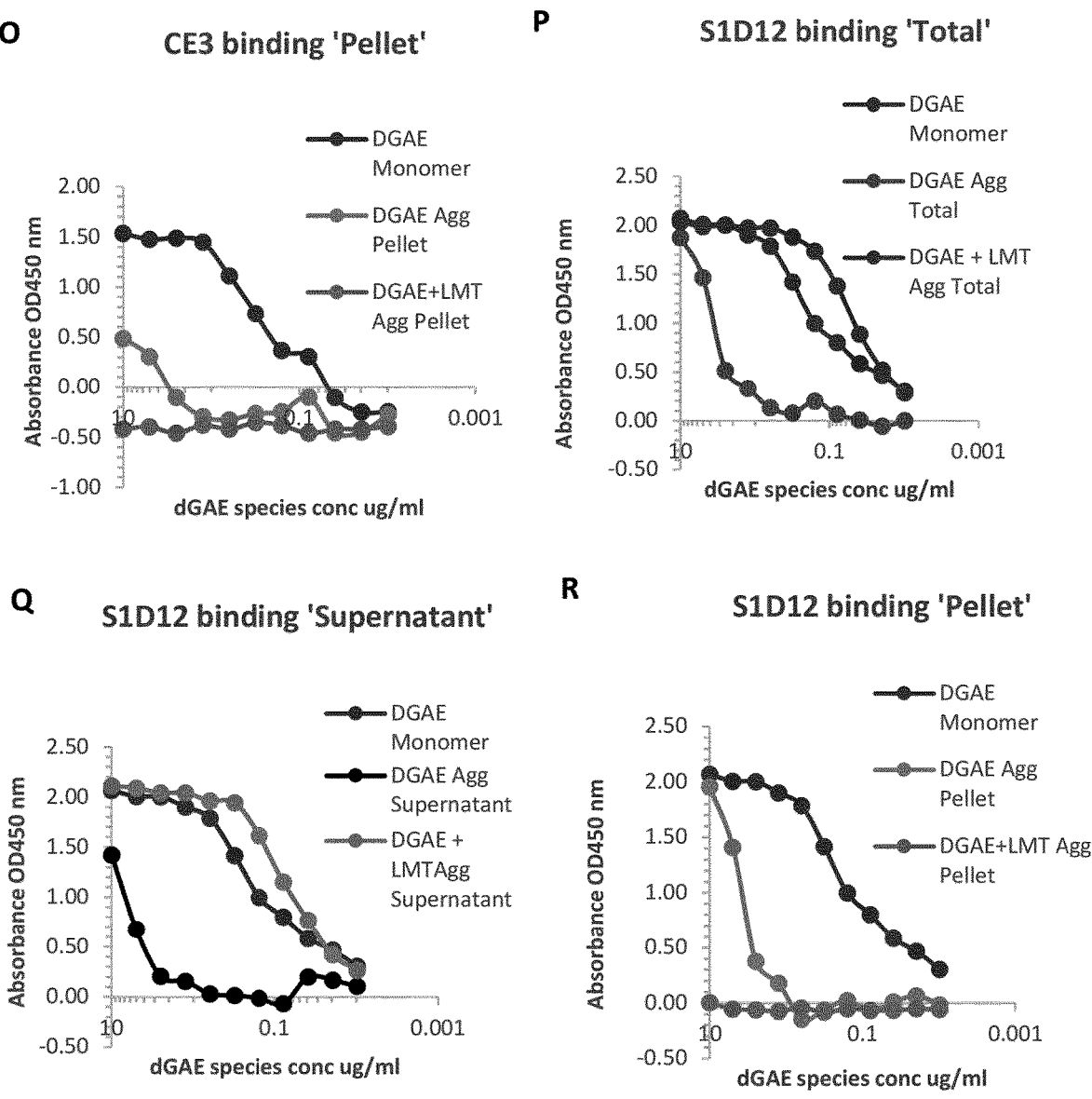

FIG. 34. Sandwich ELISA graphs showing the increase in immunoreactivity of core region scAbs to dGAE 'total', 'supernatant' and 'pellet' aggregation inhibition samples prepared in the presence of LMTM, dGAE monomer was included as assay control to indicate the binding profiles of each test scAbs to their corresponding epitopes in non-aggregated samples. (A-C) CA4 scAb, (D-F) CA9, (G-I) CB3 scAb, (J-L) CE2 scAb, (M-O) CE3, (P-R) S1D12 scAb. Lack of antibody binding in some dGAE+LMTM pellet samples corresponds to the absence protein present in this group as confirmed by SDS gel (data not included)

6

Figure 35:
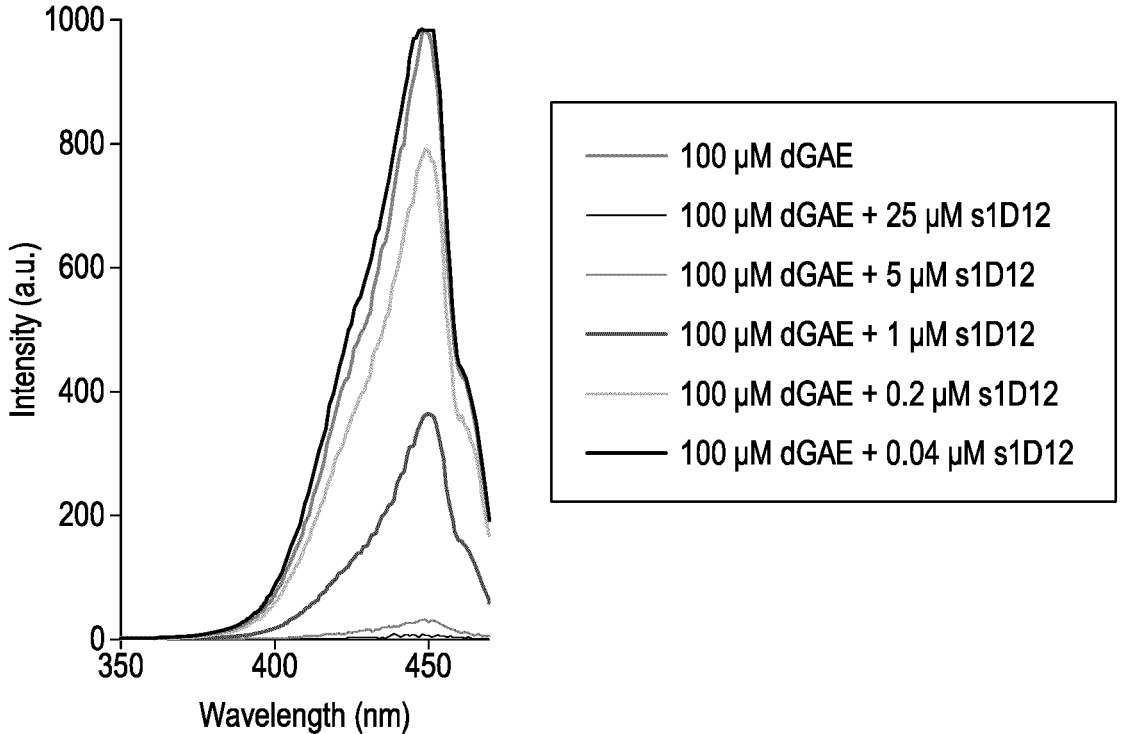

FIG. 35. An example data plot of S1D12 scAb mediated aggregation inhibition of dGAE.

Figure 36:
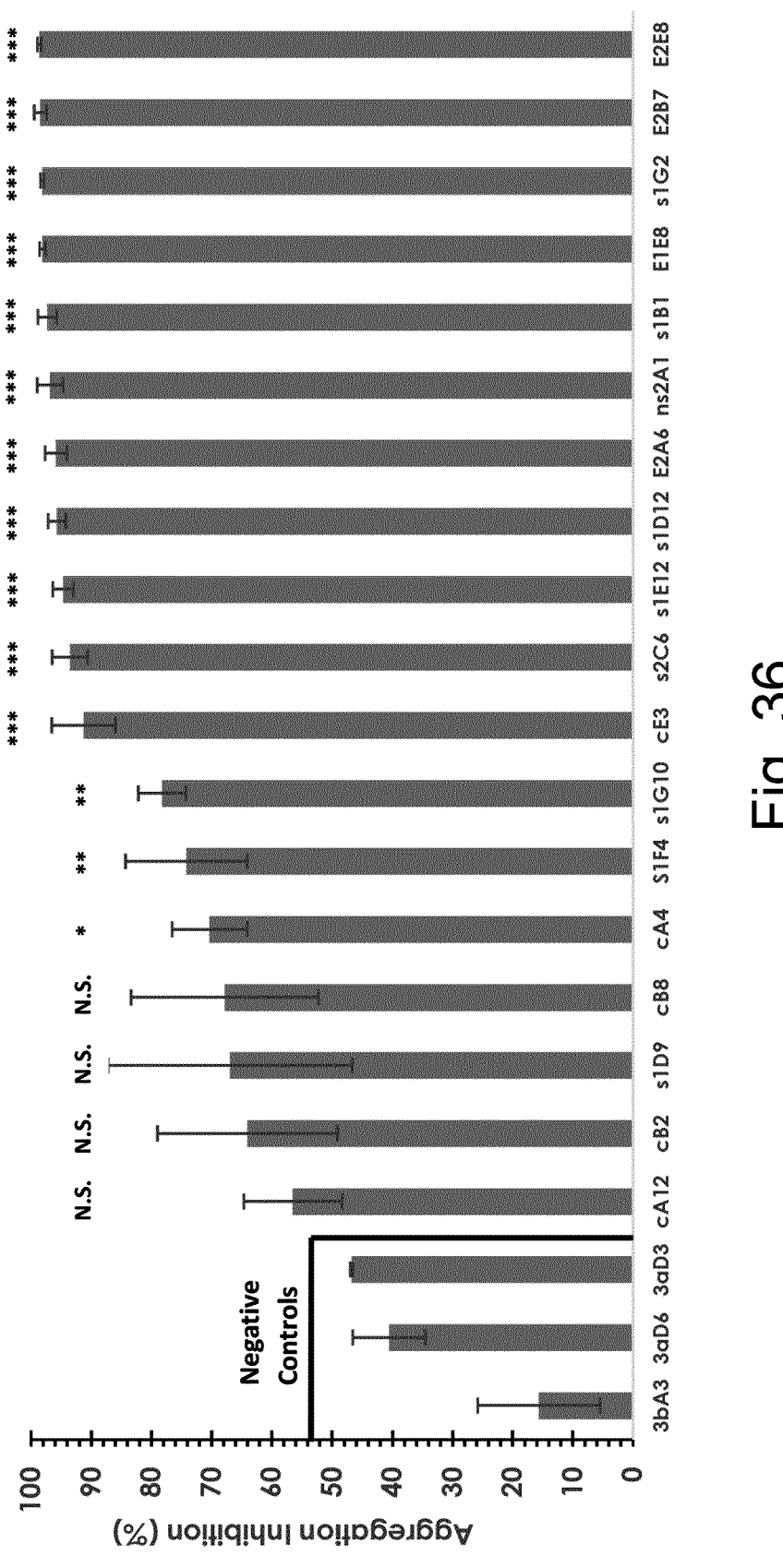

FIG. 36. Ranking of aggregation inhibition properties of anti-tau scAbs by thioflavin T assay. Aggregation inhibition dGAE was quantified by calculating the percentage change from aggregates without the presence of a scAb, scAbs 3bA3, 3aD6 and 3aD3 were used as negative controls and show no cross reactivity to dGAE (data not shown), n=3, error bars represent SD, N.S.=Not Significant*=P<0.05, =P<0.01, *=P<0.001 (one-way analysis of variance (ANOVA) and post-hoc Dunnett's test compared to scAb 3aD3).

Figure 37:
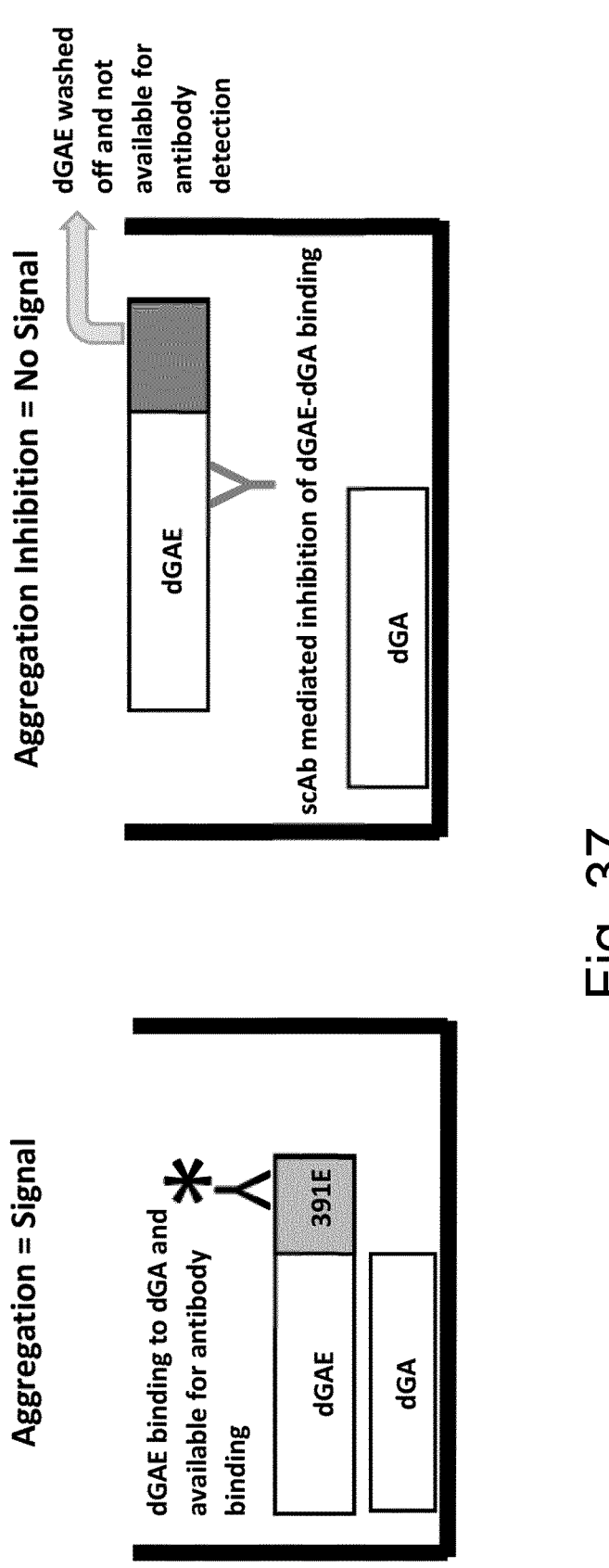

FIG. 37. Schematic representation of tau-tau immunoassay to rank the inhibitory effects of anti-tau scAbs during the aggregation of truncated tau containing the core repeat domain. (a) Tau-tau aggregation takes place when dGAE is added to the wells precoated with dGA and the presence of dGAE is detected using 391E epitope specific E2E8 scAb. (b) When dGAE was preincubated with core region binding scAbs, this binding event inhibits dGAE-dGA interaction which is measured by a loss in antibody detection by E2E8 scAb.

Figure 38:
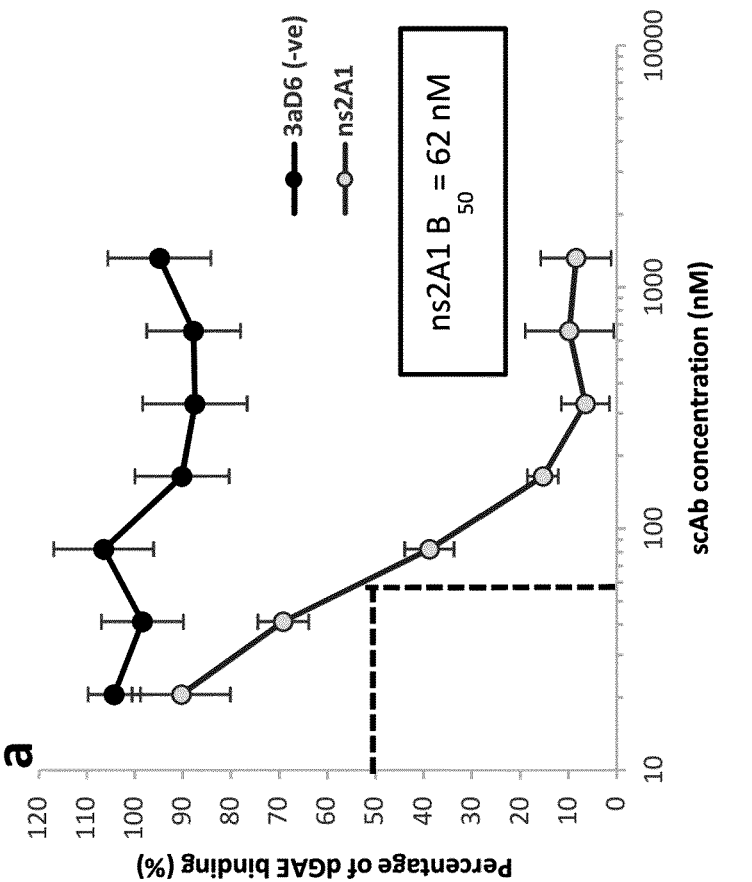

FIG. 38. Ranking of aggregation inhibition properties of anti-tau scAbs by tau-tau immunoassay (B50). A—An example of B50 quantification of NS2A1 and 3aD6 (negative control). Quantification of aggregation inhibition properties was made by calculating a B50 value (concentration of scAb where 50% of dGAE binding to dGA is evident). Error bars=SD, n=4, −ve=negative control, b—Summary of B50 ranking of the scAb panel.

Figure 39:
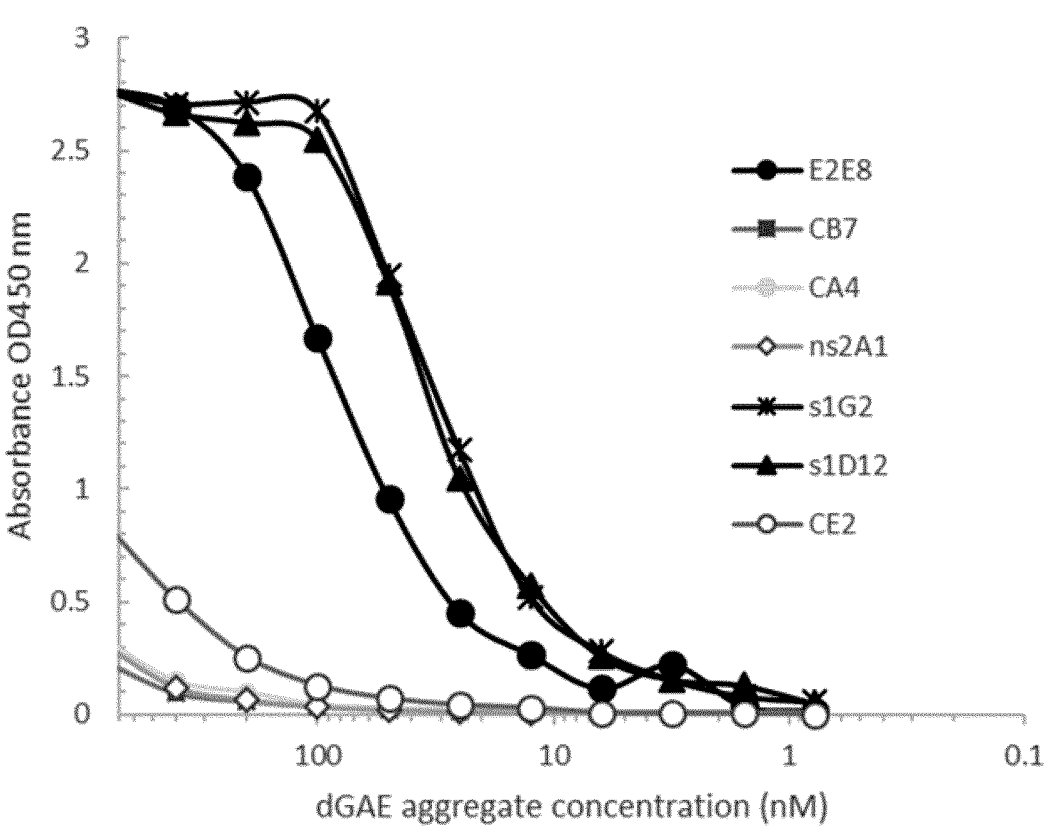

FIG. 39, mAb capture of dGAE aggregates.

Figure 40:
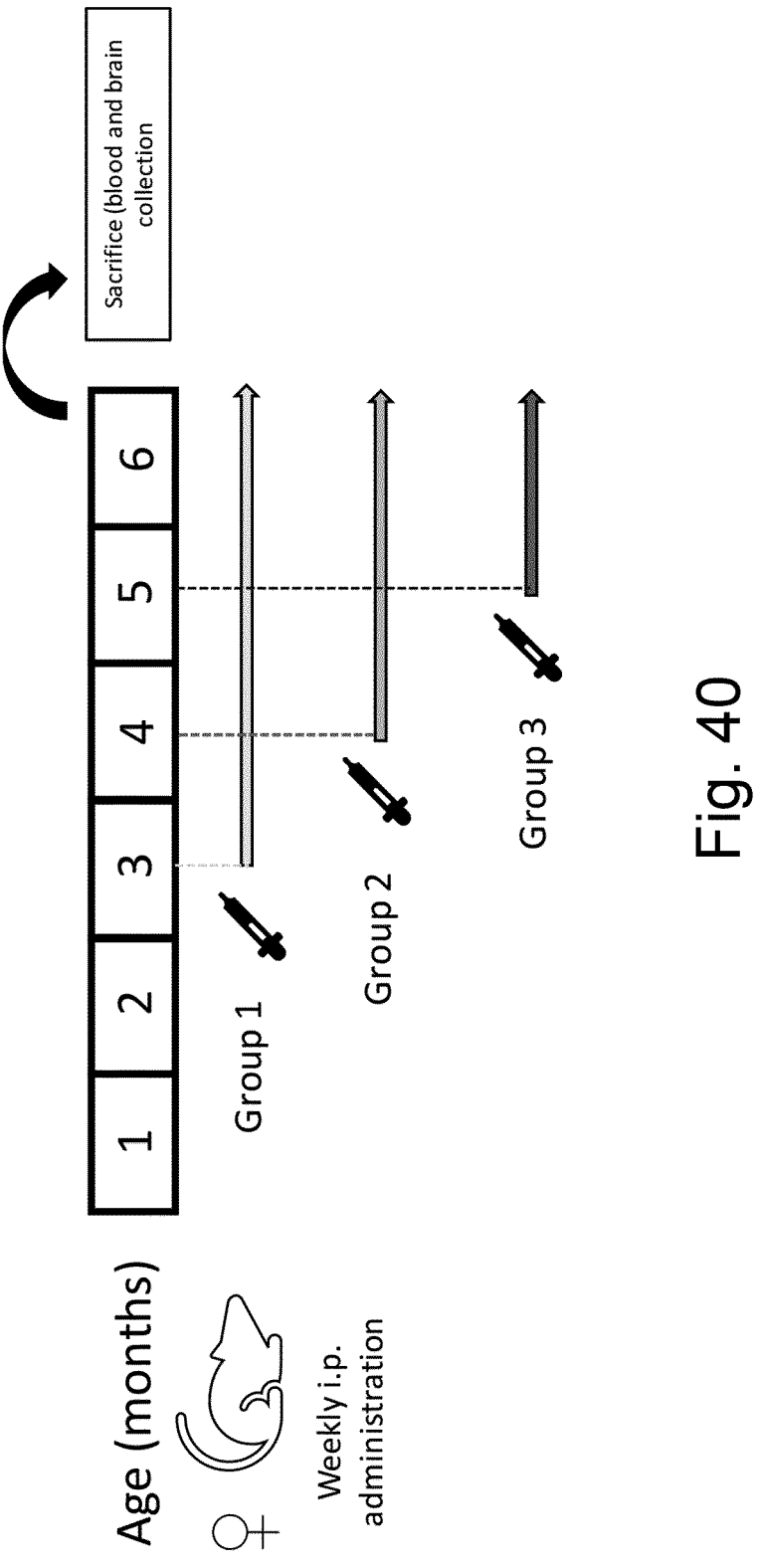

FIG. 40. Experimental design to investigate the effect of intraperitoneal administration of S1D12 in line 1, line 66 and WT mice. Animals will be injected intraperitoneally (i.p.) with either vehicle or S1D12 (10- or 50-mg/kg), once per week (Tuesdays) for twelve (Group 1), eight (Group 2) or four (Group 3) consecutive weeks. Age of mice at the end of the experiment will be the same for all three groups (i.e. 6 months).

Figure 41:
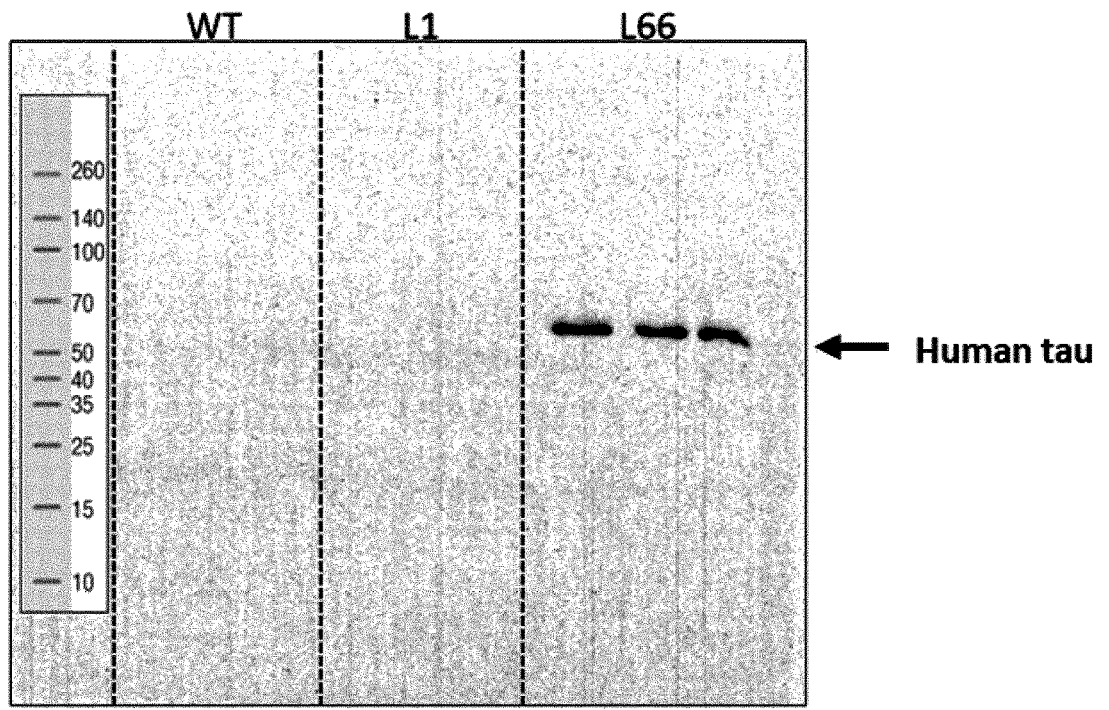

FIG. 41. Western blot showing tau labelled with a human-specific CB7 antibody. Bands are present in lanes containing 20 μg protein homogenate from 5-month-old L66$^{+/+}$ mouse brain but not in either WT or L1$^{++}$ lanes. The protein ladder superimposed on the left of the blot provides an approximation of the relative size of proteins on the gel, but it is known that the apparent size of tau is considerably greater than the actual molecular mass.

Figure 42:
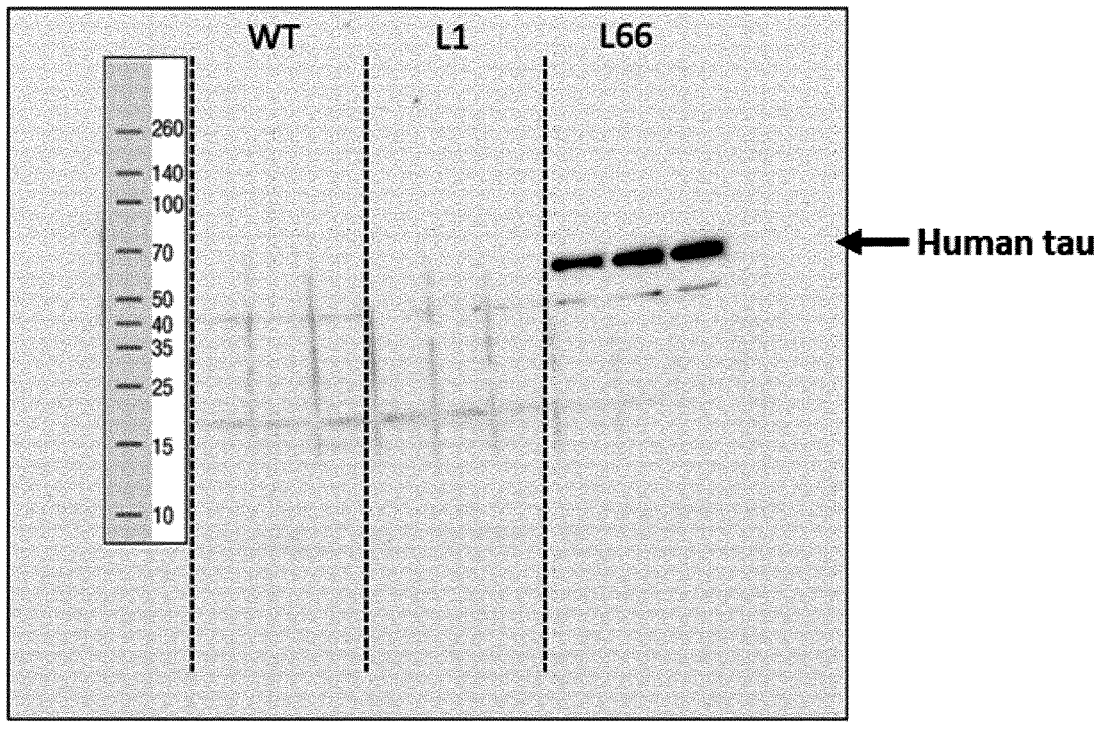

FIG. 42. Western blot showing tau labelled with human specific CC7. Results and ladder are as described in FIG. 41.

Figure 43:
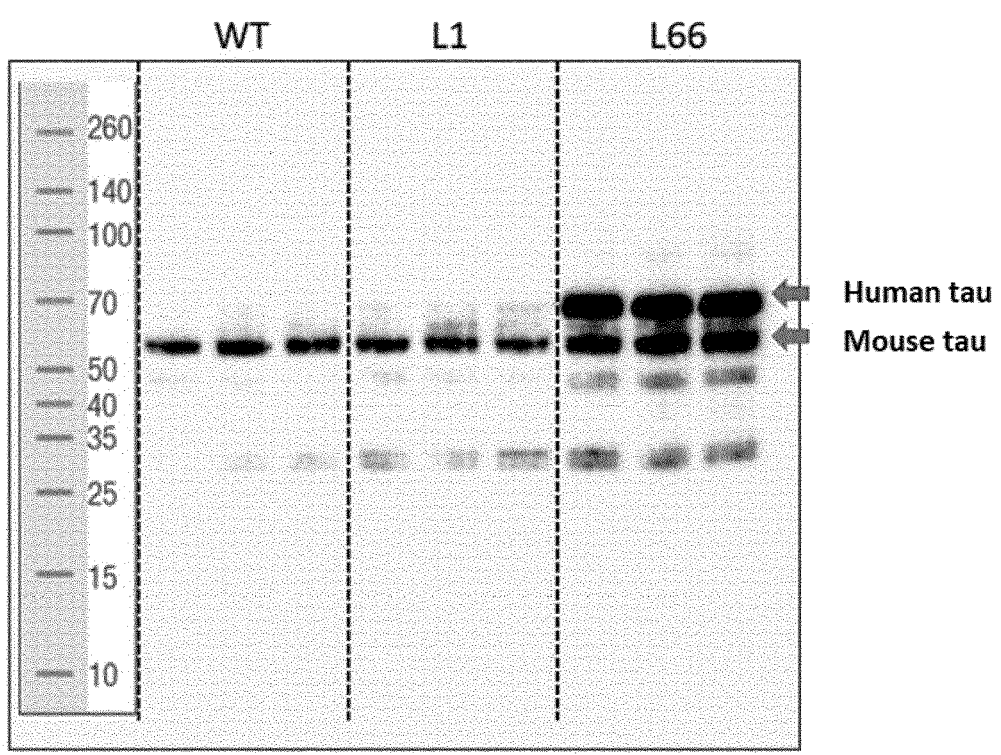

FIG. 43. Western blot labelled with S1D12 tau core antibody. Bands are present in lanes containing 20 μg protein homogenate from 5-month-old L66$^{++}$, L1 and WT mice brains. Mouse tau (indicated by the lower arrow) appears as a band of approximately 55 kDa in each of the samples. Human tau (indicated by the upper arrow) appears as a protein at 68 kDa that is present only in the L66$^{++}$ samples. Protein ladder as for FIG. 41.

Figure 44:
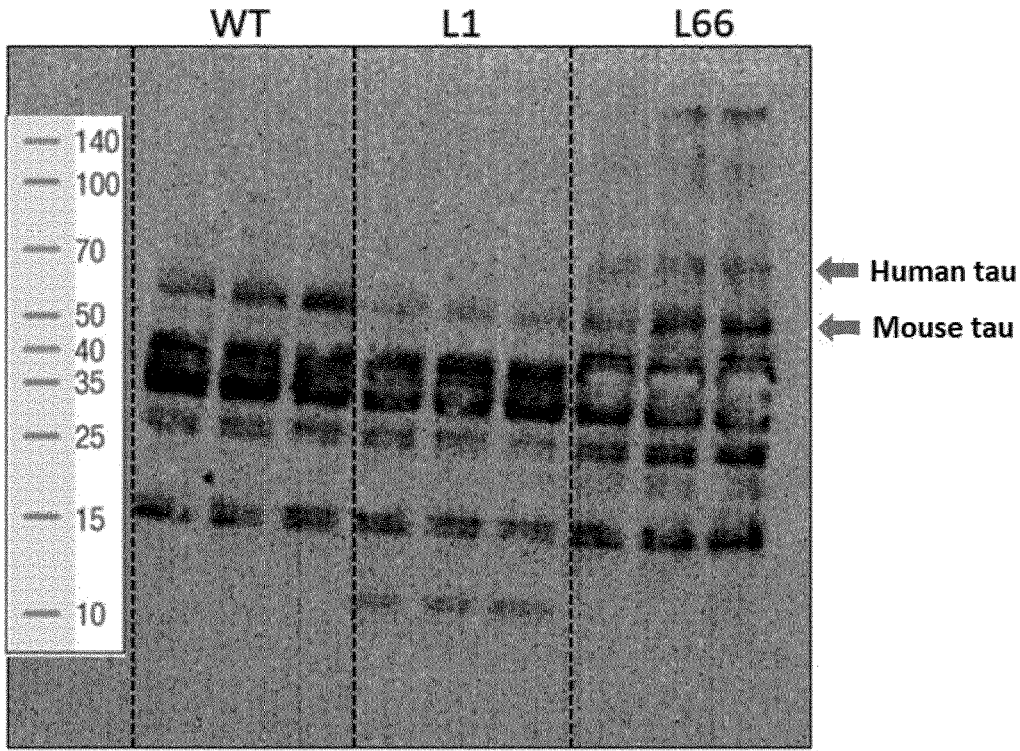

FIG. 44. Western blot labelled with S1G2 core antibody. Bands are present in lanes containing 20 μg protein homogenate from 5-month-old L66$^{++}$, L1$^{+/+}$ and WT mice brains. Mouse tau (indicated by the lower arrow) appears as a band at about 55 kDa in each of the samples. Human tau (indicated by the upper arrow) appears at about 68 kDa but only in the L66$^{+/+}$ samples. Using this antibody, a band at around 10 kDa is visible in the L1$^{+/+}$ samples. Protein ladder as for FIG. 41.

FIG. 45. Sequence comparison of human (SEQ ID NO:1) and mouse (SEQ ID NO:589) tau. The sequences shown consist of SEQ ID No. 1 for human tau (two gaps introduced to allow sequence alignment) and SEQ ID NO: 589 for mouse tau. The protein regions that contain the epitopes of candidate antibodies are superimposed. Both CB7 and CC7 binding regions in human tau are not present in mouse tau. In contrast, protein regions containing the epitopes for the antibodies S1D12 and S1G2 show 100% homology between the 2 species.

FIG. 46. A) Paired antibody ELISAs with S1D12 capture and CB7 detection show a progressive decrease in signal with advanced age in L66$^{+/+}$ mice. B) When reversing the orientation of the assay, and using CB7 as the capture along with S1G2 as detector, a similar pattern is observed.

Figures 47, 48:
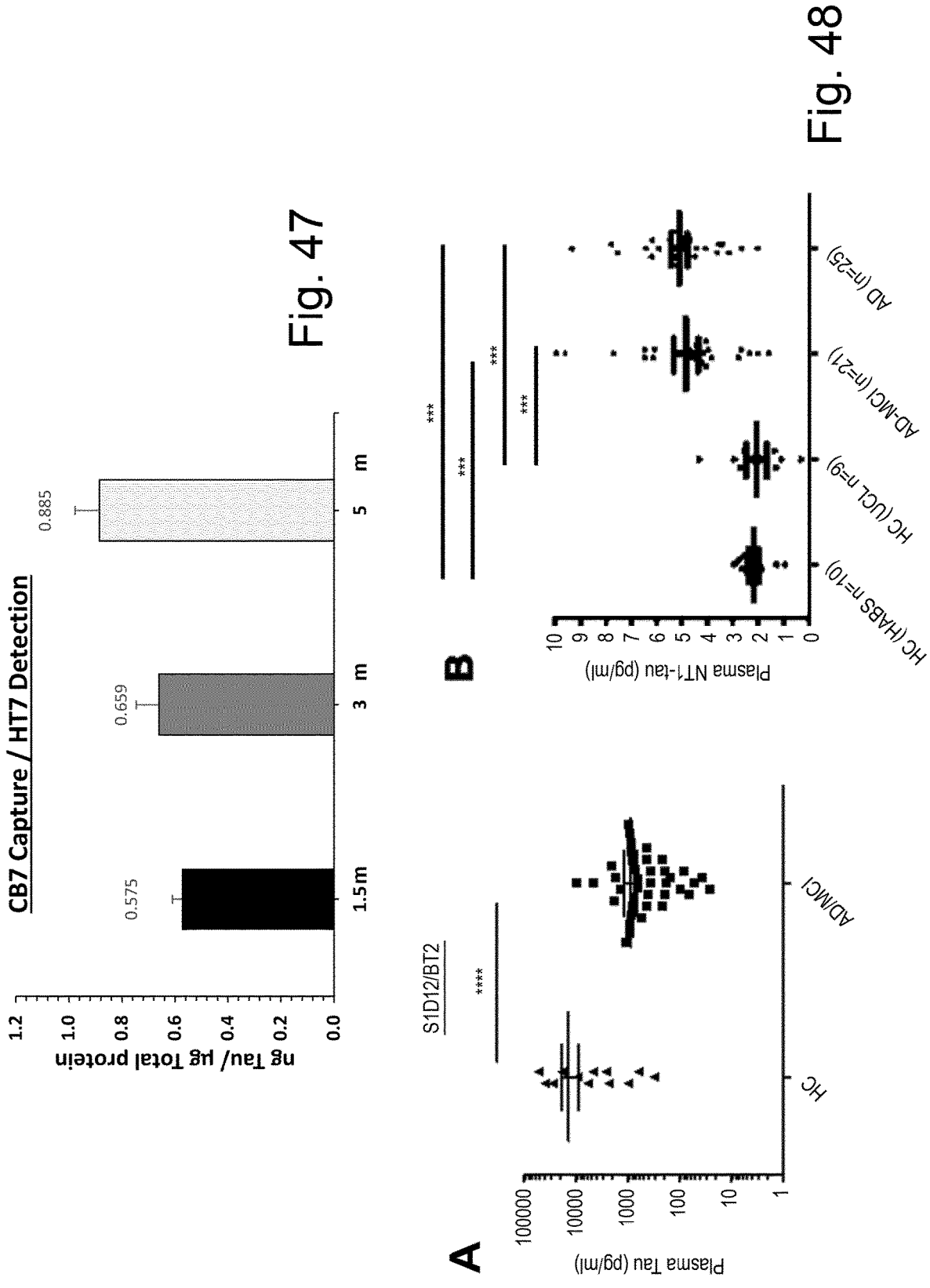

FIG. 47. Paired antibody ELISA with CB7 capture and HT7 detection shows a progressive increase in signal with age in L66$^{+/+}$ mice. This suggests an accumulation of small N-terminally intact fragments created by some sort of truncation event between the core region and the N'-terminal region of tau protein or protein fragments.

FIG. 48. (A) Plasma tau levels in healthy control (HC) and patients with a confirmed diagnosis of Alzheimer's disease (AD/MCI). The concentration of the core-proline region measured using S1D12 capture beads paired with BT2 as detector is significantly higher in healthy control than in AD samples. A total of 12 heathy control plasma samples and 42 AD/MCI samples were analysed using the Simoa® assay. ****p<0.0001 (B) NT1 assay data (Chen et al 2019) reported detecting slightly increased levels of NT-1 plasma tau in AD-MCI (AD biomarker positive-mild cognitive impairment) and AD (AD biomarker positive-clinical AD) patients compared to NC (normal control) using Tau12-BT2 antibodies.

Figures 49, 50:
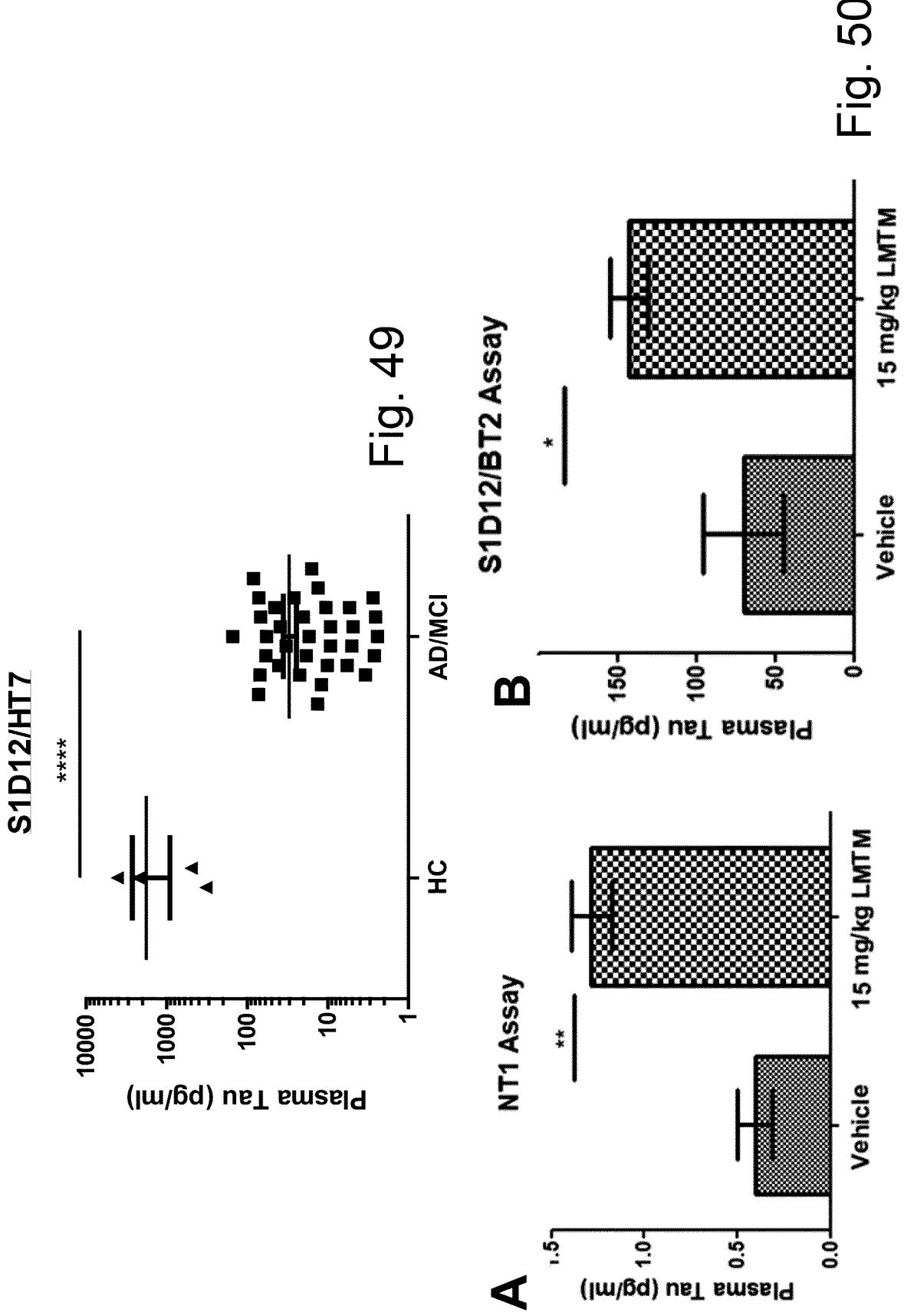

FIG. 49. Plasma tau levels in healthy control (HC) and patients with a confirmed diagnosis of Alzheimer's disease (AD/MCI). The concentration of the core-proline region measured using S1D12 capture beads paired with HT7 detector is significantly higher in healthy control than in AD samples. A total of 4 heathy control plasma samples and 34 AD/MCI samples were analysed using the Simoa® assay. ****p<0.0001

FIG. 50. Plasma tau levels are increased by LMTM treatment of L66$^{+/-}$ mice. (A) NT1 assay using BT2 and HT7 antibodies detect slightly elevated levels of human specific N terminal tau in the plasma of L66$^{+/-}$ mice receiving LMTM (15 mg/kg) (B) Similarly, the core-proline assay using S1D2 and BT2 antibodies also measured higher levels of tau in LMTM treated mice plasma with concentrations significantly higher than the levels seen using the human-specific NT1 assay. The increased levels in treated mice suggest improved clearance of pathologic tau from the brain into the blood.

Figure 51:
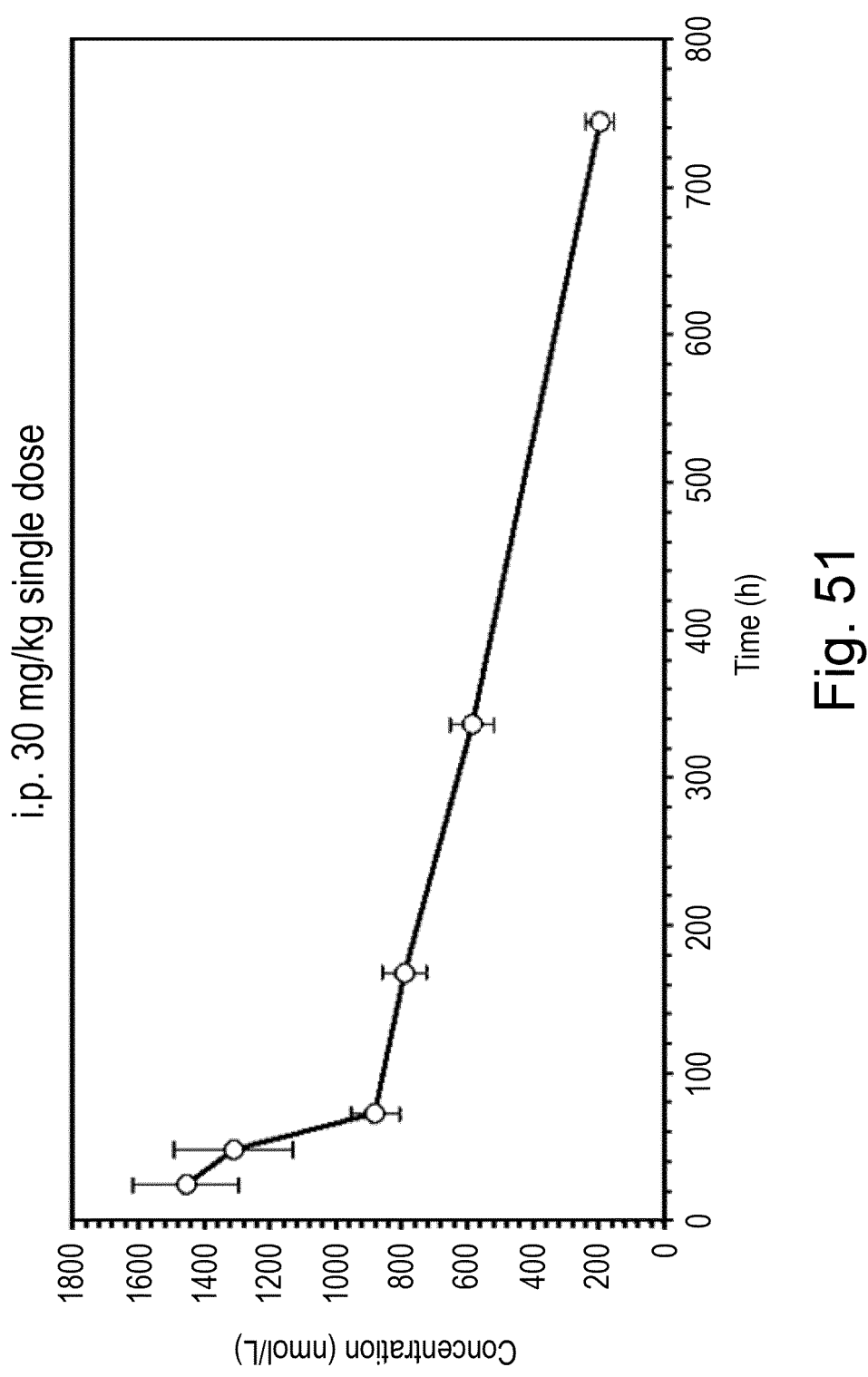

FIG. 51. Concentration of S1D12 mAb in mouse plasma at various time points. Values plotted are average concentrations in groups of mice analysed at 24, 48, 72-hours and 7-, 14- and 31-days following the administration of a single dose of S1D12 mAb at 30 mg/kg.

Figure 52:
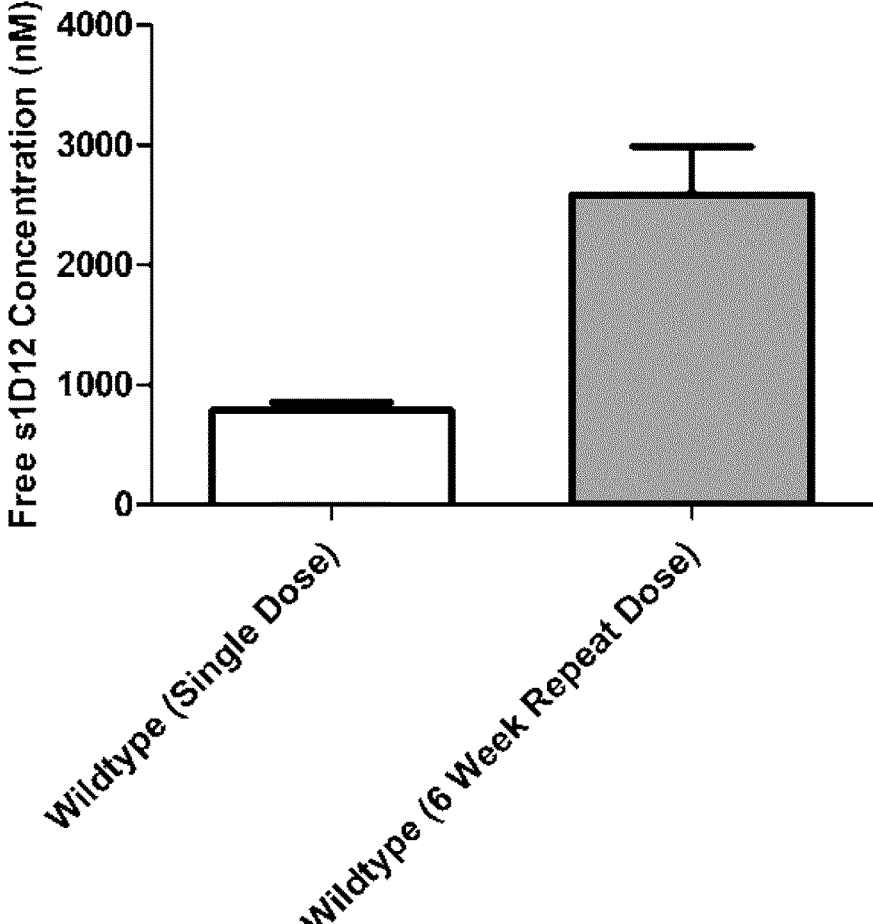

FIG. 52. Comparison of the concentrations of free S1D12 mAb in the plasma of WT mice 7 days post single or repeat dosing at 30 mg/kg. Values plotted are mean concentrations (+standard error) in groups of mice, n=6.

Figure 53:
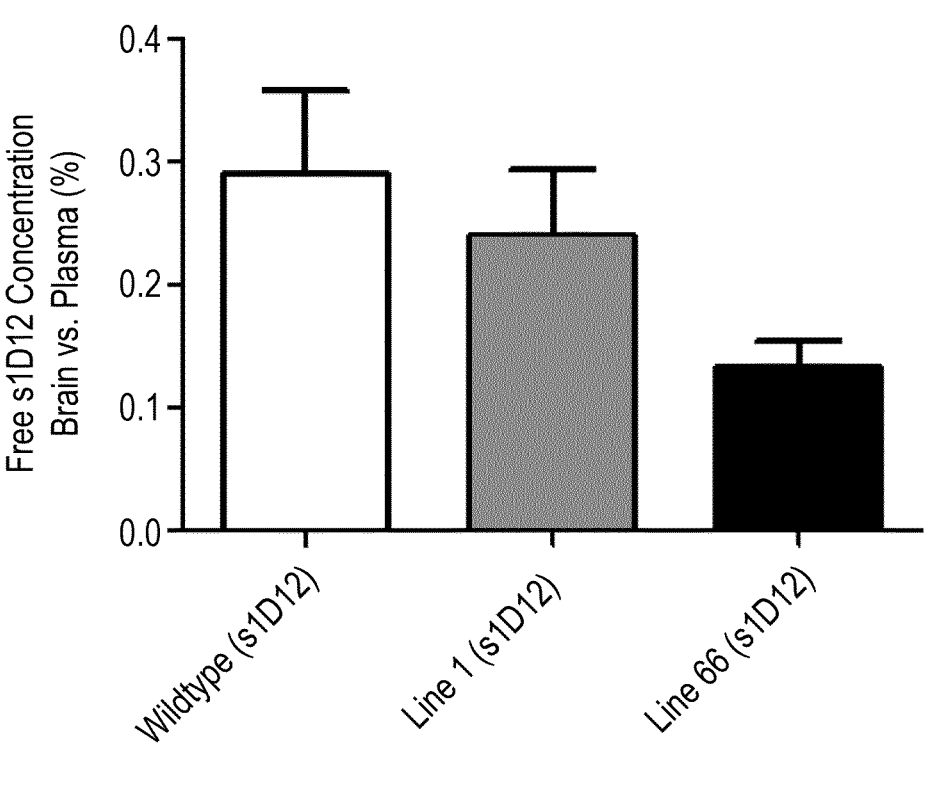

FIG. 53. Detection of S1D12 in the brain of wild type, L1 and L66++ mice receiving a weekly dose of S1D12 mAb at 30 mg/kg for 6 weeks. Values are expressed as a percentage of brain vs plasma S1D12 concentrations in groups of mice receiving the treatment (mean+standard error; n=6).

Figure 54:
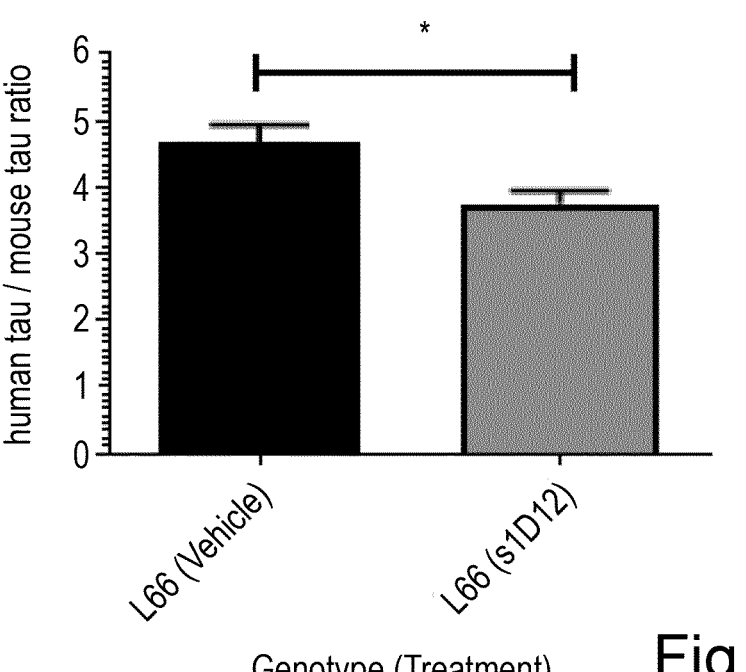

FIG. 54. Comparison of the ratio of human tau to mouse tau in the brain homogenates of L66$^{+/+}$ vehicle treated and S1D12 mAb-treated groups. A decrease in the levels of human tau was observed in mAb-treated mice brains when using a core region antibody S1G2 for detection in western blots. Values plotted are the ratio of human and mouse tau protein band densities from each group (mean+standard error; n=6). *p<0.05

Figure 55:
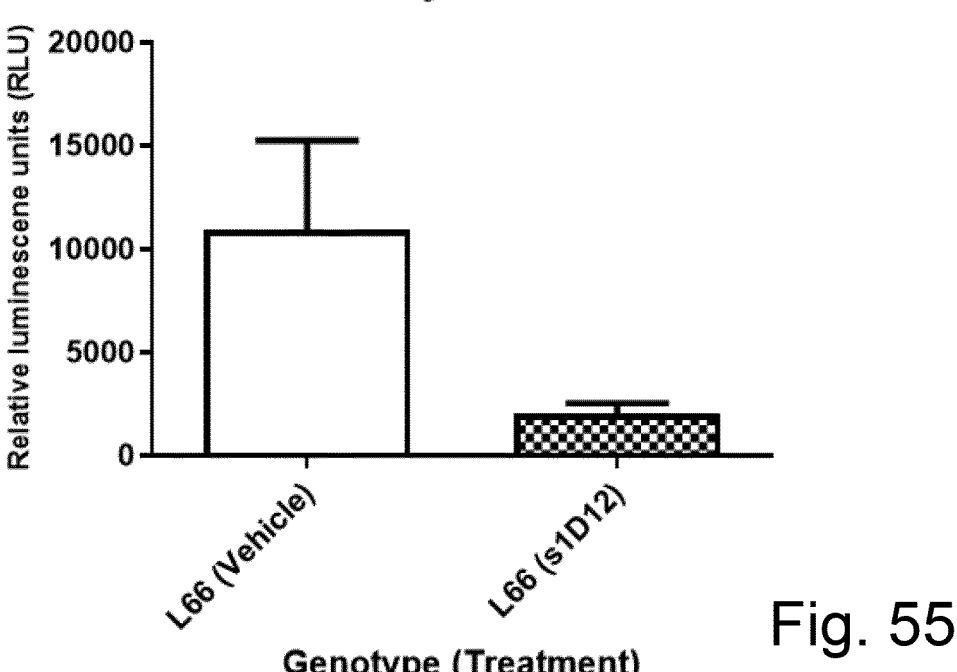

FIG. 55. Levels of sarkosyl-insoluble tau detected in the brain homogenates of vehicle- and S1D12 mAb-treated L66$^{+/+}$ mice using a core-proline region specific antibody pairing (S1G2-BT2). Between five to six-fold reduction in the levels of core-proline fragment was observed in mice receiving mAb treatment compared to the vehicle group. Individual mouse samples were analysed in duplicate and values represent the mean of relative luminescence readings from each group. (mean+standard error; n=6).

Figure 56:
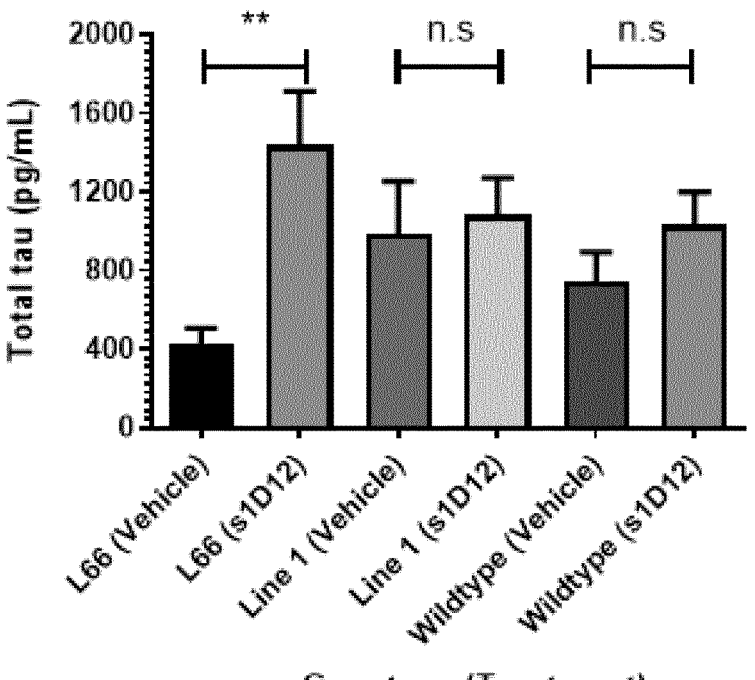

FIG. 56. Plasma tau levels are increased following S1D12 mAb treatment of mice. Using S1G2 (367-379) and BT2 (194-198) antibodies, human specific core-proline region tau levels were elevated in S1D12 mAb-treated mice compared to the vehicle group. Individual mouse samples were analysed in duplicate and values represent mean concentration of the tau fragment detected by S1G2-BT2 antibody pairing. In L66, more than a threefold increase was achieved in the treatment group, whereas in L1 and wildtype mice, the differences were not statistically significant. (n=6, mean values+standard error). Unpaired t-test was performed between vehicle and treatment groups, **P≤0.01, n.s., not significant.

Figure 57:
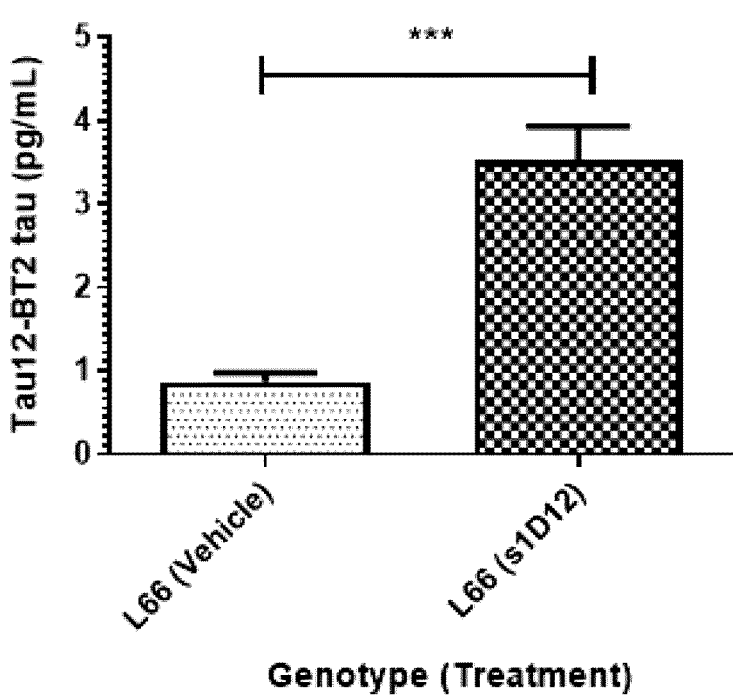

FIG. 57. Plasma tau levels of N-terminal tau is increased by S1D12 treatment in L66 mice. Using BT2 (194-198) and Tau 12 (6-18) antibodies, human specific N-terminal tau levels were elevated in S1D12 mAb-treated mice compared to the vehicle group. Individual mouse samples were analysed in duplicate and values represent mean concentration of the tau fragment detected by BT2-Tau12 antibody pairing (n=6, standard error bars); unpaired t-test was performed between vehicle and treatment groups, ***P≤0.001.

Figure 58:
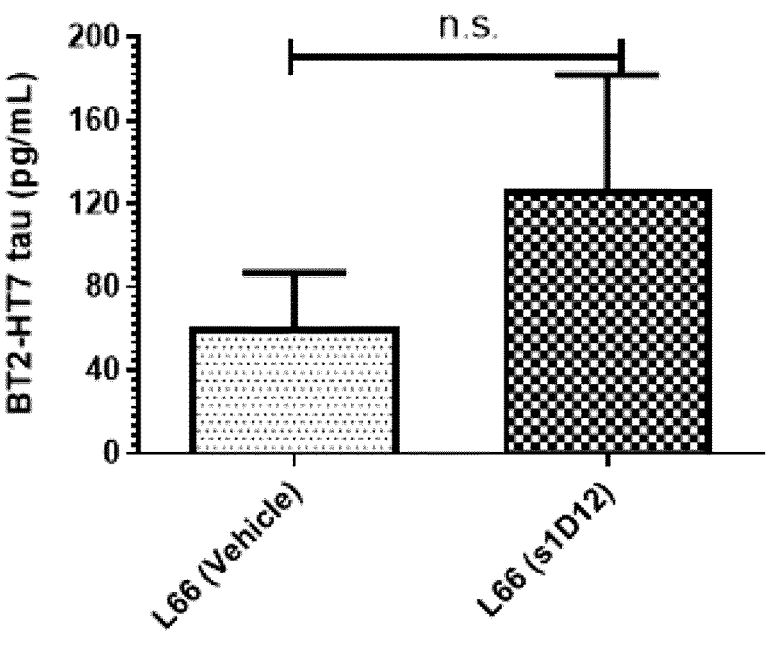

FIG. 58. Plasma tau levels of N-terminal tau is increased by S1D12 treatment in L66 mice. Using BT2 (194-198) and HT7 (159-163) antibodies, human-specific proline tau levels were elevated in S1D12 mAb-treated mice compared to the vehicle group, however the difference was not statistically significant. Individual mouse samples were analysed in duplicate and values represent mean concentration of the tau fragment detected by BT2-HT7 antibody pairing (n=6; standard error bars).

Figure 59:
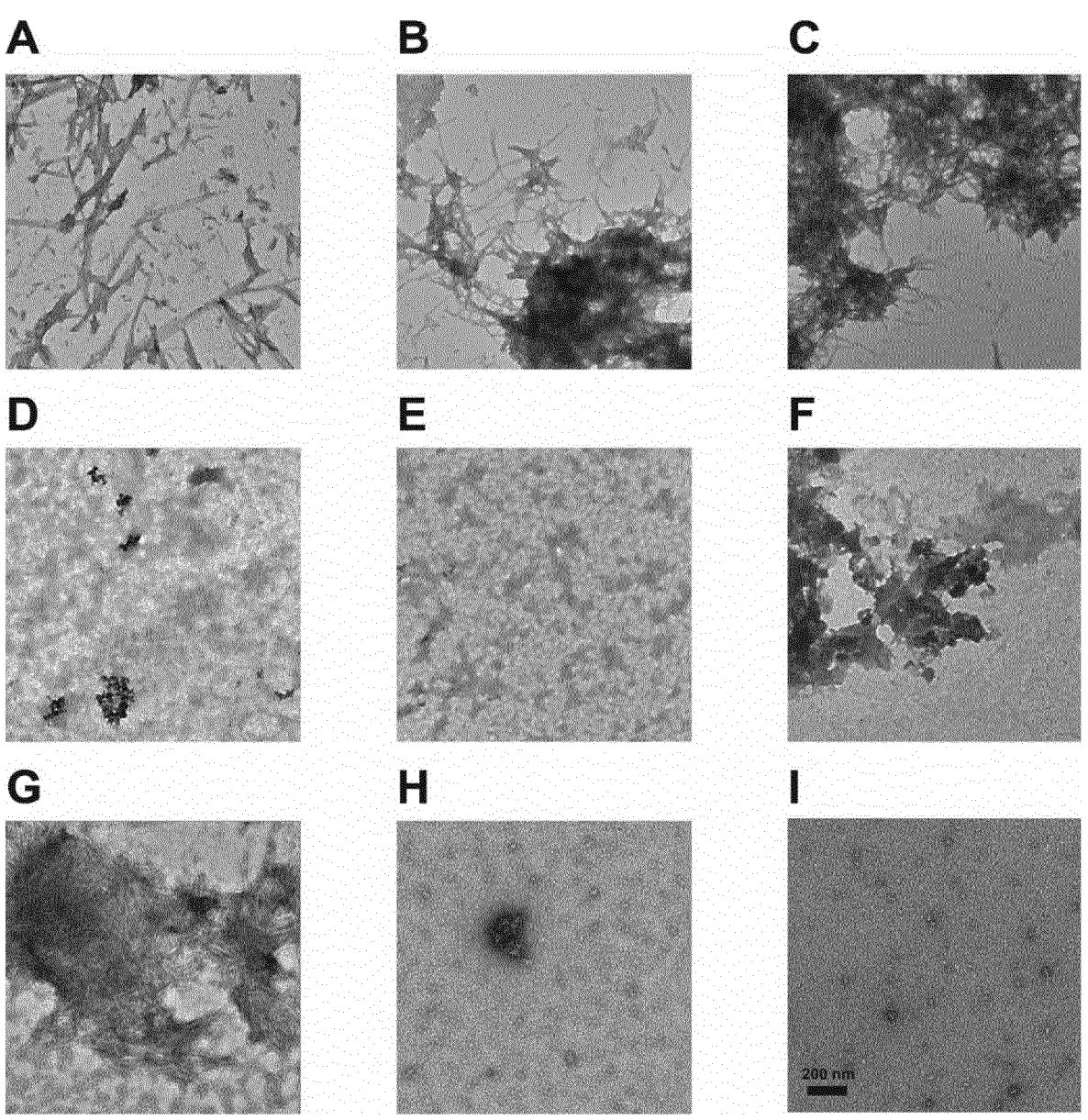

FIG. 59. Transmission electron microscopy images of dGAE assembled in the presence and absence of antibodies. (A) dGAE (100 μM); (B) dGAE (25 μM); (C) dGAE (10 μM); (D) dGAE (100 μM)+s1D12 (25 μM; 4:1); (E) dGAE (25 μM)+s1D12 (25 μM; 1:1); (F) dGAE (10 μM)+s1D12 (2.5 μM; 4:1); (G) dGAE (10 μM)+anti-ovalbumin (2.5 μM; 4:1); (H) s1D12 (25 μM); (I) anti-ovalbumin (2.5 μM). Fibrils are only observed in preparations in the absence of s1D12 (A-C) or in a control of dGAE prepared in the presence of a non-tau IgG antibody, anti-ovalbumin (G). When s1D12 is added to the assembly mixture at dGAE protein: antibody ratios of either 1:1 or 4:1 (D, E, and F), no fibril formation is observed. Fibrils are also absent from antibody controls in the absence of dGAE (H and I). Scale bar (on I for all panels), 200 nm.

Figure 60:
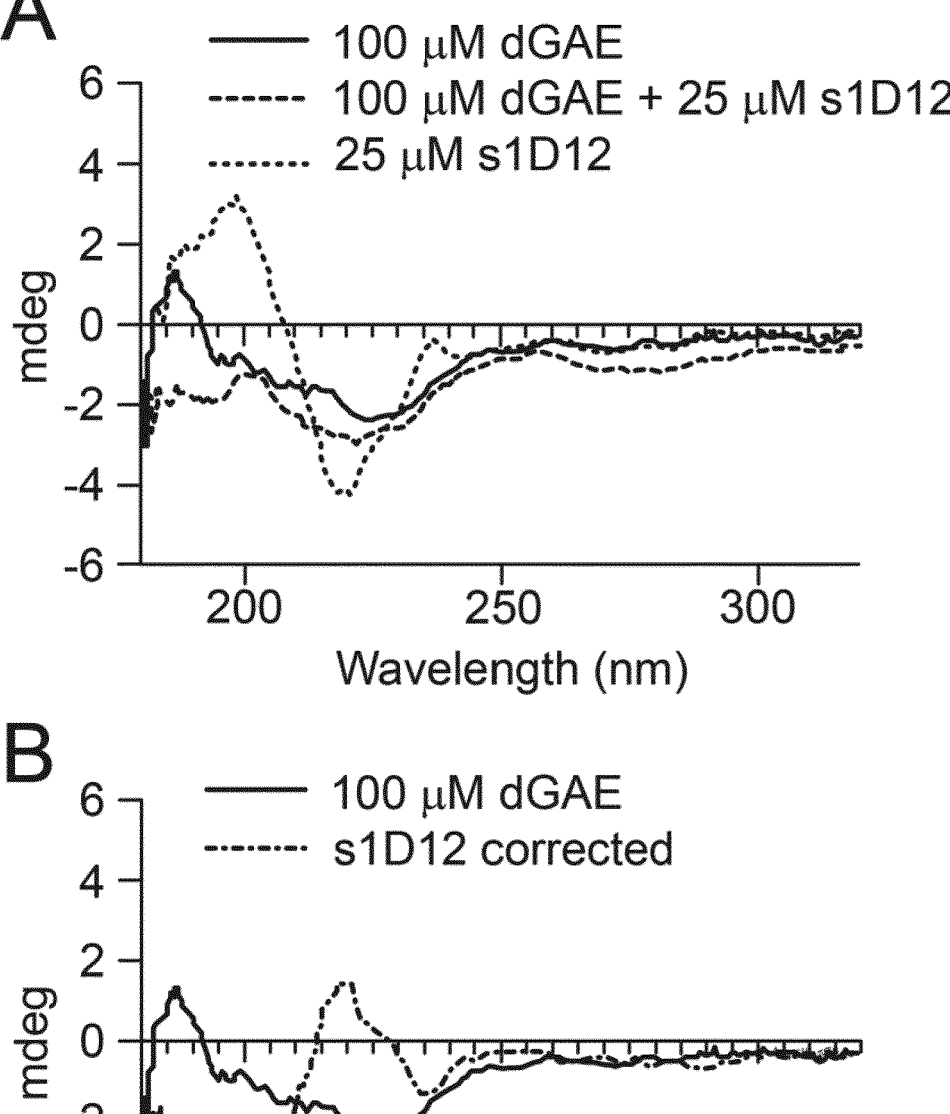

FIG. 60. CD spectra in millidegrees (mdeg) of (A) 100 μM dGAE with (dashed line) and without (solid line) 25 μM s1D12 (ratio 4:1) and antibody alone (dotted line) and (B) with the antibody spectra subtracted, dGAE (solid line) displays a β-sheet conformation (positive ~200 nm, negative ~220 nm) but shows random coil (negative at ~200 nm, positive at ~220 nm) when the s1D12 spectra is subtracted (B: dashed and dotted line), indicating that dGAE has not assembled into fibrils.

Figure 61:
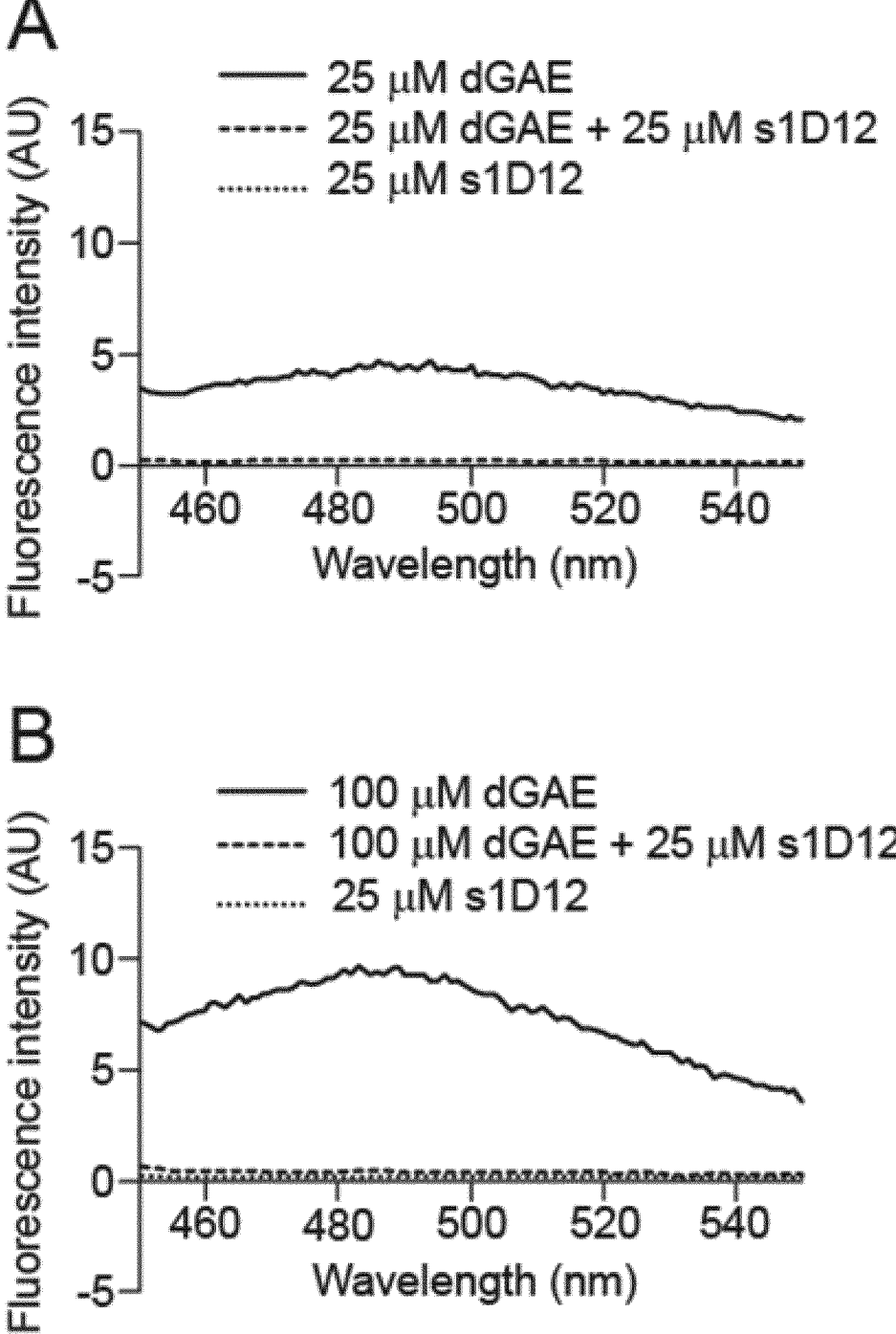

FIG. 61. Fluorescence of samples incubated with ThS. An emission peak at 483 nm is clearly observed with 25 (A, 1:1) and 100 μM (B, 4:1) dGAE (solid lines) which is abolished when s1D12 is included in the assembly mixture (dashed lines), showing that only samples that do not include s1D12 contain self-assembled amyloid fibrils. Dotted lines show that s1D12 alone does not contribute to the fluorescence.

DETAILED DESCRIPTION OF THE INVENTION

According to a first aspect, the invention provides a specific binding molecule that binds to an epitope within All residue numbers of the Tau protein sequence and structure in the present disclosure refer to the residues of SEQ ID NO:1, which is the sequence of the four repeat isoform 2N4R of human Tau protein (Uniprot ID P10636-8), or homologous positions in other species or variants thereof. Human Tau isoform 2N4R (Uniprot ID P10636-8) corresponds to amino acids 1-124, 376-394 and 461-758 of full length Tau, Uniprot ID P10636 or P10636-1, provided as SEQ ID NO:2. SEQ ID NO: 2 relates to a longer form of Tau found in the peripheral nervous system (PNS) but not the central nervous system (CNS). As used herein, references to "full-length" tau refer to SEQ ID NO: 1 (the relevant sequence for the CNS) and not to SEQ ID NO: 2 (which is not relevant in the CNS).

```
(Isoform Tau-F, also known as Tau-4, 2N4R, 441 amino acids):
>sp|P10636-8| TAU_HUMAN Isoform Tau-F of Microtubule-associated protein tau
OS = Homo sapiens OX = 9606 GN = MAPT
                                                         SEQ ID NO: 1
MAEPRQEFEVMEDHAGTYGLGDRKDQGGYTMHQDQEGDTDAGLKESPLQTPTEDGSEEPG

SETSDAKSTPTAEDVTAPLVDEGAPGKQAAAQPHTEIPEGTTAEEAGIGDTPSLEDEAAG

HVTQARMVSKSKDGTGSDDKKAKGADGKTKIATPRGAAPPGQKGQANATRIPAKTPPAPK

TPPSSGEPPKSGDRSGYSSPGSPGTPGSRSRTPSLPTPPTREPKKVAVVRTPPKSPSSAK

SRLQTAPVPMPDLKNVKSKIGSTENLKHQPGGGKVQIINKKLDLSNVQSKCGSKDNIKHV

PGGGSVQIVYKPVDLSKVTSKCGSLGNIHHKPGGGQVEVKSEKLDFKDRVQSKIGSLDNI

THVPGGGNKKIETHKLTFRENAKAKTDHGAEIVYKSPVVSGDTSPRHLSNVSSTGSIDMV

DSPQLATLADEVSASLAKQGL (Full length human Tau, Isoform PNS-Tau, 758 amino acids):
>sp|P10636-1| TAU_HUMAN Microtubule-associated protein tau OS = Homo sapiens
OX = 9606 GN = MAPT PE = 1 SV = 5
                                                         SEQ ID NO: 2
MAEPROEFEVMEDHAGTYGLGDRKDQGGYTMHQDQEGDTDAGLKESPLQTPTEDGSEEPG

SETSDAKSTPTAEDVTAPLVDEGAPGKQAAAQPHTEIPEGTTAEEAGIGDTPSLEDEAAG

HVTQEPESGKVVQEGFLREPGPPGLSHQLMSGMPGAPLLPEGPREATRQPSGTGPEDTEG

GRHAPELLKHQLLGDLHQEGPPLKGAGGKERPGSKEEVDEDRDVDESSPQDSPPSKASPA

QDGRPPQTAAREATSIPGFPAEGAIPLPVDFLSKVSTEIPASEPDGPSVGRAKGQDAPLE

FTFHVEITPNVQKEQAHSEEHLGRAAFPGAPGEGPEARGPSLGEDTKEADLPEPSEKQPA

AAPRGKPVSRVPQLKARMVSKSKDGTGSDDKKAKTSTRSSAKTLKNRPCLSPKHPTPGSS

DPLIQPSSPAVCPEPPSSPKYVSSVTSRTGSSGAKEMKLKGADGKTKIATPRGAAPPGQK

GQANATRIPAKTPPAPKTPPSSGEPPKSGDRSGYSSPGSPGTPGSRSRTPSLPTPPTREP

KKVAVVRTPPKSPSSAKSRLQTAPVPMPDLKNVKSKIGSTENLKHQPGGGKVQIINKKLD

LSNVQSKCGSKDNIKHVPGGGSVQIVYKPVDLSKVTSKCGSLGNIHHKPGGGQVEVKSEK

LDFKDRVQSKIGSLDNITHVPGGGNKKIETHKLTFRENAKAKTDHGAEIVYKSPVVSGDT

SPRHLSNVSSTGSIDMVDSPQLATLADEVSASLAKQGL
```

SEQ ID NO: 1 with a binding affinity greater than the binding affinity with which antibody mAb423 binds to an epitope within SEQ ID NO: 1.

As used herein "mouse tau" refers to Isoform Tau-A which has the sequence of Uniprot ID P10637-2, provided as SEQ ID NO: 589:

```
MADPRQEFDTMEDHAGDYTLLQDQEGDMDHGLKESPPQPPADDGAEEPG

SETSDAKSTPTAEDVTAPLVDERAPDKQAAAQPHTEIPEGITAEEAGIG

DTPNQEDQAAGHVTQARVASKDRTGNDEKKAKGADGKTGAKIATPRGAA

SPAQKGTSNATRIPAKTTPSPKTPPGSGEPPKSGERSGYSSPGSPGTPG

SRSRTPSLPTPPTREPKKVAVVRTPPKSPSASKSRLQTAPVPMPDLKNV

RSKIGSTENLKHQPGGGKVQIINKKLDLSNVQSKCGSKDNIKHVPGGGS

VQIVYKPVDLSKVTSKCGSLGNIHHKPGGGQVEVKSEKLDFKDRVQSKI

GSLDNITHVPGGGNKKIETHKLTFRENAKAKTDHGAEIVYKSPVVSGDT

SPRHLSNVSSTGSIDMVDSPQLATLADEVSASLAKQGL
``` dGAE97 refers to the 97 residues fragment of Tau (2N4R) with N-terminus at residue Asp-295 and C-terminus at residue Glu-391, as described in SEQ ID NO: 3, or at homologous positions in other species (the residues mentioned referring to the human or mouse Tau sequence, which are identical in this region). As will be apparent to the skilled person, dGAE97 also corresponds to the fragment of Isoform PNS-Tau (P10636-1) with N-ter at Asp-612 and C-ter at Glu-708.

```
SEQ ID NO: 3 (dGAE97, human/mouse, 97 amino
acids):
DNIKHVPGGGSVQIVYKPVDLSKVTSKCGSLGNIHHKPGGGQVEVKSEK

LDFKDRVQSKIGSLDNITHVPGGGNKKIETHKLTFRENAKAKTDHGAE
``` dGAE95 refers to the 95 residues fragment of Tau (2N4R) with N-terminus at residue 11e-297 and C-terminus at residue Glu-391, as described in SEQ ID NO: 4, or at homologous positions in other species (the residues mentioned referring to the human or mouse Tau sequence, which are identical in this region). As will be apparent to the skilled person, dGAE95 also corresponds to the fragment of Isoform PNS-Tau (P10636-1) with N-ter at 11e-614 and C-ter at Glu-708. This sequence may sometimes be referred to simply as "dGAE". Residues 297 to 391 of Tau (2N4R) are also known as the predominant fragment isolated from proteolytically stable core of the paired helical filament (PHF).

```
SEQ ID NO: 4 (dGAE95 or "dGAE", human/mouse, 95
amino acids):
IKHVPGGGSVQIVYKPVDLSKVTSKCGSLGNIHHKPGGGQVEVKSEKLD

FKDRVQSKIGSLDNITHVPGGGNKKIETHKLTFRENAKAKTDHGAE
```

"dGA" refers to the 94 residues fragment of Tau (2N4R) with N-terminus at residue 11e-297 and C-terminus at residue Ala-390, as described in SEQ ID NO: 5, or at homologous positions in other species (the residues mentioned referring to the human or mouse Tau sequence, which are identical in this region).

```
SEQ ID NO: 5 (dGA, human/mouse, 94 amino acids):
IKHVPGGGSVQIVYKPVDLSKVTSKCGSLGNIHHKPGGGQVEVKSEKLD

FKDRVQSKIGSLDNITHVPGGGNKKIETHKLTFRENAKAKTDHGA
``` dGAE73 refers to the fragment of Tau (2N4R) with N-terminus at residue Val-306 and C-terminus at residue Phe-378, as described in SEQ ID NO: 6, or at homologous positions in other species (the residues mentioned referring to the human or mouse Tau sequence, which are identical in this region). This fragment corresponds to residues 306-378 of the sequence identified by cryo-EM as being the core of PHFs isolated from AD brain tissue (Fitzpatrick et al, 2017; Nature). The core can extend beyond these residues but is limited by the resolution of the cryo-EM. As will be apparent to the skilled person, dGAE73 also corresponds to the fragment of Isoform PNS-Tau (P10636-1) with N-ter at Val-623 and C-ter at Phe-695.

```
SEQ ID NO: 6 (dGAE73, human/mouse, 73 amino
acids):
VQIVYKPVDLSKVTSKCGSLGNIHHKPGGGQVEVKSEKLDFKDRVQSKI

GSLDNITHVPGGGNKKIETHKLTF
```

The PHF core refers to residues 296 to 391 of Tau (2N4R) as described in SEQ ID NO: 3, or at homologous positions in other species (the residues mentioned referring to the human or mouse Tau sequence, which are identical in this region).

A further fragment of the PHF core is residues 308 to 378 of Tau (2N4R) with N-terminus at residue 11e-308 and C-terminus at residue Phe-378, as described in SEQ ID NO: 7, or at homologous positions in other species (the residues mentioned referring to the human or mouse Tau sequence, which are identical in this region).

```
SEQ ID NO: 7 (dGAE71, residues 308 to 378 of
2N4R, human/mouse, 71 amino acids):
IVYKPVDLSKVTSKCGSLGNIHHKPGGGQVEVKSEKLDFKDRVQSKIGS

LDNITHVPGGGNKKIETHKLTF
```

The epitope of the specific binding molecule may be within SEQ ID NO: 3, SEQ ID NO: 4, SEQ ID NO: 5, SEQ ID NO: 6 or SEQ ID NO: 7.

The epitope of the specific binding molecule may be within residues 297 to 391 of SEQ ID NO: 1. Residues 297 to 391 of full-length Tau are also known as the predominant fragment isolated from proteolytically stable core of the paired helical filament (PHF) or the PHF-core fragment. Therefore, the epitope of the specific binding molecule may be within the PHF or within the dGAE fragment. Accordingly, the epitope of the specific binding molecule may be within SEQ ID NO 4.

The epitope of the specific binding molecule may be within residues 297 to 390 of SEQ ID NO: 1. Residues 297 to 390 of full-length Tau are also known as the dGA fragment. Therefore, the epitope of the specific binding molecule may be within the dGA fragment. Accordingly, the epitope of the specific binding molecule may be within SEQ ID NO: 5. The epitope of the specific binding molecule may be within dGAE73 and/or dGAE71. Accordingly, the epitope of the specific binding molecule may be within SEQ ID NO: 6 and/or SEQ ID NO: 7.

The epitope of the specific binding molecule may be within residues 308 to 378 of SEQ ID NO: 1. Residues 308 to 378 of full-length Tau are also known as the PHF core. Therefore, the epitope of the specific binding molecule may be within the PHF core. Accordingly, the epitope of the specific binding molecule may be within SEQ ID NO: 7.

The epitope of the specific binding molecule may be within residues 297 to 386 of SEQ ID NO: 1. The epitope of the specific binding molecule may be within residues 306 to 391 of SEQ ID NO: 1. The epitope of the specific binding molecule may be within residues 306 to 386 of SEQ ID NO: 1.

The epitope of the specific binding molecule may be within an amino acid sequence selected from the group consisting of residues 337 to 355 of SEQ ID NO: 1, residues 367 to 379 of SEQ ID NO: 1, residues 331 to 360 of SEQ ID NO: 1, residues 355 to 367 of SEQ ID NO: 1, residues 379 to 391 of SEQ ID NO: 1, residues 297 to 390 of SEQ ID NO: 1, residues 369 to 390 of SEQ ID NO: 1, residues 337 to 368 of SEQ ID NO: 1, residues 412 to 441 of SEQ ID NO: 1, residues 1 to 49 of SEQ ID NO: 1, residues 49 to 111 of SEQ ID NO: 1, residues 147 to 157 of SEQ ID NO: 1, residues 1 to 155 of SEQ ID NO: 1, residues 1 to 238 of SEQ ID NO: 1, residues 1 to 319 of SEQ ID NO: 1, residues 13 to 25 of SEQ ID NO: 1, residues 49 to 113 of SEQ ID NO: 1, residues 49 to 155 of SEQ ID NO: 1, residues 49 to 238 of SEQ ID NO: 1, residues 113 to 238 of SEQ ID NO: 1, residues 155 to 227 of SEQ ID NO: 1, residues 155 to 238 of SEQ ID NO: 1, residues 186 to 263 of SEQ ID NO: 1, residues 186 to 350 of SEQ ID NO: 1, residues 239 to 348 of SEQ ID NO: 1, residues 266 to 359 of SEQ ID NO: 1, residues 277 to 319 of SEQ ID NO: 1, residues 319 to 331 of SEQ ID NO: 1, residues 348 to 390 of SEQ ID NO: 1, residues 348 to 441 of SEQ ID NO: 1, residues 359 to 391 of SEQ ID NO: 1, and residues 360 to 390 of SEQ ID NO: 1.

The epitope of the specific binding molecule may be within an amino acid sequence selected from the group consisting of residues 337 to 355 of SEQ ID NO: 1, residues 367 to 379 of SEQ ID NO: 1, residues 331 to 360 of SEQ ID NO: 1, residues 355 to 367 of SEQ ID NO: 1, residues 379 to 391 of SEQ ID NO: 1, residues 297 to 390 of SEQ ID NO: 1, residues 369 to 390 of SEQ ID NO: 1, residues 337 to 368 of SEQ ID NO: 1, residues 412 to 441 of SEQ ID NO: 1, residues 1 to 49 of SEQ ID NO: 1, residues 49 to 111 of SEQ ID NO: 1, and residues 147 to 157 of SEQ ID NO: 1.

The epitope of the specific binding molecule may be within an amino acid sequence selected from the group consisting of residues 337 to 355 of SEQ ID NO: 1, residues 367 to 379 of SEQ ID NO: 1, residues 331 to 360 of SEQ ID NO: 1 and residues 355 to 367 of SEQ ID NO: 1.

The epitope of the specific binding molecule may be within an amino acid sequence selected from the group consisting of residues 341 to 353 of SEQ ID NO: 1.

The epitope of specific binding molecules of the invention may be any amino acid sequence of SEQ ID NO: 1 indicated as containing critical binding residues by ELISA or alanine scanning mutagenesis, as described for example in Examples 5 to 12.

Epitopes described herein may be identified as "comprising" a certain amino acid sequence or by the phrase "the specific binding molecule binds to a polypeptide or protein molecule comprising an amino acid sequence comprising residues . . . ". As will be apparent to the skilled person, when a specific binding molecule binds a polypeptide or protein molecule comprising its epitope, it will also bind a polypeptide or protein molecule consisting of its epitope. As used herein, the phrase "the specific binding molecule binds to a polypeptide or protein molecule comprising an amino acid sequence comprising residues . . . " may therefore alternatively be substituted wherever it occurs for the phrase "the specific binding molecule binds to a polypeptide or protein molecule comprising an amino acid sequence consisting of residues . . . "; the phrase "the specific binding molecule binds to a polypeptide or protein molecule consisting of an amino acid sequence comprising residues . . . "; or the phrase "the specific binding molecule binds to a polypeptide or protein molecule consisting of an amino acid sequence consisting of residues . . . ".

The skilled person is aware that not all residues within an epitope are always essential. A specific binding molecule may retain binding to an amino acid sequence with at least 70% identity to an epitope. The specific binding molecule may bind to any of the epitopes disclosed herein or an amino acid sequence having at least 70% identity thereto.

A specific binding molecule may retain binding to an amino acid sequence with at least 70%, at least 75%, at least 80%, at least 90%, at least 95% or at least 99% identity to an epitope. The specific binding molecule may bind to any of the epitopes disclosed herein or an amino acid sequence having at least 70%, at least 75%, at least 80%, at least 90%, at least 95% or at least 99% identity thereto.

In embodiments of the invention where specific binding molecule retains binding to an amino acid sequence with less than 100% sequence identity to the amino acid sequence of SEQ ID NO: 1 (or any of SEQ ID NOS: 3 to 7 or any other epitope defined herein), the epitope sequence may be altered by substitution, addition or deletion of an appropriate number of amino acids in the sequences of SEQ ID NO: 1 (or any of SEQ ID NOs: 3 to 7 or any other epitope defined herein). In another embodiment of the invention, the epitope may be modified by the substitution, addition or deletion of up to 2 amino acids relative to SEQ ID NO: 1 (or any of SEQ ID NOS: 3 to 7 or any other epitope defined herein), with the proviso that the resultant epitope sequence has at least 85% or 90% sequence identity to SEQ ID NO: 1 (or any of SEQ ID NOS: 3 to 7 or any other epitope defined herein), as set out above. By "substitution, addition or deletion" is included combinations of substitutions, additions and deletions.

When an epitope sequence is modified by substitution of a particular amino acid residue, the substitution may be a conservative amino acid substitution. The term "conservative amino acid substitution", as used herein, refers to an amino acid substitution in which one amino acid residue is replaced with another amino acid residue having a similar side chain. Amino acids with similar side chains tend to have similar properties, and thus a conservative substitution of an amino acid important for the structure or function of a polypeptide may be expected to affect polypeptide structure/function less than a non-conservative amino acid substitution at the same position. Families of amino acid residues having similar side chains have been defined in the art, including basic side chains (e.g. lysine, arginine, histidine), acidic side chains (e.g. aspartic acid, glutamic acid), uncharged polar side chains (e.g. asparagine, glutamine, serine, threonine, tyrosine), non-polar side chains (e.g. glycine, cysteine, alanine, valine, leucine, isoleucine, proline, phenylalanine, methionine, tryptophan) and aromatic side chains (e.g. tyrosine, phenylalanine, tryptophan, histidine). Thus a conservative amino acid substitution may be considered to be a substitution in which a particular amino acid residue is substituted for a different amino acid in the same family. However, a substitution of an epitope residue may equally be a non-conservative substitution, in which one amino acid is substituted for another with a side-chain belonging to a different family.

The epitope may be at least five, at least six, at least seven, at least eight, at least nine, at least 10, at least 11, at least 12, at least 13, at least 14, at least 15, at least 16, at least 17, at least 18, at least 19 or at least 20 amino acids in length. The epitope may be five to 20 amino acids in length. The epitope may be five to 15 amino acids in length. The epitope may be five to 12 amino acids in length. The epitope may be six to 12 amino acids in length. The epitope may be seven to 12 amino acids in length.

As used herein, the term "within" means "contained within" or "fully within". No residues thought to be essential for the binding of the specific binding molecule to its target are outside of the epitope.

Residues outside the epitope do not significantly contribute to binding. For example, where the epitope of the specific binding molecule is within residues 337 to 355 of SEQ ID NO: 1, residues outside of residues 337 to 355 do not significantly contribute to binding.

The epitope may comprise any residues within SEQ ID NO: 1 bound by the specific binding molecule.

The epitope may be a continuous epitope or a discontinuous epitope.

A continuous epitope may be any consecutive residues within SEQ ID NO: 1 bound by the specific binding molecule. Consecutive residues are adjacent to one another in the primary structure of a polypeptide.

A discontinuous epitope may be any non-consecutive residues within SEQ ID NO: 1 bound by the specific binding molecule. Discontinuous epitopes are typically formed by non-consecutive residues adopting nearby positions in three-dimensional space due to the folding of a polypeptide.

Typically, a specific binding molecule binds to a polypeptide or protein molecule comprising its epitope. Therefore, the specific binding molecule may bind to SEQ ID NO: 1 or a fragment thereof. The specific molecule may bind to SEQ ID NO: 3, SEQ ID NO: 4, SEQ ID NO: 5, SEQ ID NO: 6 and/or SEQ ID NO: 7. The specific molecule may bind to the PHF or the dGAE fragment, the specific binding molecule may bind to the dGA fragment. The specific binding molecule may bind to the PHF core. The specific binding molecule may bind to a polypeptide or protein molecule comprising an amino acid sequence selected from the group consisting of residues 337 to 355 of SEQ ID NO: 1, residues 367 to 379 of SEQ ID NO: 1, residues 331 to 360 of SEQ ID NO: 1, residues 355 to 367 of SEQ ID NO: 1, residues 379 to 391 of SEQ ID NO: 1, residues 297 to 390 of SEQ ID NO: 1, residues 369 to 390 of SEQ ID NO: 1, residues 337 to 368 of SEQ ID NO: 1, residues 412 to 441 of SEQ ID NO: 1, residues 1 to 49 of SEQ ID NO: 1, residues 49 to 111 of SEQ ID NO: 1, residues 147 to 157 of SEQ ID NO: 1, residues 1 to 155 of SEQ ID NO: 1, residues 1 to 238 of SEQ ID NO: 1, residues 1 to 319 of SEQ ID NO: 1, residues 13 to 25 of SEQ ID NO: 1, residues 49 to 113 of SEQ ID NO: 1, residues 49 to 155 of SEQ ID NO: 1, residues 49 to 238 of SEQ ID NO: 1, residues 113 to 238 of SEQ ID NO: 1, residues 155 to 227 of SEQ ID NO: 1, residues 155 to 238 of SEQ ID NO: 1, residues 186 to 263 of SEQ ID NO: 1, residues 186 to 350 of SEQ ID NO: 1, residues 239 to 348 of SEQ ID NO: 1, residues 266 to 359 of SEQ ID NO: 1, residues 277 to 319 of SEQ ID NO: 1, residues 319 to 331 of SEQ ID NO: 1, residues 348 to 390 of SEQ ID NO: 1, residues 348 to 441 of SEQ ID NO: 1, residues 359 to 391 of SEQ ID NO: 1, and residues 360 to 390 of SEQ ID NO: 1.

The specific binding molecule may bind to a polypeptide or protein molecule comprising an amino acid sequence of residues 341 to 353 of SEQ ID NO: 1.

In the sequences that follow, "/" means "or" and denotes residues that the inventors have shown may vary as specified. In this context, "-" means a gap or no amino acid. X is any amino acid. For example. "N/S" means a residue which may be either N or S. Likewise, "G/-" means a residue which may be either G or absent. Likewise, "H/F/Y" means a residue may be H, F or Y. Where sequence identity values are specified, sequence identity may be calculated starting from any one of the residues separated by a "/".

The epitope of the specific binding molecule may be within an amino acid sequence comprising residues 337 to 355 of SEQ ID NO: 1. The epitope of the specific binding molecule within an amino acid sequence comprising residues 337 to 355 of SEQ ID NO: 1 may be within an amino acid sequence comprising residues 341 to 353 of SEQ ID NO: 1. Accordingly, the epitope may be within the amino acid sequence of SEQ ID NO: 8 (VEVKSEKLDFKDR).

The epitope may be within an amino acid sequence comprising residues 337 to 349 of SEQ ID NO: 1, preferably within an amino acid sequence comprising residues 337 to 355 of SEQ ID NO: 1. This epitope may be bound by the CDRs of the specific binding molecule referred to as "S1D12" herein. The epitope may comprise the amino acid sequence of SEQ ID NO: 8 (VEVKSEKLDFKDR). The epitope may comprise an amino acid sequence having at least 70%, at least 75%, at least 80%, at least 90%, at least 95% or at least 99% identity to SEQ ID NO: 8 (VEVKSEKLDFKDR). Critical residues of the epitope may be residues 343 (K), 346 (F) and/or 349 (R) (numbering according to SEQ ID NO: 1). The epitope may comprise the amino acid sequence of SEQ ID NO: 9 (XXXXXXXKXXFXXR, wherein X is any amino acid). The epitope may comprise the amino acid sequence of SEQ ID NO: 8, wherein any one or more residue other than residue number 343 (K), 346 (F) and/or 349 (R) is replaced by a non-conservative amino acid substitution (numbering according to SEQ ID NO: 1). The epitope may comprise the amino acid sequence of SEQ ID NO: 8, wherein any one or more residue other than residue number 343 (K), 346 (F) and/or 349 (R) is replaced by a conservative amino acid substitution (numbering according to SEQ ID NO: 1). The epitope may comprise the amino acid sequence of SEQ ID NO: 8, wherein any one or more residue other than residue number 343 (K), 346 (F) and/or 349 (R) is replaced by a conservative amino acid substitution (numbering according to SEQ ID NO: 1) and any one or more residue other than residue number 343 (K), 346 (F) and/or 349 (R) is replaced by a non-conservative amino acid substitution (numbering according to SEQ ID NO: 1).

The epitope may consist of residues 337 to 349 of SEQ ID NO: 1, preferably residues 337 to 355 of SEQ ID NO: 1. The epitope may consist of the amino acid sequence of SEQ ID NO: 8 (VEVKSEKLDFKDR). The epitope may consist of an amino acid sequence having at least 70%, at least 75%, at least 80%, at least 90%, at least 95% or at least 99% identity to SEQ ID NO: 8 (VEVKSEKLDFKDR).

The specific binding molecule may bind to a polypeptide or protein molecule comprising an amino acid sequence comprising residues 337 to 355 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 10 (N/S N A V G);
VHCDR2 comprises the sequence set forth in SEQ ID NO: 11 (G C S S D G T/K C Y Y/H N SALKS);
VHCDR3 comprises the sequence set forth in SEQ ID NO: 12 (G H/F/Y Y S/P I/V Y G Y D YU/SGTIDY);
VLCDR1 comprises the sequence set forth in SEQ ID NO: 13 (S G S S S N V G/-G G/R N S/D V G/A);
VLCDR2 comprises the sequence set forth in SEQ ID NO: 14 (D/N/G T N/T S R P S);

VLCDR3 comprises the sequence set forth in SEQ ID
NO: 15 (VIA T/S G D S T/S T/A H/I D/N D L/I);
or for each CDR sequence, an amino acid sequence with
(i) at least 85% identity thereto, and/or
(ii) one, two, or three amino acid substitutions relative
thereto.

Said sequence identity is at least about 85% sequence
identity and may therefore be at least 85%, at least 86%, at
least 87%, at least 88%, at least 89%, at least 90%, at least
91%, at least 92%, at least 93%, at least 94%, at least 95%,
at least 96%, at least 97%, at least 98%, or at least 99%
identity. Preferably said sequence identity is at least 90% or
at least 95%.

The specific binding molecule may comprise the CDRs
VHCDR1, VHCDR2, VHCDR3, VLCDR1. VLCDR2 and
VLCDR3, wherein each of said CDRs comprises an amino
acid sequence as follows:
VHCDR1 comprises the sequence set forth in SEQ ID
NO: 16 (NNAVG) or SEQ ID NO: 17 (SNAVG);
VHCDR2 comprises the sequence set forth in SEQ ID
NO: 18 (GCSSDGTCYYNSALKS). SEQ ID NO: 19
(GCSSDGKCYHNSALKS) or SEQ ID NO: 20
(GCSSDGKCYYNSALKS);
VHCDR3 comprises the sequence set forth in SEQ ID
NO: 21 (GHYSIYGYDYLGTIDY), SEQ ID NO: 22
(GFYSIYGYDYSGTIDY), or SEQ ID NO: 23
(GYYPVYGYDYLGTIDY);
VLCDR1 comprises the sequence set forth in SEQ ID
NO: 24 (SGSSSNVGGGNSVG) or SEQ ID NO: 25
(SGSSSNVGRNDVA);
VLCDR2 comprises the sequence set forth in SEQ ID
NO: 26 (DTNSRPS), SEQ ID NO: 27 (NTNSRPS), or
SEQ ID NO: 28 (GTTSRPS);
VLCDR3 comprises the sequence set forth in SEQ ID
NO: 29 (VTGDSTTHDDL), SEQ ID NO: 30
(VTGDSSTHDDL), or SEQ ID NO: 31 (ASGDS-
SAINDI);
or for each CDR sequence, an amino acid sequence with
(i) at least 85% identity thereto, and/or
(ii) one, two, or three amino acid substitutions relative
thereto,
wherein the specific binding molecule binds to a poly-
peptide or protein molecule comprising an amino
acid sequence comprising residues 337 to 355 of
SEQ ID NO: 1.

The specific binding molecule may comprise the CDRs
VHCDR1, VHCDR2, VHCDR3, VLCDR1. VLCDR2 and
VLCDR3, wherein each of said CDRs comprises an amino
acid sequence as follows:
VHCDR1 comprises the sequence set forth in SEQ ID
NO: 16 (NNAVG);
VHCDR2 comprises the sequence set forth in SEQ ID
NO: 18 (GCSSDGTCYYNSALKS);
VHCDR3 comprises the sequence set forth in SEQ ID
NO: 21 (GHYSIYGYDYLGTIDY);
VLCDR1 comprises the sequence set forth in SEQ ID
NO: 24 (SGSSSNVGGGNSVG);
VLCDR2 comprises the sequence set forth in SEQ ID
NO: 26 (DTNSRPS);
VLCDR3 comprises the sequence set forth in SEQ ID
NO: 29 (VTGDSTTHDDL);
or for each CDR sequence, an amino acid sequence with
(i) at least 85% identity thereto, and/or
(ii) one, two, or three amino acid substitutions relative
thereto,
wherein the specific binding molecule binds to a poly-
peptide or protein molecule comprising an amino acid sequence comprising residues 337 to 355 of SEQ ID
NO: 1. The specific binding molecule comprising
CDRs having 100% identity to those given above is
referred to as "S1D12" (or abbreviated to "1D12")
herein.

The specific binding molecule may comprise the CDRs
VHCDR1, VHCDR2, VHCDR3, VLCDR1. VLCDR2 and
VLCDR3, wherein each of said CDRs comprises an amino
acid sequence as follows:
VHCDR1 comprises the sequence set forth in SEQ ID
NO: 16 (NNAVG);
VHCDR2 comprises the sequence set forth in SEQ ID
NO: 18 (GCSSDGTCYYNSALKS);
VHCDR3 comprises the sequence set forth in SEQ ID
NO: 21 (GHYSIYGYDYLGTIDY);
VLCDR1 comprises the sequence set forth in SEQ ID
NO: 24 (SGSSSNVGGGNSVG);
VLCDR2 comprises the sequence set forth in SEQ ID
NO: 26 (DTNSRPS); and
VLCDR3 comprises the sequence set forth in SEQ ID
NO: 29 (VTGDSTTHDDL).

Any specific binding molecule disclosed herein may be
further defined by reference to one or more framework
region (FR). The framework regions (FRs) are non-CDR
sequences which together with the CDR sequences form a
variable domain.

The VH domain may have the formula: VHFR1-
VHCDR1-VHFR2-VHCDR2-VHFR3-VHCDR3-VHFR4.

The VL domain may have the formula: VLFR1-
VLCDR1-VLFR2-VLCDR2-VLFR3-VLCDR3-VLFR4.

The skilled person is able to identify CDR and framework
regions within the amino acid sequence of a variable domain
using known methods described elsewhere herein. Accord-
ingly, any specific binding molecule disclosed herein may be
defined by reference to its CDRs and FRs. In some instances,
some of the FR residues may contribute to the affinity with
which a specific binding molecule binds its target. However,
without being bound by theory, function is more likely to be
preserved when replacing an FR residue than when replac-
ing a CDR residue. FR residues may for example be
commonly replaced by corresponding residues from human
sequences during the process of humanization. FR
sequences may therefore be more tolerant of amino acid
substitutions than CDR sequences.

The specific binding molecule may comprise:
(a) framework regions (FRs) VHFR1, VHFR2, VHFR3,
VHFR4, VLFR1, VLFR2, VLFR3 and VLFR4,
wherein each of said FRs comprises an amino acid
sequence from any specific binding molecule disclosed
herein; or for each FR sequence, an amino acid
sequence with
(i) at least 50% identity thereto, and/or
(ii) one, two, three, four or five amino acid substitutions
relative thereto; and
(b) CDRs VHCDR1, VHCDR2, VHCDR3, VLCDR1,
VLCDR2 and VLCDR3, wherein each of said CDRs
comprises an amino acid sequence from any specific
binding molecule disclosed herein, or for each CDR
sequence, an amino acid sequence with
(i) at least 85% identity thereto, and/or
(ii) one, two, or three amino acid substitutions relative
thereto.

Said sequence identity in a CDR sequence is at least about
85% sequence identity and may therefore be at least 85%, at
least 86%, at least 87%, at least 88%, at least 89%, at least
90%, at least 91%, at least 92%, at least 93%, at least 94%, at least 95%, at least 96%, at least 97%, at least 98%, or at least 99% identity. Preferably said sequence identity is at least 90% or at least 95%.

Said sequence identity in a FR sequence is at least about 50% sequence identity and may therefore be at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

Where an FR sequence has at least 50% identity (but less than 100% identity) to an FR sequence disclosed as part of a specific binding molecule disclosed herein, the FR sequence may be a humanized sequence. In other words, the changes to amino acid sequence may be only those needed to humanize the sequence.

Where an FR sequence has one, two, three, four or five amino acid substitutions relative to an FR sequence disclosed as part of a specific binding molecule disclosed herein, the FR sequence may be a humanized sequence. In other words, the substitutions may be only those needed to humanize the sequence.

The specific binding molecule may comprise:
(a) framework regions (FRs) VHFR1, VHFR2, VHFR3, VHFR4, VLFR1, VLFR2, VLFR3 and VLFR4, wherein each of said FRs comprises an amino acid sequence from any specific binding molecule disclosed herein; and
(b) CDRs VHCDR1, VHCDR2, VHCDR3, VLCDR1, VLCDR2 and VLCDR3, wherein each of said CDRs comprises an amino acid sequence from any specific binding molecule disclosed herein.

Typically, each of the FRs will be from the same specific binding molecule disclosed herein. Typically, each of the CDRs will be from the same specific binding molecule disclosed herein. Typically, there will be no additional amino acid residues intervening between a defined FR and CDR; each of said FRs and each of said CDRs may therefore be said to consist of an amino acid sequence from any specific binding molecule disclosed herein.

As used herein, the phrase "comprising the CDRs" also encompasses a specific binding molecule comprising the CDRs and FRs of a specific binding molecule disclosed herein, including variants of the FRs including those described above, such as humanized FRs. It also encompasses a specific binding molecule comprising the VH and/or VL domains of a specific binding molecule disclosed herein, including variants of the FRs including those described above, such as humanized FRs. It also encompasses a specific binding molecule comprising the heavy chain and/or light chain of a specific binding molecule disclosed herein, including variants of the FRs and constant regions including those described above, such as humanized FRs and humanized constant regions.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:
VHFR1 comprises the sequence set forth in SEQ ID NO: 435 (QVQLQESGPSLVKPSQTLSLTCTVSGFSLN);
VHFR2 comprises the sequence set forth in SEQ ID NO: 436 (WRQAPGKVPESLV);
VHFR3 comprises the sequence set forth in SEQ ID NO: 437 (RLDITRDTSKNQISLSLSSVTTD-DAAVYYCTR);

VHFR4 comprises the sequence set forth in SEQ ID NO: 438 (WGPGLLVTVSS);
VLFR1 comprises the sequence set forth in SEQ ID NO: 439 (QAVLTQPSSVSGSLGQRVSITC);
VLFR2 comprises the sequence set forth in SEQ ID NO: 440 (WYQHLPGSGLKTIIY);
VLFR3 comprises the sequence set forth in SEQ ID NO: 441 (GVPDRFSGSRSGNTATLTINSLQAEDE-GDYYC);
VLFR4 comprises the sequence set forth in SEQ ID NO: 442 (VGSGTRLTVLG);
or for each FR sequence, an amino acid sequence with
(i) at least 50% identity thereto, and/or
(ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:
VHFR1 comprises the sequence set forth in SEQ ID NO: 435 (QVQLQESGPSLVKPSQTLSLTCTVSGFSLN);
VHFR2 comprises the sequence set forth in SEQ ID NO: 436 (WRQAPGKVPESLV);
VHFR3 comprises the sequence set forth in SEQ ID NO: 437 (RLDITRDTSKNQISLSLSSVTTD-DAAVYYCTR);
VHFR4 comprises the sequence set forth in SEQ ID NO: 438 (WGPGLLVTVSS);
VLFR1 comprises the sequence set forth in SEQ ID NO: 439 (QAVLTQPSSVSGSLGQRVSITC);
VLFR2 comprises the sequence set forth in SEQ ID NO: 440 (WYQHLPGSGLKTIIY);
VLFR3 comprises the sequence set forth in SEQ ID NO: 441 (GVPDRFSGSRSGNTATLTINSLQAEDE-GDYYC);
VLFR4 comprises the sequence set forth in SEQ ID NO: 442 (VGSGTRLTVLG);
or for each FR sequence, an amino acid sequence with
(i) at least 50% identity thereto, and/or
(ii) one, two, three, four or five amino acid substitutions relative thereto,
wherein the specific binding molecule binds to a polypeptide or protein molecule comprising an amino acid sequence comprising residues 337 to 355 of SEQ ID NO: 1. A specific binding molecule comprising FRs having 100% identity to those given above is referred to as "S1D12" (or abbreviated to "1D12") herein.

The specific binding molecule may comprise:
(a) framework regions (FRs) VHFR1, VHFR2. VHFR3, VHFR4, VLFR1, VLFR2, VLFR3 and VLFR4, wherein each of said FRs comprises an amino acid sequence as follows:
VHFR1 comprises the sequence set forth in SEQ ID NO: 435 (QVQLQESGPSLVKP-SQTLSLTCTVSGFSLN);
VHFR2 comprises the sequence set forth in SEQ ID NO: 436 (WRQAPGKVPESLV);
VHFR3 comprises the sequence set forth in SEQ ID NO: 437 (RLDITRDTSKNQISLSLSSVTTD-DAAVYYCTR);
VHFR4 comprises the sequence set forth in SEQ ID NO: 438 (WGPGLLVTVSS); VLFR1 comprises set the sequence forth in SEQ ID NO: 439 (QAVLTQPSSVSGSLGQRVSITC);
VLFR2 comprises the sequence set forth in SEQ ID NO: 440 (WYQHLPGSGLKTIIY);

VLFR3 comprises the sequence set forth in SEQ ID NO: 441 (GVPDRFSGSRSGNTATLTINSLQAE-DEGDYYC);

VLFR4 comprises the sequence set forth in SEQ ID NO: 442 (VGSGTRLTVLG);

or for each FR sequence, an amino acid sequence with
  (i) at least 50% identity thereto, and/or
  (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 16 (NNAVG);

VHCDR2 comprises the sequence set forth in SEQ ID NO: 18 (GCSSDGTCYYNSALKS);

VHCDR3 comprises the sequence set forth in SEQ ID NO: 21 (GHYSIYGYDYLGTIDY);

VLCDR1 comprises the sequence set forth in SEQ ID NO: 24 (SGSSSNVGGGNSVG);

VLCDR2 comprises the sequence set forth in SEQ ID NO: 26 (DTNSRPS);

VLCDR3 comprises the sequence set forth in SEQ ID NO: 29 (VTGDSTTHDDL);

or for each CDR sequence, an amino acid sequence with
  (i) at least 85% identity thereto, and/or
  (ii) one, two, or three amino acid substitutions relative thereto wherein the specific binding molecule binds to a polypeptide or protein molecule comprising an amino acid sequence comprising residues 337 to 355 of SEQ ID NO: 1. The specific binding molecule comprising FRs and CDRs having 100% identity to those given above is referred to as "S1D12" (or abbreviated to "1D12") herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 435 (QVQLQESGPSLVKP-SQTLSLTCTVSGFSLN);

VHFR2 comprises the sequence set forth in SEQ ID NO: 436 (WRQAPGKVPESLV);

VHFR3 comprises the sequence set forth in SEQ ID NO: 437 (RLDITRDTSKNQISLSLSSVTTD-DAAVYYCTR);

VHFR4 comprises the sequence set forth in SEQ ID NO: 438 (WGPGLLVTVSS);

VLFR1 comprises the sequence set forth in SEQ ID NO: 439 (QAVLTQPSSVSGSLGQRVSITC);

VLFR2 comprises the sequence set forth in SEQ ID NO: 440 (WYQHLPGSGLKTIIY);

VLFR3 comprises the sequence set forth in SEQ ID NO: 441 (GVPDRFSGSRSGNTATLTINSLQAE-DEGDYYC);

VLFR4 comprises the sequence set forth in SEQ ID NO: 442 (VGSGTRLTVLG);

or for each FR sequence, an amino acid sequence with
  (i) at least 50% identity thereto, and/or
  (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 16 (NNAVG);

VHCDR2 comprises the sequence set forth in SEQ ID NO: 18 (GCSSDGTCYYNSALKS);

VHCDR3 comprises the sequence set forth in SEQ ID NO: 21 (GHYSIYGYDYLGTIDY);

VLCDR1 comprises the sequence set forth in SEQ ID NO: 24 (SGSSSNVGGGNSVG);

VLCDR2 comprises the sequence set forth in SEQ ID NO: 26 (DTNSRPS);

VLCDR3 comprises the sequence set forth in SEQ ID NO: 29 (VTGDSTTHDDL);

wherein the specific binding molecule binds to a polypeptide or protein molecule comprising an amino acid sequence comprising residues 337 to 355 of SEQ ID NO: 1. The specific binding molecule comprising FRs and CDRs having 100% identity to those given above is referred to as "S1D12" (or abbreviated to "1D12") herein.

The specific binding molecule may comprise:

(a) A VH domain comprising the sequence set forth in SEQ ID NO: 443 (QVQLQESGPSLVKP-SQTLSLTCTVSGFSLNN-NAVGWVRQAPGKVPESLVGCSSDGTCY YNSALKSRLDITRDTSKNQISLSLSSVTTD-DAAVYYCTRGHYSIYGYDYLGTIDYWGPGLL VTVSS); and/or (b) a VL domain comprising the sequence set forth in SEQ ID NO: 444 (QAVLTQPSSVSGSLGQRVSITCSGSSSNVGGG-NSVGWYQHLPGSGLKTIIYDTNSRPSG VPDRFSGSRSGNTATLTINSLQAEDE-GDYYCVTGDSTTHDDLVGSGTRLTVLG);

or a humanized variant thereof.

The specific binding molecule may comprise:

```
(a) A heavy chain comprising the sequence set
forth in SEQ ID NO: 445
(QVQLQESGPSLVKPSQTLSLTCTVSGFSLNNNAVGWVRQAPGKVPESL

VGCSSDGTCYYNSALKSRLDITRDTSKNQISLSLSSVTTDDAAVYYCTR

GHYSIYGYDYLGTIDYWGPGLLVTVSSAKTTAPSVYPLAPVCGDTTGSS

VTLGCLVKGYFPEPVTLTWNSGSLSSGVHTFPAVLQSDLYTLSSSVTVT

SSTWPSQSITCNVAHPASSTKVDKKIEPRGPTIKPCPPCKCPAPNLLGG

PSVFIFPPKIKDVLMISLSPIVTCVVVDVSEDDPDVQISWFVNNVEVHT

AQTQTHREDYNSTLRVVSALPIQHQDWMSGKEFKCKVNNKDLPAPIERT

ISKPKGSVRAPQVYVLPPPEEEMTKKQVTLTCMVTDFMPEDIYVEWTNN

GKTELNYKNTEPVLDSDGSYFMYSKLRVEKKNWVERNSYSCSVVHEGLH

NHHTTKSFSRTPGK) ;
and/or (b) a light chain comprising the sequence set
forth in SEQ ID NO: 446
(QAVLTQPSSVSGSLGQRVSITCSGSSSNVGGGNSVGWYQHLPGSGLKT

IIYDTNSRPSGVPDRFSGSRSGNTATLTINSLQAEDEGDYYCVTGDSTT

HDDLVGSGTRLTVLGGQPKSSPSVTLFPPSSEELETNKATLVCTITDFY

PGVVTVDWKVDGTPVTQGMETTQPSKQSNNKYMASSYLTLTARAWERHS

SYSCQVTHEGHTVEKSLSRADCS) ;
``` or a humanized variant thereof.

The specific binding molecule may comprise the CDR sequences of a clone set out in Table 1 below. The epitope may be within residues 337 to 355 of SEQ ID

TABLE 1

| Clone | VH | | | VL | | | |
|---|---|---|---|---|---|---|---|
| name | CDR1 | CDR2 | CDR3 | CDR1 | CDR2 | CDR3 | Epitope |
| S1D12 | NNAVG (SEQ ID NO: 16) | SEQGCSSDGTCYYNSALKS (SEQ ID NO: 18) | GHYSIYGYDYLGTIDY (SEQ ID NO: 21) | SGSSSNVGGGNSVG (SEQ ID NO: 24) | DTNSRPS (SEQ ID NO: 26) | VTGDSTTHDDL (SEQ ID NO: 29) | 337-355 |
| S2C1 | NNAVG (SEQ ID NO: 16) | SEQGCSSDGTCYYNSALKS (SEQ ID NO: 18) | NA | NA | NA | NA | 337-355 |
| ME12 | SNAVG (SEQ ID NO: 17) | SEQGCSSDGKCYHNSALKS (SEQ ID NO: 19) | GFYSIYGYDYSGTIDY (SEQ ID NO: 22) | SGSSSNVGGGNSVG (SEQ ID NO: 24) | NTNSRPS (SEQ ID NO: 27) | VTGDSSTHDDL (SEQ ID NO: 30) | 337-355 |
| NS3D9 | SNAVG (SEQ ID NO: 17) | SEQGCSSDGKCYYNSALKS (SEQ ID NO: 20) | GYYPVYGYDYLGTIDY (SEQ ID NO: 23) | SGSSSNV-GRNDVA (SEQ ID NO: 25) | GTTSRPS (SEQ ID NO: 28) | ASGDSSAINDI (SEQ ID NO: 31) | 337-355 |

The CDRs specified herein are defined according to Kabat. The skilled person is aware that other methods for identifying CDRs are available, such as Chothia and Martin. The use of an alternative method to define CDRs may on occasion alter the residues defined as belonging to one or more CDRs. For example, alternative CDR definitions for S1D12 according to Chothia and Martin are shown in FIG. 1. Any alternative CDR definitions for the specific binding molecule sequences disclosed herein fall within the scope of the invention.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises a VHCDR1 amino acid sequence set forth in table 1;

VHCDR2 comprises a VHCDR2 amino acid sequence set forth in table 1;

VHCDR3 comprises a VHCDR3 amino acid sequence set forth in table 1;

VLCDR1 comprises a VLCDR1 amino acid sequence set forth in table 1;

VLCDR2 comprises a VLCDR2 amino acid sequence set forth in table 1; and

VLCDR3 comprises a VLCDR3 amino acid sequence set forth in table 1;

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 337 to 355 of SEQ ID NO: 1.

The specific binding molecule may bind to a polypeptide or protein molecule comprising an amino acid sequence comprising residues 337 to 355 of SEQ ID NO: 1 with a $K_D$ of less than around 500 pM. The $K_D$ may be less than around 400 pM, less than around 300 PM, less than around 200 pM or less than around 150 pM. The Ko may preferably be for binding to SEQ ID NO: 1 or to SEQ ID NO: 5. The $K_D$ for binding to SEQ ID NO: 1 may be around 50 pM to around 150 pM. The Ko for binding to SEQ ID NO: 1 may be around 101 pM or 122 pM, optionally wherein the specific binding molecule comprises the CDRs of S1D12. The $K_D$ for binding to SEQ ID NO: 5 may be around 300 pM to around 400 pM. The $K_D$ for binding to SEQ ID NO: 5 may be around 344 pM, optionally wherein the specific binding molecule comprises the CDRs of S1D12.

The specific binding molecule may comprise an amino acid sequence having at least 70%, at least 75%, at least 80%, at least 90%, at least 95% or at least 99% identity to SEQ ID NO: 32 wherein the specific binding molecule binds to a polypeptide or protein molecule comprising an amino acid sequence comprising residues 337 to 355 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 30. The CDRs may be 100% identical to the CDRs of SEQ ID NO: 32. The specific binding molecule may comprise an amino acid sequence having at least 70%, at least 75%, at least 80%, at least 90%, at least 95% or at least 99% identity to SEQ ID NO: 30 wherein CDRs are 100% identical to the CDRs of SEQ ID NO: 32. The specific binding molecule may comprise the amino acid sequence of SEQ ID NO: 32.

```
(S1D12 amino acid sequence)
                              SEQ ID NO: 32
QVQLQESGPSLVKPSQTLSLTCTVSGFSLNNNAVGWVRQAPGKVPESLV

GCSSDGTCYYNSALKSRLDITRDTSKNQISLSLSSVTTDDAAVYYCTRG

HYSIYGYDYLGTIDYWGPGLLVTVSSEGKSSGASGESKVDDQAVLTQPS

SVSGSLGQRVSITCSGSSSNVGGGNSVGWYQHLPGSGLKTIIYDTNSRP

SGVPDRFSGSRSGNTATLTINSLQAEDEGDYYCVTGDSTTHDDLVGSGT

RLTVLG
```

The epitope of the specific binding molecule may be within an amino acid sequence comprising residues 367 to 379 of SEQ ID NO: 1. Accordingly, the epitope may be within the amino acid sequence of SEQ ID NO: 33 (GNK-KIETHKLTFR).

The epitope may be within an amino acid sequence comprising residues 367 to 379 of SEQ ID NO: 1. This epitope may be bound by the CDRs of the specific binding molecule referred to as "S1G2" herein.

The epitope may comprise the amino acid sequence of SEQ ID NO: 33 (GNKKIETHKLTFR). The epitope may comprise an amino acid sequence having at least 70%, at least 75%, at least 80%, at least 90%, at least 95% or at least 99% identity to SEQ ID NO: 33 (GNKKIETHKLTFR). Critical residues of the epitope may be residues 370 (K) and/or 374 (H) (numbering according to SEQ ID NO: 1). The epitope may comprise the amino acid sequence of SEQ ID NO: 34 (XXXKXXXHXXXXX, wherein X is any amino acid). The epitope may comprise the amino acid sequence of SEQ ID NO: 33, wherein any one or more residue other than residue number 370 (K) and/or 374 (H) is replaced by a non-conservative amino acid substitution (numbering according to SEQ ID NO: 1). The epitope may comprise the amino acid sequence of SEQ ID NO: 33, wherein any one or more residue other than residue number 370 (K) and/or 374 (H) is replaced by a conservative amino acid substitution (numbering according to SEQ ID NO: 1). The epitope may comprise the amino acid sequence of SEQ ID NO: 33, wherein any one or more residue other than residue number 370 (K) and/or 374 (H) is replaced by a conservative amino acid substitution (numbering according to SEQ ID NO: 1) and any one or more residue other than residue number 370 (K) and/or 374 (H) is replaced by a non-conservative amino acid substitution (numbering according to SEQ ID NO: 1).

The epitope may consist of the amino acid sequence of SEQ ID NO: 33 (GNKKIETHKLTFR). The epitope may consist of an amino acid sequence having at least 70%, at least 75%, at least 80%, at least 90%, at least 95% or at least 99% identity to SEQ ID NO: 33 (GNKKIETHKLTFR).

The specific binding molecule may bind to a polypeptide or protein molecule comprising an amino acid sequence comprising residues 367 to 379 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 35 (S/T N/Y S/A/Y V G);

VHCDR2 comprises the sequence set forth in SEQ ID NO: 36 (G/S/N I/V DAY T/S D/T G E/Y/D/R E/T/A G/Y/F Y/F N P A/V L N/K S);

VHCDR3 comprises the sequence set forth in SEQ ID NO: 37 (S/T Y/V/A R/N A/T/G/S D/-G/-L/Y/F/-A/-Y/H G/P Y/D V Q/Y A/Y I D/E Y/R/K) or SEQ ID NO: 265 (GSYYHGGGNGMVDFFDY);

VLCDR1 comprises the sequence set forth in SEQ ID NO: 38 (S G S/R F/Y/D I/L/V G/S I/S/R S S/R/A/G V G) or in SEQ ID NO: 39 (SGSSSNVGYGNYVG)

VLCDR2 comprises the sequence set forth in SEQ ID NO: 40 (A/D S/A D/S/T G/S R P/A S);

VLCDR3 comprises the sequence set forth in SEQ ID NO: 41 (G/S S/I/V S/F/Y/T D/G/A/Q R/P/-T/-P/Q/D/G Y/R/H/N T/N G/Y V/I/L);

or for each CDR sequence, an amino acid sequence with
(i) at least 85% identity thereto, and/or
(ii) one, two, or three amino acid substitutions relative thereto.

Said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 42 (SNSVG), SEQ ID NO: 17 (SNAVG), SEQ ID NO: 44 (SYYVG), or SEQ ID NO: 45 (TNSVG);

VHCDR2 comprises the sequence set forth in SEQ ID NO: 46 (GIDTDGEEGYNPALNS), SEQ ID NO: 47 (SVDSDGYTYYNPALKS), SEQ ID NO: 48 (GIDSDGEEGYNPALNS), SEQ ID NO: 49 (GIDSDGEEGYNPALKS), SEQ ID NO: 50 (SVDSDGDTYYNPALKS), SEQ ID NO: 51 (GIDTDGEEGYNPALKS), SEQ ID NO: 52 (NIYST-GRAFYNPALKS), or SEQ ID NO: 53 (GIDTDG-EEGFNPVLKS);

VHCDR3 comprises the sequence set forth in SEQ ID NO: 54 (SYRADGLAYGYVQAIDY). SEQ ID NO: 55

(SYRTDGLAYGYVQAIDY), SEQ ID NO: 56 (SVNGHPDVYYIDR). SEQ ID NO: 57 (TYRTDG-YAYGYVQAIDY), SEQ ID NO: 58 (SYRSDG-LAYGYVQAIDY). SEQ ID NO: 59 (SANGHPDVYYIDK). SEQ ID NO: 60 (TYRTDGFAYGYVQAIDY). SEQ ID NO: 61 (SYRTDGLAYGYVQAIEY), or SEQ ID NO: 265 (GSYYHGGGNGMVDFFDY);

VLCDR1 comprises the sequence set forth in SEQ ID NO: 63 (SGSFIGISSVG); SEQ ID NO: 64 (SGSYIS-SSRVG); SEQ ID NO: 65 (SGSDLGSSRVG); SEQ ID NO: 66 (SGSY/GSSAVG): SEQ ID NO: 67 (SGRFI-GISSVG); SEQ ID NO: 68 (SGSY/GSSGVG); or SEQ ID NO: 69 (SGSYVSRSRVG);

VLCDR2 comprises the sequence set forth in SEQ ID NO: 70 (ASDGRPS); SEQ ID NO: 71 (DSSSRPS); or SEQ ID NO: 72 (AATSRAS);

VLCDR3 comprises the sequence set forth in SEQ ID NO: 73 (GSSDRTPYTGV); SEQ ID NO: 74 (GSS-DRTQYTGV); SEQ ID NO: 75 (GVFGDRNYI); SEQ ID NO: 76 (GIFGDRNYI); SEQ ID NO: 77 (GSTAPTPHTGV); SEQ ID NO: 78 (SSYQRGNTGV); SEQ ID NO: 79 (GSS-DRTQYTGL); or SEQ ID NO: 80 (GIYGDRNYI);

or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 367 to 379 of SEQ ID NO: 1.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 54 (SYRADGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 73 (GSSDRTPYTGV);

or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 367 to 379 of SEQ ID NO: 1. The specific binding molecule comprising CDRs having 100% identity to those given above is referred to as "S1G2" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 54 (SYRADGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS); and

VLCDR3 comprises the sequence set forth in SEQ ID NO: 73 (GSSDRTPYTGV).

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 447 (QVQLQESGPSLVKPSQTLSLTCTVSGFSLT);

VHFR2 comprises the sequence set forth in SEQ ID NO: 448 (WVRQAPGKAPEWVA);

VHFR3 comprises the sequence set forth in SEQ ID NO: 449 (RLSITRDTSKSQVSLSLSSVTSED-TAVYYCGR);

VHFR4 comprises the sequence set forth in SEQ ID NO: 450 (WGPGLLVTVSS);

VLFR1 comprises the sequence set forth in SEQ ID NO: 451 (QAVVTQPSSVSGSLGQRVSITC);

VLFR2 comprises the sequence set forth in SEQ ID NO: 452 (WFQQLPGSGLRTIIV);

VLFR3 comprises the sequence set forth in SEQ ID NO: 453 (GVPDRFSMSKSGNTATLTISSLQAEDEAD-YFC);

VLFR4 comprises the sequence set forth in SEQ ID NO: 454 (FGSGTRLTVLG);

or for each FR sequence, an amino acid sequence with
(i) at least 50% identity thereto, and/or
(ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 447 (QVQLQESGPSLVKPSQTLSLTCTVSGFSLT);

VHFR2 comprises the sequence set forth in SEQ ID NO: 448 (WVRQAPGKAPEWVA);

VHFR3 comprises the sequence set forth in SEQ ID NO: 449 (RLSITRDTSKSQVSLSLSSVTSED-TAVYYCGR);

VHFR4 comprises the sequence set forth in SEQ ID NO: 450 (WGPGLLVTVSS);

VLFR1 comprises the sequence set forth in SEQ ID NO: 451 (QAVVTQPSSVSGSLGQRVSITC);

VLFR2 comprises the sequence set forth in SEQ ID NO: 452 (WFQQLPGSGLRTIIV);

VLFR3 comprises the sequence set forth in SEQ ID NO: 453 (GVPDRFSMSKSGNTATLTISSLQAEDEAD-YFC);

VLFR4 comprises the sequence set forth in SEQ ID NO: 454 (FGSGTRLTVLG);

or for each FR sequence, an amino acid sequence with
(i) at least 50% identity thereto, and/or
(ii) one, two, three, four or five amino acid substitutions relative thereto, wherein the specific binding molecule binds to a polypeptide or protein molecule comprising an amino acid sequence comprising residues 367 to 379 of SEQ ID NO: 1. A specific binding molecule comprising FRs having 100% identity to those given above is referred to as "S1G2" herein.

The specific binding molecule may comprise:
(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 447 (QVQLQESGPSLVKP-SQTLSLTCTVSGFSLT);

VHFR2 comprises the sequence set forth in SEQ ID NO: 448 (WVRQAPGKAPEWVA);

VHFR3 comprises the sequence set forth in SEQ ID NO: 449 (RLSITRDTSKSQVSLSLSSVTSED-TAVYYCGR);

VHFR4 comprises the sequence set forth in SEQ ID NO: 450 (WGPGLLVTVSS);

VLFR1 comprises the sequence set forth in SEQ ID NO: 451 (QAVVTQPSSVSGSLGQRVSITC);

VLFR2 comprises the sequence set forth in SEQ ID NO: 452 (WFQQLPGSGLRTIIV);

VLFR3 comprises the sequence set forth in SEQ ID NO: 453 (GVPDRFSMSKSGNTATLTISSLQAE-DEADYFC);

VLFR4 comprises the sequence set forth in SEQ ID NO: 454 (FGSGTRLTVLG);

or for each FR sequence, an amino acid sequence with
(i) at least 50% identity thereto, and/or
(ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 54 (SYRADGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS); and

VLCDR3 comprises the sequence set forth in SEQ ID NO: 73 (GSSDRTPYTGV).

or for each CDR sequence, an amino acid sequence with
(i) at least 85% identity thereto, and/or
(ii) one, two, or three amino acid substitutions relative thereto wherein the specific binding molecule binds to a polypeptide or protein molecule comprising an amino acid sequence comprising residues 367 to 379 of SEQ ID NO: 1. The specific binding molecule comprising FRs and CDRs having 100% identity to those given above is referred to as "S1G2" herein.

The specific binding molecule may comprise:
(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 447 (QVQLQESGPSLVKP-SQTLSLTCTVSGFSLT);

VHFR2 comprises the sequence set forth in SEQ ID NO: 448 (WVRQAPGKAPEWVA);

VHFR3 comprises the sequence forth in SEQ ID NO: 449 set (RLSITRDTSKSQVSLSLSSVTSED-TAVYYCGR);

VHFR4 comprises the sequence set forth in SEQ ID NO: 450 (WGPGLLVTVSS);

VLFR1 comprises the sequence set forth in SEQ ID NO: 451 (QAVVTQPSSVSGSLGQRVSITC);

VLFR2 comprises the sequence set forth in SEQ ID NO: 452 (WFQQLPGSGLRTIIV);

VLFR3 comprises the sequence set forth in SEQ ID NO: 453 (GVPDRFSMSKSGNTATLTISSLQAE-DEADYFC);

VLFR4 comprises the sequence set forth in SEQ ID NO: 454 (FGSGTRLTVLG);

or for each FR sequence, an amino acid sequence with
(i) at least 50% identity thereto, and/or
(ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 54 (SYRADGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS); and

VLCDR3 comprises the sequence set forth in SEQ ID NO: 73 (GSSDRTPYTGV).

wherein the specific binding molecule binds to a polypeptide or protein molecule comprising an amino acid sequence comprising residues 367 to 379 of SEQ ID NO: 1. The specific binding molecule comprising FRs and CDRs having 100% identity to those given above is referred to as "S1G2" herein.

The specific binding molecule may comprise:

```
(a) A VH domain comprising the sequence set forth
in SEQ ID NO: 455
(QVQLQESGPSLVKPSQTLSLTCTVSGFSLTSNSVGWVRQAPGKAPEWV

AGIDTDGEEGYNPALNSRLSITRDTSKSQVSLSLSSVTSEDTAVYYCGR

SYRADGLAYGYVQAIDYWGPGLLVTVSS);
and/or (b) a VL domain comprising the sequence set forth
in SEQ ID NO: 456
(QAVVTQPSSVSGSLGQRVSITCSGSFIGISSVGWFQQLPGSGLRTIIV

ASDGRPSGVPDRFSMSKSGNTATLTISSLQAEDEADYFCGSSDRTPYTG

VFGSGTRLTVLG);
``` or a humanized variant thereof.

The specific binding molecule may comprise:

```
(a) A heavy chain comprising the sequence set
forth in SEQ ID NO: 457
(QVQLQESGPSLVKPSQTLSLTCTVSGFSLTSNSVGWRQAPGKAPEWVA

GIDTDGEEGYNPALNSRLSITRDTSKSQVSLSLSSVTSEDTAVYYCGRS

YRADGLAYGYVQAIDYWGPGLLVTVSSAKTTAPSVYPLAPVCGDTTGSS

VTLGCLVKGYFPEPVTLTWNSGSLSSGVHTFPAVLQSDLYTLSSSVTVT

SSTWPSQSITCNVAHPASSTKVDKKIEPRGPTIKPCPPCKCPAPNLLGG
```

```
-continued
PSVFIFPPPKIKDVLMISLSPIVTCVVVDVSEDDPDVQISWFVNNVEVHT

AQTQTHREDYNSTLRVVSALPIQHQDWMSGKEFKCKVNNKDLPAPIERT

ISKPKGSVRAPQVYVLPPPEEEMTKKQVTLTCMVTDFMPEDIYVEWTNN

GKTELNYKNTEPVLDSDGSYFMYSKLRVEKKNWVERNSYSCSVVHEGLH

NHHTTKSFSRTPGK);
and/or (b) a light chain comprising the sequence set
forth in SEQ ID NO: 458
(QAVVTQPSSVSGSLGQRVSITCSGSFIGISSVGWFQQLPGSGLRTIIV

ASDGRPSGVPDRFSMSKSGNTATLTISSLQAEDEADYFCGSSDRTPYTG

VFGSGTRLTVLGGQPKSSPSVTLFPPPSSEELETNKATLVCTITDFYPGV

VTVDWKVDGTPVTQGMETTQPSKQSNNKYMASSYLTLTARAWERHSSYS

CQVTHEGHTVEKSLSRADCS);
``` or a humanized variant thereof.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 55 (SYRTDGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 74 (GSSDRTQYTGV);

or for each CDR sequence, an amino acid sequence with
(i) at least 85% identity thereto, and/or
(ii) one, two, or three amino acid substitutions relative thereto, wherein the specific binding molecule binds to a polypeptide or protein molecule comprising an amino acid sequence comprising residues 367 to 379 of SEQ ID NO: 1. The specific binding molecule comprising CDRs having 100% identity to those given above is referred to as "S1B1" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 55 (SYRTDGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 74 (GSSDRTQYTGV).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 48 (GIDSDGEEGYNPALNS);

VHCDR3 comprises the sequence set forth in SEQ ID NO: 57 (TYRTDGYAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 74 (GSSDRTQYTGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 367 to 379 of SEQ ID NO: 1. The specific binding molecule comprising CDRs having 100% identity to those given above is referred to as "S1D9" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 48 (GIDSDGEEGYNPALNS);

VHCDR3 comprises the sequence set forth in SEQ ID NO: 57 (TYRTDGYAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 74 (GSSDRTQYTGV).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 54 (SYRADGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 74 (GSSDRTQYTGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 367 to 379 of SEQ ID NO: 1. The specific binding molecule comprising CDRs having 100% identity to those given above is referred to as "S1F4" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 54 (SYRADGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 74 (GSSDRTQYTGV).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 54 (SYRADGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 74 (GSSDRTQYTGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 367 to 379 of SEQ ID NO: 1. The specific binding molecule comprising CDRs having 100% identity to those given above is referred to as "S1G10" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 54 (SYRADGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 74 (GSSDRTQYTGV).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 51 (GIDTDGEEGYNPALKS);

VHCDR3 comprises the sequence set forth in SEQ ID NO: 60 (TYRTDGFAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 74 (GSSDRTQYTGV);

or for each CDR sequence, an amino acid sequence with
  (i) at least 85% identity thereto, and/or
  (ii) one, two, or three amino acid substitutions relative thereto, wherein the specific binding molecule binds to a polypeptide or protein molecule comprising an amino acid sequence comprising residues 367 to 379 of SEQ ID NO: 1. The specific binding molecule comprising CDRs having 100% identity to those given above is referred to as "S2C6" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 51 (GIDTDGEEGYNPALKS);

VHCDR3 comprises the sequence set forth in SEQ ID NO: 60 (TYRTDGFAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 74 (GSSDRTQYTGV).

The specific binding molecule may comprise the CDR sequences of a clone set out in Table 2 below. The epitope may be within residues 367 to 379 of SEQ ID

TABLE 2

| Clone name | VH | | | VL | | | Epitope |
|---|---|---|---|---|---|---|---|
| | CDR1 | CDR2 | CDR3 | CDR1 | CDR2 | CDR3 | |
| S1B1 | SNSVG (SEQ ID NO: 42) | GIDTDGEEGYNPALNS (SEQ ID NO: 46) | SYRTDGLAYGYVQAIDY (SEQ ID NO: 55) | SGSFIGISSVG (SEQ ID NO:63) | ASDGRPS (SEQ ID NO: 70) | GSSDRTQYTGV (SEQ ID NO: 74) | 367-379 |
| S1D2 | SNAVG (SEQ ID NO: 17) | SVDSDGTYYNPALKS (SEQ ID NO: 47) | SVNG---HPDVYYIDR (SEQ ID NO: 56) | SGSYISSSRVG (SEQ ID NO: 64) | DSSSRPS (SEQ ID NO: 71) | GVFG--DRNYI (SEQ ID NO: 75) | 367-379 |
| S1D9 | SNSVG (SEQ ID NO: 42) | GIDSDGEEGYNPALNS (SEQ ID NO: 48) | TYRTDGYAYGYVQAIDY (SEQ ID NO: 57) | SGSFIGISSVG (SEQ ID NO:63) | ASDGRPS (SEQ ID NO: 70) | GSSDRTQYTGV (SEQ ID NO: 74) | 367-379 |
| S1F4 | SNSVG (SEQ ID NO: 42) | GIDTDGEEGYNPALNS (SEQ ID NO: 46) | SYRADGLAYGYVQAIDY (SEQ ID NO: 54) | SGSFIGISSVG (SEQ ID NO:63) | ASDGRPS (SEQ ID NO: 70) | GSSDRTQYTGV (SEQ ID NO: 74) | 367-379 |
| S1G2 | SNSVG (SEQ ID NO: 42) | GIDTDGEEGYNPALNS (SEQ ID NO: 46) | SYRADGLAYGYVQAIDY (SEQ ID NO: 54) | SGSFIGISSVG (SEQ ID NO:63) | ASDGRPS (SEQ ID NO: 70) | GSSDRTPYTGV (SEQ ID NO: 73) | 367-379 |
| S1G10 | SNSVG (SEQ ID NO: 42) | GIDTDGEEGYNPALNS (SEQ ID NO: 46) | SYRADGLAYGYVQAIDY (SEQ ID NO: 54) | SGSFIGISSVG (SEQ ID NO:63) | ASDGRPS (SEQ ID NO: 70) | GSSDRTQYTGV (SEQ ID NO: 74) | 367-379 |
| S1H6 | SNAVG (SEQ ID NO: 17) | SVDSDGTYYNPALKS (SEQ ID NO: 47) | SVNG---HPDVYYIDR (SEQ ID NO: 56) | SGSDLGSSRVG (SEQ ID NO: 65) | DSSSRPS (SEQ ID NO: 71) | GIFG--DRNYI (SEQ ID NO: 76) | 367-379 |
| S1H9 | SNSVG (SEQ ID NO: 42) | GIDSDGEEGYNPALKS (SEQ ID NO: 49) | SYRSDGLAYGYVQAIDY (SEQ ID NO: 58) | SGSFIGISSVG (SEQ ID NO:63) | ASDGRPS (SEQ ID NO: 70) | GSSDRTQYTGV (SEQ ID NO: 74) | 367-379 |
| S2C3 | SNAVG (SEQ ID NO: 17) | SVDSDGTYYNPALKS (SEQ ID NO: 50) | SANG---HPDVYYIDK (SEQ ID NO: 59) | SGSYISSSRVG (SEQ ID NO: 64) | DSSSRPS (SEQ ID NO: 71) | GIFG--DRNYI (9) | 367-379 |
| S2C6 | SNSVG (SEQ ID NO: 42) | GIDTDGEEGYNPALKS (SEQ ID NO: 51) | TYRTDGFAYGYVQAIDY (SEQ ID NO 60) | SGSFIGISSVG (SEQ ID NO: 63) | ASDGRPS (SEQ ID NO: 70) | GSSDRTQYTGV (SEQ ID NO: 74) | 367-379 |
| S2D1 | SNSVG (SEQ ID NO: 42) | GIDTDGEEGYNPALNS (SEQ ID NO: 46) | SYRTDGLAYGYVQAIDY (SEQ ID NO: 55) | SGSYIGSSAVG (SEQ ID NO: 66) | ASDGRPS (SEQ ID NO: 70) | Incomplete | 367-379 |
| S2D4 | SNSVG (SEQ ID NO: 42) | GIDTDGEEGYNPALNS (SEQ ID NO: 46) | SYRTDGLAYGYVQAIEY (SEQ ID NO: 61) | SGRFIGISSVG (SEQ ID NO: 67) | ASDGRPS (SEQ ID NO: 70) | GSTAPTPHTGV (SEQ ID NO: 77) | 367-379 |

TABLE 2-continued

| Clone name | VH | | | VL | | | Epitope |
|---|---|---|---|---|---|---|---|
| | CDR1 | CDR2 | CDR3 | CDR1 | CDR2 | CDR3 | |
| CA9 | SNSVG (SEQ ID NO: 42) | GIDTDGEGYNPALNS (SEQ ID NO: 46) | SYRSDGLAYGYVQAIDY (SEQ ID NO: 58) | SGSFIGISSVG (SEQ ID NO:63) | ASDGRPS (SEQ ID NO: 70) | GSSDRTQYTGV (SEQ ID NO: 74) | 367-379 |
| CA12 | SYYVG (SEQ ID NO: 44) | NIYSTGRAFYNPALKS (SEQ ID NO: 52) | GSYYHGGGNGMVDFFDY (SEQ ID NO: 265) | SGSSSNVGYGNYVG (14) | AATSRAS (SEQ ID NO: 72) | SSYQR-GNTGV (SEQ ID NO: 78) | 367-379 |
| CB2 | TNSVG (SEQ ID NO: 45) | GIDTDGEGFNPVLKS (SEQ ID NO: 53) | SYRTDGLAYGYVQAIDY (SEQ ID NO: 55) | SGSYIGSSGVG (SEQ ID NO 68) | ASDGRPS (SEQ ID NO: 70) | GSSDRTQYTGL (SEQ ID NO: 79) | 367-379 |
| CC12 | SNSVG (SEQ ID NO: 42) | GIDSDGEGYNPALNS (SEQ ID NO: 48) | SYRADGLAYGYVQAIDY (SEQ ID NO: 54) | SGRFIGISSVG (SEQ ID NO: 67) | ASDGRPS (SEQ ID NO: 70) | GSSDRTQYTGV (SEQ ID NO: 74) | 367-379 |
| MC5 | SNAVG (SEQ ID NO: 17) | SVDSDGDTYYNPALKS (SEQ ID NO: 50) | SVNG---HPDVYYIDR (SEQ ID NO: 56) | SGSTVSRSRVG (SEQ ID NO: 69) | DSSSRPS (SEQ ID NO: 71) | GIYG--DRNYI (SEQ ID NO: 80) | 367-379 |
| MD12 | SNAVG (SEQ ID NO: 17) | SVDSDGTYYNPALKS (SEQ ID NO: 47) | SVNG---HPDVYYIDR (SEQ ID NO: 56) | SGSYISSSRVG (SEQ ID NO: 64) | DSSSRPS (SEQ ID NO: 72) | GVFG--DRNYI (SEQ ID NO: 75) | 367-379 |

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises a VHCDR1 amino acid sequence set forth in table 2;

VHCDR2 comprises a VHCDR2 amino acid sequence set forth in table 2;

VHCDR3 comprises a VHCDR3 amino acid sequence set forth in table 2;

VLCDR1 comprises a VLCDR1 amino acid sequence set forth in table 2;

VLCDR2 comprises a VLCDR2 amino acid sequence set forth in table 2; and

VLCDR3 comprises a VLCDR3 amino acid sequence set forth in table 2;

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 367 to 379 of SEQ ID NO: 1.

The specific binding molecule may bind to a polypeptide or protein molecule comprising an amino acid sequence comprising residues 367 to 379 of SEQ ID NO: 1 with a $K_D$ of less than around 500 pM. The Kc may be less than around 400 pM, less than around 300 pM, or less than around 200 pM. The $K_D$ may preferably be for binding to SEQ ID NO: 1 or to SEQ ID NO: 5. The $K_D$ for binding to SEQ ID NO: 1 may be around 100 pM to around 200 pM. The $K_D$ for binding to SEQ ID NO: 1 may be around 140 PM or 170 pM, optionally wherein the specific binding molecule comprises the CDRs of S1G2. The $K_D$ for binding to SEQ ID NO: 5 may be around 400 pM to around 500 pM. The $K_D$ for binding to SEQ ID NO: 5 may be around 447 PM, optionally wherein the specific binding molecule comprises the CDRs of S1G2.

The specific binding molecule may comprise an amino acid sequence having at least 70%, at least 75%, at least 80%, at least 90%, at least 95% or at least 99% identity to SEQ ID NO: 81 wherein the specific binding molecule binds to a polypeptide or protein molecule comprising an amino acid sequence comprising residues 367 to 379 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 81. The CDRs may be 100% identical to the CDRs of SEQ ID NO: 81. The specific binding molecule may comprise an amino acid sequence having at least 70%, at least 75%, at least 80%, at least 90%, at least 95% or at least 99% identity to SEQ ID NO: 81 wherein CDRs are 100% identical to the CDRs of SEQ ID NO: 81. The specific binding molecule may comprise the amino acid sequence of SEQ ID NO: 81.

(S1G2 amino acid sequence)

SEQ ID NO: 81

```
QVQLQESGPSLVKPSQTLSLTCTVSGFSLTSNSVGWVRQAPGKAPEWAG

IDTDGEEGYNPALNSRLSITRDTSKSQVSLSLSSVTSEDTAVYYCGRSY

RADGLAYGYVQAIDYWGPGLLVTVSSEGKSSGASGESKVDDQAVVTQPS

SVSGSLGQRVSITCSGSFIGISSVGWFQQLPGSGLRTIIVASDGRPSGV
```

-continued
```
PDRFSMSKSGNTATLTISSLQAEDEADYFCGSSDRTPYTGVFGSGTRLT

VLG
```

The specific binding molecule may comprise an amino acid sequence having at least 70%, at least 75%, at least 80%, at least 90%, at least 95% or at least 99% identity to SEQ ID NO: 412 wherein the specific binding molecule binds to a polypeptide or protein molecule comprising an amino acid sequence comprising residues 367 to 379 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 412. The CDRs may be 100% identical to the CDRs of SEQ ID NO: 412. The specific binding molecule may comprise an amino acid sequence having at least 70%, at least 75%, at least 80%, at least 90%, at least 95% or at least 99% identity to SEQ ID NO: 412 wherein CDRs are 100% identical to the CDRs of SEQ ID NO: 412. The specific binding molecule may comprise the amino acid sequence of SEQ ID NO: 412.

(S1B1 amino acid sequence)

SEQ ID NO: 412

```
QVQLQESGPSLVKPSQTLSLTCTVSGFSLSSNSVGWRQAPGKAPEWVAG

IDTDGEEGYNPALNSRLSITRDTSKSQVSLSLSSVTSEDTAVYYCVRSY

RTDGLAYGYVQAIDYWGPGLLVTVSSEGKSSGASGESKVDDQAVLTQPS

SVSGSLGQRVSITCSGSFIGISSVGWFQQLPGSGLRTVIVASDGRPSGV

PDRFSNSKSGNTATLTISSLQAEDEADYFCGSSDRTQYTGVFGSGTRLT

VLG
```

The specific binding molecule may comprise an amino acid sequence having at least 70%, at least 75%, at least 80%, at least 90%, at least 95% or at least 99% identity to SEQ ID NO: 413 wherein the specific binding molecule binds to a polypeptide or protein molecule comprising an amino acid sequence comprising residues 367 to 379 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 413. The CDRs may be 100% identical to the CDRs of SEQ ID NO: 413. The specific binding molecule may comprise an amino acid sequence having at least 70%, at least 75%, at least 80%, at least 90%, at least 95% or at least 99% identity to SEQ ID NO: 413 wherein CDRs are 100% identical to the CDRs of SEQ ID NO: 413. The specific binding molecule may comprise the amino acid sequence of SEQ ID NO: 413.

(S1D9 amino acid sequence)

SEQ ID NO: 413

```
QVQLQESGPSLVKPSQTLSLTCTVSGFSLTSNSVG

WVRQAPGKAPEWVAGIDSDGEEGYNPALNSRLSIT

RDTSKNQVSLSLSRVTSEDTAVYYCGRTYRTDGYA

YGYVQAIDYWGPGLLVTVSSEGKSSGASGESKVDD

RVMLTQPPSVSGSPGQTVSITCSGSFIGISSVGWF
```

-continued

```
QQLPGSGLRTVIFASDGRPSGVPDRFSNSKSGNTA

TLTISSLQAEDEADYFCGSSDRTQYTGVFGSGTRL

TVLS
```

The specific binding molecule may comprise an amino acid sequence having at least 70%, at least 75%, at least 80%, at least 90%, at least 95% or at least 99% identity to SEQ ID NO: 414 wherein the specific binding molecule binds to a polypeptide or protein molecule comprising an amino acid sequence comprising residues 367 to 379 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 414. The CDRs may be 100% identical to the CDRs of SEQ ID NO: 414. The specific binding molecule may comprise an amino acid sequence having at least 70%, at least 75%, at least 80%, at least 90%, at least 95% or at least 99% identity to SEQ ID NO: 414 wherein CDRs are 100% identical to the CDRs of SEQ ID NO: 414. The specific binding molecule may comprise the amino acid sequence of SEQ ID NO: 414.

```
(S1F4 amino acid sequence)
                              SEQ ID NO: 414
QVQLQESGPSLVKPSQTLSLTCTVSGFSLSSNSVG

WRQAPGKAPEWVAGIDTDGEEGYNPALNSRLSITR

DTSKSQVSLSLSSVTSEDTAVYYCVRSYRADGLAY

GYVQAIDYWGPGLLLTISSEGKSSGASGESKVDDQ

AWVTQPSSVSGSLGQRVSITCSGSFIGISSVGWFQ

QLPGSGLRTVIVASDGRPSGVPDRFSNSKSGNTAT

LTISSLQAEDEADYFCGSSDRTQYTGVFGSGTRLT

VLG
```

The specific binding molecule may comprise an amino acid sequence having at least 70%, at least 75%, at least 80%, at least 90%, at least 95% or at least 99% identity to SEQ ID NO: 415 wherein the specific binding molecule binds to a polypeptide or protein molecule comprising an amino acid sequence comprising residues 367 to 379 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 415. The CDRs may be 100% identical to the CDRs of SEQ ID NO: 415. The specific binding molecule may comprise an amino acid sequence having at least 70%, at least 75%, at least 80%, at least 90%, at least 95% or at least 99% identity to SEQ ID NO: 415 wherein CDRs are 100% identical to the CDRs of SEQ ID NO: 415. The specific binding molecule may comprise the amino acid sequence of SEQ ID NO: 415.

```
(S1G10 amino acid sequence)
                              SEQ ID NO: 415
QVQLQESGPSLVKPSQTLSLTCTVSGFSLTSNSVG
```

-continued

```
WVRQAPGKAPEWVAGIDTDGEEGYNPALNSRLSIT

RDTSKSQVSLSLSSVTSEDTAVYYCGRSYRADGLA

YGYVQAIDYWGPGLLVTVSSEGKSSGASGESKVDD

QAVLTQPSSMSGSLGQRVSITCSGSFIGISSVGWF

QQLPGSGLRTIIVASDGRPSGVPDRFSMSKSGNTA

TLTISSLQAEDEADYFCGSSDRTQYTGVFGSGTRL

TVLG
```

The specific binding molecule may comprise an amino acid sequence having at least 70%, at least 75%, at least 80%, at least 90%, at least 95% or at least 99% identity to SEQ ID NO: 416 wherein the specific binding molecule binds to a polypeptide or protein molecule comprising an amino acid sequence comprising residues 367 to 379 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 416. The CDRs may be 100% identical to the CDRs of SEQ ID NO: 416. The specific binding molecule may comprise an amino acid sequence having at least 70%, at least 75%, at least 80%, at least 90%, at least 95% or at least 99% identity to SEQ ID NO: 416 wherein CDRs are 100% identical to the CDRs of SEQ ID NO: 416. The specific binding molecule may comprise the amino acid sequence of SEQ ID NO: 416.

```
(S2C6 amino acid sequence)
                              SEQ ID NO: 416
QVQLQESGPSLVKPSQTLSLTCTVSGFSLISNSVG

WVRQAPGKAPEWAGIDTDGEEGYNPALKSQYAASD

PDTSKSQVSLSLSSVTSEDTAVYYCGRTYRTDGFA

YGYVQAIDYWGPGLLLTISSEGKSSGASGESKVDD

QAVLTQPSSVSGSLGQRVSITCSGSFIGISSVGWF

QQLPGSGLRTIIVASDGRPSGVPDRFSMSKSGNTA

TLTISSLQAEDEADYFCGSSDRTQYTGVFGSGTRL

TVLG
```

The epitope of the specific binding molecule may be within an amino acid sequence comprising residues 337 to 368 of SEQ ID NO: 1. Accordingly, the epitope may be within the amino acid sequence of SEQ ID NO: 82 (VEVKSEKLDFKDRVQSKIGSLDNITHVPGGGN).

The epitope may be within an amino acid sequence comprising residues 337 to 368 of SEQ ID NO: 1. This epitope may be bound by the CDRs of the specific binding molecule referred to as "NS2A3" herein.

The epitope may comprise the amino acid sequence of SEQ ID NO: 82 (VEVKSEKLDFKDRVQSKIGSLD-NITHVPGGGN). The epitope may comprise an amino acid sequence having at least 70%, at least 75%, at least 80%, at least 90%, at least 95% or at least 99% identity to SEQ ID NO: 82 (VEVKSEKLDFKDRVQSKIGSLD-NITHVPGGGN).

The epitope may consist of the amino acid sequence of SEQ ID NO: 82 (VEVKSEKLDFKDRVQSKIGSLD-NITHVPGGGN). The epitope may consist of an amino acid sequence having at least 70%, at least 75%, at least 80%, at least 90%, at least 95% or at least 99% identity to SEQ ID NO: 82 (VEVKSEKLDFKDRVQSKIGSLD-NITHVPGGGN).

The specific binding molecule may bind to a polypeptide or protein molecule comprising an amino acid sequence comprising residues 337 to 368 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 83 (S Y S V Y)

VHCDR2 comprises the sequence set forth in SEQ ID NO: 84 (I M Y A S G R V D Y N P A L K S)

VHCDR3 comprises the sequence set forth in SEQ ID NO: 85 (G I E N/D)

VLCDR1 comprises the sequence set forth in SEQ ID NO: 86 (R T S/N Q/E S/N V/I N/G/D N/S Y/G L S/A)

VLCDR2 comprises the sequence set forth in SEQ ID NO: 87 (Y A T Y L Y/H T)

VLCDR3 comprises the sequence set forth in SEQ ID NO: 88 (L Q Y D/G/E S/T T P L A/T)

or for each CDR sequence, an amino acid sequence with
(i) at least 85% identity thereto, and/or
(ii) one, two, or three amino acid substitutions relative thereto.

Said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 83 (SYSVY);

VHCDR2 comprises the sequence set forth in SEQ ID NO: 84 (IMYASGRVDYNPALKS);

VHCDR3 comprises the sequence set forth in SEQ ID NO: 89 (GIEN) or SEQ ID NO: 90 (GIED);

VLCDR1 comprises the sequence set forth in SEQ ID NO: 91 (RTSQSVNNYLS), SEQ ID NO: 92 (RT-NESVGNYLS), SEQ ID NO: 93 (RTSQNIDNGLA), or SEQ ID NO 94 (RTSQSVGSYLS);

VLCDR2 comprises the sequence set forth in SEQ ID NO: 95 (YATRLYT) or SEQ ID NO: 96 (YATRLHT);

VLCDR3 comprises the sequence set forth in SEQ ID NO: 97 (LQYDSTPLA), SEQ ID NO: 98 (LQYD-STPLT), SEQ ID NO: 99 (LQYESTPLA), or SEQ ID NO: 100 (LQYGTTPLA);

or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 337 to 368 of SEQ ID NO: 1.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 83 (SYSVY);

VHCDR2 comprises the sequence set forth in SEQ ID NO: 84 (IMYASGRVDYNPALKS);

VHCDR3 comprises the sequence set forth in SEQ ID NO: 89 (GIEN);

VLCDR1 comprises the sequence set forth in SEQ ID NO: 91 (RTSQSVNNYLS);

VLCDR2 comprises the sequence set forth in SEQ ID NO: 95 (YATRLYT);

VLCDR3 comprises the sequence set forth in SEQ ID NO: 97 (LQYDSTPLA);

or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 337 to 368 of SEQ ID NO: 1. The specific binding molecule comprising CDRs having 100% identity to those given above is referred to as "NS2A3" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 83 (SYSVY);

VHCDR2 comprises the sequence set forth in SEQ ID NO: 84 (IMYASGRVDYNPALKS);

VHCDR3 comprises the sequence set forth in SEQ ID NO: 89 (GIEN);

VLCDR1 comprises the sequence set forth in SEQ ID NO: 91 (RTSQSVNNYLS);

VLCDR2 comprises the sequence set forth in SEQ ID NO: 95 (YATRLYT); and

VLCDR3 comprises the sequence set forth in SEQ ID NO: 97 (LQYDSTPLA).

The specific binding molecule may comprise the CDR sequences of a clone set out in Table 3 below. The epitope may be within residues 337 to 368 of SEQ ID

TABLE 3

| Clone name | VH | | | VL | | | Epitope |
|---|---|---|---|---|---|---|---|
| | CDR1 | CDR2 | CDR3 | CDR1 | CDR2 | CDR3 | |
| NS2A3 | SYSVY (SEQ ID NO: 83) | IMYASG RVDYNP ALKS (SEQ ID NO: 84) | GIEN (SEQ ID NO: 89) | RTSQSV NNYLS (SEQ ID NO: 91) | YATRLY T (SEQ ID NO: 95) | LQYDST PLA (SEQ ID NO: 97) | 337-368 |

TABLE 3-continued

| Clone name | VH | | | VL | | | Epitope |
|---|---|---|---|---|---|---|---|
| | CDR1 | CDR2 | CDR3 | CDR1 | CDR2 | CDR3 | |
| NS2A8 | SYSVY (SEQ ID NO: 83) | IMYASG RVDYNP ALKS (SEQ ID NO: 84) | GIEN (SEQ ID NO: 89) | RTNESV GNYLS (SEQ ID NO: 92) | YATRLH T (SEQ ID NO: 96) | LQYGTT PLA (SEQ ID NO: 100) | 337-368 |
| NS2C5 | SYSVY (SEQ ID NO: 83) | IMYASG RVDYNP ALKS (SEQ ID NO: 84) | GIED (SEQ ID NO: 90) | RTSQNI DNGLA (SEQ ID NO: 93) | YATRLH T (SEQ ID NO: 96) | LQYEST PLA (SEQ ID NO: 99) | 337-368 |
| NS2C8 | SYSVY (SEQ ID NO: 83) | IMYASG RVDYNP ALKS (SEQ ID NO: 84) | GIEN (SEQ ID NO: 89) | RTSQSV NNYLS (SEQ ID NO: 91) | YATRLY T (SEQ ID NO: 95) | LQYDST PLA (SEQ ID NO: 97) | 337-368 |
| NS2D3 | SYSVY (SEQ ID NO: 83) | IMYASG RVDYNP ALKS (SEQ ID NO: 84) | GIED (SEQ ID NO: 89) | RTSQSV GSYLS (SEQ ID NO: 94) | YATRLH T (SEQ ID NO: 96) | LOYDST PLT (SEQ ID NO: 98) | 337-368 |

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises a VHCDR1 amino acid sequence set forth in table 3;

VHCDR2 comprises a VHCDR2 amino acid sequence set forth in table 3;

VHCDR3 comprises a VHCDR3 amino acid sequence set forth in table 3;

VLCDR1 comprises a VLCDR1 amino acid sequence set forth in table 3;

VLCDR2 comprises a VLCDR2 amino acid sequence set forth in table 3; and

VLCDR3 comprises a VLCDR3 amino acid sequence set forth in table 3;

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 337 to 368 of SEQ ID NO: 1.

The specific binding molecule may bind to a polypeptide or protein molecule comprising an amino acid sequence comprising residues 337 to 368 of SEQ ID NO: 1 with a $K_D$ of less than 25 nM, preferably less than 20 nM, 15 nM or 10 nM. The $K_D$ may preferably be for binding to SEQ ID NO: 1 or to SEQ ID NO: 5.

The epitope of the specific binding molecule may be within an amino acid sequence comprising residues 369 to 390 of SEQ ID NO: 1. Accordingly, the epitope may be within the amino acid sequence of SEQ ID NO: 101 (KKI-ETHKLTFRENAKAKTDHGA).

The epitope may be within an amino acid sequence comprising residues 369 to 390 of SEQ ID NO: 1. This epitope may be bound by the CDRs of the specific binding molecule referred to as "NS4E3" herein.

The epitope may comprise the amino acid sequence of SEQ ID NO: 101 (KKIETHKLTFRENAKAKTDHGA).

The epitope may comprise an amino acid sequence having at least 70%, at least 75%, at least 80%, at least 90%, at least 95% or at least 99% identity to SEQ ID NO: 101 (KKI-ETHKLTFRENAKAKTDHGA).

The epitope may consist of the amino acid sequence of SEQ ID NO: 101 (KKIETHKLTFRENAKAKTDHGA). The epitope may consist of an amino acid sequence having at least 70%, at least 75%, at least 80%, at least 90%, at least 95% or at least 99% identity to SEQ ID NO: 101 (KKI-ETHKLTFRENAKAKTDHGA).

The specific binding molecule may bind to a polypeptide or protein molecule comprising an amino acid sequence comprising residues 369 to 390 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 102 (R E S I A);

VHCDR2 comprises the sequence set forth in SEQ ID NO: 103 (G V G I D G T S Y Y S P A L K S);

VHCDR3 comprises the sequence set forth in SEQ ID NO: 104 (N Y I D F E Y);

VLCDR1 comprises the sequence set forth in SEQ ID NO: 105 (S G S S/N/Y S/N/-N/-V/-G/I Y/S/A/G E/G/S D/N/T Y/G/D V N/S/G)

VLCDR2 comprises the sequence set forth in SEQ ID NO: 106 (G/R T/N/S T/S N/T/R R P/A S); and VLCDR3 comprises the sequence set forth in SEQ ID NO: 107 (LIA/G S Y D R/T/G/S S/T G/N S/R/-N/G/S/I F/I/V);

or for each CDR sequence, an amino acid sequence with (i) at least 85% identity thereto, and/or (ii) one, two, or three amino acid substitutions relative thereto.

Said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 102 (RESIA);

VHCDR2 comprises the sequence set forth in SEQ ID NO: 103 (GVGIDGTSYYSPALKS);

VHCDR3 comprises the sequence set forth in SEQ ID NO: 104 (NYIDFEY);

VLCDR1 comprises the sequence set forth in SEQ ID NO: 108 (SGSSSNVGYEDYVN), SEQ ID NO: 109 (SGSNIAGNGVG), SEQ ID NO: 110 (SGSSNNVGSGDYVS), or SEQ ID NO: 111 (SGSY/GSTDVG);

VLCDR2 comprises the sequence set forth in SEQ ID NO: 112 (GTTNRPS), SEQ ID NO: 113 (GSTRRPS), SEQ ID NO: 114 (RNSNRPS), or SEQ ID NO: 115 (RTTTRAS); and VLCDR3 comprises the sequence set forth in SEQ ID NO: 116 (LSYDRSGSNF), SEQ ID NO: 117 (ASYDTSNRGI), SEQ ID NO: 118 (GSYDGTNSF), or SEQ ID NO: 119 (ASYDSNNSIV);

or for each CDR sequence, an amino acid sequence with
   (i) at least 85% identity thereto, and/or
   (ii) one, two, or three amino acid substitutions relative thereto,
      wherein the specific binding molecule binds to a polypeptide or protein molecule comprising an amino acid sequence comprising residues 369 to 390 of SEQ ID NO: 1.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 102 (RESIA);

VHCDR2 comprises the sequence set forth in SEQ ID NO: 103 (GVGIDGTSYYSPALKS);

VHCDR3 comprises the sequence set forth in SEQ ID NO: 104 (NYIDFEY);

VLCDR1 comprises the sequence set forth in SEQ ID NO: 108 (SGSSSNVGYEDYVN);

VLCDR2 comprises the sequence set forth in SEQ ID NO: 112 (GTTNRPS); and

VLCDR3 comprises the sequence set forth in SEQ ID NO: 116 (LSYDRSGSNF);

or for each CDR sequence, an amino acid sequence with
   (i) at least 85% identity thereto, and/or
   (ii) one, two, or three amino acid substitutions relative thereto,
wherein the specific binding molecule binds to a polypeptide or protein molecule comprising an amino acid sequence comprising residues 369 to 390 of SEQ ID NO: 1. The specific binding molecule comprising CDRs having 100% identity to those given above is referred to as "NS4E4" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 102 (RESIA);

VHCDR2 comprises the sequence set forth in SEQ ID NO: 103 (GVGIDGTSYYSPALKS);

VHCDR3 comprises the sequence set forth in SEQ ID NO: 104 (NYIDFEY);

VLCDR1 comprises the sequence set forth in SEQ ID NO: 108 (SGSSSNVGYEDYVN);

VLCDR2 comprises the sequence set forth in SEQ ID NO: 112 (GTTNRPS); and

VLCDR3 comprises the sequence set forth in SEQ ID NO: 116 (LSYDRSGSNF).

The specific binding molecule may comprise the CDR sequences of a clone set out in Table 4 below. The epitope may be within residues 369 to 390 of SEQ ID NO: 1.

TABLE 4

| Clone name | VH CDR1 | VH CDR2 | VH CDR3 | VL CDR1 | VL CDR2 | VL CDR3 | Epitope |
|---|---|---|---|---|---|---|---|
| NS3E5 | RESIA (SEQ ID NO: 102) | GVGI DGTS YYSP ALKS (SEQ ID NO: 103) | N Y I D F E Y (SEQ ID NO: 104) | S G S Y - - -I G S T D V G (SEQ ID NO: 111) | GSTR RPS (SEQ ID NO: 113) | A S Y D S N N S I V (SEQ ID NO: 119) | 369-390 |
| NS3H4 | RESIA (SEQ ID NO: 102) | GVGI DGTS YYSP ALKS (SEQ ID NO: 103) | NYID FEY (SEQ ID NO: 104) | SGSN- --IAG NGVG (SEQ ID NO: 109) | RNSN RPS (SEQ ID NO: 114) | GSYD GTN-SE (SEQ ID NO: 118) | 369-390 |
| NS4F2 | RESIA (SEQ ID NO: | GVGI DGTS YYSP ALKS (SEQ | NYID FEY (SEQ ID NO: | SGSS NNVG SGDY VS (SEQ | RTTT RAS (SEQ ID NO: | ASYD TSNR GI (SEQ ID | 369-390 |

TABLE 4-continued

| Clone name | VH CDR1 | VH CDR2 | VH CDR3 | VL CDR1 | VL CDR2 | VL CDR3 | Epitope |
|---|---|---|---|---|---|---|---|
| | | | | VH | | | |
| | | | | VL | | | |
| | 102) | ID NO: 103) | 104) | ID NO: 110) | 115) | NO: 117) | |
| NS4E3 | RESI A (SEQ ID NO: 102) | GVGI DGTS YYSP AL KS (SEQ ID NO: 103) | NYID FEY (SEQ ID NO: 104) | SGSS SNVG YEDY VN (SEQ ID NO: 108) | GTTN RPS (SEQ ID NO: 112) | LSYD RSGS NF (SEQ ID NO: 116) | 369-390 |

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises a VHCDR1 amino acid sequence set forth in table 4;
  VHCDR2 comprises a VHCDR2 amino acid sequence set forth in table 4;
  VHCDR3 comprises a VHCDR3 amino acid sequence set forth in table 4;
  VLCDR1 comprises a VLCDR1 amino acid sequence set forth in table 4;
  VLCDR2 comprises a VLCDR2 amino acid sequence set forth in table 4; and
  VLCDR3 comprises a VLCDR3 amino acid sequence set forth in table 4;
or for each CDR sequence, an amino acid sequence with
  (i) at least 85% identity thereto, and/or
  (ii) one, two, or three amino acid substitutions relative thereto,
wherein the specific binding molecule binds to a polypeptide or protein molecule comprising an amino acid sequence comprising residues 369 to 390 of SEQ ID NO: 1.

The specific binding molecule may bind to a polypeptide or protein molecule comprising an amino acid sequence comprising residues 369 to 390 of SEQ ID NO: 1 with a $K_D$ of less than 25 nM, preferably less than 20 nM, 15 nM or 10 nM. The $K_D$ may preferably be for binding to SEQ ID NO: 1 or to SEQ ID NO: 5.

The epitope of the specific binding molecule may be within an amino acid sequence comprising residues 412 to 441 of SEQ ID NO: 1. Accordingly, the epitope may be within the amino acid sequence of SEQ ID NO: 120 (SSTGSIDMVDSPQLATLADEVSASLAKQGL).

The epitope may be within an amino acid sequence comprising residues 412 to 441 of SEQ ID NO: 1. This epitope may be bound by the CDRs of the specific binding molecule referred to as "412E10" herein The epitope may comprise the amino acid sequence of SEQ ID NO: 120 (SSTGSIDMVDSPQLATLADEVSASLAKQGL). The epitope may comprise an amino acid sequence having at least 70%, at least 75%, at least 80%, at least 90%, at least 95% or at least 99% identity to SEQ ID NO: 120 (SSTGSIDMVDSPQLATLADEVSASLAKQGL).

The epitope may consist of the amino acid sequence of SEQ ID NO: 120 (SSTGSIDMVDSPQLATLADEVSASLAKQGL). The epitope may consist of an amino acid sequence having at least 70%, at least 75%, at least 80%, at least 90%, at least 95% or at least 99% identity to SEQ ID NO: 120 (SSTGSIDMVDSPQLATLADEVSASLAKQGL).

The specific binding molecule may bind to a polypeptide or protein molecule comprising an amino acid sequence comprising residues 412 to 441 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 121 (S/N D/Y S/G/A V/L A/G);
  VHCDR2 comprises the sequence set forth in SEQ ID NO: 122 (A/N S/I GAY/W S/R S/G G N/S/R K/T/I Y/E Y N P A L K S);
  VHCDR3 comprises the sequence set forth in SEQ ID NO: 123 (G I/G I/V A/G G/S V D V), or SEQ ID NO: 124 (SGGD);
  VLCDR1 comprises the sequence set forth in SEQ ID NO: 125 (S G S/G S/N N V/I G Y/R G N/D/T Y/F V G/D);
  VLCDR2 comprises the sequence set forth in SEQ ID NO: 126 (G T/A A/D/T I/S/R R A/P S/P); and
  VLCDR3 comprises the sequence set forth in SEQ ID NO: 127 (A S/T Y Q/D S/Y/R N/S Y/D/N/E A/G/D/ S-/G/M/V-/I F/V/I);
  or for each CDR sequence, an amino acid sequence with
    (i) at least 85% identity thereto, and/or
    (ii) one, two, or three amino acid substitutions relative thereto.

Said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 128 (SDSVA), SEQ ID NO: 129 (NYGVG), or SEQ ID NO: 130 (SYALG);
  VHCDR2 comprises the sequence set forth in SEQ ID NO: 131 (ASGSSGNKYYNPALKS). SEQ ID NO:

132 (NIWRGGRIEYNPALKS), or SEQ ID NO: 133 (NIYSGGSTYYNPALKS);

VHCDR3 comprises the sequence set forth in SEQ ID NO: 134 (GIIAGVDV), SEQ ID NO: 135 (GGVGSVDV), or SEQ ID NO: 124 (SGGD);

VLCDR1 comprises the sequence set forth in SEQ ID NO: 39 (SGSSSNVGYGNYVG), SEQ ID NO: 137 (SGGRNNIGRGTFVD), and SEQ ID NO: 138 (SGSSSNVGYGDYVG);

VLCDR2 comprises the sequence set forth in SEQ ID NO: 139 (GTAIRAS), SEQ ID NO: 140 (GAASRAS), SEQ ID NO: 141 (GATSRAS), or SEQ ID NO: 142 (GTDRRPP); and VLCDR3 comprises the sequence set forth in SEQ ID NO: 143 (ASYQSNYAF), SEQ ID NO: 144 (ASYDRSESVV), SEQ ID NO: 145 (ASYDSSDGGV), or SEQ ID NO 146 (ATYDYSNDMII);

or for each CDR sequence, an amino acid sequence with
  (i) at least 85% identity thereto, and/or
  (ii) one, two, or three amino acid substitutions relative thereto,
    wherein the specific binding molecule binds to a polypeptide or protein molecule comprising an amino acid sequence comprising residues 412 to 441 of SEQ ID NO: 1.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 128 (SDSVA);

VHCDR2 comprises the sequence set forth in SEQ ID NO: 131 (ASGSSGNKYYNPALKS);

VHCDR3 comprises the sequence set forth in SEQ ID NO: 134 (GIIAGVDV);

VLCDR1 comprises the sequence set forth in SEQ ID NO: 39 (SGSSSNVGYGNYVG);

VLCDR2 comprises the sequence set forth in SEQ ID NO: 139 (GTAIRAS); and

VLCDR3 comprises the sequence set forth in SEQ ID NO: 143 (ASYQSNYAF);

or for each CDR sequence, an amino acid sequence with
  (i) at least 85% identity thereto, and/or
  (ii) one, two, or three amino acid substitutions relative thereto,
wherein the specific binding molecule binds to a polypeptide or protein molecule comprising an amino acid sequence comprising residues 412 to 441 of SEQ ID NO: 1. The specific binding molecule comprising CDRs having 100% identity to those given above is referred to as "412E10" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 128 (SDSVA);

VHCDR2 comprises the sequence set forth in SEQ ID NO: 131 (ASGSSGNKYYNPALKS);

VHCDR3 comprises the sequence set forth in SEQ ID NO: 134 (GIIAGVDV);

VLCDR1 comprises the sequence set forth in SEQ ID NO: 39 (SGSSSNVGYGNYVG);

VLCDR2 comprises the sequence set forth in SEQ ID NO: 139 (GTAIRAS); and VLCDR3 comprises the sequence set forth in SEQ ID NO: 143 (ASYQSNYAF).

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 459 (QVQLQESGPSLVKPSQTLSLTCTVSGFSVI);

VHFR2 comprises the sequence set forth in SEQ ID NO: 460 (WRQAPGKVPEWLG);

VHFR3 comprises the sequence set forth in SEQ ID NO: 461 (RLSITRDTSKSQVSLSLSSVTTEDTAVYY-CAR);

VHFR4 comprises the sequence set forth in SEQ ID NO: 462 (WGRGLLVTVSS);

VLFR1 comprises the sequence set forth in SEQ ID NO: 463 (QAVLTQPSSVSGSLGQRVSITC);

VLFR2 comprises the sequence set forth in SEQ ID NO: 464 (WYQQVPGSAPKLLIY);

VLFR3 comprises the sequence set forth in SEQ ID NO: 465 (GVPDRFSGSRSGDTATLTITSLQAEDEAD-YYC);

VLFR4 comprises the sequence set forth in SEQ ID NO: 466 (FGSGTRLTVLG);

or for each FR sequence, an amino acid sequence with
  (i) at least 50% identity thereto, and/or
  (ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 459 (QVQLQESGPSLVKPSQTLSLTCTVSGFSVI);

VHFR2 comprises the sequence set forth in SEQ ID NO: 460 (WRQAPGKVPEWLG);

VHFR3 comprises the sequence set forth in SEQ ID NO: 461 (RLSITRDTSKSQVSLSLSSVTTEDTAVYY-CAR);

VHFR4 comprises the sequence set forth in SEQ ID NO: 462 (WGRGLLVTVSS);

VLFR1 comprises the sequence set forth in SEQ ID NO: 463 (QAVLTQPSSVSGSLGQRVSITC);

VLFR2 comprises the sequence set forth in SEQ ID NO: 464 (WYQQVPGSAPKLLIY);

VLFR3 comprises the sequence set forth in SEQ ID NO: 465 (GVPDRFSGSRSGDTATLTITSLQAEDEAD-YYC);

VLFR4 comprises the sequence set forth in SEQ ID NO: 466 (FGSGTRLTVLG);

or for each FR sequence, an amino acid sequence with
  (i) at least 50% identity thereto, and/or
  (ii) one, two, three, four or five amino acid substitutions relative thereto,
wherein the specific binding molecule binds to a polypeptide or protein molecule comprising an amino acid sequence comprising residues 412 to 441 of SEQ ID NO: 1. A specific binding molecule comprising FRs having 100% identity to those given above is referred to as "412E10" herein.

The specific binding molecule may comprise:
(a) framework regions (FRs) VHFR1, VHFR2, VHFR3, VHFR4, VLFR1, VLFR2, VLFR3 and VLFR4, wherein each of said FRs comprises an amino acid sequence as follows:
  VHFR1 comprises the sequence set forth in SEQ ID NO: 459 (QVQLQESGPSLVKP-SQTLSLTCTVSGFSVI);

VHFR2 comprises the sequence set forth in SEQ ID NO: 460 (WVRQAPGKVPEWLG);

VHFR3 comprises the sequence forth set in SEQ ID NO: 461 (RLSITRDTSKSQVSLSLSSVTTED-TAVYYCAR);

VHFR4 comprises the sequence set forth in SEQ ID NO: 462 (WGRGLLVTVSS);

VLFR1 comprises the sequence set forth in SEQ ID NO: 463 (QAVLTQPSSVSGSLGQRVSITC);

VLFR2 comprises the sequence set forth in SEQ ID NO: 464 (WYQQVPGSAPKLLIY);

VLFR3 comprises the sequence set forth in SEQ ID NO: 465 (GVPDRFSGSRSGDTATLTITSLQAE-DEADYYC);

VLFR4 comprises the sequence set forth in SEQ ID NO: 466 (FGSGTRLTVLG);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 128 (SDSVA);

VHCDR2 comprises the sequence set forth in SEQ ID NO: 131 (ASGSSGNKYYNPALKS);

VHCDR3 comprises the sequence set forth in SEQ ID NO: 134 (GIIAGVDV);

VLCDR1 comprises the sequence set forth in SEQ ID NO: 39 (SGSSSNVGYGNYVG);

VLCDR2 comprises the sequence set forth in SEQ ID NO: 139 (GTAIRAS); and

VLCDR3 comprises the sequence set forth in SEQ ID NO: 143 (ASYQSNYAF);

or for each CDR sequence, an amino acid sequence with (i) at least 85% identity thereto, and/or (ii) one, two, or three amino acid substitutions relative thereto wherein the specific binding molecule binds to a polypeptide or protein molecule comprising an amino acid sequence comprising residues 412 to 441 of SEQ ID NO: 1. The specific binding molecule comprising FRs and CDRs having 100% identity to those given above is referred to as "412E10" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 459 (QVQLQESGPSLVKP-SQTLSLTCTVSGFSVI);

VHFR2 comprises the sequence set forth in SEQ ID NO: 460 (WRQAPGKVPEWLG);

VHFR3 comprises the sequence set forth in SEQ ID NO: 461 (RLSITRDTSKSQVSLSLSSVTTED-TAVYYCAR);

VHFR4 comprises the sequence set forth in SEQ ID NO: 462 (WGRGLLVTVSS);

VLFR1 comprises the sequence set forth in SEQ ID NO: 463 (QAVLTQPSSVSGSLGQRVSITC);

VLFR2 comprises the sequence set forth in SEQ ID NO: 464 (WYQQVPGSAPKLLIY);

VLFR3 comprises the sequence set forth in SEQ ID NO: 465 (GVPDRFSGSRSGDTATLTITSLQAE-DEADYYC);

VLFR4 comprises the sequence set forth in SEQ ID NO: 466 (FGSGTRLTVLG);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 128 (SDSVA);

VHCDR2 comprises the sequence set forth in SEQ ID NO: 131 (ASGSSGNKYYNPALKS);

VHCDR3 comprises the sequence set forth in SEQ ID NO: 134 (GIIAGVDV);

VLCDR1 comprises the sequence set forth in SEQ ID NO: 39 (SGSSSNVGYGNYVG);

VLCDR2 comprises the sequence set forth in SEQ ID NO: 139 (GTAIRAS); and

VLCDR3 comprises the sequence set forth in SEQ ID NO: 143 (ASYQSNYAF);

wherein the specific binding molecule binds to a polypeptide or protein molecule comprising an amino acid sequence comprising residues 412 to 441 of SEQ ID NO: 1. The specific binding molecule comprising FRs and CDRs having 100% identity to those given above is referred to as "412E10" herein.

The specific binding molecule may comprise:

```
(a) A VH domain comprising the sequence
set forth in SEQ ID NO: 467
(QVQLQESGPSLVKPSQTLSLTCTVSGFSVISDSVAWVRQ

APGKVPEWLGASGSSGNKYYNPALKSRLSITRDTSKSQVS

LSLSSVTTEDTAVYYCARGIIAGVDVWGRGLLVTVSS);
and/or (b) a VL domain comprising the sequence
set forth in SEQ ID NO: 468
(QAVLTQPSSVSGSLGQRVSITCSGSSSNVGYGNYVGWY

QQVPGSAPKLLIYGTAIRASGVPDRFSGSRSGDTATLTI

TSLQAEDEADYYCASYQSNYAFFGSGTRLTVLG);
``` or a humanized variant thereof.

The specific binding molecule may comprise:

```
(a) A heavy chain comprising the sequence
set forth in SEQ ID NO: 469
(QVQLQESGPSLVKPSQTLSLTCTVSGFSVISDSVAWV

RQAPGKVPEWLGASGSSGNKYYNPALKSRLSITRDTSK

SQVSLSLSSVTTEDTAVYYCARGIIAGVDVWGRGLLVT

VSSAKTTAPSVYPLAPVCGDTTGSSVTLGCLVKGYFPE

PVTLTWNSGSLSSGVHTFPAVLQSDLYTLSSSVTVTSS

TWPSQSITCNVAHPASSTKVDKKIEPRGPTIKPCPPCK

CPAPNLLGGPSVFIFPPKIKDVLMISLSPIVTCVVVDV

SEDDPDVQISWFVNNVEVHTAQTQTHREDYNSTLRVVS

ALPIQHQDWMSGKEFKCKVNNKDLPAPIERTISKPKGS

VRAPQVYVLPPPEEEMTKKQVTLTCMVTDFMPEDIYVE

WTNNGKTELNYKNTEPVLDSDGSYFMYSKLRVEKKNWV
```

-continued

```
ERNSYSCSVVHEGLHNHHTTKSFSRTPGK) ;
and/or (b) a light chain comprising the sequence
set forth in SEQ ID NO: 470
(QAVLTQPSSVSGSLGQRVSITCSGSSSNVGYGNYVGW

YQQVPGSAPKLLIYGTAIRASGVPDRFSGSRSGDTATL

TITSLQAEDEADYYCASYQSNYAFFGSGTRLTVLGGQP

KSSPSVTLFPPSSEELETNKATLVCTITDFYPGVVTVD

WKVDGTPVTQGMETTQPSKQSNNKYMASSYLTLTARAW

ERHSSYSCQVTHEGHTVEKSLSRADCS) ;
``` or a humanized variant thereof.

The specific binding molecule may comprise the CDRs VHCDR1, VHCDR2, VHCDR3, VLCDR1,
VLCDR2 and VLCDR3, wherein each of said CDRs comprises an amino acid sequence as follows:
VHCDR1 comprises the sequence set forth in SEQ ID NO: 128 (SDSVA);
VHCDR2 comprises the sequence set forth in SEQ ID NO: 131 (ASGSSGNKYYNPALKS);
VHCDR3 comprises the sequence set forth in SEQ ID NO: 134 (GIIAGVDV);
VLCDR1 comprises the sequence set forth in SEQ ID NO: 138 (SGSSSNVGYGDYVG);
VLCDR2 comprises the sequence set forth in SEQ ID NO: 140 (GAASRAS); and
VLCDR3 comprises the sequence set forth in SEQ ID NO: 145 (ASYDSSDGGV);
or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 412 to 441 of SEQ ID NO: 1. The specific binding molecule comprising CDRs having 100% identity to those given above is referred to as "412B9" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:
VHCDR1 comprises the sequence set forth in SEQ ID NO: 128 (SDSVA);
VHCDR2 comprises the sequence set forth in SEQ ID NO: 131 (ASGSSGNKYYNPALKS);
VHCDR3 comprises the sequence set forth in SEQ ID NO: 134 (GIIAGVDV);
VLCDR1 comprises the sequence set forth in SEQ ID NO: 138 (SGSSSNVGYGDYVG);
VLCDR2 comprises the sequence set forth in SEQ ID NO: 140 (GAASRAS); and
VLCDR3 comprises the sequence set forth in SEQ ID NO: 145 (ASYDSSDGGV).

The specific binding molecule may comprise the CDRs VHCDR1, VHCDR2, VHCDR3, VLCDR1. VLCDR2 and VLCDR3, wherein each of said CDRs comprises an amino acid sequence as follows:
VHCDR1 comprises the sequence set forth in SEQ ID NO: 129 (NYGVG);
VHCDR2 comprises the sequence set forth in SEQ ID NO: 133 (NIYSGGSTYYNPALKS);

VHCDR3 comprises the sequence set forth in SEQ ID NO: 135 (GGVGSVDV);
VLCDR1 comprises the sequence set forth in SEQ ID NO: 137 (SGGRNNIGRGTFVD);
VLCDR2 comprises the sequence set forth in SEQ ID NO: 142 (GTDRRPP); and
VLCDR3 comprises the sequence set forth in SEQ ID NO: 146 (ATYDYSNDMII);
or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 412 to 441 of SEQ ID NO: 1. The specific binding molecule comprising CDRs having 100% identity to those given above is referred to as "412E6" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:
VHCDR1 comprises the sequence set forth in SEQ ID NO: 129 (NYGVG);
VHCDR2 comprises the sequence set forth in SEQ ID NO: 133 (NIYSGGSTYYNPALKS);
VHCDR3 comprises the sequence set forth in SEQ ID NO: 135 (GGVGSVDV);
VLCDR1 comprises the sequence set forth in SEQ ID NO: 137 (SGGRNNIGRGTFVD);
VLCDR2 comprises the sequence set forth in SEQ ID NO: 142 (GTDRRPP); and
VLCDR3 comprises the sequence set forth in SEQ ID NO: 146 (ATYDYSNDMII).

The specific binding molecule may comprise the CDRs VHCDR1, VHCDR2, VHCDR3, VLCDR1, VLCDR2 and VLCDR3, wherein each of said CDRs comprises an amino acid sequence as follows:
VHCDR1 comprises the sequence set forth in SEQ ID NO: 130 (SYALG);
VHCDR2 comprises the sequence set forth in SEQ ID NO: 132 (NIWRGGRIEYNPALKS);
VHCDR3 comprises the sequence set forth in SEQ ID NO: 124 (SGGD);
VLCDR1 comprises the sequence set forth in SEQ ID NO: 39 (SGSSSNVGYGNYVG);
VLCDR2 comprises the sequence set forth in SEQ ID NO: 141 (GATSRAS); and
VLCDR3 comprises the sequence set forth in SEQ ID NO: 144 (ASYDRSESVV);
or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 412 to 441 of SEQ ID NO: 1. The specific binding molecule comprising CDRs having 100% identity to those given above is referred to as "412G11" herein The specific binding molecule may comprise the CDRs VHCDR1, VHCDR2, VHCDR3, VLCDR1. VLCDR2 and VLCDR3, wherein each of said CDRs comprises an amino acid sequence as follows:
VHCDR1 comprises the sequence set forth in SEQ ID NO: 130 (SYALG);

VHCDR2 comprises the sequence set forth in SEQ ID NO: 132 (NIWRGGRIEYNPALKS);

VHCDR3 comprises the sequence set forth in SEQ ID NO: 124 (SGGD);

VLCDR1 comprises the sequence set forth in SEQ ID NO: 39 (SGSSSNVGYGNYVG);

VLCDR2 comprises the sequence set forth in SEQ ID NO: 141 (GATSRAS); and

VLCDR3 comprises the sequence set forth in SEQ ID NO: 144 (ASYDRSESVV).

The specific binding molecule may comprise the CDR sequences of a clone set out in Table 5 below. The epitope may be within residues 412 to 441 of SEQ ID NO: 1.

wherein the specific binding molecule binds to a polypeptide or protein molecule comprising an amino acid sequence comprising residues 412 to 441 of SEQ ID NO: 1.

The specific binding molecule may bind to a polypeptide or protein molecule comprising an amino acid sequence comprising residues 412 to 441 of SEQ ID NO: 1 with a $K_D$ of less than around 25 nM. The $K_D$ may be less than around 20 nM, less than around 15 nM, or less than around 10 nM. The $K_D$ may preferably be for binding to SEQ ID NO: 1 or to SEQ ID NO: 120. The $K_D$ for binding to SEQ ID NO: 1 may be around 1 nM to around 10 nM. The $K_D$ for binding

TABLE 5

| Clone name | VH | | | VL | | | Epitope |
|---|---|---|---|---|---|---|---|
| | CDR1 | CDR2 | CDR3 | CDR1 | CDR2 | CDR3 | |
| 412E10 | SDSVA (SEQ ID NO: 128) | ASGSSG NKYYNP ALKS (SEQ ID NO: 131) | GIIAGV DV (SEQ ID NO: 134) | SGSSSN VGYGNY VG (SEQ ID NO: 39) | GTAIRA S (SEQ ID NO: 139) | ASYQSN YAF (SEQ ID NO: 143) | 412-441 |
| 412B9 | SDSVA (SEQ ID NO: 128) | ASGSSG NKYYNP ALKS (SEQ ID NO: 131) | GIIAGV DV (SEQ ID NO: 134) | SGSSSN VGYGDY VG (SEQ ID NO: 138) | GAASRA S (SEQ ID NO: 140) | ASYDSS DGGV (SEQ ID NO: 145) | 412-441 |
| 412E6 | NYGVG (SEQ ID NO: 129) | NIYSGG STYYNP ALKS (SEQ ID NO: 133) | GGVGSV DV (SEQ ID NO: 135) | SGGRNN IGRGTF VD (SEQ ID NO: 137) | GTDRRP P (SEQ ID NO: 142) | ATYDYS NDMII (SEQ ID NO: 146) | 412-441 |
| 412G11 | SYALG (SEQ ID NO: 130) | NIWRGG RIEYNP ALKS (SEQ ID NO: 132) | SGGD (SEQ ID NO: 124) | SGSSSN VGYGNY VG (SEQ ID NO: 39) | GATSRA S (SEQ ID NO: 141) | ASYDRS ESVV (SEQ ID NO: 144) | 412-441 |

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises a VHCDR1 amino acid sequence set forth in table 5;

VHCDR2 comprises a VHCDR2 amino acid sequence set forth in table 5;

VHCDR3 comprises a VHCDR3 amino acid sequence set forth in table 5;

VLCDR1 comprises a VLCDR1 amino acid sequence set forth in table 5;

VLCDR2 comprises a VLCDR2 amino acid sequence set forth in table 5; and

VLCDR3 comprises a VLCDR3 amino acid sequence set forth in table 5;

or for each CDR sequence, an amino acid sequence with (i) at least 85% identity thereto, and/or (ii) one, two, or three amino acid substitutions relative thereto, to SEQ ID NO: 1 may be around 3.16 nM or 9.0 nM, optionally wherein the specific binding molecule comprises the CDRs of 412E10.

The specific binding molecule may comprise an amino acid sequence having at least 70%, at least 75%, at least 80%, at least 90%, at least 95% or at least 99% identity to SEQ ID NO: 147 wherein the specific binding molecule binds to a polypeptide or protein molecule comprising an amino acid sequence comprising residues 412 to 441 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 147. The CDRs may be 100% identical to the CDRs of SEQ ID NO: 147. The specific binding molecule may comprise an amino acid sequence having at least 70%, at least 75%, at least 80%, at least 90%, at least 95% or at least 99% identity to SEQ ID NO: 147 wherein CDRs are 100% identical to the CDRs of SEQ ID NO: 147. The specific binding molecule may comprise the amino acid sequence of SEQ ID NO: 147.

(412E10 amino acid sequence)
SEQ ID NO: 147
QVQLQESGPSLVKPSQTLSLTCTVSGFSVISDSVA

WVRQAPGKVPEWLGASGSSGNKYYNPALKSRLSIT

RDTSKSQVSLSLSSVTTEDTAVYYCARGIIAGVDV

WGRGLLVTVSSEGKSSGASGESKVDDQAVLTQPSS

VSGSLGQRVSITCSGSSSNVGYGNYVGWYQQVPGS

APKLLIYGTAIRASGVPDRFSGSRSGDTATLTITS

LQAEDEADYYCASYQSNYAFFGSGTRLTVLG

The specific binding molecule may comprise an amino acid sequence having at least 70%, at least 75%, at least 80%, at least 90%, at least 95% or at least 99% identity to SEQ ID NO: 417 wherein the specific binding molecule binds to a polypeptide or protein molecule comprising an amino acid sequence comprising residues 412 to 441 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 417. The CDRs may be 100% identical to the CDRs of SEQ ID NO: 417. The specific binding molecule may comprise an amino acid sequence having at least 70%, at least 75%, at least 80%, at least 90%, at least 95% or at least 99% identity to SEQ ID NO: 417 wherein CDRs are 100% identical to the CDRs of SEQ ID NO: 417. The specific binding molecule may comprise the amino acid sequence of SEQ ID NO: 417.

(412B9 amino acid sequence)
SEQ ID NO: 417
QVQLQESGPSLVKPSQTLSLTCTVSGFSVISDSVA

WVRQAPGKVPEWLGASGSSGNKYYNPALKSRLSIT

RDTSKSQVSLSLSSVTTEDTAVYYCARGIIAGVDV

WGRGLLVTVSSEGKSSGASGESKVDDQAVLTQPSS

VSGALGQRVSITCSGSSSNVGYGDYVGWYQQVPGS

APKLLIYGAASRASGVPDRFSGSRSGNTATLTISS

LQAEDEADYYCASYDSSDGGVFGSGTRLTVLG

The specific binding molecule may comprise an amino acid sequence having at least 70%, at least 75%, at least 80%, at least 90%, at least 95% or at least 99% identity to SEQ ID NO: 418 wherein the specific binding molecule binds to a polypeptide or protein molecule comprising an amino acid sequence comprising residues 412 to 441 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 418. The CDRs may be 100% identical to the CDRs of SEQ ID NO: 418. The specific binding molecule may comprise an amino acid sequence having at least 70%, at least 75%, at least 80%, at least 90%, at least 95% or at least 99% identity to SEQ ID NO: 418 wherein CDRs are 100% identical to the CDRs of SEQ ID NO: 418. The specific binding molecule may comprise the amino acid sequence of SEQ ID NO: 418.

(412E6 amino acid sequence)
SEQ ID NO: 418
QVQLQESGPSLVKPSETLSLTCTVSGFSLTNYGVG

WVRQAPGKALEWLGNIYSGGSTYYNPALKSRLSIT

RDTSKSQVSLSLNSVTLEDTAVYYCGRGGVGSVDV

WGPGLLVTVSSEGKSSGASGESKVDDQAVLTQPPS

VSGSPGQRVSITCSGGRNNIGRGTFVDWYQQLPGS

GLKTVIYGTDRRPPGVPDRFSGSKTGNAATLTITS

LQAEDEADYWCATYDYSNDMIILGSGTRLTVLG

The specific binding molecule may comprise an amino acid sequence having at least 70%, at least 75%, at least 80%, at least 90%, at least 95% or at least 99% identity to SEQ ID NO: 434 wherein the specific binding molecule binds to a polypeptide or protein molecule comprising an amino acid sequence comprising residues 412 to 441 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 434. The CDRs may be 100% identical to the CDRs of SEQ ID NO: 434. The specific binding molecule may comprise an amino acid sequence having at least 70%, at least 75%, at least 80%, at least 90%, at least 95% or at least 99% identity to SEQ ID NO: 434 wherein CDRs are 100% identical to the CDRs of SEQ ID NO: 434. The specific binding molecule may comprise the amino acid sequence of SEQ ID NO: 434.

(412G11 amino acid sequence)
SEQ ID NO: 434
QVRLQESGPSLVKPSQTLSLTCTVSGFSLTSYALG

WVRQAPGRAPEWIGNIWRGGRIEYNPALKSRLSIT

RDTSKSQVSLSLSSVTTEDTAVYYCSRSGGDWGPG

LLVTVSSEGKSSGASGESKVDDQAVLTQPSSVSGS

LGQRVSITCSGSSSNVGYGNYVGWYQQVPGSAPKL

LIYGATSRASGVPDRFSGSRSENTATLTISSLQAE

DEADYYCASYDRSESVVFGSGTRLTVLG

The epitope of the specific binding molecule may be within an amino acid sequence comprising residues 1 to 49 of SEQ ID NO: 1. Accordingly, the epitope may be within the amino acid sequence of SEQ ID NO: 148 (MAE-PRQEFEVMEDHAGTYGLGDRKDOG-GYTMHQDQEGDTDAGLKESPLQ).

Preferably, the epitope of the specific binding molecule within an amino acid sequence comprising residues 1 to 49 of SEQ ID NO: 1, may be within an amino acid sequence comprising residues 1 to 15 of SEQ ID NO: 1.

The epitope may be within an amino acid sequence comprising residues 1 to 49 of SEQ ID NO: 1. This epitope may be bound by the CDRs of the specific binding molecule referred to as "3aG3" herein.

The epitope may be within an amino acid sequence comprising residues 1 to 49 of SEQ ID NO: 1, preferably within an amino acid sequence comprising residues 1 to 15 of SEQ ID NO: 1. This epitope may be bound by the CDRs of the specific binding molecule referred to as "3bG4" herein.

The epitope may comprise the amino acid sequence of SEQ ID NO: 148 (MAEPRQEFEVMED-HAGTYGLGDRKDQGGYTMHQDQEGDTDAGL-KESPLQ). The epitope may comprise an amino acid sequence having at least 70%, at least 75%, at least 80%, at least 90%, at least 95% least 99% or at identity to SEQ ID NO: 148 (MAEPRQEFEVMEDHAGTYGLGDRKDQG-GYTMHQDQEGDTDAGLKESPLQ).

The epitope may consist of the amino acid sequence of SEQ ID NO: 148 (MAEPRQEFEVMED-HAGTYGLGDRKDQGGYTMHQDQEGDTDAGL-KESPLQ). The epitope may consist of an amino acid sequence having at least 70%, at least 75%, at least 80%, at least 90%, at least 95% or at least 99% identity to SEQ ID NO: 148 (MAEPRQEFEVMEDHAGTYGLGDRKDQG-GYTMHQDQEGDTDAGLKESPLQ).

The specific binding molecule may bind to a polypeptide or protein molecule comprising an amino acid sequence comprising residues 1 to 49 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 149 (S N G V G);

VHCDR2 comprises the sequence set forth in SEQ ID NO: 150 (D I S/A S S/V/G G K A/K/V Y A/S/G N/H P A L K S);

VHCDR3 comprises the sequence set forth in SEQ ID NO: 151 (C R D G G V S/T Y G Y D I/S D Y);

VLCDR1 comprises the sequence set forth in SEQ ID NO: 152 (S G S S/T S/G N I/V G G/S/Y G N/D Y/D L/V S/G);

VLCDR2 comprises the sequence set forth in SEQ ID NO: 153 (G A/V T S/N/E R/L A S); and VLCDR3 comprises the sequence set forth in SEQ ID NO: 154 (A/G S F/Y D T/S/D S/N S G G I/);

or for each CDR sequence, an amino acid sequence with (i) at least 85% identity thereto, and/or (ii) one, two, or three amino acid substitutions relative thereto.

Said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 155 (DISSSGKAYANPALKS). SEQ ID NO: 156 (DISSGGKVYGHPALKS), SEQ ID NO: 157 (DIS-SVGKKYANPALKS), or SEQ ID NO: 158 (DIASSG-KAYSNPALKS);

VHCDR3 comprises the sequence set forth in SEQ ID NO: 159 (CRDGGVSYGYDIDY), SEQ ID NO: 160 (CRDGGVSYGYDSDY), or SEQ ID NO: 161 (CRDGGVTYGYDIDY);

VLCDR1 comprises the sequence set forth in SEQ ID NO: 163 (SGSSSNIGGGNYLS), SEQ ID NO: 138

(SGSSSNVGYGDYVG), SEQ ID NO: 165 (SGSSGNVGYGDYVS), or SEQ ID NO: 166 (SGST-SNVGSGNDVS);

VLCDR2 comprises the sequence set forth in SEQ ID NO: 141 (GATSRAS), SEQ ID NO: 168 (GVTERAS), SEQ ID NO: 169 (GATNLAS), or SEQ ID NO: 170 (GATNRAS); and VLCDR3 comprises the sequence set forth in SEQ ID NO: 171 (ASFDTSSGGI), SEQ ID NO: 172 (ASYDDSSGGI), SEQ ID NO: 173 (ASYDSSSGGV), or SEQ ID NO: 174 (GSYDSNSGGI); or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 1 to 49 of SEQ ID NO: 1.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 155 (DISSSGKAYANPALKS);

VHCDR3 comprises the sequence set forth in SEQ ID NO: 159 (CRDGGVSYGYDIDY);

VLCDR1 comprises the sequence set forth in SEQ ID NO: 163 (SGSSSNIGGGNYLS);

VLCDR2 comprises the sequence set forth in SEQ ID NO: 141 (GATSRAS); and

VLCDR3 comprises the sequence set forth in SEQ ID NO: 171 (ASFDTSSGGI);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 1 to 49 of SEQ ID NO: 1. The specific binding molecule comprising CDRs having 100% identity to those given above is referred to as "3aG3" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 155 (DISSSGKAYANPALKS);

VHCDR3 comprises the sequence set forth in SEQ ID NO: 159 (CRDGGVSYGYDIDY);

VLCDR1 comprises the sequence set forth in SEQ ID NO: 163 (SGSSSNIGGGNYLS);

VLCDR2 comprises the sequence set forth in SEQ ID NO: 141 (GATSRAS); and

VLCDR3 comprises the sequence set forth in SEQ ID NO: 171 (ASFDTSSGGI).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 156 (DISSGGKVYGHPALKS);

VHCDR3 comprises the sequence set forth in SEQ ID NO: 160 (CRDGGVSYGYDSDY);

VLCDR1 comprises the sequence set forth in SEQ ID NO: 138 (SGSSSNVGYGDYVG);

VLCDR2 comprises the sequence set forth in SEQ ID NO: 168 (GVTERAS); and

VLCDR3 comprises the sequence set forth in SEQ ID NO: 172 (ASYDDSSGGI);

or for each CDR sequence, an amino acid sequence with
(i) at least 85% identity thereto, and/or
(ii) one, two, or three amino acid substitutions relative thereto, wherein the specific binding molecule binds to a polypeptide or protein molecule comprising an amino acid sequence comprising residues 1 to 49 of SEQ ID NO: 1. The specific binding molecule comprising CDRs having 100% identity to those given above is referred to as "3aD3" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 156 (DISSGGKVYGHPALKS);

VHCDR3 comprises the sequence set forth in SEQ ID NO: 160 (CRDGGVSYGYDSDY);

VLCDR1 comprises the sequence set forth in SEQ ID NO: 138 (SGSSSNVGYGDYVG);

VLCDR2 comprises the sequence set forth in SEQ ID NO: 168 (GVTERAS); and

VLCDR3 comprises the sequence set forth in SEQ ID NO: 172 (ASYDDSSGGI).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 157 (DISSVGKKYANPALKS);

VHCDR3 comprises the sequence set forth in SEQ ID NO: 161 (CRDGGVTYGYDIDY);

VLCDR1 comprises the sequence set forth in SEQ ID NO: 165 (SGSSGNVGYGDYVS);

VLCDR2 comprises the sequence set forth in SEQ ID NO: 169 (GATNLAS); and

VLCDR3 comprises the sequence set forth in SEQ ID NO: 173 (ASYDSSSGGV);

or for each CDR sequence, an amino acid sequence with
(i) at least 85% identity thereto, and/or
(ii) one, two, or three amino acid substitutions relative thereto, wherein the specific binding molecule binds to a polypeptide or protein molecule comprising an amino acid sequence comprising residues 1 to 49 of SEQ ID NO: 1. The specific binding molecule comprising CDRs having 100% identity to those given above is referred to as "3aH6" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 157 (DISSVGKKYANPALKS);

VHCDR3 comprises the sequence set forth in SEQ ID NO: 161 (CRDGGVTYGYDIDY);

VLCDR1 comprises the sequence set forth in SEQ ID NO: 165 (SGSSGNVGYGDYVS);

VLCDR2 comprises the sequence set forth in SEQ ID NO: 169 (GATNLAS); and

VLCDR3 comprises the sequence set forth in SEQ ID NO: 173 (ASYDSSSGGV).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 158 (DIASSGKAYSNPALKS);

VHCDR3 comprises the sequence set forth in SEQ ID NO: 161 (CRDGGVTYGYDIDY);

VLCDR1 comprises the sequence set forth in SEQ ID NO: 166 (SGSTSNVGSGNDVS);

VLCDR2 comprises the sequence set forth in SEQ ID NO: 170 (GATNRAS); and

VLCDR3 comprises the sequence set forth in SEQ ID NO: 174 (GSYDSNSGGI);

or for each CDR sequence, an amino acid sequence with
(i) at least 85% identity thereto, and/or
(ii) one, two, or three amino acid substitutions relative thereto, wherein the specific binding molecule binds to a polypeptide or protein molecule comprising an amino acid sequence comprising residues 1 to 49 of SEQ ID NO: 1. The specific binding molecule comprising CDRs having 100% identity to those given above is referred to as "3bG4" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 158 (DIASSGKAYSNPALKS);

VHCDR3 comprises the sequence set forth in SEQ ID NO: 161 (CRDGGVTYGYDIDY);

VLCDR1 comprises the sequence set forth in SEQ ID NO: 166 (SGSTSNVGSGNDVS);

VLCDR2 comprises the sequence set forth in SEQ ID NO: 170 (GATNRAS); and

VLCDR3 comprises the sequence set forth in SEQ ID NO: 174 (GSYDSNSGGI).

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 471 (QVQLQESGPSLVKPSQTLSLTCTISGFSLI);

VHFR2 comprises the sequence set forth in SEQ ID NO: 472 (WRQAPGKVPEWVG);

VHFR3 comprises the sequence set forth in SEQ ID NO: 473 (RLSITRDTSKSQVSLSLRSVTTED-TAVYYCVR);

VHFR4 comprises the sequence set forth in SEQ ID NO: 474 (WGPGLLVTVSS);

VLFR1 comprises the sequence set forth in SEQ ID NO: 475 (QAVLTQPSSVSKSLGQSVSITC);

VLFR2 comprises the sequence set forth in SEQ ID NO: 476 (WFQQVPGSAPKLLFY);

VLFR3 comprises the sequence set forth in SEQ ID NO: 477 (GVPDRFSGSRSGNTATLTITSLQAEDEADYYC);

VLFR4 comprises the sequence set forth in SEQ ID NO: 478 (FGSGTRLTVLG);

or for each FR sequence, an amino acid sequence with
    (i) at least 50% identity thereto, and/or
    (ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 471 (QVQLQESGPSLVKPSQTLSLTCTISGFSLI);

VHFR2 comprises the sequence set forth in SEQ ID NO: 472 (WVRQAPGKVPEWVG);

VHFR3 comprises the sequence set forth in SEQ ID NO: 473 (RLSITRDTSKSQVSLSLRSVTTED-TAVYYCVR);

VHFR4 comprises the sequence set forth in SEQ ID NO: 474 (WGPGLLVTVSS);

VLFR1 comprises the sequence set forth in SEQ ID NO: 475 (QAVLTQPSSVSKSLGQSVSITC);

VLFR2 comprises the sequence set forth in SEQ ID NO: 476 (WFQQVPGSAPKLLFY);

VLFR3 comprises the sequence set forth in SEQ ID NO: 477 (GVPDRFSGSRSGNTATLTITSLQAEDEAD-YYC);

VLFR4 comprises the sequence set forth in SEQ ID NO: 478 (FGSGTRLTVLG);

or for each FR sequence, an amino acid sequence with
    (i) at least 50% identity thereto, and/or
    (ii) one, two, three, four or five amino acid substitutions relative thereto, wherein the specific binding molecule binds to a polypeptide or protein molecule comprising an amino acid sequence comprising residues 1 to 49 of SEQ ID NO: 1. A specific binding molecule comprising FRs having 100% identity to those given above is referred to as "3bG4" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 471 (QVQLQESGPSLVKPSQTLSLTCTIS-GFSLI);

VHFR2 comprises the sequence set forth in SEQ ID NO: 472 (WVRQAPGKVPEWVG);

VHFR3 comprises the sequence set forth in SEQ ID NO: 473 (RLSITRDTSKSQVSLSLRSVTTED-TAVYYCVR);

VHFR4 comprises the sequence set forth in SEQ ID NO: 474 (WGPGLLVTVSS);

VLFR1 comprises the sequence set forth in SEQ ID NO: 475 (QAVLTQPSSVSKSLGQSVSITC);

VLFR2 comprises the sequence set forth in SEQ ID NO: 476 (WFQQVPGSAPKLLFY);

VLFR3 comprises the sequence set forth in SEQ ID NO: 477 (GVPDRFSGSRSGNTATLTITSLQAE-DEADYYC);

VLFR4 comprises the sequence set forth in SEQ ID NO: 478 (FGSGTRLTVLG);

or for each FR sequence, an amino acid sequence with
    (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 158 (DIASSGKAYSNPALKS);

VHCDR3 comprises the sequence set forth in SEQ ID NO: 161 (CRDGGVTYGYDIDY);

VLCDR1 comprises the sequence set forth in SEQ ID NO: 166 (SGSTSNVGSGNDVS);

VLCDR2 comprises the sequence set forth in SEQ ID NO: 170 (GATNRAS); and

VLCDR3 comprises the sequence set forth in SEQ ID NO: 174 (GSYDSNSGGI);

or for each CDR sequence, an amino acid sequence with
    (i) at least 85% identity thereto, and/or
    (ii) one, two, or three amino acid substitutions relative thereto wherein the specific binding molecule binds to a polypeptide or protein molecule comprising an amino acid sequence comprising residues 1 to 49 of SEQ ID NO: 1. The specific binding molecule comprising FRs and CDRs having 100% identity to those given above is referred to as "3bG4" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 471 (QVQLQESGPSLVKPSQTLSLTCTIS-GFSLI);

VHFR2 comprises the sequence set forth in SEQ ID NO: 472 (WVRQAPGKVPEWVG);

VHFR3 comprises the sequence set forth in SEQ ID NO: 473 (RLSITRDTSKSQVSLSLRSVTTED-TAVYYCVR);

VHFR4 comprises the sequence set forth in SEQ ID NO: 474 (WGPGLLVTVSS);

VLFR1 comprises the sequence set forth in SEQ ID NO: 475 (QAVLTQPSSVSKSLGQSVSITC);

VLFR2 comprises the sequence set forth in SEQ ID NO: 476 (WFQQVPGSAPKLLFY);

VLFR3 comprises the sequence set forth in SEQ ID NO: 477 (GVPDRFSGSRSGNTATLTITSLQAE-DEADYYC);

VLFR4 comprises the sequence set forth in SEQ ID NO: 478 (FGSGTRLTVLG);

or for each FR sequence, an amino acid sequence with
    (i) at least 50% identity thereto, and/or
    (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 158 (DIASSGKAYSNPALKS);

VHCDR3 comprises the sequence set forth in SEQ ID NO: 161 (CRDGGVTYGYDIDY);

VLCDR1 comprises the sequence set forth in SEQ ID NO: 166 (SGSTSNVGSGNDVS);

VLCDR2 comprises the sequence set forth in SEQ ID
NO: 170 (GATNRAS); and

VLCDR3 comprises the sequence set forth in SEQ ID
NO: 174 (GSYDSNSGGI);

wherein the specific binding molecule binds to a poly-
peptide or protein molecule comprising an amino
acid sequence comprising residues 1 to 49 of SEQ ID
NO: 1. The specific binding molecule comprising
FRs and CDRs having 100% identity to those given
above is referred to as "3bG4" herein.

The specific binding molecule may comprise:

```
(a) A VH domain comprising the
sequence set forth in SEQ ID NO: 479
(QVQLQESGPSLVKPSQTLSLTCTISGFSLISNGVG

WVRQAPGKVPEWVGDIASSGKAYSNPALKSRLSIT

RDTSKSQVSLSLRSVTTEDTAVYYCVRCRDGGVTY

GYDIDYWGPGLLVTVSS);
and/or (b) a VL domain comprising the
sequence set forth in SEQ ID NO: 480
(QAVLTQPSSVSKSLGQSVSITCSGSTSNVGSGND

VSWFQQVPGSAPKLLFYGATNRASGVPDRFSGSRS

GNTATLTITSLQAEDEADYYCGSYDSNSGGIFGSG

TRLTVLG);
``` or a humanized variant thereof.

The specific binding molecule may comprise:

```
(a) A heavy chain comprising the
sequence set forth in SEQ ID NO: 481
(QVQLQESGPSLVKPSQTLSLTCTISGFSLISNGV
```

```
-continued
GWVRQAPGKVPEWVGDIASSGKAYSNPALKSRLSI

TRDTSKSQVSLSLRSVTTEDTAVYYCVRCRDGGVT

YGYDIDYWGPGLLVTVSSAKTTAPSVYPLAPVCGD

TTGSSVTLGCLVKGYFPEPVTLTWNSGSLSSGVHT

FPAVLQSDLYTLSSSVTVTSSTWPSQSITCNVAHP

ASSTKVDKKIEPRGPTIKPCPPCKCPAPNLLGGPS

VFIFPPKIKDVLMISLSPIVTCVVVDVSEDDPDVQ

ISWFVNNVEVHTAQTQTHREDYNSTLRVVSALPIQ

HQDWMSGKEFKCKVNNKDLPAPIERTISKPKGSVR

APQVYVLPPPEEEMTKKQVTLTCMVTDFMPEDIYV

EWTNNGKTELNYKNTEPVLDSDGSYFMYSKLRVEK

KNWVERNSYSCSVVHEGLHNHHTTKSFSRTPGK);
and/or (b) a light chain comprising the
sequence set forth in SEQ ID NO: 482
(QAVLTQPSSVSKSLGQSVSITCSGSTSNVGSGND

VSWFQQVPGSAPKLLFYGATNRASGVPDRFSGSRS

GNTATLTITSLQAEDEADYYCGSYDSNSGGIFGSG

TRLTVLGGQPKSSPSVTLFPPSSEELETNKATLVC

TITDFYPGVVTVDWKVDGTPVTQGMETTQPSKQSN

NKYMASSYLTLTARAWERHSSYSCQVTHEGHTVEK

SLSRADCS);
``` or a humanized variant thereof.

The specific binding molecule may comprise the CDR
sequences of a clone set out in Table 6 below. The epitope
may be within residues 1 to 49 of SEQ ID NO: 1.

TABLE 6

| Clone | VH | | |
|---|---|---|---|
| name | CDR1 | CDR2 | CDR3 |
| 3aD3 | SNGVG (SEQ ID NO: 149) | DISSGGKVYGHP ALKS (SEQ ID NO: 156) | CRDGGVSYGYDSDY (SEQ ID NO: 160) |
| 3aH6 | SNGVG (SEQ ID NO: 149) | DISSVGKKYANP ALKS (SEQ ID NO: 157) | CRDGGVTYGYDIDY (SEQ ID NO: 161) |
| 3aG3 | SNGVG (SEQ ID NO: 149) | DISSSGKAYANP ALKS (SEQ ID NO: 155) | CRDGGVSYGYDIDY (SEQ ID NO: 159) |
| 3bG4 | SNGVG (SEQ ID NO: 149) | DIASSGKAYSNP ALKS (SEQ ID NO: 158) | CRDGGVTYGYDIDY (SEQ ID NO: 161) |

| Clone | VL | | | |
|---|---|---|---|---|
| name | CDR1 | CDR2 | CDR3 | Epitope |
| 3aD3 | SGSSSNVGYGDYV G (SEQ ID NO: 138) | GVTERAS (SEQ ID NO: 168) | ASYDDSSGGI (SEQ ID NO: 172) | 1-49 |
| 3aH6 | SGSSGNVGYGDYV S (SEQ ID NO: 165) | GATNLAS (SEQ ID NO: 169) | ASYDSSSGGV (SEQ ID NO: 173) | 1-49 |
| 3aG3 | SGSSSNIGGGNYLS (SEQ ID NO: 163) | GATSRAS (SEQ ID NO: 141) | ASFDTSSGGI (SEQ ID NO: 171) | 1-49 |

TABLE 6-continued

```
3bG4 SGSTSNVGSGNDV      GATNRAS (SEQ ID  GSYDSNSGGI (SEQ  1-49
     S (SEQ ID NO: 166) NO: 170)        ID NO: 174)
```

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises a VHCDR1 amino acid sequence set forth in table 6;

VHCDR2 comprises a VHCDR2 amino acid sequence set forth in table 6;

VHCDR3 comprises a VHCDR3 amino acid sequence set forth in table 6;

VLCDR1 comprises a VLCDR1 amino acid sequence set forth in table 6;

VLCDR2 comprises a VLCDR2 amino acid sequence set forth in table 6; and

VLCDR3 comprises a VLCDR3 amino acid sequence set forth in table 6;

or for each CDR sequence, an amino acid sequence with
(i) at least 85% identity thereto, and/or
(ii) one, two, or three amino acid substitutions relative thereto, wherein the specific binding molecule binds to a polypeptide or protein molecule comprising an amino acid sequence comprising residues 1 to 49 of SEQ ID NO: 1.

The specific binding molecule may bind to a polypeptide or protein molecule comprising an amino acid sequence comprising residues 1 to 49 of SEQ ID NO: 1 with a $K_D$ of less than around 25 nM. The $K_D$ may be less than around 20 nM, less than around 15 nM, or less than around 10 nM. The Kp may preferably be for binding to SEQ ID NO: 1 or to SEQ ID NO: 148. The $K_D$ for binding to SEQ ID NO: 1 may be around 1 nM to around 20 nM. The $K_D$ for binding to SEQ ID NO: 1 may be around 1 nM to around 10 nM. The $K_D$ for binding to SEQ ID NO: 1 may be around 19.1 nM, optionally wherein the specific binding molecule comprises the CDRs of 3aD3. The $K_D$ for binding to SEQ ID NO: 1 may be around 3.6 nM, optionally wherein the specific binding molecule comprises the CDRs of 3aH6. The K for binding to SEQ ID NO: 1 may be around 6.1 nM, optionally wherein the specific binding molecule comprises the CDRs of 3aG3. The $K_D$ for binding to SEQ ID NO: 1 may be around 8.9 nM, optionally wherein the specific binding molecule comprises the CDRs of 3bG4.

The specific binding molecule may comprise an amino acid sequence having at least 70%, at least 75%, at least 80%, at least 90%, at least 95% or at least 99% identity to SEQ ID NO: 422 wherein the specific binding molecule binds to a polypeptide or protein molecule comprising an amino acid sequence comprising residues 1 to 49 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 422. The CDRs may be 100% identical to the CDRs of SEQ ID NO: 422. The specific binding molecule may comprise an amino acid sequence having at least 70%, at least 75%, at least 80%, at least 90%, at least 95% or at least 99% identity to SEQ ID NO: 422 wherein CDRs are 100% identical to the CDRs of SEQ ID NO: 422. The specific binding molecule may comprise the amino acid sequence of SEQ ID NO: 422.

(3aD3 amino acid sequence)

SEQ ID NO: 422

QVQLQESGPSLVKPSQTLSLTCTVSGFSLTSNGVGWRRAPGKVPEWVGD

ISSGGKVYGHPALKSRLSITRDTSKSQVSLSVSSVTSEDTAVYYCVRCR

DGGVSYGYDSDYWGPGLLVTVSSEGKSSGASGESKVDDQAVVTQPSSVS

KSLGQSVSITCSGSSSNVGYGDYVGWFQQVPGSAPKLLIYGVTERASGV

PDRFSGSRSGNTATLTISSIQAEDEADYYCASYDDSSGGIFGSGTRLTV

LG

The specific binding molecule may comprise an amino acid sequence having at least 70%, at least 75%, at least 80%, at least 90%, at least 95% or at least 99% identity to SEQ ID NO: 423 wherein the specific binding molecule binds to a polypeptide or protein molecule comprising an amino acid sequence comprising residues 1 to 49 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 423. The CDRs may be 100% identical to the CDRs of SEQ ID NO: 423. The specific binding molecule may comprise an amino acid sequence having at least 70%, at least 75%, at least 80%, at least 90%, at least 95% or at least 99% identity to SEQ ID NO: 423 wherein CDRs are 100% identical to the CDRs of SEQ ID NO: 423. The specific binding molecule may comprise the amino acid sequence of SEQ ID NO: 423.

(3aH6 amino acid sequence)

SEQ ID NO: 423

QVQLQESGPSLVKPSQTLSLTCTVSGFSLSSNGVGWVRQAPGKVPEWLG

DISSVGKKYANPALKSRLSFTRDTSKSQVSLSLSSVTTEDTAVYYCVKC

RDGGVTYGYDIDYWGPGLLVTASSEGKSSGASGESKVDDQAWVTQPSSV

SGSLGQSVSITCSGSSGNVGYGDYVSWFQQFHGSAPKLLIYGATNLASG

VPARFSGSRSGNTATLTISSLHAEDEADYYCASYDSSSGGVFGSGTRLT

VLG

The specific binding molecule may comprise an amino acid sequence having at least 70%, at least 75%, at least 80%, at least 90%, at least 95% or at least 99% identity to SEQ ID NO: 424 wherein the specific binding molecule binds to a polypeptide or protein molecule comprising an amino acid sequence comprising residues 1 to 49 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 424. The CDRs may be 100% identical to the CDRs of SEQ ID NO: 424. The specific binding molecule may comprise an amino acid sequence having at least 70%, at least 75%, at least 80%, at least 90%, at least 95% or at least 99% identity to SEQ ID NO: 424 wherein CDRs are 100% identical to the CDRs of SEQ ID NO: 424. The specific binding molecule may comprise the amino acid sequence of SEQ ID NO: 424.

(3aG3 amino acid sequence)

SEQ ID NO: 424

QVQLQESGPSLVKPSQTLSLTCTVSGFSLSSNGVGWVRQAPGKVPEWVG

DISSSGKAYANPALKSRLSITRDTAKTQVFLSLSSVTTEDTAVYYCVRC

RDGGVSYGYDIDYWGPGLLVTVSSEGKSSGASGESKVDDQAVLTQPPSV

SGSPGQRVSITCSGSSSNIGGGNYLSWFQQVPGSAPKLLIYGATSRASG

VPDRFSGSRSGNTATLTISSLQAEDEADYYCASFDTSSGGIFGAGTRLT

VLG

The specific binding molecule may comprise an amino acid sequence having at least 70%, at least 75%, at least 80%, at least 90%, at least 95% or at least 99% identity to SEQ ID NO: 425 wherein the specific binding molecule binds to a polypeptide or protein molecule comprising an amino acid sequence comprising residues 1 to 49 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 425. The CDRs may be 100% identical to the CDRs of SEQ ID NO: 425. The specific binding molecule may comprise an amino acid sequence having at least 70%, at least 75%, at least 80%, at least 90%, at least 95% or at least 99% identity to SEQ ID NO: 425 wherein CDRs are 100% identical to the CDRs of SEQ ID NO: 425. The specific binding molecule may comprise the amino acid sequence of SEQ ID NO: 425.

(3bG4 amino acid sequence)

SEQ ID NO: 425

QVQLQESGPSLVKPSQTLSLTCTISGFSLISNGVGWVRQAPGKVPEWVG

DIASSGKAYSNPALKSRLSITRDTSKSQVSLSLRSVTTEDTAVYYCVRC

RDGGVTYGYDIDYWGPGLLVTVSSEGKSSGASGESKVDDQAVLTQPSSV

SKSLGQSVSITCSGSTSNVGSGNDVSWFQQVPGSAPKLLFYGATNRASG

VPDRFSGSRSGNTATLTITSLQAEDEADYYCGSYDSNSGGIFGSGTRLT

VLG

The epitope of the specific binding molecule may be within an amino acid sequence comprising residues 49 to 111 of SEQ ID NO: 1. Accordingly, the epitope may be within the amino acid sequence of SEQ ID NO: 175 (QTPT-EDGSEEPGSETSDAKSTPTAEDVTAPLVDE-GAPGKQAAAQPHTEIPEGTTAEEAGIGDT).

The epitope may be within an amino acid sequence comprising residues 49 to 111 of SEQ ID NO: 1. This epitope may be bound by the CDRs of the specific binding molecule referred to as "3bF4" herein.

The epitope may comprise the amino acid sequence of SEQ ID NO: 175 (QTPTEDGSEEPGSETSDAKSTPTAE-DVTAPLVDEGAPGKQAAAQPHTEIPEGTTAEEA-GIGDT). The epitope may comprise an amino acid sequence having at least 70%, at least 75%, at least 80%, at least 90%, at least 95% or at least 99% identity to SEQ ID NO: 175 (QTPTEDGSEEPGSETSDAKSTPTAEDVTAPLVDE-GAPGKQAAAQPHTEIPEGTTAEEAGIGDT).

The epitope may consist of the amino acid sequence of SEQ ID NO: 175 (QTPTEDGSEEPGSETSDAKSTPTAE-DVTAPLVDEGAPGKQAAAQPHTEIPEGTTAEEA-GIGDT). The epitope may consist of an amino acid sequence having at least 70%, at least 75%, at least 80%, at least 90%, at least 95% or at least 99% identity to SEQ ID NO: 175 (QTPTEDGSEEPGSETSDAKSTPTAEDVTA-PLVDEGAPGKQAAAQPHTEIPEGTTAEEAGIGDT).

The specific binding molecule may bind to a polypeptide or protein molecule comprising an amino acid sequence comprising residues 49 to 111 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 149 (S N G V G);

VHCDR2 comprises the sequence set forth in SEQ ID NO: 176 (D I/K S S V/A G K K/T Y A/G N P A L K S);

VHCDR3 comprises the sequence set forth in SEQ ID NO: 177 (C R D G G V T Y G Y D I N DY);

VLCDR1 comprises the sequence set forth in SEQ ID NO: 178 (S G S S S N V G L Y R/G N/D Y/V V T/S);

VLCDR2 comprises the sequence set forth in SEQ ID NO: 179 (G A/T T S/T R A S); and VLCDR3 comprises the sequence set forth in SEQ ID NO: 180 (A S A/F D T/S N/D D/S G G V/I);

or for each CDR sequence, an amino acid sequence with
    (i) at least 85% identity thereto, and/or
    (ii) one, two, or three amino acid substitutions relative thereto.

Said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 157 (DISSVGKKYANPALKS), or SEQ ID NO: 182 (DKSSAGKTYGNPALKS);

VHCDR3 comprises the sequence set forth in SEQ ID NO: 161 (CRDGGVTYGYDIDY), or SEQ ID NO: 184 (CRDGGVTYGYDVDY);

VLCDR1 comprises the sequence set forth in SEQ ID NO: 185 (SGSSSNVGLRNYVT), or SEQ ID NO: 186 (SGSSSNVGYGDVVS);

VLCDR2 comprises the sequence set forth in SEQ ID NO: 141 (GATSRAS), or SEQ ID NO: 188 (GTT-TRAS); and VLCDR3 comprises the sequence set forth in SEQ ID NO: 189 (ASADTNDGGV), or SEQ ID NO: 190 (ASFDSDSGGI);

or for each CDR sequence, an amino acid sequence with
    (i) at least 85% identity thereto, and/or
    (ii) one, two, or three amino acid substitutions relative thereto,
    wherein the specific binding molecule binds to a polypeptide or protein molecule comprising an amino acid sequence comprising residues 49 to 111 of SEQ ID NO: 1.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 157 (DISSVGKKYANPALKS);

VHCDR3 comprises the sequence set forth in SEQ ID NO: 161 (CRDGGVTYGYDIDY);

VLCDR1 comprises the sequence set forth in SEQ ID NO: 185 (SGSSSNVGLRNYVT);

VLCDR2 comprises the sequence set forth in SEQ ID NO: 141 (GATSRAS); and

VLCDR3 comprises the sequence set forth in SEQ ID NO: 189 (ASADTNDGGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 49 to 111 of SEQ ID NO: 1. The specific binding molecule comprising CDRs having 100% identity to those given above is referred to as "3bF4" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 157 (DISSVGKKYANPALKS);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 49 to 111 of SEQ ID NO: 1. The specific binding molecule comprising CDRs having 100% identity to those given above is referred to as "3aB7" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 182 (DKSSAGKTYGNPALKS);

VHCDR3 comprises the sequence set forth in SEQ ID NO: 184 (CRDGGVTYGYDVDY);

VLCDR1 comprises the sequence set forth in SEQ ID NO: 186 (SGSSSNVGYGDWVS); 10

VLCDR2 comprises the sequence set forth in SEQ ID NO: 188 (GTTTRAS); and

VLCDR3 comprises the sequence set forth in SEQ ID NO: 190 (ASFDSDSGGI).

The specific binding molecule may comprise the CDR sequences of a clone set out in Table 7 below. The epitope may be within residues 49 to 111 of SEQ ID NO: 1.

TABLE 7

| Clone | VH | | | VL | | | |
|---|---|---|---|---|---|---|---|
| name | CDR1 | CDR2 | CDR3 | CDR1 | CDR2 | CDR3 | Epitope |
| 3aB7 | SNGVG (SEQ ID NO: 149) | DKSSAGKTYGNPALKS (SEQ ID NO: 182) | CRDGGVTYGYDVDY (SEQ ID NO: 184) | SGSSSNVGYGDVVS (SEQ ID NO: 186) | GTTTRAS (SEQ ID NO: 188) | ASFDSDSGGI (SEQ ID NO: 190) | 49-111 |
| 3bF4 | SNGVG (SEQ ID NO: 149) | DISSVGKKYANPALKS (SEQ ID NO: 157) | CRDGGVTYGYDIDY (SEQ ID NO: 161) | SGSSSNVGLRNYVT (SEQ ID NO: 185) | GATSRAS (SEQ ID NO: 141) | ASADTNDGGV (SEQ ID NO: 189) | 49-111 |

VHCDR3 comprises the sequence set forth in SEQ ID NO: 161 (CRDGGVTYGYDIDY);

VLCDR1 comprises the sequence set forth in SEQ ID NO: 186 (SGSSSNVGYGDVVS);

VLCDR2 comprises the sequence set forth in SEQ ID NO: 141 (GATSRAS); and

VLCDR3 comprises the sequence set forth in SEQ ID NO: 189 (ASADTNDGGV).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 149 (SNGVG);

VHCDR2 comprises the sequence set forth in SEQ ID NO: 182 (DKSSAGKTYGNPALKS);

VHCDR3 comprises the sequence set forth in SEQ ID NO: 184 (CRDGGVTYGYDVDY);

VLCDR1 comprises the sequence set forth in SEQ ID NO: 186 (SGSSSNVGYGDVVS);

VLCDR2 comprises the sequence set forth in SEQ ID NO: 188 (GTTTRAS); and

VLCDR3 comprises the sequence set forth in SEQ ID NO: 190 (ASFDSDSGGI);

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises a VHCDR1 amino acid sequence set forth in table 7;

VHCDR2 comprises a VHCDR2 amino acid sequence set forth in table 7;

VHCDR3 comprises a VHCDR3 amino acid sequence set forth in table 7;

VLCDR1 comprises a VLCDR1 amino acid sequence set forth in table 7;

VLCDR2 comprises a VLCDR2 amino acid sequence set forth in table 7; and

VLCDR3 comprises a VLCDR3 amino acid sequence set forth in table 7;

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 49 to 111 of SEQ ID NO: 1.

The specific binding molecule may bind to a polypeptide or protein molecule comprising an amino acid sequence comprising residues 49 to 111 of SEQ ID NO: 1 with a $K_D$ of less than around 250 nM. The Kc may be less than around 200 nM, less than around 150 nM, or less than around 100 nM. The Ko may preferably be for binding to SEQ ID NO: 1 or to SEQ ID NO: 175. The Ko for binding to SEQ ID NO: 1 may be around 1 nM to around 20 nM. The $K_D$ for binding to SEQ ID NO: 1 may be around 50 nM to around 150 nM. The $K_D$ for binding to SEQ ID NO: 1 may be around 69 nM, optionally wherein the specific binding molecule comprises the CDRs of 3aB7. The $K_D$ for binding to SEQ ID NO: 1 may be around 140 nM, optionally wherein the specific binding molecule comprises the CDRs of 3bF4.

The specific binding molecule may comprise an amino acid sequence having at least 70%, at least 75%, at least 80%, at least 90%, at least 95% or at least 99% identity to SEQ ID NO: 420 wherein the specific binding molecule binds to a polypeptide or protein molecule comprising an amino acid sequence comprising residues 49 to 111 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 420. The CDRs may be 100% identical to the CDRs of SEQ ID NO: 420. The specific binding molecule may comprise an amino acid sequence having at least 70%, at least 75%, at least 80%, at least 90%, at least 95% or at least 99% identity to SEQ ID NO: 420 wherein CDRs are 100% identical to the CDRs of SEQ ID NO: 420. The specific binding molecule may comprise the amino acid sequence of SEQ ID NO: 420.

(3aB7 amino acid sequence)

SEQ ID NO: 420

QVQLQESGPSLVKPSQTLSLTCTVSGFSLTSNGVGWRQAPGKVPEWVGD

KSSAGKTYGNPALKSRLSITRDTSKSQVSLSLSSVTTEDTAVYYCVRCR

DGGVTYGYDVDYWGPGLLVTVSSEGKSSGASGESKVDDQAVLTQPSSVS

KSLGQSVSITCSGSSSNVGYGDVVSWFQQFPGSAPKLLIFGTTTRASGV

PDRFSGSRSGNAATLTINSLQAEDEADYYCASFDSDSGGIAGSGTRLTV

LG

The specific binding molecule may comprise an amino acid sequence having at least 70%, at least 75%, at least 80%, at least 90%, at least 95% or at least 99% identity to SEQ ID NO: 421 wherein the specific binding molecule binds to a polypeptide or protein molecule comprising an amino acid sequence comprising residues 49 to 111 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 421. The CDRs may be 100% identical to the CDRs of SEQ ID NO: 421. The specific binding molecule may comprise an amino acid sequence having at least 70%, at least 75%, at least 80%, at least 90%, at least 95% or at least 99% identity to SEQ ID NO: 421 wherein CDRs are 100% identical to the CDRs of SEQ ID NO: 421. The specific binding molecule may comprise the amino acid sequence of SEQ ID NO: 421.

(3bF4 amino acid sequence)

SEQ ID NO: 421

QVQLQESGPSLVKPSQTLSLTCTVSGFSLSSNGVGWVRQAPGKVPEWLG

DISSVGKKYANPALKSRLSFTRDTSKSQVSLSLSSVTTEDTAVYYCVKC

RDGGVTYGYDIDYWGPGLLVTVSSEGKSSGASGESKVDDQAVLTQPSSV

SKSTGQTVSITCSGSSSNVGLRNYVTWFQQVPGSAPKLLIYGATSRASG

IPDRFSGSRSGNTATLIISSLQAEDEADYYCASADTNDGGVFGSGTRLT

VLG

The epitope of the specific binding molecule may be within an amino acid sequence comprising residues 146 to 157 of SEQ ID NO: 1. Accordingly, the epitope may be within the amino acid sequence of SEQ ID NO: 191 (GKT-KIATPRGA).

The epitope may be within an amino acid sequence comprising residues 147 to 157 of SEQ ID NO: 1. This epitope may be bound by the CDRs of the specific binding molecule referred to as "3aD6" herein The epitope may comprise the amino acid sequence of SEQ ID NO: 191 (GKTKIATPRGA). The epitope may comprise an amino acid sequence having at least 70%, at least 75%, at least 80%, at least 90%, at least 95% or at least 99% identity to SEQ ID NO: 191 (GKTKIATPRGA).

The epitope may consist of the amino acid sequence of SEQ ID NO: 191 (GKTKIATPRGA). The epitope may consist of an amino acid sequence having at least 70%, at least 75%, at least 80%, at least 90%, at least 95% or at least 99% identity to SEQ ID NO: 191 (GKTKIATPRGA).

The specific binding molecule may bind to a polypeptide or protein molecule comprising an amino acid sequence comprising residues 147 to 157 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 192 (S N A V I/G);

VHCDR2 comprises the sequence set forth in SEQ ID NO: 193 (L I D V/ID G D A/T A Y D/N PAL K/ES);

VHCDR3 comprises the sequence set forth in SEQ ID NO: 194 (D/H Y G/D S/K W G Y V/A S/D D/S I D Y);

VLCDR1 comprises the sequence set forth in SEQ ID NO: 195 (S G S D/S-/S-/N-/V I/G G/Y G A/D D/Y V G);

VLCDR2 comprises the sequence set forth in SEQ ID NO: 196 (D N/A D/T N/T R P/A S); and VLCDR3 comprises the sequence set forth in SEQ ID NO: 197 (G/A T/S Y S/Q G/N A/E N/R Y/S G I/V);

or for each CDR sequence, an amino acid sequence with
   (i) at least 85% identity thereto, and/or
   (ii) one, two, or three amino acid substitutions relative thereto.

Said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 198 (SNAVI), or SEQ ID NO: 17 (SNAVG);

VHCDR2 comprises the sequence set forth in SEQ ID NO: 200 (LIDVDGDAAYDPALKS), or SEQ ID NO: 201 (LIDIDGDTAYNPALES);

VHCDR3 comprises the sequence set forth in SEQ ID NO: 202 (DYGSWGYVSDIDY), or SEQ ID NO: 203 (HYDKWGYADSIDY);

VLCDR1 comprises the sequence set forth in SEQ ID NO: 204 (SGSDIGGADVG), or SEQ ID NO: 138 (SGSSSNVGYGDYVG);

VLCDR2 comprises the sequence set forth in SEQ ID NO: 206 (DNDNRPS), or SEQ ID NO: 207 (DATTRAS); and VLCDR3 comprises the sequence set forth in SEQ ID NO: 208 (GTYSGANYGI), or SEQ ID NO: 209 (ASYQNERSGV);

or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 147 to 157 of SEQ ID NO: 1.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 198 (SNAVI);

VHCDR2 comprises the sequence set forth in SEQ ID NO: 200 (LIDVDGDAAYDPALKS);

VHCDR3 comprises the sequence set forth in SEQ ID NO: 202 (DYGSWGYVSDIDY);

VLCDR1 comprises the sequence set forth in SEQ ID NO: 204 (SGSDIGGADVG);

VLCDR2 comprises the sequence set forth in SEQ ID NO: 206 (DNDNRPS); and

VLCDR3 comprises the sequence set forth in SEQ ID NO: 208 (GTYSGANYGI):

or for each CDR sequence, an amino acid sequence with

VHCDR1 comprises the sequence set forth in SEQ ID NO: 198 (SNAVI);

VHCDR2 comprises the sequence set forth in SEQ ID NO: 200 (LIDVDGDAAYDPALKS);

VHCDR3 comprises the sequence set forth in SEQ ID NO: 202 (DYGSWGYVSDIDY);

VLCDR1 comprises the sequence set forth in SEQ ID NO: 204 (SGSDIGGADVG);

VLCDR2 comprises the sequence set forth in SEQ ID NO: 206 (DNDNRPS); and

VLCDR3 comprises the sequence set forth in SEQ ID NO: 208 (GTYSGANYGI).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 17 (SNAVG);

VHCDR2 comprises the sequence set forth in SEQ ID NO: 201 (LIDIDGDTAYNPALES);

VHCDR3 comprises the sequence set forth in SEQ ID NO: 203 (HYDKWGYADSIDY);

VLCDR1 comprises the sequence set forth in SEQ ID NO: 138 (SGSSSNVGYGDYVG);

VLCDR2 comprises the sequence set forth in SEQ ID NO: 207 (DATTRAS); and

VLCDR3 comprises the sequence set forth in SEQ ID NO: 209 (ASYQNERSGV):

or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 147 to 157 of SEQ ID NO: 1. The specific binding molecule comprising CDRs having 100% identity to those given above is referred to as "3aA6" herein.

The specific binding molecule may comprise the CDR sequences of a clone set out in Table 8 below. The epitope may be within residues 147 to 157 of SEQ ID NO: 1.

TABLE 8

| Clone | VH | | | VL | | | |
|---|---|---|---|---|---|---|---|
| name | CDR1 | CDR2 | CDR3 | CDR1 | CDR2 | CDR3 | Epitope |
| 3aA6 | SNAVG (SEQ ID NO: 17) | LIDIDGDTAYNPALES (SEQ ID NO: 201) | HYDKWGYADSIDY (SEQ ID NO: 203) | SGSSSNVGYGDYVG (SEQ ID NO: 138) | DATTRAS (SEQ ID NO: 207) | ASYQNERSGV (SEQ ID NO: 209) | 147-157 |
| 3aD6 | SNAVI (SEQ ID NO: 198) | LIDVDGDAAYDPALKS (SEQ ID NO: 200) | DYGSWGYVSDIDY (SEQ ID NO: 202) | SGSD---IGGADVG (SEQ ID NO: 204) | DNDNRPS (SEQ ID NO: 206) | GTYSGANYGI (SEQ ID NO: 208) | 147-157 |

(i) at least 85% identity thereto, and/or
(ii) one, two, or three amino acid substitutions relative thereto,
wherein the specific binding molecule binds to a polypeptide or protein molecule comprising an amino acid sequence comprising residues 147 to 157 of SEQ ID NO: 1. The specific binding molecule comprising CDRs having 100% identity to those given above is referred to as "3aD6" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises a VHCDR1 amino acid sequence set forth in table 8;

VHCDR2 comprises a VHCDR2 amino acid sequence set forth in table 8;

VHCDR3 comprises a VHCDR3 amino acid sequence set forth in table 8;

VLCDR1 comprises a VLCDR1 amino acid sequence set forth in table 8;

VLCDR2 comprises a VLCDR2 amino acid sequence set forth in table 8; and

VLCDR3 comprises a VLCDR3 amino acid sequence set forth in table 8;

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 147 to 157 of SEQ ID NO: 1.

The specific binding molecule may bind to a polypeptide or protein molecule comprising an amino acid sequence comprising residues 147 to 157 of SEQ ID NO: 1 with a Ko of less than around 50 nM. The Ko may be less than around 40 nM, less than around 30 nM, or less than around 20 nM. The $K_D$ may preferably be for binding to SEQ ID NO: 1 or to SEQ ID NO: 191. The $K_D$ for binding to SEQ ID NO: 1 may be around 10 nM to around 20 nM. The Ku for binding to SEQ ID NO: 1 may be around 16.5 nM, optionally wherein the specific binding molecule comprises the CDRs of 3aD6.

The specific binding molecule may comprise an amino acid sequence having at least 70%, at least 75%, at least 80%, at least 90%, at least 95% or at least 99% identity to SEQ ID NO: 418 wherein the specific binding molecule binds to a polypeptide or protein molecule comprising an amino acid sequence comprising residues 147 to 157 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 418. The CDRs may be 100% identical to the CDRs of SEQ ID NO: 418. The specific binding molecule may comprise an amino acid sequence having at least 70%, at least 75%, at least 80%, at least 90%, at least 95% or at least 99% identity to SEQ ID NO: 418 wherein CDRs are 100% identical to the CDRs of SEQ ID NO: 418. The specific binding molecule may comprise the amino acid sequence of SEQ ID NO: 418.

(3aA6 amino acid sequence)

SEQ ID NO: 418

QVRLQESGSSLVKPSQTLSLVCTVSGFPLTSNAVGWWVRQAPGKAPEWL

GLIDIDGDTAYNPALESRLSITRDTSKSQVSLSLSSVAIEDTAVYYCAR

HYDKWGYADSIDYWGPGLLVTVSSEGKSSGASGESKVDDQALLTQPSSV

FGSLGQRVSITCSGSSSNVGYGDYVGWYQQVPGSAPKLLIYDATTRASG

VPDRFSGSRSGNTATLTISSLQAEDEADYYCASYQNERSGVFGSGTRLT

VLG

The specific binding molecule may comprise an amino acid sequence having at least 70%, at least 75%, at least 80%, at least 90%, at least 95% or at least 99% identity to SEQ ID NO: 419 wherein the specific binding molecule binds to a polypeptide or protein molecule comprising an amino acid sequence comprising residues 147 to 157 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 419. The CDRs may be 100% identical to the CDRs of SEQ ID NO: 419. The specific binding molecule may comprise an amino acid sequence having at least 70%, at least 75%, at least 80%, at least 90%, at least 95% or at least 99% identity to SEQ ID NO: 419 wherein CDRs are 100% identical to the CDRs of SEQ ID NO: 419. The specific binding molecule may comprise the amino acid sequence of SEQ ID NO: 419.

(3aD6 amino acid sequence)

SEQ ID NO: 419

QVQLQESGPSLVKPSQTLSLTCTVSGFSLTSNAVIWVRQAPGKAPEWVA

LIDVDGDAAYDPALKSRLSITRDTSKSQVSLSLRSVTTEDTAVYYCARD

YGSWGYVSDIDYWGPGLLVTVSSEGKSSGASGESKVDDQAVLTQPSSVS

GSLGQRVSITCSGSDIGGADVGWFQQVPGSGLRTLIYDNDNRPSGVPDR

FSGSKSGNTATLTISSLQPEDEADYFCGTYSGANYGIFGSGTRLTVLG

The epitope of the specific binding molecule may be within an amino acid sequence comprising residues 379 to 391 of SEQ ID NO: 1. Accordingly, the epitope may be within the amino acid sequence of SEQ ID NO: 221 (RENAKAKTDHGAE).

The epitope may comprise the amino acid sequence of SEQ ID NO: 221 (RENAKAKTDHGAE). The epitope may comprise an amino acid sequence having at least 70%, at least 75%, at least 80%, at least 90%, at least 95% or at least 99% identity to SEQ ID NO: 221 (RENAKAKTDHGAE). The epitope may be within an amino acid sequence comprising residues 379 to 391 of SEQ ID NO: 1. This epitope may be bound by the CDRs of the specific binding molecule referred to as "E2E8" herein. Critical residues of the epitope may be residue 391 (E) (numbering according to SEQ ID NO: 1). The epitope may comprise the amino acid sequence of SEQ ID NO: 222 (XXXXXXXXXXXXE, wherein X is any amino acid). The epitope may comprise the amino acid sequence of SEQ ID NO: 8, wherein any one or more residue other than residue number 391 (E) is replaced by a non-conservative amino acid substitution (numbering according to SEQ ID NO: 1). The epitope may comprise the amino acid sequence of SEQ ID NO: 221, wherein any one or more residue other than residue number 391 (E) is replaced by a conservative amino acid substitution (numbering according to SEQ ID NO: 1). The epitope may comprise the amino acid sequence of SEQ ID NO: 221, wherein any one or more residue other than residue number 391 (E) is replaced by a conservative amino acid substitution (numbering according to SEQ ID NO: 1) and any one or more residue other than residue number 391 (E) is replaced by a non-conservative amino acid substitution (numbering according to SEQ ID NO: 1).

The epitope may comprise the amino acid sequence of SEQ ID NO: 221 (RENAKAKTDHGAE). The epitope may comprise an amino acid sequence having at least 70%, at least 75%, at least 80%, at least 90%, at least 95% or at least 99% identity to SEQ ID NO: 221 (RENAKAKTDHGAE).

The epitope may consist of the amino acid sequence of SEQ ID NO: 221 (RENAKAKTDHGAE). The epitope may consist of an amino acid sequence having at least 70%, at least 75%, at least 80%, at least 90%, at least 95% or at least 99% identity to SEQ ID NO: 221 (RENAKAKTDHGAE).

The specific binding molecule may bind to a polypeptide or protein molecule comprising an amino acid sequence comprising residues 379 to 391 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 223 (D/S R/W G V A);

VHCDR2 comprises the sequence set forth in SEQ ID NO: 224 (T M R S G G T/G I/T D/E Y/D N P A L K S);

VHCDR3 comprises the sequence set forth SEQ ID NO: 225 (G Y L S G D/I/V R/H Y A); VLCDR1 comprises the sequence set forth in SEQ ID NO: 226 (S G S R/S S D/N I/V G Y/D/A G N/D/R Y V S/G);

VLCDR2 comprises the sequence set forth in SEQ ID NO: 227 (D/S/G T/A N/R/T T/N/S R A S); and VLCDR3 comprises the sequence set forth in SEQ ID NO: 228 (A N/S I D S/T S/G R/N S/N H/L L/I);

or for each CDR sequence, an amino acid sequence with
(i) at least 85% identity thereto, and/or
(ii) one, two, or three amino acid substitutions relative thereto.

Said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 229 (DRGVA). SEQ ID NO: 230 (DWGVA), or SEQ ID NO: 231 (SWGVA);

VHCDR2 comprises the sequence set forth in SEQ ID NO: 232 (TMRSGGTIDYNPALKS). SEQ ID NO: 233 (TMRSGGGTEYNPALKS), or SEQ ID NO: 234 (TMRSGGTTDDNPALKS);

VHCDR3 comprises the sequence set forth in SEQ ID NO: 235 (GYLSGDRYA), SEQ ID NO: 236 (GYLSGIHYA), or SEQ ID NO: 237 (GYLSGVHYA);

VLCDR1 comprises the sequence set forth in SEQ ID NO: 238 (SGSRSDIGYGNYVS), SEQ ID NO: 239 (SGSSSNVGAGNYVG), SEQ ID NO: 240 (SGSSSNVGDGDYVG), or SEQ ID NO: 241 (SGSSSNVGDGRYVS);

VLCDR2 comprises the sequence set forth in SEQ ID NO: 242 (DTNTRAS), SEQ ID NO: 243 (DTTSRAS), SEQ ID NO: 170 (GATNRAS), or SEQ ID NO: 244 (SARNRAS); and VLCDR3 comprises the sequence set forth in SEQ ID NO: 245 (ANIDSSRSHL), SEQ ID NO: 246 (ASIDSGNNLL), or SEQ ID NO: 247 (ASIDTSR-SHI);

or for each CDR sequence, an amino acid sequence with
(i) at least 85% identity thereto, and/or
(ii) one, two, or three amino acid substitutions relative thereto,
wherein the specific binding molecule binds to a poly-peptide or protein molecule comprising an amino acid sequence comprising residues 379 to 391 of SEQ ID NO: 1.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 229 (DRGVA);

VHCDR2 comprises the sequence set forth in SEQ ID NO: 232 (TMRSGGTIDYNPALKS);

VHCDR3 comprises the sequence set forth in SEQ ID NO: 235 (GYLSGDRYA);

VLCDR1 comprises the sequence set forth in SEQ ID NO: 238 (SGSRSDIGYGNYVS);

VLCDR2 comprises the sequence set forth in SEQ ID NO: 242 (DTNTRAS); and

VLCDR3 comprises the sequence set forth in SEQ ID NO: 245 (ANIDSSRSHL);

or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 379 to 391 of SEQ ID NO: 1. The specific binding molecule comprising CDRs having 100% identity to those given above is referred to as "E2E8" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 229 (DRGVA);

VHCDR2 comprises the sequence set forth in SEQ ID NO: 232 (TMRSGGTIDYNPALKS);

VHCDR3 comprises the sequence set forth in SEQ ID NO: 235 (GYLSGDRYA);

VLCDR1 comprises the sequence set forth in SEQ ID NO: 238 (SGSRSDIGYGNYVS);

VLCDR2 comprises the sequence set forth in SEQ ID NO: 242 (DTNTRAS); and

VLCDR3 comprises the sequence set forth in SEQ ID NO: 245 (ANIDSSRSHL).

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 483 (QVQLQESGPSLVKPSQTLSLTCTVSGFSLT);

VHFR2 comprises the sequence set forth in SEQ ID NO: 484 (WRQAPGKALEWVG);

VHFR3 comprises the sequence set forth in SEQ ID NO: 485 (RLSITRDTSKSQVFLSLSSVTTEDMAMYY-CAR);

VHFR4 comprises the sequence set forth in SEQ ID NO: 486 (WGRGLLVTVSS);

VLFR1 comprises the sequence set forth in SEQ ID NO: 487 (QAVLTQPSSVSKSLGQSVSIAC);

VLFR2 comprises the sequence set forth in SEQ ID NO: 488 (WFQQIPGSAPKLLIY);

VLFR3 comprises the sequence set forth in SEQ ID NO: 489 (GVPDRFSGARSGNTATLTINSLQAEDEAD-YYC);

VLFR4 comprises the sequence set forth in SEQ ID NO: 490 (FGSGTRLTVLG);

or for each FR sequence, an amino acid sequence with
(i) at least 50% identity thereto, and/or
(ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 483 (QVQLQESGPSLVKPSQTLSLTCTVSGFSLT);

VHFR2 comprises the sequence set forth in SEQ ID NO: 484 (WRQAPGKALEWVG);

VHFR3 comprises the sequence set forth in SEQ ID NO: 485 (RLSITRDTSKSQVFLSLSSVTTEDMAMYY-CAR);

VHFR4 comprises the sequence set forth in SEQ ID NO: 486 (WGRGLLVTVSS);

VLFR1 comprises the sequence set forth in SEQ ID NO: 487 (QAVLTQPSSVSKSLGQSVSIAC);

VLFR2 comprises the sequence set forth in SEQ ID NO: 488 (WFQQIPGSAPKLLIY);

VLFR3 comprises the sequence set forth in SEQ ID NO: 489 (GVPDRFSGARSGNTATLTINSLQAEDEAD-YYC);

VLFR4 comprises the sequence set forth in SEQ ID NO: 490 (FGSGTRLTVLG);

or for each FR sequence, an amino acid sequence with
   (i) at least 50% identity thereto, and/or
   (ii) one, two, three, four or five amino acid substitutions relative thereto, wherein the specific binding molecule binds to a polypeptide or protein molecule comprising an amino acid sequence comprising residues 379 to 391 of SEQ ID NO: 1. A specific binding molecule comprising FRs having 100% identity to those given above is referred to as "E2E8" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 483 (QVQLQESGPSLVKP-SQTLSLTCTVSGFSLT);

VHFR2 comprises the sequence set forth in SEQ ID NO: 484 (WVRQAPGKALEWVG);

VHFR3 comprises the sequence set forth in SEQ ID NO: 485 (RLSITRDTSKSQVFLSLSSVTTED-MAMYYCAR);

VHFR4 comprises the sequence set forth in SEQ ID NO: 486 (WGRGLLVTVSS);

VLFR1 comprises the sequence set forth in SEQ ID NO: 487 (QAVLTQPSSVSKSLGQSVSIAC);

VLFR2 comprises the sequence set forth in SEQ ID NO: 488 (WFQQIPGSAPKLLIY);

VLFR3 comprises the sequence set forth in SEQ ID NO: 489 (GVPDRFSGARSGNTATLTINSLQAE-DEADYYC);

VLFR4 comprises the sequence set forth in SEQ ID NO: 490 (FGSGTRLTVLG);

or for each FR sequence, an amino acid sequence with
      (i) at least 50% identity thereto, and/or
      (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 229 (DRGVA);

VHCDR2 comprises the sequence set forth in SEQ ID NO: 232 (TMRSGGTIDYNPALKS);

VHCDR3 comprises the sequence set forth in SEQ ID NO: 235 (GYLSGDRYA);

VLCDR1 comprises the sequence set forth in SEQ ID NO: 238 (SGSRSDIGYGNYVS);

VLCDR2 comprises the sequence set forth in SEQ ID NO: 242 (DTNTRAS); and

VLCDR3 comprises the sequence set forth in SEQ ID NO: 245 (ANIDSSRSHL);

or for each CDR sequence, an amino acid sequence with
      (i) at least 85% identity thereto, and/or
      (ii) one, two, or three amino acid substitutions relative thereto wherein the specific binding molecule binds to a polypeptide or protein molecule comprising an amino acid sequence comprising residues 379 to 391 of SEQ ID NO: 1. The specific binding molecule comprising FRs and CDRs having 100% identity to those given above is referred to as "E2E8" herein.

The specific binding molecule may comprise:

(a) framework regions (FRs) VHFR1, VHFR2. VHFR3, VHFR4, VLFR1, VLFR2, VLFR3 and VLFR4, wherein each of said FRs comprises an amino acid sequence as follows:

VHFR1 comprises the sequence set forth in SEQ ID NO: 483 (QVQLQESGPSLVKP-SQTLSLTCTVSGFSLT);

VHFR2 comprises the sequence set forth in SEQ ID NO: 484 (WRQAPGKALEWVG);

VHFR3 comprises the sequence set forth in SEQ ID NO: 485 (RLSITRDTSKSQVFLSLSSVTTED-MAMYYCAR);

VHFR4 comprises the sequence set forth in SEQ ID NO: 486 (WGRGLLVTVSS);

VLFR1 comprises the sequence set forth in SEQ ID NO: 487 (QAVLTQPSSVSKSLGQSVSIAC);

VLFR2 comprises the sequence set forth in SEQ ID NO: 488 (WFQQIPGSAPKLLIY);

VLFR3 comprises the sequence set forth in SEQ ID NO: 489 (GVPDRFSGARSGNTATLTINSLQAE-DEADYYC);

VLFR4 comprises the sequence set forth in SEQ ID NO: 490 (FGSGTRLTVLG);

or for each FR sequence, an amino acid sequence with
      (i) at least 50% identity thereto, and/or
      (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 229 (DRGVA);

VHCDR2 comprises the sequence set forth in SEQ ID NO: 232 (TMRSGGTIDYNPALKS);

VHCDR3 comprises the sequence set forth in SEQ ID NO: 235 (GYLSGDRYA);

VLCDR1 comprises the sequence set forth in SEQ ID NO: 238 (SGSRSDIGYGNYVS);

VLCDR2 comprises the sequence set forth in SEQ ID NO: 242 (DTNTRAS); and

VLCDR3 comprises the sequence set forth in SEQ ID NO: 245 (ANIDSSRSHL);

wherein the specific binding molecule binds to a polypeptide or protein molecule comprising an amino acid sequence comprising residues 379 to 391 of SEQ ID NO: 1. The specific binding molecule comprising FRs and CDRs having 100% identity to those given above is referred to as "E2E8" herein.

The specific binding molecule may comprise:

```
(a) A VH domain comprising the sequence set forth
in SEQ ID NO: 491
(QVQLQESGPSLVKPSQTLSLTCTVSGFSLTDRGVAWRQAPGKALEWVG
TMRSGGTIDYNPALKSRLSITRDTSKSQVFLSLSSVTTEDMAMYYCARG
YLSGDRYAWGRGLLVTVSS);
and/or (b) a VL domain comprising the sequence set forth
in SEQ ID NO: 492
(QAVLTQPSSVSKSLGQSVSIACSGSRSDIGYGNYVSWFQQIPGSAPKL
LIYDTNTRASGVPDRFSGARSGNTATLTINSLQAEDEADYYCANIDSSR
SHLFGSGTRLTVLG);
``` or a humanized variant thereof.

The specific binding molecule may comprise:

```
(a) A heavy chain comprising the sequence set
forth in SEQ ID NO: 493
(QVQLQESGPSLVKPSQTLSLTCTVSGFSLTDRGVAWRQAPGKALEWVG

TMRSGGTIDYNPALKSRLSITRDTSKSQVFLSLSSVTTEDMAMYYCARG

YLSGDRYAWGRGLLVTVSSAKTTAPSVYPLAPVCGDTTGSSVTLGCLVK

GYFPEPVTLTWNSGSLSSGVHTFPAVLQSDLYTLSSSVTVTSSTWPSQS

ITCNVAHPASSTKVDKKIEPRGPTIKPCPPCKCPAPNLLGGPSVFIFPP

KIKDVLMISLSPIVTCVVVDVSEDDPDVQISWFVNNVEVHTAQTQTHRE

DYNSTLRVVSALPIQHQDWMSGKEFKCKVNNKDLPAPIERTISKPKGSV

RAPQVYVLPPPEEEMTKKQVTLTCMVTDFMPEDIYVEWTNNGKTELNYK

NTEPVLDSDGSYFMYSKLRVEKKNWVERNSYSCSVVHEGLHNHHTTKSF

SRTPGK);
and/or (b) a light chain comprising the sequence set
forth in SEQ ID NO: 494
(QAVLTQPSSVSKSLGQSVSIACSGSRSDIGYGNYVSWFQQIPGSAPKL

LIYDTNTRASGVPDRFSGARSGNTATLTINSLQAEDEADYYCANIDSSR

SHLFGSGTRLTVLGGQPKSSPSVTLFPPSSEELETNKATLVCTITDFYP

GVVTVDWKVDGTPVTQGMETTQPSKQSNNKYMASSYLTLTARAWERHSS

YSCQVTHEGHTVEKSLSRADCS);
``` or a humanized variant thereof.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 230 (DWGVA);

VHCDR2 comprises the sequence set forth in SEQ ID NO: 234 (TMRSGGTTDDNPALKS);

VHCDR3 comprises the sequence set forth in SEQ ID NO: 237 (GYLSGVHYA);

VLCDR1 comprises the sequence set forth in SEQ ID NO: 241 (SGSSSNVGDGRYVS);

VLCDR2 comprises the sequence set forth in SEQ ID NO: 243 (DTTSRAS); and

VLCDR3 comprises the sequence set forth in SEQ ID NO: 246 (ASIDSGNNLL);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 379 to 391 of SEQ ID NO: 1. The specific binding molecule comprising CDRs having 100% identity to those given above is referred to as "E1E8" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 230 (DWGVA);

VHCDR2 comprises the sequence set forth in SEQ ID NO: 234 (TMRSGGTTDDNPALKS);

VHCDR3 comprises the sequence set forth in SEQ ID NO: 237 (GYLSGVHYA);

VLCDR1 comprises the sequence set forth in SEQ ID NO: 241 (SGSSSNVGDGRYVS);

VLCDR2 comprises the sequence set forth in SEQ ID NO: 243 (DTTSRAS); and

VLCDR3 comprises the sequence set forth in SEQ ID NO: 246 (ASIDSGNNLL).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 230 (DWGVA);

VHCDR2 comprises the sequence set forth in SEQ ID NO: 234 (TMRSGGTTDDNPALKS);

VHCDR3 comprises the sequence set forth in SEQ ID NO: 237 (GYLSGVHYA);

VLCDR1 comprises the sequence set forth in SEQ ID NO: 239 (SGSSSNVGAGNYVG);

VLCDR2 comprises the sequence set forth in SEQ ID NO: 70 (GATNRAS); and

VLCDR3 comprises the sequence set forth in SEQ ID NO: 247 (ASIDTSRSHI);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 379 to 391 of SEQ ID NO: 1. The specific binding molecule comprising CDRs having 100% identity to those given above is referred to as "E2A6" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 230 (DWGVA);

VHCDR2 comprises the sequence set forth in SEQ ID NO: 234 (TMRSGGTTDDNPALKS);

VHCDR3 comprises the sequence set forth in SEQ ID NO: 237 (GYLSGVHYA);

VLCDR1 comprises the sequence set forth in SEQ ID NO: 239 (SGSSSNVGAGNYVG);

VLCDR2 comprises the sequence set forth in SEQ ID NO: 70 (GATNRAS); and

VLCDR3 comprises the sequence set forth in SEQ ID NO: 247 (ASIDTSRSHI).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 231 (SWGVA);

VHCDR2 comprises the sequence set forth in SEQ ID NO: 233 (TMRSGGGTEYNPALKS);

VHCDR3 comprises the sequence set forth in SEQ ID NO: 236 (GYLSGIHYA);

VLCDR1 comprises the sequence set forth in SEQ ID NO: 240 (SGSSSNVGDGDYVG);

VLCDR2 comprises the sequence set forth in SEQ ID NO: 244 (SARNRAS); and

VLCDR3 comprises the sequence set forth in SEQ ID NO: 247 (ASIDTSRSHI);

or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 379 to 391 of SEQ ID NO: 1. The specific binding molecule comprising CDRs having 100% identity to those given above is referred to as "E2B7" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 231 (SWGVA);

VHCDR2 comprises the sequence set forth in SEQ ID NO: 233 (TMRSGGGTEYNPALKS);

VHCDR3 comprises the sequence set forth in SEQ ID NO: 236 (GYLSGIHYA);

VLCDR1 comprises the sequence set forth in SEQ ID NO: 240 (SGSSSNVGDGDYVG);

VLCDR2 comprises the sequence set forth in SEQ ID NO: 244 (SARNRAS); and

VLCDR3 comprises the sequence set forth in SEQ ID NO: 247 (ASIDTSRSHI).

The specific binding molecule may comprise the CDR sequences of a clone set out in Table 9 below. The epitope may be within residues 379 to 391 of SEQ ID NO: 1.

VHCDR2 comprises a VHCDR2 amino acid sequence set forth in table 9;

VHCDR3 comprises a VHCDR3 amino acid sequence set forth in table 9;

VLCDR1 comprises a VLCDR1 amino acid sequence set forth in table 9;

VLCDR2 comprises a VLCDR2 amino acid sequence set forth in table 9; and

VLCDR3 comprises a VLCDR3 amino acid sequence set forth in table 9;

or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 379 to 391 of SEQ ID NO: 1.

The specific binding molecule may bind to a polypeptide or protein molecule comprising an amino acid sequence comprising residues 379 to 391 of SEQ ID NO: 1 with a $K_D$ of less than around 25 nM. The Ko may be less than around 20 nM, less than around 15 nM, or less than around 10 nM. The Ko may preferably be for binding to SEQ ID NO: 4. The specific binding molecule may have no detectable binding to SEQ ID NO: 1. The Ko for binding to SEQ ID NO: 4 may be around 300 pM to around 10 nM. The $K_D$ for binding to SEQ ID NO: 4 may be around 300 PM to around 500 pM. The $K_D$ for binding to SEQ ID NO: 4 may be around 1 nM to around 10 nM. The $K_D$ for binding to SEQ ID NO: 4 may be around 401 PM, optionally wherein the specific binding molecule comprises the CDRs of E1E8. The $K_D$ for binding to SEQ ID NO: 4 may be around 6.3 nM, optionally wherein the specific binding molecule comprises the CDRs of E1E8.

The specific binding molecule may comprise an amino acid sequence having at least 70%, at least 75%, at least 80%, at least 90%, at least 95% or at least 99% identity to SEQ ID NO: 248 wherein the specific binding molecule binds to a polypeptide or protein molecule comprising an amino acid sequence comprising residues 379 to 391 of SEQ ID NO: 1. The CDRs of the specific binding molecule may

TABLE 9

| Clone | VH | | | VL | | | |
|---|---|---|---|---|---|---|---|
| name | CDR1 | CDR2 | CDR3 | CDR1 | CDR2 | CDR3 | Epitope |
| E1E8 | DWGVA (SEQ ID NO: 230) | TMRSGGTTDDNPALKS (SEQ ID NO: 234) | GYLSGVHYA (SEQ ID NO: 237) | SGSSSNVGDGRYVS (SEQ ID NO: 241) | DTTSRAS (SEQ ID NO: 243) | ASIDSGNNLL (SEQ ID NO: 246) | 391'E' |
| E2A6 | DWGVA (SEQ NO: 230) | TMRSGGTTDDNPALKS (SEQ ID NO: 234) | GYLSGVHYA (SEQ ID NO: 237) | SGSSSNVGAGNYVG (SEQ ID NO: 239) | GATNRAS (SEQ ID NO: 70) | ASIDTSRSHI (SEQ ID NO: 247) | 391'E' |
| E2B7 | SWGVA (SEQ ID NO: 231) | TMRSGGGTEYNPALKS (SEQ ID NO: 233) | GYLSGIHYA (SEQ ID NO: 236) | SGSSSNVGDGDYVG (SEQ ID NO: 240) | SARNRAS (SEQ ID NO: 244) | ASIDTSRSHI (SEQ ID NO: 247) | 391'E' |
| E2E8 | DRGVA (SEQ ID NO: 229) | TMRSGGTIDYNPALKS (SEQ ID NO: 232) | GYLSGDRYA (SEQ ID NO: 235) | SGSRSDIGYGNYVS (SEQ ID NO: 238) | DTNTRAS (SEQ ID NO: 242) | ANIDSSRSHL (SEQ ID NO: 245) | 391'E' |

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises a VHCDR1 amino acid sequence set forth in table 9;

be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 248. The CDRs may be 100% identical to the CDRs of SEQ ID NO: 248. The specific binding molecule may comprise an amino acid sequence having at least 70%, at least 75%, at least 80%, at least 90%, at least 95% or at least 99% identity to SEQ ID NO: 248 wherein CDRs are 100% identical to the CDRs of SEQ ID NO: 248. The specific binding molecule may comprise the amino acid sequence of SEQ ID NO: 248.

(E2E8 amino acid sequence)

SEQ ID NO: 248

```
QVQLQESGPSLVKPSQTLSLTCTVSGFSLTDRGVAWVRQAPGKALEWVG

TMRSGGTIDYNPALKSRLSITRDTSKSQVFLSLSSVTTEDMAMYYCARG

YLSGDRYAWGRGLLVTVSSEGKSSGASGESKVDDQAVLTQPSSVSKSLG

QSVSIACSGSRSDIGYGNYVSWFQQIPGSAPKLLIYDTNTRASGVPDRF

SGARSGNTATLTINSLQAEDEADYYCANIDSSRSHLFGSGTRLTVLG
```

The specific binding molecule may comprise an amino acid sequence having at least 70%, at least 75%, at least 80%, at least 90%, at least 95% or at least 99% identity to SEQ ID NO: 250 wherein the specific binding molecule binds to a polypeptide or protein molecule comprising an amino acid sequence comprising residues 379 to 391 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 250. The CDRs may be 100% identical to the CDRs of SEQ ID NO: 250. The specific binding molecule may comprise an amino acid sequence having at least 70%, at least 75%, at least 80%, at least 90%, at least 95% or at least 99% identity to SEQ ID NO: 250 wherein CDRs are 100% identical to the CDRs of SEQ ID NO: 250. The specific binding molecule may comprise the amino acid sequence of SEQ ID NO: 250.

(E1E8 amino acid sequence)

SEQ ID NO: 250

```
QVQLQESGPSLVKPSQTLSLTCTVSGFSLTDWGVAWVRQAPGKALEWLG

TMRSGGTTDDNPALKSRLSITRDTSKSQVSLSLSSVTTEDMAMYYCARG

YLSGVHYAWGRGLLVTVSSEGKSSGASGESKVDDQAVLTQPSSVSGSLG

QSVSITCSGSSSNVGDGRYVSWFQQVPGSAPKLLIYDTTSRASGVPDRF

SGSRSGNTATLIITSLQAEDEADYYCASIDSGNNLLFGSGTRLTVLG
```

The specific binding molecule may comprise an amino acid sequence having at least 70%, at least 75%, at least 80%, at least 90%, at least 95% or at least 99% identity to SEQ ID NO: 252 wherein the specific binding molecule binds to a polypeptide or protein molecule comprising an amino acid sequence comprising residues 379 to 391 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 252. The CDRs may be 100% identical to the CDRs of SEQ ID NO: 252. The specific binding molecule may comprise an amino acid sequence having at least 70%, at least 75%, at least 80%, at least 90%, at least 95% or at least 99% identity to SEQ ID NO: 252 wherein CDRs are 100% identical to the CDRs of SEQ ID NO: 252. The specific binding molecule may comprise the amino acid sequence of SEQ ID NO: 252.

(E2A6 amino acid sequence)

SEQ ID NO: 252

```
QVQLQESGPSLVKPSQTLSLTCTVSGFSLTDWGVAWVRQAPGKALEWLG

TMRSGGTTDDNPALKSRLSITRDTSKSQVSLSLSSVTTEDMAMYYCARG

YLSGVHYAWGRGLLVTVSSEGKSSGASGESKVDDRWRTQPSSVSKSLGQ

SVSITCSGSSSNVGAGNYVGWFQQVPGSAPKLLIYGATNRASGVPARFS

GSKSGVTATLTITSLQAEDEADYYCASIDTSRSHIFGSGTRLTVLG
```

The specific binding molecule may comprise an amino acid sequence having at least 70%, at least 75%, at least 80%, at least 90%, at least 95% or at least 99% identity to SEQ ID NO: 254 wherein the specific binding molecule binds to a polypeptide or protein molecule comprising an amino acid sequence comprising residues 379 to 391 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 254. The CDRs may be 100% identical to the CDRs of SEQ ID NO: 254. The specific binding molecule may comprise an amino acid sequence having at least 70%, at least 75%, at least 80%, at least 90%, at least 95% or at least 99% identity to SEQ ID NO: 254 wherein CDRs are 100% identical to the CDRs of SEQ ID NO: 254. The specific binding molecule may comprise the amino acid sequence of SEQ ID NO: 254.

(E2B7 amino acid sequence)

SEQ ID NO: 254

```
QVQLQESGPSLVKPSQTLSLTCTVSGFSLTSWGVAWVRQAPGKALEWLG

TMRSGGGTEYNPALKSRLSITRDTSKSQVSLSLSSVTTEDMAMYYCARG

YLSGIHYAWGRGLLVSVSSEGKSSGASGESKVDDQAVLTQLSSVSGSLG

QRVSITCSGSSSNVGDGDYVGWFQQLPGSAPKLLIYSARNRASGVPDRF

SGSRSGNTATLTITSLQAEDEADYYCASIDTSRSHIFGSGTRLTVLG
```

The epitope of the specific binding molecule may be within an amino acid sequence comprising residues 113 to 238 of SEQ ID NO: 1. Accordingly, the epitope may be within the amino acid sequence of SEQ ID NO: 255 (SLEDEAAGHVTQARMVSKSKDGTGSDDKKAK-GADGKTKIATPRGAAPPGQKGQANATRIP AKTP-PAPKTPPSSGEPPKSGDRSGYSSPGSPGTPGSRSRTPS LPTPPTREPKKVAVVRTP PKSPSS).

The epitope may be within an amino acid sequence comprising residues 113 to 238 of SEQ ID NO: 1. This epitope may be bound by the CDRs of the specific binding molecule referred to as "CB11" herein The epitope may comprise the amino acid sequence of SEQ ID NO: 255 (SLEDEAAGHVTQARMVSK-SKDGTGSDDKKAKGADGKTKIATPR-GAAPPGQKGQANATRIP AKTP-PAPKTPPSSGEPPKSGDRSGYSSPGSPGTPGSRSRTPS LPTPPTREPKKVAVVRTP PKSPSS). The epitope may comprise an amino acid sequence having at least 70%, at least 75%, at least 80%, at least 90%, at least 95% or at least 99% identity to SEQ ID NO: 255 (SLEDEAAGHVTQARMVSKSKDGTGSDDKKAK-GADGKTKIATPRGAAPPGQKGQANATRIP AKTP-PAPKTPPSSGEPPKSGDRSGYSSPGSPGTPGSRSRTPS LPTPPTREPKKVAVVRTP PKSPSS).

The epitope may consist of the amino acid sequence of SEQ ID NO: 255 (SLEDEAAGHVTQARMVSK-SKDGTGSDDKKAKGADGKTKIATPR-GAAPPGQKGQANATRIP AKTP-PAPKTPPSSGEPPKSGDRSGYSSPGSPGTPGSRSRTPS LPTPPTREPKKVAVVRTP PKSPSS). The epitope may consist of an amino acid sequence having at least 70%, at least 75%, at least 80%, at least 90%, at least 95% or at least 99% identity to SEQ ID NO: 255 (SLEDEAAGHVTQARMVSKSKDGTGSDDKKAK-GADGKTKIATPRGAAPPGQKGQANATRIP AKTP-PAPKTPPSSGEPPKSGDRSGYSSPGSPGTPGSRSRTPS LPTPPTREPKKVAVVRTP PKSPSS).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 198 (SNAVI);

VHCDR2 comprises the sequence set forth in SEQ ID NO: 200 (LIDVDGDAAYDPALKS);

VHCDR3 comprises the sequence set forth in SEQ ID NO: 202 (DYGSWGYVSDIDY);

VLCDR1 comprises the sequence set forth in SEQ ID NO: 256 (SGSNIGSNDVG);

VLCDR2 comprises the sequence set forth in SEQ ID NO: 257 (DNNNRPS); and

VLCDR3 comprises the sequence set forth in SEQ ID NO: 258 (GGYAGSSSNFL);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 113 to 238 of SEQ ID NO: 1. The specific binding molecule comprising CDRs having 100% identity to those given above is referred to as "CB11" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 198 (SNAVI);

VHCDR2 comprises the sequence set forth in SEQ ID NO: 200 (LIDVDGDAAYDPALKS);

VHCDR3 comprises the sequence set forth in SEQ ID NO: 202 (DYGSWGYVSDIDY);

VLCDR1 comprises the sequence set forth in SEQ ID NO: 256 (SGSNIGSNDVG);

VLCDR2 comprises the sequence set forth in SEQ ID NO: 257 (DNNNRPS); and

VLCDR3 comprises the sequence set forth in SEQ ID NO: 258 (GGYAGSSSNFL).

The epitope of the specific binding molecule may be within an amino acid sequence comprising residues 1 to 155 of SEQ ID NO: 1. Accordingly, the epitope may be within the amino acid sequence of SEQ ID NO: 293 (MAE-PRQEFEVMEDHAGTYGLGDRKDQG-GYTMHQDQEGDTDAGLKESPLQTPTEDGSEEPGSE TSDAKSTPTAEDVTAPLVDEGAPGKQAAAQPHTEI-PEGTTAEEAGIGDTPSLEDEAAGHVTQARM VSK-SKDGTGSDDKKAKGADGKTKIATPR).

The epitope may be within an amino acid sequence comprising residues 1 to 155 of SEQ ID NO: 1. This epitope may be bound by the CDRs of the specific binding molecule referred to as "CA2" herein.

The epitope may comprise the amino acid sequence of SEQ ID NO: 293 (MAEPRQEFEVMED-HAGTYGLGDRKDQGGYTMHQDQEGDTDAGL-KESPLQTPTEDGSEEPGSE TSDAKSTPTAEDVTAPLV-DEGAPGKQAAAQPHTEIPEGTTAEEAGIGDTPSLEDE AAGHVTQARM VSKSKDGTGSDDKKAKGADGKTKI-ATPR). The epitope may comprise an amino acid sequence having at least 70%, at least 75%, at least 80%, at least 90%, at least 95% or at least 99% identity to SEQ ID NO: 293 (MAEPRQEFEVMEDHAGTYGLGDRKDQG-GYTMHQDQEGDTDAGLKESPLQTPTEDGSEEPGSE TSDAKSTPTAEDVTAPLVDEGAPGKQAAAQPHTEI-PEGTTAEEAGIGDTPSLEDEAAGHVTQARM VSK-SKDGTGSDDKKAKGADGKTKIATPR).

The epitope may consist of the amino acid sequence of SEQ ID NO: 293 (MAEPRQEFEVMED-HAGTYGLGDRKDQGGYTMHQDQEGDTDAGL-KESPLQTPTEDGSEEPGSE TSDAKSTPTAEDVTAPLV-DEGAPGKQAAAQPHTEIPEGTTAEEAGIGDTPSLEDE AAGHVTQARM VSKSKDGTGSDDKKAKGADGKTKI-ATPR). The epitope may consist of an amino acid sequence having at least 70%, at least 75%, at least 80%, at least 90%, at least 95% or at least 99% identity to SEQ ID NO: 293 (MAEPRQEFEVMEDHAGTYGLGDRKDQG-GYTMHQDQEGDTDAGLKESPLQTPTEDGSEEPGSE TSDAKSTPTAEDVTAPLVDEGAPGKQAAAQPHTEI-PEGTTAEEAGIGDTPSLEDEAAGHVTQARM VSK-SKDGTGSDDKKAKGADGKTKIATPR).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 157 (DISSVGKKYANPALKS);

VHCDR3 comprises the sequence set forth in SEQ ID NO: 161 (CRDGGVTYGYDIDY);

VLCDR1 comprises the sequence set forth in SEQ ID NO: 165 (SGSSGNVGYGDYVS);

VLCDR2 comprises the sequence set forth in SEQ ID NO: 169 (GATNLAS); and

VLCDR3 comprises the sequence set forth in SEQ ID NO: 173 (ASYDSSSGGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 1 to 155 of SEQ ID NO: 1. The specific binding molecule comprising CDRs having 100% identity to those given above is referred to as "CA2" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 157 (DISSVGKKYANPALKS);

VHCDR3 comprises the sequence set forth in SEQ ID NO: 161 (CRDGGVTYGYDIDY);

VLCDR1 comprises the sequence set forth in SEQ ID NO: 165 (SGSSGNVGYGDYVS);

VLCDR2 comprises the sequence set forth in SEQ ID NO: 169 (GATNLAS); and

VLCDR3 comprises the sequence set forth in SEQ ID NO: 173 (ASYDSSSGGV).

The epitope of the specific binding molecule may be within an amino acid sequence comprising residues 1 to 238 of SEQ ID NO: 1. Accordingly, the epitope may be within the amino acid sequence of SEQ ID NO: 260 (MAE-PRQEFEVMEDHAGTYGLGDRKDQG-GYTMHQDQEGDTDAGLKESPLQTPTEDGSEEPGSE TSDAKSTPTAEDVTAPLVDEGAPGKQAAAQPHTEI-PEGTTAEEAGIGDTPSLEDEAAGHVTQARM VSK-SKDGTGSDDKKAKGADGKTKIATPR-GAAPPGQKGQANATRIPAKTPPAPKTPPSSGEPPKSG DRSGYSSPGSPGTPGSRSRTPSLPTPPTREPKKVA-VVRTPPKSPSS).

The epitope may be within an amino acid sequence comprising residues 1 to 238 of SEQ ID NO: 1. This epitope may be bound by the CDRs of the specific binding molecule referred to as "CB6" herein.

The epitope may comprise the amino acid sequence of SEQ ID NO: 260 (MAEPRQEFEVMED-HAGTYGLGDRKDQGGYTMHQDQEGDTDAGL-KESPLQTPTEDGSEEPGSE TSDAKSTPTAEDVTAPLV-DEGAPGKQAAAQPHTEIPEGTTAEEAGIGDTPSLEDE AAGHVTQARM VSKSKDGTGSDDKKAKGADGKTKI-ATPRGAAPPGQKGQANATRIPAKTP-PAPKTPPSSGEPPKSG DRSGYSSPGSPGTPGSRSRTPSLPTPPTREPKK-VAWRTPPKSPSS). The epitope may comprise an amino acid sequence having at least 70%, at least 75%, at least 80%, at least 90%, at least 95% or at least 99% identity to SEQ ID NO: 260 (MAEPRQEFEVMED-HAGTYGLGDRKDQGGYTMHQDQEGDTDAGL-KESPLQTPTEDGSEEPGSE TSDAKSTPTAEDVTAPLV-DEGAPGKQAAAQPHTEIPEGTTAEEAGIGDTPSLED EAAGHVTQARM VSKSKDGTGSDDKKAKGADGKT-KIATPRGAAPPGQKGQANATRIPAKTP-PAPKTPPSSGEPPKSG DRSGYSSPGSPGTPGSRSRTPSLPTPPTREPKK-VAWRTPPKSPSS).

The epitope may consist of the amino acid sequence of SEQ ID NO: 260 (MAEPRQEFEVMED-HAGTYGLGDRKDQGGYTMHQDQEGDTDAGL-KESPLQTPTEDGSEEPGSE TSDAKSTPTAEDVTAPLV-DEGAPGKQAAAQPHTEIPEGTTAEEAGIGDTPSLEDE AAGHVTQARM VSKSKDGTGSDDKKAKGADGKTKI-ATPRGAAPPGQKGQANATRIPAKTP-PAPKTPPSSGEPPKSG DRSGYSSPGSPGTPGSRSRTPSLPTPPTREPKK-VAWRTPPKSPSS). The epitope may consist of an amino acid sequence having at least 70%, at least 75%, at least 80%, at least 90%, at least 95% or least 99% at identity to SEQ ID NO: 260 (MAEPRQEFEVMED-HAGTYGLGDRKDQGGYTMHQDQEGDTDAGL-KESPLQTPTEDGSEEPGSE TSDAKSTPTAEDVTAPLV-DEGAPGKQAAAQPHTEIPEGTTAEEAGIGDTPSLEDE AAGHVTQARM VSKSKDGTGSDDKKAKGADGKTKI-ATPRGAAPPGQKGQANATRIPAKTP-PAPKTPPSSGEPPKSG DRSGYSSPGSPGTPGSRSRTPSLPTPPTREPKK-VAWRTPPKSPSS).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 157 (DISSVGKKYANPALKS);

VHCDR3 comprises the sequence set forth in SEQ ID NO: 161 (CRDGGVTYGYDIDY);

VLCDR1 comprises the sequence set forth in SEQ ID NO: 261 (SGSSSNIGTGNYVG);

VLCDR2 comprises the sequence set forth in SEQ ID NO: 262 (GAVTRAS); and

VLCDR3 comprises the sequence set forth in SEQ ID NO: 263 (ASYDSTSGGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 1 to 238 of SEQ ID NO: 1. The specific binding molecule comprising CDRs having 100% identity to those given above is referred to as "CB6" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 157 (DISSVGKKYANPALKS);

VHCDR3 comprises the sequence set forth in SEQ ID NO: 161 (CRDGGVTYGYDIDY);

VLCDR1 comprises the sequence set forth in SEQ ID NO: 261 (SGSSSNIGTGNYVG);

VLCDR2 comprises the sequence set forth in SEQ ID NO: 262 (GAVTRAS); and

VLCDR3 comprises the sequence set forth in SEQ ID NO: 263 (ASYDSTSGGV).

The epitope of the specific binding molecule may be within an amino acid sequence comprising residues 1 to 319 of SEQ ID NO: 1. Accordingly, the epitope may be within the amino acid sequence of SEQ ID NO: 264 (MAE-PRQEFEVMEDHAGTYGLGDRKDQG-GYTMHQDQEGDTDAGLKESPLQTPTEDGSEEPGSE TSDAKSTPTAEDVTAPLVDEGAPGKQAAAQPHTEI-PEGTTAEEAGIGDTPSLEDEAAGHVTQARM VSK-SKDGTGSDDKKAKGADGKTKIATPR-GAAPPGQKGQANATRIPAKTPPAPKTPPSSGEPPKSG DRSGYSSPGSPGTPGSRSRTPSLPTPPTREPKK-VAWRTPPKSPSSAKSRLQTAPVPMPDLKNVK SKIG-STENLKHQPGGGKVQIINKKLDLSNVQSKCGSKD-NIKHVPGGGSVQIVYKPVDLSKVT).

The epitope may be within an amino acid sequence comprising residues 1 to 319 of SEQ ID NO: 1. This epitope may be bound by the CDRs of the specific binding molecules referred to as "CA7". "CA8", and "CB10" herein.

The epitope within an amino acid sequence comprising residues 1 to 319 of SEQ ID NO: 1 may preferably be within an amino acid sequence comprising residues 37 to 49 of SEQ ID NO: 1. This epitope may be bound by the CDRs of at least the specific binding molecule referred to as "CA7" herein.

The epitope may comprise the amino acid sequence of SEQ ID NO: 264 (MAEPRQEFEVMED-HAGTYGLGDRKDQGGYTMHQDQEGDTDAGL-KESPLQTPTEDGSEEPGSE TSDAKSTPTAEDVTAPLV-DEGAPGKQAAAQPHTEIPEGTTAEEAGIGDTPSLEDE AAGHVTQARM VSKSKDGTGSDDKKAKGADGKTKI-ATPRGAAPPGQKGQANATRIPAKTP-PAPKTPPSSGEPPKSG DRSGYSSPGSPGTPGSRSRTPSLPTPPTREPKKVA-VVRTPPKSPSSAKSRLQTAPVPMPDLKNVK SKIG-STENLKHQPGGGKVQIINKKLDLSNVQSKCGSKD-NIKHVPGGGSVQIVYKPVDLSKVT). The epitope may comprise an amino acid sequence having at least 70%, at least 75%, at least 80%, at least 90%, at NO: 264 least 95% or at least 99% identity to SEQ ID NO: 264 (MAEPRQEFE-VMEDHAGTYGLGDRKDQG-GYTMHQDQEGDTDAGLKESPLQTPTEDGSEEPGSE TSDAKSTPTAEDVTAPLVDEGAPGKQAAAQPHTEI-PEGTTAEEAGIGDTPSLEDEAAGHVTQARM VSK-SKDGTGSDDKKAKGADGKTKIATPR-GAAPPGQKGQANATRIPAKTPPAPKTPPSSGEPPKSG DRSGYSSPGSPGTPGSRSRTPSLPTPPTREPKKVA-VVRTPPKSPSSAKSRLQTAPVPMPDLKNVK SKIG-STENLKHQPGGGKVQIINKKLDLSNVQSKCGSKD-NIKHVPGGGSVQIVYKPVDLSKVT).

The epitope may consist of the amino acid sequence of SEQ ID NO: 264 (MAEPRQEFEVMED-HAGTYGLGDRKDQGGYTMHQDQEGDTDAGL-KESPLQTPTEDGSEEPGSE TSDAKSTPTAEDVTAPLV-DEGAPGKQAAAQPHTEIPEGTTAEEAGIGDTPSLEDE AAGHVTQARM VSKSKDGTGSDDKKAKGADGKTKI-ATPRGAAPPGQKGQANATRIPAKTP-PAPKTPPSSGEPPKSG DRSGYSSPGSPGTPGSRSRTPSLPTPPTREPKK-VAWVRTPPKSPSSAKSRLQTAPVPMPDLKNVK SKIG-STENLKHQPGGGKVQIINKKLDLSNVQSKCGSKD-NIKHV PGGGSVQIVYKPVDLSKVT). The epitope may consist of an amino acid sequence having at least 70%, at least 75%, at least 80%, at least 90%, at or 99% identity ID 264 least 95% at least to SEQ NO: 264 (MAEPRQEFE-VMEDHAGTYGLGDRKDQG-GYTMHQDQEGDTDAGLKESPLQTPTEDGSEEPGSE TSDAKSTPTAEDVTAPLVDEGAPGKQAAAQPHTEI-PEGTTAEEAGIGDTPSLEDEAAGHVTQARM VSK-SKDGTGSDDKKAKGADGKTKIATPR-GAAPPGQKGQANATRIPAKTPPAPKTPPSSGEPPKSG DRSGYSSPGSPGTPGSRSRTPSLPTPPTREPKKVA-VVRTPPKSPSSAKSRLQTAPVPMPDLKNVK SKIG-STENLKHQPGGGKVQIINKKLDLSNVQSKCGSKD-NIKHVPGGGSVQIVYKPVDLSKVT).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 44 (SYYVG);

VHCDR2 comprises the sequence set forth in SEQ ID NO: 52 (NIYSTGRAFYNPALKS);

VHCDR3 comprises the sequence set forth in SEQ ID NO: 265 (GSYYHGGGNGMVDFFDY);

VLCDR1 comprises the sequence set forth in SEQ ID NO: 39 (SGSSSNVGYGNYVG);

VLCDR2 comprises the sequence set forth in SEQ ID NO: 72 (AATSRAS); and

VLCDR3 comprises the sequence set forth in SEQ ID NO: 78 (SSYQRGNTGV);

or for each CDR sequence, an amino acid sequence with
  (i) at least 85% identity thereto, and/or
  (ii) one, two, or three amino acid substitutions relative thereto,
wherein the specific binding molecule binds to a polypeptide or protein molecule comprising an amino acid sequence comprising residues 1 to 319 of SEQ ID NO: 1. The specific binding molecule comprising CDRs having 100% identity to those given above is referred to as "CA7" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 44 (SYYVG);

VHCDR2 comprises the sequence set forth in SEQ ID NO: 52 (NIYSTGRAFYNPALKS);

VHCDR3 comprises the sequence set forth in SEQ ID NO: 265 (GSYYHGGGNGMVDFFDY);

VLCDR1 comprises the sequence set forth in SEQ ID NO: 39 (SGSSSNVGYGNYVG);

VLCDR2 comprises the sequence set forth in SEQ ID NO: 72 (AATSRAS); and

VLCDR3 comprises the sequence set forth in SEQ ID NO: 78 (SSYQRGNTGV).

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 495 (RVRLQGSGPSLVKPSQTLSLTCTVSGFSFD);

VHFR2 comprises the sequence set forth in SEQ ID NO: 496 (WRQAPGKALEWLG);

VHFR3 comprises the sequence set forth in SEQ ID NO: 497 (RLSITRDTSKSQVSLSVSSVTIED-TALYYCVR);

VHFR4 comprises the sequence set forth in SEQ ID NO: 498 (WSPGLLVTVSS);

VLFR1 comprises the sequence set forth in SEQ ID NO: 499 (QWVRTQPSSVSGSLGQRVSITC);

VLFR2 comprises the sequence set forth in SEQ ID NO: 500 (WFQQVPGSAPKLLIY);

VLFR3 comprises the sequence set forth in SEQ ID NO: 501 (GVPDRFSGSRSGNTATLTIDSLQAEDEAD-YYC);

VLFR4 comprises the sequence set forth in SEQ ID NO: 502 (FGSGTRLTVLG);

or for each FR sequence, an amino acid sequence with
  (i) at least 50% identity thereto, and/or
  (ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 495 (RVRLQGSGPSLVKPSQTLSLTCTVSGFSFD);

VHFR2 comprises the sequence set forth in SEQ ID NO: 496 (WVRQAPGKALEWLG);

VHFR3 comprises the sequence set forth in SEQ ID NO: 497 (RLSITRDTSKSQVSLSVSSVTIED-TALYYCVR);

VHFR4 comprises the sequence set forth in SEQ ID NO: 498 (WSPGLLVTVSS);

VLFR1 comprises the sequence set forth in SEQ ID NO: 499 (QVVRTQPSSVSGSLGQRVSITC);

VLFR2 comprises the sequence set forth in SEQ ID NO: 500 (WFQQVPGSAPKLLIY);

VLFR3 comprises the sequence set forth in SEQ ID NO: 501 (GVPDRFSGSRSGNTATLTIDSLQAEDEAD-YYC);

VLFR4 comprises the sequence set forth in SEQ ID NO: 502 (FGSGTRLTVLG);

or for each FR sequence, an amino acid sequence with
  (i) at least 50% identity thereto, and/or (ii) one, two, three, four or five amino acid substitutions relative thereto, wherein the specific binding molecule binds to a polypeptide or protein molecule comprising an amino acid sequence comprising residues 1 to 319 of SEQ ID NO: 1. A specific binding molecule comprising FRs having 100% identity to those given above is referred to as "CA7" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 495 (RVRLQGSGPSLVKP-SQTLSLTCTVSGFSFD);

VHFR2 comprises the sequence set forth in SEQ ID NO: 496 (WRQAPGKALEWLG);

VHFR3 comprises the sequence set forth in SEQ ID NO: 497 (RLSITRDTSKSQVSLSVSSVTIED-TALYYCVR);

VHFR4 comprises the sequence set forth in SEQ ID NO: 498 (WSPGLLVTVSS);

VLFR1 comprises the sequence set forth in SEQ ID NO: 499 (QVVRTQPSSVSGSLGQRVSITC);

VLFR2 comprises the sequence set forth in SEQ ID NO: 500 (WFQQVPGSAPKLLIY);

VLFR3 comprises the sequence set forth in SEQ ID NO: 501 (GVPDRFSGSRSGNTATLTIDSLQAE-DEADYYC);

VLFR4 comprises the sequence set forth in SEQ ID NO: 502 (FGSGTRLTVLG);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 44 (SYYVG);

VHCDR2 comprises the sequence set forth in SEQ ID NO: 52 (NIYSTGRAFYNPALKS);

VHCDR3 comprises the sequence set forth in SEQ ID NO: 265 (GSYYHGGGNGMVDFFDY);

VLCDR1 comprises the sequence set forth in SEQ ID NO: 39 (SGSSSNVGYGNYVG);

VLCDR2 comprises the sequence set forth in SEQ ID NO: 72 (AATSRAS); and

VLCDR3 comprises the sequence set forth in SEQ ID NO: 78 (SSYQRGNTGV).

or for each CDR sequence, an amino acid sequence with (i) at least 85% identity thereto, and/or (ii) one, two, or three amino acid substitutions relative thereto wherein the specific binding molecule binds to a polypeptide or protein molecule comprising an amino acid sequence comprising residues 1 to 319 of SEQ ID NO: 1. The specific binding molecule comprising FRs and CDRs having 100% identity to those given above is referred to as "CA7" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 495 (RVRLQGSGPSLVKP-SQTLSLTCTVSGFSFD);

VHFR2 comprises the sequence set forth in SEQ ID NO: 496 (WRQAPGKALEWLG);

VHFR3 comprises the sequence set forth in SEQ ID NO: 497 (RLSITRDTSKSQVSLSVSSVTIED-TALYYCVR);

VHFR4 comprises the sequence set forth in SEQ ID NO: 498 (WSPGLLVTVSS);

VLFR1 comprises the sequence set forth in SEQ ID NO: 499 (QVVRTQPSSVSGSLGQRVSITC);

VLFR2 comprises the sequence set forth in SEQ ID NO: 500 (WFQQVPGSAPKLLIY);

VLFR3 comprises the sequence set forth in SEQ ID NO: 501 (GVPDRFSGSRSGNTATLTIDSLQAE-DEADYYC);

VLFR4 comprises the sequence set forth in SEQ ID NO: 502 (FGSGTRLTVLG);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 44 (SYYVG);

VHCDR2 comprises the sequence set forth in SEQ ID NO: 52 (NIYSTGRAFYNPALKS);

VHCDR3 comprises the sequence set forth in SEQ ID NO: 265 (GSYYHGGGNGMVDFFDY);

VLCDR1 comprises the sequence set forth in SEQ ID NO: 39 (SGSSSNVGYGNYVG);

VLCDR2 comprises the sequence set forth in SEQ ID NO: 72 (AATSRAS); and

VLCDR3 comprises the sequence set forth in SEQ ID NO: 78 (SSYQRGNTGV), wherein the specific binding molecule binds to a polypeptide or protein molecule comprising an amino acid sequence comprising residues 1 to 319 of SEQ ID NO: 1. The specific binding molecule comprising FRs and CDRs having 100% identity to those given above is referred to as "CA7" herein.

The specific binding molecule may comprise:

```
(a) A VH domain comprising the sequence set forth
in SEQ ID NO: 503
(RVRLQGSGPSLVKPSQTLSLTCTVSGFSFDSYYVGWRQAPGKALEWLG
NIYSTGRAFYNPALKSRLSITRDTSKSQVSLSVSSVTIEDTALYYCVRG
SYYHGGGNGMVDFFDYWSPGLLVTVSS);
and/or
```

```
(b) a VL domain comprising the sequence set forth
in SEQ ID NO: 504
(QVVRTQPSSVSGSLGQRVSITCSGSSSNVGYGNYVGWFQQVPGSAPKL
LIYAATSRASGVPDRFSGSRSGNTATLTIDSLQAEDEADYYCSSYQRGN
TGVFGSGTRLTVLG);
``` or a humanized variant thereof.

The specific binding molecule may comprise:

```
(a) A heavy chain comprising the sequence set
forth in SEQ ID NO: 505
(RVRLQGSGPSLVKPSQTLSLTCTVSGFSFDSYYVGWRQAPGKALEWLG

NIYSTGRAFYNPALKSRLSITRDTSKSQVSLSVSSVTIEDTALYYCVRG

SYYHGGGNGMVDFFDYWSPGLLVTVSSAKTTAPSVYPLAPVCGDTTGSS
```

-continued

VTLGCLVKGYFPEPVTLTWNSGSLSSGVHTFPAVLQSDLYTLSSSVTVT

SSTWPSQSITCNVAHPASSTKVDKKIEPRGPTIKPCPPCKCPAPNLLGG

PSVFIFPPPKIKDVLMISLSPIVTCVVVDVSEDDPDVQISWFVNNVEVHT

AQTQTHREDYNSTLRVVSALPIQHQDWMSGKEFKCKVNNKDLPAPIERT

ISKPKGSVRAPQVYVLPPPEEEMTKKQVTLTCMVTDFMPEDIYVEWTNN

GKTELNYKNTEPVLDSDGSYFMYSKLRVEKKNWVERNSYSCSVVHEGLH

NHHTTKSFSRTPGK);
and/or (b) a light chain comprising the sequence set
forth in SEQ ID NO: 506
(QWVRTQPSSVSGSLGQRVSITCSGSSSNVGYGNYVGWFQQVPGSAPKL

LIYAATSRASGVPDRFSGSRSGNTATLTIDSLQAEDEADYYCSSYQRGN

TGVFGSGTRLTVLGGQPKSSPSVTLFPPSSEELETNKATLVCTITDFYP

GVVTVDWKVDGTPVTQGMETTQPSKQSNNKYMASSYLTLTARAWERHSS

YSCQVTHEGHTVEKSLSRADCS);

or a humanized variant thereof.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 266 (SNAVV);

VHCDR2 comprises the sequence set forth in SEQ ID NO: 267 (AIDKDGDTIYNPALKS);

VHCDR3 comprises the sequence set forth in SEQ ID NO: 268 (DPSGWGYPDVDY);

VLCDR1 comprises the sequence set forth in SEQ ID NO: 269 (SGTY/GSSDVG);

VLCDR2 comprises the sequence set forth in SEQ ID NO: 270 (GTSSRPS); and

VLCDR3 comprises the sequence set forth in SEQ ID NO: 271 (ATYESSYHNSV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 1 to 319 of SEQ ID NO: 1. The specific binding molecule comprising CDRs having 100% identity to those given above is referred to as "CA8" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 266 (SNAVV);

VHCDR2 comprises the sequence set forth in SEQ ID NO: 267 (AIDKDGDTIYNPALKS);

VHCDR3 comprises the sequence set forth in SEQ ID NO: 268 (DPSGWGYPDVDY);

VLCDR1 comprises the sequence set forth in SEQ ID NO: 269 (SGTY/GSSDVG);

VLCDR2 comprises the sequence set forth in SEQ ID NO: 270 (GTSSRPS); and

VLCDR3 comprises the sequence set forth in SEQ ID NO: 271 (ATYESSYHNSV).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 272 (SNTVA);

VHCDR2 comprises the sequence set forth in SEQ ID NO: 273 (EINSGGSTYYNPALKS);

VHCDR3 comprises the sequence set forth in SEQ ID NO: 274 (GARSTYAAY);

VLCDR1 comprises the sequence set forth in SEQ ID NO: 275 (SGSSSDVGYSTWVY);

VLCDR2 comprises the sequence set forth in SEQ ID NO: 276 (HISNRAS); and

VLCDR3 comprises the sequence set forth in SEQ ID NO: 277 (AAYDSSNNVWI);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 1 to 319 of SEQ ID NO: 1. The specific binding molecule comprising CDRs having 100% identity to those given above is referred to as "CB10" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 272 (SNTVA);

VHCDR2 comprises the sequence set forth in SEQ ID NO: 273 (EINSGGSTYYNPALKS);

VHCDR3 comprises the sequence set forth in SEQ ID NO: 274 (GARSTYAAY);

VLCDR1 comprises the sequence set forth in SEQ ID NO: 275 (SGSSSDVGYSTWVY);

VLCDR2 comprises the sequence set forth in SEQ ID NO: 276 (HISNRAS); and

VLCDR3 comprises the sequence set forth in SEQ ID NO: 277 (AAYDSSNNVWI).

The epitope of the specific binding molecule may be within an amino acid sequence comprising residues 13 to 25 of SEQ ID NO: 1. Accordingly, the epitope may be within the amino acid sequence of SEQ ID NO: 278 (DHAGTYGLGDRKD).

The epitope may be within an amino acid sequence comprising residues 13 to 25 of SEQ ID NO: 1. This epitope may be bound by the CDRs of the specific binding molecule referred to as "CB7" herein.

The epitope may comprise the amino acid sequence of SEQ ID NO: 278 (DHAGTYGLGDRKD). The epitope may comprise an amino acid sequence having at least 70%, at least 75%, at least 80%, at least 90%, at least 95% or at least 99% identity to SEQ ID NO: 278 (DHAGTYGLGDRKD).

The epitope may consist of the amino acid sequence of SEQ ID NO: 278 (DHAGTYGLGDRKD). The epitope may consist of an amino acid sequence having at least 70%, at least 75%, at least 80%, at least 90%, at least 95% or at least 99% identity to SEQ ID NO: 278 (DHAGTYGLGDRKD).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 279 (NYRVG);

VHCDR2 comprises the sequence set forth in SEQ ID NO: 280 (NIRSGGTTWYNPALKS);

VHCDR3 comprises the sequence set forth in SEQ ID NO: 281 (DSSGDLYAYDY);

VLCDR1 comprises the sequence set forth in SEQ ID NO: 282 (SGSSSNVGYGNYMA);

VLCDR2 comprises the sequence set forth in SEQ ID NO: 141 (GATSRAS); and

VLCDR3 comprises the sequence set forth in SEQ ID NO: 263 (ASYDSTSGGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 13 to 25 of SEQ ID NO: 1. The specific binding molecule comprising CDRs having 100% identity to those given above is referred to as "CB7" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 279 (NYRVG);

VHCDR2 comprises the sequence set forth in SEQ ID NO: 280 (NIRSGGTTWYNPALKS);

VHCDR3 comprises the sequence set forth in SEQ ID NO: 281 (DSSGDLYAYDY);

VLCDR1 comprises the sequence set forth in SEQ ID NO: 282 (SGSSSNVGYGNYMA);

VLCDR2 comprises the sequence set forth in SEQ ID NO: 141 (GATSRAS); and

VLCDR3 comprises the sequence set forth in SEQ ID NO: 263 (ASYDSTSGGV).

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 507 (QVQLQESGPSLVKPSQTLSLTCTVSGFSLT);

VHFR2 comprises the sequence set forth in SEQ ID NO: 508 (WRQAPGKALEWVS);

VHFR3 comprises the sequence set forth in SEQ ID NO: 509 (RLSITADTSKSQVSLSLSSVTTEDTAVYY-CAR);

VHFR4 comprises the sequence set forth in SEQ ID NO: 510 (WGPGLLVTVSS);

VLFR1 comprises the sequence set forth in SEQ ID NO: 511 (QAVLTQPSSVSRSLGQSVSMTC);

VLFR2 comprises the sequence set forth in SEQ ID NO: 512 (WFQQVPGSAPKLLIY);

VLFR3 comprises the sequence set forth in SEQ ID NO: 513 (GVPDRFSGSRSGNTATLTISSLQAEDEAD-YYC);

VLFR4 comprises the sequence set forth in SEQ ID NO:514 (FGSGTRLTVLG);

or for each FR sequence, an amino acid sequence with (i) at least 50% identity thereto, and/or (ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 507 (QVQLQESGPSLVKPSQTLSLTCTVSGFSLT);

VHFR2 comprises the sequence set forth in SEQ ID NO: 508 (WVRQAPGKALEWVS);

VHFR3 comprises the sequence set forth in SEQ ID NO: 509 (RLSITADTSKSQVSLSLSSVTTEDTAVYY-CAR);

VHFR4 comprises the sequence set forth in SEQ ID NO: 510 (WGPGLLVTVSS);

VLFR1 comprises the sequence set forth in SEQ ID NO: 511 (QAVLTQPSSVSRSLGQSVSMTC);

VLFR2 comprises the sequence set forth in SEQ ID NO: 512 (WFQQVPGSAPKLLIY);

VLFR3 comprises the sequence set forth in SEQ ID NO: 513 (GVPDRFSGSRSGNTATLTISSLQAEDEAD-YYC);

VLFR4 comprises the sequence set forth in SEQ ID NO: 514 (FGSGTRLTVLG);

or for each FR sequence, an amino acid sequence with (i) at least 50% identity thereto, and/or (ii) one, two, three, four or five amino acid substitutions relative thereto, wherein the specific binding molecule binds to a polypeptide or protein molecule comprising an amino acid sequence comprising residues 13 to 25 of SEQ ID NO: 1. A specific binding molecule comprising FRs having 100% identity to those given above is referred to as "CB7" herein.

The specific binding molecule may comprise:

(a) framework regions (FRs) VHFR1, VHFR2. VHFR3, VHFR4, VLFR1, VLFR2, VLFR3 and VLFR4, wherein each of said FRs comprises an amino acid sequence as follows:

VHFR1 comprises the sequence set forth in SEQ ID NO: 507 (QVQLQESGPSLVKP-SQTLSLTCTVSGFSLT);

VHFR2 comprises the sequence set forth in SEQ ID NO: 508 (WRQAPGKALEWVS);

VHFR3 comprises the sequence set forth in SEQ ID NO: 509 (RLSITADTSKSQVSLSLSSVTTED-TAVYYCAR);

VHFR4 comprises the sequence set forth in SEQ ID NO: 510 (WGPGLLVTVSS);

VLFR1 comprises the sequence set forth in SEQ ID NO: 511 (QAVLTQPSSVSRSLGQSVSMTC);

VLFR2 comprises the sequence set forth in SEQ ID NO: 512 (WFQQVPGSAPKLLIY);

VLFR3 comprises the sequence set forth in SEQ ID NO: 513 (GVPDRFSGSRSGNTATLTISSLQAE-DEADYYC);

VLFR4 comprises the sequence set forth in SEQ ID NO: 514 (FGSGTRLTVLG);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 279 (NYRVG);

VHCDR2 comprises the sequence set forth in SEQ ID NO: 280 (NIRSGGTTWYNPALKS);

VHCDR3 comprises the sequence set forth in SEQ ID NO: 281 (DSSGDLYAYDY);

VLCDR1 comprises the sequence set forth in SEQ ID NO: 282 (SGSSSNVGYGNYMA);

VLCDR2 comprises the sequence set forth in SEQ ID NO: 141 (GATSRAS); and

VLCDR3 comprises the sequence set forth in SEQ ID
NO: 263 (ASYDSTSGGV);

or for each CDR sequence, an amino acid sequence with
(i) at least 85% identity thereto, and/or
(ii) one, two, or three amino acid substitutions relative
thereto wherein the specific binding molecule binds to a poly-
peptide or protein molecule comprising an amino acid
sequence comprising residues 13 to 25 of SEQ ID NO:
1. The specific binding molecule comprising FRs and
CDRs having 100% identity to those given above is
referred to as "CB7" herein.

The specific binding molecule may comprise:

(a) framework regions (FRs) VHFR1, VHFR2, VHFR3,
VHFR4, VLFR1, VLFR2, VLFR3 and VLFR4,
wherein each of said FRs comprises an amino acid
sequence as follows:
VHFR1 comprises the sequence set forth in SEQ ID
NO: 507 (QVQLQESGPSLVKP-
SQTLSLTCTVSGFSLT);
VHFR2 comprises the sequence set forth in SEQ ID
NO: 508 (WVRQAPGKALEWVS);
VHFR3 comprises the sequence set forth in SEQ ID
NO: 509 (RLSITADTSKSQVSLSLSSVTTED-
TAVYYCAR);
VHFR4 comprises the sequence set forth in SEQ ID
NO: 510 (WGPGLLVTVSS);
VLFR1 comprises the sequence set forth in SEQ ID
NO: 511 (QAVLTQPSSVSRSLGQSVSMTC);
VLFR2 comprises the sequence set forth in SEQ ID
NO: 512 (WFQQVPGSAPKLLIY);
VLFR3 comprises the sequence set forth in SEQ ID
NO: 513 (GVPDRFSGSRSGNTATLTISSLQAE-
DEADYYC);
VLFR4 comprises the sequence set forth in SEQ ID
NO: 514 (FGSGTRLTVLG);
or for each FR sequence, an amino acid sequence with
(i) at least 50% identity thereto, and/or
(ii) one, two, three, four or five amino acid substi-
tutions relative thereto; and (b) the CDRs VHCDR1. VHCDR2, VHCDR3, VLCDR1,
VLCDR2 and VLCDR3, wherein each of said CDRs
comprises an amino acid sequence as follows:
VHCDR1 comprises the sequence set forth in SEQ ID
NO: 279 (NYRVG);
VHCDR2 comprises the sequence set forth in SEQ ID
NO: 280 (NIRSGGTTWYNPALKS);
VHCDR3 comprises the sequence set forth in SEQ ID
NO: 281 (DSSGDLYAYDY);
VLCDR1 comprises the sequence set forth in SEQ ID
NO: 282 (SGSSSNVGYGNYMA);
VLCDR2 comprises the sequence set forth in SEQ ID
NO: 141 (GATSRAS); and
VLCDR3 comprises the sequence set forth in SEQ ID
NO: 263 (ASYDSTSGGV);
wherein the specific binding molecule binds to a poly-
peptide or protein molecule comprising an amino
acid sequence comprising residues 13 to 25 of SEQ
ID NO: 1. The specific binding molecule comprising
FRs and CDRs having 100% identity to those given
above is referred to as "CB7" herein.

The specific binding molecule may comprise:

```
(a) A VH domain comprising the sequence set forth
in SEQ ID NO: 515
```

```
-continued
(QVQLQESGPSLVKPSQTLSLTCTVSGFSLTNYRVGWRQAPGKALEWVS
NIRSGGTTWYNPALKSRLSITADTSKSQVSLSLSSVTTEDTAVYYCARD
SSGDLYAYDYWGPGLLVTVSS);
and/or
```

```
(b) a VL domain comprising the sequence set forth
in SEQ ID NO: 516
(QAVLTQPSSVSRSLGQSVSMTCSGSSSNVGYGNYMAWFQQVPGSAPKL
LIYGATSRASGVPDRFSGSRSGNTATLTISSLQAEDEADYYCASYDSTS
GGVFGSGTRLTVLG);
``` or a humanized variant thereof.

The specific binding molecule may comprise:

```
(a) A heavy chain comprising the sequence set
forth in SEQ ID NO: 517
(QVQLQESGPSLVKPSQTLSLTCTVSGFSLTNYRVGWRQAPGKALEWVS

NIRSGGTTWYNPALKSRLSITADTSKSQVSLSLSSVTTEDTAVYYCARD

SSGDLYAYDYWGPGLLVTVSSAKTTAPSVYPLAPVCGDTTGSSVTLGCL

VKGYFPEPVTLTWNSGSLSSGVHTFPAVLQSDLYTLSSSVTVTSSTWPS

QSITCNVAHPASSTKVDKKIEPRGPTIKPCPPCKCPAPNLLGGPSVFIF

PPKIKDVLMISLSPIVTCVVVDVSEDDPDVQISWFVNNVEVHTAQTQTH

REDYNSTLRVVSALPIQHQDWMSGKEFKCKVNNKDLPAPIERTISKPKG

SVRAPQVYVLPPPEEEMTKKQVTLTCMVTDFMPEDIYVEWTNNGKTELN

YKNTEPVLDSDGSYFMYSKLRVEKKNWVERNSYSCSVVHEGLHNHHTTK

SFSRTPGK);
and/or
```

```
(b) a light chain comprising the sequence set
forth in SEQ ID NO: 518
(QAVLTQPSSVSRSLGQSVSMTCSGSSSNVGYGNYMAWFQQVPGSAPKL

LIYGATSRASGVPDRFSGSRSGNTATLTISSLQAEDEADYYCASYDSTS

GGVFGSGTRLTVLGGQPKSSPSVTLFPPSSEELETNKATLVCTITDFYP

GVVTVDWKVDGTPVTQGMETTQPSKQSNNKYMASSYLTLTARAWERHSS

YSCQVTHEGHTVEKSLSRADCS);
``` or a humanized variant thereof.

The epitope of the specific binding molecule may be
within an amino acid sequence comprising residues 145 to
157 of SEQ ID NO: 1. Accordingly, the epitope may be
within the amino acid sequence of SEQ ID NO: 283
(ADGKTKIATPRGA).

The epitope may be within an amino acid sequence
comprising residues 145 to 157 of SEQ ID NO: 1. This
epitope may be bound by the CDRs of the specific binding
molecule referred to as "CC7" herein.

The epitope may comprise the amino acid sequence of
SEQ ID NO: 283 (ADGKTKIATPRGA). The epitope may
comprise an amino acid sequence having at least 70%, at
least 75%, at least 80%, at least 90%, at least 95% or at least
99% identity to SEQ ID NO: 283 (ADGKTKIATPRGA).

The epitope may consist of the amino acid sequence of
SEQ ID NO: 283 (ADGKTKIATPRGA). The epitope may
consist of an amino acid sequence having at least 70%, at
least 75%, at least 80%, at least 90%, at least 95% or at least
99% identity to SEQ ID NO: 283 (ADGKTKIATPRGA).

The specific binding molecule may comprise the CDRs
VHCDR1, VHCDR2, VHCDR3, VLCDR1, VLCDR2 and
VLCDR3, wherein each of said CDRs comprises an amino
acid sequence as follows:
VHCDR1 comprises the sequence set forth in SEQ ID
NO: 198 (SNAVI);

VHCDR2 comprises the sequence set forth in SEQ ID NO: 200 (LIDVDGDAAYDPALKS);

VHCDR3 comprises the sequence set forth in SEQ ID NO: 202 (DYGSWGYVSDIDY);

VLCDR1 comprises the sequence set forth in SEQ ID NO: 292 (SGSYITGSSVG);

VLCDR2 comprises the sequence set forth in SEQ ID NO: 284 (DNNDRPS); and

VLCDR3 comprises the sequence set forth in SEQ ID NO: 285 (ASYDTSNIGL);

or for each CDR sequence, an amino acid sequence with
(i) at least 85% identity thereto, and/or
(ii) one, two, or three amino acid substitutions relative thereto, wherein the specific binding molecule binds to a polypeptide or protein molecule comprising an amino acid sequence comprising residues 145 to 157 of SEQ ID NO: 1. The specific binding molecule comprising CDRs having 100% identity to those given above is referred to as "CC7" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 198 (SNAVI);

VHCDR2 comprises the sequence set forth in SEQ ID NO: 200 (LIDVDGDAAYDPALKS);

VHCDR3 comprises the sequence set forth in SEQ ID NO: 202 (DYGSWGYVSDIDY);

VLCDR1 comprises the sequence set forth in SEQ ID NO: 292 (SGSYITGSSVG);

VLCDR2 comprises the sequence set forth in SEQ ID NO: 284 (DNNDRPS); and

VLCDR3 comprises the sequence set forth in SEQ ID NO: 285 (ASYDTSNIGL).

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 519 (QVQLQESGPSLVKPSQTLSLTCTVSGFSLT);

VHFR2 comprises the sequence set forth in SEQ ID NO: 520 (WVRQAPGKAPEWVA);

VHFR3 comprises the sequence set forth in SEQ ID NO: 521 (RLSITRDTSKSQVSLSLRSVTTEDTAVYY-CAR);

VHFR4 comprises the sequence set forth in SEQ ID NO: 522 (WGPGLLVTVSS);

VLFR1 comprises the sequence set forth in SEQ ID NO: 523 (RWRTQPSSVSGSLGQRVSITC);

VLFR2 comprises the sequence set forth in SEQ ID NO: 524 (WFQQVPGSGLKTVIY);

VLFR3 comprises the sequence set forth in SEQ ID NO: 525 (GVPDRFSGSKSGDTATLTISSLQAEDEAD-YYC);

VLFR4 comprises the sequence set forth in SEQ ID NO: 526 (FGSGTRLTVLG);

or for each FR sequence, an amino acid sequence with
(i) at least 50% identity thereto, and/or
(ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 519 (QVQLQESGPSLVKPSQTLSLTCTVSGFSLT);

VHFR2 comprises the sequence set forth in SEQ ID NO: 520 (WRQAPGKAPEWVA);

VHFR3 comprises the sequence set forth in SEQ ID NO: 521 (RLSITRDTSKSQVSLSLRSVTTEDTAVYY-CAR);

VHFR4 comprises the sequence set forth in SEQ ID NO: 522 (WGPGLLVTVSS);

VLFR1 comprises the sequence set forth in SEQ ID NO: 523 (RVVRTQPSSVSGSLGQRVSITC);

VLFR2 comprises the sequence set forth in SEQ ID NO: 524 (WFQQVPGSGLKTVIY);

VLFR3 comprises the sequence set forth in SEQ ID NO: 525 (GVPDRFSGSKSGDTATLTISSLQAEDEAD-YYC);

VLFR4 comprises the sequence set forth in SEQ ID NO: 526 (FGSGTRLTVLG);

or for each FR sequence, an amino acid sequence with
(i) at least 50% identity thereto, and/or
(ii) one, two, three, four or five amino acid substitutions relative thereto, wherein the specific binding molecule binds to a polypeptide or protein molecule comprising an amino acid sequence comprising residues 145 to 157 of SEQ ID NO: 1. A specific binding molecule comprising FRs having 100% identity to those given above is referred to as "CC7" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 519 (QVQLQESGPSLVKP-SQTLSLTCTVSGFSLT);

VHFR2 comprises the sequence set forth in SEQ ID NO: 520 (WWRQAPGKAPEWVA);

VHFR3 comprises the sequence set forth in SEQ ID NO: 521 (RLSITRDTSKSQVSLSLRSVTTED-TAVYYCAR);

VHFR4 comprises the sequence set forth in SEQ ID NO: 522 (WGPGLLVTVSS);

VLFR1 comprises the sequence set forth in SEQ ID NO: 523 (RWRTQPSSVSGSLGQRVSITC);

VLFR2 comprises the sequence set forth in SEQ ID NO: 524 (WFQQVPGSGLKTVIY);

VLFR3 comprises the sequence set forth in SEQ ID NO: 525 (GVPDRFSGSKSGDTATLTISSLQAE-DEADYYC);

VLFR4 comprises the sequence set forth in SEQ ID NO: 526 (FGSGTRLTVLG);

or for each FR sequence, an amino acid sequence with
(i) at least 50% identity thereto, and/or
(ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 198 (SNAVI);

VHCDR2 comprises the sequence set forth in SEQ ID NO: 200 (LIDVDGDAAYDPALKS);

VHCDR3 comprises the sequence set forth in SEQ ID NO: 202 (DYGSWGYVSDIDY);

VLCDR1 comprises the sequence set forth in SEQ ID NO: 292 (SGSYITGSSVG);

VLCDR2 comprises the sequence set forth in SEQ ID NO: 284 (DNNDRPS); and

VLCDR3 comprises the sequence set forth in SEQ ID NO: 285 (ASYDTSNIGL);

or for each CDR sequence, an amino acid sequence with (i) at least 85% identity thereto, and/or (ii) one, two, or three amino acid substitutions relative thereto wherein the specific binding molecule binds to a polypeptide or protein molecule comprising an amino acid sequence comprising residues 145 to 157 of SEQ ID NO: 1. The specific binding molecule comprising FRs and CDRs having 100% identity to those given above is referred to as "CC7" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 519 (QVQLQESGPSLVKP-SQTLSLTCTVSGFSLT);

VHFR2 comprises the sequence set forth in SEQ ID NO: 520 (WVRQAPGKAPEWVA);

VHFR3 comprises the sequence set forth in SEQ ID NO: 521 (RLSITRDTSKSQVSLSLRSVTTED-TAVYYCAR);

VHFR4 comprises the sequence set forth in SEQ ID NO: 522 (WGPGLLVTVSS);

VLFR1 comprises the sequence set forth in SEQ ID NO: 523 (RWRTQPSSVSGSLGQRVSITC);

VLFR2 comprises the sequence set forth in SEQ ID NO: 524 (WFQQVPGSGLKTVIY);

VLFR3 comprises the sequence set forth in SEQ ID NO: 525 (GVPDRFSGSKSGDTATLTISSLQAE-DEADYYC);

VLFR4 comprises the sequence set forth in SEQ ID NO: 526 (FGSGTRLTVLG);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 198 (SNAVI);

VHCDR2 comprises the sequence set forth in SEQ ID NO: 200 (LIDVDGDAAYDPALKS);

VHCDR3 comprises the sequence set forth in SEQ ID NO: 202 (DYGSWGYVSDIDY);

VLCDR1 comprises the sequence set forth in SEQ ID NO: 292 (SGSYITGSSVG);

VLCDR2 comprises the sequence set forth in SEQ ID NO: 284 (DNNDRPS); and

VLCDR3 comprises the sequence set forth in SEQ ID NO: 285 (ASYDTSNIGL);

wherein the specific binding molecule binds to a polypeptide or protein molecule comprising an amino acid sequence comprising residues 145 to 157 of SEQ ID NO: 1. The specific binding molecule comprising FRs and CDRs having 100% identity to those given above is referred to as "CC7" herein.

The specific binding molecule may comprise:

```
(a) A VH domain comprising the sequence set forth
in SEQ ID NO: 527
(QVQLQESGPSLVKPSQTLSLTCTVSGFSLTSNAVIWRQAPGKAPEWVA
LIDVDGDAAYDPALKSRLSITRDTSKSQVSLSLRSVTTEDTAVYYCARD
YGSWGYVSDIDYWGPGLLVTVSS);
and/or (b) a VL domain comprising the sequence set forth
in SEQ ID NO: 528
(RVVRTQPSSVSGSLGQRVSITCSGSYITGSSVGWFQQVPGSGLKTVIY
DNNDRPSGVPDRFSGSKSGDTATLTISSLQAEDEADYYCASYDTSNIGL
FGSGTRLTVLG);
``` or a humanized variant thereof.

The specific binding molecule may comprise:

```
(a) A heavy chain comprising the sequence set
forth in SEQ ID NO: 529
(QVQLQESGPSLVKPSQTLSLTCTVSGFSLTSNAVIWVRQAPGKAPEWV

ALIDVDGDAAYDPALKSRLSITRDTSKSQVSLSLRSVTTEDTAVYYCAR

DYGSWGYVSDIDYWGPGLLVTVSSAKTTAPSVYPLAPVCGDTTGSSVTL

GCLVKGYFPEPVTLTWNSGSLSSGVHTFPAVLQSDLYTLSSSVTVTSST

WPSQSITCNVAHPASSTKVDKKIEPRGPTIKPCPPCKCPAPNLLGGPSV

FIFPPKIKDVLMISLSPIVTCVVVDVSEDDPDVQISWFVNNVEVHTAQT

QTHREDYNSTLRVVSALPIQHQDWMSGKEFKCKVNNKDLPAPIERTISK

PKGSVRAPQVYVLPPPEEEMTKKQVTLTCMVTDFMPEDIYVEWTNNGKT

ELNYKNTEPVLDSDGSYFMYSKLRVEKKNWVERNSYSCSVVHEGLHNHH

TTKSFSRTPGK);
and/or (b) a light chain comprising the sequence set
forth in SEQ ID NO: 530
(RVVRTQPSSVSGSLGQRVSITCSGSYITGSSVGWFQQVPGSGLKTVIY

DNNDRPSGVPDRFSGSKSGDTATLTISSLQAEDEADYYCASYDTSNIGL

FGSGTRLTVLGGQPKSSPSVTLFPPSSEELETNKATLVCTITDFYPGVV

TVDWKVDGTPVTQGMETTQPSKQSNNKYMASSYLTLTARAWERHSSYSC

QVTHEGHTVEKSLSRADCS);
``` or a humanized variant thereof.

The epitope of the specific binding molecule may be within an amino acid sequence comprising residues 155 to 227 of SEQ ID NO: 1. Accordingly, the epitope may be within the amino acid sequence of SEQ ID NO: 294 (RGAAPPGQKGQANATRIPAKTP-PAPKTPPSSGEPPKSGDRSGYSSPGSPGTPGSRSRTPS LPTP PTREPKKVA).

The epitope may be within an amino acid sequence comprising residues 155 to 227 of SEQ ID NO: 1. This epitope may be bound by the CDRs of the specific binding molecules referred to as "CB12" and "CC3" herein.

The epitope may comprise the amino acid sequence of SEQ ID NO: 294 (RGAAPPGQKGQANATRIPAKTP-PAPKTPPSSGEPPKSGDRSGYSSPGSPGTPGSRSRTPS LPTP PTREPKKVA). The epitope may comprise an amino acid sequence having at least 70%, at least 75%, at least 80%, at least 90%, at least 95% or at least 99% identity to SEQ ID NO: 294 (RGAAPPGQKGQANATRIPAKTP-PAPKTPPSSGEPPKSGDRSGYSSPGSPGTPGSRSRTPS LPTP PTREPKKVA).

The epitope may consist of the amino acid sequence of SEQ ID NO: 294 (RGAAPPGQKGQANATRIPAKTP-PAPKTPPSSGEPPKSGDRSGYSSPGSPGTPGSRSRTPS LPTP PTREPKKVA). The epitope may consist of an amino acid sequence having at least 70%, at least 75%, at least 80%, at least 90%, at least 95% or at least 99% identity to SEQ ID NO: 294 (RGAAPPGQKGQANATRIPAKTP-PAPKTPPSSGEPPKSGDRSGYSSPGSPGTPGSRSRTPSL PTP PTREPKKVA).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 182 (DKSSAGKTYGNPALKS);

VHCDR3 comprises the sequence set forth in SEQ ID NO: 286 (CRDGGVSYGYDVDY);

VLCDR1 comprises the sequence set forth in SEQ ID NO: 287 (SGSSSNVGGDYVG);

VLCDR2 comprises the sequence set forth in SEQ ID NO: 288 (DTTSRPS); and

VLCDR3 comprises the sequence set forth in SEQ ID NO: 289 (ASVDKTTGGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 155 to 227 of SEQ ID NO: 1. The specific binding molecule comprising CDRs having 100% identity to those given above is referred to as "CB12" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 182 (DKSSAGKTYGNPALKS);

VHCDR3 comprises the sequence set forth in SEQ ID NO: 286 (CRDGGVSYGYDVDY);

VLCDR1 comprises the sequence set forth in SEQ ID NO: 287 (SGSSSNVGGDYVG);

VLCDR2 comprises the sequence set forth in SEQ ID NO: 288 (DTTSRPS); and

VLCDR3 comprises the sequence set forth in SEQ ID NO: 289 (ASVDKTTGGV).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 182 (DKSSAGKTYGNPALKS);

VHCDR3 comprises the sequence set forth in SEQ ID NO: 286 (CRDGGVSYGYDVDY);

VLCDR1 comprises the sequence set forth in SEQ ID NO: 290 (SGSSSNVGYGTYVS);

VLCDR2 comprises the sequence set forth in SEQ ID NO: 188 (GTTTRAS); and

VLCDR3 comprises the sequence set forth in SEQ ID NO: 291 (ASYDTGSGGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 155 to 227 of SEQ ID NO: 1. The specific binding molecule comprising CDRs having 100% identity to those given above is referred to as "CC3" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 182 (DKSSAGKTYGNPALKS);

VHCDR3 comprises the sequence set forth in SEQ ID NO: 286 (CRDGGVSYGYDVDY);

VLCDR1 comprises the sequence set forth in SEQ ID NO: 290 (SGSSSNVGYGTYVS);

VLCDR2 comprises the sequence set forth in SEQ ID NO: 188 (GTTTRAS); and

VLCDR3 comprises the sequence set forth in SEQ ID NO: 291 (ASYDTGSGGV).

The epitope of the specific binding molecule may be within an amino acid sequence comprising residues 155 to 238 of SEQ ID NO: 1. Accordingly, the epitope may be within the amino acid sequence of SEQ ID NO: 295 (RGAAPPGQKGQANATRIPAKTP-PAPKTPPSSGEPPKSGDRSGYSSPGSPGTPGSRSRTPS LPTP PTREPKKVAVVRTPPKSPSS).

The epitope may be within an amino acid sequence comprising residues 155 to 238 of SEQ ID NO: 1. This epitope may be bound by the CDRs of the specific binding molecule referred to as "CA1" herein.

The epitope may comprise the amino acid sequence of SEQ ID NO: 295 (RGAAPPGQKGQANATRIPAKTP-PAPKTPPSSGEPPKSGDRSGYSSPGSPGTPGSRSRTPS LPTP PTREPKKVAVVRTPPKSPSS). The epitope may comprise an amino acid sequence having at least 70%, at least 75%, at least 80%, at least 90%, at least 95% or at least 99% identity to SEQ ID NO: (RGAAPPGQKGQANATRI-PAKTP-PAPKTPPSSGEPPKSGDRSGYSSPGSPGTPGSRSRTPSL PTP PTREPKKVAVVRTPPKSPSS).

The epitope may consist of the amino acid sequence of SEQ ID NO: 295 (RGAAPPGQKGQANATRIPAKTP-PAPKTPPSSGEPPKSGDRSGYSSPGSPGTPGSRSRTPS LPTP PTREPKKVAVVRTPPKSPSS). The epitope may consist of an amino acid sequence having at least 70%, at least 75%, at least 80%, at least 90%, at least 95% or at least 99% identity to SEQ ID NO: 295 (RGAAPPGQKGQANATRIPAKTP-PAPKTPPSSGEPPKSGDRSGYSSPGSPGTPGSRSRTPS LPTP PTREPKKVAVVRTPPKSPSS).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 198 (SNAVI);

VHCDR2 comprises the sequence set forth in SEQ ID NO: 296 (DIRADGATNYNAALKS);

VHCDR3 comprises the sequence set forth in SEQ ID NO: 297 (PGNYYYGAGRDVARLAD);

VLCDR1 comprises the sequence set forth in SEQ ID NO: 298 (SGSSSNIGGGNAVG);

VLCDR2 comprises the sequence set forth in SEQ ID NO: 288 (DTTSRPS); and

VLCDR3 comprises the sequence set forth in SEQ ID NO: 299 (AAMDSSSLIGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 155 to 238 of SEQ ID NO: 1. The specific binding molecule comprising CDRs having 100% identity to those given above is referred to as "CA1" herein. The epitope of the specific binding molecule may be within an amino acid sequence comprising residues 186 to 263 of SEQ ID NO: 1. Accordingly, the epitope may be within the amino acid sequence of SEQ ID NO: 300 (GEPPKSGDRSGYSSPGSPGTPGSRSRTPSLPTPP-TREPKKVAVVRTPPKSPSSAKSRLQTAPVP MPDLKNVKSKIGST).

The epitope may be within an amino acid sequence comprising residues 186 to 263 of SEQ ID NO: 1. This epitope may be bound by the CDRs of the specific binding molecule referred to as "CA3" herein.

The epitope may comprise the amino acid sequence of SEQ ID NO: 300 (GEPPKSGDRSGYSSPGSPGTPGSRSRTPSLPTPP-TREPKKVAVVRTPPKSPSSAKSRLQT APVPMPDLKNVKSKIGST). The epitope may comprise an amino acid sequence having at least 70%, at least 75%, at least 80%, at least 90%, at least 95% or at least 99% identity to SEQ ID NO: 300 (GEPPKSGDRSGYSSPGSPGTPGSRSRTPSLPTPP-TREPKKVAVVRTPPKSPSSAKSRLQT APVPMPDLKNVKSKIGST).

The epitope may consist of the amino acid sequence of SEQ ID NO: 300 (GEPPKSGDRSGYSSPGSPGTPGSRSRTPSLPTPP-TREPKKVAVVRTPPKSPSSAKSRLQT APVPMPDLKNVKSKIGST). The epitope may consist of an amino acid sequence having at least 70%, at least 75%, at least 80%, at least 90%, at least 95% or at least 99% identity to SEQ ID NO: 300 (GEPPKSGDRSGYSSPGSPGTPGSRSRTPSLPTPP-TREPKKVAVVRTPPKSPSSAKSRLQT APVPMPDLKNVKSKIGST).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 182 (DKSSAGKTYGNPALKS);

VHCDR3 comprises the sequence set forth in SEQ ID NO: 184 (CRDGGVTYGYDVDY);

VLCDR1 comprises the sequence set forth in SEQ ID NO: 301 (SGSSGNIGYDDYVS);

VLCDR2 comprises the sequence set forth in SEQ ID NO: 302 (GATRRSS); and

VLCDR3 comprises the sequence set forth in SEQ ID NO: 303 (ASYDSSGGGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 186 to 263 of SEQ ID NO: 1. The specific binding molecule comprising CDRs having 100% identity to those given above is referred to as "CA3" herein.

The epitope of the specific binding molecule may be within an amino acid sequence comprising residues 186 to 350 of SEQ ID NO: 1. Accordingly, the epitope may be within the amino acid sequence of SEQ ID NO: 304 (GEPPKSGDRSGYSSPGSPGTPGSRSRTPSLPTPP-TREPKKVAVVRTPPKSPSSAKSRLQTAPVP MPDLKNVKSKIGSTENLKHQPGGGKVQIINKKLDL-SNVQSKCGSKDNIKHVPGGGSVQIVYKPVDL SKVTSKCGSLGNIHHKPGGGQVEVKSEKLDFKDRV).

The epitope may be within an amino acid sequence comprising residues 186 to 350 of SEQ ID NO: 1. This epitope may be bound by the CDRs of the specific binding molecule referred to as "CD2" herein.

The epitope may comprise the amino e of SEQ ID NO: 304 (GEPPKSGDRSGYSSPGSPGTPGSRSRTPSLPTPP-TREPKKVAVVRTPPKSPSSAKSRLQTAPVP MPDLKNVKSKIGSTENLKHQPGGGKVQIINKKLDL-SNVQSKCGSKDNIKHVPGGGSVQIVYKPVDL SKVTSKCGSLGNIHHKPGGGQVEVKSEKLDFKDRV). The epitope may comprise an amino acid sequence having at least 70%, at least 75%, at least 80%, at least 90%, at least 95% or at least 99% identity to SEQ ID NO: 304 (GEPPKSGDRSGYSSPGSPGTPGSRSRTPSLPTPP-TREPKKVAVVRTPPKSPSSAKSRLQTAPVP MPDLKNVKSKIGSTENLKHQPGGGKVQIINKKLDL-SNVQSKCGSKDNIKHVPGGGSVQIVYKPVDL SKVTSKCGSLGNIHHKPGGGQVEVKSEKLDFKDRV).

The epitope may consist of the amino acid sequence of SEQ ID NO: 304 (GEPPKSGDRSGYSSPGSPGTPGSRSRTPSLPTPP-TREPKKVAVVRTPPKSPSSAKSRLQTAPVP MPDLKNVKSKIGSTENLKHQPGGGKVQIINKKLDL-SNVQSKCGSKDNIKHVPGGGSVQIVYKPVDL SKVTSKCGSLGNIHHKPGGGQVEVKSEKLDFKDRV). The epitope may consist of an amino acid sequence having at least 70%, at least 75%, at least 80%, at least 90%, at least 95% or at least 99% identity to SEQ ID NO: 304 (GEPPKSGDRSGYSSPGSPGTPGSRSRTPSLPTPP-TREPKKVAVVRTPPKSPSSAKSRLQTAPVP MPDLKNVKSKIGSTENLKHQPGGGKVQIINKKLDL-SNVQSKCGSKDNIKHVPGGGSVQIVYKPVDL SKVTSKCGSLGNIHHKPGGGQVEVKSEKLDFKDRV).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 198 (SNAVI);

VHCDR2 comprises the sequence set forth in SEQ ID NO: 200 (LIDVDGDAAYDPALKS);

VHCDR3 comprises the sequence set forth in SEQ ID NO: 202 (DYGSWGYVSDIDY);

VLCDR1 comprises the sequence set forth in SEQ ID NO: 305 (SGSNIGDADVG);

VLCDR2 comprises the sequence set forth in SEQ ID NO: 306 (YNENRPS); and

VLCDR3 comprises the sequence set forth in SEQ ID NO: 307 (GSYAGDTYNHGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 186 to 350 of SEQ ID NO: 1. The specific binding molecule comprising CDRs having 100% identity to those given above is referred to as "CD2" herein.

The epitope of the specific binding molecule may be within an amino acid sequence comprising residues 239 to 348 of SEQ ID NO: 1. Accordingly, the epitope may be within the amino acid sequence of SEQ ID NO: 308 (AKSRLQTAPVPMPDLKNVKSKIG-STENLKHQPGGGKVQIINKKLDLSNVQSKCGSKD-NIKHVPGG GSVQIVYKPVDL-SKVTSKCGSLGNIHHKPGGGQVEVKSEKLDFKD).

The epitope may be within an amino acid sequence comprising residues 239 to 348 of SEQ ID NO: 1. This epitope may be bound by the CDRs of the specific binding molecule referred to as "CB9" herein.

The epitope may comprise the amino acid sequence of 308 (AKSRLQTAPVPMPDLKNVKSKIG-STENLKHQPGGGKVQIINKKLDLSNVQSKCGSKD-NIKHVPGG GSVQIVYKPVDL-SKVTSKCGSLGNIHHKPGGGQVEVKSEKLDFKD). The epitope may comprise an amino acid sequence having at least 70%, at least 75%, at least 80%, at least 90%, at least 95% or at least 99% identity to 308 (AKSRLQTAPVPMPDLKNVKSKIG-STENLKHQPGGGKVQIINKKLDLSNVQSKCGSKD-NIKHVPGG GSVQIVYKPVDL-SKVTSKCGSLGNIHHKPGGGQVEVKSEKLDFKD).

The epitope may consist of the amino acid sequence of 308 (AKSRLQTAPVPMPDLKNVKSKIG-STENLKHQPGGGKVQIINKKLDLSNVQSKCGSKD-NIK HVPGGGSVQIVYKPVDL-SKVTSKCGSLGNIHHKPGGGQVEVKSEKLDFKD). The epitope may consist of an amino acid sequence having at least 70%, at least 75%, at least 80%, at least 90%, at least 95% or at least 99% identity to 308 (AKSRLQTAPVPMPDLKNVKSKIG-STENLKHQPGGGKVQIINKKLDLSNVQSKCGSKD-NIKHVPGG GSVQIVYKPVDL-SKVTSKCGSLGNIHHKPGGGQVEVKSEKLDFKD).

The specific binding molecule may comprise the CDRs VHCDR1, VHCDR2, VHCDR3, VLCDR1. VLCDR2 and VLCDR3, wherein each of said CDRs comprises an amino acid sequence as follows: VHCDR1 comprises the sequence set forth in SEQ ID NO: 42 (SNSVG); VHCDR2 comprises the sequence set forth in SEQ ID NO: 48 (GIDSDGEEGY-NPALNS); VHCDR3 comprises the sequence set forth in SEQ ID NO: 54 (SYRADGLAYGYVQAIDY); VLCDR1 comprises the sequence set forth in SEQ ID NO: 67 (SGR-FIGISSVG); VLCDR2 comprises the sequence set forth in SEQ ID NO: 70 (ASDGRPS); and VLCDR3 comprises the sequence set forth in SEQ ID NO: 74 (GSSDRTQYTGV); or for each CDR sequence, an amino acid sequence with
   (i) at least 85% identity thereto, and/or
   (ii) one, two, or three amino acid substitutions relative thereto,
wherein the specific binding molecule binds to a polypeptide or protein molecule comprising an amino acid sequence comprising residues 239 to 348 of SEQ ID NO: 1. The specific binding molecule comprising CDRs having 100% identity to those given above is referred to as "CB9" herein.

The epitope of the specific binding molecule may be within an amino acid sequence comprising residues 266 to 359 of SEQ ID NO: 1. Accordingly, the epitope may be within the amino acid sequence of SEQ ID NO: 309 (LKHQPGGGKVQIINKKLDLSNVQSKCGSKD-

NIKHVPGGGSVQIVYKPVDLSKVTSKOGSLGNIHH KPGGGQVEVKSEKLDFKDRVQSKIGSLDN).

The epitope may be within an amino acid sequence comprising residues 266 to 359 of SEQ ID NO: 1. This epitope may be bound by the CDRs of the specific binding molecule referred to as "CG11" herein.

The epitope may comprise the amino acid sequence of SEQ ID NO: 309 (LKHQPGGGKVQIINKKLDL-SNVQSKCGSKDNIKHVPGGGSVQIVYKPVDL-SKVTSKOGSLGNIHH KPGGGQVEVKSEKLDFKDRVQSKIGSLDN). The epitope may comprise an amino acid sequence having at least 70%, at least 75%, at least 80%, at least 90%, at least 95% or at least 99% identity to SEQ ID NO: 309 (LKHQPGGGKVQIINKKLDLSNVQSKCGSKD-NIKHVPGGGSVQIVYKPVDLSKVTSKCGSLGNIHH KPGGGQVEVKSEKLDFKDRVQSKIGSLDN).

The epitope may consist of the amino acid sequence of SEQ ID NO: 309 (LKHQPGGGKVQIINKKLDL-SNVQSKCGSKDNIKHVPGGGSVQIVYKPVDL-SKVTSKCGSLGNIHH KPGGGQVEVKSEKLDFKDRVQSKIGSLDN). The epitope may consist of an amino acid sequence having at least 70%, at least 75%, at least 80%, at least 90%, at least 95% or at least 99% identity to SEQ ID NO: 309 (LKHQPGGGKVQIINKKLDLSNVQSKCGSKD-NIKHVPGGGSVQIVYKPVDLSKVTSKOGSLGNIHH KPGGGQVEVKSEKLDFKDRVQSKIGSLDN).

The specific binding molecule may comprise the CDRs VHCDR1, VHCDR2, VHCDR3, VLCDR1. VLCDR2 and VLCDR3, wherein each of said CDRs comprises an amino acid sequence as follows:
   VHCDR1 comprises the sequence set forth in SEQ ID NO: 310 (NYPVG);
   VHCDR2 comprises the sequence set forth in SEQ ID NO: 311 (NIENDGSANYASALKS);
   VHCDR3 comprises the sequence set forth in SEQ ID NO: 312 (EFGGSDGYTYFVDIDY);
   VLCDR1 comprises the sequence set forth in SEQ ID NO: 313 (SGSSSNVGYGNYVS);
   VLCDR2 comprises the sequence set forth in SEQ ID NO: 141 (GATSRAS); and
   VLCDR3 comprises the sequence set forth in SEQ ID NO: 314 (ASYDGSSSGV);
or for each CDR sequence, an amino acid sequence with
   (i) at least 85% identity thereto, and/or
   (ii) one, two, or three amino acid substitutions relative thereto,
wherein the specific binding molecule binds to a polypeptide or protein molecule comprising an amino acid sequence comprising residues 266 to 359 of SEQ ID NO: 1. The specific binding molecule comprising CDRs having 100% identity to those given above is referred to as "CG11" herein.

The epitope of the specific binding molecule may be within an amino acid sequence comprising residues 277 to 319 of SEQ ID NO: 1. Accordingly, the epitope may be within the amino acid sequence of SEQ ID NO: 315 (IINKKLDLSNVQSKCGSKDNIKHVPGGGSVQI-VYKPVDLSKVT).

The epitope may be within an amino acid sequence comprising residues 277 to 319 of SEQ ID NO: 1. This epitope may be bound by the CDRs of the specific binding molecule referred to as "CA10" herein.

The epitope may comprise the amino acid sequence of SEQ ID NO: 315 (IINKKLDLSNVQSKCGSKD-NIKHVPGGGSVQIVYKPVDLSKVT). The epitope may comprise an amino acid sequence having at least 70%, at least 75%, at least 80%, at least 90%, at least 95% or at least 99% identity to SEQ ID NO 315 (IINKKLDLSNVQSKCG-SKDNIKHVPGGGSVQIVYKPVDLSKVT).

The epitope may consist of the amino acid sequence of SEQ ID NO: 315 (IINKKLDLSNVQSKCGSKD- NIKHVPGGGSVQIVYKPVDLSKVT). The epitope may consist of an amino acid sequence having at least 70%, at least 75%, at least 80%, at least 90%, at least 95% or at least 99% identity to SEQ ID NO: 315 (IINKKLDL-SNVQSKCGSKDNIKHVPGGGSVQIVYKPVDLSKVT).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 157 (DISSVGKKYANPALKS);

VHCDR3 comprises the sequence set forth in SEQ ID NO: 161 (CRDGGVTYGYDIDY); 20

VLCDR1 comprises the sequence set forth in SEQ ID NO: 316 (SGSSSNVGYGNYVT);

VLCDR2 comprises the sequence set forth in SEQ ID NO: 317 (DATTRVS); and

VLCDR3 comprises the sequence set forth in SEQ ID NO: 318 (AAHDSSSGGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 277 to 319 of SEQ ID NO: 1. The specific binding molecule comprising CDRs having 100% identity to those given above is referred to as "CA10" herein

The epitope of the specific binding molecule may be within an amino acid sequence comprising residues 297 to 390 of SEQ ID NO: 1. Accordingly, the epitope may be within the amino acid sequence of SEQ ID NO: 5 (IKHVPGGGSVQIVYKPVDL- SKVTSKCGSLGNIHHKPGGGQVEVKSEKLDFKDRV QSKIGSLDNITH VPGGGNKKI-ETHKLTFRENAKAKTDHGA).

The epitope may be within an amino acid sequence comprising residues 297 to 390 of SEQ ID NO: 1. This epitope may be bound by the CDRs of the specific binding molecule referred to as "CC12" herein.

The epitope may comprise the amino acid sequence of SEQ ID NO: 5 (IKHVPGGGSVQIVYKPVDL-SKVTSKCGSLGNIHHKPGGGQVEVKSEKLDFKDRV QSKIGSLDNITH VPGGGNKKI-ETHKLTFRENAKAKTDHGA). The epitope may comprise an amino acid sequence having at least 70%, at least 75%, at least 80%, at least 90%, at least 95% or at least 99% identity to SEQ ID NO: 5 (IKHVPGGGSVQIVYKPVDL- 55 SKVTSKCGSLGNIHHKPGGGQVEVKSEKLDFKDRV QSKIGSLDNITH VPGGGNKKI-ETHKLTFRENAKAKTDHGA).

The epitope may consist of the amino acid sequence of SEQ ID NO: 5 (IKHVPGGGSVQIVYKPVDL- 60 SKVTSKCGSLGNIHHKPGGGQVEVKSEKLDFKDRV QSKIGSLDNITH VPGGGNKKI-ETHKLTFRENAKAKTDHGA). The epitope may consist of an amino acid sequence having at least 70%, at least 75%, at least 80%, at least 90%, at least 95% or at least 99% identity to SEQ ID NO 5 (IKHVPGGGSVQIVYKPVDL-SKVTSKCGSLGNIHHKPGGGQVEVKSEKLDFKDRV

QSKIGSLDNITH VPGGGNKKI-ETHKLTFRENAKAKTDHGA).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 48 (GIDSDGEEGYNPALNS);

VHCDR3 comprises the sequence set forth in SEQ ID NO: 54 (SYRADGLAYGYVQAIDY);

VLCDR1 comprises the sequence set forth in SEQ ID NO: 67 (SGRFIGISSVG);

VLCDR2 comprises the sequence set forth in SEQ ID NO: 70 (ASDGRPS); and

VLCDR3 comprises the sequence set forth in SEQ ID NO: 74 (GSSDRTQYTGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 297 to 390 of SEQ ID NO: 1. The specific binding molecule comprising CDRs having 100% identity to those given above is referred to as "CC12" herein.

The epitope of the specific binding molecule may be within an amino acid sequence comprising residues 319 to 331 of SEQ ID NO: 1. Accordingly, the epitope may be within the amino acid sequence of SEQ ID NO: 319 (TSKCGSLGNIHHK).

The epitope may be within an amino acid sequence comprising residues 319 to 331 of SEQ ID NO: 1. This epitope may be bound by the CDRs of the specific binding molecule referred to as "CE2" or "E1B8" herein. Critical residues of the epitope may be residues 323 (G), 324 (S), 325 (L), 326 (G), 327 (N) and/or 328 (I) (numbering according to SEQ ID NO: 1). The epitope may comprise the amino acid sequence of SEQ ID NO: 320 (XXXXGSLGNIXXX, wherein X is any amino acid). The epitope may comprise the amino acid sequence of SEQ ID NO: 319, wherein any one or more residue other than residue number 323 (G), 324 (S), 325 (L), 326 (G), 327 (N) and/or 328 (I) is replaced by a non-conservative amino acid substitution (numbering according to SEQ ID NO: 1). The epitope may comprise the amino acid sequence of SEQ ID NO: 319, wherein any one or more residue other than residue number 323 (G), 324 (S), 325 (L), 326 (G), 327 (N) and/or 328 (I) is replaced by a conservative amino acid substitution (numbering according to SEQ ID NO: 1). The epitope may comprise the amino acid sequence of SEQ ID NO: 319, wherein any one or more residue other than residue number 323 (G), 324 (S), 325 (L), 326 (G), 327 (N) and/or 328 (I) is replaced by a conservative amino acid substitution (numbering according to SEQ ID NO: 1) and any one or more residue other than residue number 323 (G), 324 (S), 325 (L), 326 (G), 327 (N) and/or 328 (I) is replaced by a non-conservative amino acid substitution (numbering according to SEQ ID NO: 1).

The epitope may comprise the amino acid sequence of SEQ ID NO: 319 (TSKCGSLGNIHHK). The epitope may comprise an amino acid sequence having at least 70%, at least 75%, at least 80%, at least 90%, at least 95% or at least 99% identity to SEQ ID NO: 319 (TSKCGSLGNIHHK).

The epitope may consist of the amino acid sequence of SEQ ID NO: 319 (TSKCGSLGNIHHK). The epitope may consist of an amino acid sequence having at least 70%, at least 75%, at least 80%, at least 90%, at least 95% or at least 99% identity to SEQ ID NO: 319 (TSKCGSLGNIHHK).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 310 (NYPVG);

VHCDR2 comprises the sequence set forth in SEQ ID NO: 311 (NIENDGSANYASALKS);

VHCDR3 comprises the sequence set forth in SEQ ID NO: 312 (EFGGSDGYTYFVDIDY);

VLCDR1 comprises the sequence set forth in SEQ ID NO: 313 (SGSSSNVGYGNYVS);

VLCDR2 comprises the sequence set forth in SEQ ID NO: 141 (GATSRAS); and

VLCDR3 comprises the sequence set forth in SEQ ID NO: 314 (ASYDGSSSGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 319 to 331 of SEQ ID NO: 1. The specific binding molecule comprising CDRs having 100% identity to those given above is referred to as "CE2" or "E1B8" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 310 (NYPVG);

VHCDR2 comprises the sequence set forth in SEQ ID NO: 311 (NIENDGSANYASALKS);

VHCDR3 comprises the sequence set forth in SEQ ID NO: 312 (EFGGSDGYTYFVDIDY);

VLCDR1 comprises the sequence set forth in SEQ ID NO: 313 (SGSSSNVGYGNYVS);

VLCDR2 comprises the sequence set forth in SEQ ID NO: 141 (GATSRAS); and

VLCDR3 comprises the sequence set forth in SEQ ID NO: 314 (ASYDGSSSGV).

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 531 (QVQLQESGPSLVKPSQTLSLTCTVSGFSLT);

VHFR2 comprises the sequence set forth in SEQ ID NO: 532 (WRQAPGKALEWIG);

VHFR3 comprises the sequence set forth in SEQ ID NO: 533 (RLSITRDTSKNQVSLSLSSATTED-TAVYYCGR);

VHFR4 comprises the sequence set forth in SEQ ID NO: 534 (WGPGLLVTVSS);

VLFR1 comprises the sequence set forth in SEQ ID NO: 535 (QAVLTQPSSVSKSLGQSVSITC);

VLFR2 comprises the sequence set forth in SEQ ID NO: 536 (WFQQVPGSAPKILIY);

VLFR3 comprises the sequence set forth in SEQ ID NO: 537 (GVPDRFSGSRSGNTATLTITSLQAEDEAD-YYC);

VLFR4 comprises the sequence set forth in SEQ ID NO: 538 (FGSGTRLTVLG);

or for each FR sequence, an amino acid sequence with (i) at least 50% identity thereto, and/or (ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 531 (QVQLQESGPSLVKPSQTLSLTCTVSGFSLT);

VHFR2 comprises the sequence set forth in SEQ ID NO: 532 (WRQAPGKALEWIG);

VHFR3 comprises the sequence set forth in SEQ ID NO: 533 (RLSITRDTSKNQVSLSLSSATTED-TAVYYCGR);

VHFR4 comprises the sequence set forth in SEQ ID NO: 534 (WGPGLLVTVSS);

VLFR1 comprises the sequence set forth in SEQ ID NO: 535 (QAVLTQPSSVSKSLGQSVSITC);

VLFR2 comprises the sequence set forth in SEQ ID NO: 536 (WFQQVPGSAPKILIY);

VLFR3 comprises the sequence set forth in SEQ ID NO: n537 (GVPDRFSGSRSGNTATLTITSLQAEDEAD-YYC);

VLFR4 comprises the sequence set forth in SEQ ID NO: 538 (FGSGTRLTVLG);

or for each FR sequence, an amino acid sequence with (i) at least 50% identity thereto, and/or (ii) one, two, three, four or five amino acid substitutions relative thereto, wherein the specific binding molecule binds to a polypeptide or protein molecule comprising an amino acid sequence comprising residues 319 to 331 of SEQ ID NO: 1. A specific binding molecule comprising FRs having 100% identity to those given above is referred to as "CE2" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 531 (QVQLQESGPSLVKP-SQTLSLTCTVSGFSLT);

VHFR2 comprises the sequence set forth in SEQ ID NO: 532 (WVRQAPGKALEWIG);

VHFR3 comprises the sequence set forth in SEQ ID NO: 533 (RLSITRDTSKNQVSLSLSSATTED-TAVYYCGR);

VHFR4 comprises the sequence set forth in SEQ ID NO: 534 (WGPGLLVTVSS);

VLFR1 comprises the sequence set forth in SEQ ID NO: 535 (QAVLTQPSSVSKSLGQSVSITC);

VLFR2 comprises the sequence set forth in SEQ ID NO: 536 (WFQQVPGSAPKILIY);

VLFR3 comprises the sequence set forth in SEQ ID NO: 537 (GVPDRFSGSRSGNTATLTITSLQAE-DEADYYC);

VLFR4 comprises the sequence set forth in SEQ ID NO: 538 (FGSGTRLTVLG);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 310 (NYPVG);

VHCDR2 comprises the sequence set forth in SEQ ID NO: 311 (NIENDGSANYASALKS);

VHCDR3 comprises the sequence set forth in SEQ ID NO: 312 (EFGGSDGYTYFVDIDY);

VLCDR1 comprises the sequence set forth in SEQ ID NO: 313 (SGSSSNVGYGNYVS);

VLCDR2 comprises the sequence set forth in SEQ ID NO: 141 (GATSRAS); and

VLCDR3 comprises the sequence set forth in SEQ ID NO: 314 (ASYDGSSSGV);

or for each CDR sequence, an amino acid sequence with (i) at least 85% identity thereto, and/or (ii) one, two, or three amino acid substitutions relative thereto wherein the specific binding molecule binds to a polypeptide or protein molecule comprising an amino acid sequence comprising residues 319 to 331 of SEQ ID NO: 1. The specific binding molecule comprising FRs and CDRs having 100% identity to those given above is referred to as "CE2" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 531 (QVQLQESGPSLVKP-SQTLSLTCTVSGFSLT);

VHFR2 comprises the sequence set forth in SEQ ID NO: 532 (WVRQAPGKALEWIG);

VHFR3 comprises the sequence set forth in SEQ ID NO: 533 (RLSITRDTSKNQVSLSLSSATTED-TAVYYCGR);

VHFR4 comprises the sequence set forth in SEQ ID NO: 534 (WGPGLLVTVSS);

VLFR1 comprises the sequence set forth in SEQ ID NO: 535 (QAVLTQPSSVSKSLGQSVSITC);

VLFR2 comprises the sequence set forth in SEQ ID NO: 536 (WFQQVPGSAPKILIY);

VLFR3 comprises the sequence set forth in SEQ ID NO: 537 (GVPDRFSGSRSGNTATLTITSLQAE-DEADYYC);

VLFR4 comprises the sequence set forth in SEQ ID NO: 538 (FGSGTRLTVLG);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 310 (NYPVG);

VHCDR2 comprises the sequence set forth in SEQ ID NO: 311 (NIENDGSANYASALKS);

VHCDR3 comprises the sequence set forth in SEQ ID NO: 312 (EFGGSDGYTYFVDIDY);

VLCDR1 comprises the sequence set forth in SEQ ID NO: 313 (SGSSSNVGYGNYVS);

VLCDR2 comprises the sequence set forth in SEQ ID NO: 141 (GATSRAS); and

VLCDR3 comprises the sequence set forth in SEQ ID NO: 314 (ASYDGSSSGV);

wherein the specific binding molecule binds to a polypeptide or protein molecule comprising an amino acid sequence comprising residues 319 to 331 of SEQ ID NO: 1. The specific binding molecule comprising FRs and CDRs having 100% identity to those given above is referred to as "CE2" herein.

The specific binding molecule may comprise:

```
(a) A VH domain comprising the sequence set forth
in SEQ ID NO: 539
(QVQLQESGPSLVKPSQTLSLTCTVSGFSLTNYPVGWRQAPGKALEWIG
NIENDGSANYASALKSRLSITRDTSKNQVSLSLSSATTEDTAVYYCGRE
FGGSDGYTYFVDIDYWGPGLLVTVSS);
and/or (b) a VL domain comprising the sequence set forth
in SEQ ID NO: 540
(QAVLTQPSSVSKSLGQSVSITCSGSSSNVGYGNYVSWFQQVPGSAPKI
LIYGATSRASGVPDRFSGSRSGNTATLTITSLQAEDEADYYCASYDGSS
SGVFGSGTRLTVLG);
``` or a humanized variant thereof.

The specific binding molecule may comprise:

```
(a) A heavy chain comprising the sequence set
forth in SEQ ID NO: 541
(QVQLQESGPSLVKPSQTLSLTCTVSGFSLTNYPVGWRQAPGKALEWIG

NIENDGSANYASALKSRLSITRDTSKNQVSLSLSSATTEDTAVYYCGRE

FGGSDGYTYFVDIDYWGPGLLVTVSSAKTTAPSVYPLAPVCGDTTGSSV

TLGCLVKGYFPEPVTLTWNSGSLSSGVHTFPAVLQSDLYTLSSSVTVTS

STWPSQSITCNVAHPASSTKVDKKIEPRGPTIKPCPPCKCPAPNLLGGP

SVFIFPPKIKDVLMISLSPIVTCVVVDVSEDDPDVQISWFVNNVEVHTA

QTQTHREDYNSTLRVVSALPIQHQDWMSGKEFKCKVNNKDLPAPIERTI

SKPKGSVRAPQVYVLPPPEEEMTKKQVTLTCMVTDFMPEDIYVEWTNNG

KTELNYKNTEPVLDSDGSYFMYSKLRVEKKNWVERNSYSCSVVHEGLHN

HHTTKSFSRTPGK);
and/or (b) a light chain comprising the sequence set
forth in SEQ ID NO: 542
(QAVLTQPSSVSKSLGQSVSITCSGSSSNVGYGNYVSWFQQVPGSAPKI

LIYGATSRASGVPDRFSGSRSGNTATLTITSLQAEDEADYYCASYDGSS

SGVFGSGTRLTVLGGQPKSSPSVTLFPPSSEELETNKATLVCTITDFYP

GVVTVDWKVDGTPVTQGMETTQPSKQSNNKYMASSYLTLTARAWERHSS

YSCQVTHEGHTVEKSLSRADCS);
``` or a humanized variant thereof.

The epitope of the specific binding molecule may be within an amino acid sequence comprising residues 331 to 360 of SEQ ID NO: 1. Accordingly, the epitope may be within the amino acid sequence of SEQ ID NO: 321 (KPGGGQVEVKSEKLDFKDRVQSKIGSLDNI).

The epitope may be within an amino acid sequence comprising residues 331 to 360 of SEQ ID NO: 1. This epitope may be bound by the CDRs of the specific binding molecule referred to as "CE3" herein.

The epitope may comprise the amino acid sequence of SEQ ID NO: 321 (KPGGGQVEVKSEKLDFKDRVQSKIGSLDNI). The epitope may comprise an amino acid sequence having at least 70%, at least 75%, at least 80%, at least 90%, at least 95% or at least 99% identity to SEQ ID NO: 321 (KPGGGQVEVKSEKLDFKDRVQSKIGSLDNI).

The epitope may consist of the amino acid sequence of SEQ ID NO: 321 (KPGGGQVEVKSEKLDFKDRVQSKIGSLDNI). The epitope may consist of an amino acid sequence having at least 70%, at least 75%, at least 80%, at least 90%, at least 95% or at least 99% identity to SEQ ID NO: 321 (KPGGGQVEVKSEKLDFKDRVQSKIGSLDNI).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 17 (SNAVG);

VHCDR2 comprises the sequence set forth in SEQ ID NO: 20 (GCSSDGKCYYNSALKS);

VHCDR3 comprises the sequence set forth in SEQ ID NO: 23 (GYYPVYGYDYLGTIDY);

VLCDR1 comprises the sequence set forth in SEQ ID NO: 25 (SGSSSNVGRNDVA);

VLCDR2 comprises the sequence set forth in SEQ ID NO: 28 (GTTSRPS); and

VLCDR3 comprises the sequence set forth in SEQ ID NO: 31 (ASGDSSAINDI);

or for each CDR sequence, an amino acid sequence with
(i) at least 85% identity thereto, and/or
(ii) one, two, or three amino acid substitutions relative thereto, wherein the specific binding molecule binds to a polypeptide or protein molecule comprising an amino acid sequence comprising residues 331 to 360 of SEQ ID NO: 1. The specific binding molecule comprising CDRs having 100% identity to those given above is referred to as "CE3" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 17 (SNAVG);

VHCDR2 comprises the sequence set forth in SEQ ID NO: 20 (GCSSDGKCYYNSALKS);

VHCDR3 comprises the sequence set forth in SEQ ID NO: 23 (GYYPVYGYDYLGTIDY);

VLCDR1 comprises the sequence set forth in SEQ ID NO: 25 (SGSSSNVGRNDVA);

VLCDR2 comprises the sequence set forth in SEQ ID NO: 28 (GTTSRPS); and

VLCDR3 comprises the sequence set forth in SEQ ID NO: 31 (ASGDSSAINDI).

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 543 (QVRLQESGPSLVKPSQTLSVTCTVSGFSLI);

VHFR2 comprises the sequence set forth in SEQ ID NO: 544 (WRQAPGKVPESLA);

VHFR3 comprises the sequence set forth in SEQ ID NO: n545 (RLDITRDTSKNQISLSLSSVTTD-DAAVYYCTR);

VHFR4 comprises the sequence set forth in SEQ ID NO: 546 (WGPGLLVTVSS);

VLFR1 comprises the sequence set in SEQ ID forth NO: 547 (QAVLTQPSSVSGSLGQRVSITC);

VLFR2 comprises the sequence set forth in SEQ ID NO: 548 (WFQQLPGSGLRTIIY);

VLFR3 comprises the sequence set forth in SEQ ID NO: 549 (GIPDRFSGSKSGVTATLTIDSLQAEDEAD-YFC);

VLFR4 comprises the sequence set forth in SEQ ID NO: 550 (FGSGTRLTVLG);

or for each FR sequence, an amino acid sequence with
(i) at least 50% identity thereto, and/or
(ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 543 (QVRLQESGPSLVKPSQTLSVTCTVSGFSLI);

VHFR2 comprises the sequence set forth in SEQ ID NO: 544 (WVRQAPGKVPESLA);

VHFR3 comprises the sequence set forth in SEQ ID NO: 545 (RLDITRDTSKNQISLSLSSVTTD-DAAVYYCTR);

VHFR4 comprises the sequence set forth in SEQ ID NO: 546 (WGPGLLVTVSS);

VLFR1 comprises the sequence set SEQ forth in ID NO: 547 (QAVLTQPSSVSGSLGQRVSITC);

VLFR2 comprises the sequence set forth in SEQ ID NO: 548 (WFQQLPGSGLRTIIY);

VLFR3 comprises the sequence set forth in SEQ ID NO: 549 (GIPDRFSGSKSGVTATLTIDSLQAEDEAD-YFC);

VLFR4 comprises the sequence set forth in SEQ ID NO: 550 (FGSGTRLTVLG);

or for each FR sequence, an amino acid sequence with
(i) at least 50% identity thereto, and/or
(ii) one, two, three, four or five amino acid substitutions relative thereto, wherein the specific binding molecule binds to a polypeptide or protein molecule comprising an amino acid sequence comprising residues 331 to 360 of SEQ ID NO: 1. A specific binding molecule comprising FRs having 100% identity to those given above is referred to as "CE3" herein.

The specific binding molecule may comprise:
(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 543 (QVRLQESGPSLVKP-SQTLSVTCTVSGFSLI);

VHFR2 comprises the sequence set forth in SEQ ID NO: 544 (WVRQAPGKVPESLA);

VHFR3 comprises the sequence set forth in SEQ ID NO: 545 (RLDITRDTSKNQISLSLSSVTTD-DAAVYYCTR);

VHFR4 comprises the sequence set forth in SEQ ID NO: 546 (WGPGLLVTVSS);

VLFR1 comprises the sequence set forth in SEQ ID NO: 547 (QAVLTQPSSVSGSLGQRVSITC);

VLFR2 comprises the sequence set forth in SEQ ID NO: 548 (WFQQLPGSGLRTIIY);

VLFR3 comprises the sequence set forth in SEQ ID NO: 549 (GIPDRFSGSKSGVTATLTIDSLQAE-DEADYFC);

VLFR4 comprises the sequence set forth in SEQ ID NO: 550 (FGSGTRLTVLG);

or for each FR sequence, an amino acid sequence with
(i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 17 (SNAVG);

VHCDR2 comprises the sequence set forth in SEQ ID NO: 20 (GCSSDGKCYYNSALKS);

VHCDR3 comprises the sequence set forth in SEQ ID NO: 23 (GYYPVYGYDYLGTIDY);

VLCDR1 comprises the sequence set forth in SEQ ID NO: 25 (SGSSSNVGRNDVA);

VLCDR2 comprises the sequence set forth in SEQ ID NO: 28 (GTTSRPS); and

VLCDR3 comprises the sequence set forth in SEQ ID NO: 31 (ASGDSSAINDI);

or for each CDR sequence, an amino acid sequence with (i) at least 85% identity thereto, and/or (ii) one, two, or three amino acid substitutions relative thereto wherein the specific binding molecule binds to a polypeptide or protein molecule comprising an amino acid sequence comprising residues 331 to 360 of SEQ ID NO: 1. The specific binding molecule comprising FRs and CDRs having 100% identity to those given above is referred to as "CE3" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 543 (QVRLQESGPSLVKPSQTLSVTCTVSGFSLI);

VHFR2 comprises the sequence set forth in SEQ ID NO: 544 (WVRQAPGKVPESLA);

VHFR3 comprises the sequence set forth in SEQ ID NO: 545 (RLDITRDTSKNQISLSLSSVTTDDAAVYYCTR);

VHFR4 comprises the sequence set forth in SEQ ID NO: 546 (WGPGLLVTVSS);

VLFR1 comprises the sequence set forth in SEQ ID NO: 547 (QAVLTQPSSVSGSLGQRVSITC);

VLFR2 comprises the sequence set forth in SEQ ID NO: 548 (WFQQLPGSGLRTIIY);

VLFR3 comprises the sequence set forth in SEQ ID NO: 549 (GIPDRFSGSKSGVTATLTIDSLQAEDEADYFC);

VLFR4 comprises the sequence set forth in SEQ ID NO: 550 (FGSGTRLTVLG);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 17 (SNAVG);

VHCDR2 comprises the sequence set forth in SEQ ID NO: 20 (GCSSDGKCYYNSALKS);

VHCDR3 comprises the sequence set forth in SEQ ID NO: 23 (GYYPVYGYDYLGTIDY);

VLCDR1 comprises the sequence set forth in SEQ ID NO: 25 (SGSSSNVGRNDVA);

VLCDR2 comprises the sequence set forth in SEQ ID NO: 28 (GTTSRPS); and

VLCDR3 comprises the sequence set forth in SEQ ID NO: 31 (ASGDSSAINDI);

wherein the specific binding molecule binds to a polypeptide or protein molecule comprising an amino acid sequence comprising residues 331 to 360 of SEQ ID NO: 1. The specific binding molecule comprising FRs and CDRs having 100% identity to those given above is referred to as "CE3" herein.

The specific binding molecule may comprise:

```
(a) A VH domain comprising the sequence set forth
in SEQ ID NO: 551
(QVRLQESGPSLVKPSQTLSVTCTVSGFSLISNAVGWRQAPGKVPESLA
GCSSDGKCYYNSALKSRLDITRDTSKNQISLSLSSVTTDDAAVYYCTRG
YYPVYGYDYLGTIDYWGPGLLVTVSS);
and/or (b) a VL domain comprising the sequence set forth
in SEQ ID NO: 552
(QAVLTQPSSVSGSLGQRVSITCSGSSSNVGRNDVAWFQQLPGSGLRTI
IYGTTSRPSGIPDRFSGSKSGVTATLTIDSLQAEDEADYFCASGDSSAI
NDIFGSGTRLTVLG);
``` or a humanized variant thereof.

The specific binding molecule may comprise:

```
(a) A heavy chain comprising the sequence set
forth in SEQ ID NO: 553
(QVRLQESGPSLVKPSQTLSVTCTVSGFSLISNAVGWVRQAPGKVPESL

AGCSSDGKCYYNSALKSRLDITRDTSKNQISLSLSSVTTDDAAVYYCTR

GYYPVYGYDYLGTIDYWGPGLLVTVSSAKTTAPSVYPLAPVCGDTTGSS

VTLGCLVKGYFPEPVTLTWNSGSLSSGVHTFPAVLQSDLYTLSSSVTVT

SSTWPSQSITCNVAHPASSTKVDKKIEPRGPTIKPCPPCKCPAPNLLGG

PSVFIFPPKIKDVLMISLSPIVTCVVVDVSEDDPDVQISWFVNNVEVHT

AQTQTHREDYNSTLRVVSALPIQHQDWMSGKEFKCKVNNKDLPAPIERT

ISKPKGSVRAPQVYVLPPPEEEMTKKQVTLTCMVTDFMPEDIYVEWTNN

GKTELNYKNTEPVLDSDGSYFMYSKLRVEKKNWVERNSYSCSVVHEGLH

NHHTTKSFSRTPGK);
and/or (b) a light chain comprising the sequence set
forth in SEQ ID NO: 554
(QAVLTQPSSVSGSLGQRVSITCSGSSSNVGRNDVAWFQQLPGSGLRTI

IYGTTSRPSGIPDRFSGSKSGVTATLTIDSLQAEDEADYFCASGDSSAI

NDIFGSGTRLTVLGGQPKSSPSVTLFPPSSEELETNKATLVCTITDFYP

GVVTVDWKVDGTPVTQGMETTQPSKQSNNKYMASSYLTLTARAWERHSS

YSCQVTHEGHTVEKSLSRADCS);
``` or a humanized variant thereof.

The epitope of the specific binding molecule may be within an amino acid sequence comprising residues 348 to 390 of SEQ ID NO: 1. Accordingly, the epitope may be within the amino acid sequence of SEQ ID NO: 322 (DRVQSKIGSLDNITHVPGGGNKKI-ETHKLTFRENAKAKTDHGA).

The epitope may be within an amino acid sequence comprising residues 348 to 390 of SEQ ID NO: 1. This epitope may be bound by the CDRs of the specific binding molecule referred to as "CA6" herein.

The epitope may comprise the amino id sequence of SEQ ID NO: 322 (DRVQSKIGSLDNITHVPGGGNKKI-ETHKLTFRENAKAKTDHGA). The epitope may comprise an amino acid sequence having at least 70%, at least 75%, at least 80%, at least 90%, at least 95% or at least 99% identity to SEQ ID NO: 322 (DRVQSKIGSLD-NITHVPGGGNKKIETHKLTFRENAKAKTDHGA).

The epitope may consist of the amino acid sequence of SEQ ID NO: 322 (DRVQSKIGSLDNITHVPGGGNKKI-ETHKLTFRENAKAKTDHGA). The epitope may consist of an amino acid sequence having at least 70%, at least 75%, at least 80%, at least 90%, at least 95% or at least 99% identity to SEQ ID NO: 322 (DRVQSKIGSLD-NITHVPGGGNKKIETHKLTFRENAKAKTDHGA).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 323 (DKSSGGKTYGNPALKS);

VHCDR3 comprises the sequence set forth in SEQ ID NO: 161 (CRDGGVTYGYDIDY);

VLCDR1 comprises the sequence set forth in SEQ ID NO: 324 (SGSRNNIGYGNHVG);

VLCDR2 comprises the sequence set forth in SEQ ID NO: 207 (DATTRAS); and

VLCDR3 comprises the sequence set forth in SEQ ID NO: 325 (ASFDRGSGGI);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 348 to 390 of SEQ ID NO: 1. The specific binding molecule comprising CDRs having 100% identity to those given above is referred to as "CA6" herein.

The epitope of the specific binding molecule may be within an amino acid sequence comprising residues 348 to 441 of SEQ ID NO: 1. Accordingly, the epitope may be within the amino acid sequence of SEQ ID NO: 326 (DRVQSKIGSLDNITHVPGGGNKKI-ETHKLTFRENAKAKTDHGAEIVYKSPVVSGDT-SPRHLSNVSS TGSIDMVDSPQLAT-LADEVSASLAKQGL).

The epitope may be within an amino acid sequence comprising residues 348 to 441 of SEQ ID NO: 1. This epitope may be bound by the CDRs of the specific binding molecule referred to as "CA11" herein.

The epitope may comprise the amino acid sequence of SEQ ID NO: 326 (DRVQSKIGSLDNITHVPGGGNKKI-ETHKLTFRENAKAKTDHGAEIVYKSPVVSGDT-SPRHLSNVSS TGSIDMVDSPQLAT-LADEVSASLAKQGL). The epitope may comprise an amino acid sequence having at least 70%, at least 75%, at least 80%, at least 90%, at least 95% or at least 99% identity to SEQ ID NO: 326 (DRVQSKIGSLDNITHVPGGGNK-KIETHKLTFRENAKAKTDHGAEIVYKSPVVSGDT-SPRHLSNVSS TGSIDMVDSPQLAT-LADEVSASLAKQGL).

The epitope may consist of the amino acid sequence of SEQ ID NO: 326 (DRVQSKIGSLDNITHVPGGGNKKI-ETHKLTFRENAKAKTDHGAEIVYKSPVVSGDT-SPRHLSNVSS TGSIDMVDSPQLAT-LADEVSASLAKQGL). The epitope may consist of an amino acid sequence having at least 70%, at least 75%, at least 80%, at least 90%, at least 95% or at least 99% identity to SEQ ID NO: 326 (DRVQSKIGSLDNITHVPGGGNK-KIETHKLTFRENAKAKTDHGAEIVYKSPVVSGDT-SPRHLSNVSS TGSIDMVDSPQLAT-LADEVSASLAKQGL).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 272 (SNTVA);

VHCDR2 comprises the sequence set forth in SEQ ID NO: 273 (EINSGGSTYYNPALKS);

VHCDR3 comprises the sequence set forth in SEQ ID NO: 274 (GARSTYAAY);

VLCDR1 comprises the sequence set forth in SEQ ID NO: 327 (SGSGSNIGAGNWVS);

VLCDR2 comprises the sequence set forth in SEQ ID NO: 328 (GATSRPS); and

VLCDR3 comprises the sequence set forth in SEQ ID NO: 329 (AAYDSGSSIV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 348 to 441 of SEQ ID NO: 1. The specific binding molecule comprising CDRs having 100% identity to those given above is referred to as "CA11" herein.

The epitope of the specific binding molecule may be within an amino acid sequence comprising residues 355 to 367 of SEQ ID NO: 1. Accordingly, the epitope may be within the amino acid sequence of SEQ ID NO: 330 (GSLD-NITHVPGGG).

The epitope may be within an amino acid sequence comprising residues 355 to 367 of SEQ ID NO: 1. This epitope may be bound by the CDRs of the specific binding molecule referred to as "CA4" herein. Critical residues of the epitope may be residues 358 (D), 360 (I), 361 (T), 362 (H) and/or 364 (P) (numbering according to SEQ ID NO: 1). The epitope may comprise the amino acid sequence of SEQ ID NO: 331 (XXXDXITHXPXXX, wherein X is any amino acid). The epitope may comprise the amino acid sequence of SEQ ID NO: 330, wherein any one or more residue other than residue number 358 (D), 360 (I), 361 (T), 362 (H) and/or 364 (P) (numbering according to SEQ ID NO: 1) is replaced by a non-conservative amino acid substitution (numbering according to SEQ ID NO: 1). The epitope may comprise the amino acid sequence of SEQ ID NO: 330, wherein any one or more residue other than residue number 358 (D), 360 (I), 361 (T), 362 (H) and/or 364 (P) (numbering according to SEQ ID NO: 1) is replaced by a conservative amino acid substitution (numbering according to SEQ ID NO: 1). The epitope may comprise the amino acid sequence of SEQ ID NO: 330, wherein any one or more residue other than residue number 358 (D), 360 (I), 361 (T), 362 (H) and/or 364 (P) (numbering according to SEQ ID NO: 1) is replaced by a conservative amino acid substitution (numbering according to SEQ ID NO: 1) and any one or more residue other than residue number 358 (D), 360 (I), 361 (T), 362 (H) and/or 364 (P) (numbering according to SEQ ID NO: 1) is replaced by a non-conservative amino acid substitution (numbering according to SEQ ID NO: 1).

The epitope may comprise the amino acid sequence of SEQ ID NO: 330 (GSLDNITHVPGGG). The epitope may comprise an amino acid sequence having at least 70%, at least 75%, at least 80%, at least 90%, at least 95% or at least 99% identity to SEQ ID NO: 330 (GSLDNITHVPGGG).

The epitope may consist of the amino acid sequence of SEQ ID NO: 330 (GSLDNITHVPGGG). The epitope may consist of an amino acid sequence having at least 70%, at least 75%, at least 80%, at least 90%, at least 95% or at least 99% identity to SEQ ID NO: 330 (GSLDNITHVPGGG).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 83 (SYSVY);

VHCDR2 comprises the sequence set forth in SEQ ID NO: 84 (IMYASGRVDYNPALKS);

VHCDR3 comprises the sequence set forth in SEQ ID NO: 89 (GIEN);

VLCDR1 comprises the sequence set forth in SEQ ID NO: 91 (RTSQSVNNYLS);

VLCDR2 comprises the sequence set forth in SEQ ID NO: 95 (YATRLYT); and

VLCDR3 comprises the sequence set forth in SEQ ID NO: 97 (LQYDSTPLA);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 355 to 367 of SEQ ID NO: 1. The specific binding molecule comprising CDRs having 100% identity to those given above is referred to as "CA4" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 83 (SYSVY);

VHCDR2 comprises the sequence set forth in SEQ ID NO: 84 (IMYASGRVDYNPALKS);

VHCDR3 comprises the sequence set forth in SEQ ID NO: 89 (GIEN);

VLCDR1 comprises the sequence set forth in SEQ ID NO: 91 (RTSQSVNNYLS);

VLCDR2 comprises the sequence set forth in SEQ ID NO: 95 (YATRLYT); and

VLCDR3 comprises the sequence set forth in SEQ ID NO: 97 (LQYDSTPLA).

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 555 (QVQLQESGPSLVKPSQTLSLTCTVSGFSLT);

VHFR2 comprises the sequence set forth in SEQ ID NO: 556 (WVRQAPGQALEWIS);

VHFR3 comprises the sequence set forth in SEQ ID NO: 557 (RLSITRDTSKSQFSLSLSSVTTED-TAVYYCTR);

VHFR4 comprises the sequence set forth in SEQ ID NO: 558 (WGPGLLVTVSS);

VLFR1 comprises the sequence set forth in SEQ ID NO: 559 (DIQVTQSPSSLSASLTERVSITC);

VLFR2 comprises the sequence set forth in SEQ ID NO: 560 (WYQQKPGQAPKLLIY);

VLFR3 comprises the sequence set forth in SEQ ID NO: 561 (DVPSRFSGSGSGTDYTLTITSLEADD-TATYYC);

VLFR4 comprises the sequence set forth in SEQ ID NO: 562 (FGGGTNVEIK);

or for each FR sequence, an amino acid sequence with (i) at least 50% identity thereto, and/or (ii) one, two, three, four or five amino acid substitutions relative thereto.

The specific binding molecule may comprise framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 555 (QVQLQESGPSLVKPSQTLSLTCTVSGFSLT);

VHFR2 comprises the sequence set forth in SEQ ID NO: 556 (WVRQAPGQALEWIS);

VHFR3 comprises the sequence set forth in SEQ ID NO: 557 (RLSITRDTSKSQFSLSLSSVTTED-TAVYYCTR);

VHFR4 comprises the sequence set forth in SEQ ID NO: 558 (WGPGLLVTVSS);

VLFR1 comprises the sequence set forth in SEQ ID NO: 559 (DIQVTQSPSSLSASLTERVSITC);

VLFR2 comprises the sequence set forth in SEQ ID NO: 560 (WYQQKPGQAPKLLIY);

VLFR3 comprises the sequence set forth in SEQ ID NO: 561 (DVPSRFSGSGSGTDYTLTITSLEADD-TATYYC);

VLFR4 comprises the sequence set forth in SEQ ID NO: 562 (FGGGTNVEIK);

or for each FR sequence, an amino acid sequence with (i) at least 50% identity thereto, and/or (ii) one, two, three, four or five amino acid substitutions relative thereto, wherein the specific binding molecule binds to a polypeptide or protein molecule comprising an amino acid sequence comprising residues 355 to 367 of SEQ ID NO: 1. A specific binding molecule comprising FRs having 100% identity to those given above is referred to as "CA4" herein.

The specific binding molecule may comprise:

(a) framework regions (FRs) VHFR1, VHFR2. VHFR3, VHFR4, VLFR1, VLFR2, VLFR3 and VLFR4, wherein each of said FRs comprises an amino acid sequence as follows:

VHFR1 comprises the sequence set forth in SEQ ID NO: 555 (QVQLQESGPSLVKP-SQTLSLTCTVSGFSLT);

VHFR2 comprises the sequence set forth in SEQ ID NO: 556 (WVRQAPGQALEWIS);

VHFR3 comprises the sequence set forth in SEQ ID NO: 557 (RLSITRDTSKSQFSLSLSSVTTED-TAVYYCTR);

VHFR4 comprises the sequence set forth in SEQ ID NO: 558 (WGPGLLVTVSS);

VLFR1 comprises the sequence set forth in SEQ ID NO: 559 (DIQVTQSPSSLSASLTERVSITC);

VLFR2 comprises the sequence set forth in SEQ ID NO: 560 (WYQQKPGQAPKLLIY);

VLFR3 comprises the sequence set forth in SEQ ID NO: 561 (DVPSRFSGSGSGTDYTLTITSLEADD-TATYYC);

VLFR4 comprises the sequence set forth in SEQ ID NO: 562 (FGGGTNVEIK);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 83 (SYSVY);

VHCDR2 comprises the sequence set forth in SEQ ID NO: 84 (IMYASGRVDYNPALKS);

VHCDR3 comprises the sequence set forth in SEQ ID NO: 89 (GIEN);

VLCDR1 comprises the sequence set forth in SEQ ID NO: 91 (RTSQSVNNYLS);

VLCDR2 comprises the sequence set forth in SEQ ID NO: 95 (YATRLYT); and

VLCDR3 comprises the sequence set forth in SEQ ID NO: 97 (LQYDSTPLA);

or for each CDR sequence, an amino acid sequence with (i) at least 85% identity thereto, and/or (ii) one, two, or three amino acid substitutions relative thereto wherein the specific binding molecule binds to a polypeptide or protein molecule comprising an amino acid sequence comprising residues 355 to 367 of SEQ ID NO: 1. The specific binding molecule comprising FRs and CDRs having 100% identity to those given above is referred to as "CA4" herein.

The specific binding molecule may comprise:

(a) framework regions (FRs) VHFR1, VHFR2, VHFR3, VHFR4, VLFR1, VLFR2, VLFR3 and VLFR4, wherein each of said FRs comprises an amino acid sequence as follows:

VHFR1 comprises the sequence set forth in SEQ ID NO: 555 (QVQLQESGPSLVKPSQTLSLTCTVSGFSLT);

VHFR2 comprises the sequence set forth in SEQ ID NO: 556 (WRQAPGQALEWIS);

VHFR3 comprises the sequence set forth in SEQ ID NO: 557 (RLSITRDTSKSQFSLSLSSVTTEDTAVYYCTR);

VHFR4 comprises the sequence set forth in SEQ ID NO: 558 (WGPGLLVTVSS);

VLFR1 comprises the sequence set forth in SEQ ID NO: 559 (DIQVTQSPSSLSASLTERVSITC);

VLFR2 comprises the sequence set forth in SEQ ID NO: 560 (WYQQKPGQAPKLLIY);

VLFR3 comprises the sequence set forth in SEQ ID NO: 561 (DVPSRFSGSGSGTDYTLTITSLEADDTATYYC);

VLFR4 comprises the sequence set forth in SEQ ID NO: 562 (FGGGTNVEIK);

or for each FR sequence, an amino acid sequence with (i) at least 50% identity thereto, and/or (ii) one, two, three, four or five amino acid substitutions relative thereto; and (b) the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 83 (SYSVY);

VHCDR2 comprises the sequence set forth in SEQ ID NO: 84 (IMYASGRVDYNPALKS);

VHCDR3 comprises the sequence set forth in SEQ ID NO: 89 (GIEN);

VLCDR1 comprises the sequence set forth in SEQ ID NO: 91 (RTSQSVNNYLS);

VLCDR2 comprises the sequence set forth in SEQ ID NO: 95 (YATRLYT); and

VLCDR3 comprises the sequence set forth in SEQ ID NO: 97 (LQYDSTPLA);

wherein the specific binding molecule binds to a polypeptide or protein molecule comprising an amino acid sequence comprising residues 355 to 367 of SEQ ID NO: 1. The specific binding molecule comprising FRs and CDRs having 100% identity to those given above is referred to as "CA4" herein.

The specific binding molecule may comprise:

```
(a) A VH domain comprising the sequence set forth
in SEQ ID NO: 563
(QVQLQESGPSLVKPSQTLSLTCTVSGFSLTSYSVYWRQAPGQALEWIS
IMYASGRVDYNPALKSRLSITRDTSKSQFSLSLSSVTTEDTAVYYCTRG
IENWGPGLLVTVSS);
and/or
```

```
(b) a VL domain comprising the sequence set forth
in SEQ ID NO: 564
(DIQVTQSPSSLSASLTERVSITCRTSQSVNNYLSWYQQKPGQAPKLLI
YYATRLYTDVPSRFSGSGSGTDYTLTITSLEADDTATYYCLQYDSTPLA
FGGGTNVEIK);
``` or a humanized variant thereof.

The specific binding molecule may comprise:

```
(a) A heavy chain comprising the sequence set
forth in SEQ ID NO: 565
(QVQLQESGPSLVKPSQTLSLTCTVSGFSLTSYSVYWRQAPGQALEWIS

IMYASGRVDYNPALKSRLSITRDTSKSQFSLSLSSVTTEDTAVYYCTRG

IENWGPGLLVTVSSAKTTAPSVYPLAPVCGDTTGSSVTLGCLVKGYFPE

PVTLTWNSGSLSSGVHTFPAVLQSDLYTLSSSVTVTSSTWPSQSITCNV

AHPASSTKVDKKIEPRGPTIKPCPPCKCPAPNLLGGPSVFIFPPKIKDV

LMISLSPIVTCVVVDVSEDDPDVQISWFVNNVEVHTAQTQTHREDYNST

LRVVSALPIQHQDWMSGKEFKCKVNNKDLPAPIERTISKPKGSVRAPQV

YVLPPPEEEMTKKQVTLTCMVTDFMPEDIYVEWTNNGKTELNYKNTEPV

LDSDGSYFMYSKLRVEKKNWVERNSYSCSVVHEGLHNHHTTKSFSRTPG

K);
and/or
```

```
(b) a light chain comprising the sequence set
forth in SEQ ID NO: 566
(DIQVTQSPSSLSASLTERVSITCRTSQSVNNYLSWYQQKPGQAPKLLI

YYATRLYTDVPSRFSGSGSGTDYTLTITSLEADDTATYYCLQYDSTPLA

FGGGTNVEIKGQPKSSPSVTLFPPSSEELETNKATLVCTITDFYPGVVT

VDWKVDGTPVTQGMETTQPSKQSNNKYMASSYLTLTARAWERHSSYSCQ

VTHEGHTVEKSLSRADCS);
``` or a humanized variant thereof.

The epitope of the specific binding molecule may be within an amino acid sequence comprising residues 359 to 391 of SEQ ID NO: 1. Accordingly, the epitope may be within the amino acid sequence of SEQ ID NO: 332 (NITHVPGGGNKKIETHKLTFRENAKAKTDHGAE).

The epitope may be within an amino acid sequence comprising residues 359 to 391 of SEQ ID NO: 1. This epitope may be bound by the CDRs of the specific binding molecule referred to as "CB2" herein.

The epitope may comprise the amino acid sequence of SEQ ID NO: 332 (NITHVPGGGNKKI- ETHKLTFRENAKAKTDHGAE). The epitope may comprise an amino acid sequence having at least 70%, at least 75%, at least 80%, at least 90%, at least 95% or at least 99% identity to SEQ ID NO: 332 (NITHVPGGGNKKI-ETHKLTFRENAKAKTDHGAE).

The epitope may consist of the amino acid sequence of SEQ ID NO: 332 (NITHVPGGGNKKI-ETHKLTFRENAKAKTDHGAE). The epitope may consist of an amino acid sequence having at least 70%, at least 75%, at least 80%, at least 90%, at least 95% or at least 99% identity to SEQ ID NO: 332 (NITHVPGGGNKKI-ETHKLTFRENAKAKTDHGAE).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 45 (TNSVG);
VHCDR2 comprises the sequence set forth in SEQ ID NO: 53 (GIDTDGEEGFNPVLKS);
VHCDR3 comprises the sequence set forth in SEQ ID NO: 55 (SYRTDGLAYGYVQAIDY);
VLCDR1 comprises the sequence set forth in SEQ ID NO: 68 (SGSY/GSSGVG);
VLCDR2 comprises the sequence set forth in SEQ ID NO: 70 (ASDGRPS); and
VLCDR3 comprises the sequence set forth in SEQ ID NO: 79 (GSSDRTQYTGL):
or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 359 to 391 of SEQ ID NO: 1. The specific binding molecule comprising CDRs having 100% identity to those given above is referred to as "CB2" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 45 (TNSVG);
VHCDR2 comprises the sequence set forth in SEQ ID NO: 53 (GIDTDGEEGFNPVLKS);
VHCDR3 comprises the sequence set forth in SEQ ID NO: 55 (SYRTDGLAYGYVQAIDY);
VLCDR1 comprises the sequence set forth in SEQ ID NO: 68 (SGSY/GSSGVG);
VLCDR2 comprises the sequence set forth in SEQ ID NO: 70 (ASDGRPS); and
VLCDR3 comprises the sequence set forth in SEQ ID NO: 79 (GSSDRTQYTGL).

The epitope of the specific binding molecule may be within an amino acid sequence comprising residues 360 to 390 of SEQ ID NO: 1. Accordingly, the epitope may be within the amino acid sequence of SEQ ID NO: 333 (ITHVPGGGNKKIETHKLTFRENAKAKTDHGA).

The epitope may be within an amino acid sequence comprising residues 360 to 390 of SEQ ID NO: 1. This epitope may be bound by the CDRs of the specific binding molecule referred to as "CB3" herein.

The epitope may comprise the amino acid sequence of SEQ ID NO: 333 (ITHVPGGGNKKI-ETHKLTFRENAKAKTDHGA). The epitope may comprise an amino acid sequence having at least 70%, at least 75%, at least 80%, at least 90%, at least 95% or at least 99% identity to SEQ ID NO: 333 (ITHVPGGGNKKI-ETHKLTFRENAKAKTDHGA).

The epitope may consist of the amino acid sequence of SEQ ID NO: 333 (ITHVPGGGNKKI-ETHKLTFRENAKAKTDHGA). The epitope may consist of an amino acid sequence having at least 70%, at least 75%, at least 80%, at least 90%, at least 95% or at least 99% identity to SEQ ID NO: 333 (ITHVPGGGNKKI-ETHKLTFRENAKAKTDHGA).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 334 (SVAVN);
VHCDR2 comprises the sequence set forth in SEQ ID NO: 335 (GIISNGGTGYNPALKS);
VHCDR3 comprises the sequence set forth in SEQ ID NO: 336 (GVEWEGSMDY);
VLCDR1 comprises the sequence set forth in SEQ ID NO: 337 (SGSSSNVGAGSYVG);
VLCDR2 comprises the sequence set forth in SEQ ID NO: 338 (GATKRAS); and
VLCDR3 comprises the sequence set forth in SEQ ID NO: 339 (VSYQTDFTLV);
or for each CDR sequence, an amino acid sequence with
(i) at least 85% identity thereto, and/or
(ii) one, two, or three amino acid substitutions relative thereto,
wherein the specific binding molecule binds to a polypeptide or protein molecule comprising an amino acid sequence comprising residues 360 to 390 of SEQ ID NO: 1. The specific binding molecule comprising CDRs having 100% identity to those given above is referred to as "CB3" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 334 (SVAVN);
VHCDR2 comprises the sequence set forth in SEQ ID NO: 335 (GIISNGGTGYNPALKS);
VHCDR3 comprises the sequence set forth in SEQ ID NO: 336 (GVEWEGSMDY);
VLCDR1 comprises the sequence set forth in SEQ ID NO: 337 (SGSSSNVGAGSYVG);
VLCDR2 comprises the sequence set forth in SEQ ID NO: 338 (GATKRAS); and
VLCDR3 comprises the sequence set forth in SEQ ID NO: 339 (VSYQTDFTLV).

The epitope of the specific binding molecule may be within an amino acid sequence comprising residues 367 to 379 of SEQ ID NO: 1. Accordingly, the epitope may be within the amino acid sequence of SEQ ID NO: 33 (GNK-KIETHKLTFR).

The epitope may be within an amino acid sequence comprising residues 367 to 379 of SEQ ID NO: 1. This epitope may be bound by the CDRs of the specific binding molecules referred to as "CA9" and "CA12" herein. Critical residues of the epitope may be residues 370 (K), and/or 374 (H) (numbering according to SEQ ID NO: 1). The epitope may comprise the amino acid sequence of SEQ ID NO: 34 (XXXKXXXHXXXX, wherein X is any amino acid). The epitope may comprise the amino acid sequence of SEQ ID NO: 33, wherein any one or more residue other than residue number 370 (K), and/or 374 (H) is replaced by a non-conservative amino acid substitution (numbering according to SEQ ID NO: 1). The epitope may comprise the amino acid sequence of SEQ ID NO: 33, wherein any one or more residue other than residue number 370 (K), and/or 374 (H) is replaced by a conservative amino acid substitution (numbering according to SEQ ID NO: 1). The epitope may comprise the amino acid sequence of SEQ ID NO: 33, wherein any one or more residue other than residue number 370 (K), and/or 374 (H) is replaced by a conservative amino acid substitution (numbering according to SEQ ID NO: 1) and any one or more residue other than residue number 370 (K), and/or 374 (H) is replaced by a non-conservative amino acid substitution (numbering according to SEQ ID NO: 1).

The epitope may comprise the amino acid sequence of SEQ ID NO: 33 (GNKKIETHKLTFR). The epitope may comprise an amino acid sequence having at least 70%, at least 75%, at least 80%, at least 90%, at least 95% or at least 99% identity to SEQ ID NO: 33 (GNKKIETHKLTFR).

The epitope may consist of the amino acid sequence of SEQ ID NO: 33 (GNKKIETHKLTFR). The epitope may consist of an amino acid sequence having at least 70%, at least 75%, at least 80%, at least 90%, at least 95% or at least 99% identity to SEQ ID NO: 33 (GNKKIETHKLTFR).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 58 (SYRSDGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS); and

VLCDR3 comprises the sequence set forth in SEQ ID NO: 74 (GSSDRTQYTGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 367 to 379 of SEQ ID NO: 1. The specific binding molecule comprising CDRs having 100% identity to those given above is referred to as "CA9" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 58 (SYRSDGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS); and

VLCDR3 comprises the sequence set forth in SEQ ID NO: 74 (GSSDRTQYTGV).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 44 (SYYVG);

VHCDR2 comprises the sequence set forth in SEQ ID NO: 52 (NIYSTGRAFYNPALKS);

VHCDR3 comprises the sequence set forth in SEQ ID NO: 265 (GSYYHGGGNGMVDFFDY);

VLCDR1 comprises the sequence set forth in SEQ ID NO: 39 (SGSSSNVGYGNYVG);

VLCDR2 comprises the sequence set forth in SEQ ID NO: 72 (AATSRAS); and

VLCDR3 comprises the sequence set forth in SEQ ID NO: 78 (SSYQRGNTGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 367 to 379 of SEQ ID NO: 1. The specific binding molecule comprising CDRs having 100% identity to those given above is referred to as "CA12" herein The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 44 (SYYVG);

VHCDR2 comprises the sequence set forth in SEQ ID NO: 52 (NIYSTGRAFYNPALKS);

VHCDR3 comprises the sequence set forth in SEQ ID NO: 265 (GSYYHGGGNGMVDFFDY);

VLCDR1 comprises the sequence set forth in SEQ ID NO: 39 (SGSSSNVGYGNYVG);

VLCDR2 comprises the sequence set forth in SEQ ID NO: 72 (AATSRAS); and

VLCDR3 comprises the sequence set forth in SEQ ID NO: 78 (SSYQRGNTGV).

The epitope of the specific binding molecule may be within an amino acid sequence comprising residues 49 to 113 of SEQ ID NO: 1. Accordingly, the epitope may be within the amino acid sequence of SEQ ID NO: 340 (QTPTEDGSEEPGSETSDAKSTPTAEDVTAPLVDEGAPGKQAAAQPHTEIPEGTTAEEAGIGDTPS).

The epitope may be within an amino acid sequence comprising residues 49 to 113 of SEQ ID NO: 1. This epitope may be bound by the CDRs of the specific binding molecule referred to as "CB5" herein.

The epitope may comprise the amino acid sequence of SEQ ID NO: 340 (QTPTEDGSEEPGSETSDAKSTPTAEDVTAPLVDEGAPGKQAAAQPHTEIPEGTTAEEAGIGDTPS).

The epitope may comprise an amino acid sequence having at least 70%, at least 75%, at least 80%, at least 90%, at least 95% or at least 99% identity to SEQ ID NO: 340 (QTPTEDGSEEPGSETSDAKSTPTAEDVTAPLVDEGAPGKQAAAQPHTEIPEGTTAEEAGIGDTPS).

The epitope may consist of the amino acid sequence of SEQ ID NO: 340 (QTPTEDGSEEPGSETSDAKSTPTAEDVTAPLVDEGAPGKQAAAQPHTEIPEGTTAEEAGIGDTPS).

The epitope may consist of an amino acid sequence having at least 70%, at least 75%, at least 80%, at least 90%, at least 95% or at least 99% identity to SEQ ID NO: 340 (QTPTEDGSEEPGSETSDAKSTPTAEDVTAPLVDEGAPGKQAAAQPHTEIPEGTTAEEAGIGDTPS).

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 341 (DITSGGRTYGNLALKS);

VHCDR3 comprises the sequence set forth in SEQ ID NO: 160 (CRDGGVSYGYDSDY);

VLCDR1 comprises the sequence set forth in SEQ ID NO: 342 (SGSSSNVGSGDHVN);

VLCDR2 comprises the sequence set forth in SEQ ID NO: 343 (RTTNRAS); and

VLCDR3 comprises the sequence set forth in SEQ ID NO: 344 (ASHDNNSGGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 49 to 113 of SEQ ID NO: 1. The specific binding molecule comprising CDRs having 100% identity to those given above is referred to as "CB5" herein.

The epitope of the specific binding molecule may be within an amino acid sequence comprising residues 49 to 155 of SEQ ID NO: 1. Accordingly, the epitope may be within the amino acid sequence of SEQ ID NO: 345 (QTPT-EDGSEEPGSETSDAKSTPTAEDVTAPLVDE-GAPGKQAAAQPHTEIPEGTTAEEAGIGDTPS LEDEAAGHVTQARMVSKSKDGTGSDDKKAKGAD-GKTKIATPR).

The epitope may be within an amino acid sequence comprising residues 49 to 155 of SEQ ID NO: 1. This epitope may be bound by the CDRs of the specific binding molecules referred to as "CC4" and "CD1" herein.

The epitope may comprise the amino acid sequence of SEQ ID NO: 345 (QTPTEDGSEEPGSETSDAKSTPTAE-DVTAPLVDEGAPGKQAAAQPHTEIPEGTTAEEA-GIGDTPS LEDEAAGHVTQARMVSKSKDGTGSDDK-KAKGADGKTKIATPR). The epitope may comprise an amino acid sequence having at least 70%, at least 75%, at least 80%, at least 90%, at least 95% or at least 99% identity to SEQ ID NO 345 (QTPTEDGSEEPGSETSDAKSTP-TAEDVTAPLVDEGAPGKQAAAQPHTEIPEGTTAEEA-GIGDTPS LEDEAAGHVTQARMVSKSKDGTGSDDK-KAKGADGKTKIATPR).

The epitope may consist of the amino acid sequence of SEQ ID NO: 345 (QTPTEDGSEEPGSETSDAKSTPTAE-DVTAPLVDEGAPGKQAAAQPHTEIPEGTTAEEA-GIGDTPS LEDEAAGHVTQARMVSKSKDGTGSDDK-KAKGADGKTKIATPR). The epitope may consist of an amino acid sequence having at least 70%, at least 75%, at least 80%, at least 90%, at least 95% or at least 99% identity ID to SEQ NO: 345 (QTPTEDGSEEPGSETSDAKSTP-TAEDVTAPLVDEGAPGKQAAAQPHTEIPEGTTAEEA-GIGDTPS LEDEAAGHVTQARMVSKSKDGTGSDDK-KAKGADGKTKIATPR).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 158 (DIASSGKAYSNPALKS);

VHCDR3 comprises the sequence set forth in SEQ ID NO: 161 (CRDGGVTYGYDIDY);

VLCDR1 comprises the sequence set forth in SEQ ID NO: 346 (SGSSSNVGYTNLGYSNLVT);

VLCDR2 comprises the sequence set forth in SEQ ID NO: 170 (GATNRAS); and

VLCDR3 comprises the sequence set forth in SEQ ID NO: 347 (ASYDSSNGGI);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 49 to 155 of SEQ ID NO: 1. The specific binding molecule comprising CDRs having 100% identity to those given above is referred to as "CC4" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 182 (DKSSAGKTYGNPALKS);

VHCDR3 comprises the sequence set forth in SEQ ID NO: 286 (CRDGGVSYGYDVDY);

VLCDR1 comprises the sequence set forth in SEQ ID NO: 290 (SGSSSNVGYGTYVS);

VLCDR2 comprises the sequence set forth in SEQ ID NO: 188 (GTTTRAS); and

VLCDR3 comprises the sequence set forth in SEQ ID NO: 291 (ASYDTGSGGV):

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 49 to 155 of SEQ ID NO: 1. The specific binding molecule comprising CDRs having 100% identity to those given above is referred to as "CD1" herein.

The epitope of the specific binding molecule may be within an amino acid sequence comprising residues 49 to 238 of SEQ ID NO: 1. Accordingly, the epitope may be within the amino acid sequence of SEQ ID NO: 348 (QTPT-EDGSEEPGSETSDAKSTPTAEDVTAPLVDE-GAPGKQAAAQPHTEIPEGTTAEEAGIGDTPS LEDEAAGHVTQARMVSKSKDGTGSDDKKAKGAD-GKTKIATPRGAAPPGQKGQANATRIPAKTPP APKTPPSSGEPPKSGDRSGYSSPGSPGTPGSRSRTPS LPTPPTREPKKVAVVRTPPKSPSS).

The epitope may be within an amino acid sequence comprising residues 49 to 238 of SEQ ID NO: 1. This epitope may be bound by the CDRs of the specific binding molecule referred to as "CC5" herein.

The epitope may comprise the amino sequence of SEQ ID NO: 348 (QTPTEDGSEEPGSETSDAKSTPTAEDVTA-PLVDEGAPGKQAAAQPHTEIPEGTTAEEAGIGDTPS LEDEAAGHVTQARMVSKSKDGTGSDDKKAKGAD-GKTKIATPRGAAPPGQKGQANATRIPAKTPP APKTPPSSGEPPKSGDRSGYSSPGSPGTPGSRSRTPSL PTPPTREPKKVAVVRTPPKSPSS). The epitope may comprise an amino acid sequence having at least 70%, at least 75%, at least 80%, at least 90%, least or at 99% identity SEQ least to ID NO: 348 at 95% (QTPTEDGSEEPGSETSDAK-STPTAEDVTAPLVDEGAPGKQAAAQPHTEIPEGT-TAEEA- GIGDTPS LEDEAAGHVTQARMVSKSKDGTGSDDK-KAKGADGKTKIATPRGAAPPGQKGQANATRIPAKTPP APKTPPSSGEPPKSGDRSGYSSPGSPGTPGSRSRTPSLP TPPTREPKKVAVVRTPPKSPSS).

The epitope may consist of the amino acid sequence of SEQ ID NO: 348 (QTPTEDGSEEPGSETSDAKSTPTAE-DVTAPLVDEGAPGKQAAAQPHTEIPEGTTAEEA-GIGDTPS LEDEAAGHVTQARMVSKSKDGTGSDDK-KAKGADGKTKIATPRGAAPPGQKGQANATRIPAKTPP APKTPPSSGEPPKSGDRSGYSSPGSPGTPGSRSRTPSL PTPPTREPKKVAVVRTPPKSPSS). The epitope may consist of an amino acid sequence having at least 70%, at least 75%, at least 80%, at least 90%, at least 95% or at least 99% identity to SEQ ID NO: 348 (QTPTEDGSEEPGSETSDAK-STPTAEDVTAPLVDEGAPGKQAAAQPHTEIPEGT-TAEEAGIGDTPS LEDEAAGHVTQARMVSK-SKDGTGSDDKKAKGADGKTKIATPRGAAPPGQKGQ ANATRIPAKTPP APKTPPSSGEPPKSGDRSGYSSPGSPGTPGSRSRTPS LPTPPTREPKKVAVVRTPPKSPSS).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 259 (SNGVG);

VHCDR2 comprises the sequence set forth in SEQ ID NO: 349 (DISSVGKKYASPALKS);

VHCDR3 comprises the sequence set forth in SEQ ID NO: 161 (CRDGGVTYGYDIDY);

VLCDR1 comprises the sequence set forth in SEQ ID NO: 39 (SGSSSNVGYGNYVG);

VLCDR2 comprises the sequence set forth in SEQ ID NO: 141 (GATSRAS); and

VLCDR3 comprises the sequence set forth in SEQ ID NO: 350 (ASYDSSNGGV):

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 49 to 238 of SEQ ID NO: 1. The specific binding molecule comprising CDRs having 100% identity to those given above is referred to as "CC5" herein.

The epitope of the specific binding molecule may be within an amino acid sequence comprising residues 373 to 385 of SEQ ID NO: 1. Accordingly, the epitope may be within the amino acid sequence of SEQ ID NO: 351 (THKLTFRENAKAK).

The epitope may be within an amino acid sequence comprising residues 373 to 385 of SEQ ID NO: 1. This epitope may be bound by the CDRs of the specific binding molecule referred to as "MD9" or "MoD9" herein.

The epitope may comprise the amino acid sequence of SEQ ID NO: 351 (THKLTFRENAKAK). The epitope may comprise an amino acid sequence having at least 70%, at least 75%, at least 80%, at least 90%, at least 95% or at least 99% identity to SEQ ID NO: 351 (THKLTFRENAKAK).

The epitope may consist of the amino acid sequence of SEQ ID NO: 351 (THKLTFRENAKAK). The epitope may consist of an amino acid sequence having at least 70%, at least 75%, at least 80%, at least 90%, at least 95% or at least 99% identity to SEQ ID NO: 351 (THKLTFRENAKAK).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 102 (RESIA);

VHCDR2 comprises the sequence set forth in SEQ ID NO: 103 (GVGIDGTSYYSPALKS);

VHCDR3 comprises the sequence set forth in SEQ ID NO: 104 (NYIDFEY);

VLCDR1 comprises the sequence set forth in SEQ ID NO: 352 (SGSSSNVGIYDVS);

VLCDR2 comprises the sequence set forth in SEQ ID NO: 353 (GTNNRPS); and

VLCDR3 comprises the sequence set forth in SEQ ID NO: 354 (AAGDSSTIAV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 373 to 385 of SEQ ID NO: 1. The specific binding molecule comprising CDRs having 100% identity to those given above is referred to as "MD9" or "MoD9" herein.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 102 (RESIA);

VHCDR2 comprises the sequence set forth in SEQ ID NO: 103 (GVGIDGTSYYSPALKS);

VHCDR3 comprises the sequence set forth in SEQ ID NO: 104 (NYIDFEY);

VLCDR1 comprises the sequence set forth in SEQ ID NO: 352 (SGSSSNVGIYDVS);

VLCDR2 comprises the sequence set forth in SEQ ID NO: 353 (GTNNRPS); and

VLCDR3 comprises the sequence set forth in SEQ ID NO: 354 (AAGDSSTIAV).

The epitope of the specific binding molecule may be within an amino acid sequence comprising residues 275 to 305 and/or residues 337 to 368 of SEQ ID NO: 1. Accordingly, the epitope may be within the amino acid sequence of SEQ ID NO: 355 (VQIINKKLDLSNVQSKCGSKD-NIKHVPGGGS) and/or SEQ ID NO: 356 (VEVKSEKLDFKDRVQSKIGSLDNITHVPGGGN).

The epitope may be within an amino acid sequence comprising residues 275 to 305 and/or residues 337 to 368 of SEQ ID NO: 1. This epitope may be bound by the CDRs of the specific binding molecule referred to as "NS1G7" herein.

The epitope may comprise the amino acid sequence of SEQ ID NO: 355 (VQIINKKLDLSNVQSKCGSKD-NIKHVPGGGS) and/or SEQ ID NO: 356 (VEVKSEKLDFKDRVQSKIGSLDNITHVPGGGN). The epitope may comprise an amino acid sequence having at least 70%, at least 75%, at least 80%, at least 90%, at least 95% or at least 99% identity to SEQ ID NO: 355 (VQI-INKKLDLSNVQSKCGSKDNIKHVPGGGS) and/or SEQ ID NO: 356 (VEVKSEKLDFKDRVQSKIGSLD-NITHVPGGGN).

The epitope may consist of the amino acid sequence of SEQ ID NO: 355 (VQIINKKLDLSNVQSKCGSKD-NIKHVPGGGS) and/or SEQ ID NO: 356

(VEVKSEKLDFKDRVQSKIGSLDNITHVPGGGN). The epitope may consist of an amino acid sequence having at least 70%, at least 75%, at least 80%, at least 90%, at least 95% or at least 99% identity to SEQ ID NO: 355 (VQI-INKKLDLSNVQSKCGSKDNIKHVPGGGS) and/or SEQ ID NO: 356 (VEVKSEKLDFKDRVQSKIGSLD-NITHVPGGGN).

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 357 (SYGVG);

VHCDR2 comprises the sequence set forth in SEQ ID NO: 358 (SISSGGTTFYNPALKS);

VHCDR3 comprises the sequence set forth in SEQ ID NO: 359 (DVHIYYNDYGAAYGDRDY);

VLCDR1 comprises the sequence set forth in SEQ ID NO: 360 (SGSSSNIGGGNYVS);

VLCDR2 comprises the sequence set forth in SEQ ID NO: 361 (GTTSRAS); and

VLCDR3 comprises the sequence set forth in SEQ ID NO: 362 (ASYDTNSGSV);

or for each CDR sequence, an amino acid sequence with
(i) at least 85% identity thereto, and/or
(ii) one, two, or three amino acid substitutions relative thereto, wherein the specific binding molecule binds to a polypeptide or protein molecule comprising an amino acid sequence comprising residues 275 to 305 and/or residues 337 to 368 of SEQ ID NO: 1. The specific binding molecule comprising CDRs having 100% identity to those given above is referred to as "NS1G7" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 357 (SYGVG);

VHCDR2 comprises the sequence set forth in SEQ ID NO: 358 (SISSGGTTFYNPALKS);

VHCDR3 comprises the sequence set forth in SEQ ID NO: 359 (DVHIYYNDYGAAYGDRDY);

VLCDR1 comprises the sequence set forth in SEQ ID NO: 360 (SGSSSNIGGGNYVS);

VLCDR2 comprises the sequence set forth in SEQ ID NO: 361 (GTTSRAS); and

VLCDR3 comprises the sequence set forth in SEQ ID NO: 362 (ASYDTNSGSV).

The specific binding molecule may comprise the CDR sequences of a clone set out in Table 10 below.

TABLE 10

| Clone name | VH CDR1 | VH CDR2 | VH CDR3 | VL CDR1 | VL CDR2 | VL CDR3 | Epitope |
|---|---|---|---|---|---|---|---|
| CB11 | SNAVI (SEQ ID NO: 198) | LIDVDGDAAYDPALKS (SEQ ID NO: 200) | DYGSWGYVSDIDY (SEQ ID NO: 202) | SGSNIGSNDVG (SEQ ID NO: 256) | DNNNRP S (SEQ ID NO: 257) | GGYAGSSSNFL (SEQ ID NO: 258) | 113-238 |
| CA2 | SNGVG (SEQ ID NO: 259) | DISSVGKKYANPALKS (SEQ ID NO: 157) | CRDGGVTYGYDIDY (SEQ ID NO: 161) | SGSSGNVGYGDYVS (SEQ ID NO: 165) | GATNLAS (SEQ ID NO: 169) | ASYDSSSGGV (SEQ ID NO: 173) | 1-155 |
| CB6 | SNGVG (SEQ ID NO: 259) | DISSVGKKYANPALKS (SEQ ID NO: 157) | CRDGGVTYGYDIDY (SEQ ID NO: 161) | SGSSSNIGTGNYVG (SEQ ID NO: 261) | GAVTRA S (SEQ ID NO: 262) | ASYDSTSGGV (SEQ ID NO: 263) | 1-238 |
| CA7 | SYYVG (SEQ ID NO: 44) | NIYSTGRAFYNPALKS (SEQ ID NO: 52) | GSYYHGGGNGMVDFFD Y (SEQ ID NO: 265) | SGSSSNVGYGNYVG (SEQ ID NO: 39) | AATSRAS (SEQ ID NO: 72) | SSYQRGNTGV (SEQ ID NO: 78) | 1-319 |
| CA8 | SNAVV (SEQ ID NO: 266) | AIDKDGDTIYNPALKS (SEQ ID NO: 267) | DPSGWGYPDVDY (SEQ ID NO: 268) | SGTYIGSSDVG (SEQ ID NO: 269) | GTSSRP S (SEQ ID NO: 270) | ATYESSYHNSV (SEQ ID NO: 271) | 1-319 |
| CB10 | SNTVA (SEQ ID NO: 272) | EINSGGSTYYNPALK S (SEQ ID NO: 273) | GARSTYAAY (SEQ ID NO: 274) | SGSSSDVGYSTWVY (SEQ ID NO: 275) | HISNRAS (SEQ ID NO: 276) | AAYDSSNNVWI (SEQ ID NO: 277) | 1-319 |
| CB7 | NYRVG (SEQ ID NO: 279) | NIRSGGTTWYNPALK S (SEQ ID NO: 280) | DSSGDLYAYDY (SEQ ID NO: 281) | SGSSSNVGYGNYMA (SEQ ID NO: 282) | GATSRA S (SEQ ID NO: 141) | ASYDSTSGGV (SEQ ID NO: 263) | 13-25 |
| CC7 | SNAVI (SEQ ID NO: 198) | LIDVDGDAAYDPALKS (SEQ ID NO: 200) | DYGSWGYVSDIDY (SEQ ID NO: 202) | SGSYITGSSVG (SEQ ID NO: 292) | DNNDRP S (SEQ ID NO: 284) | ASYDTSNIGL (SEQ ID NO: 285) | 145-157 |
| CB12 | SNGVG (SEQ ID NO: 259) | DKSSAGKTYGNPALK S (SEQ ID NO: 182) | CRDGGVSYGYDVDY (SEQ ID NO: 286) | SGSSSNVGGDYVG (SEQ ID NO: 287) | DTTSRPS (SEQ ID NO: 288) | ASVDKTTGGV (SEQ ID NO: 289) | 155-227 |
| CC3 | SNGVG (SEQ ID NO: 259) | DKSSAGKTYGNPALK S (SEQ ID NO: 182) | CRDGGVSYGYDVDY (SEQ ID NO: 286) | SGSSSNVGYGTYVS (SEQ ID NO: 290) | GTTTRAS (SEQ ID NO: 188) | ASYDTGSGGV (SEQ ID NO: 291) | 155-227 |
| CA1 | SNAVI (SEQ ID NO: 198) | DIRADGATNYNAALK S (SEQ ID NO: 296) | PGNYYYGAGRDVARLA D (SEQ ID NO: 297) | SGSSSNIGGGNAVG (SEQ ID NO: 298) | DTTSRPS (SEQ ID NO: 288) | AAMDSSSLIGV (SEQ ID NO: 299) | 155-238 |

TABLE 10-continued

| Clone name | VH CDR1 | CDR2 | CDR3 | VL CDR1 | CDR2 | CDR3 | Epitope |
|---|---|---|---|---|---|---|---|
| CA3 | SNGVG S (SEQ ID NO: 259) | DKSSAGKTYGNPALK (SEQ ID NO: 182) | CRDGGVTYGYDVDY (SEQ ID NO: 184) | SGSSGNIGYDDYVS (SEQ ID NO: 301) | GATRRS S (SEQ ID NO: 302) | ASYDSSGGGV (SEQ ID NO: 303) | 186-263 |
| CD2 | SNAVI (SEQ ID NO: 198) | LIDVDGDAAYDPALKS (SEQ ID NO: 200) | DYGSWGYVSDIDY (SEQ ID NO: 202) | SGSNIGDADVG (SEQ ID NO: 305) | YNENRP S (SEQ ID NO: 306) | GSYAGDTYNHG V (SEQ ID NO: 307) | 186-350 |
| CB9 | SNSVG (SEQ ID NO: 42) | GIDSDGEEGYNPALN S (SEQ ID NO: 48) | SYRADGLAYGYVQAIDY (SEQ ID NO: 54) | SGRFIGISSVG (SEQ ID NO: 67) | ASDGRP S (SEQ ID NO: 70) | GSSDRTQYTGV (SEQ ID NO: 74) | 239-348 |
| CG11 | NYPVG (SEQ ID NO: 310) | NIENDGSANYASALK S (SEQ ID NO: 311) | EFGGSDGYTYFVDIDY (SEQ ID NO: 312) | SGSSSNVGYGNYVS (SEQ ID NO: 313) | GATSRA S (SEQ ID NO: 141) | ASYDGSSSGV (SEQ ID NO: 314) | 266-359 |
| CA10 | SNGVG (SEQ ID NO: 259) | DISSVGKKYANPALKS (SEQ ID NO: 157) | CRDGGVTYGYDIDY (SEQ ID NO: 161) | SGSSSNVGYGNYVT (SEQ ID NO: 316) | DATTRVS (SEQ ID NO: 317) | AAHDSSSGGV (SEQ ID NO: 318) | 277-319 |
| CC12 | SNSVG (SEQ ID NO: 42) | GIDSDGEEGYNPALN S (SEQ ID NO: 48) | SYRADGLAYGYVQAIDY (SEQ ID NO: 54) | SGRFIGISSVG (SEQ ID NO: 67) | ASDGRP S (SEQ ID NO: 70) | GSSDRTQYTGV (SEQ ID NO: 74) | 297-390 |
| CE2/ E1B8 | NYPVG (SEQ ID NO: 310) | NIENDGSANYASALK S (SEQ ID NO: 311) | EFGGSDGYTYFVDIDY (SEQ ID NO: 312) | SGSSSNVGYGNYVS (SEQ ID NO: 313) | GATSRA S (SEQ ID NO: 141) | ASYDGSSSGV (SEQ ID NO: 314) | 319-331 |
| CE3 | SNAVG (SEQ ID NO: 17) | GCSSDGKCYYNSALK S (SEQ ID NO: 20) | GYYPVYGYDYLGTIDY (SEQ ID NO: 23) | SGSSSNVGRNDVA (SEQ ID NO: 25) | GTTSRP S (SEQ ID NO: 28) | ASGDSSAINDI (SEQ ID NO: 31) | 331-360 |
| CA6 | SNGVG (SEQ ID NO: 259) | DKSSGGKTYGNPALK S (SEQ ID NO: 323) | CRDGGVTYGYDIDY (SEQ ID NO: 161) | SGSRNNIGYGNHVG (SEQ ID NO: 324) | DATTRAS (SEQ ID NO: 207) | ASFDRGSGGI (SEQ ID NO: 325) | 348-390 |
| CA11 | SNTVA (SEQ ID NO: 272) | EINSGGSTYYNPALK S (SEQ ID NO: 273) | GARSTYAAY (SEQ ID NO: 274) | SGSGSNIGAGNWVS (SEQ ID NO: 327) | GATSRP S (SEQ ID NO: 328) | AAYDSGSSIV (SEQ ID NO: 329) | 348-441 |
| CA4 | SYSVY (SEQ ID NO: 83) | IMYASGRVDYNPALK S (SEQ ID NO: 84) | GIEN (SEQ ID NO: 89) | RTSQSVNNYLS (SEQ ID NO: 91) | YATRLYT (SEQ ID NO: 95) | LQYDSTPLA (SEQ ID NO: 97) | 355-367 |
| CB2 | TNSVG (SEQ ID NO: 45) | GIDTDGEEGFNPVLK S (SEQ ID NO: 53) | SYRTDGLAYGYVQAIDY (SEQ ID NO: 55) | SGSYIGSSGVG (SEQ ID NO: 68) | ASDGRP S (SEQ ID NO: 70) | GSSDRTQYTGL (SEQ ID NO: 79) | 359-391 |
| CB3 | SVAVN (SEQ ID NO: 334) | GIISNGGTGYNPALKS (SEQ ID NO: 335) | GVEWEGSMDY (SEQ ID NO: 336) | SGSSSNVGAGSYVG (SEQ ID NO: 337) | GATKRA S (SEQ ID NO: 338) | VSYQTDFTLV (SEQ ID NO: 339) | 360-390 |
| CA9 | SNSVG (SEQ ID NO: 42) | GIDTDGEEGYNPALN S (SEQ ID NO: 46) | SYRSDGLAYGYVQAIDY (SEQ ID NO: 58) | SGSFIGISSVG (SEQ ID NO: 63) | ASDGRP S (SEQ ID NO: 70) | GSSDRTQYTGV (SEQ ID NO: 74) | 367-379 |
| CA12 | SYYVG (SEQ ID NO: 44) | NIYSTGRAFYNPALKS (SEQ ID NO: 52) | GSYYHGGGNGMVDFFD Y (SEQ ID NO: 265) | SGSSSNVGYGNYVG (SEQ ID NO: 39) | AATSRAS (SEQ ID NO: 72) | SSYQRGNTGV (SEQ ID NO: 78) | 367-379 |
| CB5 | SNGVG (SEQ ID NO: 259) | DITSGGRTYGNLALK S (SEQ ID NO: 341) | CRDGGVSYGYDSDY (SEQ ID NO: 160) | SGSSSNVGSGDHVN (SEQ ID NO: 342) | RTTNRA S (SEQ ID NO: 343) | ASHDNNSGGV (SEQ ID NO: 344) | 49-113 |
| CC4 | SNGVG (SEQ ID NO: 259) | DIASSGKAYSNPALKS (SEQ ID NO: 158) | CRDGGVTYGYDIDY (SEQ ID NO: 161) | SGSSSNVGYTNLGYSNL VT (SEQ ID NO: 346) | GATNRA S (SEQ ID NO: 170) | ASYDSSNGGI (SEQ ID NO: 347) | 49-155 |
| CD1 | SNGVG (SEQ ID NO: 259) | DKSSAGKTYGNPALK S (SEQ ID NO: 182) | CRDGGVSYGYDVDY (SEQ ID NO: 286) | SGSSSNVGYGTYVS (SEQ ID NO: 290) | GTTTRAS (SEQ ID NO: 188) | ASYDTGSGGV (SEQ ID NO: 291) | 49-155 |
| CC5 | SNGVG (SEQ ID NO: 259) | DISSVGKKYASPALKS (SEQ ID NO: 349) | CRDGGVTYGYDIDY (SEQ ID NO: 161) | SGSSSNVGYGNYVG (SEQ ID NO: 39) | GATSRA S (SEQ ID NO: 141) | ASYDSSNGGV (SEQ ID NO: 350) | 49-238 |

TABLE 10-continued

| Clone | VH | | | VL | | | |
| name | CDR1 | CDR2 | CDR3 | CDR1 | CDR2 | CDR3 | Epitope |
| MD9/ MoD9 | RESIA (SEQ ID NO: 102) | GVGIDGTSYYSPALK S (SEQ ID NO: 103) | NYIDFEY (SEQ ID NO: 104) | SGSSSNVGIYDVS (SEQ ID NO: 352) | GTNNRP S (SEQ ID NO: 353) | AAGDSSTIAV (SEQ ID NO: 354) | 373-385 |
| NS1G7 | SYGVG (SEQ ID NO: 357) | SISSGGTTFYNPALKS (SEQ ID NO: 358) | DVHIYYNDYGAAYGDRD Y (SEQ ID NO: 359) | SGSSSNIGGGNYVS (SEQ ID NO: 360) | GTTSRA S (SEQ ID NO: 361) | ASYDTNSGSV (SEQ ID NO: 362) | 275-305, 337-368 |

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises a VHCDR1 amino acid sequence set forth in table 10;

VHCDR2 comprises a VHCDR2 amino acid sequence set forth in table 10;

VHCDR3 comprises a VHCDR3 amino acid sequence set forth in table 10;

VLCDR1 comprises a VLCDR1 amino acid sequence set forth in table 10;

VLCDR2 comprises a VLCDR2 amino acid sequence set forth in table 10; and

VLCDR3 comprises a VLCDR3 amino acid sequence set forth in table 10;

or for each CDR sequence, an amino acid sequence with (i) at least 85% identity thereto, and/or (ii) one, two, or three amino acid substitutions relative thereto, wherein the specific binding molecule binds to an epitope within SEQ ID NO: 1, optionally wherein the specific binding molecule has a Ko of less than around 25 nM.

The $K_D$ may be less than around 20 nM, less than around 15 nM, or less than around 10 nM. The $K_D$ may preferably be for binding to SEQ ID NO: 1 or to SEQ ID NO: 5. The $K_D$ for binding to SEQ ID NO: 1 may be around 1 nM to around 20 nM. The $K_D$ for binding to SEQ ID NO: 1 may be around 1 nM to around 10 nM. The $K_D$ for binding to SEQ ID NO: 1 may be around 1.23 nM to 6.9 nM, optionally wherein the specific binding molecule comprises the CDRs of CC7. The $K_D$ for binding to SEQ ID NO: 1 may be around 1.3 nM to 3.61 nM, optionally wherein the specific binding molecule comprises the CDRs of CA4. The $K_D$ for binding to SEQ ID NO: 1 may be around 3.79 nM to 16.7 nM, optionally wherein the specific binding molecule comprises the CDRs of CE3. The $K_D$ for binding to SEQ ID NO: 1 may be around 5.03 nM to 11 nM, optionally wherein the specific binding molecule comprises the CDRs of CE2. The $K_D$ for binding to SEQ ID NO: 1 may be around 3.7 nM to 5.19 nM, optionally wherein the specific binding molecule comprises the CDRs of CB7.

The specific binding molecule may comprise an amino acid sequence having at least 70%, at least 75%, at least 80%, at least 90%, at least 95% or at least 99% identity to SEQ ID NO: 363 wherein the specific binding molecule binds to a polypeptide or protein molecule comprising an amino acid sequence comprising residues 1-155 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 363. The CDRs may be 100% identical to the CDRs of SEQ ID NO: 363. The specific binding molecule may comprise an amino acid sequence having at least 70%, at least 75%, at least 80%, at least 90%, at least 95% or at least 99% identity to SEQ ID NO: 363 wherein CDRs are 100% identical to the CDRs of SEQ ID NO: 363. The specific binding molecule may comprise the amino acid sequence of SEQ ID NO: 363.

(CA2 amino acid sequence)
```
                                      SEQ ID NO: 363
QVQLQESGPSLVKPSQTLSLTCTVSGFSLSSVAVNWVRQAPGKVPEWLG

GIISNGGTGYNPALKSRLSITRDTSKSQVSLALTHVTTEDTAVYYCGRG

VEWEGSMDYLGPGLLVTVSSEGKSSGSGSETKVDDQSVLTQPSSVSGFL

GQRVTITCSGSSSNVGAGSYVGWYQQVPGSGLRILIYGATKRASGLPDR

FSGSRSGNTATLTISSLQAEDEADYYCVSYQTDFTLVFGSGTRLTVLG
```

The specific binding molecule may comprise an amino acid sequence having at least 70%, at least 75%, at least 80%, at least 90%, at least 95% or at least 99% identity to SEQ ID NO: 364 wherein the specific binding molecule binds to a polypeptide or protein molecule comprising an amino acid sequence comprising residues 13-25 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 364. The CDRs may be 100% identical to the CDRs of SEQ ID NO: 364. The specific binding molecule may comprise an amino acid sequence having at least 70%, at least 75%, at least 80%, at least 90%, at least 95% or at least 99% identity to SEQ ID NO: 364 wherein CDRs are 100% identical to the CDRs of SEQ ID NO: 364. The specific binding molecule may comprise the amino acid sequence of SEQ ID NO: 364.

(CB7 amino acid sequence)
```
                                      SEQ ID NO: 364
QVQLQESGPSLVKPSQTLSLTCTVSGFSLTNYRVGWVRQAPGKALEWVS

NIRSGGTTWYNPALKSRLSITADTSKSQVSLSLSSVTTEDTAVYYCARD

SSGDLYAYDYWGPGLLVTVSSEGKSSGASGESKVDDQAVLTQPSSVSRS

LGQSVSMTCSGSSSNVGYGNYMAWFQQVPGSAPKLLIYGATSRASGVPD

RFSGSRSGNTATLTISSLQAEDEADYYCASYDSTSGGVFGSGTRLTVLG
```

The specific binding molecule may comprise an amino acid sequence having at least 70%, at least 75%, at least 80%, at least 90%, at least 95% or at least 99% identity to SEQ ID NO: 365 wherein the specific binding molecule binds to a polypeptide or protein molecule comprising an amino acid sequence comprising residues 145 to 157 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 365. The CDRs may be 100% identical to the CDRs of SEQ ID NO: 365. The specific binding molecule may comprise an amino acid sequence having at least 70%, at least 75%, at least 80%, at least 90%, at least 95% or at least 99% identity to SEQ ID NO: 365 wherein CDRs are 100% identical to the CDRs of SEQ ID NO: 365. The specific binding molecule may comprise the amino acid sequence of SEQ ID NO: 365.

```
(CC7 amino acid sequence)
                                    SEQ ID NO: 365
QVQLQESGPSLVKPSQTLSLTCTVSGFSLTSNAVIWVRQAPGKAPEWVA

LIDVDGDAAYDPALKSRLSITRDTSKSQVSLSLRSVTTEDTAVYYCARD

YGSWGYVSDIDYWGPGLLVTVSSEGKSSGASGESKVDDRVVRTQPSSVS

GSLGQRVSITCSGSYITGSSVGWFQQVPGSGLKTVIYDNNDRPSGVPDR

FSGSKSGDTATLTISSLQAEDEADYYCASYDTSNIGLFGSGTRLTVLG
```

The specific binding molecule may comprise an amino acid sequence having at least 70%, at least 75%, at least 80%, at least 90%, at least 95% or at least 99% identity to SEQ ID NO: 366 wherein the specific binding molecule binds to a polypeptide or protein molecule comprising an amino acid sequence comprising residues 319 to 331 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 366. The CDRs may be 100% identical to the CDRs of SEQ ID NO: 366. The specific binding molecule may comprise an amino acid sequence having at least 70%, at least 75%, at least 80%, at least 90%, at least 95% or at least 99% identity to SEQ ID NO: 366 wherein CDRs are 100% identical to the CDRs of SEQ ID NO: 366. The specific binding molecule may comprise the amino acid sequence of SEQ ID NO: 366.

```
(CE2/E1B8 amino acid sequence)
                                    SEQ ID NO: 366
QVQLQESGPSLVKPSQTLSLTCTVSGFSLTNYPVGWRQAPGKALEWIGN

IENDGSANYASALKSRLSITRDTSKNQVSLSLSSATTEDTAVYYCGREF

GGSDGYTYFVDIDYWGPGLLVTVSSEGKSSGASGESKVDDQAVLTQPSS

VSKSLGQSVSITCSGSSNVGYGNYVSWFQQVPGSAPKILIYGATSRAS

GVPDRFSGSRSGNTATLTITSLQAEDEADYYCASYDGSSSGVFGSGTRL

TVLG
```

The specific binding molecule may comprise an amino acid sequence having at least 70%, at least 75%, at least 80%, at least 90%, at least 95% or at least 99% identity to SEQ ID NO: 367 wherein the specific binding molecule binds to a polypeptide or protein molecule comprising an amino acid sequence comprising residues 331 to 360 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 367. The CDRs may be 100% identical to the CDRs of SEQ ID NO: 367. The specific binding molecule may comprise an amino acid sequence having at least 70%, at least 75%, at least 80%, at least 90%, at least 95% or at least 99% identity to SEQ ID NO: 367 wherein CDRs are 100% identical to the CDRs of SEQ ID NO: 367. The specific binding molecule may comprise the amino acid sequence of SEQ ID NO: 367.

```
SEQ ID NO 367: (CE3 amino acid sequence)
QVRLQESGPSLVKPSQTLSVTCTVSGFSLISNAVGWVRQAPGKVPESLA

GCSSDGKCYYNSALKSRLDITRDTSKNQISLSLSSVTTDDAAVYYCTRG

YYPVYGYDYLGTIDYWGPGLLVTVSSEGKSSGASGESKVDDQAVLTQPS

SVSGSLGQRVSITCSGSSSNVGRNDVAWFQQLPGSGLRTIIYGTTSRPS

GIPDRFSGSKSGVTATLTIDSLQAEDEADYFCASGDSSAINDIFGSGTR

LTVLG
```

The specific binding molecule may comprise an amino acid sequence having at least 70%, at least 75%, at least 80%, at least 90%, at least 95% or at least 99% identity to SEQ ID NO: 368 wherein the specific binding molecule binds to a polypeptide or protein molecule comprising an amino acid sequence comprising residues 355 to 367 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 368. The CDRs may be 100% identical to the CDRs of SEQ ID NO: 368. The specific binding molecule may comprise an amino acid sequence having at least 70%, at least 75%, at least 80%, at least 90%, at least 95% or at least 99% identity to SEQ ID NO: 368 wherein CDRs are 100% identical to the CDRs of SEQ ID NO: 368. The specific binding molecule may comprise the amino acid sequence of SEQ ID NO: 368.

```
(CA4 amino acid sequence)
                                    SEQ ID NO: 368
QVQLQESGPSLVKPSQTLSLTCTVSGFSLTSYSVYWRQAPGQALEWISI

MYASGRVDYNPALKSRLSITRDTSKSQFSLSLSSVTTEDTAVYYCTRGI

ENWGPGLLVTVSSEGKSSGASGESKVDDDIQVTQSPSSLSASLTERVSI

TCRTSQSVNNYLSWYQQKPGQAPKLLIYYATRLYTDVPSRFSGSGSGTD

YTLTITSLEADDTATYYCLQYDSTPLAFGGGTNVEIK
```

The specific binding molecule may comprise an amino acid sequence having at least 70%, at least 75%, at least 80%, at least 90%, at least 95% or at least 99% identity to SEQ ID NO: 369 wherein the specific binding molecule binds to a polypeptide or protein molecule comprising an amino acid sequence comprising residues 359 to 391 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 369. The CDRs may be 100% identical to the CDRs of SEQ ID NO: 369. The specific binding molecule may comprise an amino acid sequence having at least 70%, at least 75%, at least 80%, at least 90%, at least 95% or at least 99% identity to SEQ ID NO: 369 wherein CDRs are 100% identical to the CDRs of SEQ ID NO: 369. The specific binding molecule may comprise the amino acid sequence of SEQ ID NO: 369.

(CB2 amino acid sequence)

SEQ ID NO: 369

```
QVQLQESGPSLVKPSQTLSLTCTVSGFSLSTNSVGWRQAPGKAPEWVAG

IDTDGEEGFNPVLKSRLSITRDTSKSQVSLSLSNVTSEDTAVYYCGRSY

RTDGLAYGYVQAIDYWGPGLLVTISSEGKSSGASGESKVDDQSVLTQPS

SVSGSPGQTVSITCSGSYIGSSGVGWFQQLPGSGLRTIIVASDGRPSGV

PDRFSMSKSGNTATLTISSLQAEDEADYFCGSSDRTQYTGLFGSGTRLT

VLG
```

The specific binding molecule may comprise an amino acid sequence having at least 70%, at least 75%, at least 80%, at least 90%, at least 95% or at least 99% identity to SEQ ID NO: 370 wherein the specific binding molecule binds to a polypeptide or protein molecule comprising an amino acid sequence comprising residues 360 to 390 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 370. The CDRs may be 100% identical to the CDRs of SEQ ID NO: 370. The specific binding molecule may comprise an amino acid sequence having at least 70%, at least 75%, at least 80%, at least 90%, at least 95% or at least 99% identity to SEQ ID NO: 370 wherein CDRs are 100% identical to the CDRs of SEQ ID NO: 370. The specific binding molecule may comprise the amino acid sequence of SEQ ID NO: 370.

(CB3 amino acid sequence)

SEQ ID NO: 370

```
QVQLQESGPSLVKPSQTLSLTCTVSGFSLSSVAVNWRQAPGKVPEWLGG

IISNGGTGYNPALKSRLSITRDTSKSQVSLALTHVTTEDTAVYYCGRGV

EWEGSMDYLGPGLLVTVSSEGKSSGSGSETKVDDQSVLTQPSSVSGFLG

QRVTITCSGSSSNVGAGSYVGWYQQVPGSGLRILIYGATKRASGLPDRF

SGSRSGNTATLTISSLQAEDEADYYCVSYQTDFTLVFGSGTRLTVLG
```

The specific binding molecule may comprise an amino acid sequence having at least 70%, at least 75%, at least 80%, at least 90%, at least 95% or at least 99% identity to SEQ ID NO: 371 wherein the specific binding molecule binds to a polypeptide or protein molecule comprising an amino acid sequence comprising residues 367 to 379 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 371. The CDRs may be 100% identical to the CDRs of SEQ ID NO: 371. The specific binding molecule may comprise an amino acid sequence having at least 70%, at least 75%, at least 80%, at least 90%, at least 95% or at least 99% identity to SEQ ID NO: 371 wherein CDRs are 100% identical to the CDRs of SEQ ID NO: 371. The specific binding molecule may comprise the amino acid sequence of SEQ ID NO: 371.

(CA9 amino acid sequence)

SEQ ID NO: 371

```
QVQLQESGPSLVKPSQTLSLTCTVSGFSLTSNSVGWVRQAPGKAPEWVA

GIDTDGEEGYNPALNSRLSITRDTSKSQVSLSLSSVTSEDTAVYYCGRS

YRSDGLAYGYVQAIDYWGPGLLVTVSSEGKSSGASGESKVDDQAVLTQP

ASVSGSLGQRVSITCSGSFIGISSVGWFQQLPGSGLRTIIVASDGRPSG

VPDRFSMSKSGNTATLTISSLQAEDEADYFCGSSDRTQYTGVFGSGTRL

TVLG
```

The specific binding molecule may comprise an amino acid sequence having at least 70%, at least 75%, at least 80%, at least 90%, at least 95% or at least 99% identity to SEQ ID NO: 372 wherein the specific binding molecule binds to a polypeptide or protein molecule comprising an amino acid sequence comprising residues 367 to 379 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 372. The CDRs may be 100% identical to the CDRs of SEQ ID NO: 372. The specific binding molecule may comprise an amino acid sequence having at least 70%, at least 75%, at least 80%, at least 90%, at least 95% or at least 99% identity to SEQ ID NO: 372 wherein CDRs are 100% identical to the CDRs of SEQ ID NO: 372. The specific binding molecule may comprise the amino acid sequence of SEQ ID NO: 372.

(CA12 amino acid sequence)

SEQ ID NO: 372

```
QVQLQGSGPSLVKPSQTLSLTCTVSGFSFDSYYVGWVRQAPGKALEWLG

NIYSTGRAFYNPALKSRLSITRDTSKSQVSLSVSSVTIEDTALYYCVRG

SYYHGGGNGMVDFFDYWSPGLLVTVSSEGKSSGASGESKVDDQWVRTQP

SSVSGSLGQRVSITCSGSSSNVGYGNYVGWFQQVPGSAPKLLIYAATSR

ASGVPDRFSGSRSGNTATLTIDSLQAEDEADYYCSSYQRGNTGVFGSGT

RLTVLG
```

The specific binding molecule may comprise an amino acid sequence having at least 70%, at least 75%, at least 80%, at least 90%, at least 95% or at least 99% identity to SEQ ID NO: 373 wherein the specific binding molecule binds to a polypeptide or protein molecule comprising an amino acid sequence comprising residues 373 to 385 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 373. The CDRs may be 100% identical to the CDRs of SEQ ID NO: 373. The specific binding molecule may comprise an amino acid sequence having at least 70%, at least 75%, at least 80%, at least 90%, at least 95% or at least 99% identity to SEQ ID NO: 373 wherein CDRs are 100% identical to the CDRs of SEQ ID NO: 373. The specific binding molecule may comprise the amino acid sequence of SEQ ID NO: 373.

```
(MD9/MoD9 amino acid sequence)
                                        SEQ ID NO: 373
QVRLQESGPSLVKSSQTLSLTCTVSGFSLTRESIAWVRQAPGKVPEWLG

GVGIDGTSYYSPALKSRLSITRDTSKSQASLSLSSVATEDTAMYYCARN

YIDFEYWGPGLLVTVSSEGKSSGASGESKVDDQAVLTQLSSVSGSLGQR

ISITCSGSSSNVGIYDVSWFQQLPGSGLRTVIYGTNNRPSGVPDRFSGS

RSGNTATLTISSLQSEDEAIYYCAAGDSSTIAVFGSGTRLTVLG
```

The specific binding molecule may comprise an amino acid sequence having at least 70%, at least 75%, at least 80%, at least 90%, at least 95% or at least 99% identity to SEQ ID NO: 374 wherein the specific binding molecule binds to a polypeptide or protein molecule comprising an amino acid sequence comprising residues 275 to 305 and/or 337 to 368 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 374. The CDRs may be 100% identical to the CDRs of SEQ ID NO: 374. The specific binding molecule may comprise an amino acid sequence having at least 70%, at least 75%, at least 80%, at least 90%, at least 95% or at least 99% identity to SEQ ID NO: 374 wherein CDRs are 100% identical to the CDRs of SEQ ID NO: 374. The specific binding molecule may comprise the amino acid sequence of SEQ ID NO: 374. SEQ ID NO: 374 (NS1G7 amino acid sequence) QVQLQESGPSLVKP-SQTLSLTCTVSGFSLTSYGVGWVRQAPGKTLEWIS-SISSGGTTFYNPALKS RLSITRDTSESQVSLSLSSVT-TEDTAVYYCTRDVHIYYNDYGAAYGDRDYWGPGLL-VTVSSEGKS SGASGESKVDDQAVVTQPPSVSGSPGQRVSITCSGSS SNIGGGNYVSWYQQLPGSGLRTLIYGT TSRASGVPDRFSGSGSGNTATLTISSLQAEDEADYY-CASYDTNSGSVFGSGTRLTVLG The epitope of the specific binding molecule may be within an amino acid sequence comprising residues 297 to 390 of SEQ ID NO: 1. Accordingly, the epitope may be within the amino acid sequence of SEQ ID NO: 5 (IKHVPGGGSVQIVYKPVDL-SKVTSKCGSLGNIHHKPGGGQVEVKSEKLDFKDRV QSKIGSLDNITH VPGGGNKKI-ETHKLTFRENAKAKTDHGA).

The epitope may be within an amino acid sequence comprising residues 297 to 390 of SEQ ID NO: 1. This epitope may be bound by the CDRs of the specific binding molecule referred to as "S1E12" herein.

The epitope may comprise the amino acid sequence of SEQ ID NO: 5 (IKHVPGGGSVQIVYKPVDL-SKVTSKCGSLGNIHHKPGGGQVEVKSEKLDFKDRV QSKIGSLDNITH VPGGGNKKI-ETHKLTFRENAKAKTDHGA). The epitope may comprise an amino acid sequence having at least 70%, at least 75%, at least 80%, at least 90%, at least 95% or at least 99% identity to SEQ ID NO: 5 (IKHVPGGGSVQIVYKPVDL-SKVTSKCGSLGNIHHKPGGGQVEVKSEKLDFKDRV QSKIGSLDNITH VPGGGNKKI-ETHKLTFRENAKAKTDHGA).

The epitope may consist of the amino acid sequence of SEQ ID NO: 5 (IKHVPGGGSVQIVYKPVDL-SKVTSKCGSLGNIHHKPGGGQVEVKSEKLDFKDRV QSKIGSLDNITH VPGGGNKKI-ETHKLTFRENAKAKTDHGA). The epitope may consist of an amino acid sequence having at least 70%, at least 75%, at least 80%, at least 90%, at least 95% or at least 99% identity to SEQ ID NO: 5 (IKHVPGGGSVQIVYKPVDL-SKVTSKCGSLGNIHHKPGGGQVEVKSEKLDFKDRVQ SKIGSLDNITH VPGGGNKKI-ETHKLTFRENAKAKTDHGA).

The specific binding molecule may bind to a polypeptide or protein molecule comprising an amino acid sequence comprising residues 297 to 390 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 136 (S/R/D/T N/E/Y/H S/G V/I G/A);

VHCDR2 comprises the sequence set forth in SEQ ID NO: 162 (G I/V D/G/N T/VY/S D G E/T/R E/S/T G/Y/E Y/F N/S P/S A/V L N/K S);

VHCDR3 comprises the sequence set forth in SEQ ID NO: 164 (S/N/D/T Y/-/S R/-/K A/-/G/S/T D/-G/-L/-AY A/-/G Y/-/W G/-Y/-/H V/Y Q/I/Y A/D/Q I/F D/E Y);

VLCDR1 comprises the sequence set forth in SEQ ID NO: 167 (S G S F/N/S/Y I/S G/N I/S/V S/A/G S/Y/ G-/G-/D-/Y V G/T/S);

VLCDR2 comprises the sequence set forth in SEQ ID NO: 181 (A/R/D S/N/A D/R/T G/N R P/A S); and VLCDR3 comprises the sequence set forth in SEQ ID NO: 183 (G/A S S/Y/H D I-R/Q/D T/S/N Q/W/R Y/G/I T/S G/A V/L);

or for each CDR sequence, an amino acid sequence with
    (i) at least 85% identity thereto, and/or
    (ii) one, two, or three amino acid substitutions relative thereto.

Said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

The specific binding molecule may comprise the CDRs VHCDR1, VHCDR2, VHCDR3, VLCDR1. VLCDR2 and VLCDR3, wherein each of said CDRs comprises an amino acid sequence as follows:

VHCDR1 comprises the sequence set forth in SEQ ID NO: 42 (SNSVG), SEQ ID NO: 187 (SHSVG), SEQ ID NO: 45 (TNSVG), SEQ ID NO: 102 (RESIA), or SEQ ID NO: 199 (DYGIG);

VHCDR2 comprises the sequence set forth in SEQ ID NO: 46 (GIDTDGEEGYNPALNS), SEQ ID NO: 205 (GINYDGRTEYNSALKS), SEQ ID NO: 103 (GVGIDGTSYYSPALKS), SEQ ID NO: 53 (GIDTDGEEGFNPVLKS), or SED ID NO: 48 (GIDSDGEEGYNPALNS);

VHCDR3 comprises the sequence set forth in SEQ ID NO: 54 (SYRADGLAYGYVQAIDY). SEQ ID NO: 55 (SYRTDGLAYGYVQAIDY), SEQ ID NO: 210 (TYRSDGYAYGYVQAIDY), SEQ ID NO: 104 (NYIDFEY), or SEQ ID NO: 211 (DSKGGWGHVYQFDY);

VLCDR1 comprises the sequence set forth in SEQ ID NO: 63 (SGSFIGISSVG), SEQ ID NO: 68 (SGSY/ GSSGVG), SEQ ID NO: 212 (SGSNIGSASVT), or SEQ ID NO: 213 (SGSSSNVGYGDYVS);

VLCDR2 comprises the sequence set forth in SEQ ID NO: 70 (ASDGRPS), SEQ ID NO: 214 (RNRNRPS), or SEQ ID NO: 215 (DATNRAS); and VLCDR3 comprises the sequence set forth in SEQ ID NO: 74 (GSSDRTQYTGV), SEQ ID NO: 79 (GSS- DRTQYTGL), SEQ ID NO: 216 (ASHDNRISAV), or SEQ ID NO: 217 (GSYQSWGSGV);

or for each CDR sequence, an amino acid sequence with
   (i) at least 85% identity thereto, and/or
   (ii) one, two, or three amino acid substitutions relative thereto,
      wherein the specific binding molecule binds to a polypeptide or protein molecule comprising an amino acid sequence comprising residues 297 to 390 of SEQ ID NO: 1.

The specific binding molecule may bind to a polypeptide or protein molecule comprising an amino acid sequence comprising residues 297 to 390 of SEQ ID NO: 1. Said specific binding molecule may comprise the CDRs VHCDR1, VHCDR2, VHCDR3, VLCDR1, VLCDR2 and VLCDR3, wherein each of said CDRs comprises an amino acid sequence as follows:
   VHCDR1 comprises the sequence set forth in SEQ ID NO: 426 (S/T N/H S V G);
   VHCDR2 comprises the sequence set forth in SEQ ID NO: 427 (G I D T/S D G E E G Y/F N P A/V L N/K S);
   VHCDR3 comprises the sequence set forth in SEQ ID NO: 428 (S/T Y R A/T/S D G LAY GY VQAID Y);
   VLCDR1 comprises the sequence set forth in SEQ ID NO: 429 (S G S FAY I G I/S S S/G V G);
   VLCDR2 comprises the sequence set forth in SEQ ID NO: 70 (A S D G R P S); and
   VLCDR3 comprises the sequence set forth in SEQ ID NO: 432 (G S S D R T Q Y T G V/L);
   or for each CDR sequence, an amino acid sequence with
      (i) at least 85% identity thereto, and/or
      (ii) one, two, or three amino acid substitutions relative thereto.

Said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

The specific binding molecule may comprise the CDRs VHCDR1, VHCDR2, VHCDR3, VLCDR1. VLCDR2 and VLCDR3, wherein each of said CDRs comprises an amino acid sequence as follows:
   VHCDR1 comprises the sequence set forth in SEQ ID NO: 42 (SNSVG), SEQ ID NO: 187 (SHSVG) or SEQ ID NO: 45 (TNSVG);
   VHCDR2 comprises the sequence set forth in SEQ ID NO: 46 (GIDTDGEEGYNPALNS), SEQ ID NO: 53 (GIDTDGEEGFNPVLKS), or SED ID NO: 48 (GIDSDGEEGYNPALNS);
   VHCDR3 comprises the sequence set forth in SEQ ID NO: 54 (SYRADGLAYGYVQAIDY). SEQ ID NO: 55 (SYRTDGLAYGYVQAIDY), or SEQ ID NO: 210 (TYRSDGYAYGYVQAIDY);
   VLCDR1 comprises the sequence set forth in SEQ ID NO: 63 (SGSFIGISSVG), or SEQ ID NO: 68 (SGSY/GSSGVG);
   VLCDR2 comprises the sequence set forth in SEQ ID NO: 70 (ASDGRPS); and
   VLCDR3 comprises the sequence set forth in SEQ ID NO: 74 (GSSDRTQYTGV), or SEQ ID NO: 79 (GSSDRTQYTGL);
   or for each CDR sequence, an amino acid sequence with
      (i) at least 85% identity thereto, and/or (ii) one, two, or three amino acid substitutions relative thereto,
      wherein the specific binding molecule binds to a polypeptide or protein molecule comprising an amino acid sequence comprising residues 297 to 390 of SEQ ID NO: 1.

The specific binding molecule may comprise the CDRs VHCDR1, VHCDR2, VHCDR3, VLCDR1. VLCDR2 and VLCDR3, wherein each of said CDRs comprises an amino acid sequence as follows:
   VHCDR1 comprises the sequence set forth in SEQ ID NO: 42 (SNSVG);
   VHCDR2 comprises the sequence set forth in SEQ ID NO: 46 (GIDTDGEEGYNPALNS);
   VHCDR3 comprises the sequence set forth in SEQ ID NO: 54 (SYRADGLAYGYVQAIDY);
   VLCDR1 comprises the sequence set forth in SEQ ID NO: 63 (SGSFIGISSVG);
   VLCDR2 comprises the sequence set forth in SEQ ID NO: 70 (ASDGRPS); and
   VLCDR3 comprises the sequence set forth in SEQ ID NO: 74 (GSSDRTQYTGV);
   or for each CDR sequence, an amino acid sequence with
      (i) at least 85% identity thereto, and/or
      (ii) one, two, or three amino acid substitutions relative thereto,
wherein the specific binding molecule binds to a polypeptide or protein molecule comprising an amino acid sequence comprising residues 297 to 390 of SEQ ID NO: 1. The specific binding molecule comprising CDRs having 100% identity to those given above is referred to as "S1E12" herein.

The specific binding molecule may comprise the CDRs VHCDR1. VHCDR2, VHCDR3, VLCDR1. VLCDR2 and VLCDR3, wherein each of said CDRs comprises an amino acid sequence as follows:
   VHCDR1 comprises the sequence set forth in SEQ ID NO: 42 (SNSVG);
   VHCDR2 comprises the sequence set forth in SEQ ID NO: 46 (GIDTDGEEGYNPALNS);
   VHCDR3 comprises the sequence set forth in SEQ ID NO: 54 (SYRADGLAYGYVQAIDY);
   VLCDR1 comprises the sequence set forth in SEQ ID NO: 63 (SGSFIGISSVG);
   VLCDR2 comprises the sequence set forth in SEQ ID NO: 70 (ASDGRPS); and
   VLCDR3 comprises the sequence set forth in SEQ ID NO: 74 (GSSDRTQYTGV).

The specific binding molecule may comprise the CDRs VHCDR1, VHCDR2, VHCDR3, VLCDR1. VLCDR2 and VLCDR3, wherein each of said CDRs comprises an amino acid sequence as follows:
   VHCDR1 comprises the sequence set forth in SEQ ID NO: 45 (TNSVG);
   VHCDR2 comprises the sequence set forth in SEQ ID NO: 53 (GIDTDGEEGFNPVLKS);
   VHCDR3 comprises the sequence set forth in SEQ ID NO: 55 (SYRTDGLAYGYVQAIDY);
   VLCDR1 comprises the sequence set forth in SEQ ID NO: 68 (SGSY/GSSGVG);
   VLCDR2 comprises the sequence set forth in SEQ ID NO: 70 (ASDGRPS); and
   VLCDR3 comprises the sequence set forth in SEQ ID NO: 79 (GSSDRTQYTGL):
   or for each CDR sequence, an amino acid sequence with
      (i) at least 85% identity thereto, and/or (ii) one, two, or three amino acid substitutions relative thereto, wherein the specific binding molecule binds to a polypeptide or protein molecule comprising an amino acid sequence comprising residues 297 to 390 of SEQ ID NO: 1. The specific binding molecule comprising CDRs having 100% identity to those given above is referred to as "NS2A1" herein.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 45 (TNSVG);

VHCDR2 comprises the sequence set forth in SEQ ID NO: 53 (GIDTDGEEGFNPVLKS);

VHCDR3 comprises the sequence set forth in SEQ ID NO: 55 (SYRTDGLAYGYVQAIDY);

VLCDR1 comprises the sequence set forth in SEQ ID NO: 68 (SGSY/GSSGVG);

VLCDR2 comprises the sequence set forth in SEQ ID NO: 70 (ASDGRPS); and

VLCDR3 comprises the sequence set forth in SEQ ID NO: 79 (GSSDRTQYTGL).

The specific binding molecule may comprise the CDR sequences of a clone set out in Table 11 below. The epitope may be within residues 297 to 390 of SEQ ID NO: 1.

TABLE 11

| Clone name | VH | | | VL | | | Epitope |
|---|---|---|---|---|---|---|---|
| | CDR1 | CDR2 | CDR3 | CDR1 | CDR2 | CDR3 | |
| NS2B6 | RESIA (SEQ ID NO: 102) | GVGIDGTSYYSPALK S (SEQ ID NO: 103) | N--------YIDFEY (SEQ ID NO: 104) | SGSNIGSAS---VT (SEQ ID NO: 212) | RNRNRPS (SEQ ID NO: 214) | GSY-QSWGSGV (SEQ ID NO: 217) | 297-390 |
| NS1B2 | DYGIG (SEQ ID NO: 199) | GINYDGRTEYNSALK S (SEQ ID NO: 205) | DSKG---GWGHVYQFDY (SEQ ID NO: 211) | SGSSSNVGYGDYV S (SEQ ID NO: 213) | DATNRAS (SEQ ID NO: 215) | ASH-DNR.ISAV (SEQ ID NO: 216) | 297-390 |
| S1A5 | SNSVG (SEQ ID NO: 42) | GIDTDGEEGYNPALN S (SEQ ID NO: 46) | TYRSDGYAYGYVQAID Y (SEQ ID NO: 210) | NA | NA | NA | 297-390 |
| S1A12 | SNSVG (SEQ ID NO: 42) | GIDTDGEEGYNPALN S (SEQ ID NO: 46) | TYRSDGYAYGYVQAID Y (SEQ ID NO: 210) | SGSFIGISS---VG (SEQ ID NO: 63) | ASDGRPS (SEQ ID NO: 70) | GSSDRTQYTG V (SEQ ID NO: 74) | 297-390 |
| S1E12 | SNSVG (SEQ ID NO: 42) | GIDTDGEEGYNPALN S (SEQ ID NO: 46) | SYRADGLAYGYVQAID Y (SEQ ID NO: 54) | SGSFIGISS---VG (SEQ ID NO: 63) | ASDGRPS (SEQ ID NO: 70) | GSSDRTQYTG V (SEQ ID NO: 74) | 297-390 |
| S1D5 | SHSVG (SEQ ID NO: 187) | GIDSDGEEGYNPALN S (SEQ ID NO: 48) | SYRADGLAYGYVQAID Y (SEQ ID NO: 54) | SGSFIGISS---VG (SEQ ID NO: 63) | ASDGRPS (SEQ ID NO: 70) | GSSDRTQYTG V (SEQ ID NO: 74) | 297-390 |
| NS2A1 | TNSVG (SEQ ID NO: 45) | GIDTDGEEGFNPVLK S (SEQ ID NO: 53) | SYRTDGLAYGYVQAID Y (SEQ ID NO: 55) | SGSYIGSSG---VG (SEQ ID NO: 68) | ASDGRPS (SEQ ID NO: 70) | GSSDRTQYTG L (SEQ ID NO: 79) | 297-390 |

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises a VHCDR1 amino acid sequence set forth in table 11;

VHCDR2 comprises a VHCDR2 amino acid sequence set forth in table 11;

VHCDR3 comprises a VHCDR3 amino acid sequence set forth in table 11;

VLCDR1 comprises a VLCDR1 amino acid sequence set forth in table 11;

VLCDR2 comprises a VLCDR2 amino acid sequence set forth in table 11; and

VLCDR3 comprises a VLCDR3 amino acid sequence set forth in table 11;

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 297 to 390 of SEQ ID NO: 1.

The specific binding molecule may bind to a polypeptide or protein molecule comprising an amino acid sequence comprising residues 297 to 390 of SEQ ID NO: 1 with a $K_D$ of less than around 25 nM. The $K_D$ may be less than around 20 nM, less than around 15 nM, or less than around 10 nM. The $K_D$ may preferably be for binding to SEQ ID NO: 1 or SEQ ID NO: 5. The $K_D$ for binding to SEQ ID NO: 1 may be around 500 pM to around 15 nM. The Kc for binding to SEQ ID NO: 1 may be around 500 pM to around 1 nM. The $K_D$ for binding to SEQ ID NO: 1 may be around 829 pM, optionally wherein the specific binding molecule comprises the CDRs of S1E12. The Kc for binding to SEQ ID NO: 1 may be around 1 nM to around 15 nM. The $K_D$ for binding to SEQ ID NO: 1 may be around 2.9 nM to 10 nM, optionally wherein the specific binding molecule comprises the CDRs of NS2A1. The $K_D$ for binding to SEQ ID NO: 5 may be around 1 nM to around 15 nM. The $K_D$ for binding to SEQ ID NO: 1 may be around 3 nM to 8 nM. The $K_D$ for binding to SEQ ID NO: 1 may be around 5.4 nM, optionally wherein the specific binding molecule comprises the CDRs of NS2A1.

The specific binding molecule may comprise an amino acid sequence having at least 70%, at least 75%, at least 80%, at least 90%, at least 95% or at least 99% identity to SEQ ID NO: 218 wherein the specific binding molecule binds to a polypeptide or protein molecule comprising an amino acid sequence comprising residues 297 to 390 of SEQ ID NO: 1. The CDRs of the specific binding molecule may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the CDRs of SEQ ID NO: 218. The CDRs may be 100% identical to the CDRs of SEQ ID NO: 218. The specific binding molecule may comprise an amino acid sequence having at least 70%, at least 75%, at least 80%, at least 90%, at least 95% or at least 99% identity to SEQ ID NO: 218 wherein CDRs are 100% identical to the CDRs of SEQ ID NO: 218. The specific binding molecule may comprise the amino acid sequence of SEQ ID NO: 218.

(S1E12 amino acid sequence)

SEQ ID NO: 218

```
QVQLQESGPSLVKPSQTLSLTCTVSGFSLGSNSVGWVRQAPGKAPEWVA

GIDTDGEEGYNPALNSRLSITRDTSKSQVSLSLSSVTSEDTAVYYCGRS

YRADGLAYGYVQAIDYWGPGLLVTVSSEGKSSGASGESKVDDRVVRTQP

SSVSGSLGQRVSITCSGSFIGISSVGWFQQLPGSGLRTIIVASDGRPSG

VPDRFSMSKSGNTATLTISSLQAEDEADYFCGSSDRTQYTGVFGSGTRL

TVLG
```

The specific binding molecule may comprise an amino acid sequence having at least 70%, at least 75%, at least 80%, at least 90%, at least 95% or at least 99% identity to SEQ ID NO: 220 wherein the specific binding molecule binds to a polypeptide or protein molecule comprising an amino acid sequence comprising residues 297 to 390 of SEQ ID NO: 1. The CDRs of the specific binding molecule may be at least 85%, at least 86%, at least 87%, at least 88%, at least 89%, at least 90%, at least 91% at least 92%, at least 93%, at least 94%, at least 95%, at least 96%, at least 97%, at least 98%, or at least 99% identical to the CDRs of SEQ ID NO: 220. The CDRs may be 100% identical to the CDRs of SEQ ID NO: 220. The specific binding molecule may comprise an amino acid sequence having at least 70%, at least 75%, at least 80%, at least 90%, at least 95% or at least 99% identity to SEQ ID NO: 220 wherein CDRs are 100% identical to the CDRs of SEQ ID NO: 220. The specific binding molecule may comprise the amino acid sequence of SEQ ID NO: 220.

(NS2A1 amino acid sequence)

SEQ ID NO: 220

```
QVQLQESGPSLVKPSQTLSLTCTVSGFSLSTNSVGWVRQAPGKAPEWVA

GIDTDGEEGFNPVLKSRLSITRDTSKSQVSLSLSNVTSEDTAVYYCGRS

YRTDGLAYGYVQAIDYWGPGLLVTISSEGKSSGASGESKVDDQSVLTQP

SSVSGSPGQTVSITCSGSYIGSSGVGWFQQLPGSGLRTIIVASDGRPSG

VPDGFSMSKSGNTATLTISSLQAEDEADYFCGSSDRTQYTGLFGSGTRL

TVLG
```

CDRs disclosed herein in connection with different clones may be combined into a specific binding molecule.

The specific binding molecule may comprise one or more CDR sequences disclosed herein in connection a clone identified in any one of tables 1 to 11 wherein the remaining CDR sequences are disclosed herein in connection one or more other clones identified in any one of tables 1 to 11. The specific binding molecule may comprise CDRs from two, three, four, five or six clones identified in any one of tables 1 to 11.

The specific binding molecule may comprise the CDRs VHCDR1, VHCDR2, VHCDR3, VLCDR1, VLCDR2 and VLCDR3, wherein each of said CDRs comprises an amino acid sequence as follows:

VHCDR1 comprises a VHCDR1 amino acid sequence set forth in any one of tables 1 to 11;

VHCDR2 comprises a VHCDR2 amino acid sequence set forth in any one of tables 1 to 11;

VHCDR3 comprises a VHCDR3 amino acid sequence set forth in any one of tables 1 to 11;

VLCDR1 comprises a VLCDR1 amino acid sequence set forth in any one of tables 1 to 11;

VLCDR2 comprises a VLCDR2 amino acid sequence set forth in any one of tables 1 to 11; and VLCDR3 comprises a VLCDR3 amino acid sequence set forth in any one of tables 1 to 11;

or for each CDR sequence, an amino acid sequence with (i) at least 85% identity thereto, and/or (ii) one, two, or three amino acid substitutions relative thereto, wherein the specific binding molecule binds to an epitope within SEQ ID NO: 1.

The specific binding molecule may comprise the CDRs of a clone selected from the group consisting of S1D12, E2E8, E1E8. E2A6, E2B7, NS2A1, S1E12, S1B1. S1D9, S1F4, S1G2. S1G10, S2C6, MD9, 412E10, 412B9, 412E6, 412G11, CA2, CA4, CA9, CA12, CB2, CB3, CB7, CC7, CE2, CE3, 3aA6, 3aD6, 3aB7, 3bF4, 3aD3, 3aH6, 3aG3, 3bG4 and NS1G7;

or for each CDR sequence, an amino acid sequence with (i) at least 85% identity thereto, and/or (ii) one, two, or three amino acid substitutions relative thereto, wherein the specific binding molecule binds to an epitope within SEQ ID NO: 1.

The specific binding molecule may comprise the CDRs of a clone selected from the group consisting of S1D12, E2E8, E1E8, E2A6, E2B7, NS2A1, S1E12, S1B1, S1D9, S1F4, S1G2, S1G10, S2C6, MD9, 412E10, 412B9, 412E6, 412G11, CA2, CA4, CA9, CA12, CB2, CB3, CB7, CC7, CE2, CE3, 3aA6, 3aD6, 3aB7, 3bF4, 3aD3, 3aH6, 3aG3, 3bG4 and NS1G7.

Without being bound by theory, the specific binding molecule is thought to bind to its target monovalently. The specific binding molecule may be a monovalent binder.

The specific binding molecule may bind to SEQ ID NO: 1 or a fragment thereof with a $K_D$ of less than 25 nM, less than 20 nM, less than 15 nM, less than 10 nM, less than 8 nM, less than 6 nM, less than 5 nM, less than 4 nM, less than 3 nM, less than 2 nM, less than 1 nM, less than 0.5 nM, less than 0.4 nM, less than 0.3 nM, less than 0.2 nM or less than 0.15 nM.

The specific binding molecule may bind to SEQ ID NO: 1 or a fragment thereof with a $K_D$ of less than 10 nM.

The specific binding molecule may have a $K_D$ of 5 to 25 nM. The specific binding molecule may have a $K_D$ of 5 to 20 nM. The specific binding molecule may have a Kc of 6 to 25 nM. The specific binding molecule may have a $K_D$ of 6 to 20 nM.

The specific binding molecule may compete for binding to the same epitope as the epitope bound by mAb423. Without being bound by theory, the epitope of mAb423 is thought to be DHGAE, corresponding to residues 387-391 of SEQ ID NO: 1. It is thought that the binding of mAb423 is Glu-391 specific. Accordingly, mAb423 does not bind to DHGA, corresponding to residues 387-390 of SEQ ID NO: 1. The specific binding molecule may therefore compete for binding to DHGAE, corresponding to residues 387 to 391 of SEQ ID NO: 1. Any specific binding molecule disclosed herein with an epitope comprising one or more of residues 387 to 391 of SEQ ID NO:1 may therefore compete for binding to the same epitope as the epitope bound by mAb423. For example, a specific binding molecule with an epitope within an amino acid sequence comprising residues 369 to 390 of SEQ ID NO: 1 may compete for binding to the same epitope as the epitope bound by mAb423. Preferably, the specific binding molecules that compete for binding to the same epitope as the epitope bound by mAb423 are Glu-391 specific. The specific binding molecule that competes for binding to the same epitope as the epitope bound by mAb423 may therefore be selected from the group consisting of E1E8, E2A6, E2B7, E2E8 and E1B8.

The epitopes of clones directed to the dGAE fragment may include residues thought to be involved in the formation of the "C shaped" architecture of the PHF core (see FIGS. 2 to 4). The binding of such clones may impair the formation of the "C shaped" architecture of the PHF core or inhibit binding of subunits to existing oligomers by steric hinderance and/or inhibiting the association of key residues.

The specific binding molecule may compete with the binding of a first region within residues 296 to 391 of SEQ ID NO: 1 to a second region within residues 296 to 391 of SEQ ID NO: 1. Accordingly, the specific binding molecule may compete with the binding of a first region within the dGAE fragment to a second region within the dGAE fragment.

The specific binding molecule may compete with the binding of a first region within residues 296 to 390 of SEQ ID NO: 1 to a second region within residues 296 to 390 of SEQ ID NO: 1. Accordingly, the specific binding molecule may compete with the binding of a first region within the dGA fragment to a second region within the dGA fragment.

The specific binding molecule may compete with the binding of a first region within residues 308 to 378 of SEQ ID NO: 1 to a second region within residues 308 to 378 of SEQ ID NO: 1. Accordingly, the specific binding molecule may compete with the binding of a first region within dGAE73 and/or dGAE71 to a second region within dGAE73 and/or dGAE71.

The specific binding molecule may compete with the binding of a first region within residues 296 to 386 of SEQ ID NO: 1 to a second region within residues 296 to 386 of SEQ ID NO: 1.

The specific binding molecule may compete with the binding of a first region within residues 306 to 391 of SEQ ID NO: 1 to a second region within residues 306 to 391 of SEQ ID NO: 1.

The specific binding molecule may compete with the binding of a first region within residues 306 to 386 of SEQ ID NO: 1 to a second region within residues 306 to 386 of SEQ ID NO: 1.

The first and second region may be within the same polypeptide molecule. Accordingly, the specific binding molecule may inhibit the formation of a hairpin structure of the PHF core. The specific binding molecule may inhibit the folding of the PHF core.

The PHF core is composed of eight β-sheets (β 1-8) that run along the length of the protofilament, adopting a C-shaped architecture.

Starting from the termini of the PHF, there is a heterotypic cross-β interface formed between β 1-2 and β 8. The N-terminal end of the ordered core is formed by the hexapeptide $_{306}VQIVYK_{311}$, (SEQ ID NO: 430) which forms a complementary packing interface with residues 373-378 from the opposing β 8 by face-to-face packing of hydrophobic groups. The specific binding molecule may compete with the binding of residues 306 to 311 of SEQ ID NO: 1 to residues 373 to 378 of SEQ ID NO: 1. Any specific binding molecule disclosed herein with an epitope overlapping either 306 to 311 of SEQ ID NO: 1 or residues 373 to 378 of SEQ ID NO: 1 may compete with the binding of residues 306 to 311 of SEQ ID NO: 1 to residues 373 to 378 of SEQ ID NO: 1. For example, a specific binding molecule with an epitope within residues 367 to 379 of SEQ ID NO: 1 may compete with the binding of residues 306 to 311 of SEQ ID NO: 1 to residues 373 to 378 of SEQ ID NO: 1. For instance, a specific binding molecule comprising the CDRs of S1G2 (or a derivative thereof) may compete with the binding of residues 306 to 311 of SEQ ID NO: 1 to residues 373 to 378 of SEQ ID NO: 1.

Strands β 2 (residues 313-322 of SEQ ID NO: 1) and β 8 (residues 368-378 of SEQ ID NO: 1) pack against each other through a polar-zipper motif. The specific binding molecule may compete with the binding of residues 313 to 322 of SEQ ID NO: 1 to residues 368 to 378 of SEQ ID NO: 1. Any specific binding molecule disclosed herein with an epitope overlapping either 313 to 322 of SEQ ID NO: 1 or residues 368 to 378 of SEQ ID NO: 1 may compete with the binding of residues 313 to 322 of SEQ ID NO: 1 to residues 368 to 378 of SEQ ID NO: 1. For example, a specific binding molecule with an epitope within residues 367 to 379 of SEQ ID NO: 1 may compete with the binding of residues 313 to 322 of SEQ ID NO: 1 to residues 368 to 378 of SEQ ID NO: 1. For instance, a specific binding molecule comprising the CDRs of S1G2 (or a derivative thereof) may compete with the binding of residues 313 to 322 of SEQ ID NO: 1 to residues 368 to 378 of SEQ ID NO: 1.

A hydrophobic cluster of L324, I326 and V363 stabilizes the region immediately after a turn in the PHF core and the cross-β interface between β 3 and β 7 is further cemented by hydrogen bonds between the sidechains of H328 and T361. The specific binding molecule may compete with the binding of residues 327 to 331 of SEQ ID NO: 1 to residues 356 to 363 of SEQ ID NO: 1. Any specific binding molecule disclosed herein with an epitope overlapping either 324 to 331 of SEQ ID NO: 1 or residues 356 to 363 of SEQ ID NO: 1 may compete with the binding of residues 327 to 331 of SEQ ID NO: 1 to residues 356 to 363 of SEQ ID NO: 1.

For example, a specific binding molecule with an epitope within residues 319 to 331 of SEQ ID NO: 1 may compete with the binding of residues 327 to 331 of SEQ ID NO: 1 to residues 356 to 363 of SEQ ID NO: 1. For instance, a specific binding molecule comprising the CDRs of CE2 (or a derivative thereof) may compete with the binding of residues 327 to 331 of SEQ ID NO: 1 to residues 356 to 363 of SEQ ID NO: 1.

As a further example, a specific binding molecule with an epitope within residues 355 to 367 of SEQ ID NO: 1 may compete with the binding of residues 327 to 331 of SEQ ID NO: 1 to residues 356 to 363 of SEQ ID NO: 1. For instance, a specific binding molecule comprising the CDRs of CA4 (or a derivative thereof) may compete with the binding of residues 327 to 331 of SEQ ID NO: 1 to residues 356 to 363 of SEQ ID NO: 1.

The two "sides" of the PHF core meet through a β-helix structure that is defined by three β-strands in residues 337 to 368 of SEQ ID NO: 1 (β 4-6). The "hinge" region of the PHF core may be defined as residues 337 to 355 of SEQ ID NO: 1 and may alternatively be defined as the "critical abnormal fold". Two-residue (E342, K343) and three-residue ($_{347}$KDR$_{349}$) β-arc corners punctuate the triangular β-helix geometry, which is closed with a pivotal ~ 70° glycine conformation (G355). Hydrophobic clustering, aliphatic stacking (V339, L344, V350 and I354) and aromatic stacking (F346) stabilize the interior of the β-helix. Any specific binding molecule disclosed herein with an epitope overlapping residues 337 to 355 of SEQ ID NO: 1 may compete with the binding of residues 337 to 355 of SEQ ID NO: 1 to residues 337 to 355 of SEQ ID NO: 1. For example, a specific binding molecule with an epitope within residues 337 to 355 of SEQ ID NO: 1 may compete with the binding of residues 337 to 355 of SEQ ID NO: 1 to residues 337 to 355 of SEQ ID NO: 1. For instance, a specific binding molecule comprising the CDRs of S1D12 (or a derivative thereof) may compete with the binding of residues 337 to 355 of SEQ ID NO: 1 to residues 337 to 355 of SEQ ID NO: 1.

Specific binding molecules competing for binding of regions described above may have utility in preventing the formation of the PHF core structure and therefore inhibiting tau aggregation. A combination of specific binding molecules competing for binding of multiple regions described above may have increased utility in preventing the formation of the PHF core structure and therefore inhibiting tau aggregation.

Alternatively, the first and second region may be within different polypeptide molecules. Accordingly, the specific binding molecule may inhibit the binding of a first polypeptide to a second polypeptide. The first and second polypeptides may comprise the PHF core.

As illustrated in FIGS. 5 and 6, a new dGAE unit progressively unfolds and becomes aligned with the structure of an existing oligomer. This attachment sequence may be understood in terms of 3 stages corresponding to progressive binding of key segments of dGAE and their epitopes into the oligomer. As can be seen, the hinge region recognised by S1D12 is the primary site of attachment, followed by progressive symmetrical binding of the other domains.

The specific binding molecule may compete with the binding of a first polypeptide comprising the amino acid sequence GGGQVEVKSEKLDFKDRVQSK (SEQ ID NO: 375-corresponding to residues 333 to 353 of SEQ ID NO: 1) to a second polypeptide comprising the PHF core. The specific binding molecule may compete with the binding of a first polypeptide comprising residues 333 to 353 of SEQ ID NO: 1 to a second polypeptide comprising residues 333 to 353 of SEQ ID NO: 1. Any specific binding molecule disclosed herein with an epitope overlapping residues 333 to 353 of SEQ ID NO: 1 may compete with the binding of a first polypeptide comprising residues 333 to 353 of SEQ ID NO: 1 to a second polypeptide comprising the PHF core and/or residues 333 to 353 of SEQ ID NO: 1. For example, a specific binding molecule with an epitope within residues 337 to 355 of SEQ ID NO: 1 may compete with the binding of a first polypeptide comprising residues 333 to 353 of SEQ ID NO: 1 to a second polypeptide comprising the PHF core and/or residues 333 to 353 of SEQ ID NO: 1. For instance, a specific binding molecule comprising the CDRs of S1D12 (or a derivative thereof) may compete with the binding of a first polypeptide comprising residues 333 to 353 of SEQ ID NO: 1 to a second polypeptide comprising the PHF core and/or residues 333 to 353 of SEQ ID NO: 1.

The specific binding molecule may compete with the binding of a first polypeptide comprising the amino acid sequence CGSLGNIHHKPG (SEQ ID NO: 376-corresponding to residues 322 to 333 of SEQ ID NO: 1) to a second polypeptide comprising the PHF core. The specific binding molecule may compete with the binding of a first polypeptide comprising residues 322 to 333 of SEQ ID NO: 1 to a second polypeptide comprising residues 322 to 333 of SEQ ID NO: 1. Any specific binding molecule disclosed herein with an epitope overlapping residues 322 to 333 of SEQ ID NO: 1 may compete with the binding of a first polypeptide comprising residues 322 to 333 of SEQ ID NO: 1 to a second polypeptide comprising the PHF core and/or residues 322 to 333 of SEQ ID NO: 1. For example, a specific binding molecule with an epitope within residues 319 to 331 of SEQ ID NO: 1 may compete with the binding of a first polypeptide comprising residues 322 to 333 of SEQ ID NO: 1 to a second polypeptide comprising the PHF core and/or residues 322 to 333 of SEQ ID NO: 1. For instance, a specific binding molecule comprising the CDRs of CE2 (or a derivative thereof) may compete with the binding of a first polypeptide comprising residues 322 to 333 of SEQ ID NO: 1 to a second polypeptide comprising the PHF core and/or residues 322 to 333 of SEQ ID NO: 1.

The specific binding molecule may compete with the binding of a first polypeptide comprising the amino acid sequence SLDNITHVP (SEQ ID NO: 377-corresponding to residues 356 to 364 of SEQ ID NO: 1) to a second polypeptide comprising the PHF core. The specific binding molecule may compete with the binding of a first polypeptide comprising residues 356 to 364 of SEQ ID NO: 1 to a second polypeptide comprising residues 356 to 364 of SEQ ID NO: 1. Any specific binding molecule disclosed herein with an epitope overlapping residues 356 to 364 of SEQ ID NO: 1 may compete with the binding of a first polypeptide comprising residues 356 to 364 of SEQ ID NO: 1 to a second polypeptide comprising the PHF core and/or residues 356 to 364 of SEQ ID NO: 1. For example, a specific binding molecule with an epitope within residues 355 to 367 of SEQ ID NO: 1 may compete with the binding of a first polypeptide comprising residues 356 to 364 of SEQ ID NO: 1 to a second polypeptide comprising the PHF core and/or residues 356 to 364 of SEQ ID NO: 1. For instance, a specific binding molecule comprising the CDRs of CA4 (or a derivative thereof) may compete with the binding of a first polypeptide comprising residues 356 to 364 of SEQ ID NO: 1 to a second polypeptide comprising the PHF core and/or residues 356 to 364 of SEQ ID NO: 1.

The specific binding molecule may compete with the binding of a first polypeptide comprising the amino acid sequence VQIVYKPVD (SEQ ID NO: 378-corresponding to residues 306 to 314 of SEQ ID NO: 1) to a second polypeptide comprising the PHF core. The specific binding molecule may compete with the binding of a first polypeptide comprising residues 306 to 314 of SEQ ID NO: 1 to a second polypeptide comprising residues 306 to 314 of SEQ ID NO: 1. Any specific binding molecule disclosed herein with an epitope overlapping residues 306 to 314 of SEQ ID NO: 1 may compete with the binding of a first polypeptide comprising residues 306 to 314 of SEQ ID NO: 1 to a second polypeptide comprising the PHF core and/or residues 306 to 314 of SEQ ID NO: 1. For example, a specific binding molecule with an epitope comprising residues 306 to 314 of SEQ ID NO: 1 may compete with the binding of a first polypeptide comprising residues 306 to 314 of SEQ ID NO: 1 to a second polypeptide comprising the PHF core and/or residues 306 to 314 of SEQ ID NO: 1.

The specific binding molecule may compete with the binding of a first polypeptide comprising the amino acid sequence KKIETHKLTF (SEQ ID NO: 379-corresponding to residues 369 to 378 of SEQ ID NO: 1) to a second polypeptide comprising the PHF core. The specific binding molecule may compete with the binding of a first polypeptide comprising residues 369 to 378 of SEQ ID NO: 1 to a second polypeptide comprising residues 369 to 378 of SEQ ID NO: 1. Any specific binding molecule disclosed herein with an epitope overlapping residues 369 to 378 of SEQ ID NO: 1 may compete with the binding of a first polypeptide comprising residues 369 to 378 of SEQ ID NO: 1 to a second polypeptide comprising the PHF core and/or residues 369 to 378 of SEQ ID NO: 1. For example, a specific binding molecule with an epitope within residues 367 to 379 of SEQ ID NO: 1 may compete with the binding of a first polypeptide comprising residues 369 to 378 of SEQ ID NO: 1 to a second polypeptide comprising the PHF core and/or residues 369 to 378 of SEQ ID NO: 1. For instance, a specific binding molecule comprising the CDRs of S1G2 (or a derivative thereof) may compete with the binding of a first polypeptide comprising residues 369 to 378 of SEQ ID NO: 1 to a second polypeptide comprising the PHF core and/or residues 369 to 378 of SEQ ID NO: 1.

Without being bound by theory, in any embodiment where the binding of a specific binding molecule competes with the binding of a first region within residues 296 to 391 of SEQ ID NO: 1 to a second region within residues 296 to 391 of SEQ ID NO: 1 (or within the other ranges or residues of SEQ ID NO: 1 set out above), the specific binding molecule may inhibit the tau aggregation. This applies whether the first and second region are within the same or different polypeptide molecules. Any suitable test for determining competitive binding or for screening inhibitors of tau aggregation may therefore be used to confirm that a specific binding molecule competes with the binding of a first region within residues 296 to 391 of SEQ ID NO: 1 to a second region within residues 296 to 391 of SEQ ID NO: 1.

Suitable screening methods include a thioflavin T-assay, a tau-tau immunoassay and an assay for assessing the effects of aggregated tau in cell culture. A suitable assay for assessing the effects of aggregated tau in cell culture is disclosed in UK application no. GB2010620.9 filed on 10 Jul. 2020, and in international (PCT) application no. PCT/EP2021/069138 filed on 9 Jul. 2021 and claiming priority to UK application no. GB2010620.9, both of which are hereby incorporated by reference in their entirety.

The invention provides specific binding molecules with high affinities for their ligands. A specific binding molecule with high affinity for its ligand is advantageous in the present invention, as, generally, less of a specific binding molecule with high affinity for its ligand is required to achieve a particular effect than of a specific binding molecule with lower affinity for the same ligand. For instance, if the specific binding molecule is for therapeutic use, it can be expected that a lower dosage would be required of a specific binding molecule with high affinity for its ligand than of a specific binding molecule with lower affinity for the same ligand. This may be advantageous for the patient, who might require fewer or smaller doses of the specific binding molecule, e.g. antibody, and would also be more economical, as less of the specific binding molecule would be required for the therapy.

The affinity of a binding molecule for its ligand (or binding partner), such as the affinity of an antibody for its target antigen, can be quantitatively defined by the dissociation constant ($K_D$) for a complex of the binding molecule and ligand. The $K_D$ value of a specific binding molecule, e.g. an antibody, corresponds to the ratio of the binding molecule dissociation rate (i.e. how quickly it dissociates from its ligand) to the binding molecule association rate (i.e. how quickly it binds its ligand). A lower $K_D$ value corresponds to a higher binding affinity of the binding molecule for its ligand. Kc may be measured under any suitable conditions for binding of specific binding molecule to its ligand, preferably under conditions identified as optimal. Methods as described in the Examples may be used. Alternatively, any other conditions identified as promoting the binding of the specific binding molecule of the invention to a peptide comprising the epitope within SEQ ID NO: 1 bound by the specific binding molecule may be used. A number of methods by which the Kc of an interaction between a specific binding molecule and its ligand may be calculated are well-known in the art. Known techniques include SPR (e.g.

Biacore) and polarization-modulated oblique-incidence reflectivity difference (OI-RD).

The specific binding molecule may be an isolated specific binding molecule.

As indicated, the specific binding molecule of the invention comprises 6 CDRs consisting of polypeptide sequences. As used herein, "protein" and "polypeptide" are interchangeable, and each refer to a sequence of 2 or more amino acids joined by one or more peptide bonds. Thus, the specific binding molecule may be a polypeptide. Alternatively, the specific binding molecule may comprise one or more polypeptides which comprise the CDR sequences. Preferably, the specific binding molecule of the invention is an antibody or an antibody fragment.

When a CDR sequence is modified by substitution of a particular amino acid residue, the substitution may be a conservative amino acid substitution. However, a substitution of a CDR residue may equally be a non-conservative substitution, in which one amino acid is substituted for another with a side-chain belonging to a different family.

Wherever the invention provides a CDR sequence comprising one, two, or three amino acid substitutions relative to a specified CDR sequence, said one, two, or three amino acid substitutions may be conservative amino acid substitutions. Preferably the CDR sequence comprises two conservative amino acid substitutions. More preferably the CDR sequence comprises one conservative amino acid substitution.

When a FR sequence is modified by substitution of a particular amino acid residue, the substitution may be a conservative amino acid substitution. However, a substitution of a FR residue may equally be a non-conservative substitution, in which one amino acid is substituted for another with a side-chain belonging to a different family.

Wherever the invention provides a FR sequence comprising one, two, three, four or five amino acid substitutions relative to a specified FR sequence, said one, two, three, four or five amino acid substitutions may be conservative amino acid substitutions. Preferably the FR sequence comprises four conservative amino acid substitutions. Preferably the FR sequence comprises three conservative amino acid substitutions. Preferably the FR sequence comprises two conservative amino acid substitutions. More preferably the FR sequence comprises one conservative amino acid substitution.

Amino acid substitutions or additions in the scope of the invention may be made using a proteinogenic amino acid encoded by the genetic code, a proteinogenic amino acid not encoded by the genetic code, or a non-proteinogenic amino acid. Preferably any amino acid substitution or addition is made using a proteinogenic amino acid. The amino acids making up the sequence of the CDRs may include amino acids which do not occur naturally, but which are modifications of amino acids which occur naturally. Providing these non-naturally occurring amino acids do not alter the sequence and do not affect specificity, they may be used to generate CDRs described herein without reducing sequence identity, i.e. are considered to provide an amino acid of the CDR. For example derivatives of the amino acids such as methylated amino acids may be used. The specific binding molecule of the invention be a non-natural molecule, i.e. not a molecule found in nature.

Modifications to the amino acid sequences of the CDRs set out in herein may be made using any suitable technique, such as site-directed mutagenesis of the encoding DNA sequence or solid state synthesis.

Specific binding molecules of the invention comprise CDRs as described herein. Additionally, such molecules may contain linker moieties or framework sequences to allow appropriate presentation of the CDRs. Additional sequences may also be present which may conveniently confer additional properties, e.g. peptide sequences which allow isolation or identification of the molecules containing the CDRs such as those described hereinbefore. In such cases a fusion protein may be generated.

The CDRs of the specific binding molecule of the invention may be defined as having a certain percentage sequence identity to one or more SEQ ID NOs described herein. Sequence identity may be assessed by any convenient method. However, for determining the degree of sequence identity between sequences, computer programmes that make pairwise or multiple alignments of sequences are useful, for instance EMBOSS Needle or EMBOSS stretcher (both Rice, P, et al., Trends Genet., 16, (6) pp 276-277, 2000) may be used for pairwise sequence alignments while Clustal Omega (Sievers F et al., Mol. Syst. Biol. 7:539, 2011) or MUSCLE (Edgar, R. C., Nucleic Acids Res. 32 (5): 1792-1797, 2004) may be used for multiple sequence alignments, though any other appropriate programme may be used. Whether the alignment is pairwise or multiple, it must be performed globally (i.e. across the entirety of the reference sequence) rather than locally.

Sequence alignments and % identity calculations may be determined using for instance standard Clustal Omega parameters: matrix Gonnet, gap opening penalty 6, gap extension penalty 1. Alternatively, the standard EMBOSS Needle parameters may be used: matrix BLOSUM62, gap opening penalty 10, gap extension penalty 0.5. Any other suitable parameters may alternatively be used.

For the purposes of this application, where there is dispute between sequence identity values obtained by different methods, the value obtained by global pairwise alignment using EMBOSS Needle with default parameters shall be considered valid.

Wherever the invention provides a CDR sequence with at least 85% identity to a specified CDR sequence, said sequence identity is at least about 85% sequence identity and may therefore be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity. Preferably said sequence identity is at least 90% or at least 95%.

As stated above, the specific binding molecule of the invention is preferably an antibody or an antibody fragment. An "antibody" is an immunoglobulin having the features described hereinbefore. Also contemplated by the invention are variants of naturally occurring antibodies which retain the CDRs but are presented in a different framework, as discussed hereinafter and which function in the same way, i.e. retain specificity for the antigen. Thus, antibodies include functional equivalents or homologues in which naturally occurring domains have been replaced in part or in full with natural or non-natural equivalents or homologues which function in the same way.

When the specific binding molecule of the invention is an antibody, it is preferably a monoclonal antibody. By "monoclonal antibody" is meant an antibody preparation consisting of a single antibody species, i.e. all antibodies in the preparation have the same amino acid sequences, including the same CDRs, and thus bind the same epitope on their target antigen (by "target antigen" is meant the antigen containing the epitope bound by a particular antibody, i.e. the target antigen of an anti-2N4R antibody is 2N4R) with the same effect. In other words, the antibody of the invention is preferably not part of a polyclonal mix of antibodies.

In an antibody, as described above, the CDR sequences are located in the variable domains of the heavy and light chains. The CDR sequences sit within a polypeptide framework, which positions the CDRs appropriately for antigen binding. Thus, the remainder of the variable domains (i.e. the parts of the variable domain sequences which do not form a part of any one of the CDRs) constitute framework regions. The N-terminus of a mature variable domain forms framework region 1 (FR1); the polypeptide sequence between CDR1 and CDR2 forms FR2; the polypeptide sequence between CDR2 and CDR3 forms FR3; and the polypeptide sequence linking CDR3 to the constant domain forms FR4. In an antibody of the invention the variable region framework regions may have any appropriate amino acid sequence such that the antibody binds to SEQ ID NO: 1 or a fragment thereof via its CDRs. The constant regions may be the constant regions of any mammalian (preferably human) antibody isotype.

In certain embodiments of the invention the specific binding molecule may be multi-specific, e.g. a bi-specific monoclonal antibody. A multi-specific binding molecule contains regions or domains (antigen-binding regions) which bind to at least two different molecular binding partners, e.g. bind to two or more different antigens or epitopes. In the case of a bi-specific antibody, the antibody comprises two heavy and light chains, in the formation as described above, except that the variable domains of the two heavy chains and the two light chains, respectively, are different, and thus form two different antigen-binding regions. In a multi-specific (e.g. bi-specific) binding molecule, e.g. monoclonal antibody, of the invention, one of the antigen-binding regions has the CDR sequences of a specific binding molecule of the invention as defined herein, and thus binds SEQ ID NO: 1 or a fragment thereof. The other antigen-binding region(s) of the multi-specific binding molecule of the invention are different to the antigen-binding regions formed by CDRs of the invention, e.g. have CDRs with sequences different to those defined herein for the specific binding molecule of the invention. The additional (e.g. second) antigen-binding region(s) of the specific binding molecule, e.g. in the bi-specific antibody, may also bind SEQ ID NO: 1 or a fragment thereof, but at a different epitope to the first antigen-binding region which binds to SEQ ID NO: 1 or a fragment thereof (which has the CDRs of the specific binding molecule of the invention). Alternatively, the additional (e.g. second) antigen-binding region(s) may bind additional (e.g. a second), different antigen(s) which is (are) not SEQ ID NO: 1 or a fragment thereof. In an alternative embodiment, the two or more antigen-binding regions in the specific binding molecule, e.g. in an antibody, may each bind to the same antigen, i.e. provide a multivalent (e.g. bivalent) molecule.

The specific binding molecule may be an antibody fragment or synthetic construct capable of binding human SEQ ID NO: 1 or a fragment thereof. Antibody fragments are discussed in Rodrigo et al., Antibodies, Vol. 4 (3), p. 259-277, 2015. Antibody fragments of the invention are preferably monoclonal (i.e. they are not part of a polyclonal mix of antibody fragments). Antibody fragments include, for example, Fab, F(ab')₂, Fab' and Fv fragments. Fab fragments are discussed in Roitt et al, Immunology second edition (1989), Churchill Livingstone, London. A Fab fragment consists of the antigen-binding domain of an antibody, i.e. an individual antibody may be seen to contain two Fab fragments, each consisting of a light chain and its conjoined N-terminal section of the heavy chain. Thus, a Fab fragment contains an entire light chain and the VH and CH1 domains of the heavy chain to which it is bound. Fab fragments may be obtained by digesting an antibody with papain.

F(ab')₂ fragments consist of the two Fab fragments of an antibody, plus the hinge regions of the heavy domains, including the disulphide bonds linking the two heavy chains together. In other words, a F(ab')₂ fragment can be seen as two covalently joined Fab fragments. F(ab')₂ fragments may be obtained by digesting an antibody with pepsin. Reduction of F(ab')₂ fragments yields two Fab' fragments, which can be seen as Fab fragments containing an additional sulfhydryl group which can be useful for conjugation of the fragment to other molecules.

Fv fragments consist of just the variable domains of the light and heavy chains. These are not covalently linked and are held together only weakly by non-covalent interactions. Fv fragments can be modified to produce a synthetic construct known as a single chain Fv (scFv) molecule. Such a modification is typically performed recombinantly, by engineering the antibody gene to produce a fusion protein in which a single polypeptide comprises both the VH and VL domains, scFv fragments generally include a peptide linker covalently joining the VH and VL regions, which contributes to the stability of the molecule. The linker may comprise from 1 to 20 amino acids, such as for example 1, 2, 3 or 4 amino acids, 5, 10 or 15 amino acids, or other intermediate numbers in the range 1 to 20 as convenient. The peptide linker may be formed from any generally convenient amino acid residues, such as glycine and/or serine. One example of a suitable linker is Gly4Ser. Multimers of such linkers may be used, such as for example a dimer, a trimer, a tetramer or a pentamer, e.g. (Gly4Ser) 2, (Gly4Ser) 3, (Gly4Ser) 4 or (Gly4Ser) 5. However, it is not essential that a linker be present, and the VL domain may be linked to the VH domain by a peptide bond. An scFv is herein defined as an antibody fragment.

The specific binding molecule may be an analogue of an scFv. For example, the scFv may be linked to other specific binding molecules (for example other scFvs. Fab antibody fragments and chimeric IgG antibodies (e.g. with human frameworks)). The scFv may be linked to other scFvs so as to form a multimer which is a multi-specific binding protein, for example a dimer, a trimer or a tetramer. Bi-specific scFvs are sometimes referred to as diabodies, tri-specific scFvs as triabodies and tetra-specific scFvs as tetrabodies. In other embodiments the scFv of the invention may be bound to other, identical scFv molecules, thus forming a multimer which is mono-specific but multi-valent, e.g. a bivalent dimer or a trivalent trimer may be formed. Synthetic constructs that can be used include CDR peptides. These are synthetic peptides comprising antigen-binding determinants. Peptide mimetics can also be used. These molecules are usually conformationally-restricted organic rings that mimic the structure of a CDR loop and that include antigen-interactive side chains.

The specific binding molecule may be a scAb (single-chain antibody). A scAb may comprise an scFv. The scFv may comprise a variable heavy domain and a variable light domain optionally joined by a flexible protein linker as described above. A scAb may further comprise a light chain constant domain. The light chain constant domain may be human, such as a human Ck domain.

The antibody or antibody fragment of the invention may be a chimeric antibody, or preferably may be humanised. This is particularly the case for monoclonal antibodies and antibody fragments. Humanised or chimeric antibodies or antibody fragments are desirable when the molecule is to be used as a human therapeutic. Therapeutic treatment of humans with murine antibodies can be ineffective for a number of reasons, e.g. a short in vivo half-life of the antibody; weak effector functions mediated by the mouse heavy chain constant region due to low recognition of the murine heavy chain constant region by Fc receptors on human immune effector cells; patient sensitisation to the antibody, and generation of a human anti-mouse antibody (HAMA) response; and neutralisation of the mouse antibody by HAMA leading to loss of therapeutic efficacy.

As detailed above, the isotype of an antibody is defined by the sequence of its heavy chain constant regions. The chimeric antibody of the invention may have the constant regions of any human antibody isotype, and any sub-class within each isotype. For instance, the chimeric antibody may have the Fc regions of an IgA, IgD, IgE, IgG or IgM antibody (i.e. the chimeric antibody may comprise the constant domains of heavy chains $\alpha$, $\delta$, $\epsilon$, $\gamma$, or $\mu$, respectively), though preferably the antibody of the invention is of the IgG isotype. Thus, the chimeric antibody of the invention may be of any isotype. The light chain of the chimeric antibody may be either a $\kappa$ or $\lambda$ light chain, i.e. it may comprise the constant region of a human $\lambda$ light chain or a human $\kappa$ light chain. A chimeric antibody fragment is, correspondingly, an antibody fragment comprising constant domains (e.g. an Fab, Fab' or $F(ab')_2$ fragment). The constant domains of a chimeric antibody fragment of the invention may be as described above for a chimeric monoclonal antibody.

Chimeric antibodies may be generated using any suitable technique, e.g. recombinant DNA technology in which the DNA sequence of the murine variable domain is fused to the DNA sequence of the human constant domain(s) so as to encode a chimeric antibody. A chimeric antibody fragment may be obtained either by using recombinant DNA technology to produce a DNA sequence encoding such a polypeptide, or by processing a chimeric antibody of the invention to produce the desired fragments, as described above. Chimeric antibodies can be expected to overcome the problems of a short in vivo half-life and weak effector functions associated with using a murine antibody in human therapy, and may reduce the probability of patient sensitisation and HAMA occurring. However, patient sensitisation and HAMA may still occur when a chimeric antibody is administered to a human patient, due to the presence of murine sequences in the variable domains.

Preferably the antibody or antibody fragment of the invention is therefore fully humanised. A humanised antibody is an antibody derived from another species, e.g. a mouse, in which not only are the constant domains of the antibody chains replaced with human constant domains, but the amino acid sequences of the variable regions are modified, in particular to replace the foreign (e.g. murine) framework sequences with human framework sequences, such that, preferably, the only non-human sequences in the antibody are the CDR sequences. A humanised antibody can overcome all the problems associated with therapeutic use of a non-human antibody in a human, including avoiding or minimising the probability of patient sensitisation and HAMA occurring.

Antibody humanisation is generally performed by a process known as CDR grafting, though any other technique in the art may be used. CDR grafting is well described in Williams, D. G, et al., Antibody Engineering Vol. 1, edited by R. Kontermann and S. DObel, Chapter 21, pp. 319-339. In this process, a chimeric antibody as described above is first generated. Subsequent humanisation of the foreign, e.g. murine, variable domains involves intercalating the murine CDRs from each immunoglobulin chain within the FRs of the most appropriate human variable region. This is done by aligning the murine variable domains with databases of known human variable domains (e.g. IMGT or Kabat). Appropriate human framework regions are identified from the best aligned variable domains, e.g. domains with high sequence identity between the human and murine framework regions, domains containing CDRs of the same length, domains having the most similar structures (based on homology modelling), etc. The murine CDR sequences are then grafted into the lead human framework sequences at the appropriate locations using recombinant DNA technology, and the humanised antibodies then produced and tested for binding to the target antigen. The process of antibody humanisation is known and understood by the skilled individual, who can perform the technique without further instruction. Antibody humanisation services are also offered by a number of commercial companies, e.g. GenScript (USA/China) or MRC Technology (UK). Humanised antibody fragments can be easily obtained from humanised antibodies, as described above.

Thus, the antibody or antibody fragment of the invention may be derived from any species, e.g. it may be a murine antibody or antibody fragment. It is preferred, however, that the antibody or antibody fragment is a chimeric antibody or antibody fragment, i.e. that only the variable domains of the antibody or antibody fragment are non-human, and the constant domains are all human. Optimally, the antibody or antibody fragment of the invention is a humanised antibody or antibody fragment.

The invention also provides a composition comprising the specific binding molecule described above. At least 90% of the specific binding molecules in the composition that bind to an epitope within SEQ ID NO: 1 bind with a $K_D$ of less than 25 nM, preferably less than 20 nM, 15 nM or 10 nM. Techniques by which $K_D$ of the binding molecule may be measured, and conditions under which the $K_D$ may be measured, are described above. In an alternative embodiment, a composition is provided comprising the specific binding molecule of the invention in which at least 90% of the specific binding molecules in the composition that bind to an epitope within SEQ ID NO: 1 have the CDRs as described hereinbefore, and preferably contain two copies of the CDRs in each molecule (e.g. in an antibody). In a yet further embodiment, a composition is provided comprising the specific binding molecule of the invention in which the specific binding molecule is an antibody or fragment thereof and at least 90% of the antibodies or fragments in said composition are said antibodies or fragments of the invention (i.e. contain the CDRs as described hereinbefore, preferably contain two copies of the CDRs described hereinbefore). Further preferred compositions according to the invention comprise antibody fragments, monoclonal antibodies or their fragments, chimeric antibodies or their fragments, or humanized antibodies or their fragments, of the invention.

In an alternative statement of the first aspect of the invention, the invention provides a specific binding molecule that binds to an epitope within SEQ ID NO: 1. In this alternative first aspect, the specific binding molecule of the invention is defined without reference to the binding affinity with which antibody mAb423. This alternative first aspect of the invention is disclosed in combination with any and all of the features identified above in relation to the first aspect of the invention and any and all of the features identified below in relation to subsequent aspects of the invention.

According to a second aspect, the invention provides a composition comprising a specific binding molecule according to the first aspect of the invention, wherein at least 90% of the specific binding molecules in the composition that bind an epitope within SEQ ID NO: 1 bind with a $K_D$ of less than 25 nM.

The term "composition" as used herein means a product (e.g. a solution or preparation) containing at least the specific binding molecule of the invention. The composition should be made up in a form in which the specific binding molecule may be stably stored, i.e. a form in which the specific binding molecule does not degrade or become denatured, or lose its structure or activity. Suitable conditions in which an antibody may be stored are well known to the skilled person. The composition of the invention may be a liquid composition (i.e. a solution), such as an aqueous composition (i.e. a solution made up in water) or a composition made up in solvent, such as one or more organic solvents, or primarily in a solvent. Such a solvent may be polar or non-polar. Alternatively, the composition may be a powder, such a lyophilised powder, or may be in any other suitable form for the storage of a specific binding molecule.

At least 90% of the specific binding molecules in the composition that bind to SEQ ID NO: 1 bind with a $K_D$ of less than 25 nM, preferably less than 20 nM, 15 nM or 10 nM. Preferably at least 95%, 96%, 97%, 98% or 99% of the specific binding molecules in the composition that bind to SEQ ID NO: 1 bind with a Kn of less than 25 nM, 20 nM, 15 nM or 10 nM. In this embodiment the specific binding molecule has the definition described hereinbefore but is not necessarily a specific binding molecule of the invention, i.e. all specific binding molecules which bind SEQ ID NO: 1 are assessed to determine if at least 90% have the required $K_D$. Preferably the specific binding molecules to be assessed are antibodies or their fragments. The skilled person is able to calculate the $K_D$ of the binding of a specific binding molecule to its ligand. Conditions under which the $K_D$ of specific binding molecules of the invention may be calculated, and methods by which this may be achieved, are mentioned above. By 90% is meant 90% of the number of specific binding molecules which bind SEQ ID NO: 1 (i.e. 9 out of 10 specific binding molecules which bind SEQ ID NO: 1), not 90% w/w. As noted, at least 90% of the specific binding molecules which bind SEQ ID NO: 1 bind with a $K_D$ of less than 25 nM, preferably less than 20 nM, 15 nM or 10 nM. This does not preclude that the composition contains any concentration of specific binding molecules which bind other antigens. This provides a composition in which the molecules which bind to SEQ ID NO: 1 are largely uniform, i.e. have similar functionality.

At least 90% of the specific binding molecules in the composition that bind an epitope within SEQ ID NO: 1 may bind with a $K_D$ of less than 25 nM, preferably less than 20 nM, 15 nM or 10 nM.

At least 95% of the specific binding molecules in the composition that bind an epitope within SEQ ID NO: 1 may bind with a $K_D$ of less than 25 nM, preferably less than 20 nM, 15 nM or 10 nM.

At least 99% of the specific binding molecules in the composition that bind an epitope within SEQ ID NO: 1 may bind with a $K_D$ of less than 25 nM, preferably less than 20 nM, 15 nM or 10 nM.

The composition (and preparation) of the invention may contain additives, which may be advantageous for storage of a specific binding molecule such as an antibody or antibody fragment. For instance, if the composition is a liquid, the composition may advantageously comprise a high concentration of a cryoprotective agent, such as glycerol or ethylene glycol, e.g. at least 20%, at least 25%, at least 30%, at least 40% or at least 50% glycerol or ethylene glycol. Percentages may be expressed as w/w or v/v. A cryoprotective agent prevents the composition from freezing at low temperature, protecting the specific binding molecule from ice damage during storage. Concentrated sucrose (e.g. at least 250 mM, at least 500 mM, at least 750 mM or at least 1M sucrose) may advantageously be comprised within a liquid composition. Liquid compositions may also comprise one or more antioxidants, e.g. 3-mercaptoethanol or dithiothreitol, one or more metal chelating agents, e.g. ethylenediaminetetraacetic acid (EDTA), and one or more carrier proteins, particularly bovine serum albumin (BSA). The liquid composition may preferably comprise up to 1% BSA, e.g. 0.1-0.5% BSA. The composition of the invention may be at a pH of 5-8, e.g. 6-8, 7-8 or 7-7.5. The pH may be maintained by addition of a buffer to the composition, e.g. Tris (i.e. tris(hydroxymethyl)aminomethane), HEPES or MOPS. For instance, the composition may contain 5-50 mM HEPES, e.g. 10-20 mM HEPES. Lyophilised compositions (or compositions) of the invention may contain one or more stabilisers, such as a polyol, e.g. glycerol or sorbitol, and/or a sugar, e.g. sucrose, trehalose or mannitol. The composition may also contain additional components as described for compositions described hereinafter.

According to a third aspect, the invention provides a nucleic acid molecule comprising a nucleic acid sequence encoding a specific binding molecule according to the first aspect of the invention.

The nucleic acid sequence may be selected from the group consisting of SEQ ID NOS: 43, 219, 249, 251, 253, 380 to 411, and 431 or a nucleic acid sequence with at least 70% identity to any one of SEQ ID NOS: 43, 219, 249, 251, 253, 380 to 411, and 431. Preferably the nucleic acid sequence may have at least 75%, at least 80%, at least 90%, at least 95% or at least 99% identity to any one of SEQ ID NOS: 43, 219, 249, 251, 253, 380 to 411, and 431.

```
(S1D12 nucleotide sequence)
                              SEQ ID NO: 380
CAGGTGCAGCTGCAGGAGTCGGGACCCAGCCTGGTGAAGC

CCTCACAGACCCTCTCCCTCACCTGCACGGTCTCTGGATT

CTCATTGAACAACAATGCTGTAGGCTGGGTCCGCCAGGCT

CCAGGAAAGGTGCCGGAGTCGCTTGTGGGTTGTAGCAGTG

ATGGAACGTGTTACTATAATTCGGCCCTGAAATCCCGGCT

CGACATCACCAGGGACACCTCCAAGAACCAGATCTCCCTG

TCACTGAGCAGCGTTACAACTGACGACGCGGCCGTGTACT

ATTGTACAAGAGGCCATTATAGTATTTATGGTTATGACTA

TCTTGGCACTATCGACTACTGGGGCCCAGGACTCCTGGTC

ACCGTCTCCTCAGAAGGTAAATCTTCTGGCGCGTCTGGCG

AGTCTAAAGTGGATGACCAGGCTGTGCTGACTCAGCCGTC

CTCCGTGTCCGGGTCCCTGGGCCAGAGGGTCTCCATCACC

TGCTCTGGAAGCAGCAGCAACGTCGGGGGTGGTAATAGTG

TGGGCTGGTACCAACACCTCCCAGGCTCAGGCCTCAAAAC
```

-continued

CATCATCTATGATACTAACAGTCGACCCTCGGGGGTCCCG

GACCGATTCTCTGGCTCCAGGTCTGGCAACACGGCCACCC

TAACCATCAACTCGCTCCAGGCTGAGGACGAGGGTGATTA

TTACTGTGTAACGGGTGACAGCACTACTCATGATGATCTT

GTCGGCAGCGGGACCAGGCTGACCGTCCTGGGG (S1E12 nucleotide sequence)
SEQ ID NO: 219
CAGGTGCAGTTGCAGGAGTCGGGACCCAGCCTGGTGAAGC

CCTCACAGACCCTCTCCCTCACCTGCACGGTCTCCGGATT

CTCATTAGGCAGCAATTCTGTAGGCTGGGTCCGCCAGGCT

CCAGGAAAGGCGCCGGAGTGGGTTGCTGGTATAGATACTG

ATGGAGAAGAAGGCTATAATCCAGCCCTTAACTCCCGGCT

CAGCATCACCAGGGACACCTCCAAGAGTCAGGTCTCTTTG

TCATTGAGCAGCGTGACAAGTGAGGACACGGCCGTGTACT

ACTGTGGAAGAAGTTATAGGGCTGATGGTCTTGCTTACGG

TTATGTCCAAGCCATCGACTACTGGGGCCCAGGACTCCTG

GTCACCGTCTCCTCAGAAGGTAAATCTTCTGGCGCGTCTG

GCGAGTCTAAAGTGGATGACAGGGTCGTGCGGACTCAACC

GTCCTCCGTGTCTGGGTCCCTGGGCCAGAGGGTCTCCATC

ACCTGCTCTGGAAGCTTCATCGGTATTAGTAGTGTAGGCT

GGTTCCAACAGCTCCCAGGATCGGGCCTCAGAACCATCAT

CGTGGCGAGTGACGGTCGACCCTCAGGGGTCCCCGACCGA

TTCTCTATGTCCAAATCGGGCAACACAGCCACCCTGACCA

TCAGCTCGCTCCAGGCTGAGGACGAGGCCGATTATTTCTG

TGGAAGTAGTGATAGGACTCAATATACTGGAGTTTTCGGC

AGCGGGACCAGGCTGACCGTCCTGGGT (S1G2 nucleotide sequence)
SEQ ID NO: 381
CAGGTGCAGCTGCAGGAGTCGGGACCCAGCCTGGTGAAGC

CCTCACAGACCCTCTCCCTCACCTGCACGGTCTCTGGATT

CTCATTAACCAGCAATTCTGTGGGCTGGGTCCGACAGGCT

CCAGGAAAGGCGCCGGAGTGGGTTGCTGGTATAGATACTG

ATGGAGAAGAAGGCTATAATCCAGCCCTTAACTCCCGGCT

CAGCATCACCAGGGACACCTCCAAGAGTCAAGTCTCTTTG

TCATTGAGCAGCGTGACAAGTGAGGACACGGCCGTGTACT

ACTGTGGAAGAAGTTATAGGGCTGATGGTCTTGCTTACGG

TTATGTCCAAGCCATCGACTACTGGGGCCCAGGACTCCTG

GTCACCGTCTCCTCAGAAGGTAAATCTTCTGGCGCGTCTG

GCGAGTCTAAAGTGGATGACCAGGCCGTGGTGACTCAGCC

GTCCTCCGTGTCTGGGTCCCTGGGCCAGAGGGTCTCCATC

ACCTGCTCTGGAAGCTTCATCGGTATTAGTAGTGTAGGCT

GGTTCCAACAGCTCCCAGGATCGGGCCTCAGAACCATCAT

CGTGGCGAGTGACGGTCGACCCTCAGGGGTCCCCGACCGA

-continued

TTCTCTATGTCCAAATCGGGCAACACAGCCACCCTGACCA

TCAGCTCGCTCCAGGCTGAGGACGAGGCCGATTATTTCTG

TGGAAGTAGTGATAGGACTCCTTATACTGGGGTCTTCGGC

AGCGGGACCAGGCTGACCGTCCTGGGT (S1B1 nucleotide sequence)
SEQ ID NO: 388
CAGGTGCAGCTGCAGGAGTCGGGACCCAGCCTGGTGAAGC

CCTCACAGACCCTCTCCCTCACCTGCACGGTCTCTGGATT

CTCATTGTCCAGCAATTCTGTGGGCTGGGTCCGACAGGCT

CCAGGAAAGGCGCCGGAGTGGGTTGCTGGTATAGATACTG

ATGGAGAAGAAGGCTATAATCCAGCCCTTAACTCCCGGCT

CAGCATCACCAGGGACACCTCCAAGAGTCAAGTCTCTTTG

TCATTGAGCAGCGTGACAAGTGAGGACACGGCCGTGTACT

ACTGTGTAAGAAGTTATAGGACTGATGGTCTTGCTTACGG

TTATGTCCAAGCCATCGACTACTGGGGCCCAGGACTCCTG

GTCACCGTCTCCTCAGAAGGTAAATCTTCTGGCGCGTCTG

GCGAGTCTAAAGTGGATGACCAGGCTGTGCTGACTCAGCC

GTCCTCCGTGTCTGGGTCCCTGGGCCAGAGGGTCTCCATC

ACCTGCTCTGGAAGCTTCATCGGTATTAGTAGTGTAGGCT

GGTTCCAACAGCTCCCAGGATCGGGCCTCAGAACCGTCAT

CGTTGCGAGTGACGGTCGACCCTCAGGGGTCCCCGACCGA

TTCTCTAACTCCAAATCGGGCAACACAGCCACCCTGACCA

TCAGCTCGCTCCAGGCTGAGGACGAGGCCGATTATTTCTG

TGGAAGTAGTGATAGGACTCAATATACTGGAGTTTTCGGC

AGCGGGACCAGGCTGACCGTCCTTGGT (CA4 nucleotide sequence)
SEQ ID NO: 382
CAGGTTCAGCTGCAGGAGTCGGGACCCAGCCTGGTGAAGC

CCTCACAGACCCTCTCCCTCACCTGCACGGTCTCTGGATT

CTCATTAACCAGCTATTCCGTATACTGGGTCCGCCAGGCT

CCAGGCCAGGCACTGGAGTGGATTAGTATTATGTATGCTA

GTGGAAGAGTAGACTATAACCCGGCCCTGAAATCCCGGCT

CAGCATCACCAGGGACACCTCCAAGAGTCAATTCTCCCTG

TCATTGAGCAGCGTGACAACTGAGGACACGGCCGTCTACT

ACTGTACAAGAGGAATCGAAAACTGGGGCCCCGGACTCCT

GGTCACCGTCTCCTCAGAAGGTAAATCTTCTGGCGCGTCT

GGCGAGTCTAAAGTGGATGACGACATCCAGGTGACCCAGT

CTCCGTCCTCCCTGTCTGCATCTCTAACAGAGAGAGTCTC

CATCACTTGCCGGACCAGTCAGAGCGTTAACAATTACTTA

AGCTGGTATCAGCAGAAACCAGGGCAAGCTCCTAAGCTCC

TGATCTATTATGCAACCAGATTGTACACCGATGTCCCATC

CCGGTTCAGTGGCAGTGGATCTGGGACAGATTACACCCTC

-continued

ACCATCACCAGCCTGGAGGCGGACGACACTGCAACTTATT

ACTGTCTACAATATGATAGTACACCTCTTGCATTCGGCGG

TGGGACCAACGTGGAAATCAAACGG

(CE2/E1B8 nucleotide sequence)
                    SEQ ID NO: 383
CAGGTGCAGCTGCAGGAGTCGGGACCCAGCCTGGTGAAGC

CCTCACAGACCCTCTCCCTCACCTGCACGGTCTCTGGATT          10

CTCATTAACCAACTATCCTGTAGGCTGGGTCCGCCAGGCT

CCAGGAAAGGCACTGGAGTGGATTGGTAACATAGAAAATG

ATGGAAGTGCGAACTATGCCTCGGCCCTGAAATCCCGACT          15

CAGCATCACCAGGGACACCTCCAAGAACCAAGTCTCCCTG

TCACTGAGCAGCGCGACAACTGAGGACACGGCCGTTTACT

ACTGTGGAAGAGAATTCGGTGGGAGTGATGGTTATACTTA

TTTCGTTGATATCGACTACTGGGGCCCAGGACTCCTGGTC

ACCGTCTCCTCAGAAGGTAAATCTTCTGGCGCGTCTGGCG

AGTCTAAAGTGGATGACCAGGCTGTGCTGACTCAGCCGTC

CTCCGTGTCCAAGTCCCTGGGCCAGAGTGTCTCCATCACC

TGCTCTGGAAGCAGCAGCAACGTTGGATATGGTAATTATG

TGAGCTGGTTCCAACAGGTCCCAGGATCAGCCCCCAAAAT          30

CCTCATCTATGGTGCAACCAGTCGAGCCTCGGGGGTCCCC

GACCGATTCTCCGGCTCCAGGTCTGGCAACACAGCGACTC

TGACCATCACCTCGCTCCAGGCTGAGGACGAGGCCGATTA

TTACTGTGCATCTTATGACGGCAGTAGCAGTGGTGTTTTC

GGCAGCGGGACCAGGCTGACCGTCCTGGGT (E2E8 nucleotide sequence)
                    SEQ ID NO: 249
CAGGTGCAGCTGCAGGAGTCGGGACCCAGCCTGGTGAAGC          40

CCTCACAGACCCTCTCCCTCACCTGCACGGTCTCTGGATT

CTCATTAACCGACCGTGGTGTAGCCTGGGTCCGCCAGGCT

CCAGGAAAGGCACTGGAGTGGGTTGGTACTATGCGTAGTG

GTGGAACGATAGACTATAACCCGGCCCTGAAATCCCGGCT

CAGCATCACCAGGGACACCTCCAAGAGCCAAGTTTTCCTG

TCACTGAGCAGCGTCACAACTGAGGACATGGCCATGTACT

ACTGTGCCAGAGGTTATTTGAGCGGTGATCGTTATGCCTG

GGGCCGAGGACTCCTGGTCACCGTCTCCTCAGAAGGTAAA

TCTTCTGGCGCGTCTGGCGAGTCTAAAGTGGATGACCAGG          55

CTGTGCTGACTCAGCCGTCCTCCGTGTCCAAGTCCCTGGG

CCAGAGTGTCTCCATCGCCTGCTCTGGAAGCAGGAGCGAC

ATTGGATATGGTAATTATGTGAGCTGGTTCCAACAGATCC          60

CAGGATCAGCCCCCAAACTCCTTATTTATGATACAAACAC

TCGGGCCTCGGGGGTCCCCGACCGATTCTCCGGCGCCAGG

TCTGGCAACACAGCAACACTGACCATCAACTCGCTCCAGG

CTGAGGACGAGGCCGATTATTACTGTGCAAATATTGACAG

-continued

TAGTCGCAGTCATCTTTTCGGCAGTGGCACCAGACTGACC

GTCCTGGGT (E1E8 nucleotide sequence)
                    SEQ ID NO: 251
CAGGTGCAGCTGCAGGAGTCGGGACCCAGCCTGGTGAAGC

CCTCACAGACCCTCTCCCTCACCTGCACGGTCTCTGGATT

CTCATTAACTGACTGGGGTGTAGCTTGGGTCCGCCAGGCT

CCAGGAAAGGCACTGGAGTGGCTTGGTACGATGCGTAGTG

GTGGGACTACAGACGATAACCCGGCCCTGAAATCCCGCCT

CAGCATCACCAGGGACACCTCTAAGAGCCAAGTCTCCCTG

TCACTGAGCAGCGTGACAACTGAGGACATGGCCATGTACT

ACTGTGCCAGAGGTTATTTGAGTGGTGTGCATTATGCCTG

GGGCCGAGGACTCCTGGTCACCGTCTCCTCAGAAGGTAAA

TCTTCTGGCGCGTCTGGCGAGTCTAAAGTGGATGACCAGG

CTGTGCTGACTCAGCCGTCCTCCGTATCTGGGTCCCTGGG

CCAGAGTGTCTCCATCACCTGCTCTGGAAGCAGCAGCAAC

GTGGGAGATGGTAGATATGTGAGCTGGTTCCAACAGGTCC

CAGGATCAGCCCCCAAACTCCTCATCTATGATACAACCAG

TCGAGCCTCGGGGGTTCCCGACCGATTCTCCGGCTCCAGG

TCTGGCAACACAGCGACTCTCATCATCACCTCGCTCCAGG

CTGAGGACGAGGCCGATTATTACTGTGCATCTATTGACAG

CGGTAACAATCTTCTTTTCGGCAGCGGCACCAGGCTGACC

GTCCTGGGT (NS2A1 nucleotide sequence)
                    SEQ ID NO: 431
CAGGTGCAGTTGCAGGAGTCGGGACCCAGCCTCGTGAAGC

CCTCACAGACCCTCTCCCTCACCTGCACGGTCTCTGGATT

CTCATTAAGCACTAATTCTGTGGGCTGGGTCCGACAGGCT

CCAGGAAAGGCGCCGGAGTGGGTTGCTGGTATAGATACTG

ATGGAGAAGAAGGCTTTAATCCAGTCCTTAAGTCCCGGCT

CAGCATCACCAGGGACACCTCCAAGAGTCAAGTCTCTTTG

TCATTGAGCAACGTGACAAGTGAAGACACGGCCGTGTACT

ACTGTGGAAGAAGTTATAGGACTGATGGTCTTGCTTACGG

TTATGTCCAAGCCATCGACTACTGGGGCCCAGGACTCCTG

GTCACTATCTCCTCAGAAGGTAAATCTTCTGGCGCGTCTG

GCGAGTCTAAAGTGGATGACCAGTCTGTGCTGACTCAGCC

GTCCTCCGTGTCCGGGTCCCCGGGCCAGACAGTCTCCATC

ACCTGCTCTGGAAGCTATATCGGTAGTAGTGGTGTAGGCT

GGTTCCAACAGCTCCCAGGATCGGGCCTCAGAACCATCAT

CGTGGCGAGTGACGGTCGACCCTCAGGGGTCCCCGACGGA

TTCTCTATGTCCAAATCGGGCAACACAGCCACCCTGACCA

TCAGCTCGCTCCAGGCTGAGGACGAGGCCGATTATTTCTG

-continued

TGGAAGTAGTGATAGGACTCAATATACTGGACTTTTCGGC

AGCGGGACCAGGCTGACCGTCCTGGGT (CE3 nucleotide sequence)

SEQ ID NO: 384

CAGGTGCGACTGCAGGAGTCGGGACCCAGCCTGGTGAAGC

CCTCACAGACCCTCTCCGTCACCTGCACGGTCTCTGGATT

CTCATTGATCAGCAATGCTGTAGGCTGGGTCCGCCAGGCT

CCAGGAAAGGTGCCGGAGTCGCTTGCTGGTTGTAGCAGTG

ATGGAAAGTGTTACTATAACTCGGCCCTGAAATCCCGGCT

CGACATCACCAGGGACACCTCGAAGAACCAGATCTCCCTG

TCACTGAGCAGCGTCACAACTGACGACGCGGCCGTGTACT

ACTGTACAAGAGGCTATTATCCTGTTTATGGTTATGACTA

TCTTGGCACTATCGACTACTGGGGCCCCGGACTCCTGGTC

ACCGTCTCCTCAGAAGGTAAATCTTCTGGCGCGTCTGGCG

AGTCTAAAGTGGATGACCAAGCTGTGCTGACTCAACCGTC

CTCCGTGTCTGGGTCCCTGGGCCAGAGGGTCTCCATCACC

TGCTCTGGAAGCAGCAGCAACGTTGGTAGAAATGATGTAG

CCTGGTTCCAACAACTCCCAGGATCAGGCCTCAGAACCAT

CATCTATGGTACTACCAGTCGACCCTCAGGTATCCCGGAC

CGATTCTCCGGCTCCAAGTCTGGCGTTACGGCCACCCTGA

CCATCGACTCGCTCCAGGCTGAGGACGAGGCCGATTATTT

CTGTGCCTCTGGTGACAGTAGTGCCATTAATGATATTTTC

GGCAGCGGGACCAGGCTGACCGTCCTGGGT (CB7 nucleotide sequence)

SEQ ID NO: 385

CAGGTGCAGCTGCAGGAGTCGGGACCCAGCCTGGTGAAGC

CCTCACAGACCCTCTCCCTCACCTGCACGGTCTCTGGATT

CTCATTAACCAACTATCGTGTAGGTTGGGTCCGCCAGGCT

CCAGGAAAGGCACTGGAGTGGGTTAGTAACATACGGAGTG

GTGGAACTACATGGTATAACCCGGCCCTGAAATCCCGGCT

CAGCATCACCGCGGACACCTCCAAGAGCCAAGTCTCCCTG

TCACTGAGCAGCGTGACAACTGAGGACACGGCCGTATATT

ATTGTGCAAGAGATTCCTCTGGTGATCTTTATGCGTATGA

TTACTGGGGCCCAGGACTCCTGGTCACCGTCTCCTCAGAA

GGTAAATCTTCTGGCGCGTCTGGCGAGTCTAAAGTGGATG

ACCAGGCCGTGCTGACTCAGCCGTCCTCCGTGTCCAGGTC

CCTGGGCCAGAGTGTCTCCATGACCTGCTCTGGAAGCAGC

AGCAACGTTGGATATGGTAATTATATGGCCTGGTTCCAAC

AGGTTCCAGGATCAGCCCCCAAACTCCTCATCTATGGTGC

AACCAGTCGAGCCTCGGGGGTCCCCGACCGATTCTCCGGC

TCCAGGTCTGGCAACACAGCGACTCTGACCATCAGCTCGC

TCCAGGCTGAGGACGAGGCCGATTACTACTGTGCATCTTA

TGACAGCACTAGCGGGGGTGTCTTCGGCAGCGGGACCAGG

-continued

CTGACCGTCCTGGGT (CC7 nucleotide sequence)

SEQ ID NO: 386

CAGGTGCAGCTGCAGGAGTCGGGACCCAGCCTGGTGAAGC

CCTCACAGACCCTCTCCCTCACCTGCACGGTCTCTGGATT

CTCACTAACCAGCAATGCTGTGATCTGGGTCCGGCAGGCT

CCAGGAAAGGCGCCGGAGTGGGTTGCTTTGATAGATGTTG

ATGGAGATGCAGCCTATGACCCAGCCCTTAAGTCCCGCCT

CAGCATCACCAGGGACACCTCCAAGAGTCAAGTCTCCCTT

TCACTGCGCAGCGTGACAACTGAGGACACGGCCGTGTACT

ACTGTGCAAGAGACTATGGTAGTTGGGGTTATGTTTCCGA

CATCGACTACTGGGGCCCAGGACTCCTGGTCACCGTCTCC

TCAGAAGGTAAATCTTCTGGCGCGTCTGGCGAGTCTAAAG

TGGATGACAGGGTCGTGCGGACTCAACCGTCCTCCGTGTC

TGGGTCCCTGGGCCAGAGGGTCTCCATCACCTGCTCTGGA

AGCTACATCACTGGTAGTTCTGTAGGCTGGTTCCAACAGG

TCCCAGGATCGGGCCTCAAAACCGTCATCTATGACAATAA

CGATCGACCCTCAGGGGTCCCCGACCGATTCTCTGGCTCC

AAGTCGGGCGACACAGCCACCCTGACCATCAGCTCGCTCC

AGGCTGAGGACGAGGCCGATTATTACTGTGCATCTTATGA

CACCAGTAACATTGGTCTTTTCGGCAGCGGGACCAGGCTG

ACCGTCCTGGGT (412E10 nucleotide sequence)

SEQ ID NO: 387

CAGGTGCAGCTGCAGGAGTCGGGACCCAGCCTGGTGAAGC

CCTCACAGACCCTCTCCCTCACCTGCACGGTCTCTGGCTT

CTCTGTAATAAGCGATTCTGTAGCCTGGGTCCGCCAGGCT

CCAGGAAAGTGCCGGAGTGGCTTGGTGCTAGCGGCAGTT

CTGGAAACAAATACTATAACCCGGCCCTAAAATCCCGGCT

CAGCATCACCAGGGACACCTCCAAGAGCCAAGTCTCCCTG

TCACTGAGCAGCGTGACAACTGAGGATACGGCCGTGTACT

ACTGTGCGAGAGGTATTATCGCCGGTGTAGATGTCTGGGG

CCGAGGACTCCTGGTCACCGTCTCCTCAGAAGGTAAATCT

TCTGGCGCGTCTGGCGAGTCTAAAGTGGATGACCAGGCTG

TGCTGACTCAGCCGTCCTCCGTGTCTGGGTCCCTGGGCCA

GAGGGTCTCCATCACCTGCTCTGGAAGCAGCAGCAACGTT

GGATATGGTAATTATGTGGGCTGGTACCAACAGGTCCCAG

GATCAGCCCCCAAACTCCTCATCTATGGTACAGCCATTCG

AGCCTCGGGGGTCCCCGACCGATTCTCCGGCTCCAGGTCT

GGGGACACAGCCACCCTTACCATCACCTCGCTCCAGGCTG

AGGACGAGGCCGATTACTACTGTGCATCTTATCAGAGTAA

TTACGCTTTTTTCGGCAGCGGGACCAGGCTGACCGTCCTG

-continued
GGT (E2B7 nucleotide sequence)
SEQ ID NO: 43
CAGGTGCAGCTGCAGGAGTCGGGACCCAGCCTGGTGAAGC

CCTCACAGACCCTCTCCCTCACCTGCACGGTCTCTGGATT

CTCATTAACCAGCTGGGGTGTAGCTTGGGTCCGCCAGGCT

CCAGGAAAGGCACTGGAGTGGCTTGGTACCATGCGTAGTG

GTGGTGGTACAGAATATAATCCGGCCCTGAAATCCCGCCT

CAGCATCACCAGGGACACCTCCAAGAGCCAAGTCTCCCTG

TCACTGAGCAGCGTGACAACTGAGGACATGGCCATGTACT

ACTGTGCCAGAGGTTATTTGAGTGGTATTCATTATGCCTG

GGGCCGAGGACTCCTAGTCTCCGTCTCCTCAGAAGGTAAA

TCTTCTGGCGCGTCTGGCGAGTCTAAAGTGGATGACCAGG

CTGTGCTGACTCAGCTGTCCTCCGTGTCTGGGTCCCTGGG

CCAGAGGGTCTCCATCACCTGCTCTGGAAGCAGCAGCAAC

GTTGGAGATGGTGATTATGTGGGCTGGTTCCAACAGCTCC

CAGGATCAGCCCCCAAACTCCTCATCTATAGTGCGCGCAA

TCGAGCCTCGGGGGTCCCCGACCGATTCTCCGGCTCCAGG

TCTGGCAACACAGCGACTCTAACCATCACCTCGCTCCAGG

CTGAGGACGAGGCCGATTATTACTGTGCATCTATTGACAC

CAGTCGCTCTCACATTTTCGGCAGCGGGACCAGACTGACC

GTCCTGGGT (E2A6 nucleotide sequence)
SEQ ID NO: 253
CAGGTGCAGCTGCAGGAGTCGGGACCCAGCCTGGTGAAGC

CCTCACAGACCCTCTCCCTCACCTGCACGGTCTCTGGATT

CTCATTAACTGACTGGGGTGTAGCTTGGGTCCGCCAGGCT

CCAGGAAAGGCACTGGAGTGGCTTGGTACGATGCGTAGTG

GTGGGACTACAGACGATAACCCGGCCCTGAAATCCCGCCT

CAGCATCACCAGGGACACCTCTAAGAGCCAAGTCTCCCTG

TCACTGAGCAGCGTGACAACTGAGGACATGGCCATGTACT

ACTGTGCCAGAGGTTATTTGAGTGGTGTGCATTATGCCTG

GGGCCGAGGACTCCTGGTCACCGTCTCCTCAGAAGGTAAA

TCTTCTGGCGCGTCTGGCGAGTCTAAAGTGGATGACCGGG

TCGTGCGGACTCAGCCGTCCTCCGTGTCCAAGTCCCTGGG

CCAGAGTGTCTCCATCACCTGCTCTGGAAGCAGCAGCAAC

GTTGGAGCTGGTAATTATGTGGGCTGGTTCCAACAGGTCC

CAGGATCAGCCCCCAAACTCCTCATCTATGGTGCAACCAA

TCGAGCCTCGGGGGTCCCCGCCCGATTCTCAGGCTCCAAG

TCTGGCGTCACAGCGACTCTAACCATCACCTCGCTCCAGG

CTGAGGACGAGGCCGATTATTACTGTGCATCTATTGACAC

CAGTCGCTCTCACATTTTCGGCAGCGGGACCAGGCTGACC

GTCCTGGGT

-continued
S1D9 nucleotide sequence
SEQ ID NO: 389
CAGGTGCAGCTGCAGGAGTCGGGACCCAGCCTGGTGAAGC

CCTCACAGACCCTCTCCCTCACCTGCACGGTCTCTGGATT

CTCATTAACCAGCAATTCTGTGGGCTGGGTCCGACAGGCT

CCAGGAAAGGCGCCGGAGTGGGTTGCTGGTATAGATAGTG

ATGGAGAAGAAGGCTATAATCCAGCCCTTAACTCCCGGCT

CAGCATCACCAGGGACACCTCCAAGAATCAAGTCTCTTTG

TCATTGAGCAGAGTGACAAGTGAGGACACGGCCGTTTACT

ACTGTGGAAGAACTTATAGGACTGATGGTTATGCTTACGG

TTATGTCCAAGCCATCGACTACTGGGGCCCAGGACTCCTG

GTCACCGTCTCCTCAGAAGGTAAATCTTCTGGCGCGTCTG

GCGAGTCTAAAGTGGATGACCGGGTCATGCTGACTCAGCC

ACCCTCCGTGTCCGGGTCCCCGGGCCAGACGGTATCCATC

ACCTGCTCTGGAAGCTTCATCGGTATTAGTAGTGTAGGCT

GGTTCCAACAGCTCCCAGGATCGGGCCTCAGAACCGTCAT

TTTTGCGAGTGACGGTCGACCCTCAGGGGTCCCCGATCGA

TTCTCTAACTCCAAATCGGGCAACACAGCCACCCTGACCA

TCAGCTCGCTCCAGGCTGAGGACGAGGCCGATTATTTCTG

TGGAAGTAGTGATAGGACTCAATATACTGGAGTTTTCGGC

AGCGGGACCAGGCTGACCGTCCTGAGT (S1F4 nucleotide sequence)
SEQ ID NO: 390
CAGGTGCAGTTGCAAGAGTCGGGACCCAGCCTGGTGAAGC

CCTCACAGACCCTCTCCCTCACCTGCACGGTCTCTGGATT

CTCATTAAGTAGCAATTCTGTCGGCTGGGTCCGACAGGCT

CCAGGAAAGGCGCCGGAGTGGGTTGCTGGTATAGATACTG

ATGGAGAAGAAGGCTATAATCCAGCCCTTAACTCCCGGCT

CAGCATCACCAGGGACACCTCCAAGAGTCAAGTCTCATTG

TCATTGAGCAGCGTTACAAGTGAGGACACGGCCGTGTACT

ACTGTGTAAGAAGTTATAGAGCTGATGGTCTTGCTTACGG

TTATGTCCAAGCCATCGACTACTGGGGCCCAGGACTCCTG

CTCACCATCTCCTCAGAAGGTAAATCTTCTGGCGCGTCTG

GCGAGTCTAAAGTGGATGACCAGGCCGTGGTGACTCAGCC

GTCCTCCGTGTCTGGGTCCCTGGGCCAGAGGGTCTCCATC

ACCTGCTCTGGAAGCTTCATCGGTATTAGTAGTGTAGGCT

GGTTCCAACAGCTCCCAGGATCGGGCCTCAGAACCGTCAT

CGTGGCGAGTGACGGTCGACCCTCAGGGGTCCCCGACCGA

TTCTCTAACTCCAAATCGGGCAACACAGCCACCCTGACCA

TCAGCTCGCTCCAGGCTGAGGACGAGGCCGATTATTTCTG

TGGAAGTAGTGATAGGACTCAATATACTGGAGTTTTCGGC

AGCGGGACCAGGCTGACCGTCCTGGGT

-continued
(S1G10 nucleotide sequence)

SEQ ID NO: 391

CAGGTTCAGTTGCAGGAGTCGGGACCCAGCCTGGTGAAGC

CCTCACAGACCCTCTCCCTCACCTGCACGGTCTCTGGATT

CTCATTAACCAGCAATTCTGTGGGCTGGGTCCGACAGGCT

CCAGGAAAGGCGCCGGAGTGGGTTGCTGGTATAGATACTG

ATGGAGAAGAAGGCTATAATCCAGCCCTTAACTCCCGGCT

CAGCATCACCAGGGACACCTCCAAGAGTCAAGTCTCATTG

TCATTGAGCAGCGTGACAAGTGAGGACACGGCCGTGTACT

ACTGTGGAAGAAGTTATAGAGCTGATGGTCTTGCTTACGG

TTATGTCCAAGCCATCGACTACTGGGGCCCAGGACTCCTG

GTCACCGTCTCCTCAGAAGGTAAATCTTCTGGCGCGTCTG

GCGAGTCTAAAGTGGATGACCAGGCTGTGCTGACTCAGCC

GTCCTCCATGTCCGGGTCCCTGGGCcAGAGGGTCTCCATC

ACCTGTTCTGGAAGCTTCATCGGTATTAGTAGTGTAGGCT

GGTTCCAACAGCTCCCAGGATCGGGCCTCAGAACCATCAT

CGTGGCGAGTGACGGTCGACCCTCAGGGGTCCCCGACCGA

TTCTCTATGTCCAAATCGGGCAACACAGCCACCCTGACCA

TCAGCTCGCTCCAGGCTGAGGACGAGGCCGATTATTTCTG

TGGAAGTAGTGATAGGACTCAATATACTGGAGTTTTCGGC

AGCGGGACCAGGCTGACCGTCCTGGGT (S2C6 nucleotide sequence)

SEQ ID NO: 392

CAGGTGCAGCTGCAGGAGTCGGGACCCAGCCTGGTGAAGC

CCTCACAGACCCTCTCCCTCACCTGCACGGTCTCTGGATT

CTCATTAATCAGCAATTCTGTGGGCTGGGTCCGACAGGCT

CCAGGAAAGGCGCCGGAGTGGGTTGCTGGTATAGATACTG

ATGGAGAAGAAGGCTATAATCCAGCCCTTAAGTCCCAATA

TGCAGCTAGTGATCCGGACACCTCCAAGAGTCAAGTCTCC

TTGTCATTGAGCAGCGTGACAAGTGAGGACACGGCCGTGT

ACTACTGTGGAAGAACTTATAGGACTGATGGTTTTGCTTA

TGGTTATGTCCAAGCCATCGACTACTGGGGCCCAGGACTC

CTGCTCACTATCTCCTCAGAAGGTAAATCTTCTGGCGCGT

CTGGCGAGTCTAAAGTGGATGACCAGGCTGTGCTGACTCA

GCCGTCCTCCGTGTCTGGGTCCCTGGGCCAGAGGGTCTCC

ATCACCTGCTCTGGAAGCTTTATTGGTATTAGTAGTGTAG

GCTGGTTCCAACAGCTCCCAGGATCGGGCCTCAGAACCAT

CATCGTGGCGAGTGACGGTCGACCCTCAGGGGTCCCCGAC

CGATTCTCTATGTCCAAATCGGGCAACACAGCCACCCTGA

CCATCAGCTCGCTCCAGGCTGAGGACGAGGCCGATTATTT

CTGTGGAAGTAGTGATAGGACTCAATATACTGGAGTTTTC

GGCAGCGGGACCAGGCTGACCGTCCTGGGT (MD9/MoD9 nucleotide sequence)

-continued

SEQ ID NO: 393

CAGGTGCGGCTGCAGGAGTCGGGACCCAGCCTGGTGAAGT

CCTCACAGACCCTCTCCCTCACCTGCACGGTCTCTGGATT

CTCATTAACCAGGGAATCTATAGCCTGGGTCCGCCAGGCT

CCAGGAAAGGTGCCGGAGTGGCTTGGTGGTGTAGGCATTG

ATGGAACCTCATACTATAGCCCGGCCCTGAAATCCCGGCT

CAGTATCACGAGGGACACCTCCAAGAGCCAAGCCTCCCTG

TCACTGAGCAGCGTGGCAACTGAGGACACGGCCATGTATT

ACTGTGCACGTAATTATATTGATTTCGAGTACTGGGGCCC

AGGACTCCTGGTCACCGTCTCCTCAGAAGGTAAATCTTCT

GGCGCGTCTGGCGAGTCTAAAGTGGATGACCAGGCTGTGC

TGACTCAACTGTCCTCCGTATCTGGGTCCCTGGGCCAGAG

GATCTCCATCACCTGCTCTGGAAGCAGCAGCAACGTTGGT

ATATATGATGTGTCTTGGTTCCAACAACTCCCAGGATCAG

GCCTCAGAACCGTCATCTATGGTACTAACAATCGACCCTC

GGGTGTCCCGGACCGATTCTCCGGCTCCAGGTCTGGCAAC

ACGGCCACCCTGACTATCAGCTCTCTCCAGTCTGAGGACG

AGGCCATTTATTACTGTGCTGCTGGTGACAGCAGTACTAT

TGCTGTTTTCGGCAGCGGGACCAGGCTGACCGTCCTGGGT (412B9 nucleotide sequence)

SEQ ID NO: 394

CAGGTGCAGCTGCAGGAGTCGGGACCCAGCCTGGTGAAGC

CCTCACAGACCCTCTCCCTCACCTGCACGGTCTCTGGATT

CTCTGTAATAAGCGATTCTGTAGCCTGGGTCCGCCAGGCT

CCAGGAAAAGTGCCGGAGTGGCTTGGTGCTAGCGGCAGTT

CTGGAAACAAATACTATAACCCGGCCCTAAAATCCCGGCT

CAGCATCACCAGGGACACCTCCAAGAGCCAAGTCTCCCTG

TCACTGAGCAGCGTGACAACTGAGGATACGGCCGTGTACT

ACTGTGCGAGAGGTATTATCGCCGGTGTAGATGTCTGGGG

CCGAGGACTCCTGGTCTCCGTCTCCTCAGAAGGTAAATCT

TCTGGCGCGTCTGGCGAGTCTAAAGTGGATGACCAGGCTG

TGCTGACTCAGCCGTCCTCCGTGTCTGGGGCCCTGGGCCA

GAGGGTCTCCATCACCTGCTCTGGAAGCAGCAGCAACGTT

GGATATGGTGATTATGTGGGCTGGTACCAACAGGTCCCAG

GATCAGCCCCCAAACTCCTCATCTATGGTGCAGCCAGTCG

AGCCTCGGGGGTCCCCGACCGATTCTCTGGCTCCAGGTCT

GGCAACACAGCGACTCTGACCATCAGCTCGCTCCAGGCTG

AGGACGAGGCCGATTATTACTGTGCATCTTATGACAGCAG

TGACGGTGGTGTTTTCGGCAGCGGGACCAGGCTGACCGTC

CTGGGT (412E6 nucleotide sequence)

SEQ ID NO: 395

CAGGTGCAGCTGCAGGAGTCGGGACCCAGCCTGGTGAAGC

-continued

CCTCAGAGACCCTCTCCCTCACCTGCACGGTCTCTGGATT

CTCATTAACAAACTATGGTGTGGGCTGGGTCCGCCAGGCT

CCAGGAAAGGCACTGGAGTGGCTTGGTAACATATATAGTG

GTGGGTCTACATACTATAACCCGGCCCTGAAATCCCGACT

CAGCATCACCAGGGACACCTCCAAGAGCCAAGTCTCCCTG

TCACTGAACAGCGTGACACTTGAGGACACGGCCGTTTATT

ACTGTGGAAGAGGAGGTGTTGGGAGTGTCGACGTCTGGGG

CCCAGGACTCCTGGTCACCGTCTCCTCAGAAGGTAAATCT

TCTGGCGCGTCTGGCGAGTCTAAAGTGGATGACCAGGCTG

TGCTGACTCAGCCGCCCTCCGTGTCCGGTTCCCAGGCCA

GAGGGTCTCCATCACCTGCTCTGGAGGCAGGAATAACATC

GGGCGTGGTACCTTTGTGGACTGGTACCAGCAACTCCCAG

GATCAGGCCTCAAAACCGTCATCTATGGTACTGACCGTCG

ACCACCGGGGGTCCCGGACCGATTCTCCGGCTCCAAGACT

GGCAACGCGGCCACCCTGACCATCACCTCCCTCCAGGCTG

AGGACGAGGCCGATTATTGGTGTGCTACTTATGATTACAG

TAATGATATGATTATTCTCGGCAGCGGGACCAGGCTGACC

GTCCTGGGT (412G11 nucleotide sequence)

SEQ ID NO: 396

CAGGTGCGGCTGCAGGAGTCGGGACCCAGCCTGGTGAAGC

CCTCACAGACCCTCTCCCTCACCTGTACGGTCTCTGGATT

CTCATTAACCAGCTATGCTTTAGGCTGGGTCCGCCAGGCT

CCAGGAAGGGCTCCGGAGTGGATTGGTAACATATGGAGGG

GTGGACGAATAGAATATAACCCGGCCCTGAAATCCCGGCT

CAGCATCACTAGGGACACCTCCAAGAGCCAAGTCTCGCTG

TCACTGAGCAGCGTGACAACTGAGGATACGGCCGTGTACT

ACTGTTCAAGAAGTGGCGGCGACTGGGGCCCAGGACTCCT

GGTCACCGTCTCCTCAGAAGGTAAATCTTCTGGCGCGTCT

GGCGAGTCTAAAGTGGATGACCAGGCTGTGCTGACTCAGC

CGTCCTCCGTGTCTGGGTCCCTGGGCCAGAGGGTCTCCAT

CACCTGCTCTGGAAGCAGCAGCAACGTTGGATATGGTAAT

TATGTGGGCTGGTACCAACAGGTCCCAGGATCAGCCCCCA

AACTCCTCATCTATGGTGCAACCAGTCGAGCCTCGGGGGT

CCCCGACCGATTCTCCGGCTCCAGGTCTGAGAACACAGCC

ACCCTGACCATCAGCTCCCTCCAGGCTGAGGACGAGGCCG

ATTATTACTGTGCGTCTTATGATAGGAGTGAGAGTGTTGT

GTTCGGCAGCGGGACCAGACTGACCGTCCTGGGT (CA2 nucleotide sequence)

SEQ ID NO: 397

CAGGTTCAGCTGCAGGAGTCGGGACCCAGCCTGGTGAAGC

CCTCACAGACCCTCTCCCTCACCTGCACGGTCTCTGGATT

CTCATTAAGCAGCGTCGCTGTAAACTGGGTCCGCCAGGCT

-continued

CCAGGAAAGGTGCCGGAGTGGCTTGGTGGCATTATTAGTA

ATGGAGGCACAGGCTATAATCCGGCCCTGAAATCTCGGCT

GAGCATCACCAGGGACACCTCCAAGAGCCAAGTCTCCCTG

GCACTGACCCACGTGACAACTGAGGACACGGCCGTGTACT

ACTGTGGAAGGGGAGTTGAATGGGAGGGCTCTATGGACTA

CTTGGGCCCAGGACTCCTGGTCACCGTCTCCTCAGAAGGT

AAATCTTCTGGCTCTGGCTCTGAGACTAAAGTGGATGACC

AGTCTGTGCTGACTCAGCCGTCCTCCGTGTCCGGGTTCCT

GGGCCAGAGGGTCACCATCACCTGCTCTGGAAGCAGCAGC

AACGTTGGAGCTGGTAGTTATGTGGGCTGGTACCAGCAGG

TCCCAGGATCGGGCCTCAGAATCCTCATCTATGGTGCAAC

CAAGCGAGCCTCGGGACTCCCCGACCGATTCTCCGGCTCC

AGGTCTGGGAACACAGCCACCCTGACCATCAGCTCGCTCC

AGGCTGAGGACGAGGCCGATTATTACTGCGTATCTTATCA

GACTGATTTTACTTTAGTTTTCGGCAGCGGGACCAGGCTG

ACCGTCCTAGGT (CA9 nucleotide sequence)

SEQ ID NO: 398

CAGGTGCAGCTTCAGGAGTCGGGACCCAGCCTGGTGAAGC

CCTCACAGACCCTCTCCCTCACCTGCACGGTCTCTGGATT

CTCATTAACCAGCAATTCTGTGGGCTGGGTCCGACAGGCT

CCAGGAAAGGCGCCGGAGTGGGTTGCTGGTATAGATACTG

ATGGAGAAGAAGGCTATAATCCAGCCCTTAACTCCCGGCT

CAGCATCACCAGGGACACCTCCAAGAGTCAAGTCTCTTTG

TCATTGAGCAGCGTGACAAGTGAGGACACGGCCGTGTACT

ACTGTGGAAGAAGTTATAGGAGTGATGGTCTTGCTTACGG

TTATGTCCAAGCCATCGACTACTGGGGCCCAGGACTCCTG

GTCACCGTCTCCTCAGAAGGTAAATCTTCTGGCGCGTCTG

GCGAGTCTAAAGTGGATGACCAAGCTGTGCTGACTCAGCC

GGCCTCCGTGTCTGGGTCCCTGGGCCAGAGGGTCTCCATC

ACCTGTTCTGGAAGCTTCATCGGTATTAGTAGTGTAGGCT

GGTTCCAACAGCTCCCAGGATCGGGCCTCAGAACCATCAT

CGTGGCGAGTGACGGTCGACCCTCAGGGGTCCCCGACCGA

TTCTCTATGTCCAAATCGGGCAACACAGCCACCCTGACCA

TCAGCTCGCTCCAGGCTGAGGACGAGGCCGATTATTTCTG

TGGAAGTAGTGATAGGACTCAATATACTGGAGTTTTCGGC

AGCGGGACCAGGCTGACCGTCCTGGGT (CA12 nucleotide sequence)

SEQ ID NO: 399

CAGGTGCAGCTGCAGGGGTCGGGACCCAGCCTGGTGAAGC

CCTCACAGACCCTCTCCCTCACCTGCACGGTCTCTGGATT

CTCTTTTGACAGCTATTATGTAGGCTGGGTCCGCCAGGCT

-continued

-continued

CCAGGAAAGGCACTGGAGTGGCTTGGTAATATATATAGTA

ATGGAGGCACAGGCTATAATCCGGCCCTGAAATCTCGGCT

CTGGAAGGGCATTCTATAACCCGGCCCTGAAATCCCGGCT

GAGCATCACCAGGGACACCTCCAAGAGCCAAGTCTCCCTG

CAGCATCACCAGGGACACCTCCAAGAGCCAAGTCTCCCTA

GCACTGACCCACGTGACAACTGAGGACACGGCCGTGTACT

TCAGTGAGCAGCGTGACAATTGAGGACACGGCCCTGTACT

ACTGTGGAAGGGGAGTTGAATGGGAGGGCTCTATGGACTA

ACTGTGTCAGAGGCTCGTATTATCACGGTGGTGGCAATGG

CTTGGGCCCAGGACTCCTGGTCACCGTCTCCTCAGAAGGT

GATGGTCGACTTTTTCGACTACTGGAGCCCAGGACTCCTG

AAATCTTCTGGCTCTGGCTCTGAGACTAAAGTGGATGACC

GTCACCGTCTCCTCAGAAGGTAAATCTTCTGGCGCGTCTG

AGTCTGTGCTGACTCAGCCGTCCTCCGTGTCCGGGTTCCT

GCGAGTCTAAAGTGGATGACCAGGTCGTGCGGACTCAGCC

GGGCCAGAGGGTCACCATCACCTGCTCTGGAAGCAGCAGC

GTCCTCCGTGTCTGGGTCCCTGGGCCAGAGGGTCTCCATC

AACGTTGGAGCTGGTAGTTATGTGGGCTGGTACCAGCAGG

ACCTGCTCTGGAAGCAGCAGCAATGTTGGATATGGTAATT

TCCCAGGATCGGGCCTCAGAATCCTCATCTATGGTGCAAC

ATGTGGGCTGGTTCCAACAGGTGCCAGGGTCAGCCCCCAA

CAAGCGAGCCTCGGGACTCCCCGACCGATTCTCCGGCTCC

ACTCCTCATCTATGCTGCAACCAGTCGAGCCTCGGGGGTC

AGGTCTGGGAACACAGCCACCCTGACCATCAGCTCGCTCC

CCCGACCGATTCTCCGGCTCCAGGTCTGGGAATACAGCCA

AGGCTGAGGACGAGGCCGATTATTACTGCGTATCTTATCA

CCCTGACCATCGACTCGCTCCAGGCTGAGGACGAGGCCGA

GACTGATTTTACTTTAGTTTTCGGCAGCGGGACCAGGCTG

TTATTACTGTTCATCTTATCAACGCGGTAACACTGGTGTT

ACCGTCCTAGGT

TTCGGCAGCGGGACCAGGCTGACCGTCCTGGGT (CB7 nucleotide sequence)

(CB2 nucleotide sequence)

SEQ ID NO: 402

SEQ ID NO: 400

CAGGTGCAGCTGCAGGAGTCGGGACCCAGCCTGGTGAAGC

CAGGTTCAGCTTCAGGAGTCGGGACCCAGCCTGGTGAAGC

CCTCACAGACCCTCTCCCTCACCTGCACGGTCTCTGGATT

CCTCACAGACCCTCTCCCTCACCTGCACGGTCTCTGGATT

CTCATTAACCAACTATCGTGTAGGTTGGGTCCGCCAGGCT

CTCATTAAGCACTAATTCTGTGGGCTGGGTCCGACAGGCT

CCAGGAAAGGCACTGGAGTGGGTTAGTAACATACGGAGTG

CCAGGAAAGGCGCCGGAGTGGGTTGCTGGTATAGATACTG

GTGGAACTACATGGTATAACCCGGCCCTGAAATCCCGGCT

ATGGAGAAGAAGGCTTTAATCCAGTCCTTAAGTCCCGGCT

CAGCATCACCGCGGACACCTCCAAGAGCCAAGTCTCCCTG

CAGCATCACCAGGGACACCTCCAAGAGTCAAGTCTCTTTG

TCACTGAGCAGCGTGACAACTGAGGACACGGCCGTATATT

TCATTGAGCAACGTGACAAGTGAAGACACGGCCGTGTACT

ATTGTGCAAGAGATTCCTCTGGTGATCTTTATGCGTATGA

ACTGTGGAAGAAGTTATAGGACTGATGGTCTTGCTTACGG

TTACTGGGGCCCAGGACTCCTGGTCACCGTCTCCTCAGAA

TTATGTCCAAGCCATCGACTACTGGGGCCCAGGACTCCTG

GGTAAATCTTCTGGCGCGTCTGGCGAGTCTAAAGTGGATG

GTCACTATCTCCTCAGAAGGTAAATCTTCTGGCGCGTCTG

ACCAGGCCGTGCTGACTCAGCCGTCCTCCGTGTCCAGGTC

GCGAGTCTAAAGTGGATGACCAGTCTGTGCTGACTCAGCC

CCTGGGCCAGAGTGTCTCCATGACCTGCTCTGGAAGCAGC

GTCCTCCGTGTCCGGGTCCCCGGGCCAGACAGTCTCCATC

AGCAACGTTGGATATGGTAATTATATATGGCCTGGTTCCAAC

ACCTGCTCTGGAAGCTATATCGGTAGTAGTGGTGTAGGCT

AGGTTCCAGGATCAGCCCCCAAACTCCTCATCTATGGTGC

GGTTCCAACAGCTCCCAGGATCGGGCCTCAGAACCATCAT

AACCAGTCGAGCCTCGGGGGTCCCCGACCGATTCTCCGGC

CGTGGCGAGTGACGGTCGACCCTCAGGGGTCCCCGACCGA

TCCAGGTCTGGCAACACAGCGACTCTGACCATCAGCTCGC

TTCTCTATGTCCAAATCGGGCAACACAGCCACCCTGACCA

TCCAGGCTGAGGACGAGGCCGATTACTACTGTGCATCTTA

TCAGCTCGCTCCAGGCTGAGGACGAGGCCGATTATTTCTG

TGACAGCACTAGCGGGGGTGTCTTCGGCAGCGGGACCAGG

TGGAAGTAGTGATAGGACTCAATATACTGGACTTTTCGGC

CTGACCGTCCTGGGT

AGCGGGACCAGGCTGACCGTCCTGGGT (CC7 nucleotide sequence)

(CB3 nucleotide sequence)

SEQ ID NO: 403

SEQ ID NO: 401

CAGGTGCAGCTGCAGGAGTCGGGACCCAGCCTGGTGAAGC

CAGGTTCAGCTGCAGGAGTCGGGACCCAGCCTGGTGAAGC

CCTCACAGACCCTCTCCCTCACCTGCACGGTCTCTGGATT

CCTCACAGACCCTCTCCCTCACCTGCACGGTCTCTGGATT

CTCACTAACCAGCAATGCTGTGATCTGGGTCCGGCAGGCT

CTCATTAAGCAGCGTCGCTGTAAACTGGGTCCGCCAGGCT

CCAGGAAAGGCGCCGGAGTGGGTTGCTTTGATAGATGTTG

CCAGGAAAGGTGCCGGAGTGGCTTGGTGGCATTATTAGTA

-continued

-continued

ATGGAGATGCAGCCTATGACCCAGCCCTTAAGTCCCGCCT

CAGCATCACCAGGGACACCTCCAAGAGTCAAGTCTCCCTT

TCACTGCGCAGCGTGACAACTGAGGACACGGCCGTGTACT

ACTGTGCAAGAGACTATGGTAGTTGGGGTTATGTTTCCGA

CATCGACTACTGGGGCCCAGGACTCCTGGTCACCGTCTCC

TCAGAAGGTAAATCTTCTGGCGCGTCTGGCGAGTCTAAAG

TGGATGACAGGGTCGTGCGGACTCAACCGTCCTCCGTGTC

TGGGTCCCTGGGCCAGAGGGTCTCCATCACCTGCTCTGGA

AGCTACATCACTGGTAGTTCTGTAGGCTGGTTCCAACAGG

TCCCAGGATCGGGCCTCAAAACCGTCATCTATGACAATAA

CGATCGACCCTCAGGGGTCCCCGACCGATTCTCTGGCTCC

AAGTCGGGCGACACAGCCACCCTGACCATCAGCTCGCTCC

AGGCTGAGGACGAGGCCGATTATTACTGTGCATCTTATGA

CACCAGTAACATTGGTCTTTTCGGCAGCGGGACCAGGCTG

ACCGTCCTGGGT (3aA6 nucleotide sequence)

SEQ ID NO: 404

CAGGTGCGGCTGCAGGAGTCGGGATCCAGTCTGGTGAAGC

CCTCACAGACCCTCTCCCTCGTCTGCACGGTCTCTGGATT

CCCATTAACCAGCAATGCTGTAGGCTGGGTCCGCCAGGCT

CCAGGAAAGGCGCCGGAGTGGCTAGGTCTCATAGATATTG

ATGGAGACACAGCCTATAACCCAGCCCTTGAGTCCCGGCT

CAGCATCACCAGGGACACCTCCAAGAGTCAAGTCTCCCTG

TCACTGAGCAGCGTGGCAATTGAGGACACGGCCGTGTACT

ATTGTGCTCGTCATTATGATAAATGGGGTTATGCTGATTC

GATCGACTACTGGGGCCCAGGACTCCTGGTCACCGTCTCC

TCAGAAGGTAAATCTTCTGGCGCGTCTGGCGAGTCTAAAG

TGGATGACCAGGCCCTGCTGACTCAGCCGTCCTCCGTGTT

TGGTTCCCTGGGCCAGAGGGTCTCCATCACCTGCTCTGGA

AGCAGCAGCAACGTTGGATATGGTGATTATGTAGGCTGGT

ACCAACAGGTCCCAGGATCAGCCCCCAAACTCCTCATCTA

TGATGCAACCACTCGAGCCTCGGGGGTCCCCGACCGATTC

TCCGGCTCCAGGTCTGGGAACACAGCCACCCTGACCATCA

GCTCGCTCCAGGCTGAGGACGAGGCCGATTATTACTGTGC

ATCTTATCAGAATGAAAGAAGTGGTGTTTTCGGCAGCGGG

ACCAGGCTGACCGTCCTGGGT (3aD6 nucleotide sequence)

SEQ ID NO: 405

CAGGTGCAGCTGCAGGAGTCGGGACCCAGCCTGGTGAAGC

CCTCACAGACCCTCTCCCTCACCTGCACGGTCTCTGGATT

CTCACTAACCAGCAATGCTGTGATCTGGGTCCGGCAGGCT

CCAGGAAAGGCGCCGGAGTGGGTTGCTTTGATAGATGTTG

ATGGAGATGCAGCCTATGACCCAGCCCTTAAGTCCCGCCT

CAGCATCACCAGGGACACCTCCAAGAGTCAAGTCTCCCTT

TCACTGCGCAGCGTGACAACTGAGGACACGGCCGTGTACT

ACTGTGCAAGAGACTATGGTAGTTGGGGTTATGTTTCCGA

CATCGACTACTGGGGCCCAGGACTCCTGGTCACCGTCTCC

TCAGAAGGTAAATCTTCTGGCGCGTCTGGCGAGTCTAAAG

TGGATGACCAGGCTGTGCTGACTCAGCCGTCCTCCGTGTC

TGGGTCCCTGGGCCAGAGGGTCTCCATCACCTGCTCTGGA

AGCGACATCGGTGGTGCTGATGTAGGCTGGTTCCAACAGG

TCCCAGGATCGGGCCTCAGAACCCTCATCTATGATAATGA

CAATCGACCCTCAGGGGTCCCCGACCGATTCTCTGGCTCC

AAGTCGGGCAACACAGCCACCCTGACCATCAGCTCGCTCC

AGCCTGAGGATGAGGCCGATTATTTCTGTGGCACTTATTC

TGGTGCTAACTATGGTATTTTTGGCAGCGGGACCAGGCTG

ACCGTCCTGGGT (3aB7 nucleotide sequence)

SEQ ID NO: 406

CAGGTTCAGCTGCAGGAGTCGGGACCCAGCCTGGTGAAGC

CCTCACAGACCCTCTCCCTCACCTGCACGGTCTCTGGATT

CTCATTAACTAGCAATGGTGTAGGCTGGGTCCGCCAGGCT

CCAGGAAAGGTGCCGGAGTGGGTTGGTGATAAAAGCAGTG

CTGGAAAGACATACGGTAACCCGGCCCTGAAATCCCGGCT

CAGCATCACCAGGGACACCTCCAAGAGCCAAGTCTCCCTG

TCACTGAGCAGCGTGACAACTGAGGACACGGCCGTGTACT

ACTGTGTAAGATGCAGGGATGGTGGTGTGACTTATGGTTA

TGACGTCGACTACTGGGGCCCAGGACTCCTGGTCACCGTC

TCCTCAGAAGGTAAATCTTCTGGCGCGTCTGGCGAGTCTA

AAGTGGATGACCAGGCTGTGCTGACTCAGCCGTCCTCCGT

GTCCAAGTCCCTGGGCCAGAGTGTCTCCATCACCTGCTCT

GGAAGCAGCAGCAACGTTGGATATGGTGATGTTGTGAGCT

GGTTCCAACAGTTCCCAGGATCAGCCCCCAAACTCCTCAT

TTTCGGTACAACGACTCGAGCCTCGGGGGTCCCCGACCGA

TTCTCCGGCTCCAGGTCTGGCAACGCAGCGACTCTAACCA

TCAACTCTCTCCAGGCTGAGGACGAGGCCGACTATTACTG

TGCGTCTTTTGATAGTGATAGCGGTGGAATTGCCGGCAGC

GGGACCAGGCTGACCGTCCTGGGT (3bF4 nucleotide sequence)

SEQ ID NO: 407

CAGGTGCAGCTGCAGGAGTCGGGACCCAGCCTGGTGAAGC

CCTCACAGACCCTCTCCCTCACCTGCACGGTCTCTGGATT

CTCCTTGAGTAGCAATGGTGTAGGCTGGGTCCGCCAGGCT

CCAGGAAAGGTGCCGGAGTGGCTTGGTGATATAAGCAGTG

TTGGAAAAAAAATACGCTAACCCGGCCCTGAAATCTCGGCT

-continued

CAGCTTCACTAGGGACACCTCCAAGAGCCAAGTGTCCCTG

TCACTGAGCAGCGTGACAACTGAGGACACGGCCGTGTACT

ATTGTGTAAAATGCAGGGATGGTGGTGTGACTTATGGTTA

TGATATCGACTACTGGGGCCCAGGACTCCTGGTCACCGTC

TCCTCAGAAGGTAAATCTTCTGGCGCGTCTGGCGAGTCTA

AAGTGGATGACCAGGCTGTGCTGACTCAGCCGTCCTCCGT

GTCTAAGTCCACGGGCCAGACTGTCTCCATCACCTGCTCT

GGAAGCAGCAGCAACGTTGGGTTACGTAATTATGTGACCT

GGTTCCAACAGGTCCCAGGATCAGCCCCCAAACTCCTCAT

CTATGGTGCAACCAGTCGAGCCTCGGGGATCCCCGACCGA

TTCTCCGGCTCCAGGTCTGGCAACACAGCGACTCTGATCA

TCAGCTCGCTCCAGGCTGAGGACGAGGCCGATTATTACTG

TGCATCTGCTGACACCAATGACGGTGGTGTTTTCGGCAGC

GGGACCAGGCTGACCGTCCTGGGT (3aD3 nucleotide sequence)
SEQ ID NO: 408

CAGGTGCAGCTGCAGGAGTCGGGACCCAGCCTGGTGAAGC

CCTCACAGACCCTCTCCCTCACCTGCACGGTCTCTGGATT

CTCATTAACTAGCAATGGTGTAGGCTGGGTCCGCCGGGCT

CCAGGAAAGGTGCCGGAGTGGGTTGGTGATATAAGCAGTG

GTGGAAAAGTATACGGGCACCCGGCCCTGAAATCCCGGCT

CAGCATCACCAGGGACACCTCCAAGAGCCAAGTCTCCCTG

TCAGTGAGCAGCGTGACAAGTGAGGACACGGCCGTGTACT

ACTGTGTAAGATGCAGGGATGGTGGTGTGAGTTATGGTTA

TGATAGCGACTACTGGGGCCCAGGACTCCTGGTCACCGTC

TCCTCAGAAGGTAAATCTTCTGGCGCGTCTGGCGAGTCTA

AAGTGGATGACCAGGCTGTGGTGACTCAGCCGTCCTCCGT

GTCCAAGTCCCTGGGCCAGAGTGTCTCCATCACCTGCTCT

GGAAGCAGCAGCAACGTTGGATATGGTGATTATGTGGGCT

GGTTCCAACAGGTCCCAGGATCAGCCCCCAAACTCCTCAT

CTATGGTGTAACCGAGCGAGCCTCGGGGGTCCCCGACCGA

TTCTCCGGCTCCAGGTCTGGCAACACAGCGACTCTGACCA

TCAGCTCGATCCAGGCTGAGGACGAGGCCGATTATTACTG

TGCATCTTATGACGACAGTAGCGGTGGTATTTTCGGCAGC

GGGACCAGGCTGACCGTCCTGGGT (3aH6 nucleotide sequence)
SEQ ID NO: 409

CAGGTGCAGCTGCAGGAGTCGGGACCCAGCCTGGTGAAGC

CCTCACAGACCCTCTCCCTCACCTGCACGGTCTCTGGATT

CTCCTTGAGTAGCAATGGTGTAGGCTGGGTCCGCCAGGCT

CCAGGAAAGGTGCCGGAGTGGCTTGGTGATATAAGCAGTG

TTGGAAAAAAATACGCTAACCCGGCCCTGAAATCTCGGCT

CAGCTTCACTAGGGACACCTCCAAGAGCCAAGTGTCCCTG

-continued

TCACTGAGCAGCGTGACAACTGAGGACACGGCCGTGTACT

ATTGTGTAAAATGCAGGGATGGTGGTGTGACTTATGGTTA

TGATATCGACTACTGGGGCCCAGGACTACTGGTCACCGCC

TCCTCAGAAGGTAAATCTTCTGGCGCGTCTGGCGAGTCTA

AAGTGGATGACCAGGCCGTGGTGACTCAGCCGTCCTCCGT

GTCTGGGTCCCTGGGCCAGAGTGTCTCCATCACCTGCTCC

GGAAGCTCCGGCAACGTTGGCTATGGCGATTATGTGAGTT

GGTTCCAACAATTCCACGGATCGGCCCCCAAACTCCTCAT

CTATGGTGCAACCAATCTTGCCTCGGGAGTTCCCGCCCGA

TTCTCCGGCTCCAGGTCTGGCAACACGGCCACCCTTACTA

TCAGCTCGCTCCACGCTGAGGACGAGGCCGATTACTATTG

TGCATCTTATGACAGCAGTAGCGGCGGTGTGTTCGGCAGC

GGGACCAGGCTGACCGTCCTGGGT (3aG3 nucleotide sequence)
SEQ ID NO: 410

CAGGTGCAGCTGCAGGAGTCGGGACCCAGCCTGGTGAAGC

CCTCACAGACCCTCTCCCTCACCTGCACGGTCTCTGGATT

CTCATTAAGTAGTAATGGTGTAGGCTGGGTCCGCCAGGCT

CCAGGAAAGGTGCCGGAGTGGGTTGGTGATATAAGTAGTA

GTGGAAAAGCATACGCTAATCCGGCCCTGAAATCCCGGCT

CAGCATCACCAGGGACACCGCCAAGACCCAAGTCTTCCTG

TCACTGAGCAGCGTGACAACTGAGGACACGGCCGTGTACT

ACTGTGTAAGATGCAGGGATGGTGGTGTAAGTTATGGTTA

TGATATCGACTACTGGGGCCCAGGACTCCTGGTCACCGTC

TCCTCAGAAGGTAAATCTTCTGGCGCGTCTGGCGAGTCTA

AAGTGGATGACCAGGCTGTGCTGACTCAGCCACCCTCCGT

GTCCGGGTCCCCGGGCCAGAGGGTATCCATTACCTGCTCT

GGAAGCAGCAGCAACATCGGGGGTGGTAATTATCTGAGCT

GGTTCCAACAGGTCCCAGGATCAGCCCCCAAACTCCTCAT

CTATGGTGCAACCAGTCGAGCCTCGGGGGTCCCCGACCGA

TTCTCCGGCTCCAGATCTGGCAACACAGCGACTCTGACAA

TCAGCTCGCTCCAGGCTGAGGACGAGGCCGATTATTACTG

TGCATCTTTTGACACCAGTAGCGGTGGTATTTTCGGCGCC

GGGACCAGGCTGACCGTCCTGGGT (3bG4 nucleotide sequence)
SEQ ID NO: 411

CAGGTGCAGCTTCAGGAGTCGGGACCCAGCCTGGTGAAGC

CCTCACAGACCCTCTCCCTCACCTGCACAATCTCTGGATT

CTCATTAATCAGCAATGGTGTAGGCTGGGTCCGCCAGGCT

CCAGGAAAGGTGCCGGAGTGGGTTGGTGATATTGCTAGTA

GTGGAAAGGCATACAGTAACCCGGCCCTGAAATCCCGGCT

CAGCATCACCAGGGACACCTCCAAGAGCCAAGTCTCCCTG

```
-continued
TCACTGAGGAGCGTGACAACTGAGGACACGGCCGTGTACT

ACTGTGTAAGATGCAGGGATGGTGGTGTGACTTATGGTTA

TGATATCGACTACTGGGGCCCAGGACTCCTGGTCACCGTC

TCCTCAGAAGGTAAATCTTCTGGCGCGTCTGGCGAGTCTA

AAGTGGATGACCAGGCTGTGCTGACTCAGCCGTCATCCGT

GTCCAAGTCCCTGGGCCAGAGTGTCTCCATCACCTGCTCC

GGAAGCACTAGCAACGTTGGAAGTGGTAATGATGTGAGCT

GGTTCCAACAGGTCCCAGGATCAGCCCCCAAACTCCTCTT

CTACGGTGCAACCAACCGAGCCTCGGGGGTCCCCGACCGA

TTCTCCGGCTCCAGGTCTGGCAACACAGCGACTCTGACCA

TCACCTCGCTTCAGGCTGAGGACGAGGCCGATTATTACTG

TGGATCTTATGACAGCAATAGCGGTGGTATTTTCGGCAGT

GGGACCAGGCTGACCGTCCTGGGT
```

(NS1G7 nucleotide sequence)
```
                            SEQ ID NO: 412
CAGGTGCAGCTGCAGGAATCAGGACCCAGCCTGGTGAAGC

CCTCACAGACCCTCTCCCTCACCTGCACGGTCTCTGGATT

CTCATTAACCAGCTATGGTGTAGGCTGGGTCCGCCAGGCT

CCAGGAAAGACACTGGAGTGGATTAGTAGCATATCTAGTG

GTGGAACTACTTTCTATAACCCGGCCCTGAAATCCCGCCT

CAGCATCACCAGGGACACCTCCGAGAGCCAAGTCTCCCTG

TCACTGAGCAGCGTGACGACTGAGGACACGGCCGTGTACT

ACTGTACAAGAGACGTGCATATTTACTATAATGATTATGG

TGCTGCTTATGGTGACAGGGACTACTGGGGCCCAGGACTC

CTGGTCACCGTCTCCTCAGAAGGTAAATCTTCTGGCGCGT

CTGGCGAGTCTAAAGTGGATGACCAGGCTGTGGTGACTCA

GCCACCCTCCGTGTCCGGGTCCCCGGGCCAGAGGGTATCC

ATCACCTGCTCTGGAAGCAGCAGCAACATCGGGGGTGGTA

ATTATGTGAGCTGGTACCAACAACTCCCAGGATCGGGCCT

CAGAACCCTCATCTATGGTACAACCAGTCGAGCCTCGGGG

GTCCCCGACCGGTTTTCCGGCTCCGGATCTGGCAACACAG

CGACTCTGACCATCAGCTCGCTCCAAGCTGAAGACGAGGC

CGATTATTACTGTGCATCTTATGACACGAATAGCGGTAGT

GTTTTCGGCAGTGGGACCAGGCTGACCGTCCTGGGT
```

The nucleic acid sequence may comprise a nucleic acid sequence encoding a variable domain disclosed herein. The variable domain may be a VH domain and/or a VL domain. Typically, the nucleic acid sequence comprises a nucleic acid sequence encoding a VH domain and a nucleic acid sequence encoding a VL domain. The nucleic acid sequence encoding a VH domain may be a nucleic acid sequence encoding a VH domain of any of SEQ ID NOs: 43, 219, 249, 251, 253, 380 to 411, and 431. The nucleic acid sequence encoding a VH domain may be selected from the group consisting of SEQ ID NOs: 567, 569, 571, 573, 575, 577, 579, 581, 583, 585 and 587 or a nucleic acid sequence with at least 70% identity to any one of SEQ ID NOs: 567, 569, 571, 573, 575, 577, 579, 581, 583, 585 and 587. Preferably the nucleic acid sequence may have at least 75%, at least 80%, at least 90%, at least 95% or at least 99% identity to any one of SEQ ID NOs: 567, 569, 571, 573, 575, 577, 579, 581, 583, 585 and 587. The nucleic acid sequence encoding a VL domain may be a nucleic acid sequence encoding a VL domain of any of SEQ ID NOs: 43, 219, 249, 251, 253, 380 to 411, and 431. The nucleic acid sequence encoding a VL domain may be selected from the group consisting of SEQ ID NOs: 568, 570, 572, 574, 576, 578, 580, 582, 584, 586 and 588 or a nucleic acid sequence with at least 70% identity to any one of SEQ ID NOs: 568, 570, 572, 574, 576, 578, 580, 582, 584, 586, and 588. Preferably the nucleic acid sequence may have at least 75%, at least 80%, at least 90%, at least 95% or at least 99% identity to any one of SEQ ID NOs: 568, 570, 572, 574, 576, 578, 580, 582, 584, 586 and 588.

(S1D12 VH nucleotide sequence)
```
                            SEQ ID NO: 567
CAGGTGCAGCTGCAGGAGTCGGGACCCAGCCTGGTGAAGC

CCTCACAGACCCTCTCCCTCACCTGCACGGTCTCTGGATT

CTCATTGAACAACAATGCTGTAGGCTGGGTCCGCCAGGCT

CCAGGAAAGGTGCCGGAGTCGCTTGTGGGTTGTAGCAGTG

ATGGAACGTGTTACTATAATTCGGCCCTGAAATCCCGGCT

CGACATCACCAGGGACACCTCCAAGAACCAGATCTCCCTG

TCACTGAGCAGCGTTACAACTGACGACGCGGCCGTGTACT

ATTGTACAAGAGGCCATTATAGTATTTATGGTTATGACTA

TCTTGGCACTATCGACTACTGGGGCCCAGGACTCCTGGTC

ACCGTCTCCTCA
```

(S1D12 VL nucleotide sequence)
```
                            SEQ ID NO: 568
CAGGCTGTGCTGACTCAGCCGTCCTCCGTGTCCGGGTCCC

TGGGCCAGAGGGTCTCCATCACCTGCTCTGGAAGCAGCAG

CAACGTCGGGGGTGGTAATAGTGTGGGCTGGTACCAACAC

CTCCCAGGCTCAGGCCTCAAAACCATCATCTATGATACTA

ACAGTCGACCCTCGGGGGTCCCGGACCGATTCTCTGGCTC

CAGGTCTGGCAACACGGCCACCCTAACCATCAACTCGCTC

CAGGCTGAGGACGAGGGTGATTATTACTGTGTAACGGGTG

ACAGCACTACTCATGATGATCTTGTCGGCAGCGGGACCAG

GCTGACCGTCCTGGGG
```

(S1G2 VH nucleotide sequence)
```
                            SEQ ID NO: 569
CAGGTGCAGCTGCAGGAGTCGGGACCCAGCCTGGTGAAGC

CCTCACAGACCCTCTCCCTCACCTGCACGGTCTCTGGATT

CTCATTAACCAGCAATTCTGTGGGCTGGGTCCGACAGGCT

CCAGGAAAGGCGCCGGAGTGGGTTGCTGGTATAGATACTG

ATGGAGAAGAAGGCTATAATCCAGCCCTTAACTCCCGGCT

CAGCATCACCAGGGACACCTCCAAGAGTCAAGTCTCTTTG

TCATTGAGCAGCGTGACAAGTGAGGACACGGCCGTGTACT
```

-continued
ACTGTGGAAGAAGTTATAGGGCTGATGGTCTTGCTTACGG

TTATGTCCAAGCCATCGACTACTGGGGCCCAGGACTCCTG

GTCACCGTCTCCTCA

(S1G2 VL nucleotide sequence)
                            SEQ ID NO: 570
CAGGCCGTGGTGACTCAGCCGTCCTCCGTGTCTGGGTCCC

TGGGCCAGAGGGTCTCCATCACCTGCTCTGGAAGCTTCAT

CGGTATTAGTAGTGTAGGCTGGTTCCAACAGCTCCCAGGA

TCGGGCCTCAGAACCATCATCGTGGCGAGTGACGGTCGAC

CCTCAGGGGTCCCCGACCGATTCTCTATGTCCAAATCGGG   15

CAACACAGCCACCCTGACCATCAGCTCGCTCCAGGCTGAG

GACGAGGCCGATTATTTCTGTGGAAGTAGTGATAGGACTC

CTTATACTGGGGTCTTCGGCAGCGGGACCAGGCTGACCGT

CCTGGGT (CB7 VH nucleotide sequence)
                            SEQ ID NO: 571
CAGGTGCAGCTGCAGGAGTCGGGACCCAGCCTGGTGAAGC   25

CCTCACAGACCCTCTCCCTCACCTGCACGGTCTCTGGATT

CTCATTAACCAACTATCGTGTAGGTTGGGTCCGCCAGGCT

CCAGGAAAGGCACTGGAGTGGGTTAGTAACATACGGAGTG   30

GTGGAACTACATGGTATAACCCGGCCCTGAAATCCCGGCT

CAGCATCACCGCGGACACCTCCAAGAGCCAAGTCTCCCTG

TCACTGAGCAGCGTGACAACTGAGGACACGGCCGTATATT

ATTGTGCAAGAGATTCCTCTGGTGATCTTTATGCGTATGA   35

TTACTGGGGGCCCAGGACTCCTGGTCACCGTCTCCTCA (CB7 VL nucleotide sequence)
                            SEQ ID NO: 572
CAGGCCGTGCTGACTCAGCCGTCCTCCGTGTCCAGGTCCC

TGGGCCAGAGTGTCTCCATGACCTGCTCTGGAAGCAGCAG

CAACGTTGGATATGGTAATTATATGGCCTGGTTCCAACAG

GTTCCAGGATCAGCCCCCAAACTCCTCATCTATGGTGCAA   45

CCAGTCGAGCCTCGGGGGTCCCCGACCGATTCTCCGGCTC

CAGGTCTGGCAACACAGCGACTCTGACCATCAGCTCGCTC

CAGGCTGAGGACGAGGCCGATTACTACTGTGCATCTTATG

ACAGCACTAGCGGGGGTGTCTTCGGCAGCGGGACCAGGCT

GACCGTCCTGGGT (CC7 VH nucleotide sequence)
                            SEQ ID NO: 573
CAGGTGCAGCTGCAGGAGTCGGGACCCAGCCTGGTGAAGC

CCTCACAGACCCTCTCCCTCACCTGCACGGTCTCTGGATT

CTCACTAACCAGCAATGCTGTGATCTGGGTCCGGCAGGCT   60

CCAGGAAAGGCGCCGGAGTGGGTTGCTTTGATAGATGTTG

ATGGAGATGCAGCCTATGACCCAGCCCTTAAGTCCCGCCT

CAGCATCACCAGGGACACCTCCAAGAGTCAAGTCTCCCTT

TCACTGCGCAGCGTGACAACTGAGGACACGGCCGTGTACT

-continued
ACTGTGCAAGAGACTATGGTAGTTGGGGTTATGTTTCCGA

CATCGACTACTGGGGCCCAGGACTCCTGGTCACCGTCTCC

TCA (CC7 VL nucleotide sequence)
                            SEQ ID NO: 574
AGGGTCGTGCGGACTCAACCGTCCTCCGTGTCTGGGTCCC

TGGGCCAGAGGGTCTCCATCACCTGCTCTGGAAGCTACAT

CACTGGTAGTTCTGTAGGCTGGTTCCAACAGGTCCCAGGA

TCGGGCCTCAAAACCGTCATCTATGACAATAACGATCGAC

CCTCAGGGGTCCCCGACCGATTCTCTGGCTCCAAGTCGGG

CGACACAGCCACCCTGACCATCAGCTCGCTCCAGGCTGAG

GACGAGGCCGATTATTACTGTGCATCTTATGACACCAGTA

ACATTGGTCTTTTCGGCAGCGGGACCAGGCTGACCGTCCT

GGGT (CA4 VH nucleotide sequence)
                            SEQ ID NO: 575
CAGGTTCAGCTGCAGGAGTCGGGACCCAGCCTGGTGAAGC

CCTCACAGACCCTCTCCCTCACCTGCACGGTCTCTGGATT

CTCATTAACCAGCTATTCCGTATACTGGGTCCGCCAGGCT

CCAGGCCAGGCACTGGAGTGGATTAGTATTATGTATGCTA

GTGGAAGAGTAGACTATAACCCGGCCCTGAAATCCCGGCT

CAGCATCACCAGGGACACCTCCAAGAGTCAATTCTCCCTG

TCATTGAGCAGCGTGACAACTGAGGACACGGCCGTCTACT

ACTGTACAAGAGGAATCGAAAACTGGGGCCCCGGACTCCT

GGTCACCGTCTCCTCA (CA4 VL nucleotide sequence)
                            SEQ ID NO: 576
GACATCCAGGTGACCCAGTCTCCGTCCTCCCTGTCTGCATC

TCTAACAGAGAGAGTCTCCATCACTTGCCGGACCAGTCAG

AGCGTTAACAATTACTTAAGCTGGTATCAGCAGAAACCAG

GGCAAGCTCCTAAGCTCCTGATCTATTATGCAACCAGATT

GTACACCGATGTCCCATCCCGGTTCAGTGGCAGTGGATCT

GGGACAGATTACACCCTCACCATCACCAGCCTGGAGGCGG

ACGACACTGCAACTTATTACTGTCTACAATATGATAGTAC

ACCTCTTGCATTCGGCGGTGGGACCAACGTGGAAATCAAA

CGG (3bG4 VH nucleotide sequence)
                            SEQ ID NO: 577
CAGGTGCAGCTTCAGGAGTCGGGACCCAGCCTGGTGAAGC

CCTCACAGACCCTCTCCCTCACCTGCACAATCTCTGGATT

CTCATTAATCAGCAATGGTGTAGGCTGGGTCCGCCAGGCT

CCAGGAAAGGTGCCGGAGTGGGTTGGTGATATTGCTAGTA

GTGGAAAGGCATACAGTAACCCGGCCCTGAAATCCCGGCT

CAGCATCACCAGGGACACCTCCAAGAGCCAAGTCTCCCTG

-continued

TCACTGAGGAGCGTGACAACTGAGGACACGGCCGTGTACT

ACTGTGTAAGATGCAGGGATGGTGGTGTGACTTATGGTTA

TGATATCGACTACTGGGGCCCAGGACTCCTGGTCACCGTC

TCCTCA (3bG4 VL nucleotide sequence)
SEQ ID NO: 578
CAGGCTGTGCTGACTCAGCCGTCATCCGTGTCCAAGTCCC

TGGGCCAGAGTGTCTCCATCACCTGCTCCGGAAGCACTAG

CAACGTTGGAAGTGGTAATGATGTGAGCTGGTTCCAACAG

GTCCCAGGATCAGCCCCCAAACTCCTCTTCTACGGTGCAA

CCAACCGAGCCTCGGGGGTCCCCGACCGATTCTCCGGCTC

CAGGTCTGGCAACACAGCGACTCTGACCATCACCTCGCTT

CAGGCTGAGGACGAGGCCGATTATTACTGTGGATCTTATG

ACAGCAATAGCGGTGGTATTTTCGGCAGTGGGACCAGGCT

GACCGTCCTGGGT (CA7 VH nucleotide sequence)
SEQ ID NO: 579
CGGGTGCGGCTGCAGGGGTCGGGACCCAGCCTGGTGAAAC CtTCACAGACCCTCTCCCTCACCTGCACGGTCTCTGGATTCT

CTTTTGACAGCTATTATGTAGGCTGGGTCCGCCAGGCTCC

AGGAAAGGCACTGGAGTGGCTTGGTAATATATATAGTACT

GGAAGGGCATTCTATAACCCCGGCCCTGAAATCCCGGCTCA

GCATCACCAGGGACACCTCCAAGAGCCAAGTCTCCCTATC

AGTGAGCAGCGTGACAATTGAGGACACGGCCCTGTACTAC

TGTGTCAGAGGCTCGTATTATCACGGTGGTGGCAATGGGA

TGGTCGACTTTTTCGACTACTGGAGCCCAGGACTCCTGGT

CACCGTCTCCTCA (CA7 VL nucleotide sequence)
SEQ ID NO: 580
CAGGTCGTGCGGACTCAGCCGTCCTCCGTGTCTGGGTCCC

TGGGCCAGAGGGTCTCCATCACCTGCTCTGGAAGCAGCAG

CAATGTTGGATATGGTAATTATGTGGGCTGGTTCCAACAG

GTGCCAGGGTCAGCCCCCAAACTCCTCATCTATGCTGCAA

CCAGTCGAGCCTCGGGGGTCCCCGACCGATTCTCCGGCTC

CAGGTCTGGGAATACAGCCACCCTGACCATCGACTCGCTC

CAGGCTGAGGACGAGGCCGATTATTACTGTTCATCTTATC

AACGCGGTAACACTGGTGTTTTCGGCAGCGGGACCAGGCT

GACCGTCCTGGGT (E2E8 VH nucleotide sequence)
SEQ ID NO: 581
CAGGTGCAGCTGCAGGAGTCGGGACCCAGCCTGGTGAAGC

CCTCACAGACCCTCTCCCTCACCTGCACGGTCTCTGGATT

CTCATTAACCGACCGTGGTGTAGCCTGGGTCCGCCAGGCT

CCAGGAAAGGCACTGGAGTGGGTTGGTACTATGCGTAGTG

GTGGAACGATAGACTATAACCCGGCCCTGAAATCCCGGCT

-continued

CAGCATCACCAGGGACACCTCCAAGAGCCAAGTTTTCCTG

TCACTGAGCAGCGTCACAACTGAGGACATGGCCATGTACT

ACTGTGCCAGAGGTTATTTGAGCGGTGATCGTTATGCCTG

GGGCCGAGGACTCCTGGTCACCGTCTCCTCA (E2E8 VL nucleotide sequence)
SEQ ID NO: 582
CAGGCTGTGCTGACTCAGCCGTCCTCCGTGTCCAAGTCCC

TGGGCCAGAGTGTCTCCATCGCCTGCTCTGGAAGCAGGAG

CGACATTGGATATGGTAATTATGTGAGCTGGTTCCAACAG

ATCCCAGGATCAGCCCCCAAACTCCTTATTTATGATACAA

ACACTCGGGCCTCGGGGGTCCCCGACCGATTCTCCGGCGC

CAGGTCTGGCAACACAGCAACACTGACCATCAACTCGCTC

CAGGCTGAGGACGAGGCCGATTATTACTGTGCAAATATTG

ACAGTAGTCGCAGTCATCTTTTCGGCAGTGGCACCAGACT

GACCGTCCTGGGT (412E10 VH nucleotide sequence)
SEQ ID NO: 583
CAGGTGCAGCTGCAGGAGTCGGGACCCAGCCTGGTGAAGC

CCTCACAGACCCTCTCCCTCACCTGCACGGTCTCTGGCTT

CTCTGTAATAAGCGATTCTGTAGCCTGGGTCCGCCAGGCT

CCAGGAAAAGTGCCGGAGTGGCTTGGTGCTAGCGGCAGTT

CTGGAAACAAATACTATAACCCGGCCCTAAAATCCCGGCT

CAGCATCACCAGGGACACCTCCAAGAGCCAAGTCTCCCTG

TCACTGAGCAGCGTGACAACTGAGGATACGGCCGTGTACT

ACTGTGCGAGAGGTATTATCGCCGGTGTAGATGTCTGGGG

CCGAGGACTCCTGGTCACCGTCTCCTCA (412E10 VL nucleotide sequence)
SEQ ID NO: 584
CAGGCTGTGCTGACTCAGCCGTCCTCCGTGTCTGGGTCCC

TGGGCCAGAGGGTCTCCATCACCTGCTCTGGAAGCAGCAG

CAACGTTGGATATGGTAATTATGTGGGCTGGTACCAACAG

GTCCCAGGATCAGCCCCCAAACTCCTCATCTATGGTACAG

CCATTCGAGCCTCGGGGGTCCCCGACCGATTCTCCGGCTC

CAGGTCTGGGGACACAGCCACCCTTACCATCACCTCGCTC

CAGGCTGAGGACGAGGCCGATTACTACTGTGCATCTTATC

AGAGTAATTACGCTTTTTTCGGCAGCGGGACCAGGCTGAC

CGTCCTGGGT (CE2 VH nucleotide sequence)
SEQ ID NO: 585
CAGGTGCAGCTGCAGGAGTCGGGACCCAGCCTGGTGAAGC

CCTCACAGACCCTCTCCCTCACCTGCACGGTCTCTGGATT

CTCATTAACCAACTATCCTGTAGGCTGGGTCCGCCAGGCT

CCAGGAAAGGCACTGGAGTGGATTGGTAACATAGAAAATG

ATGGAAGTGCGAACTATGCCTCGGCCCTGAAATCCCGACT

-continued

CAGCATCACCAGGGACACCTCCAAGAACCAAGTCTCCCTG

TCACTGAGCAGCGCGACAACTGAGGACACGGCCGTTTACT

ACTGTGGAAGAGAATTCGGTGGGAGTGATGGTTATACTTA

TTTCGTTGATATCGACTACTGGGGCCCAGGACTCCTGGTC

ACCGTCTCCTCA (CE2 VL nucleotide sequence)
SEQ ID NO: 586
CAGGCTGTGCTGACTCAGCCGTCCTCCGTGTCCAAGTCCC

TGGGCCAGAGTGTCTCCATCACCTGCTCTGGAAGCAGCAG

CAACGTTGGATATGGTAATTATGTGAGCTGGTTCCAACAG

GTCCCAGGATCAGCCCCCAAAATCCTCATCTATGGTGCAA

CCAGTCGAGCCTCGGGGGTCCCCGACCGATTCTCCGGCTC

CAGGTCTGGCAACACAGCGACTCTGACCATCACCTCGCTC

CAGGCTGAGGACGAGGCCGATTATTACTGTGCATCTTATG

ACGGCAGTAGCAGTGGTGTTTTCGGCAGCGGGACCAGGCT

GACCGTCCTGGGT (CE3 VH nucleotide sequence)
SEQ ID NO: 587
CAGGTGCGACTGCAGGAGTCGGGACCCAGCCTGGTGAAGC

CCTCACAGACCCTCTCCGTCACCTGCACGGTCTCTGGATT

CTCATTGATCAGCAATGCTGTAGGCTGGGTCCGCCAGGCT

CCAGGAAAGGTGCCGGAGTCGCTTGCTGGTTGTAGCAGTG

ATGGAAAGTGTTACTATAACTCGGCCCTGAAATCCCGGCT

CGACATCACCAGGGACACCTCGAAGAACCAGATCTCCCTG

TCACTGAGCAGCGTCACAACTGACGACGCGGCCGTGTACT

ACTGTACAAGAGGCTATTATCCTGTTTATGGTTATGACTA

TCTTGGCACTATCGACTACTGGGGCCCCGGACTCCTGGTC

ACCGTCTCCTCA (CE3 VL nucleotide sequence)
SEQ ID NO: 588
CAAGCTGTGCTGACTCAACCGTCCTCCGTGTCTGGGTCCC

TGGGCCAGAGGGTCTCCATCACCTGCTCTGGAAGCAGCAG

CAACGTTGGTAGAAATGATGTAGCCTGGTTCCAACAACTC

CCAGGATCAGGCCTCAGAACCATCATCTATGGTACTACCA

GTCGACCCTCAGGTATCCCGGACCGATTCTCCGGCTCCAA

GTCTGGCGTTACGGCCACCCTGACCATCGACTCGCTCCAG

GCTGAGGACGAGGCCGATTATTTCTGTGCCTCTGGTGACA

GTAGTGCCATTAATGATATTTTCGGCAGCGGGACCAGGCT

GACCGTCCTGGGT

It will be appreciated by those of ordinary skill in the art that, as a result of the degeneracy of the genetic code, there are many nucleotide sequences that may encode any given amino acid sequences, such as a CDR as described herein. By degenerate nucleotide sequences is meant two (or more) nucleotide sequences which encode the same protein (or protein sequence), specifically in the open reading frame of the reference nucleotide sequence which begins at position 1 (i.e. in which codon 1 of the encoding sequence corresponds to positions 1-3 of the reference nucleotide sequence).

The nucleic acid molecule of the invention may be an isolated nucleic acid molecule and may further include DNA or RNA or chemical derivatives of DNA or RNA. The term "nucleic acid molecule" specifically includes single and double stranded forms of DNA and RNA.

Methods for preparing a nucleic acid molecule encoding a specific binding molecule of the invention are well known in the art, e.g. conventional polymerase chain reaction (PCR) cloning techniques can be used to construct the nucleic acid molecule of the invention. The nucleotide sequence encoding the specific binding molecule of the invention may be codon-optimised for expression in cells of a particular type or origin, e.g. the sequence may be hamster-optimised for expression in CHO cells.

According to a fourth aspect, the invention provides a construct comprising a nucleic acid molecule of the third aspect of the invention.

The construct is conveniently a recombinant construct comprising the nucleic acid molecule of the invention. In the construct, the nucleic acid molecule of the invention may be flanked by restriction sites (i.e. nucleotide sequences recognised by one or more restriction enzymes) to enable easy cloning of the nucleic acid molecule of the invention. In the construct of the invention the nucleotide sequence encoding the specific binding molecule of the invention may conveniently be operably linked within said construct to an expression control sequence, which may be heterologous to the nucleic acid molecule, i.e. non-native. Such an expression control sequence is typically a promoter, though the nucleotide sequence encoding the specific binding molecule may alternatively or additionally be operably linked to other expression control sequences such as a terminator sequence, an operator sequence, an enhancer sequence or suchlike. Accordingly, the construct may comprise a native or non-native promoter.

The term "operably linked" refers to the association of two or more nucleic acid molecules on a single nucleic acid fragment so that the function of one is affected by the other. For example, a promoter is operably linked to a coding sequence when it is capable of affecting the expression of that coding sequence (i.e. the coding sequence is under the transcriptional control of the promoter). Coding sequences may be operably linked to regulatory sequences in sense or antisense orientation.

The term "expression control sequence" refers to nucleotide sequences located upstream (5' non-coding sequences), within, or downstream (3' non-coding sequences) of a coding sequence, and which influence transcription, RNA processing or stability, or translation of the associated coding sequence. Expression control sequences may include promoters, operators, enhancers, translation leader sequences, a TATA box, a B recognition element and suchlike. As used herein, the term "promoter" refers to a nucleotide sequence capable of controlling the expression of a coding sequence or RNA. Suitable examples are provided hereinafter. In general, a coding sequence is located 3' to a promoter sequence. Promoters may be derived in their entirety from a native gene, or be composed of different elements derived from different promoters found in nature, or even comprise synthetic nucleotide segments. It is further recognised that since in most cases the exact boundaries of regulatory sequences have not been completely defined, nucleic acid fragments of different lengths may have identical regulatory activity.

Methods for preparing a construct of the invention are well known in the art, e.g. conventional polymerase chain reaction (PCR) cloning techniques can be used to construct the nucleic acid molecule of the invention which may be inserted into suitable constructs (e.g. containing an expression control sequence) using known methods.

According to a fifth aspect, the invention provides a vector comprising a nucleic acid molecule of the third aspect of the invention or a construct of the fourth aspect of the invention.

The term "vector" as used herein refers to a vehicle into which the nucleic acid molecule or construct of the invention may be introduced (e.g. be covalently inserted) from which the specific binding molecule or mRNA encoding it may be expressed and/or the nucleic acid molecule/construct of the invention may be cloned. The vector may accordingly be a cloning vector or an expression vector.

The nucleic acid molecule or construct of the invention may be inserted into a vector using any suitable methods known in the art, for example, without limitation, the vector and nucleic acid molecule may be digested using appropriate restriction enzymes and then may be ligated with the nucleic acid molecule having matching sticky ends, or as appropriate the digested nucleic acid molecule may be ligated into the digested vector using blunt-ended cloning.

The vector may be a bacterial or prokaryotic vector, or it may be a eukaryotic vector, particularly a mammalian vector. The nucleic acid molecule or construct of the invention may be produced in or introduced into a general purpose cloning vector, particularly a bacterial cloning vector, e.g. an *Escherichia coli* cloning vector. Examples of such vectors include pUC19, pBR322, pBluescript vectors (Stratagene Inc.) and pCR TOPO® from Invitrogen Inc., e.g. pCR2.1-TOPO.

The nucleic acid molecule or construct of the invention may be sub-cloned into an expression vector for expression of the specific binding molecule of the invention, particularly a mammalian expression vector. Expression vectors can contain a variety of expression control sequences. In addition to control sequences that govern transcription and translation, vectors may contain additional nucleic acid sequences that serve other functions, including for example vector replication, selectable markers etc.

The expression vector should have the necessary 5' upstream and 3' downstream regulatory elements such as promoter sequences, e.g. the cytomegalovirus (CMV), PGK or EF1a promoter, particularly the human CMV (HCMV) promoter, ribosome recognition and binding TATA box, a Kozak sequence at the translation start site, and the 3 ' UTR AATAAA transcription termination sequence for efficient gene transcription and translation in its respective host cell. Other promoters include the constitutive simian virus 40 (SV40) early promoter, the mouse mammary tumour virus (MMTV) promoter, the HIV LTR promoter, the MoMuLV promoter, the avian leukaemia virus promoter, the EBV immediate early promoter, and the Rous sarcoma virus promoter. Human gene promoters may also be used, including, but not limited to the actin promoter, the myosin promoter, the haemoglobin promoter, and the creatine kinase promoter. In certain embodiments inducible promoters may be used. These provide a molecular switch capable of turning expression of the nucleic acid molecule on or off. Examples of inducible promoters include, but are not limited to, a metallothionine promoter, a glucocorticoid promoter, a progesterone promoter, or a tetracycline promoter. Further, the expression vector may contain 5' and 3' untranslated regulatory sequences that may function as enhancer sequences, and/or terminator sequences that can facilitate or enhance efficient transcription of the nucleic acid molecule.

Examples of vectors are plasmids, autonomously replicating sequences, and transposable elements. Additional exemplary vectors include, without limitation, phagemids, cosmids, artificial chromosomes such as yeast artificial chromosome (YAC), bacterial artificial chromosome (BAC), or PI-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g. herpes simplex virus), poxvirus, baculovirus, papillomavirus, and papovavirus (e.g. SV40).

Particularly preferred expression vectors are those disclosed in Kettleborough et al. (Protein Eng, Vol. 4 (7): 773-783, 1991), which were specifically designed to express chimeric or reshaped human light and heavy chains in mammalian cells. These vectors contain the human cytomegalovirus (HCMV) enhancer and promoter for transcription, an appropriate human light or heavy chain constant region, a gene such as neomycin resistance (neo) for selection of transformed cells, and the SV40 origin of replication for DNA replication in host cells.

According to a sixth aspect, the invention provides a host cell comprising a nucleic acid molecule of the third aspect of the invention, a construct of the fourth aspect of the invention or a vector of the fifth aspect of the invention.

The host cell may be a prokaryotic (e.g. bacterial) or eukaryotic (e.g. mammalian) cell. A prokaryotic cell may in particular be used as a cloning host for the nucleic acid molecule, construct or vector of the invention. Suitable prokaryotic cells for use as cloning hosts include without limitation, eubacteria, such as Gram-negative or Gram-positive organisms, for example, Enterobacteriaceae such as *Escherichia*, in particular *E, coli*, and Bacilli such as *B, subtilis*. The cloning host may alternatively be a eukaryotic cell such as a fungal cell, e.g. *Pichia pastoris*, or a yeast cell, or even a higher eukaryotic cell such as a mammalian cell.

The host cell of the invention may alternatively be a production host, i.e. a cell used to express and produce the specific binding molecule of the invention. The production host cell may be a prokaryotic cell, as defined above, but is preferably a eukaryotic cell. The production host may be a fungal cell, such as *Pichia pastoris* or a yeast cell, but is preferably a mammalian cell, particularly a rodent cell, a human cell or a cell of an alternative primate.

Particular examples of cells which may constitute a production host according to the invention include Cos cells, such as COS-7 cells, HEK293 cells, CHO cells, though any suitable cell type or line may be used.

The nucleic acid molecule, construct or vector of the invention may be integrated into the host cell chromosome or may be maintained extra-chromosomally. The nucleic acid molecule, construct or vector may be introduced into a host cell by any method known in the art. Such methods include, in particular, for prokaryotic cells transformation, transduction and conjugation. Transformation refers to the genetic alteration of a competent bacterium by direct uptake of DNA. Transduction refers to infection of a bacterium using a bacteriophage in order to introduce DNA of interest. Conjugation refers to the direct transfer of genetic material between bacterial cells in direct contact.

For eukaryotic cells, nucleic acid molecules, constructs and vectors may be introduced by transfection or transduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into viral particles or virions prior to contact with a cell. The skilled person is well aware of appropriate methods for introducing such genetic material into a host cell.

According to a seventh aspect, the invention provides a method of preparing a specific binding molecule according to the first aspect of the invention comprising:

i) introducing into a host cell a nucleic acid molecule of the third aspect of the invention, a construct of the fourth aspect of the invention or a vector of the fifth aspect of the invention;

ii) expressing the nucleic acid molecule such that the specific binding molecule is produced; and iii) collecting the specific binding molecule, preferably by purification.

The host cell used in the method is as described above with reference to a host cell provided by the invention. Methods of introducing a nucleic acid molecule, construct or vector of the invention into a host cell are as described above. Advantageously, the nucleic acid molecule, construct or vector of the invention comprises a selectable marker such that host cells into which it has been introduced may be selected. Examples of selectable markers include antibiotic resistance genes, such as an ampicillin resistance gene (e.g. 13-lactamase), a kanamycin resistance gene or a chloramphenicol resistance gene (e.g. chloramphenicol acetyl transferase). Selectable markers particularly suitable for use in mammalian host cells include hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

Cells into which a nucleic acid molecule, construct or vector have been introduced may then be easily selected as appropriate, e.g. by exposure to the compound to which the selectable marker confers resistance. In a particular embodiment of the invention CHO cells lacking the DHFR genes are transfected or transduced with a vector of the invention carrying a DHFR gene, restoring DHFR function in the cells. Transfected cells are then selected by culture in medium lacking thymidine, which DHFR is required to synthesise. By "expression" of the nucleic acid molecule of the invention is meant that the gene, i.e. the nucleotide sequence, within the nucleic acid molecule, which encodes the specific binding molecule of the invention, is transcribed and translated so as to produce the specific binding molecule of the invention. Expression of the nucleic acid molecule, to produce the specific binding molecule of the invention, may be constitutive or inducible, depending on the promoter used to drive expression of the gene. It is straightforward for the skilled person to express a gene in a host cell, though it may be necessary for expression conditions to be optimised. This is well within the ability of the skilled person.

The specific binding molecule produced by the production host is finally collected. "Collection" of the specific binding molecule produced by this method simply means that it is separated from the production host cells. Collection does not necessarily entail isolation of the specific binding molecule, though preferably the specific binding molecule is isolated by purification. The specific binding molecule may be produced, such that it is secreted from the host cells, e.g. the specific binding molecule may be produced with a signal sequence. If the specific binding molecule is secreted by the host cells it can, at its most simple, be collected simply by isolating the culture supernatant by e.g. centrifugation of the culture. The specific binding molecule would thus be collected as it would be separated from the production host cells. Antibody heavy and light chains are natively encoded with N-terminal signal sequences, and are thus secreted from cells which produce them. Preferably, the specific binding molecule of the invention is produced such that it is secreted from the host cells, e.g. it may be produced with a signal sequence (and thus the nucleic acid molecule of the invention may encode a specific binding molecule with a signal sequence). Upon translocation of the polypeptide chains across the relevant membrane (the cell surface membrane in bacteria, the ER membrane in eukaryotes), the signal sequence is cleaved, yielding a mature polypeptide sequence. Specific binding molecules with and without signal sequences fall under the scope of this invention.

If the specific binding molecule of the invention is not produced such that it is secreted from the host cells, the specific binding molecule may be collected by harvesting and lysing the host cells producing the molecule. The individual skilled in the art can readily perform this task. Host cells may be harvested by centrifugation, and lysed by e.g. sonication, French Press, chemical lysis using a protein extraction reagent (e.g. BugBuster®, EMD Millipore (USA)), or a mammalian cell lysis kit as produced by e.g. AbCam (UK) or Sigma-Aldrich (USA)). The specific binding molecule of the invention is preferably then purified. Methods for purification of specific binding molecules are described earlier. Purification is preferably achieved such that the specific binding molecule is at least 50% (e.g. 60%, 70%, 80%, 90%, 95%) pure, when assessed on a w/w basis relative to other components present in the solution or composition (excluding the solvent).

Alternatively, the specific binding molecule may be prepared by any suitable method of cell-free synthesis.

According to an eighth aspect, the invention provides a specific binding molecule obtainable by a method according to the seventh aspect of the invention.

A specific binding molecule obtainable by the above method falls under the scope of this invention (i.e. which has the characteristics of a molecule obtained when such a method is used, even if that specific method is not used). The invention also extends to specific binding molecules which are obtained by using that method. Such a specific binding molecule has the characteristics of the specific binding molecule provided by the invention which is described above. A specific binding molecule obtainable by the above method is a polypeptide, preferably an antibody or a fragment of an antibody.

According to a ninth aspect, the invention provides a pharmaceutical composition comprising a specific binding molecule according to the first aspect of the invention or a composition according to a second aspect of the invention and one or more pharmaceutically acceptable diluents, carriers or excipients.

The compositions of the invention may be formulated in any convenient manner according to techniques and procedures known in the pharmaceutical art. The specific binding molecule may be presented in the form of a pharmaceutically acceptable salt and in such cases the compositions are prepared accordingly. "Pharmaceutically acceptable" as used herein refers to ingredients that are compatible with other ingredients of the compositions as well as physiologically acceptable to the recipient. The nature of the composition and carriers or excipient materials, dosages etc, may be selected in routine manner according to choice and the desired route of administration, purpose of treatment etc. Dosages may likewise be determined in routine manner and may depend upon the nature of the molecule, purpose of treatment, age of patient, mode of administration etc.

The pharmaceutical composition may be prepared for administration to a subject by any suitable means. Such administration may be e.g. oral, rectal, nasal, topical, vaginal or parenteral. Oral administration as used herein includes buccal and sublingual administration. Topical administration as used herein includes transdermal administration. Parenteral administration as defined herein includes subcutaneous, intramuscular, intravenous, intraperitoneal and intradermal administration.

Pharmaceutical compositions as disclosed herein include liquid solutions or syrups, solid compositions such as powders, granules, tablets or capsules, creams, ointments and any other style of composition commonly used in the art. Suitable pharmaceutically acceptable diluents, carriers and excipients for use in such compositions are well known in the art.

For instance, suitable excipients include lactose, maize starch or derivatives thereof, stearic acid or salts thereof, vegetable oils, waxes, fats and polyols. Suitable carriers or diluents include carboxymethylcellulose (CMC), methylcellulose, hydroxypropylmethylcellulose (HPMC), dextrose, trehalose, liposomes, polyvinyl alcohol, pharmaceutical grade starch, mannitol, lactose, magnesium stearate, sodium saccharin, talcum, cellulose, glucose, sucrose (and other sugars), magnesium carbonate, gelatin, oil, alcohol, detergents and emulsifiers such as polysorbates. Stabilising agents, wetting agents, emulsifiers, sweeteners etc, may also be used.

Liquid pharmaceutical compositions, whether they be solutions, suspensions or other like form, may include one or more of the following: sterile diluents such as water for injection, saline solution, preferably physiological, Ringer's solution, isotonic sodium chloride, fixed oils such as synthetic mono- or diglycerides which may serve as a solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as EDTA; buffers such as acetates, citrates or phosphates and agents for the adjustment of tonicity such as sodium chloride or dextrose. A parenteral preparation can be enclosed in ampoules, disposable syringes or multiple dose vials made of glass or plastic. An injectable pharmaceutical composition is preferably sterile.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials. Conveniently a specific binding molecule of the invention may be provided to a subject in a daily, weekly or monthly dose, or a dose in an intermediate frequency, e.g. a dose may be provided every 2, 3, 4, 5 or 6 days, every 2, 3, 4, 5 or 6 weeks, every 2, 3, 4, 5 or 6 months, annually or biannually. The dose may be provided in the amount of from 10 ng/kg to 100 mg/kg, e.g. 1 µg/kg to 10 mg/kg body weight, for example from 10

µg/kg to 1 mg/kg. The skilled clinician will be able to calculate an appropriate dose for a patient based on all relevant factors, e.g. age, height, weight, the condition to be treated and its severity. The pharmaceutical composition of the invention may further comprise at least one second therapeutically active agent, i.e. the composition may comprise both the specific binding molecule of the invention and another therapeutic agent. The second therapeutically active agent may be e.g. a drug molecule or a second specific binding molecule. The second specific binding molecule may bind a ligand which is not human tau or to a different epitope on human tau. The second therapeutically active agent may be a second agent for treatment of the condition during the treatment of which the specific binding molecule of the invention is administered to a subject, i.e. the specific binding molecule of the invention and the second therapeutic agent in the composition are both intended to treat the same illness or condition.

The pharmaceutical composition may further comprise at least one second therapeutically active agent.

The at least one second therapeutically active agent may comprise at least one second specific binding molecule according to the invention. A combination of specific binding molecules competing for binding of multiple regions described above may have increased utility in preventing the formation of the PHF core structure and therefore inhibiting tau aggregation.

In a particular embodiment the pharmaceutical composition may comprise a specific binding molecule that competes with the binding of residues 337 to 355 of SEQ ID NO: 1 to residues 337 to 355 of SEQ ID NO: 1.

The pharmaceutical composition may further comprise one or more specific binding molecules selected from the group consisting of:

a specific binding molecule that competes with the binding of residues 327 to 331 of SEQ ID NO: 1 to residues 356 to 363 of SEQ ID NO: 1;

a specific binding molecule that competes with the binding of residues 306 to 311 of SEQ ID NO: 1 to residues 373 to 378 of SEQ ID NO: 1; and, a specific binding molecule may compete with the binding of residues 313 to 322 of SEQ ID NO: 1 to residues 368 to 378 of SEQ ID NO: 1.

In a particular embodiment the pharmaceutical composition may comprise a specific binding molecule that competes with the binding of a first polypeptide comprising residues 333 to 353 of SEQ ID NO: 1 to a second polypeptide comprising residues 333 to 353 of SEQ ID NO: 1.

The pharmaceutical composition may further comprise one or more specific binding molecules selected from the group consisting of:

a specific binding molecule that competes with the binding of a first polypeptide comprising residues 369 to 378 of SEQ ID NO: 1 to a second polypeptide comprising residues 369 to 378 of SEQ ID NO: 1;

a specific binding molecule that competes with the binding of a first polypeptide comprising residues 322 to 333 of SEQ ID NO: 1 to a second polypeptide comprising residues 322 to 333 of SEQ ID NO: 1; and a specific binding molecule may compete with the binding of a first polypeptide comprising residues 356 to 364 of SEQ ID NO: 1 to a second polypeptide comprising residues 356 to 364 of SEQ ID NO: 1.

The pharmaceutical composition may therefore comprise:
i, a first specific binding molecule comprising the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 16 (NNAVG);

VHCDR2 comprises the sequence set forth in SEQ ID NO: 18 (GCSSDGTCYYNSALKS);

VHCDR3 comprises the sequence set forth in SEQ ID NO: 21 (GHYSIYGYDYLGTIDY);

VLCDR1 comprises the sequence set forth in SEQ ID NO: 24 (SGSSSNVGGGNSVG);

VLCDR2 comprises the sequence set forth in SEQ ID NO: 26 (DTNSRPS);

VLCDR3 comprises the sequence set forth in SEQ ID NO: 29 (VTGDSTTHDDL);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 337 to 355 of SEQ ID NO: 1; and one or more further specific binding molecules selected from the group consisting of:

ii, a specific binding molecule comprising the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 42 (SNSVG);

VHCDR2 comprises the sequence set forth in SEQ ID NO: 46 (GIDTDGEEGYNPALNS);

VHCDR3 comprises the sequence set forth in SEQ ID NO: 54 (SYRADGLAYGYVQAIDY);

VLCDR1 comprises the sequence set forth in SEQ ID NO: 63 (SGSFIGISSVG);

VLCDR2 comprises the sequence set forth in SEQ ID NO: 70 (ASDGRPS);

VLCDR3 comprises the sequence set forth in SEQ ID NO: 73 (GSSDRTPYTGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 367 to 379 of SEQ ID NO: 1;

iii, a specific binding molecule comprising the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 310 (NYPVG);

VHCDR2 comprises the sequence set forth in SEQ ID NO: 311 (NIENDGSANYASALKS);

VHCDR3 comprises the sequence set forth in SEQ ID NO: 312 (EFGGSDGYTYFVDIDY);

VLCDR1 comprises the sequence set forth in SEQ ID NO: 313 (SGSSSNVGYGNYVS);

VLCDR2 comprises the sequence set forth in SEQ ID NO: 141 (GATSRAS); and

VLCDR3 comprises the sequence set forth in SEQ ID NO: 314 (ASYDGSSSGV);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 319 to 331 of SEQ ID NO: 1; and iv, a specific binding molecule comprising the CDRs VHCDR1, VHCDR2, VHCDR3, VLCDR1, VLCDR2 and VLCDR3, wherein each of said CDRs comprises an amino acid sequence as follows:

VHCDR1 comprises the sequence set forth in SEQ ID NO: 83 (SYSVY);

VHCDR2 comprises the sequence set forth in SEQ ID NO: 84 (IMYASGRVDYNPALKS);

VHCDR3 comprises the sequence set forth in SEQ ID NO: 89 (GIEN);

VLCDR1 comprises the sequence set forth in SEQ ID NO: 91 (RTSQSVNNYLS);

VLCDR2 comprises the sequence set forth in SEQ ID NO: 95 (YATRLYT); and

VLCDR3 comprises the sequence set forth in SEQ ID NO: 97 (LQYDSTPLA);

or for each CDR sequence, an amino acid sequence with (i) at least 85% identity thereto, and/or (ii) one, two, or three amino acid substitutions relative thereto, wherein the specific binding molecule binds to a polypeptide or protein molecule comprising an amino acid sequence comprising residues 355 to 367 of SEQ ID NO: 1

The pharmaceutical composition may comprise a specific binding molecule comprising the CDRs of S1D12 and one or more further specific binding molecules comprising the CDRs of a specific binding molecule selected from the group consisting of S1G2, CE2 and CA4.

The at least one second therapeutically active agent may be any suitable symptomatic treatment for a tauopathy, such as any suitable symptomatic treatment for AD. The at least one second therapeutically active agent may be selected from the group consisting of an acetylcholinesterase (ACE) inhibitor, an NMDA receptor antagonist, a tau aggregation inhibitor and a β-amyloid aggregation inhibitor.

The acetylcholinesterase inhibitor (AChEI) may be selected from the group consisting of rivastigmine, galantamine, donepezil and tacrine.

Rivastigmine is a non-selective pseudoreversible acetylcholinesterase inhibitor that inhibits both butyrylcholinesterase (BuChE) and acetylcholinesterase (unlike donepezil, which selectively inhibits acetylcholinesterase). It is thought to work by inhibiting these cholinesterase enzymes, which would otherwise break down the brain neurotransmitter acetylcholine.

Galantamine is a weak competitive and reversible cholinesterase inhibitor in all areas of the body and also a potent allosteric potentiating ligand of human nicotinic acetylcholine receptors (nAChRs) α4β2, α7/5-HT3, α3β4, and α6β4 in certain areas of the brain. It increases the concentration and thereby action of acetylcholine in certain parts of the brain. It has shown activity in modulating the nicotinic cholinergic receptors on cholinergic neurons to increase acetylcholine release.

Donepezil binds and inactivates reversibly and non-competitively the cholinesterases, thus inhibiting hydrolysis of acetylcholine. It is selective for AChE over BuChE. This results in increased acetylcholine concentrations at cholinergic synapses. In addition to its actions as an acetylcholinesterase inhibitor, donepezil has been found to act as a potent agonist of the σ1 receptor (Ki=14.6 nM), and has been shown to produce specific anti-amnestic effects in animals mainly via this action.

Tacrine is not preferred because it is associated with significant liver toxicity.

The NMDA receptor antagonist may be memantine. Memantine is an NMDA receptor antagonist, which reduces certain types of brain activity by binding to NMDA receptors on brain cells and blocking the activity of the neurotransmitter glutamate. At normal levels, glutamate aids in memory and learning, but if levels are too high, glutamate appears to overstimulate nerve cells, killing them through excitotoxicity. Memantine is a low-affinity voltage-dependent uncompetitive antagonist at glutamatergic NMDA receptors. By binding to the NMDA receptor with a higher affinity than $Mg^{2+}$ ions, memantine is able to inhibit the prolonged influx of $Ca^{2+}$ ions, particularly from extrasynaptic receptors, which forms the basis of neuronal excitotoxicity. Memantine acts as a non-competitive antagonist at different neuronal nicotinic acetylcholine receptors (nAChRs) at potencies possibly similar to the NMDA and 5-HT3 receptors, but this is difficult to ascertain with accuracy because of the rapid desensitization of nAChR responses in these experiments. It has also been reported that memantine can increase extracellular acetylcholine in the nucleus accumbens and the ventral tegmental areas (see Shearman, E, Rossi, S, Szasz, B, Juranyi, Z. Fallon, S et al. (2006) Changes in cerebral neurotransmitters and metabolites induced by acute donepezil and memantine administrations: A microdialysis study. Brain Research Bulletin 69:204-213).

The tau aggregation inhibitor may be a methylthioninium (MT)-containing compound. WO96/30766 describes MT-containing compounds for use in the treatment and prophylaxis of various "tauopathy" diseases. One example compound was methylthioninium chloride ("MTC") commonly known as methylene blue, which is the chloride salt of the oxidized form of methylthioninium (MT) i.e. $MT^+$. MT is a redox molecule and, depending on environmental conditions (e.g., pH, oxygen, reducing agents), exists in equilibrium between a reduced [leucomethylthioninium (LMT)] and an oxidized form ($MT^+$).

The MT containing compound may be an LMT compound. Preferably the LMT compound is an "LMTX" compound of the type described in WO2007/110627 or WO2012/107706.

The MT containing compound may be an $MT^+$ compound. Preferably the MT compound is an MT+compound of the type described in WO96/30766 or WO2007/110630.

Without being bound by theory, an MT containing compound may enhance the activity of a specific binding molecule of the invention by increasing the availability of the epitope bound by the specific binding molecule.

The β-amyloid aggregation inhibitor may be any suitable substance that inhibits the aggregation of β-amyloid. For instance, it may be a molecule that can interact with β-amyloid to block aggregation of β-amyloid. The β-amyloid aggregation inhibitor may bind to Aβ (1-42).

According to a tenth aspect, the invention provides a specific binding molecule according to the first aspect of the invention, a composition according to the second aspect of the invention or a pharmaceutical composition according to the ninth aspect of the invention for use in therapy.

By therapy is meant the treatment of a subject. By "therapy" as used herein is meant the treatment of any medical condition. Such treatment may be prophylactic (i.e. preventative), curative (or treatment intended to be curative), or palliative (i.e. treatment designed merely to limit, relieve or improve the symptoms of a condition). A subject, as defined herein, refers to any mammal, e.g. a farm animal such as a cow, horse, sheep, pig or goat, a pet animal such as a rabbit, cat or dog, or a primate such as a monkey, chimpanzee, gorilla or human. Most preferably the subject is a human.

The invention therefore has general use in medicine. Accordingly, the invention provides a specific binding molecule according to the first aspect of the invention, a composition according to the second aspect of the invention or a pharmaceutical composition according to the ninth aspect of the invention for use in medicine or for use as a medicament.

Preferably, the specific binding molecule of the first aspect of the invention binds to an epitope within residues 296 to 391 of SEQ ID NO: 1.

Most preferably, the specific binding molecule comprises the CDRs of a specific binding molecule selected from the group consisting of S1D12, S1G2, CE2 and CA4.

According to an eleventh aspect, the invention provides a specific binding molecule according to the first aspect of the invention, a composition according to the second aspect of the invention or a pharmaceutical composition according to the ninth aspect of the invention for use in treatment of a tauopathy.

Preferably, the specific binding molecule of the first aspect of the invention binds to an epitope within residues 296 to 391 of SEQ ID NO: 1.

Most preferably, the specific binding molecule comprises the CDRs of a specific binding molecule selected from the group consisting of S1D12, S1G2, CE2 and CA4.

Aggregation of the tau protein is a hallmark of diseases referred to as "tauopathies". Various tauopathy disorders that have been recognized which feature prominent tau pathology in neurons and/or glia and this term has been used in the art for several years. The similarities between these pathological inclusions and the characteristic tau inclusions in diseases such as AD indicate that the structural features are shared and that it is the topographic distribution of the pathology that is responsible for the different clinical phenotypes observed. In particular, cryo-electron microscope structures of aggregated Tau in AD, Pick's disease (a subtype of Frontotemporal Dementia), chronic traumatic encephalopathy (CTE) and cortico-basal degeneration (CBD) have been obtained previously, and all show common conformational features, indicating that compounds that have the ability to modulate Tau aggregation in e.g. PHFs (as observed in AD), may also modulate aggregation of Tau in other tauopathies. In addition to specific diseases discussed below, those skilled in the art can identify tauopathies by combinations of cognitive or behavioural symptoms, plus additionally through the use of appropriate ligands for aggregated tau as visualised using PET or MRI, such as those described in WO02/075318.

Aspects of the present invention relate to "tauopathies". As well as Alzheimer's disease (AD), the pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Relevant dementias include frontotemporal dementia (FTD); parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD); Dementia with Argyrophilic grains (AgD); Dementia pugilistica (DP) wherein despite different topography, NFTs are similar to those observed in AD (Bouras et al., 1992); Chronic traumatic encephalopathy (CTE), a tauopathy including DP as well as repeated and sports-related concussion (McKee, et al., 2009). Others are discussed in Wischik et al. 2000, for detailed discussion-especially Table 5.1).

Abnormal tau in NFTs is found also in Down's Syndrome (DS) (Flament et al., 1990), and in dementia with Lewy bodies (DLB) (Harrington et al., 1994). Tau-positive NFTs are also found in Postencephalitic parkinsonism (PEP) (Charpiot et al., 1992). Glial tau tangles are observed in Subacute sclerosing panencephalitis (SSPE) (Ikeda et al., 1995). Other tauopathies include Niemann-Pick disease type C (NPC) (Love et al., 1995); Sanfilippo syndrome type B (or mucopolysaccharidosis III B, MPS III B) (Ohmi, et al., 2009); myotonic dystrophies (DM), DM1 (Sergeant, et al., 2001 and references cited therein) and DM2 (Maurage et al., 2005). Additionally, there is a growing consensus in the literature that a tau pathology may also contribute more generally to cognitive deficits and decline, including in mild cognitive impairment (MCI) (see e.g. Braak, et al., 2003, Wischik et al., 2018).

All of these diseases, which are characterized primarily or partially by abnormal tau aggregation, are referred to herein as "tauopathies" or "diseases of tau protein aggregation". In aspects of the invention relating to tauopathies, the tauopathy may be selected from any tauopathy defined herein. Without wishing to be bound by theory, the present inventors believe that all structures solved for tauopathies encompass the dGAE region of Tau. As such, specific binding molecules that stabilise a conformation of dGAE that is not prone to assembly by binding to dGAE can reasonably be expected to apply to all tau diseases including but not limited to AD.

The tauopathy may be selected from the group consisting of Alzheimer's disease, Primary age-related tauopathy (PART), Neurofibrillary tangle-predominant senile dementia, Chronic traumatic encephalopathy (CTE), Progressive supranuclear palsy (PSP), Corticobasal degeneration (CBD), Frontotemporal dementia (FTD), Frontotemporal dementia and parkinsonism linked to chromosome 17 (FTDP-17), Pick disease, disinhibition-dementia-parkinsonism-amyotrophy complex (DDPAC), pallido-ponto-nigral degeneration (PPND), Guam-ALS syndrome; pallido-nigro-luysian degeneration (PNLD), Dementia with Argyrophilic grains (AgD), Down's Syndrome (DS), dementia with Lewy bodies (DLB), Postencephalitic parkinsonism (PEP), Dementia pugilistica (DP), traumatic brain injury (TBI), stroke, ischemia, Lytico-bodig disease (Parkinson-dementia complex of Guam), Ganglioglioma, Gangliocytoma, Meningioangiomatosis, Postencephalitic parkinsonism, Subacute sclerosing panencephalitis (SSPE), Lead encephalopathy, tuberous sclerosis, Pantothenate kinase-associated neurodegeneration, lipofuscinosis and mild cognitive impairment (MCI).

The tauopathy may be Alzheimer's disease.

The invention also embraces treatment as a prophylactic measure. The treatment may be prophylactic treatment. The treatment may be by active immunization or passive immunization.

Active tau immunization has been shown to reduce tau pathology by targeting single or multiple phospho-epitopes, the amino terminus, full-length normal and mutant tau or aggregated tau. Reductions in pathological tau are achieved with few reported adverse effects, and the long-lasting immune response makes active immunization a promising option. However, elicitation of antibodies against a native protein always carries the risk of adverse immune reactions and detrimental targeting of the normal protein.

Passive immunization offers a potential solution to the safety concerns that arise from active strategies. Patients will not develop their own antibodies, and the effects of immunization are likely to be transient, which reduces the risk of immunological adverse effects. Passive immunization also offers greater specificity for the epitope that is being targeted.

Antibodies could also modify disease progression by blocking the spread of tau pathology.

The specific binding molecule according to the first aspect of the invention, a composition according to the second aspect of the invention or a pharmaceutical composition according to the ninth aspect of the invention may therefore be for use in treatment of an early stage tauopathy and/or a tauopathy characterised by mild symptoms. The specific binding molecule may be for use in treatment of mild cognitive impairment (MCI).

The specific binding molecule according to the first aspect of the invention, a composition according to the second aspect of the invention or a pharmaceutical composition according to the ninth aspect of the invention may be for use in treatment of a tauopathy in a subject at risk of developing a tauopathy. The subject at risk of developing a tauopathy may be identified by any suitable means, such as one or more of medical history, physical examination, neurological examination, brain imaging, mental status tests (such as the Mini-Mental State Exam (MMSE) and the Mini-Cog test), computerised cognitive tests (such as the Cantab Mobile, Cognigram, Cognivue, Cognision and Automated Neuropsychological Assessment Metrics (ANAM) devices), mood assessment and genetic testing.

The skilled person is aware that a tauopathy diagnosis may not always be definitive until post-mortem. Accordingly, the specific binding molecule may be for use in treatment of a tauopathy in a subject at risk of developing a tauopathy. The subject may be suspected of having a tauopathy. The subject may have one or more symptoms of a tauopathy. The specific binding molecule may be for use in slowing progression of a tauopathy or suspected tauopathy.

The term "treatment" includes "combination" treatments and therapies, in which two or more treatments or therapies for the same tauopathy, are combined, for example, sequentially or simultaneously. These may be symptomatic or disease modifying treatments.

The particular combination would be at the discretion of the physician. In combination treatments, the therapeutically active substances (i.e., a specific binding molecule, composition or pharmaceutical composition as described herein, plus one or more other therapeutically active substances) may be administered simultaneously or sequentially, and may be administered in individually varying dose schedules and via different routes. For example, when administered sequentially, the therapeutically active substances can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutically active substances.

An example of a combination treatment of the invention would be a specific binding molecule in combination with an ACE inhibitor, an NMDA receptor antagonist or a tau aggregation inhibitor.

A further example of a combination treatment of the invention would be a specific binding molecule comprising the CDRs of S1D12 and one or more further specific binding molecules comprising the CDRs of a specific binding mol-
ecule of the invention. The further specific binding molecule
may for example be selected from the group consisting of
S1G2, CE2 and CA4.

In other embodiments the treatment is a "monotherapy",
which is to say that the specific binding molecule is not used
in combination (within the meaning discussed above) with
another active agent for treating the same tauopathy in the
subject.

According to a twelfth aspect, the invention provides a
method of treating a tauopathy, comprising administering to
a subject in need thereof a specific binding molecule accord-
ing to the first aspect of the invention, a composition
according to the second aspect of the invention or a phar-
maceutical composition according to the ninth aspect of the
invention.

Preferably, the specific binding molecule of the first
aspect of the invention binds to an epitope within residues
296 to 391 of SEQ ID NO: 1.

Most preferably, the specific binding molecule comprises
the CDRs of a specific binding molecule selected from the
group consisting of S1D12, S1G2, CE2 and CA4.

The term "therapeutically-effective amount," where used
herein, pertains to that amount of an agent used in the
practice of the combination methodologies of the invention
which is effective for producing some desired therapeutic
effect, commensurate with a reasonable benefit/risk ratio,
when administered in accordance with a desired treatment
regimen.

As explained above the invention also embraces treatment
as a prophylactic measure. For example, the invention
provides a method of prophylactic treatment of a tauopathy
in a subject, which method comprises administering to said
subject a specific binding molecule according to the first
aspect of the invention, a composition according to the
second aspect of the invention or a pharmaceutical compo-
sition according to the ninth aspect of the invention.

The term "prophylactically effective amount" where used
herein, pertains to that amount of a compound of the
invention, or a material, composition or dosage from com-
prising said compound, which is effective for producing
some desired prophylactic effect, commensurate with a
reasonable benefit/risk ratio, when administered in accor-
dance with a desired treatment regimen. "Prophylaxis" in
the context of the present specification should not be under-
stood to circumscribe complete success i.e. complete pro-
tection or complete prevention. Rather prophylaxis in the
present context refers to a measure which is administered in
advance of detection of a symptomatic condition with the
aim of preserving health by helping to delay, mitigate or
avoid that particular condition.

According to a thirteenth aspect, the invention provides
an in vitro method of inhibiting aggregation of a tau protein
or a fragment thereof comprising contacting the tau protein
or a fragment thereof with a specific binding molecule
according to the first aspect of the invention.

Preferably, the specific binding molecule of the first
aspect of the invention binds to an epitope within residues
296 to 391 of SEQ ID NO: 1.

Most preferably, the specific binding molecule comprises
the CDRs of a specific binding molecule selected from the
group consisting of S1D12, S1G2, CE2 and CA4.

The method may be selected from the group consisting of
a thioflavin T-assay, a tau-tau immunoassay and an assay for
assessing the effects of aggregated tau in cell culture. A
suitable assay for assessing the effects of aggregated tau in
cell culture is disclosed in UK application no. GB2010620.9 filed on 10 Jul. 2020, and in international (PCT) application
no. PCT/EP2021/069138 filed on 9 Jul. 2021 and claiming
priority to UK application no. GB2010620.9, both of which
are hereby incorporated by reference in their entirety.

The invention therefore provides a screening method for
measuring the effect of a specific binding molecule on the
aggregation of tau protein. The tau protein may be human
tau. The human tau may comprise the amino acid sequence
of SEQ ID NO: 1, SEQ ID NO: 3, SEQ ID NO: 4, SEQ ID
NO: 5, SEQ ID NO: 6 or SEQ ID NO: 7.

In this context, by "fragment" is meant any region of the
tau protein capable of aggregation in vitro. For example, tau
protein fragments include SEQ ID NO: 3, SEQ ID NO: 4,
SEQ ID NO: 5, SEQ ID NO: 6 and SEQ ID NO: 7.

In this context, by "contacting" is meant "exposing to". It
does not require directionality; the tau protein or a fragment
thereof may be exposed to the specific binding molecule or
the specific binding molecule may be exposed to the tau
protein or a fragment thereof. The contacting occurs under
conditions permissive for aggregation of the tau protein or
fragment thereof.

According to a fourteenth aspect, the invention provides
an in vitro method for detecting a tau protein or a fragment
thereof in a sample comprising contacting the sample with
a specific binding molecule of the first aspect of the inven-
tion.

In a preferred embodiment, the specific binding molecule
may comprise the CDRs of a specific binding molecule
selected from the group consisting of S1D12, S1G2 and
E2E8.

The sample may be defined as a "patient sample" or a
"biological sample". The sample may be from a subject
suffering from or at risk of a tauopathy.

Samples are typically obtained prior to the methods of the
invention being performed. The methods of the invention are
in vitro or ex vivo methods accordingly. In some alternative
embodiments, the method may further comprise a step or
steps of sample collection.

The sample may be a plasma, a whole blood sample, a
brain lysate or cerebrospinal fluid (CSF) sample. Preferably,
the sample is a plasma sample.

The sample may be processed in any suitable way prior to
detecting the tau protein or a fragment thereof in a sample.
The tau protein or fragment thereof may be isolated,
extracted and/or purified from the sample. The isolation,
extraction and/or purification may be performed by any
suitable technique.

The method of the invention may further comprise an
initial step of isolating, extracting and/or purifying the tau
protein or fragment thereof from the sample. The method
may therefore further comprise isolating the tau protein or
fragment thereof from the sample. The method may further
comprise extracting the tau protein or fragment thereof from
the sample. The method may further comprise purifying the
tau protein or fragment thereof from the sample.

The step of obtaining the sample and/or the step of
isolating, extracting and/or purifying the tau protein or
fragment thereof from the sample may occur in a different
location to the subsequent steps of the method. Accordingly,
the method may further comprise a step of transporting the
sample and/or transporting the tau protein or fragment
thereof.

The sample (the term "sample" includes the tau protein or
fragment thereof isolated and/or purified therefrom) may be
denatured, for example by treatment with sodium dodecyl
sulphate (SDS). The method may further comprise a step of
denaturing the tau protein or fragment thereof prior to contacting the sample with the specific binding molecule. The denaturing may preferably be by contacting the sample with sodium dodecyl sulphate (SDS). The sample may therefore comprise denatured protein. The tau protein or a fragment thereof may be denatured.

The term "detecting" as used herein encompasses quantitative or qualitative detection. "Detecting" may include measuring and/or quantifying the amount (or level) of a tau protein or a fragment thereof in a sample.

The tau protein or fragment thereof may be detected using an immunoassay. Immunoassays have the potential to be miniaturised to run on a microfluidics device or test-strip and may be more suited for clinical point-of-care applications. Embodiments of the invention which incorporate an immunoassay may therefore be used in situ by a primary healthcare provider for assistance in prescribing a treatment for an individual patient.

The amount (or level) of a tau protein or a fragment thereof in a sample may be measured using a homogeneous or heterogeneous immunoassay.

Thus, in some embodiments, the amount (or level) of a tau protein or a fragment thereof may be measured in solution by binding to specific binding molecules of the invention that are present in excess, whereby binding alters detectable properties of the label. The amount of tau protein or a fragment thereof present will therefore affect the amount of the label with a particular detectable property. As is well known in the art, the label may comprise a radioactive label, a fluorescent label or an enzyme having a chromogenic or chemiluminescent substrate that is coloured or caused or allowed to fluoresce when acted on by the enzyme.

Alternatively, a heterogeneous format may be used in which the at least one tau protein or a fragment thereof is captured by surface-bound antibodies for separation and quantification. In some embodiments, a sandwich assay may be used in which a surface-bound tau protein or a fragment thereof is quantified by binding a labelled secondary antibody.

Suitably, the immunoassay may comprise an enzyme immunoassay (EIA) in which the label is an enzyme such, for example, as horseradish peroxidase (HRP). Suitable substrates for HRP are well known in the art and include, for example, ABTS, OPD, AmplexRed, DAB, AEC, TMB, homovanillic acid and luminol. In some embodiments, an ELISA immunoassay may be used; a sandwich ELISA assay may be particularly preferred.

The immunoassay may be competitive or non-competitive. Thus, in some embodiments, the amount of a tau protein or a fragment thereof may be measured directly by a homogeneous or heterogeneous method, as described above. Alternatively, the amount of a tau protein or a fragment thereof in the sample may be sequestered in solution with a specific binding molecule which is present in excess, and the amount of specific binding molecule remaining then determined by binding to surface-bound tau protein or a fragment thereof to give an indirect read-out of the amount of tau protein or a fragment thereof in the original sample. In another variant, the tau protein or a fragment thereof may be caused to compete for binding to a surface bound specific binding molecule with a known amount of a labelled tau protein or a fragment thereof.

The surface bound specific binding molecule or tau protein or a fragment thereof may be immobilised on any suitable surface of the kind known in the art. For instance, the specific binding molecule or tau protein or a fragment thereof may be immobilised on a surface of a well or plate or on the surface of a plurality of magnetic or non-magnetic beads.

In some embodiments, the immunoassay may be a competitive assay, further comprising a known amount of the tau protein or a fragment thereof, which is the same as the one to be quantified in the sample, but tagged with a detectable label. The labelled tau protein or a fragment thereof may be affinity-bound to a suitable surface by a specific binding molecule to the tau protein or a fragment thereof. Upon adding the sample, a proportion of the labelled tau protein or a fragment thereof may be displaced from the surface-bound specific binding molecule, thereby providing a measure of the level of tau protein or a fragment thereof in the sample.

In some embodiments, the immunoassay may comprise surface-bound tau protein or a fragment thereof, which is the same as the tau protein or a fragment thereof that is to be quantitated in the sample, and a known amount of specific binding molecule to the tau protein or a fragment thereof in solution in excess. The sample is first mixed with the specific binding molecule in solution such that a proportion of the specific binding molecules bind with the tau protein or a fragment thereof in the sample. The amount of unbound specific binding molecules remaining can then be measured by binding to the surface-bound tau protein or a fragment thereof.

In some embodiments, the immunoassay may comprise a labelled secondary antibody to the tau protein or a fragment thereof or to a primary antibody to the tau protein or a fragment thereof for quantifying the amount of the tau protein or a fragment thereof bound to surface-bound antibodies or the amount of primary antibody bound to the tau protein or a fragment thereof immobilised on a surface.

Measuring the level of a tau protein or a fragment thereof may be by equipment for measuring the level of a tau protein or a fragment thereof in a sample comprising a sample collection device and an immunoassay. The equipment may further comprise a detector for detecting labelled tau protein or a fragment thereof or labelled antibodies to the tau protein or a fragment thereof in the immunoassay. Suitable labels are mentioned above, but in a preferred embodiment, the label may be an enzyme having a chromogenic or chemiluminescent substrate that is coloured or caused or allowed to fluoresce when acted on by the enzyme.

The immunoassay or equipment may be incorporated into a miniaturised device for measuring the level of a tau protein or a fragment thereof in a biological sample. Suitably, the device may comprise a lab-on-a-chip.

Measuring levels of tau protein or a fragment thereof may be by a device for measuring the level of at least one tau protein or a fragment thereof in a sample obtained from a patient, the device comprising one or more parts defining an internal channel having an inlet port and a reaction zone, in which a tau protein or a fragment thereof in a sample may be reacted with an immobilised primary antibody for the tau protein or a fragment thereof for capturing the tau protein or a fragment thereof, or a primary antibody for the tau protein or a fragment thereof in excess in solution after mixing with the sample upstream of the reaction zone may be reacted with tau protein or a fragment thereof, which is the same as the one to be measured in the sample, but immobilised on a surface within the reaction zone, for quantifying directly or indirectly the amount of the tau protein or a fragment thereof in the sample.

The captured tau protein or a fragment thereof or primary antibody may then be detected using a secondary antibody to the tau protein or a fragment thereof or primary antibody, which is tagged with an enzyme.

As described above, the enzyme may have a chromogenic or chemiluminescent substrate that is coloured or caused or allowed to fluoresce when acted on by the enzyme. Suitably, the one or more parts of the device defining the channel, at least adjacent the reaction zone, may be transparent to light, at least in a range of wavelengths encompassing the colour or fluorescence of the substrate to allow detection of a reaction between the tau protein or a fragment thereof or primary antibody and the secondary antibody using a suitable detector such, for example, as a photodiode, positioned outside the channel or further channel.

In some embodiments, the device may comprise a plurality of channels, each with its own inlet port, for measuring the levels of a plurality of different tau protein or a fragments thereof in the sample in parallel. Therefore, each channel may include a different respective immobilised primary antibody or tau protein or a fragment thereof.

Suitably, the device may comprise one or more selectively operable valves associated with the one or more inlet ports for controlling the admission of a sequence of different reagents into to the channels such, for example, as the sample, wash solutions, primary antibody, secondary antibody and enzyme substrate.

The device therefore may comprise a microfluidics device. The channel may include a reaction zone. Microfluidics devices are known to those skilled in the art. A review of microfluidic immunoassays or protein diagnostic chip microarrays is provided by Chin et al. 2012. *Lab on a Chip.* 2012; 12:2118-2134. A microfluidics device suitable for carrying out an ELISA immunoassay at a point-of-care is disclosed by Chan C D, Laksanasopin T, Cheung Y K, Steinmiller D et al. "Microfluidics-based diagnostics of infectious diseases in the developing world". *Nature Medicine.* 2011; 17 (8): 1015-1019, the contents of which are incorporated herein by reference.

The specific binding molecule may be a specific binding molecule according to the first aspect of the invention. The epitope of the specific binding molecule may be within SEQ ID NO: 1, SEQ ID NO: 3, SEQ ID NO: 4, SEQ ID NO: 5, SEQ ID NO: 6 or SEQ ID NO: 7. The specific binding molecule may bind to SEQ ID NO:1, SEQ ID NO: 3, SEQ ID NO: 4, SEQ ID NO: 5, SEQ ID NO: 6 or SEQ ID NO: 7.

The specific binding molecule may bind to an epitope within residues 296 to 391 of SEQ ID NO: 1 wherein the sample is a plasma sample.

The method may comprise contacting a sample with at least one specific binding molecule of the first aspect of the invention. The method may comprise contacting the sample with a first specific binding molecule that binds to an epitope within residues 296 to 391 of SEQ ID NO: 1 and contacting the sample with a second specific binding molecule that binds to an epitope within SEQ ID NO: 1.

The first and/or second specific binding molecule may be a specific binding molecule according to the first aspect of the invention. The first or second specific binding molecule may be a known specific binding molecule such as HT7, BT2, Tau12 or Tau146.

The first specific binding molecule may bind to SEQ ID NO: 1 or a fragment thereof with a $K_D$ of less than 25 nM, less than 20 nM, less than 15 nM, less than 10 nM, less than 8 nM, less than 6 nM, less than 5 nM, less than 4 nM, less than 3 nM, less than 2 nM, less than 1 nM, less than 0.5 nM, less than 0.4 nM, less than 0.3 nM, less than 0.2 nM or less than 0.15 nM. A high affinity first specific binding molecule may be especially advantageous in embodiments where the first specific binding molecule is a surface bound specific binding molecule. A preferred high affinity first specific binding molecule is a specific binding molecule comprising the CDRs of S1D12.

The first specific binding molecule may bind to an epitope within residues 296 to 391 of SEQ ID NO: 1. Preferably, the first specific binding molecule binds to an epitope within residues 337 to 355 of SEQ ID NO: 1.

The second specific binding molecule may bind to the same epitope or to a different epitope than the first specific binding molecule. The skilled person will understand that an appropriate pair of antibodies may permit detection of particular tau fragments of interest. For instance, where the epitope of the first specific binding molecule and the second specific binding molecule are widely spaced across the sequence of SEQ ID NO:1 (such as binding to an N-terminal region and to a C-terminal region respectively), the method may selectively detect full length and longer fragments of tau; shorter fragments of tau that are only bound by one of the specific binding molecules (or by neither) will not be detected.

The ability to interrogate and determine the levels of various tau species or fragments in patient samples is crucial in early AD diagnosis. The invention provides a method for determining the concentrations of different tau species accordingly. The method may use spiked samples. The method may use pairings of specific binding molecules directed towards selected epitopes of the tau protein. Accordingly, the method may be a sandwich ELISA assay.

The second specific binding molecule may bind to an epitope within residues 367 to 379 of SEQ ID NO: 1. A preferred second specific binding molecule is a specific binding molecule comprising the CDRs of S1G2.

When the first specific binding molecule binds to an epitope within residues 337 to 355 of SEQ ID NO: 1 and the second specific binding molecule binds to an epitope within residues 367 to 379 of SEQ ID NO: 1, the method may detect SEQ ID NO:1, SEQ ID NO: 3, SEQ ID NO: 4, SEQ ID NO: 5, SEQ ID NO: 6 and SEQ ID NO: 7. Since cleavage within the from proteolytically stable core of the paired helical filament (PHF) is thought to be uncommon, this embodiment may therefore detect total tau comprising the PHF.

The second specific binding molecule may bind to an epitope within residues 379 to 391 of SEQ ID NO: 1. A preferred second specific binding molecule is a specific binding molecule comprising the CDRs of E2E8.

As described herein, specific binding molecules that bind to an epitope within residues 379 to 391 of SEQ ID NO: 1 may be "E-specific"; that E391 may be critical for binding. When the first specific binding molecule binds to an epitope within residues 337 to 355 of SEQ ID NO: 1 and the second specific binding molecule binds to an epitope within residues 379 to 391 of SEQ ID NO: 1, the method may detect SEQ ID NO:1, SEQ ID NO: 3 and SEQ ID NO: 4. Since E-specific specific binding molecules do not detect SEQ ID NO: 5, SEQ ID NO: 6 or SEQ ID NO: 7, this embodiment may therefore detect dGAE and full length tau but not fragments lacking E391 such as dGA.

The second specific binding molecule may bind to an epitope within residues 13 to 25 of SEQ ID NO: 1. A preferred second specific binding molecule is a specific binding molecule comprising the CDRs of CB7.

When the first specific binding molecule binds to an epitope within residues 337 to 355 of SEQ ID NO: 1 and the second specific binding molecule binds to an epitope within residues 13 to 25 of SEQ ID NO: 1, the method may detect SEQ ID NO:1. However, this embodiment will not detect isolated SEQ ID NO: 3, SEQ ID NO: 4, SEQ ID NO: 5, SEQ ID NO: 6 and SEQ ID NO: 7 as these fragments omit residues 13 to 25 of SEQ ID NO: 1. Since the epitopes used in this embodiment are spaced widely apart, this embodiment may therefore detect full-length tau.

The method may comprise contacting the sample with at least one pair of first and second specific binding molecules, wherein the pair of first and second specific binding molecules may be any two specific binding molecules of the invention. Preferred pairs of first and second specific binding molecule include:

A first specific binding molecule that binds to an epitope within residues 337 to 355 of SEQ ID NO: 1 and a second specific binding molecule that binds to an epitope within residues 367 to 379 of SEQ ID NO: 1;

A first specific binding molecule that binds to an epitope within residues 337 to 355 of SEQ ID NO: 1 and a second specific binding molecule that binds to an epitope within residues 379 to 391 of SEQ ID NO: 1; and A first specific binding molecule that binds to an epitope within residues 337 to 355 of SEQ ID NO: 1 and a second specific binding molecule that binds to an epitope within residues 13 to 25 of SEQ ID NO: 1.

The method may comprise contacting the sample with at least two or at least three pairs of first and second specific binding molecules. For instance, the method may comprise contacting the sample with:

A first specific binding molecule that binds to an epitope within residues 337 to 355 of SEQ ID NO: 1 and a second specific binding molecule that binds to an epitope within residues 367 to 379 of SEQ ID NO: 1;

A first specific binding molecule that binds to an epitope within residues 337 to 355 of SEQ ID NO: 1 and a second specific binding molecule that binds to an epitope within residues 379 to 391 of SEQ ID NO: 1; and A first specific binding molecule that binds to an epitope within residues 337 to 355 of SEQ ID NO: 1 and a second specific binding molecule that binds to an epitope within residues 13 to 25 of SEQ ID NO: 1.

Where the method comprises contacting the sample with two or more pairs of specific binding molecules, each pair of specific binding molecules is typically contacted to the sample separately and/or in parallel. The sample may therefore be aliquoted prior to contacting the sample with the pairs of specific binding molecules. A separate aliquot may be contacted with each pair of specific binding molecules. Contacting in parallel may be contacting at the same time or simultaneously. Contacting in parallel may be contacting at essentially the same time or essentially simultaneously. Contacting in parallel may be not contacting sequentially or contacting one after another. Contacting in parallel typically means each pair of specific binding molecules is contacted to the sample in a separate vessel. Contacting in parallel typically means that each pair of specific binding molecules may independently interact with the sample.

Each pair of specific binding molecules may be configured to detect a different tau protein or a fragment thereof. For example:

A first pair of specific binding molecules that bind to an epitope within residues 337 to 355 of SEQ ID NO: 1 and to an epitope within residues 367 to 379 of SEQ ID NO: 1, respectively, may be configured to detect total tau comprising the PHF;

A second pair of specific binding molecules that bind to an epitope within residues 337 to 355 of SEQ ID NO: 1 and to an epitope within residues 379 to 391 of SEQ ID NO: 1, respectively, may be configured to detect dGAE and full length tau but not fragments lacking E391 such as dGA; and A third pair of specific binding molecules that bind to an epitope within residues 337 to 355 of SEQ ID NO: 1 and to an epitope within residues 13 to 25 of SEQ ID NO: 1, respectively, may be configured to detect full-length tau.

The method may further comprise a step of determining the levels of the different tau proteins or a fragment(s) thereof. The method may further comprise a step of comparing the levels of the different tau proteins or a fragment(s) thereof.

In a specific embodiment, the method comprises detecting a tau protein or a fragment thereof in a sample comprising:
   a) contacting the sample with a first pair of specific binding molecules comprising a specific binding molecule comprising the CDRs of S1D12 and a specific binding molecule comprising the CDRs of S1G2;
   b) contacting the sample with a second pair of specific binding molecules comprising a specific binding molecule comprising the CDRs of S1D12 and a specific binding molecule comprising the CDRs of E2E8; and
   c) contacting the sample with a third pair of specific binding molecules comprising a specific binding molecule comprising the CDRs of S1D12 and a specific binding molecule comprising the CDRs of CB7;
      wherein each pair of specific binding molecules is contacted to the sample in parallel.

The invention provides distinguishing and/or determining the levels of hT40, dGAE and dGA in a sample accordingly.

According to a fifteenth aspect, the invention provides a diagnostic method comprising contacting a sample with a specific binding molecule of the first aspect of the invention.

The diagnostic method may comprise the in vitro method for detecting a tau protein or a fragment thereof in a sample according to the fourteenth aspect.

The method may further comprise diagnosing a tauopathy if a tau protein or a fragment thereof is detected.

The specific binding molecule may bind to an epitope within residues 296 to 391 of SEQ ID NO: 1. Preferably, the specific binding molecule binds to an epitope within residues 337 to 355 of SEQ ID NO: 1 or to an epitope within residues 367 to 379 of SEQ ID NO: 1

An advantage of the present invention is the provision of a diagnostic test for a tauopathy which can be performed using a plasma sample. Plasma samples are easier, faster and safer to obtain than CSF samples. However, very limited published data are available supporting a diagnostic test for a tauopathy, particularly Alzheimer's disease, in a plasma sample. The complexities of extracellular tau and the limited progress towards developing a blood-based screen for Alzheimer's disease are reviewed in Chen et al (2019) Alzheimers Dement. 15 (3): 487-496. Chen et al concluded that "most plasma tau is full length". None of the antibodies described targeted residues 296 to 391 of full-length Tau (see FIG. 1A). The authors suggest using N-terminal assays in a diagnostic context. Two N-terminal assays are described:
   NT1 requires a minimal sequence of residues 6 to 198 of full-length tau.
   NT2 requires a longer sequence of residues 6 to 224 of full-length tau.

Chen et al suggest use of the NT1 assay, rather than the NT2 assay is preferred in a diagnostic context. Chen et al therefore teach away from using a specific binding molecule that binds to an epitope within residues 296 to 391 of SEQ ID NO: 1.

The levels of tau measured when using our core capture antibody S1D12 as part of an antibody pair is 1,000-fold more than the typical values seen for the existing NT1 assay in human plasma. In contrast to the reported NT1 assay, where AD/MCI patients typically show higher assay values than healthy controls, for assays using S1D12 capture this pattern is surprisingly reversed with health control samples showing higher tau fragment values than AD/MCI patients. The levels of tau detected using the core capture antibody are significantly greater than previously reported and suggests that the use of S1D12 reveals large amounts of previously undetected tau fragments in biological samples. The use of a specific binding molecule comprising the CDRs of S1D12 therefore provides a surprisingly sensitive AD/MCI diagnostic assay with improved performance over the existing NT1 assay in human plasma samples. These findings translate to higher levels of core-proline fragments in healthy control and form the basis of a regular monitoring test to identify patients worthy of additional screening, i.e. a potential predictor of early onset of disease.

The method may comprise contacting the sample with a pair of specific binding molecules that bind to an epitope within residues 337 to 355 of SEQ ID NO: 1 and to an epitope within residues 367 to 379 of SEQ ID NO: 1, respectively.

Preferably, the method comprises contacting the sample with a pair of specific binding molecules comprising a first specific binding molecule comprising the CDRs of S1D12 and a second specific binding molecule comprising the CDRs of S1G2.

In a study using human plasma samples disclosed herein, the inventors have unexpectedly shown an ability to discriminate between AD patients and healthy controls using a combination of S1D12 and S1G2. While the combination of S1D12 and CB7 (which binds an N-terminal epitope of Tau13-25) does not show an overall difference in values between AD and healthy control groups. CB7 binds within the NT1 region of Chen et al (2019) and overlaps with the epitope of the Tau12 antibody (6-18) used in NT1. These data therefore show an unexpected advantage of using a first specific binding molecule comprising the CDRs of S1D12 and a second specific binding molecule comprising the CDRs of S1G2 to diagnose Alzheimer's disease.

The diagnostic method may comprise contacting a plasma sample with a pair of specific binding molecules comprising a first specific binding molecule comprising the CDRs of S1D12 and a second specific binding molecule comprising the CDRs of S1G2, wherein the tauopathy is Alzheimer's disease.

A specific binding molecule used in the method of the fourteenth of the fifteenth aspects of the invention may be a specific binding molecule comprising the CDRs of CB7 and/or CC7. The epitopes of CB7 and CC7 fall in regions of tau with no homology between the human and mouse tau sequences. The diagnostic utility of these specific binding molecules is demonstrated by their ability to recognise the presence of pathologic human tau in a transgenic mouse brain against a background of endogenous mouse tau protein. These specific binding molecules may therefore be utilised to track the fragmentation patterns of pathologic tau species during aging and in relation to any pharmacologic treatments that may affect the (human) tau protein, its aggregation, movement between compartments in the body (e.g. between brain and blood) and its pattern of fragmentation.

The in vitro method for detecting a tau protein or a fragment thereof according to the fifteenth aspect of the invention, or the diagnostic method according to the sixteenth aspect of the invention may comprise contacting the sample with a pair of first and second specific binding molecules, wherein the pair of first and second specific binding molecules wherein the first specific binding molecule binds within the core region of tau (such as to an epitope within residues 337 to 355 or 367 to 379 of SEQ ID NO: 1) and the second specific binding molecule binds to an epitope within residues 13 to 25 of SEQ ID NO: 1. The first specific binding molecule may comprise the CDRs of S1D12 or S1G2. The second specific binding molecule may comprise the CDRs of CB7. Such pairings have the advantage of detecting tau fragments that contain the amino acids spanning from 13-379 of SEQ ID NO:1. The inventors have shown that such fragments decrease with aging in L66$^{+/+}$ mice, suggesting that either a truncation or epitope occlusion event is occurring or that multiple events of this nature are occurring during the aging of L66$^{+/+}$ mice. Methods enabling detection of tau fragments that contain the amino acids spanning from 13-379 of SEQ ID NO:1 may therefore provide an early marker for pathology associated events.

The in vitro method for detecting a tau protein or a fragment thereof according to the fifteenth aspect of the invention, or the diagnostic method according to the sixteenth aspect of the invention may comprise contacting the sample with a pair of first and second specific binding molecules, wherein the pair of first and second specific binding molecules wherein the first specific binding molecule binds N-terminally to the core region of tau (such as to an epitope within residues 147 to 163, resides 159 to 163, or 147 to 157 of SEQ ID NO: 1) and the second specific binding molecule binds to an epitope within residues 13 to 25 of SEQ ID NO: 1. The first specific binding molecule may comprise the CDRs of HT7, or an alternative specific binding molecule disclosed herein with a nearby or overlapping epitope, such as 3aA6 and 3aD6 which bind to the adjacent epitope within residues 147 to 157 of SEQ ID NO: 1. The second specific binding molecule may comprise the CDRs of CB7. Such pairings have the advantage of detecting tau fragments that contain the amino acids spanning from 13-163 or 13-157 of SEQ ID NO: 1. The inventors have shown that such fragments increase with aging in L66$^{+/+}$ mice, suggesting that levels of smaller, truncated fragments of human tau increase during the aging of L66$^{+/+}$ mice. Methods enabling detection of tau fragments that contain the amino acids spanning from 13-163 or 13-157 of SEQ ID NO:1 may therefore provide an early marker for pathology associated events.

The in vitro method for detecting a tau protein or a fragment thereof according to the fifteenth aspect of the invention, or the diagnostic method according to the sixteenth aspect of the invention may comprise contacting the sample with a pair of first and second specific binding molecules, wherein the pair of first and second specific binding molecules are a pair identified in Table 26 or 27, or a pair comprising the CDRs of each of a pair of antibodies identified in Table 26 or 27 or are a pair of antibodies targeting the same, adjacent of overlapping epitopes as a pair of antibodies identified in Table 26 or 27.

According to a sixteenth aspect, the invention provides a diagnostic device for use in a method according to the fifteenth aspect of the invention.

221

222

The device may comprise any suitable components described in connection with the fourteenth aspect of the invention.

The device may comprise equipment for measuring the level of a tau protein or a fragment thereof in a sample comprising a sample collection device and an immunoassay. The equipment may further comprise a detector for detecting labelled tau protein or a fragment thereof or labelled antibodies to the tau protein or a fragment thereof in the immunoassay.

The immunoassay or equipment may be incorporated into a miniaturised device for measuring the level of a tau protein or a fragment thereof in a biological sample. Suitably, the device may comprise a lab-on-a-chip.

The device may comprise one or more parts defining an internal channel having an inlet port and a reaction zone.

In some embodiments, the device may comprise a plurality of channels, each with its own inlet port, for measuring the levels of a plurality of different tau protein or a fragment (s) thereof in the sample in parallel. Therefore, each channel may include a different respective immobilised primary antibody or tau protein or a fragment thereof.

Suitably, the device may comprise one or more selectively operable valves associated with the one or more inlet ports for controlling the admission of a sequence of different reagents into to the channels such, for example, as the sample, wash solutions, primary antibody, secondary antibody and enzyme substrate.

The device therefore may comprise a microfluidics device. The channel may include a reaction zone. Microfluidics devices are known to those skilled in the art. A review of microfluidic immunoassays or protein diagnostic chip microarrays is provided by Chin et al. 2012. *Lab on a Chip*. 2012; 12:2118-2134. A microfluidics device suitable for carrying out an ELISA immunoassay at a point-of-care is disclosed by Chan C D, Laksanasopin T, Cheung Y K, Steinmiller D et al. "Microfluidics-based diagnostics of infectious diseases in the developing world". *Nature Medicine*. 2011; 17 (8): 1015-1019, the contents of which are incorporated herein by reference.

According to a seventeenth aspect, the invention provides a kit comprising a specific binding molecule according to the first aspect of the invention and reagents for detecting a tau protein or a fragment thereof in a sample.

The kit may comprise a first specific binding molecule that binds to an epitope within residues 296 to 391 of SEQ ID NO: 1 and a second specific binding molecule that binds to an epitope within SEQ ID NO: 1.

The kit may comprise any suitable components described in connection with the fourteenth aspect of the invention.

The kit may comprise an enzyme such, for example, as horseradish peroxidase (HRP). Suitable substrates for HRP are well known in the art and include, for example, ABTS, OPD, AmplexRed, DAB, AEC, TMB, homovanillic acid and luminol.

The kit may comprise one or more specific binding molecules or tau protein or a fragment thereof immobilised on a surface of a well or plate or on the surface of a plurality of magnetic or non-magnetic beads.

The kit may comprise a labelled secondary antibody to the tau protein or a fragment thereof or to a primary antibody to the tau protein or a fragment thereof for quantifying the amount of the tau protein or a fragment thereof bound to surface-bound antibodies or the amount of primary antibody bound to the tau protein or a fragment thereof immobilised on a surface.

The present invention will now be described by way of reference to the following Examples and accompanying Drawings which are present for the purposes of illustration only and are not to be construed as being limiting on the invention.

Example 1: Sheep Immunisation Using Tau Protein Antigens and Analysis of Antigen Specific Immune Response Two Welsh bred sheep were hyperimmunised with full length tau protein (2N4R, referred as hT40 in this study) and truncated tau (dGAE, representing the core repeat region corresponding to amino acids 297-391 of hT40) separately to generate antigen specific immune response. For primary immunisation, 500 µg of hT40 or dGAE was mixed with Freund's complete adjuvant in a final volume of up to 2 ml and administered per sheep. For subsequent boosts at 4 weeks intervals, 250 µg of each antigen was mixed with Freund's incomplete adjuvant and administered per sheep. The immune responses were monitored by performing binding ELISA using polyclonal sera collected after 10-14 days of subsequent boosts (FIG. 7).

ELISA plates were coated with 1 µg/ml hT40 or dGAE by incubation at 37° C. for 1 h or 4° C. overnight, followed by blocking with PBS containing 2% Marvel (MPBS) at 37° C. for 1 h. After each step the plates were washed three times with PBS containing 0.1% tween 20 (PBST) and three times with PBS. Sheep polyclonal sera was added to designated wells (pre-immune and subsequent boost samples), double diluted in PBS across the plate and incubated at room temperature for 1 h. Anti-sheep IgG HRP conjugated secondary antibody (Sigma A3415) was added to the wells and incubated as before. The resulting immunoreaction was developed by adding SureBlue TMB substrate solution, the reaction was stopped using 1 M H2SO4 and the absorbance values measured using a microplate reader at absorbance 450 nm.

Antigen specific immune response was achieved after the first boost for both hT40 and dGAE immunised sheep (FIGS. 7a and 7b) and the levels peaked at boost 2, 3 and 4 without any further improvement in antibody titre. Therefore after 4th boost immunisation, approx. 350 ml of blood was collected from each sheep, PBLs separated using standard techniques and stored in RNA later solution for the extraction of mRNA and further amplification of antibody genes for library construction.

Example 2: Construction of Phage Display Antibody Libraries from the Immunorepertoire of Sheep Peripheral blood lymphocytes (PBLs) were prepared from sheep blood using Accuspin system Histopaque 1077 columns (Sigma. Cat No: A7054) according to manufacturer's instructions. Total RNA was extracted using RNeasy midi kit (QIAGEN) and cDNA was synthesised by RT-PCR using sheep antibody constant region-specific primers (OvCHFOR 5'-GAC TTT CGG GGC TGT GGT GGA GGC-3' (SEQ ID NO: 634), OvCKFOR 5'-GA TGG TTT GAA GAG GGA GAC GGA TGG CTG AGC-3' (SEQ ID NO: 635), OvCL-FOR 5'-A CAG GGT GAC CGA GGG TGC GGA CTT GG-3' (SEQ ID NO:636)). Sheep IgG VH and VN/VK repertoires were created by PCR amplification as per published methods using V region specific primers (Charlton et al., 2000). For joining of antibody genes, PCR products were enzymatically digested and ligated using the restriction sites Ascl for heavy chain and Mlul for light chain at the 15 amino acid cellulase linker region incorporated through PCR design. The cloning sites Ncol and Notl were incorporated to the ligated DNA through PCR and the resultant scFv DNA fragments were cloned into a phagemid vector pHEN 2a (Hoogenboom et al 1991). Separate VH-VA and VH-VK antibody phage display libraries were created by transformation of electrocompetent *E, coli* TG1 cells (Lucigen Corp).

Two separate phage display libraries were constructed for dGAE and hT40 immunisation hereby referred to as tau antibody library 1 and library 2 respectively. These resultant VH-VA and VH-VK libraries were rescued separately through helper phage infection following published methods (Charlton et al., 2001) and subjected to biopanning including forced epitope selection for the isolation of phage binders with desired specificity and binding affinity.

Example 3: Selection and Screening of dGAE and hT40 Phage Display Antibody Libraries Several biopanning strategies were employed to isolate tau protein specific binders from Library 1 and Library 2.

Helper phage rescued Library 1 was subjected to three selection campaigns as outlined in Table 11. Screening of phage monoclonals using ELISA identified several phage binders, which showed specific binding to the antigens used for selection namely dGA (representing amino acid sequences 297-390 of hT40) and dGAE. These phage binders were grouped into two-(1) dGAE specific binders-(2) dGAE cross reactive binders which recognised dGAE, dGA and hT40. DNA sequencing revealed rich diversity in the selected positive phage population and unique phage clones were reformatted into single chain antibodies (scAbs) by cloning the respective scFv gene (VH-linker-VL) into the bacterial expression vector pIMS147 (reference) using Ncol and Notl restriction enzymes. Unique sequences from these selections were given in a separate document along with sequence IDs.

In order to distinguish between positive clones arising from different selection strategies, the following nomenclature was used.

All positive clones from Library 1 selection 1 were given a prefix 'E' (dGAE panning)

All positive clones from Library 1 selection 2 were given a prefix 'NS' (non-stringent dGA panning) All positive clones from Library 1 selection 2 were given a prefix 'S' (stringent dGA panning) All positive clones from Library 1 where a repeat of selection 2 strategy was performed were given a prefix 'M'

TABLE 12

Showing the three different selection strategies for Library 1 and the concentrations of dGA or dGAE antigen used for different rounds of panning.

| | | | |
|---|---|---|---|
| Library 1 Selection 1 | Pan 1 - 50 µg/ml dGAE | Pan 2 - 10 µg/ml dGAE | Pan 2 - 1 µg/ml dGAE |
| Library 1 Selection 2 | Pan 1 - 100 µg/ml dGA | Pan 2 - 50 µg/ml dGAE | Pan 2 - 10 µg/ml dGAE |
| Library 1 Selection 3 | Pan 1 - 100 µg/ml dGAE | Pan 2 - 10 µg/ml dGAE | Pan 2 - 1 µg/ml dGAE |

Similarly, helper phage rescued Library 2 was subjected to five different selection campaigns using the following antigens as outlined in Table 2 and unique phage binders to respective antigens were reformatted into scAbs as described previously. Antigens used for selection are— hT40, R1-3 (representing amino acids in the region 266-359 on hT40) and biotinylated 412-441 (representing amino acids in the region 412-441 on hT40). In selection strategies 4 and 5, a step to deselect dGA binding phage population was introduced to encourage the enrichment of clones outside of 297-390 region on the tau protein.

TABLE 13

Showing the five different selection strategies for Library 2 and the concentrations of various antigens used for different rounds of panning.

| | | | |
|---|---|---|---|
| Library 2 Selection 1 | Pan 1 - 100 µg/ml hT40 | Pan 2 - 10 µg/ml hT40 | Pan 2 - 1 µg/ml hT40 |
| Library 2 Selection 2 | Pan 1 - 100 µg/ml R1-3 | Pan 2 - 50 µg/ml R1-3 | Pan 2 - 10 µg/ml R1-3 |
| Library 2 Selection 3 | Pan 1 - 100 µg/ml 412-441 | Pan 2 - 10 µg/ml 412-441 | Pan 2 - 1 µg/ml 412-441 |
| Library 2 Selection 4 | Pan 1 - 100 µg/ml hT4Z | Pan 2 - 50 µg/ml hT40 dGA deselection | Pan 2 - 10 µg/ml hT40 |
| Library 2 Selection 5 | Pan 1 - 100 µg/ml hT40 | Pan 2 - 10 µg/ml hT40 dGA deselection | Pan 2 - 0.1 µg/ml hT40 |

In order to distinguish between positive clones arising from different selection strategies, the following nomenclature was used.

All positive clones from Library 2 selection 1 and selection 2 were given a prefix 'C' All positive clones from Library 2 selection 3 were given a prefix '412' All positive clones from Library 2 selection 4 and selection 5 were given prefixes '3a' and '3b' respectively

Example 4: Expression of Reformatted scAbs in Bacterial System and Purification Using Affinity Chromatography Bacterial stocks of positive clones were grown in Terrific Broth (TB) medium supplemented with PO4 salts, 100 μg/ml ampicillin and 1% w/v glucose to reach desired cell density, induced with 1 mM IPTG and expressed scAbs in the periplasm was released using the osmotic shock solution (100 ml 200 Mm Tris-HCl-20% sucrose, 200 μl 0.5 M EDTA and 0.5 mg lysozyme followed by 5 Mm MgSO4) and incubating on ice for 15 minutes each. Recombinant anti-tau scAbs present in crude periplasmic extracts were purified using IMAC columns via binding of hexa Histidine tagged protein to activated Ni-sepharose beads and elution using 200 mM Imidazole. Eluted protein samples were dialysed against 1×PBS pH 7.4 and purity analysed on 4-12% Bis-Tris gels using SDS-PAGE. All expressed scAbs were found to be 90% pure. Protein concentrations were determined by running a standard scAb of known concentration alongside unknown samples using SDS-PAGE and comparing the intensities of the protein bands using ImageJ. Alternatively, absorbance values at 280 nm were measured using Ultraspec 6300 pro UV/Visible spectrophotometer (Amersham, Biosciences) and final scAb concentrations determined from the values obtained.

Example 5: Mapping of Specific Binding Regions and Affinity Ranking of Anti-Tau scAbs A series of binding ELISA was performed using various truncated versions of the tau protein and 13mer peptide libraries spanning the entire hT40 molecule for mapping the epitopes of anti-tau scAbs (Full list of protein antigens used is given in Table 14). In general, ELISA plates were coated with 1 μg/ml hT40 or dGA or dGAE or other truncated versions of the protein and in the case of biotinylated peptides, plates were coated with 5 μg/ml Streptavidin followed by 1 μg/ml biotinylated peptide. The plates were blocked with 2% MPBS and scAb samples added at desired starting concentrations and double diluted across the plate. Binding was detected using anti-Human C Kappa HRP conjugated secondary antibody and the resulting immunoreaction was developed and absorbance values measured as described above.

For affinity ranking ELISA, plates were coated with 1 μg/ml hT40 or dGA or dGAE as before and blocked as normal. Anti-tau scAbs at a starting concentration of 25 μg/ml or 1 μg/ml was added to designated wells and a serial dilution in 1×PBS was performed for each sample. Binding reaction was determined as before, and the scAbs were ranked based on their absorbance values and top binding scAbs were selected for affinity studies using Surface Plasmon Resonance technology.

TABLE 14

Listing various truncated versions of hT40 and biotinylated peptide antigens used for epitope mapping of anti-tau scAbs.

| | | | |
|---|---|---|---|
| Tau 1-49 | m186-350 | m268-391 | N biotin 306-323 |
| Tau 1-201 | C2-186-319 | m352-441 | N biotin 301-325 |
| Tau 1-227 | 42a-186-350 | m348-441 | N biotin 331-360 |
| B1-1-391 | m113-319 | Tau 275-305 | N biotin 301-359 |
| Tau 1-251 | m113-201 | Tau 323-335 | N biotin 337-355 |
| Tau 1-319 | m113-251 | Tau 297-315 | C biotin 337-355 |
| Tau 1-155 | m186-251 | dGAE (297-391) | N biotin 339-351 |
| Tau 1-286 | m186-390 + D/GA/S | dGA (297-390) | N biotin 341-353 |
| Tau 1-391 | m186-319/+ GAE/DHGAE | Tau 337-368 | N biotin 379-390 |
| Tau 1-238 | m221-441 | Tau 377-390 | N biotin 390-414 |
| m113-238 | m239-441 | Tau 306-336 | hT40 13mer library N terminal biotinylated |
| m113-155 | m221-319 | Tau 377-391 | |
| m186-441 | m239-319 | Tau 360-378 | |
| m186-391 | m268-441 | N biotin 412-441 | |

Example 6: Detailed Mapping of Core Region Binding Anti-Tau scAbs

Positive scAbs from Library 1 selections-'E', 'NS' 'S' and 'M' clones (as described previously) were checked for hT40, dGA and dGAE binding using direct binding ELISA, scAbs specifically binding to dGAE were grouped as 'E' dependant and showed no cross reactivity towards hT40. Selected E specific scAbs and their specific binding to dGAE is shown below (FIG. 8A-E).

TABLE 15

A summary of specific scAb binding to various tau truncations and protein fragments representing regions of the tau molecule. A further narrowing down of binding regions was achieved for some scAbs, including those showing positive reactivity to shorter epitopes within 13mer peptides is also shown

| scAb clones | Tau proteins/fragments with positive scAb reactivity | Shortest region bound on hT40 |
|---|---|---|
| E1E8 | 297-391 (dGAE) | 391'E' |
| E2A6 | 297-391 (dGAE) | 391'E' |
| E2B7 | 297-391 (dGAE) | 391'E' |
| E2E8 | 297-391 (dGAE) | 391'E' |
| E1B8 | 297-390 (dGA), 297-391 (dGAE), 313-336 | 313-336 |

Similarly, dGA binding 'NS', 'S' and 'M' group scAbs were subjected to further antigen binding ELISA using shorter tau proteins and biotinylated 13mer peptides as shown below (FIGS. 10A-F) and (FIGS. 11A-R).

TABLE 16

A summary of specific scAb binding to various tau truncations and protein fragments representing regions of the tau molecule. A further narrowing down of epitopes was achieved for some scAbs, including those showing positive reactivity to shorter epitopes, contained within 13mers, or recognising two epitopes are shown.

| scAb clones | Tau proteins/fragments with positive scAb reactivity | Shortest region bound on hT40 |
|---|---|---|
| NS3E5 | hT40, 297-390 (dGA), 297-391 (dGAE), 369-390, 369-391 | 369-390 |
| NS3H4 | hT40, 297-390 (dGA), 297-391 (dGAE), 369-390, 369-391 | 369-390 |
| NS4F2 | hT40, 297-390 (dGA), 297-391 (dGAE), 369-390, 369-391 | 369-390 |
| NS4E3 | hT40, 297-390 (dGA), 297-391 (dGAE), 369-390, 369-391 | 369-390 |
| NS3D9 | hT40, 297-390 (dGA), 297-391 (dGAE), 266-359, 337-368 | 337-355 |
| NS1G7 | hT40, 297-390 (dGA), 297-391 (dGAE), 275-305, 337-368 | 275-305, 337-368 |
| NS2A3 | hT40, 297-390 (dGA), 297-391 (dGAE), 337-368 | 337-368 |
| NS2A8 | hT40, 297-390 (dGA), 297-391 (dGAE), 337-368 | 337-368 |
| NS2C5 | hT40, 297-390 (dGA), 297-391 (dGAE), 337-368 | 337-368 |
| NS2C8 | hT40, 297-390 (dGA), 297-391 (dGAE), 337-368 | 337-368 |
| NS2D3 | hT40, 297-390 (dGA), 297-391 (dGAE), 337-368 | 337-368 |
| NS2A1 | hT40, 297-390 (dGA), 297-391 (dGAE) | No binding to 13mer peptides |
| NS2B6 | hT40, 297-390 (dGA), 297-391 (dGAE) | 297-390 |
| NS1B2 | hT40, 297-390 (dGA), 297-391 (dGAE) | 297-390 |
| S1A5 | hT40, 297-390 (dGA), 297-391 (dGAE) | 297-390 |
| S1A12 | hT40, 297-390 (dGA), 297-391 (dGAE) | 297-390 |
| S1E12 | hT40, 297-390 (dGA), 297-391 (dGAE) | 297-390 |
| S1D5 | hT40, 297-390 (dGA), 297-391 (dGAE) | 297-390 |
| S1D12 | hT40, 297-390 (dGA), 297-391 (dGAE), 186-350, 266-359, 337-368 | 337-355 |
| S2C1 | hT40, 297-390 (dGA), 297-391 (dGAE), 186-350, 266-359, 337-368 | 337-355 |
| S1B1 | hT40, 297-390 (dGA), 297-391 (dGAE) | 367-379 |
| S1D2 | hT40, 297-390 (dGA), 297-391 (dGAE), 369-390, 369-391 | 367-379 |
| S1D9 | hT40, 297-390 (dGA), 297-391 (dGAE) | 367-379 |
| S1F4 | hT40, 297-390 (dGA), 297-391 (dGAE), 369-390, 369-391 | 367-379 |
| S1G2 | hT40, 297-390 (dGA), 297-391 (dGAE), 369-390, 369-391 | 367-379 |
| S1G10 | hT40, 297-390 (dGA), 297-391 (dGAE), 369-390, 369-391 | 367-379 |
| S1H6 | hT40, 297-390 (dGA), 297-391 (dGAE), 369-390, 369-391 | 367-379 |
| S1H9 | hT40, 297-390 (dGA), 297-391 (dGAE), 369-390, 369-391 | 367-379 |
| S2C3 | hT40, 297-390 (dGA), 297-391 (dGAE), 369-390, 369-391 | 367-379 |
| S2C6 | hT40, 297-390 (dGA), 297-391 (dGAE), 369-390, 369-391 | 367-379 |
| S2C7 | hT40, 297-390 (dGA), 297-391 (dGAE), 369-390, 369-391 | 367-379 |
| S2D1 | hT40, 297-390 (dGA), 297-391 (dGAE), 369-390, 369-391 | 367-379 |
| S2D4 | hT40, 297-390 (dGA), 297-391 (dGAE), 369-390, 369-391 | 367-379 |
| S2D3 | hT40, 297-390 (dGA), 297-391 (dGAE), 369-390, 369-391, 275-305 | 367-379, 275-305 |
| MD9/MoD9 | hT40, 297-390 (dGA), 297-391 (dGAE), 369-390, 369-391 | 373-385 |
| ME12 | hT40, 297-390 (dGA), 297-391 (dGAE), 341-353, 337-349, 339-351 | 337-355 |
| MC5 | hT40, 297-390 (dGA), 297-391 (dGAE), 369-390, 369-391 | 367-379 |
| MD12 | hT40, 297-390 (dGA), 297-391 (dGAE), 369-390, 369-391 | 367-379 |

Example 7: Detailed Mapping of Binding of 'C', 412', '3a' and '3b' Series Clones 'C', '412', '3a' and '3b' group scAbs were subjected to further antigen binding ELISA using shorter tau proteins and biotinylated 13mer peptides as shown below (FIG. 12A-F) and (FIG. 13A-R).

TABLE 17

A summary of 'C' group scAb binding to various tau truncations and protein fragments representing regions of the tau molecule. A further narrow down of binding regions achieved for some scAbs, including those showing positive reactivity to shorter epitopes and 13mers peptide libraries are shown.

| scAb clones | Tau proteins/fragments with positive scAb reactivity | Shortest region bound on hT40 |
|---|---|---|
| CA1 | hT40, 1-238, 1-319, 1-155, 155-238 | 155-238 |
| CA2 | hT40, 1-49, 1-319, 1-155, 186-350, 348-441 | 1-155 |
| CA3 | hT40, 1-319, 186-350 | 186-263 |

TABLE 17-continued

A summary of 'C' group scAb binding to various tau truncations and protein fragments representing regions of the tau molecule. A further narrow down of binding regions achieved for some scAbs, including those showing positive reactivity to shorter epitopes and 13mers peptide libraries are shown.

| scAb clones | Tau proteins/fragments with positive scAb reactivity | Shortest region bound on hT40 |
|---|---|---|
| CA4 | hT40, 239-441, 297-390 (dGA) | 355-367 |
| CA6 | hT40, 239-441, 348-441 | 348-390 |
| CA7 | hT40, 1-319 | 1-319 |
| CA8 | hT40, 1-319 | 1-319 |
| CA9 | hT40, 239-441, 348-441, 297-390 (dGA) | 367-379 |
| CA10 | hT40, 1-319 | 227-319 |
| CA11 | hT40, 239-441, 348-441 | 348-441 |
| CA12 | hT40, 297-390 (dGA) | 367-379 |
| CB2 | hT40, 348-441 | 359-391 |
| CB3 | hT40, 297-390 (dGA) | 360-390 |
| CB5 | hT40, 1-319 | 49-113 |
| CB6 | hT40, 1-49, 1-155, 1-319, 113-251 | 1-238 |

TABLE 17-continued

A summary of 'C' group scAb binding to various tau truncations and protein fragments representing regions of the tau molecule. A further narrow down of binding regions achieved for some scAbs, including those showing positive reactivity to shorter epitopes and 13mers peptide libraries are shown.

| scAb clones | Tau proteins/fragments with positive scAb reactivity | Shortest region bound on hT40 |
|---|---|---|
| CB7 | hT40, 1-49, 1-155, 1-319 | 13-25 |
| CB9 | hT40, 239-441 | 239-348 |
| CB10 | hT40, 1-49, 1-319 | 1-319 |
| CB11 | hT40, 1-319 | 113-238 |
| CB12 | hT40, 1-49, 1-155, 1-319, 113-251, 186-350, 266-359 (R1-3), 297-441 | 115-227 |
| CC3 | hT40, 1-49, 1-155, 1-319, 186-350 | 155-227 |
| CC4 | hT40, 1-155, 1-319 | 49-155 |
| CC5 | hT40, 1-49, 1-155, 1-319, 113-251, 186-350 | 49-238 |
| CC7 | hT40, 1-319 | 145-157 |
| CC12 | hT40, 239-441, 297-390 (dGA) | 297-390 |
| CD1 | hT40, 1-49, 1-155, 1-319, 113-251, 186-350, 239-441, 266-359 (R1-3), 297-441 | 49-155 |
| CD2 | hT40, 1-319, 113-319, 113-251, 186-350 | 186-350 |
| CE2 | hT40, 266-359 (R1-3) | 319-331 |
| CE3 | hT40, 266-359 (R1-3) | 331-360 |
| CG11 | hT40, 186-350, 266-359 (R1-3) | 266-359 |

TABLE 18

A summary of '3a' & '3b' series scAbs binding to various tau truncations and protein fragments representing regions of the tau molecule. A further narrow down of binding regions achieved for some scAbs, including those showing positive reactivity to shorter epitopes and 13mers peptide libraries are also shown.

| scAb clones | Tau proteins/fragments with positive scAb reactivity | Short epitope on hT40 |
|---|---|---|
| 3aD3 | 1-155, 1-111, 1-49 | 1-49 |
| 3aH6 | 1-155, 1-111, 1-49 | 1-49 |
| 3aG3 | 1-155, 1-111, 1-49 | 1-49 |
| 3bG4 | 1-155, 1-111, 1-49 | 1-49 |
| 3aB7 | 1-155, 1-111 | 49-111 |
| 3bF4 | 1-155, 1-111 | 49-111 |
| 3aA6 | 1-155, 113-251, 145-157 | 147-157 |
| 3aD6 | 1-155, 113-251, 145-157 | 147-157 |

Example 8: Determination of Critical Binding Residues on Selected scAbs Using Alanine Scanning Mutagenesis (ASM)

To further elucidate epitopes of the scAb panel, and identify the critical amino acids needed for binding, alanine scanning mutagenesis of the parent 13 aa peptides for scAbs CE2, S1D12, CA4 and S1G2 was performed. For clones CE2 and CA4, no reactivity was observed for the first and last three overlapping amino acids in the 13mer peptide library which was used for epitope mapping and therefore only the 7 core amino acid sequences were subjected to alanine substitution for these antibodies. Briefly, 5 μg/ml streptavidin (Thermo Fisher) was adsorbed to Nunc 96-well MaxiSorp plates and following incubation at 37° C., for 1 h, the plates were washed as normal and blocked with 2% MPBS. N-terminally biotinylated peptides (ProImmune Ltd) were added to the plates and incubated for 1 h at 37° C. Subsequently, test scAbs at starting concentrations of 100-500 nM was added and double diluted across the plate for each peptide and incubated for 1 h at 37° C. Rest of the ELISA was conducted as described above and the plates were read at absorbance 450 nm. Immunoreactivity of the scAb of interest was quantified as the % of scAb was bound for each peptide at a chosen concentration (FIG. 15-20).

Example 9: CE2 Binding Region on hT40: 319-331

TABLE 19

Amino acid sequences of the parent peptide and alanine substituted peptides for identifying the critical binding sequences for CE2 scAb

| ASM positions | Peptide Sequences |
|---|---|
| Parent | TSKCGSLGNIHHK (SEQ ID NO: 590) |
| 322A | TSKAGSLGNIHHK (SEQ ID NO: 591) |
| 323A | TSKCASLGNIHHK (SEQ ID NO: 592) |
| 324A | TSKCGALGNIHHK (SEQ ID NO: 593) |
| 325A | TSKCGSAGNIHHK (SEQ ID NO: 594) |
| 326A | TSKCGSLANIHHK (SEQ ID NO: 595) |
| 327A | TSKCGSLGAIHHK (SEQ ID NO: 596) |
| 328A | TSKCGSLGNAHHK (SEQ ID NO: 597) |

Example 10: S1D12 & ME12 Binding Region on hT40: 341-353

TABLE 20

Amino acid sequences of the parent peptide and alanine substituted peptides for identifying the critical binding sequences for S1D12 scAb and ME12 scAb

| ASM positions | Peptide Sequences |
|---|---|
| Parent | SEKLDFKDRVQSK (SEQ ID NO: 598) |
| 341A | AEKLDFKDRVQSK (SEQ ID NO: 599) |
| 342A | SAKLDFKDRVQSK (SEQ ID NO: 600) |
| 343A | SEALDFKDRVQSK (SEQ ID NO: 601) |
| 344A | SEKADFKDRVQSK (SEQ ID NO: 602) |
| 345A | SEKLAFKDRVQSK (SEQ ID NO: 603) |
| 346A | SEKLDAKDRVQSK (SEQ ID NO: 604) |
| 347A | SEKLDFADRVQSK (SEQ ID NO: 605) |
| 348A | SEKLDFKARVQSK (SEQ ID NO: 606) |
| 349A | SEKLDFKDAVQSK (SEQ ID NO: 607) |
| 350A | SEKLDFKDRAQSK (SEQ ID NO: 608) |
| 351A | SEKLDFKDRVASK (SEQ ID NO: 609) |
| 352A | SEKLDFKDRVQAK (SEQ ID NO: 610) |
| 353A | SEKLDFKDRVQSA (SEQ ID NO: 611) |

Example 11: CA4 Binding Region on hT40: 355-367

TABLE 21

Amino acid sequences of the parent peptide
and alanine substituted peptides
for identifying the critical
binding sequences for CA4 scAb

| Peptide | Sequence |
| --- | --- |
| Parent | GSLDNITHVPGGG (SEQ ID NO: 612) |
| 358A | GSLANITHVPGGG (SEQ ID NO: 613) |
| 359A | GSLDAITHVPGGG (SEQ ID NO: 614) |
| 360A | GSLDNATHVPGGG (SEQ ID NO: 615) |
| 361A | GSLDNIAHVPGGG (SEQ ID NO: 616) |
| 362A | GSLDNITAVPGGG (SEQ ID NO: 617) |
| 363A | GSLDNITHAPGGG (SEQ ID NO: 618) |
| 364A | GSLDNITHVAGGG (SEQ ID NO: 619) |

Example 12: Clones with Binding Region 367-379 on hT40

Several antibody clones were shown to bind to the region 367-379 on hT40 molecule (Table 16 & 17) and were grouped together and subjected to detailed analysis of critical binding residues using ASM peptides as described above. Amino acid sequences of the parent peptide and alanine substituted mutants are given in Table 22. Binding profiles of S1G2 scAb to the parent peptide and mutants are shown in FIG. 19A-C. Similarly, percentage binding of other scAbs in the same group recognising hT40 367-379 to various alanine substituted mutants and the parent peptide are shown in FIG. 20A-J

TABLE 22

Amino acid sequences of the parent peptide
and alanine substituted peptides for
identifying the critical binding sequences
for S1G2 and related scAbs binding
to 367-379 region

| Peptide | Sequence |
| --- | --- |
| Parent | GNKKIETHKLTFR (SEQ ID NO: 620) |
| 367A | ANKKIETHKLTFR (SEQ ID NO: 621) |
| 368A | GAKKIETHKLTFR (SEQ ID NO: 622) |
| 369A | GNAKIETHKLTFR (SEQ ID NO: 623) |
| 370A | GNKAIETHKLTFR (SEQ ID NO: 624) |
| 371A | GNKKAETHKLTFR (SEQ ID NO: 625) |
| 372A | GNKKIATHKLTFR (SEQ ID NO: 626) |
| 373A | GNKKIEAHKLTFR (SEQ ID NO: 627) |
| 374A | GNKKIETAKLTFR (SEQ ID NO: 628) |
| 375A | GNKKIETHALTFR (SEQ ID NO: 629) |
| 376A | GNKKIETHKATFR (SEQ ID NO: 630) |

TABLE 22-continued

Amino acid sequences of the parent peptide
and alanine substituted peptides for
identifying the critical binding sequences
for S1G2 and related scAbs binding
to 367-379 region

| Peptide | Sequence |
| --- | --- |
| 377A | GNKKIETHKLAFR (SEQ ID NO: 631) |
| 378A | GNKKIETHKLTAR (SEQ ID NO: 632) |
| 379A | GNKKIETHKLTFA (SEQ ID NO: 633) |

Example 13: Ranking of Relative Binding Affinities of Anti-Tau scAbs Using hT40 Binding ELISA The relative binding affinities of anti-tau scAbs were ranked by performing hT40 antigen binding ELISA as described previously.

Example 14: Analysis of the Binding Kinetics of Anti-Tau scAbs Using Biacore X100™

Surface plasmon resonance (SPR) is widely regarded as the gold standard for real time measurement of protein-protein interactions such as antibody binding. All SPR experiments were carried out using a Biacore X100 machine and HBS EP+ running buffer (GE Healthcare). A 'capture' method was followed for affinity measurements, where an anti-human constant kappa chain (HuCk) antibody was conjugated to the surface of a CM5 sensor chip using an amine coupling kit and scAb molecules were immobilised via their HuCk domain. Amine coupling is a very common approach for immobilising the ligand to the chip surface. The chip surface has a dextran matrix derivatised with carboxyl groups, which after activation with N-hydroxysuccinimide (NHS) and 1-ethyl-3-(3-dimethylaminopropyl) carbodiimide (EDC), form reactive succinimide esters which allows the covalent capturing of the ligand via any available primary amine groups (e.g. Lysine) on the ligand (in this case anti-HuCk antibody). The capture antibody was diluted 1/100 in 10 mM Sodium acetate buffer pH 5.0 and passed over the activated chip surface for a period of at least 420 s. Final ligand immobilisation levels over 12,000 RU were deemed to be satisfactory.

Following immobilisation, the level of each scAb to be captured was identified using the standard SPR equation with a theoretical RMax of 100 RU. Analyte MW refers to the molecular weight of hT40 or dGA/dGAE molecules, while ligand MW refers to the molecular weight of the scAbs tested. RL is the desired capture level and S refers to the stoichiometric ratio:

$$R\max = \frac{\text{Anaylte } MW}{\text{ligand } MW} \times Rl \times S$$

The scAb to be tested was added only to flow cell 2 so that flow cell 1 could act as a control to subtract any interaction with the analyte and the chip surface. Both single and multi-cycle runs were utilised using wizards developed in the Biacore X100 control software which are both accepted methods of kinetic analysis (Karlsson, R., et al. Analyzing a kinetic titration series using affinity biosensors (2006) Analytical Biochemistry 349:136-47). The multi-cycle protocol was as follows-Three start-up cycles composed of an initial capture, to the desired level, of the scAb to be tested was performed followed by a 30 s injection of glycine buffer pH 2.0 after each cycle to regenerate the chip surface. The regeneration step removed any captured scAb whilst leaving the capture antibody intact and able to repeat the capture for the next cycle. Following three start-up cycles increasing concentrations (0.15625 nM-100 nM) of the target to be tested were added to the chip surface after the desired scAb capture. The target was added for a 120 s association period and 420 s dissociation period followed by another regeneration, 30 s injection of glycine buffer pH 2.0 in between each cycle.

The single cycle kinetics protocol was similar and utilised the same level of scAb capture. Three start-up cycles were used followed by 5 increasing concentrations of the analyte (6.25 nM-100 nM) for an association period of 120 s followed by a dissociation period of 420 s for each concentration. In single cycle kinetics the regeneration step was performed only after the final analyte concentration was added. Binding responses were analysed in Biacore X100 evaluation software and data fitted to a 1:1 binding model to obtain kinetic and affinity characterisation. Kinetic rates and equilibrium binding constants of lead scAbs are given in Table No: 23-26.

TABLE 23

Kinetic rates and equilibrium binding constants of lead scAbs for T441

| Top clones (scAbs) | ka (1/Ms) | kd (1/s) | kD (M) for hT40 binding |
|---|---|---|---|
| S1D12 | $1.252 \times 10^6$ | $1.5 \times 10^{-4}$ | 122 pM |
| S1G2 | $1.057 \times 10^6$ | $1.8 \times 10^{-4}$ | 170 pM |
| S1E12 | $3.85 \times 10^5$ | $3.19 \times 10^{-4}$ | 829 pM |
| CC7 | $2.957 \times 10^5$ | $3.659 \times 10^{-4}$ | 1.23 nM |
| NS2A1 | $2.521 \times 10^5$ | $7.393 \times 10^{-4}$ | 2.9 nM |
| CA4 | $4.581 \times 10^5$ | $1.654 \times 10^{-3}$ | 3.61 nM |
| CE3 | $1.745 \times 10^5$ | $6.620 \times 10^{-4}$ | 3.79 nM |
| 412-E10 | $2.71 \times 10^5$ | $8.5 \times 10^{-4}$ | 3.16 nM |
| CE2 | $2.137 \times 10^5$ | $1.077 \times 10^{-3}$ | 5.03 nM |
| CB7 | $1.334 \times 10^5$ | $6.936 \times 10^{-4}$ | 5.19 nM |
| E1B8 | To be determined | | |
| E2E8 | No T441 binding | | |
| MoD9 | To be determined | | |

TABLE 24

Kinetic rates and equilibrium binding constants of lead scAbs for dGA or dGAE

| Top clones (scAbs) | ka (1/Ms) | Kd (1/s) | kD (M) for truncated tau binding |
|---|---|---|---|
| S1D12 | $1.21 \times 10^6$ | $4.18 \times 10^{-4}$ | 344 pM (dGA) |
| S1G2 | $7.83 \times 10^5$ | $3.499 \times 10^{-4}$ | 447 pM (dGA) |
| S1E12 | $2.99 \times 10^6$ | $1.627 \times 10^{-3}$ | 543 pM (dGA) |
| NS2A1 | $1.88 \times 10^5$ | $1.02 \times 10^{-3}$ | 5.4 nM (dGA) |
| E1B8 | $1.37 \times 10^5$ | $2.42 \times 10^{-3}$ | 17.7 nM (dGA) |
| E2E8 | $4.77 \times 10^5$ | $1.915 \times 10^{-4}$ | 401 pM (dGAE) |
| E1E8 | $1.535 \times 10^5$ | $1.4 \times 10^{-3}$ | 6.3 nM (dGAE) |
| MoD9 | To be determined | | |
| CE2 | To be determined | | |

TABLE 25

Kinetic rates and equilibrium binding constants of '3a' and '3b'scAbs for hT40

| scAb clones | ka (1/Ms) | kd (1/s) | kD (nM) for htau40 binding |
|---|---|---|---|
| 3aA6 | $1.900 \times 10^4$ | $1.880 \times 10^{-2}$ | 989 nM |
| 3aB7 | $2.072 \times 10^5$ | $1.435 \times 10^{-2}$ | 69 nM |
| 3aD3 | $5.444 \times 10^5$ | $1.038 \times 10^{-2}$ | 19.1 nM |
| 3aD6 | $4.021 \times 10^5$ | $6.641 \times 10^{-3}$ | 16.5 nM |
| 3aH6 | $2.757 \times 10^6$ | $9.868 \times 10^{-3}$ | 3.6 nM |
| 3aG3 | $6.294 \times 10^4$ | $3.869 \times 10^{-4}$ | 6.1 nM |
| 3bA3 | $1.472 \times 10^4$ | $4.643 \times 10^{-3}$ | 315 nM |
| 3bC1 | $3.056 \times 10^4$ | $4.231 \times 10^{-3}$ | 138 nM |
| 3bF4 | $1.093 \times 10^5$ | $1.532 \times 10^{-2}$ | 140 nM |
| 3bG4 | $6.669 \times 10^6$ | $5.966 \times 10^{-2}$ | 8.9 nM |

TABLE 26

Summary of equilibrium binding constants and binding regions of top anti-tau scAbs

| Top clones (scAbs) | Epitope | KD for hT40 binding |
|---|---|---|
| CB7 | 13-25 | 5.19 nM |
| CC7 | 145-157 | 1.23 nM |
| NS2A1 | 297-390 | 2.9 nM |
| S1E12 | 297-390 | 829 pM |
| E1B8 | 316-336 | Not available |
| CE2 | 319-331 | 5.03 nM |
| CE3 | 331-360 | 3.79 nM |
| S1D12 | 337-349 | 122 pM |
| CA4 | 355-367 | 3.61 nM |
| S1G2 | 367-379 | 170 pM |
| MoD9 | 373-385 | |
| E2E8 | 391 | No hT40 binding |
| 412-E10 | 412-441 | 3.16 nM |

Example 15: IgG Reformatting

Top anti-tau scAbs were reformatted into sheep-mouse (IgG2a) chimeric mAbs by inserting respective VH and VL genes into our dual plasmid eukaryotic vector system (pEE2a) encoding constant heavy and light chain genes of mouse IgG2a separately and expressing recombinant mAbs in a mammalian expression system. Based on the DNA sequencing data, VH and VL genes of shortlisted anti-tau scAbs were custom synthesised separately by introducing the cloning sites BssHII and BstEll (for VH genes) and BssHII and Xhol (for VL genes) at their 5 and 3' end respectively (GeneArt custom gene synthesis service by Thermofisher). Custom synthesised VH and VL genes of respective scAbs and the eukaryotic expression vectors pEE2aMH (encoding mouse IgG2a constant regions) and pEE2aML (mouse N/K constant domain) were digested with restriction enzymes mentioned above. DNA bands corresponding to antibody variable regions and pEE2a heavy and light chain vector backbones were isolated and purified using DNA gel extraction and purification following QIAquick gel extraction kit manufacturer's instructions. Purified DNA fragments were ligated and used to transform electrocompetent E, coli TG1 cells for plasmid propagation. DNA sequencing of extracted plasmid confirmed successful reformatting into sheep-mouse chimeric mAbs. Large scale preparation of heavy and light chain plasmids for each anti-tau mAb clone was performed (Qiagen Plasmid Mega kit) and used to transfect Human Embryonic Kidney (HEK293F) cells grown in suspension using polyethylenimine (PEI). The transfected cells were grown for 8 days before harvesting cell culture supernatants which were then purified using Protein A beads following standard protocols. Purified mAbs were confirmed for T40 binding using ELISA and their affinities (kD) values obtained by running Biacore assays as described previously, with changes as described below.

Example 16: Analysis of the Binding Kinetics of Anti-Tau mAbs Using Biacore X100™

For anti-tau mAb SPR measurements, htau40 was conjugated to the surface of a CM5 sensor chip using amine coupling as explained previously. Briefly, 2 µg/mL htau40 in 10 mM Sodium acetate buffer (pH 4.0) was passed over the activated chip surface (EDC/NHS) in flow cell 2 for a period for 45 s followed by blocking with 1 M ethanolamine-HCl PH 8.5. Flow cell 1 was set up as reference control and blocked simultaneously. Final immobilisation level of htau40 (Rmax) was approximately 250 RU. Following a minimum of three start-up cycles, increasing concentrations (0.78 nM-25 nM) of the mAb in HBS-EP+ buffer was added at a rate of 30 µL/min to the chip. The mAb was added for a 120 s association period and 600 s dissociation period followed by a regeneration cycle of 30 s injection of glycine buffer pH 1.5 in between each cycle. Binding responses were analysed in Biacore X100 evaluation software and data fitted to a 1:1 binding model to obtain kinetic and affinity characterisation. Kinetic rates and equilibrium binding constants of lead anti-tau mAbs are given in the table below

TABLE 27

Kinetic rates and equilibrium binding constants of lead anti-tau mAbs for hT40 (TBD, to be determined)

| Top clones (mAbs) | ka (1/Ms) | kd (1/s) | kD (M) for hT40 binding |
|---|---|---|---|
| S1D12 | $4.058 \times 10^5$ | $4.093 \times 10^{-5}$ | 101 pM |
| S1G2 | $3.398 \times 10^5$ | $4.748 \times 10^{-5}$ | 140 pM |
| S1E12 | TBD | TBD | TBD |
| CC7 | $4.576 \times 10^6$ | $3.164 \times 10^{-2}$ | 6.9 nM |
| NS2A1 | $8.937 \times 10^5$ | $2.621 \times 10^{-3}$ | 10 nM |
| CA4 | $1.020 \times 10^6$ | $1.276 \times 10^{-3}$ | 1.3 nM |
| CE3 | $1.030 \times 10^5$ | $1.718 \times 10^{-3}$ | 16.7 nM |
| 412-E10 | $1.658 \times 10^6$ | $1.497 \times 10^{-2}$ | 9.0 nM |
| CE2 | $4.579 \times 10^5$ | $5.218 \times 10^{-3}$ | 11 nM |
| CB7 | $2.568 \times 10^6$ | $9.451 \times 10^{-3}$ | 3.7 nM |

Example 17: Determination of Limits of Detection (LoD) for High Affinity Anti-Tau Antibody Pairs The diverse panel of high affinity anti-tau antibodies (scAb and mAb formats) were paired in various combinations and tested in a Sandwich (or Capture) ELISA format to calculate their limits of detection (LoD) and their ability to differentiate between different tau species. Biologically, tau exists in 6 different isoforms and is subjected to numerous post translational modifications, some of them playing a significant role in the progression of neurodegeneration.

Figure 22:
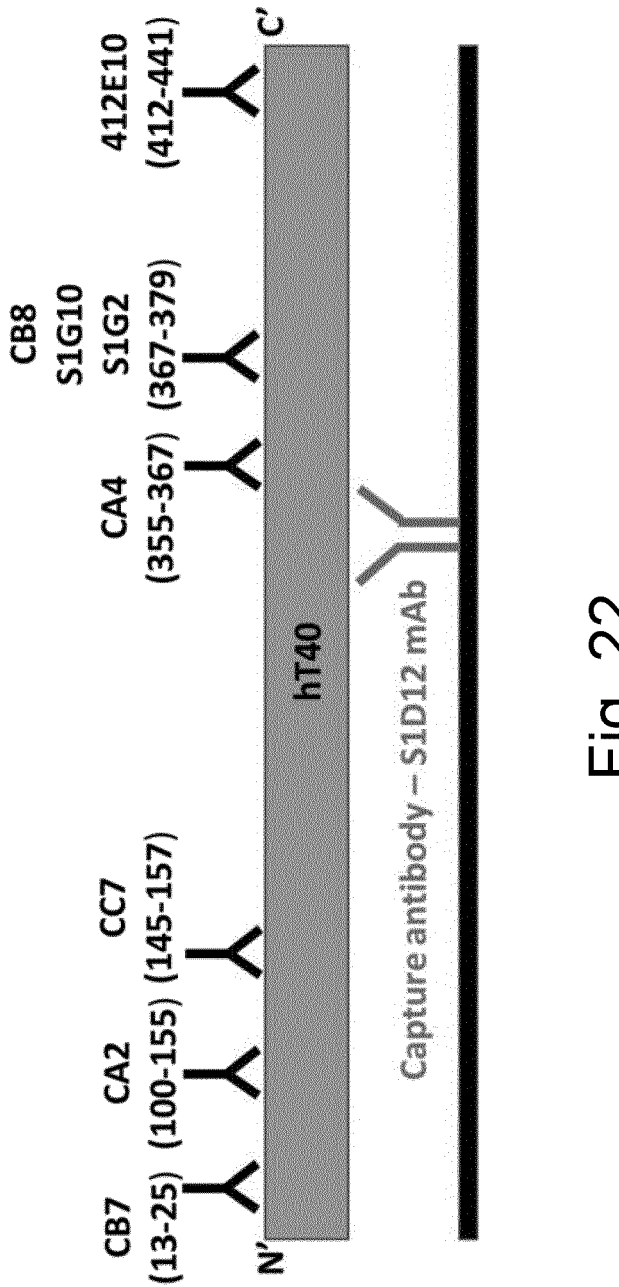

For Sandwich ELISA using colourimetric detection, 96 well Maxisorp plates were coated with the capture antibody S1D12 mAb at 1 µg/ml for 1 h at RT followed by blocking with 2% MPBS as normal. Full length tau (hT40), at 1 µg/ml starting concentration was added to designated wells and double diluted across rest of the plates and left to incubate at R/T for 1 h. A series of detection scAbs with varying epitope recognition properties were added at 10 µg/ml to designated wells (FIG. 22). For colourimetric detection HRP conjugated anti-HuCk secondary antibody was used and the resulting immunoreaction was developed and absorbance at 450 nm measured as described previously. Cut-off point for a positive binding event was an absorbance value of 0.3 following background subtraction. In order to enhance the assay sensitivity, a chemiluminescent detection method was adopted where 50 µL SuperSignal ELISA Femto Substrate (Thermo Scientific) was added to each well following incubation with anti-HuCK HRP antibody and subsequent washing. The luminescence was read using Clariostar Plus microplate reader. A further modification to this protocol was done where various detection scAbs were directly conjugated with HRP and detected using chemiluminescent protocol as before. The lowest levels of detection achieved using different detection scAbs and a comparison of colourimetric and chemiluminescent methods of detection are shown in Table 28

TABLE 28

The LoDs achieved using S1D12 mAb capture and various detection scAbs and a comparison of colourimetric and chemiluminescent methods of detection

| Detection scAb (Epitope) | Tau-441 affinities (Biacore) | LoD (ng/ml) colourimetric detection | LoD (ng/ml) chemi-luminescence detection | LoD (ng/ml) direct HRP conjugation of detection scAb & chemi-luminescence |
|---|---|---|---|---|
| CB7 (13-25) | 5.2 (nM) | 15 | 3.33 | |
| CA2 (100-155) | — | 6 | 0.37 | |
| CC7 (145-157) | 1.2 (nM) | 6 | 3.33 | |
| CA4 (355-367) | 3.6 (nM) | 6 | 0.37 | |
| S1G10 (367-379) | 0.4 (nM) | 2 | 0.12 | |
| CB8 (367-379) | 0.6 (nM) | 2 | 1.11 | |
| S1G2 (367-379) | 0.6 (nM) | 2 | 0.12 | 0.04 |
| 412E10 (412-441) | 3.3 (nM) | 20 | 0.37 | |
| E2E8 (E dependant) | 0.4 (nM) (dGAE) | — | | |

Figure 24:
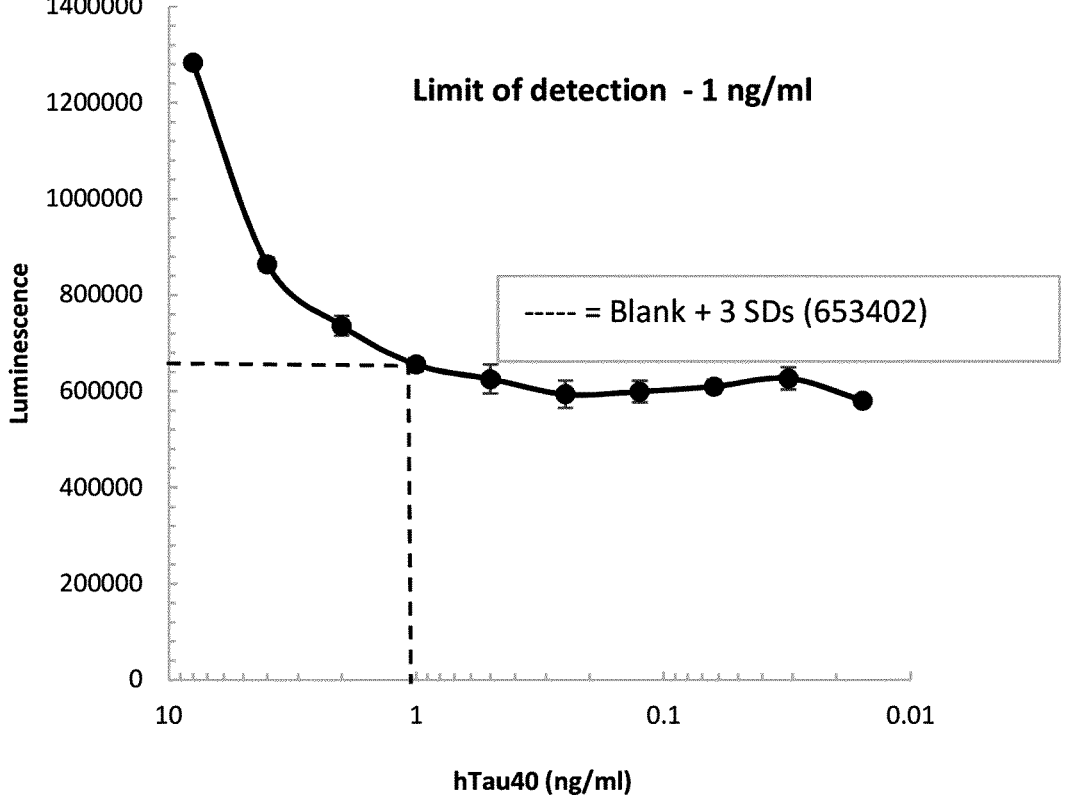

Similarly, a sandwich ELISA format was set up using S1G2 mAb at 1 µg/ml as the capture antibody and HRP conjugated S1D12 mAb for detection. The assay was conducted using chemiluminescent protocol described above. The assay setup and quantification of the limit of detection are shown in FIGS. 23 and 24

Example 18: Interrogation of Mixed Samples and their Quantification Using Antibody Pairs The ability to interrogate and determine the levels of various tau species or fragments in patient samples is crucial in early AD diagnosis. To this end, an experiment was set up to assess whether the concentrations of different tau species could be determined in spiked samples using various antibody pairings directed towards specific regions of the tau protein. Four spiked samples were prepared with varying concentrations and types of tau species-sample A with 5 nM full length human tau (hT40), sample B with 3.3 nM dGA, 3.3 nM dGAE and 3.3 nM hT40 (9.9 nM total protein), sample C with 2 nM dGA, and sample D with 1 nM hT40 and 4 nM dGA (5 nM total protein). These samples were analysed by performing three separate 'blind' sandwich ELISAs using S1D12 mAb to capture the different species in the mixture and detection using scAbs with specific epitopes.

For ELISA #1, wells were coated with S1D12 mAb, blocked and 20 nM hT40 was added to the first well for standard curve plotting. Four spiked samples were added to the first wells of designated rows and all samples were double diluted in PBS across the plate including the standard. The samples were incubated at RT for 1 h, washed as normal and 1 µg/ml CB7 scAb was added to each well and incubated as before. Secondary antibody anti HuCk HRP was added and the reaction was developed and read as described previously. For ELISA #2, 20 nM dGAE was added to the first well and double diluted across the plate for standard curve plotting. As for ELISA #1, spiked samples of unknown protein concentrations were added to respective wells in doubling dilutions. The detection antibody used was 'E' specific E2E8 scAb and rest of the ELISA was performed as described above. For ELISA #3, a standard curve was plotted using average absorbance values obtained from binding events of hT40, dGA and dGAE all at starting concentration of 20 nM. As before, four spiked samples were tested for binding using S1D12 capture mAb and core binding S1G2 detection scAb. Based on ELISA signals of unknown spiked samples, the types of tau fragments present in the mixture and their individual concentrations were determined as shown in FIGS. 25, 26 and 27. A summary of tau types and their concentrations used to spike these samples and the deduced concentrations from ELISAs are given in Table 29.

TABLE 28

Summary of various tau species and their concentrations in the spiked samples and their deduced concentrations and reactivity using three different antibody pairings in a sandwich ELISA format.

| Samples | Concentrations of various tau species in the sample mix | ELISA #1 S1D12-CB7 Reactivity & deduced concentration of samples | ELISA #2 S1D12-E2E8 Reactivity & deduced concentration of samples | ELISA #3 S1D12-S1G2 Reactivity & deduced concentration of samples |
|---|---|---|---|---|
| A | 5 nM hT40 | 5 nM N terminal | None | 3 nM core |
| B | 3.3 nM hT40 + 3.3 nM dGA + 3.3 nM dGAE | 4 nM N terminal | 3.2 nM 'E' specific | ~9 nM core |
| C | 2 nM dGA | None | None | 1 nM |
| D | 1 nM hT40 + 4 nM dGA | 1.5 nM N terminal | None | 3.2 nM core |

Example 19: SDS Treatment of dGAE Aggregates and Restoration of Immunoreactivity The immunoreactivity of core region scAbs is lost when dGA/dGAE fragments are aggregated which could be due to the non-availability of respective epitopes in this conformation. We have noticed Sodium dodecyl sulphate (SDS) can break apart dGA/dGAE aggregates and separate them into smaller fragments by performing an SDS-PAGE. This has been replicated and tested using an ELISA as described below.

For aggregation, 1000 µL 100 µM dGAE+10 µL 10 mM DTT was added to a 'LoBind' microfuge tubes and agitated at 700 RPM/37° C., for 24 hours. Resulting sample centrifuged at 17,000×g/4° C., for 60 min and supernatant discarded to remove left over monomer. Pellet resuspended in half the original volume for future experiments and hereafter referred to as 'aggregates'. 1 µl of aggregates was added to 1 ml of PBS and SDS was added to a final concentration of 1% (w/v). This was left to incubate on lab bench for 1 h with gentle agitation every 15 minutes. In order to neutralise the SDS effect on ELISA, Triton X-100 added to a final concentration of 3% (v/v) and mixed gently by pipetting to prevent any bubble formation. 200 µl added of this mix was to the first well of an ELISA plate coated with 1 µg/ml S1D12 mAb and blocked with 2% MPBS. Similarly aggregates treated with only SDS or Triton X-100, untreated aggregates, dGAE monomers treated with only SDS or SDS+Titon X-100 were also added to designated wells as controls. All samples were then double diluted across the plate in final volumes of 100 µl. The final column was left with no protein to act as a blank. This was allowed to stand at room temperature for 1 hour followed by the addition of detection scAb-S1G2 at 10 µg/ml. Anti-HuCk HRP labelled secondary antibody was added as described previously and ELISA data generated was represented using the graph below. In addition, limits of detection (LoD) of various core binding antibody pairing for SDS Triton X-100 treated dGAE aggregates were calculated using the above describe ELISA method and substituting capture mAbs and detection scAbs as shown in Table 30.

TABLE 30 shows the limits of detection (LoD) of various capture mAb-detection scAb pairing for SDS Triton X-100 treated dGAE aggregates in a sandwich ELISA system.

| | Capture System | | | | | |
|---|---|---|---|---|---|---|
| | S1D12 mAb | | 423 mAb | | Direct immobilisation of dGAE aggregates | |
| Detection scAb | Untreated dGAE agg. | +SDS Triton dGAE agg. | Untreated dGAE agg. | +SDS Triton dGAE agg. | Untreated dGAE agg. | +SDS Triton dGAE agg. |
| S1G2 scAb | 250 ng/ml | 2 ng/ml | NB | 30 ng/ml | NB | 16 ng/ml |
| CA9 scAb | | 4 ng/ml | | | | 40 ng/ml |

TABLE 30-continued shows the limits of detection (LoD) of various capture mAb-detection scAb pairing for SDS
Triton X-100 treated dGAE aggregates in a sandwich ELISA system.

| | Capture System | | | | | |
| --- | --- | --- | --- | --- | --- | --- |
| | S1D12 mAb | | 423 mAb | | Direct immobilisation of dGAE aggregates | |
| Detection scAb | Untreated dGAE agg. | +SDS Triton dGAE agg. | Untreated dGAE agg. | +SDS Triton dGAE agg. | Untreated dGAE agg. | +SDS Triton dGAE agg. |
| CA12 scAb | 2 ng/ml | | | | | 16 ng/ml |
| CB8 scAb | 4 ng/ml | | | | | 30 ng/ml |

NB denotes no binding

Example 20: Antibody Based Detection of Various Tau Fragments in Transgenic Mice Brain Lysate Collection Mouse brain lysates were prepared from wildtype, Line 1, Line 66+/+ and Line 66+/- (Melis et al., 2015, all surplus from Charles River, part of study R0144). All animals were female, 7-8 months old except Line 66+/+ which were 5 months old. The Line 66 mouse construct (FIG. 23) contains human tau cDNA coding for the longest human tau isoform (2N4R tau; 441 amino acids) with two point mutations at P301S and G335D. The L1 cDNA construct (FIG. 23) contains human tau cDNA coding for amino acid residues 296-390 with a signal sequence and related sequences in a murine Thy-1 expression cassette. For brain lysate preparation, half brains were sectioned into four and the individual sections were homogenised in 400 µl of ice cold RIPA buffer (Cell signalling Technology) containing protease and phosphatase inhibitors. Total protein concentrations for individual samples were established by BCA-assay and each sample was subsequently diluted to 1 mg/ml for future experiments.

For capture ELISA, 100 UL S1D12 capture mAb was used to coat a nunc 96 well Maxisorp plate at 1 µg/ml and incubated for 1 hour at 37° C. Plate was washed as previously and then blocked for 1 hour at 37° C., in 2% MPBS. Brain homogenate samples (50 ng total protein) from each mouse type were added to the first wells and double diluted across the plate in PBS. These samples were left to incubate at RT for 1 hour. Various detection scAbs encompassing epitopes of interest were then added to the plate at 1 µg/ml and incubated for 1 h at RT. Secondary antibody used was anti-HuCk HRP and the assays were developed as described previously. Using S1D12 mAb capture and two separate scAb detectors, S-1G2 (FIG. 24A) and C-B7 (FIG. 24B), it was possible to differentiate between L1 and L66 samples and the wild type. When s1G2 scAb was used, tau protein was detected in 50 µg of total brain protein in all four different sample types. However, with C-B7 scAb, hT40 tau was specifically detected in L66 samples and an increase was observed in L66 homozygous group compared to L66 heterozygous samples. Therefore S1D12-CB7 pair was able to differentiate L66 from L1 and wild type with the use of an N' terminally directed detection scAb which is due to a difference in sequence homology between mouse and human tau (Hernandez et al., 2019). Over the whole protein there is approximately 77% homology at the amino acid level, but the proteins differ significantly in the N'-terminal region.

Example 21: Antibody Based Detection of Tau Fragments in Transgenic Mice Plasma Collection Plasma samples from WT, L1, L66+/- and L66$^{+/+}$ of various ages (1.5-9 months) were taken as described. Mice were terminally anaesthetized using an overdose of sodium pentobarbital and blood was collected through cardiac puncture through a Plastipak syringe pre-rinsed with heparinised saline heparin (10 U/ml) (Heparin sodium salt; Sigma-Aldrich) and transferred into a plastic vial containing lithium heparin anticoagulant (Sarstedt Ltd.) Blood samples, kept on ice for no more than 30 minutes, were centrifuged to obtain plasma at 2000× g for 5 minutes at 6° C. Plasma samples were stored at −20° C.

For mouse plasma capture ELISA, 100 µL capture mAb was coated to the bottom of a black nunc 96 well 'maxisorp' plate at 2.5 µg/ml and incubated for 1 hour at 37° C. After washing and blocking as normal, several known standard solutions were set up in triplicate starting at 20 ng/ml of the desired protein before double diluted in the remaining wells. Mouse samples were added to wells in duplicate with a blank in between each sample group. Line1 plasma was diluted 1:10 before addition to plate to account for its high concentration while other samples were diluted 1:2 to account for potential matrix effects. These samples were left to incubate at RT for 1 hour. HRP-conjugated secondary scAb (conjugation carried out according to manufacturer's guidelines, Abcam) was added to each well and left to incubate at RT for 1 hour. The ELISA was developed using SuperSignal ELISA Femto Substrate (Thermo Scientific) and total luminescence was read on Clariostar Plus plate reader (BMG Labtech). Tau concentrations were established using a 4-parameter fit on concentration curves generated from recombinant tau protein spiked into samples at known concentration. For WT and L66 hT40 was used as a calibrator while dGA was used for L1 calibration.

Using S1D12 capture and S1G2 detection we were able to detect varying levels of 'core region' containing tau fragments in samples from WT, L1, L66+/- and L66+/+. In WT and L66, the levels detected were in low ng/ml (WT at 5 month: 1.947 ng/ml, WT at 9 month: 2.177 ng/ml); (L66+/- at 5 month: 0.567 ng/ml), L66+/+ at 5 month: 1.937 ng/ml). However higher concentrations of core region tau species were detected in L1 samples (5 month: 12.355 ng/ml, 9 month 13.661 ng/ml). This is in agreement with the genetic makeup of L1 mouse which contains a truncated 3 repeat fragment corresponding residues 296-390 of hT40 and a signal sequence that drives this towards the endoplasmic reticulum. This could explain the presence of elevated levels of repeat domain core containing fragments in L1 mouse plasma that was detected using our core region pair, S1D12 mAb and S1G2 scAb. This region also shares sequence homology with mouse tau protein which is reflected by base level detection of the core in WT, L66+/+ and L66+/- plasma samples.

In addition, using a second capture-detection antibody pairing, we have successfully shown the detection of human specific tau fragments in Line66 mice which express the longest tau isoform (hT40, 441 amino acids) containing 4 repeat regions with point mutations P301S and G335D (Melis et al., 2014). Using S1D12 mAb as the capture antibody and CB7 scAb detection, Line 66+/+ mouse plasma at 1.5 months showed the presence of detectable levels of human tau as compared to the wild type mouse of same age (FIG. 32A). The detection scAb CB7 (epitope 13-25 on hT40) does not cross react with endogenous mouse tau protein in Line66 transgenic model since the N terminal amino acid sequences differs considerably with between human and mouse tau. In addition, using S1D12-S1G2 pairing we have shown similar levels of core repeat region tau fragments which share close sequence homology in transgenic and wild type animals (FIG. 32B) This demonstrates the utility of our panel of antibody pairs in detecting various tau fragments and truncations in transgenic mice samples which can be translated into a diagnostic setting to interrogate the presence of different tau species in diseased vs cognitively normal human samples.

Example 22: Antibody Based Detection of Tau Fragments in Plasma Samples from AD Patients Six plasma samples from individuals with an AD diagnosis and 6 samples from aged matched controls were sourced (Logical Biological, Kent UK), divided into 100 μl aliquots and stored at −80° C. (Table 31)

TABLE 31

Demographic characteristics of human plasma samples used in this study including the age, sex and ethnicity of cognitively normal controls and patients with confirmed AD diagnosis. Mini-Mental Sate Examination (MMSE) scores of AD patients are also shown.

| | Donor Number | Age | MMSE | Sex | Ethnicity |
|---|---|---|---|---|---|
| Age- | PL 361 | 64 | — | F | Caucasian |
| Matched | PL 362 | 61 | — | M | Caucasian |
| Control | PL 363 | 61 | — | M | Caucasian |
| | PL 364 | 63 | — | M | African American |
| | PL 365 | 61 | — | F | Caucasian |
| | PL 366 | 66 | — | F | African American |
| AD | PL 505 | 62 | 27 | F | Caucasian |
| | PL 506 | 63 | 25 | F | Caucasian Italian |
| | PL 507 | 64 | 26 | M | Hispanic |
| | PL 508 | 57 | 25 | M | African American |
| | PL 509 | 64 | 21 | M | African American |
| | PL 510 | 63 | 27 | F | Caucasian |

For sandwich ELISA, 100 μl S1D12 capture mAb was coated to the bottom of a black nunc 96 well 'maxisorp' plate at 2.5 μg/ml and incubated for 1 hour at 37° C. Plate was washed as previously and then blocked for 1 hour at 37° C., in 2% MPBS. Several known hT40 standard solutions were set up in triplicate starting at 8 ng/ml and diluted 2-fold in the remaining wells using 50% sheep plasma as a diluent to account for any plasma matrix effects. 100 μl of each human sample diluted 1:2 in PBS were added to wells in duplicate with a blank in between each sample group. Samples were diluted 1:2 to account for potential matrix effects. These samples were left to incubate at 4° C., overnight. HRP-conjugated secondary scAb ((S-1G2 and C-B7) (conjugation carried out according to manufacturer's guidelines, Abcam)) was added to each well and left to incubate at RT for 1 hour. The ELISA was developed using SuperSignal ELISA Femto Substrate (Thermo Scientific) and total luminescence was read on a plate reader (BMG Labtech). Tau concentrations were established using a 4-parameter fit on concentration curves generated from recombinant human tau protein spiked into samples at known concentration.

Tau was detected in both patient groups (FIG. 33). Interestingly different levels were detected depending on the combination of capture/detection antibody used. This data provides a proof of concept that using different pairs of antibodies depending on their epitopes will allow us to detect different fragments of tau within plasma. Further antibody pairs will be used to fully interrogate the nature of tau fragments in plasma.

TABLE 32

Summarises plasma tau levels of individual samples in AD and control groups using the capture-detection pairs as shown (*Below assay limit of detection, ** Above assay limit of detection)

| | Donor Number | S1G2-HRP Detection (ng/ml) | CB7-HRP Detection (ng/ml) |
|---|---|---|---|
| Age- | PL 361 | * | 1.89 |
| Matched | PL 362 | * | 1.04 |
| Control | PL 363 | 0.036 | 1.89 |
| | PL 364 | 0.565 | 1.93 |
| | PL 365 | * | * |
| | PL 366 | 0.74 | 1.84 |
| AD | PL 505 | * | * |
| | PL 506 | * | 6.75 |
| | PL 507 | 2.13 | 2.7 |
| | PL 508 | 1.83 | ** |
| | PL 509 | 0.63 | * |
| | PL 510 | 1.38 | 1.96 |

Example 23: LMT Mediated Inhibition of dGAE Aggregates and Restoration of Immunoreactivity The truncated core repeat domain dGAE (297-391), is the predominant fragment that constitutes bulk of the PHF core in AD (Wischik et al, 1988). During dGAE aggregation in vitro, scAb binding regions on dGA/dGAE are 'hidden' or 'occluded' which leads to a loss of immunoreactivity in aggregation samples. Here we have shown the occlusion of binding regions in aggregated dGAE samples and the recovery of immunoreactivity in the presence of LMTM, a tau-aggregation inhibitor. The scAbs tested for binding are core region specific S1D12, CA4, CB3, CE2, CE3 and CA9 (binding regions given in Table 22). For preparing the aggregates, 10 μl 10 mM DTT was added to 1000 μl 100 μM dGAE and agitated with/without LMTM (1:5 ratio) at 700 rpm for 24 h at 37° C. Following overnight agitation, one third of each sample was kept aside as 'total' and the rest was spun down at 16000× g for 30 min and separated into 'supernatant' and 'pellet'. The pellet was then resuspended in half the original volume for further experiments. The immunoreactivities of core region specific scAbs towards dGAE aggregates formed with/without LMTM was tested using a sandwich ELISA format using a 'E' specific monoclonal antibody 423 mAb. This mAb has been shown to specifically bind to the Pronase resistant core structure in the PHFs (Wischik et al, 1988). ELISA plates were coated with 10 μg/ml 423 mAb and blocked as normal. Doubling dilutions of dGAE aggregate 'total', 'supernatant' and 'pellet' samples at 10 μg/ml starting concentration were added to designated wells in doubling dilutions in 1×PBS, dGAE monomer (non-aggregated) was included as assay control. All double dilutions were done in final volumes of 100 µl. This was left to incubate on lab bench for 1 h followed by the addition of test scAbs at 10 µg/ml. Anti-HuCk HRP labelled secondary antibody was added as described previously and ELISA data generated is represented using the graph below.

TABLE 33

Core binding scAbs tested in epitope occlusion assays and their specific binding regions on Ht40

| scAbs tested | Binding regions on hT40 |
| --- | --- |
| S-1D12 | 337-355 |
| CA4 | 355-367 |
| C-B3 | 360-390 |
| C-E2 | 319-331 |
| C-E3 | 297-356 |
| C-A9 | 367-379 |

All scAbs tested showed increased binding to aggregated dGAE 'total' and 'supernatant' samples, when aggregation was conducted in the presence of LMTM. This proves the opening or revealing of occluded antibody binding regions on dGAE where LMTM is preventing the aggregation event, leading to an increased immunoreactivity (FIG. 34).

Tau Aggregation Inhibition Assays

Example 24: ScAb-Mediated dGAE Aggregation Inhibition (Thioflavin T Assay)

Antibody mediated blocking of the tau aggregation cascade and subsequently halting its associated neurodegenerative effects would be a key end point to demonstrate the therapeutic potential of these scAbs. By incubating 100 µM dGAE and 10 mM DTT at 37° C., on a thermomixer at 700 rpm for 24 hours, "pathology mimicking" aggregates which have the morphology of paired helical filaments are formed. This aggregation can be quantified by adding a final concentration of 12.5 µM Thioflavin T (fluorescent dye) which binds to fibril-like β-sheets. Fluorescence was measured with a constant emission wavelength of 480 nm and a scanning excitation wavelength of 350-470 nm using a Varian Cary Eclipse fluorescence spectrophotometer. Maximal fluorescence measurements were used as an indicator of dGAE aggregation (approximately 450 nm excitation). The assay was optimised using a range of S1D12 scAb concentrations (0.04 to 25 UM) and tested for levels of aggregation inhibition as shown in FIG. 35.

Based on FIG. 35, 10 µM scAb was deemed an adequate concentration to compare and rank individual scAb-mediated dGAE aggregation inhibition events. This data is summarised below in FIG. 30: Non-binding, negative controls showed inhibition of up to 47%. A similar inhibition (40%) was seen using 10 µM bovine serum albumin as a negative control (data not shown). Despite this level of non-specific steric inhibition by controls, the anti-tau scAb panel achieved a much greater level of aggregation inhibition, statistically significant for all the anti-tau scAbs (P<0.05) with the exception of CA12, CB2, S1D9 and CB8.

Example 25: ScAb-Mediated Aggregation Inhibition (Tau-Tau Immunoassay)

To further support and rank the anti-aggregation properties of the anti-tau scAb panel, an ELISA-based aggregation inhibition assay was developed (adapted from Wischik et al., 1996).

The adapted method is as follows: dGA (1000 nM) was adsorbed to a Nunc 96-well MaxiSorp plate and incubated for 1 h at 37° C. Plates were subsequently washed 3 times with PBST which was performed after each 1 h incubation. The plates were blocked with 2% (w/v) dried milk powder in PBS for 1 h at 37° C. Double diluting concentrations of test scAbs were incubated with 100 nM of dGAE in binding buffer (25 mM KPIPES, 50 mM NaCl, 0.05% Tween 20, 1% fish skin gelatine; pH 6.8) overnight at 4° C., on a separate polypropylene plate and subsequently added to the blocked immuno-plate for 1 h at 37° C., scAb E2E8 (dGAE-specific) was added to the plates at 1 in 250 dilution as detection antibody (1:250 dilution) and incubated for 1 h at 37° C. The secondary antibody used was HRP-conjugated Anti-mouse IgG (1:1000 dilution, Sigma) and incubated at RT for 1 h. The plate was subsequently developed, and readings taken at absorbance 450 nm. The assay set up is summarised in FIG. 37.

By using a dGAE-specific antibody for detection, this allowed the quantification of the amount of scAb required to prevent 50% of 100 nM dGAE binding to 1000 nM dGA. This quantification has been termed a B50 value and an example of how this is calculated is shown in FIG. 38 as is a summary of the B50 values achieved for various scAbs. A Bbc was achieved for all anti-tau scAbs ranging from a molar ratio of 2.2 to 1 to as low as 0.5 to 1 (scAb to tau ratio). In this assay, negative control scAbs CB7 and 3aD6 showed no inhibition with no B50 value achieved (>10000 nM).

Example 26: Ranking of Tau mAbs Based on their Ability to Capture dGAE Aggregates The aggregation cascade of natively unfolded tau into insoluble filaments is a defining pathological feature of AD. Therefore, it is logical to target aggregated tau filaments for both therapeutic and diagnostic purposes. The following experiment was performed to assess the ability of our dGA mAb panel to bind aggregated dGAE using a capture ELISA method. Aggregates were prepared by incubating 100 µM dGAE and 10 mM dTT for 24 h at 37° C. with shaking at 700 RPM. The following day, dGAE aggregates were centrifuged at 17,000×g for 20 min and the supernatant was removed. The remaining pellet was washed with 10 mM phosphate buffer and centrifuged as above. Washing was repeated a further two times to remove any remaining dGAE monomer. The dGAE pellet was resuspended in 100 µl of 10 mM phosphate buffer. (Using a separate capture ELISA based quantification, we have worked out the efficiency of our dGAE aggregation as 80%)

For assessing the mAb panel for aggregate binding, designated rows of a maxisorp plate were coated with 1 µg/ml of each of the capture mAbs (S1D12, S1G2, CA4, NS2A1, CE2, E2E8 and CB7) and blocked as before. Following washing, 800 nM aggregated dGAE was added to the designated wells, double diluted across the plate and incubated for 1 h at RT. The plate was washed again and 1 µg/ml S1G2 scAb was added as detection antibody and incubated for 1 h at RT. To the row where S1G2 mAb was used for capture, 1 g/ml s1D12 scAb was added as capture antibody instead of S1G2. The assay was developed using HRP labelled HuCK as described previously.

Capture ELISA graph indicates that S1D12 and S1G2 mAbs are most efficient at capturing aggregated dGAE, along with E2E8 mAb which like the 423 mAb is a '391E' binder.

Prophetic Example 27: Study Protocol: Effect of S1D12 Treatment in the Line 1 and Line 66 Tau Transgenic Mouse Models

1. Rationale

The main purpose of this study will be to determine the effect of systemic administration of mAb S1D12 on tau pathology and in tau clearance in 6-month-old tau transgenic female mice.

The study will be conducted in accordance with the European Communities Council Directive (63/2010/EU) and a project license with local ethical approval under the UK Animals (Scientific Procedures) Act (1986). GLP compliance is not claimed for this study.

2. Materials
2.1. Test Item

| Test item | S1D12 |
|---|---|
| | The item will be supplied by Scottish Biologics Facility (SBF); Liberty Building, Foresterhill Road, Aberdeen AB25 2ZP (UK). |

2.2 Test Item Formulation

| Doses | Test item will be administered intraperitoneally at 10- and 50-mg/kg (injection volume: 5 ml/kg). Each dose will be prepared . . . |
|---|---|
| Frequency of preparation | . . . |
| Stability | . . . |

2.3 Vehicle for Test Item

| Vehicle | PBS . . . |
|---|---|
| Storage conditions | . . . |

3. Test System
3.1 Animals and Housing

| Species (Strain) | Mouse (NMRI wild-type and NMRI-derived transgenic line 1 and line 66 mice) |
|---|---|
| Supplier | Charles River (UK) |
| Number required and sex | 200 (20 wild-type, 90 line 1 and 90 line 66) female mice. |
| Number per cage | 5 (same genotype and treatment group)*. |
| Bedding | Corn cob bedding, plus environmental enrichment of paperwool and cardboard tubes (supplied by DBM Scotland Ltd). |
| Minimum acclimatisation | 1 week prior to dosing |

*Animals may be housed alternatively if it is considered necessary by the Lead Scientist, senior animal technician or a veterinary surgeon (e.g. excessive aggression, ill health). Such changes will be recorded in the study file.

3.6 Randomisation

Randomisation of animals will be performed according to genotype and body weight recorded at the beginning of the study.

4. Study Design

Three cohorts of animals at different ages at the start of the experiment will be used (i.e. 3-, 4- and 5-month) and will be allocated into three corresponding groups according to genotype (wild-type, WT; line 1, L1; line 66, L66), dose of S1D12 administered (0-, 10- or 50-mg/kg) and duration of treatment (12 weeks: Group 1; 8 weeks: Group 2; 4 weeks: Group 3) (see table 24 for group size).

TABLE 24

Number of animals assigned to the study (numbers may change due to potential health issues throughout the dosing phase of the experiment).

| | Group 1 | | | Group 2 | | | Group 3 | | |
|---|---|---|---|---|---|---|---|---|---|
| Dose | 0 mg/kg | 10 mg/kg | 50 mg/kg | 0 mg/kg | 10 mg/kg | 50 mg/kg | 0 mg/kg | 10 mg/kg | 50 mg/kg |
| WT | / | / | / | / | / | / | 10 | / | 10 |
| L1 | 10 | 10 | 10 | 10 | 10 | 10 | 10 | 10 | 10 |
| L66 | 10 | 10 | 10 | 10 | 10 | 10 | 10 | 10 | 10 |

The overall experimental design is outlined in FIG. 35.

Animals will be injected intraperitoneally (i.p.) with either vehicle or S1D12 (10- or 50-mg/kg), once per week (Tuesdays) for twelve (Group 1), eight (Group 2) or four (group 3) consecutive weeks. Age of mice at the end of the experiment will be the same for all three groups (i.e. 6 months).

At the end of the study, mice will be anaesthetized using an overdose of sodium pentobarbital administered intraperitoneally. The anesthetized animal will be placed on its back on a rack and a cut along the sternum will be performed to expose the heart. Blood will be collected via cardiac puncture through a Plastipak syringe pre-rinsed with heparinized saline Heparin (10U/ml): (sodium salt from porcine intestinal mucosa; Sigma-Aldrich, CAS No. 9041 Aug. 1) and transferred into a plastic vials containing lithium heparin anticoagulant (Sarstedt Ltd, Additive: lithium heparin; Capacity: 500 µL).

Blood samples, kept on ice for no more than 30 minutes, will be centrifuged to obtain plasma at 2000×g for 5 min at 6° C. [Centrifuge Sigma 3-16KL (3225 RPM, rotor: 11180)]. Plasma samples will be stored at −20° C., and transferred to SBF for tau level quantification.

After blood collection, each mouse will be perfused with heparinized saline for 2-3 minutes and the entire brain removed, dissected on ice and split in two halves, one for histological characterization and the other for biochemical analyses (details of histological and biochemistry analyses will be provided in the final report).

4.1 Clinical Signs

All animals will be observed for reaction to treatment during each day of dosing and throughout the week. Where possible, the onset, intensity and duration of any signs will be recorded. The cages will be inspected daily for evidence of blood and abnormal urine and/or faeces.

4.2 Body Weights

Body weight of the animals will be recorded two times per week (Tuesdays and Fridays) and dosing volumes calculated accordingly.

Example 28: Epitope Mapping and Binding Affinities of Reformatted Anti-Tau mAbs For anti-tau mAb SPR measurements (Biacore X100™) and epitope mapping, the same methodologies described above (see Example 16) were followed. Kinetic rates and equilibrium binding constants of additional anti-tau mAbs and the regions recognised on hT40 are given in the Table 25 below

TABLE 25

| Clones (mAbs) | ka (1/Ms) | kd (1/s) | kD (M) for hT40 binding | hT40 binding region |
|---|---|---|---|---|
| 3aH6 | $3.128 \times 10^{6}$ | $1.522 \times 10^{-4}$ | 49 pM | 1-15 |
| 3bG4 | $4.540 \times 10^{6}$ | $2.964 \times 10^{-4}$ | 65 pM | 1-15 |
| 3aG3 | $1.532 \times 10^{7}$ | $4.751 \times 10^{-3}$ | 310 pM | 1-15 |
| 3bD11 | $2.671 \times 10^{6}$ | $3.979 \times 10^{-3}$ | 1.490 nM | 37-49 |
| E1B8 | $3.238 \times 10^{5}$ | $1.367 \times 10^{-3}$ | 4.22 nM | 319-331 |
| MD9 | $6.620 \times 10^{4}$ | $1.462 \times 10^{-3}$ | 22 nM | 373-385 |
| *Tau12 | $1.030 \times 10^{5}$ | $1.718 \times 10^{-3}$ | 1.44 nM | 6-18 |

Kinetic rates, equilibrium binding constants and binding regions of newly converted anti-tau mAbs. *Commercially sourced Tau12 mAb binding kinetics and an affinity value was also measured and included in the table.

Example 29: Antibodies Show Specificity to Human Tau in L66+/+ Brain Homogenates Western blots with brain homogenates prepared from 3 animals of each genotype: wild-type (WT) mice; L66+/+ mouse; and L1+/+ mouse brain (all 5 months old) show specificity for human tau using CB7 (hT40 13-26) and CC7 (hT40 145-157) antibodies (Genotype and phenotype descriptions for L1 and L66+/+ are provided in the initial filing document). Protein equivalent to 20 µg from each brain extract was separated using 4-20% bis-tris gels and run in 1×MES buffer. FIG. 41 shows a blot stained with CB7 antibody. A clear band is visible in the lanes containing L66+/+ samples, but no other bands are detectable (WT or L1+ (+). FIG. 42 shows a similar outcome when a blot containing the same sample preparations is interrogated with the CC7 antibody. Once again, a band having relative mobility of 65 kDa is visible in the L66 sample with no other reactive bands present.

When these results are compared with western blots obtained with the core domain antibody binders S1D12 (hT40 337-355) (FIG. 3) and S1G2 (hT40 367-379) (FIG. 44) the results are very different with numerous bands visible in each mouse sample. A band is detected in each sample (WT, L66+/+ and L1+/+) with an apparent molecular weight of approximately 55 kDa. This band most likely corresponds to endogenous mouse tau which is of a similar size. In the L66+/+ samples, a second band running at approximately 68 kDa is also detected. The presence of numerous other bands indicates proteolytic truncation of tau within brain homogenates. In addition, in FIG. 44 the S1G2 antibody is able to detect the pathologic 10-kDa tau fragment that is capable of seeding disease in other cells.

The amino acid sequences of the human and mouse tau regions that contain the epitopes of CB7, CC7, S1D12 and S1G2 are superimposed for comparison (FIG. 45). It is clear that both CB7 and CC7 epitopes fall in areas with no homology between the human and mouse tau sequences; however, in the core region, the sequences are identical. Together these blots and sequence analysis (FIGS. 41-45) highlight the diagnostic utility of these antibodies as they are able to recognise the presence of pathologic human tau in a transgenic mouse brain against a background of endogenous mouse tau protein. These antibodies could be utilised to track the fragmentation patterns of pathologic tau species during aging and in relation to any pharmacologic treatments that may affect the (human) tau protein, its aggregation, movement between compartments in the body (e.g. between brain and blood) and its pattern of fragmentation.

Example 30: Core and N-Terminal Antibody Pairings Detect Age-Related Tau Protein Truncations or Occlusion of Core Regions in Ageing L66 Mice Brains from L66+/+ mice of various ages (1.5-month, n=11; 3-month, n=11; and 5-month, n=8) were homogenised as previously described and protein content quantified by BCA assay. These brain homogenates were then screened in paired antibody ELISAs to assess age-related changes in the tau fragmentation pattern. Brain homogenates were included in a sandwich ELISA in duplicate and tau values were determined against the linear section of an hTau40 standard curve.

When using S1D12 antibody to capture tau from these brain homogenates and CB7 as the detector antibody, a marked decrease in tau signals was observed with increasing age (FIG. 46A). This finding was confirmed by changing the orientation of the assay and using CB7 as the capture antibody and S1G2 as detector (FIG. 46B). Since the pairings used in this assay detect tau fragments that contain the amino acids spanning from 13-379, any truncation or occlusion of epitopes as a result of pathology-related aggregation that masks the core will result in lower tau detection. The progressive loss of signal that is observed here suggests that either a truncation or epitope occlusion event is occurring or that multiple events of this nature are occurring during the aging of L66+/+ mice.

Example 31: Shorter N-Terminal Human Tau Fragments Appear to Increase with Age in L66+/+ Mice In order to gain further insights into the protein fragmentation state of the tau matrix in the samples investigated above, the levels of a smaller N'-terminal fragment were determined using the CB7 antibody capture paired with HT7, a commercial antibody with an epitope in the region tau159-163. Interestingly, there was a trend towards an increase in signal as the L66+/+ mice aged. So, as the longer core to N'-terminal tau fragment decreases with age (FIG. 46), the levels of smaller, truncated fragments of human tau increase in this transgenic mouse line (FIG. 47).

Example 32: Ultrasensitive Assays for the Detection of Tau Fragments in Biological Fluids Utilising Single Molecule Array (Simoa®) technology we have lowered the limit of detection of our assays substantially, in some instances to below 1 µg/ml tau protein (or protein fragment). Simoa® is a bead-based technology where a capture antibody is coated on to magnetic beads which can then be concentrated out of solution using a magnet. A biotinylated detector is added which binds to the captured molecule of interest. Streptavidin B Galactosidase (SBG) binds to the detector and subsequently hydrolyses resorufin β-D-galactopyranoside (RPG) into a fluorescent product that is used for detection of the immunocomplex. Table 26 summarises the antibody pairings and limits of detection for assays successfully transferred to the Simoa® system.

TABLE 26

| Assay | Capture antibody | Detector antibody | Simoa ® limit of detection (pg/ml) |
|---|---|---|---|
| Core (Tau 337-379) | S1D12 (Binding region hT40 337-355) | S1G2 (Binding region hT40 367-379) | 0.75 |
| Core - proline (Tau 159-379) | S1G2 | HT7 (Binding region hT40 159-163) | 0.32 |
| | S1D12 | HT7 | 0.32 |
| | S1D12 | BT2 (Binding region hT40 194-198) | 0.32 |
| Core - N' (Tau 1-379) | S1D12 | Tau12 (Binding region hT40 6-18) | 0.75 |
| | S1G2 | Tau12 | 1.6 |
| | S1G2 | 3bG4 (Binding region hT40 1-15) | 20 |
| Full-length (Tau 1-441) | CB7 (Binding region hT40 13-25) | Tau46 (Binding region hT40 409-441) | 2.2 |
| N' - proline (Tau 6-198) | CB7 | BT2 | 0.75 |
| | CB7 | HT7 | 2.2 |
| | Tau12 | HT7 | 2.2 |
| Core - C' (Tau 337-441) | S1G2 | Tau46 | 2.2 |

Assays that have successfully been transferred to Simoa ®. Capture antibody is coated to magnetic beads and the detector antibody is biotinylated. Limits of detection for each assay are included.

Example 33: Differing Levels of Tau Fragmentation in Post-Mortem CSF

Human post-mortem CSF samples were acquired from the South West Dementia Brain Bank (SWDBB) and split into 3 groups based on histopathological diagnoses. These groups were healthy control (HC, n=6), mild/moderate AD (n=15) and severe AD (n=12). Protein content for each CSF sample was quantified by BCA assay to ensure tau levels were determined independently of total protein concentration. These samples were then screened in Simoa® experiments utilising a number of different antibody pairings as summarised in Table 27 below.

TABLE 27

| Assay | Capture antibody | Detector antibody | Tau protein fragment detected (numbers refer to amino acids in the hT40 protein) |
|---|---|---|---|
| Core | S1D12 | S1G2 | 337-379 |
| NT1 | BT2 | Tau12 | 6-198 |
| Core - N' | S1D12 | Tau12 | 6-349 |
| Full Length | CB7 | Tau46 | 13-441 |
| Core - C' | S1D12 | Tau46 | 337-441 |
| Core - BT2' | S1D12 | BT2 | 194-359 |
| Core - HT7' | S1D12 | HT7 | 159-349 |

Table summarising the assays used for post-mortem CSF screening. The capture and detector antibodies used in each assay are stated along with the minimum tau fragment that each assay measures.

The Simoa® experiments used for CSF screening utilised a 2-step protocol. First a standard curve of hTau40 (540 pg/ml-0.7 pg/ml) was created by spiking recombinant hTau40 into Tau 2.0 diluent and triple diluting. CSF samples were diluted 1:10 in Tau 2.0 diluent and subsequently again 1:100 in Tau 2.0 diluent based on previous experiments which showed that a 1:2000 dilution was optimal for the standard curve. Tau levels were read from a 4-parameter-fit standard curve, multiplied by the dilution factor and analysed for statistical differences using GraphPad prism v5.

The levels of tau fragments detected by the core assay and the previously reported NT1 assay show a statistically significant increase associated with disease severity (Table 28). The NT1 assay uses a commercial antibody pairing, BT2 and Tau12, that measures the N-terminal region of the human tau protein (that encompasses hT40 6-198) in CSF and blood (Chen et al. 2019). Using the Simoa® NT1 assay, Chen et al reported an increase in CSF tau levels in subjects with AD biomarker positive-mild cognitive impairment (AD-MCI) and AD biomarker positive-clinical AD (AD) compared to normal control (NC). However, the levels detected were the in pg/ml range, with mean values of 220-230 pg/ml in AD-MCI and AD patients (Chen et al. 2019). The results reported in Table 28 are similar, where an increase in the level of tau fragments detected by both the NT1 and core assays is observed in the post-mortem CSF samples of mild-moderate and severe AD groups compared to the control group. In contrast to Chen et al, however, we detected ng/ml quantities of these assay-specific tau fragments. No other fragments tested showed significant differences due to the disease. Full-length tau and, to a lesser degree, the other long fragments are present in much lower levels than those detected using either the core or NT1 assay. This provides further proof that tau exists as a matrix of small truncated fragments with very few longer or full-length fragments and our antibody pairings can differentiate these fragments in biological samples such as CSF.

TABLE 28

Results of Simoa ® experiments utilising 7 different antibody pairings to detect tau fragments in post-mortem CSF samples. The antibody pairings for each assay are as follows: NT1 (BT2-Tau12), Core (S1D12-S1G2), Core-N' (S1D12-Tau12), Full-length (CB7-Tau46), Core-C' (S1D12-Tau46), Core-BT2 (S1D12-BT2) and Core-HT7 (S1D12-HT7). There is a significant increase in NT1 and core tau levels in CSF samples associated with disease severity and the quantities detected in post-mortem CSF samples are greater than those in patient CSF (ng/ml levels in post-mortem samples vs pg/ml in patient CSF as reported by Chen et al. 2019). The other fragments tested did not show any differences between disease and control groups and the levels of these tau protein fragments were far lower than those measured in either the core or NT1 assays.

| | | | | | | | Assay | | | | |
| Category | n | Age (yr) | Sex (F) | PM Delay (h) | Total Protein (mg/ml) | NT1 (6-198) (ng/ml) | Core (337-379) (ng/ml) | Core-N (6-349) (ng/ml) | Full-length (13-441) (ng/ml) | Core-C (337-441) (ng/ml) | Core-HT7 (194-359) (ng/ml) | CoreBT2 (159-349) (ng/ml) |
|---|---|---|---|---|---|---|---|---|---|---|---|---|
| Control | 6 | 75.33 | 50% | 47.33 (9.8) | 5.17 (0.7) | 62.66 (14.1) | 163.65 (33.5) | 40.87 (10.3) | 4.52 (0.6) | 9.29 (5.1) | 2.57 (1) | 6.46 (2.5) |
| Mild/ Moderate AD | 15 | 87.73 | 60% | 67.58 (12.5) | 5.44 (0.4) | 83.17 (22.6) | 184.07 (48.1) | 34.92 (6.9) | 3.99 (0.5) | 7.61 (2.6) | 4.3 (1.2) | 7.95 (2) |
| Severe AD | 12 | 79.75 | 50% | 44.88 (5.1) | 5.27 (0.5) | 257.06 (79) | 542.9 (136.2) | 53.88 (10.7) | 3.85 (0.5) | 10.68 (2.4) | 6.07 (2.1) | 11.39 (3.6) |
| | | | | | P values | 0.0379* | 0.0165* | 0.3262 | 0.7786 | 0.7491 | 0.4894 | 0.5396 |

Data presented as mean (standard error). There was no correlation detected due to age, sex, post-mortem (PM) delay or total protein.

Example 34: Measuring Tau Fragment Levels in AD and Healthy Control Plasma Samples Human plasma samples were sourced from the commercial supplier Logical Biological Ltd. Healthy control (HC, n=12) and samples from individuals with a diagnosis of AD (AD/MCI, n=42) were aliquoted into low bind microfuge tubes and stored at −80° C.

The Simoa® experiments used for plasma screening utilised a 3-step protocol optimised for use with plasma samples. A standard curve (540 pg/ml-0.7 pg/ml) was created by spiking recombinant hTau40 into Tau 2.0 diluent and triple diluting. Plasma samples were diluted 1:100 and added in duplicate to the Simoa® plate followed by the addition of respective capture beads. Different antibody pairings used for plasma screening is explained in Table 5. In general, the capture antibody coated beads are mixed with diluted plasma samples, added to the plates and incubated for 30 min at 30° C., with shaking. Following the incubation, the plates were washed using the Simoa® plate washer before the addition of 0.2 µg/ml biotinylated detector antibody which was left to incubate as before for 10 min. The plates were then washed again before the addition of SBG and a final 10 min incubation. After the final incubation and wash steps the plates were transferred to the Simoa® reader and plasma tau concentrations generated against a 4-parameter fit curve.

TABLE 28

| Assay | Capture Antibody | Detector Antibody | Tau Protein Fragment Measured (numbers refer to amino acids in the tau protein) |
|---|---|---|---|
| Core | S1D12 | S1G2 | 337-379 |
| NT1 | BT2 | Tau12 | 6-198 |
| Core - Tau12 | S1D12 | Tau12 | 6-349 |
| Core - HT7 | S1D12 | HT7 | 159-349 |
| Core - BT2 | S1D12 | BT2 | 194-359 |
| BT2 - HT7 | BT2 | HT7 | 159-198 |
| Core - C' | S1D12 | Tau46 | 337-441 |
| BT2 - S1G2 | BT2 | 1G2 | 194-379 |

Table summarises the antibody pairings used for Simoa ® assays for human plasma sample screening. The capture and detector antibodies used in each assay are stated along with the tau fragment each assay (the numbers refer to the amino acid positions in the full-length human tau protein hT40).

Human plasma screening data were subsequently analysed in Graphpad Prism v5. Interestingly, we have observed significantly higher levels of plasma tau fragments in age-matched, healthy control group compared to the AD group as detected using various capture-detector antibody pairings (Table 29).

TABLE 29

Results of Simoa ® experiments utilising 8 different pairings detecting tau fragments in human plasma samples. Assay antibody pairings are as follows; NT1 (BT2-Tau12), Core (S1D12-S1G2), Core-Tau12 (S1D12-Tau12), Core-HT7 (S1D12-HT7), Core-BT2 (S1D12-BT2), BT2-HT7 (BT2-HT7), Core-C' (S1D12-Tau46), BT2-S1G2 (BT2-S1G2). There is a significant decrease in core-proline tau levels (measured using core-HT7 and core-BT2 assays where S1D12 is the capture antibody) in patients with an AD diagnosis (AD/MCI) compared with health control (HC) plasma. The levels of tau measured when using our core capture antibody S1D12 as part of an antibody pair is 1,000-fold more than the typical values seen for the existing NT1 assay in human plasma. In contrast to the reported NT1 assay, where AD/MCI patients typically show higher assay values than healthy controls, for assays using S1D12 capture this pattern is reversed with health control samples showing higher tau fragment values than AD/MCI patients.

| Category | n | Average Age (yr) | Average Sex (M) | Average MMSE score | NT1 (6-198) (pg/ml) | Core (337-379) (pg/ml) | Core-Tau12 (6-349) (pg/ml) | Core-HT7 (194-359) (pg/ml) | Core-BT2 (159-349) (pg/ml) | BT2-HT7 (159-198) (pg/ml) | Core-C (337-441) (pg/ml) | BT2-S1G2 (192-379) (pg/ml) |
|---|---|---|---|---|---|---|---|---|---|---|---|---|
| AD/MCI | 12 | 62 | 44.4% | 21 | 0.19 | n.d. | 0.67 | 30.24 | 899.6 | 44.51 | n.d. | n.d. |
| Healthy Control | 9 | 56 | 41.6% | NA | 0.145 | n.d. | 0.67 | 1,802 | 13,619 | 123.8 | n.d. | n.d. |

TABLE 29-continued

Results of Simoa ® experiments utilising 8 different pairings detecting tau fragments in human plasma samples. Assay antibody pairings are as follows; NT1 (BT2-Tau12), Core (S1D12-S1G2), Core-Tau12 (S1D12-Tau12), Core-HT7 (S1D12-HT7), Core-BT2 (S1D12-BT2), BT2-HT7 (BT2-HT7), Core-C' (S1D12-Tau46), BT2-S1G2 (BT2-S1G2). There is a significant decrease in core-proline tau levels (measured using core-HT7 and core-BT2 assays where S1D12 is the capture antibody) in patients with an AD diagnosis (AD/MCI) compared with health control (HC) plasma. The levels of tau measured when using our core capture antibody S1D12 as part of an antibody pair is 1,000-fold more than the typical values seen for the existing NT1 assay in human plasma. In contrast to the reported NT1 assay, where AD/MCI patients typically show higher assay values than healthy controls, for assays using S1D12 capture this pattern is reversed with health control samples showing higher tau fragment values than AD/MCI patients.

| Category | n | Average Age (yr) | Average Sex (M) | Average MMSE score | NT1 (6-198) (pg/ml) | Core (337-379) (pg/ml) | Core-Tau12 (6-349) (pg/ml) | Core-HT7 (194-359) (pg/ml) | Core-BT2 (159-349) (pg/ml) | BT2-HT7 (159-198) (pg/ml) | Core-C (337-441) (pg/ml) | BT2-S1G2 (192-379) (pg/ml) |
|---|---|---|---|---|---|---|---|---|---|---|---|---|
| Assay limit of detection (pg/ml) | | | | | 0.25 | 2.2 | 0.25 | 0.25 | 0.75 | 0.25 | 2.2 | 2.2 |

Data presented as mean. n.d.—not detected (signals below blank)

Example 35: Core Capture Antibody S1D12 can Measure Ng Levels of Tau in Human Plasma When S1D12-BT2 or S1D12-HT7 pairings are used in Simoa® assay, nanogram levels of tau fragments are detected in human plasma (Table 29). All studies reported so far have measured pg/ml concentration of tau fragments in plasma with highest levels ~850 µg/ml (Sparks et al 2012; Rani et al 2017). Interestingly, and contrary to the NT1 assay, this core-BT2 assay measures 1,000- to 10,000-fold more tau fragments and the levels are higher in healthy controls compared to AD patients (FIG. 8). Similarly, with the core-HT7 assay, ng/ml concentration of tau was detected in healthy control plasma and the levels were lower in AD/MCI plasma. Both findings translate to higher levels of core-proline fragments in healthy control and form the basis of a regular monitoring test to identify patients worthy of additional screening, i.e. a potential predictor of early onset of disease. The levels of tau detected using the core capture antibody is significantly greater than previously reported and suggests that the use of S1D12 reveals large amounts of previously undetected tau fragments in biological samples which can be considered as a tau protein mixture (full-length tau protein and populations of tau protein fragments) that can be referred to as a 'tauosome'. The decrease in tau levels in the plasma of AD/MCI patients suggests that perhaps defective clearance of tau from the brain is a critical factor in the pathogenesis of AD.

Example 36: Monitoring the "Treatment Effects" of LMTM by Detecting Tau Levels in the Plasma of L66$^{+/-}$ Mice The effect of the tau aggregation inhibitor LMTM on the levels of plasma tau in a L66$^{+/-}$ mouse line was investigated with two assays, both utilising the 3-step Simoa® protocols described above. Using the human specific NT1 assay (BT2 capture with Tau12 detection), low levels of tau (0.41±0.09 pg/ml) were detected in the plasma of 5-month-old L66$^{+/-}$ that were treated with vehicle control solution (FIG. 50A). At the same time, an increase in tau levels was measured in the plasma of L66$^{+/-}$ mice that had received an oral administration of LMTM (15 mg/kg) during the time period (1.28±0.11 pg/ml). This suggests that LMTM facilitates solubilisation of pathologic tau from the brain into the blood of mice receiving treatment.

This hypothesis was supported by our core-proline antibody assay in which S1D12 antibody coated capture beads and BT2 detector was used (FIG. 50B). This assay detects both human and mouse tau which explains the higher levels of tau detected. Again, there was an increase in plasma tau in LMTM treated L66$^{+/-}$ mice with 70±25 µg/ml tau detected in the vehicle group and 142.08±12.08 pg/ml in the 15 mg/kg LMTM treatment group.

Example 37: S1D12 mAb as a Potential Therapeutic Agent

Two pilot experiments were conducted in order to investigate the therapeutic effect of S1D12 mAb, its pharmacokinetic properties and potential clinical adverse events associated with antibody administration and finally to show the mAbs efficacy and low toxicity after 1 month of repeat administration in vivo in a mouse model of AD.

1) Pharmacokinetic study (PK) to provide information about the delivery of S1D12 mAb into the brain and plasma as a measure of its bioavailability.
2) Repeat-dosing study to provide efficacy data and confirm no toxicity after 1-month administration of S1D12.

For the PK study, a total of 42 female NMRI mice (Swiss-type mouse, Naval Medical Research Institute) aged 6 months were allocated into six groups according to sample collection time (Table 30 for group size). Animals were injected intraperitoneally with S1D12 (30 mg/kg) and sacrificed 24-, 48-, 72-hours and 7-, 14- and 31-days after injection to collect blood and brain samples. A control group was also included in which animals were sacrificed to collect blood and brain, but no test item was administered.

TABLE 30

| Mice (n) | Gender | Route of administration | S1D12 dose (mg.kg) | Injection volume (ml/kg) | Time point |
|---|---|---|---|---|---|
| 6 | F | i.p | 30 | 5 | 24 hours |
| 6 | F | i.p | 30 | 5 | 48 hours |
| 6 | F | i.p | 30 | 5 | 72 hours |
| 6 | F | i.p | 30 | 5 | 7 days |
| 6 | F | i.p | 30 | 5 | 14 days |
| 6 | F | i.p. | 30 | 5 | 31 Days |
| 6 | F | controls | no dose | na | na |

Number of animals allocated in the PK study. i.p., intraperitoneal; na, not applicable.

Blood samples were centrifuged to obtain plasma at 2000×g for 5 min at 6° C., and samples were stored at −20° C. After blood collection, each mouse was perfused with heparinized saline for 2-3 minutes and the entire brain removed rapidly and snap frozen in liquid nitrogen and stored at −80° C. Similarly, tissue samples such as the liver (right lobe), spleen, kidney (right kidney), muscle (thigh), heart and lung (right inferior lobe) were quickly snap frozen in liquid nitrogen after dissection.

The concentration of S1D12 mAb in mouse plasma was determined using an antigen-capture ELISA with dGAE (representing amino acids 297-391 of hT40), as described previously. Briefly, dGAE (1 µg/mL) was used to coat ELISA plates and blocked with 2% Marvel. For the standard curve, 5 nM S1D12 mAb was double diluted across plate in PBS and plasma samples were added to respective wells in duplicate at dilutions of 1:1000 and 1:5000. Following washing, HRP-conjugated anti-mouse IgG as detector was added, and the assay developed using TMB solution as normal. The absorbance at 450 nm was read using a Clariostar plate reader (BMG Labtech) and MARS Clariostar software used to calculate S1D12 concentration from a standard curve.

Individual mouse plasma concentrations of S1D12 mAb were determined from 4 individual experiments performed in duplicate. Average values from each group (representing a time point) was plotted (FIG. 10) and the in vivo half-life, $C_{max}$ and $T_{max}$ calculated by performing a non-compartmental analysis of the plasma data using the PKSolver2.0 software (FIG. 51, Table 31). Similarly, the ability of S1D12 mAb to cross the blood brain barrier (BBB) was evaluated by determining antibody levels in mouse brain homogenate by performing the dGAE ligand binding ELISA as described above. Here a higher coating concertation of dGAE at 10 µg/ml was used to compete off antibody binding to tau present in the brain. Based on the analysis of brain homogenates, between 0.2 to 0.47% of plasma S1D12 was able to cross the BBB and a $T_{max}$ of 48 h and $C_{max}$ of 6.2 nM was achieved in the brain.

TABLE 31

| Parameter | Unit | Value |
|---|---|---|
| $t_{1/2}$ | h | 256.1778139 |
| $T_{max}$ | h | 24 |
| $C_{max}$ | nmol/L | 1455.005514 |

Pharmacokinetic parameters of S1D12 after the administration of a single dose at 30 mg/kg in NMRI mice.
$t_{1/2}$ is the elimination half-life from plasma, $C_{max}$ - peak plasma concentration, $T_{max}$ - time of peak plasma concentration.

In a six-week repeat-dose study, a total of 12 WT, 12 Line 1 (L1) and 12 Line 66 homozygotes (L66+/*) female mice aged 2-months at the beginning of the study were used (Table 32 for group size). Mice in each genotype were injected intraperitoneally (i.p.) with either vehicle or S1D12 (30 mg/kg), once per week, for six consecutive weeks.

All animals were observed for reaction to treatment during each day of dosing and throughout the week. Mice treated with S1D12 were culled seven days after the last dosing whereas vehicle-treated animals were sacrificed the following day, i.e. 8 days post-treatment. Mice were anaesthetized using an overdose of sodium pentobarbital administered intraperitoneally for blood collection. Blood was transferred to plastic vials containing lithium heparin anticoagulant, centrifuged to obtain the plasma and the entire brain was removed as described previously. Plasma and brain samples (stored at −20° C., and −80° C., respectively) were subjected to further biochemical analysis.

TABLE 32

| Genotype (n) | Gender | Route of administration | Treatment | Injection volume (ml/kg) |
|---|---|---|---|---|
| Wild type (6) | F | i.p | Vehicle | 5 |
| Wild type (6) | F | i.p | S1D12 (30 mg/kg) | 5 |
| Line 1 (6) | F | i.p | Vehicle | 5 |
| Line 1 (6) | F | i.p | S1D12 (30 mg/kg) | 5 |
| Line 66 (6) | F | i.p | Vehicle | 5 |
| Line 66 (6) | F | i.p | S1D12 (30 mg/kg) | 5 |

Animals allocated in the repeat dose study. i.p. intraperitoneal.

Example 38: Quantification of S1D12 mAb in the Blood and Brain of Mice Following Repeat Dosing Free S1D12 mAb concentration in the plasma and brain homogenates of wild-type (WT), L1 and L66$^{+/+}$ mice was determined using dGAE ligand binding ELISA as described previously (FIGS. 42 and 43). More than a 3-fold increase in S1D12 concentration was achieved in WT mice plasma following repeat dosing at 30 mg/kg S1D12 once per week for 6 weeks (FIG. 52). Between 0.15-0.3% of plasma S1D12 antibody was shown to cross the blood brain barrier and could be detected in the brain homogenates of WT, L1 and L66$^{+/+}$ mice (FIG. 53).

Example 39: Assessment of Pathologic Human Tau in L66$^{++}$ Brain Homogenates Following 6-Week S1D12 mAb Therapy A hemisphere of each Line 66$^{+/+}$ mouse brain was suspended in RIPA buffer and homogenised. Samples were left on ice for 1 hour and subsequently centrifuged for 10 minutes at 10,000×g at 4° C. The supernatant was collected, and the total protein was quantified using a BCA Protein Assay Kit. Brain homogenate supernatant from each mouse was separated via sodium dodecyl sulphate polyacrylamide gel electrophoresis (SDS-PAGE) with MES running buffer. Gels were subsequently transferred on to a 0.22 µm PVDF membrane, blocked in 2% Marvel before being incubated overnight at 4° C., with S1G2 antibody (367-379 region of hT40) in the same blocking agent. Following washing, the secondary antibody, sheep anti-mouse IgG-HRP, was added, and the membrane was washed five times with PBST and developed with Clarity Western ECL Substrate and read using a BioSpectrum Gel imaging System (UVP). Results were analysed using ImageJ-Fiji (NIH, Version 1.53) where densitometric analysis was performed and the ratio of human to mouse tau densities was calculated.

A decrease in the ratio of human tau to mouse tau in the brains of L66 mAb treated mice was observed compared to the vehicle control group, when a core region specific S1G2 antibody was used for detection (FIG. 54).

Example 40: Assessment of Pathologic Insoluble Tau in L66+/Mouse Brain Homogenates Following 6-week S1D12 mAb Therapy For the extraction of pathology specific insoluble tau, a hemisphere of each Line 66$^{+/+}$ mouse brain was resuspended in TBS buffer supplemented with 1×Halt™ Protease and Phosphatase Inhibitor Cocktail and homogenised. Samples were processed to collect the supernatant as before and the total protein was quantified using a BCA Protein Assay Kit. Each brain homogenate supernatant was mixed with a final concentration of 1% sarkosyl, spun down at 200,000×g for 45 min (fixed angle rotor) and the supernatants retained. Pellets were washed with TBS+1% sarkosyl, spun down again at 200,000×g for 45 min and the resulting pellets were subsequently suspended in 70% formic acid and neutralised with 1 M Tris-base.

Formic acid extraction of sarkosyl-insoluble tau was subsequently analysed by an S1G2-BT2 chemiluminescence sandwich ELISA. Briefly, S1G2 mAb was added to a black 96 well Nunc MaxiSorp plate, and blocked with 2% Marvel. Formic acid-extracted sarkosyl insoluble tau diluted in PBS was added to respective wells and incubated overnight at 4° C. Biotinylated-BT2 at a concentration of 50 ng/ml was used as the detector antibody, incubated for 1 h at 37° C., and a streptavidin poly-HRP was added and incubated as before. For signal generation, SuperSignal™ ELISA Femto Substrate was added to the plate and read within 5 minutes of addition with a ClarioStar Plus plate reader (BMG Labtech). Mean results for L66$^{+/+}$ (vehicle treated) and L66$^{+/+}$ (S1D12 mAb treated) are displayed as relative luminescence units.

The levels of sarkosyl-insoluble tau are reduced in L66$^{+/+}$ mice treated with a repeat dose of S1D12 mAb compared to the vehicle treated group (FIG. 55). The core-proline region fragment is specifically detected using the antibody pairing S1G2-BT2 and a 5-6-fold decrease in mAb-treated mice suggests antibody-mediated clearance of pathology-associated tau from the brain into the blood (further supported by plasma tau analysis data in the following section).

Example 41: Assessment of Plasma Tau Levels in L66$^{+/+}$ Mice Following S1D12 Immunotherapy Using Simoa® Assays In order to monitor the 'treatment effect' of S1D12 mAb, plasma tau samples from vehicle- and antibody-treated L66$^{+/+}$ mice were assessed via multiple Simoa® assays to fully investigate changes in the 'tauosome'. Three-step assays were performed and analysed as per previously described plasma screening methods in this document. Details of the antibody-conjugated beads, biotinylated detectors and plasma dilutions used are shown in Table 33 below:

TABLE 33

| Assay | Capture antibody | Detector antibody | Tau fragment measured (represents amino acid regions on hT40) | Mouse plasma dilution |
|---|---|---|---|---|
| Assay 1 | S1G2 | BT2 | 194-379 | 1:100 |
| Assay 2 | BT2 | HT7 | 159-198 | 1:6 |
| Assay 3 | BT2 | Tau12 | 6-198 | 1:6 |

Antibody pairings used for Simoa ® assays for screening S1D12-treated mouse plasma samples. The capture and detector antibodies used in each assay are given together with the tau fragment that each assay measures and the dilution of mouse plasma required for each antibody pairing.

An increase in plasma tau was detected in mice treated with S1D12 mAb when using a core and proline region specific antibody pairing (S1G2-BT2) in the Simoa® assay. This assay can detect both human and mouse tau and a significant increase in the tau levels was observed in L66$^{+/+}$ mice receiving the antibody treatment (1438±275 µg/ml) vs (425±83 µg/ml) (FIG. 56). The differences in L1 and wild-type groups were not statistically significant. Using the human specific NT1 assay (BT2 capture with Tau12 detection), a four-fold increase in tau levels was measured in the plasma of S1D12 treated L66 mice (3.2±0.42 pg/ml) compared to the levels seen in vehicle-treated group (0.87±0.11 pg/ml) during the same time period (FIG. 57). When using a human-specific, proline region antibody pairing (BT2-HT7), a two-fold increase in plasma tau was observed with S1D12 immunotherapy, however this difference did not reach statistical significance (127±55 µg/ml vs 61±26 µg/ml for S1D12 mAb and vehicle group, respectively) (FIG. 58).

In earlier experiments both LMTM and S1D12 were shown in in vitro aggregation inhibition assays to prevent, block and/or slow the accumulation of potentially disease-causing tau protein aggregates (see FIGS. 34, 35, 36 and 38). As an extension to these in vitro observations and similar to the in vivo findings in LMTM-treated mice shown previously (see FIGS. 50a and 50b), the increase in N-terminal and core-proline tau in the plasma of S1D12 mAb group provides evidence of an antibody-mediated clearance of pathologic tau from the brain in these mice.

Example 42: Tau Aggregation Inhibition Assays In Vitro dGAE protein was diluted into 10 mM phosphate buffer, pH 7.4 (PB) with monoclonal antibody s1D12 at a ratio of 4:1 protein: Ab (100 µM dGAE+25 µM s1D12 and 10 µM dGAE+2.5 µM s1D12) or 1:1 (25 µM dGAE+25 µM s1D12).

As a positive control, dGAE was prepared at a final concentration of 10, 25 or 100 µM in 10 mM PB. Negative controls consisted of dGAE with a non-tau IgG antibody at a ratio of 4:1 (10 µM dGAE+2.5 µM anti-ovalbumin), or antibody alone (25 or 2.5 µM s1D12 and 2.5 µM anti-ovalbumin). Samples were agitated at 700 rpm at 37° C., for 3 days.

Transmission electron microscopy (TEM), circular dichroism (CD) and Thioflavin S (ThS) assays were performed as detailed in Al-Hilaly et, al. (2018) J. Mol. Biol. 430, 4119-4131. Briefly, TEM grids were prepared by adding 4 µL of sample to a carbon-coated grid followed by a wash with milli-Q filtered water then staining twice with 2% uranyl acetate. Grids were air dried and then imaged using a JEOL electron microscope operating at 80 kV.

For CD, 60 µL sample was placed in a 0.1 mm quartz cuvette and placed into a JASCO spectropolarimeter. 100 µL ThS in 20 mM MOPS buffer was added to 50 µL of each sample to a final concentration of 20 µM, mixed well, incubated at room temperature for 10 minutes then fluorescence intensity measured in a Cary Eclipse spectrophotometer using an excitation wavelength of 440 nm. Baseline readings from 10 mM PB were subtracted from CD and ThS measurements.

The findings from these three experiments indicate that s1D12 inhibits the assembly of dGAE into fibrils in vitro.

Firstly, dGAE fibrils were readily observed by TEM in samples using concentrations as low as 10 µM; at the same concentration in the presence of s1D12, no fibrils were present suggesting inhibition of assembly. Fibrils were present when using the same molar ratios of dGAE: Ab with a non-tau antibody, showing that the inhibitory effect is specific.

Circular dichroism reports on secondary structure characteristics of proteins in solution. Although 10 and 25 µM dGAE were too low in concentration to be observed using CD, and the signal is dominated by the characteristic-sheet signal expected from the antibody structure. At 100 µM dGAE, a random coil confirmation is revealed when the antibody CD signal is subtracted from the dGAE signal. This further indicates that for s1D12: dGAE at a ratio of 4:1, dGAE cannot assemble into β-sheet rich fibrils. Finally, Thioflavin S was used to report on the presence of fibrils. ThS is a dye that binds to amyloid, the underlying structure in dGAE fibrils, and fluoresces at a characteristic wavelength of around 483 nm when excited with light of a wavelength of 440 nm. A positive signal was clearly observed for 25 and 100 μM dGAE fibrils. However, when incubated with s1D12 at ratios of either 4:1 or 1:1, this signal was abolished, supporting the previous observations that no fibrils are present when dGAE is incubated with s1D12.

Collectively, these results provide evidence that (i) s1D12 specifically inhibits the assembly of dGAE into fibrils and (ii) these assays can be utilized to determine the inhibitory activity of other antibodies in disrupting formation of fibrils that strongly resemble the paired helical filaments that are present in the tau pathology characteristic of Alzheimer's disease.

---

The invention claimed is:

1. An anti-tau antibody or an antigen-binding fragment thereof that binds amino acids 337-355 of SEQ ID NO:1, wherein the anti-tau antibody or antigen-binding fragment thereof comprises a VH domain comprising the sequence of SEQ ID NO:443 and a VL domain comprising the sequence of SEQ ID NO:444.

2. The anti-tau antibody or antigen-binding fragment thereof of claim 1, wherein the anti-tau antibody is a humanized antibody and/or a monoclonal antibody, and/or the antigen-binding fragment thereof is a Fab or F(ab')2 antibody fragment, or an scFv molecule.

3. A composition comprising multiple anti-tau antibodies or antigen-binding fragments thereof according to claim 1, wherein at least 90% of the anti-tau antibodies or antigen-binding fragments thereof in the composition bind an epitope comprising amino acids 337-355 of SEQ ID NO: 1 with a $K_D$ of less than 25 nM.

4. A pharmaceutical composition comprising the anti-tau antibody or antigen-binding fragment according to claim 1 and one or more pharmaceutically acceptable diluents, carriers or excipients.

5. A kit for detecting a tau protein or a fragment thereof that comprises amino acids 337-355 of SEQ ID NO:1 in a sample, comprising the anti-tau antibody according to claim 1 and reagents for detecting immunocomplexes of the anti-tau antibody with the tau protein or a fragment thereof in the sample by an immunoassay.

6. An isolated nucleic acid molecule comprising a nucleic acid sequence encoding the anti-tau antibody or antigen-binding fragment thereof according to claim 1.

7. The nucleic acid molecule of claim 6, wherein the nucleic acid sequence comprises the sequence of SEQ ID NO: 380.

8. A construct comprising the nucleic acid molecule according to claim 6.

9. A vector comprising the construct of claim 8.

10. An isolated host cell comprising the construct of claim 8.

11. A method of preparing an anti-tau antibody comprising: i) introducing into an isolated host cell the nucleic acid molecule of claim 6; ii) expressing the nucleic acid molecule such that the anti-tau antibody is produced; and iii) purifying and collecting the anti-tau antibody.

12. An anti-tau antibody obtained by the method according to claim 11.

13. An in vitro method of inhibiting aggregation of a tau protein or a fragment thereof, comprising i) incubating the tau protein or fragment thereof with dithiothreitol (DTT) to induce aggregation of the tau protein or fragment thereof; ii) contacting the aggregated tau protein or a fragment thereof with the anti-tau antibody or antigen-binding fragment thereof according to claim 1 or bovine serum albumin as a negative control; iii) detecting reduced levels of aggregation of the aggregated tau protein or fragment thereof treated with the anti-tau antibody or antigen-binding fragment thereof compared to the negative control using a Thioflavin T assay; and wherein the tau protein or fragment thereof comprises amino acids 297-391 of SEQ ID NO: 1.

14. An in vitro method for detecting a tau protein or a fragment thereof that comprises amino acids 337-355 of SEQ ID NO:1 in a sample, comprising contacting the sample with the anti-tau antibody of claim 1 to form an immunocomplex and detecting the immunocomplex of the anti-tau antibody with the tau protein or fragment thereof by an immunoassay.

15. The in vitro method for detecting a tau protein or a fragment thereof according to claim 14, wherein:

(i) the sample is a plasma sample; and/or (ii) the method further comprises a step of denaturing the tau protein or fragment thereof prior to contacting the sample with the anti-tau antibody.

16. A diagnostic method comprising contacting a patient sample that comprises a tau protein or a fragment thereof comprising amino acids 337-355 of SEQ ID NO: 1 with the anti-tau antibody of claim 1 and determining whether the tau protein or the fragment thereof is present in the sample to form an immunocomplex, and detecting the immunocomplex of the anti-tau antibody with the tau protein or fragment thereof by an immunoassay.

\* \* \* \* \*

SEQUENCE LISTING

```
<160> NUMBER OF SEQ ID NOS: 589

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320
```

```
Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
        435                 440

<210> SEQ ID NO 2
<211> LENGTH: 758
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
        130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
        210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
```

-continued

```
               245                250                255

Pro Gly Phe Pro Ala Glu Gly Ala Ile Pro Leu Pro Val Asp Phe Leu
           260                265                270

Ser Lys Val Ser Thr Glu Ile Pro Ala Ser Glu Pro Asp Gly Pro Ser
           275                280                285

Val Gly Arg Ala Lys Gly Gln Asp Ala Pro Leu Glu Phe Thr Phe His
           290                295                300

Val Glu Ile Thr Pro Asn Val Gln Lys Glu Gln Ala His Ser Glu Glu
305                310                315                320

His Leu Gly Arg Ala Ala Phe Pro Gly Ala Pro Gly Glu Gly Pro Glu
               325                330                335

Ala Arg Gly Pro Ser Leu Gly Glu Asp Thr Lys Glu Ala Asp Leu Pro
               340                345                350

Glu Pro Ser Glu Lys Gln Pro Ala Ala Ala Pro Arg Gly Lys Pro Val
               355                360                365

Ser Arg Val Pro Gln Leu Lys Ala Arg Met Val Ser Lys Ser Lys Asp
               370                375                380

Gly Thr Gly Ser Asp Asp Lys Lys Ala Lys Thr Ser Thr Arg Ser Ser
385                390                395                400

Ala Lys Thr Leu Lys Asn Arg Pro Cys Leu Ser Pro Lys His Pro Thr
               405                410                415

Pro Gly Ser Ser Asp Pro Leu Ile Gln Pro Ser Ser Pro Ala Val Cys
               420                425                430

Pro Glu Pro Pro Ser Ser Pro Lys Tyr Val Ser Ser Val Thr Ser Arg
               435                440                445

Thr Gly Ser Ser Gly Ala Lys Glu Met Lys Leu Lys Gly Ala Asp Gly
               450                455                460

Lys Thr Lys Ile Ala Thr Pro Arg Gly Ala Ala Pro Pro Gly Gln Lys
465                470                475                480

Gly Gln Ala Asn Ala Thr Arg Ile Pro Ala Lys Thr Pro Pro Ala Pro
               485                490                495

Lys Thr Pro Pro Ser Ser Gly Glu Pro Pro Lys Ser Gly Asp Arg Ser
               500                505                510

Gly Tyr Ser Ser Pro Gly Ser Pro Gly Thr Pro Gly Ser Arg Ser Arg
               515                520                525

Thr Pro Ser Leu Pro Thr Pro Pro Thr Arg Glu Pro Lys Lys Val Ala
               530                535                540

Val Val Arg Thr Pro Pro Lys Ser Pro Ser Ser Ala Lys Ser Arg Leu
545                550                555                560

Gln Thr Ala Pro Val Pro Met Pro Asp Leu Lys Asn Val Lys Ser Lys
               565                570                575

Ile Gly Ser Thr Glu Asn Leu Lys His Gln Pro Gly Gly Gly Lys Val
               580                585                590

Gln Ile Ile Asn Lys Lys Leu Asp Leu Ser Asn Val Gln Ser Lys Cys
               595                600                605

Gly Ser Lys Asp Asn Ile Lys His Val Pro Gly Gly Gly Ser Val Gln
               610                615                620

Ile Val Tyr Lys Pro Val Asp Leu Ser Lys Val Thr Ser Lys Cys Gly
625                630                635                640

Ser Leu Gly Asn Ile His His Lys Pro Gly Gly Gly Gln Val Glu Val
               645                650                655

Lys Ser Glu Lys Leu Asp Phe Lys Asp Arg Val Gln Ser Lys Ile Gly
               660                665                670
```

-continued

```
Ser Leu Asp Asn Ile Thr His Val Pro Gly Gly Gly Asn Lys Lys Ile
        675             680             685

Glu Thr His Lys Leu Thr Phe Arg Glu Asn Ala Lys Ala Lys Thr Asp
        690             695             700

His Gly Ala Glu Ile Val Tyr Lys Ser Pro Val Val Ser Gly Asp Thr
705             710             715             720

Ser Pro Arg His Leu Ser Asn Val Ser Ser Thr Gly Ser Ile Asp Met
            725             730             735

Val Asp Ser Pro Gln Leu Ala Thr Leu Ala Asp Glu Val Ser Ala Ser
            740             745             750

Leu Ala Lys Gln Gly Leu
        755

<210> SEQ ID NO 3
<211> LENGTH: 97
<212> TYPE: PRT
<213> ORGANISM: Homo sapiens

<400> SEQUENCE: 3

Asp Asn Ile Lys His Val Pro Gly Gly Gly Ser Val Gln Ile Val Tyr
1               5               10              15

Lys Pro Val Asp Leu Ser Lys Val Thr Ser Lys Cys Gly Ser Leu Gly
            20              25              30

Asn Ile His His Lys Pro Gly Gly Gly Gln Val Glu Val Lys Ser Glu
        35              40              45

Lys Leu Asp Phe Lys Asp Arg Val Gln Ser Lys Ile Gly Ser Leu Asp
        50              55              60

Asn Ile Thr His Val Pro Gly Gly Gly Asn Lys Lys Ile Glu Thr His
65              70              75              80

Lys Leu Thr Phe Arg Glu Asn Ala Lys Ala Lys Thr Asp His Gly Ala
                85              90              95

Glu

<210> SEQ ID NO 4
<211> LENGTH: 95
<212> TYPE: PRT
<213> ORGANISM: Homo sapiens

<400> SEQUENCE: 4

Ile Lys His Val Pro Gly Gly Gly Ser Val Gln Ile Val Tyr Lys Pro
1               5               10              15

Val Asp Leu Ser Lys Val Thr Ser Lys Cys Gly Ser Leu Gly Asn Ile
            20              25              30

His His Lys Pro Gly Gly Gly Gln Val Glu Val Lys Ser Glu Lys Leu
        35              40              45

Asp Phe Lys Asp Arg Val Gln Ser Lys Ile Gly Ser Leu Asp Asn Ile
        50              55              60

Thr His Val Pro Gly Gly Gly Asn Lys Lys Ile Glu Thr His Lys Leu
65              70              75              80

Thr Phe Arg Glu Asn Ala Lys Ala Lys Thr Asp His Gly Ala Glu
                85              90              95

<210> SEQ ID NO 5
<211> LENGTH: 94
<212> TYPE: PRT
<213> ORGANISM: Homo sapiens
```

```
<400> SEQUENCE: 5

Ile Lys His Val Pro Gly Gly Gly Ser Val Gln Ile Val Tyr Lys Pro
1               5                   10                  15

Val Asp Leu Ser Lys Val Thr Ser Lys Cys Gly Ser Leu Gly Asn Ile
            20                  25                  30

His His Lys Pro Gly Gly Gly Gln Val Glu Val Lys Ser Glu Lys Leu
        35                  40                  45

Asp Phe Lys Asp Arg Val Gln Ser Lys Ile Gly Ser Leu Asp Asn Ile
    50                  55                  60

Thr His Val Pro Gly Gly Gly Asn Lys Lys Ile Glu Thr His Lys Leu
65                  70                  75                  80

Thr Phe Arg Glu Asn Ala Lys Ala Lys Thr Asp His Gly Ala
                85                  90

<210> SEQ ID NO 6
<211> LENGTH: 73
<212> TYPE: PRT
<213> ORGANISM: Homo sapiens

<400> SEQUENCE: 6

Val Gln Ile Val Tyr Lys Pro Val Asp Leu Ser Lys Val Thr Ser Lys
1               5                   10                  15

Cys Gly Ser Leu Gly Asn Ile His His Lys Pro Gly Gly Gly Gln Val
            20                  25                  30

Glu Val Lys Ser Glu Lys Leu Asp Phe Lys Asp Arg Val Gln Ser Lys
        35                  40                  45

Ile Gly Ser Leu Asp Asn Ile Thr His Val Pro Gly Gly Gly Asn Lys
    50                  55                  60

Lys Ile Glu Thr His Lys Leu Thr Phe
65                  70

<210> SEQ ID NO 7
<211> LENGTH: 71
<212> TYPE: PRT
<213> ORGANISM: Homo sapiens

<400> SEQUENCE: 7

Ile Val Tyr Lys Pro Val Asp Leu Ser Lys Val Thr Ser Lys Cys Gly
1               5                   10                  15

Ser Leu Gly Asn Ile His His Lys Pro Gly Gly Gly Gln Val Glu Val
            20                  25                  30

Lys Ser Glu Lys Leu Asp Phe Lys Asp Arg Val Gln Ser Lys Ile Gly
        35                  40                  45

Ser Leu Asp Asn Ile Thr His Val Pro Gly Gly Gly Asn Lys Lys Ile
    50                  55                  60

Glu Thr His Lys Leu Thr Phe
65                  70

<210> SEQ ID NO 8
<211> LENGTH: 13
<212> TYPE: PRT
<213> ORGANISM: artificial sequence
<220> FEATURE:
<223> OTHER INFORMATION: S1D12 epitope

<400> SEQUENCE: 8

Val Glu Val Lys Ser Glu Lys Leu Asp Phe Lys Asp Arg
1               5                   10
```

```
<210> SEQ ID NO 9
<211> LENGTH: 14
<212> TYPE: PRT
<213> ORGANISM: artificial sequence
<220> FEATURE:
<223> OTHER INFORMATION: S1D12 general epitope
<220> FEATURE:
<221> NAME/KEY: MISC_FEATURE
<222> LOCATION: (1)..(13)
<223> OTHER INFORMATION: Where X is any amino acid

<400> SEQUENCE: 9

Xaa Xaa Xaa Xaa Xaa Xaa Xaa Lys Xaa Xaa Phe Xaa Xaa Arg
1               5                   10

<210> SEQ ID NO 10
<211> LENGTH: 5
<212> TYPE: PRT
<213> ORGANISM: artificial sequence
<220> FEATURE:
<223> OTHER INFORMATION: 337-355 VHCDR1 consensus
<220> FEATURE:
<221> NAME/KEY: MISC_FEATURE
<222> LOCATION: (1)..(1)
<223> OTHER INFORMATION: N or S

<400> SEQUENCE: 10

Xaa Asn Ala Val Gly
1               5

<210> SEQ ID NO 11
<211> LENGTH: 16
<212> TYPE: PRT
<213> ORGANISM: artificial sequence
<220> FEATURE:
<223> OTHER INFORMATION: 337-355 VHCDR2 consensus
<220> FEATURE:
<221> NAME/KEY: MISC_FEATURE
<222> LOCATION: (7)..(7)
<223> OTHER INFORMATION: T or K
<220> FEATURE:
<221> NAME/KEY: MISC_FEATURE
<222> LOCATION: (10)..(10)
<223> OTHER INFORMATION: Y or H

<400> SEQUENCE: 11

Gly Cys Ser Ser Asp Gly Xaa Cys Tyr Xaa Asn Ser Ala Leu Lys Ser
1               5                   10                  15

<210> SEQ ID NO 12
<211> LENGTH: 16
<212> TYPE: PRT
<213> ORGANISM: artificial sequence
<220> FEATURE:
<223> OTHER INFORMATION: 337-355 VHCDR3 consensus
<220> FEATURE:
<221> NAME/KEY: MISC_FEATURE
<222> LOCATION: (2)..(2)
<223> OTHER INFORMATION: H or F or Y
<220> FEATURE:
<221> NAME/KEY: MISC_FEATURE
<222> LOCATION: (4)..(4)
<223> OTHER INFORMATION: S or P
<220> FEATURE:
<221> NAME/KEY: MISC_FEATURE
<222> LOCATION: (5)..(5)
<223> OTHER INFORMATION: I or V
<220> FEATURE:
<221> NAME/KEY: MISC_FEATURE
<222> LOCATION: (11)..(11)
<223> OTHER INFORMATION: L or S
```

-continued

```
<400> SEQUENCE: 12

Gly Xaa Tyr Xaa Xaa Tyr Gly Tyr Asp Tyr Xaa Gly Thr Ile Asp Tyr
1               5                   10                  15

<210> SEQ ID NO 13
<211> LENGTH: 14
<212> TYPE: PRT
<213> ORGANISM: artificial sequence
<220> FEATURE:
<223> OTHER INFORMATION: 337-355 VLCDR1 consensus
<220> FEATURE:
<221> NAME/KEY: MISC_FEATURE
<222> LOCATION: (8)..(8)
<223> OTHER INFORMATION: G or nothing
<220> FEATURE:
<221> NAME/KEY: MISC_FEATURE
<222> LOCATION: (10)..(10)
<223> OTHER INFORMATION: G or R
<220> FEATURE:
<221> NAME/KEY: MISC_FEATURE
<222> LOCATION: (12)..(12)
<223> OTHER INFORMATION: S or D
<220> FEATURE:
<221> NAME/KEY: MISC_FEATURE
<222> LOCATION: (14)..(14)
<223> OTHER INFORMATION: G or A

<400> SEQUENCE: 13

Ser Gly Ser Ser Ser Asn Val Xaa Gly Xaa Asn Xaa Val Xaa
1               5                   10

<210> SEQ ID NO 14
<211> LENGTH: 7
<212> TYPE: PRT
<213> ORGANISM: artificial sequence
<220> FEATURE:
<223> OTHER INFORMATION: 337-355 VLCDR2 consensus
<220> FEATURE:
<221> NAME/KEY: MISC_FEATURE
<222> LOCATION: (1)..(1)
<223> OTHER INFORMATION: D or N or G
<220> FEATURE:
<221> NAME/KEY: MISC_FEATURE
<222> LOCATION: (3)..(3)
<223> OTHER INFORMATION: N or T

<400> SEQUENCE: 14

Xaa Thr Xaa Ser Arg Pro Ser
1               5

<210> SEQ ID NO 15
<211> LENGTH: 11
<212> TYPE: PRT
<213> ORGANISM: artificial sequence
<220> FEATURE:
<223> OTHER INFORMATION: 337-355 VLCDR3 consensus
<220> FEATURE:
<221> NAME/KEY: MISC_FEATURE
<222> LOCATION: (1)..(1)
<223> OTHER INFORMATION: V or A
<220> FEATURE:
<221> NAME/KEY: MISC_FEATURE
<222> LOCATION: (2)..(2)
<223> OTHER INFORMATION: T or S
<220> FEATURE:
<221> NAME/KEY: MISC_FEATURE
<222> LOCATION: (6)..(6)
<223> OTHER INFORMATION: T or S
<220> FEATURE:
<221> NAME/KEY: MISC_FEATURE
<222> LOCATION: (7)..(7)
<223> OTHER INFORMATION: T or A
<220> FEATURE:
```

-continued

```
<221> NAME/KEY: MISC_FEATURE
<222> LOCATION: (8)..(8)
<223> OTHER INFORMATION: H or I
<220> FEATURE:
<221> NAME/KEY: MISC_FEATURE
<222> LOCATION: (9)..(9)
<223> OTHER INFORMATION: D or N
<220> FEATURE:
<221> NAME/KEY: MISC_FEATURE
<222> LOCATION: (11)..(11)
<223> OTHER INFORMATION: L or I

<400> SEQUENCE: 15

Xaa Xaa Gly Asp Ser Xaa Xaa Xaa Xaa Asp Xaa
1               5                   10

<210> SEQ ID NO 16
<211> LENGTH: 5
<212> TYPE: PRT
<213> ORGANISM: artificial sequence
<220> FEATURE:
<223> OTHER INFORMATION: VHCDR1 S1D12, S2C1

<400> SEQUENCE: 16

Asn Asn Ala Val Gly
1               5

<210> SEQ ID NO 17
<211> LENGTH: 5
<212> TYPE: PRT
<213> ORGANISM: artificial sequence
<220> FEATURE:
<223> OTHER INFORMATION: VHCDR1 ME12, NS3D9; VHCDR1 S1D2, S1H6, S2C3;
      VHCDR1 MC5, MD12; VHCDR1 3aA6, VHCDR1 CE3

<400> SEQUENCE: 17

Ser Asn Ala Val Gly
1               5

<210> SEQ ID NO 18
<211> LENGTH: 16
<212> TYPE: PRT
<213> ORGANISM: artificial sequence
<220> FEATURE:
<223> OTHER INFORMATION: VHCDR2 S1D12, S2C1

<400> SEQUENCE: 18

Gly Cys Ser Ser Asp Gly Thr Cys Tyr Tyr Asn Ser Ala Leu Lys Ser
1               5                   10                  15

<210> SEQ ID NO 19
<211> LENGTH: 16
<212> TYPE: PRT
<213> ORGANISM: artificial sequence
<220> FEATURE:
<223> OTHER INFORMATION: VHCDR2 ME12

<400> SEQUENCE: 19

Gly Cys Ser Ser Asp Gly Lys Cys Tyr His Asn Ser Ala Leu Lys Ser
1               5                   10                  15

<210> SEQ ID NO 20
<211> LENGTH: 16
<212> TYPE: PRT
<213> ORGANISM: artificial sequence
<220> FEATURE:
<223> OTHER INFORMATION: VHCDR2 NS3D9, CE3

<400> SEQUENCE: 20
```

-continued

```
Gly Cys Ser Ser Asp Gly Lys Cys Tyr Tyr Asn Ser Ala Leu Lys Ser
1               5                   10                  15

<210> SEQ ID NO 21
<211> LENGTH: 16
<212> TYPE: PRT
<213> ORGANISM: artificial sequence
<220> FEATURE:
<223> OTHER INFORMATION: VHCDR3 S1D12

<400> SEQUENCE: 21

Gly His Tyr Ser Ile Tyr Gly Tyr Asp Tyr Leu Gly Thr Ile Asp Tyr
1               5                   10                  15

<210> SEQ ID NO 22
<211> LENGTH: 16
<212> TYPE: PRT
<213> ORGANISM: artificial sequence
<220> FEATURE:
<223> OTHER INFORMATION: VHCDR3 ME12

<400> SEQUENCE: 22

Gly Phe Tyr Ser Ile Tyr Gly Tyr Asp Tyr Ser Gly Thr Ile Asp Tyr
1               5                   10                  15

<210> SEQ ID NO 23
<211> LENGTH: 16
<212> TYPE: PRT
<213> ORGANISM: artificial sequence
<220> FEATURE:
<223> OTHER INFORMATION: VHCDR3 NS3D9, CE3

<400> SEQUENCE: 23

Gly Tyr Tyr Pro Val Tyr Gly Tyr Asp Tyr Leu Gly Thr Ile Asp Tyr
1               5                   10                  15

<210> SEQ ID NO 24
<211> LENGTH: 14
<212> TYPE: PRT
<213> ORGANISM: artificial sequence
<220> FEATURE:
<223> OTHER INFORMATION: VLCDR1 S1D12, ME12

<400> SEQUENCE: 24

Ser Gly Ser Ser Ser Asn Val Gly Gly Gly Asn Ser Val Gly
1               5                   10

<210> SEQ ID NO 25
<211> LENGTH: 13
<212> TYPE: PRT
<213> ORGANISM: artificial sequence
<220> FEATURE:
<223> OTHER INFORMATION: VLCDR1 NS3D9, CE3

<400> SEQUENCE: 25

Ser Gly Ser Ser Ser Asn Val Gly Arg Asn Asp Val Ala
1               5                   10

<210> SEQ ID NO 26
<211> LENGTH: 7
<212> TYPE: PRT
<213> ORGANISM: artificial sequence
<220> FEATURE:
<223> OTHER INFORMATION: VLCDR2 S1D12

<400> SEQUENCE: 26
```

-continued

```
Asp Thr Asn Ser Arg Pro Ser
1               5

<210> SEQ ID NO 27
<211> LENGTH: 7
<212> TYPE: PRT
<213> ORGANISM: artificial sequence
<220> FEATURE:
<223> OTHER INFORMATION: VLCDR2 ME12

<400> SEQUENCE: 27

Asn Thr Asn Ser Arg Pro Ser
1               5

<210> SEQ ID NO 28
<211> LENGTH: 7
<212> TYPE: PRT
<213> ORGANISM: artificial sequence
<220> FEATURE:
<223> OTHER INFORMATION: VLCDR2 NS3D9, CE3

<400> SEQUENCE: 28

Gly Thr Thr Ser Arg Pro Ser
1               5

<210> SEQ ID NO 29
<211> LENGTH: 11
<212> TYPE: PRT
<213> ORGANISM: artificial sequence
<220> FEATURE:
<223> OTHER INFORMATION: VLCDR3 S1D12

<400> SEQUENCE: 29

Val Thr Gly Asp Ser Thr Thr His Asp Asp Leu
1               5                   10

<210> SEQ ID NO 30
<211> LENGTH: 11
<212> TYPE: PRT
<213> ORGANISM: artificial sequence
<220> FEATURE:
<223> OTHER INFORMATION: VLCDR3 ME12

<400> SEQUENCE: 30

Val Thr Gly Asp Ser Ser Thr His Asp Asp Leu
1               5                   10

<210> SEQ ID NO 31
<211> LENGTH: 11
<212> TYPE: PRT
<213> ORGANISM: artificial sequence
<220> FEATURE:
<223> OTHER INFORMATION: VLCDR3 NS3D9, CE3

<400> SEQUENCE: 31

Ala Ser Gly Asp Ser Ser Ala Ile Asn Asp Ile
1               5                   10

<210> SEQ ID NO 32
<211> LENGTH: 251
<212> TYPE: PRT
<213> ORGANISM: artificial sequence
<220> FEATURE:
<223> OTHER INFORMATION: S1D12 amino acid sequence

<400> SEQUENCE: 32

Gln Val Gln Leu Gln Glu Ser Gly Pro Ser Leu Val Lys Pro Ser Gln
```

```
1               5                10               15

Thr Leu Ser Leu Thr Cys Thr Val Ser Gly Phe Ser Leu Asn Asn Asn
            20               25               30

Ala Val Gly Trp Val Arg Gln Ala Pro Gly Lys Val Pro Glu Ser Leu
            35               40               45

Val Gly Cys Ser Ser Asp Gly Thr Cys Tyr Tyr Asn Ser Ala Leu Lys
    50               55               60

Ser Arg Leu Asp Ile Thr Arg Asp Thr Ser Lys Asn Gln Ile Ser Leu
65               70               75               80

Ser Leu Ser Ser Val Thr Thr Asp Asp Ala Ala Val Tyr Tyr Cys Thr
            85               90               95

Arg Gly His Tyr Ser Ile Tyr Gly Tyr Asp Tyr Leu Gly Thr Ile Asp
            100              105              110

Tyr Trp Gly Pro Gly Leu Leu Val Thr Val Ser Ser Glu Gly Lys Ser
            115              120              125

Ser Gly Ala Ser Gly Glu Ser Lys Val Asp Asp Gln Ala Val Leu Thr
    130              135              140

Gln Pro Ser Ser Val Ser Gly Ser Leu Gly Gln Arg Val Ser Ile Thr
145              150              155              160

Cys Ser Gly Ser Ser Ser Asn Val Gly Gly Gly Asn Ser Val Gly Trp
            165              170              175

Tyr Gln His Leu Pro Gly Ser Gly Leu Lys Thr Ile Ile Tyr Asp Thr
            180              185              190

Asn Ser Arg Pro Ser Gly Val Pro Asp Arg Phe Ser Gly Ser Arg Ser
            195              200              205

Gly Asn Thr Ala Thr Leu Thr Ile Asn Ser Leu Gln Ala Glu Asp Glu
    210              215              220

Gly Asp Tyr Tyr Cys Val Thr Gly Asp Ser Thr Thr His Asp Asp Leu
225              230              235              240

Val Gly Ser Gly Thr Arg Leu Thr Val Leu Gly
            245              250
```

```
<210> SEQ ID NO 33
<211> LENGTH: 13
<212> TYPE: PRT
<213> ORGANISM: Homo sapiens

<400> SEQUENCE: 33

Gly Asn Lys Lys Ile Glu Thr His Lys Leu Thr Phe Arg
1               5                10

<210> SEQ ID NO 34
<211> LENGTH: 13
<212> TYPE: PRT
<213> ORGANISM: artificial sequence
<220> FEATURE:
<223> OTHER INFORMATION: S1G2, CA9, CA12 general epitope
<220> FEATURE:
<221> NAME/KEY: MISC_FEATURE
<222> LOCATION: (1)..(13)
<223> OTHER INFORMATION: Where X is any amino acid

<400> SEQUENCE: 34

Xaa Xaa Xaa Lys Xaa Xaa Xaa His Xaa Xaa Xaa Xaa Xaa
1               5                10

<210> SEQ ID NO 35
<211> LENGTH: 5
<212> TYPE: PRT
```

```
<213> ORGANISM: artificial sequence
<220> FEATURE:
<223> OTHER INFORMATION: 367 to 379 VHCDR1 consensus
<220> FEATURE:
<221> NAME/KEY: MISC_FEATURE
<222> LOCATION: (1)..(1)
<223> OTHER INFORMATION: S or T
<220> FEATURE:
<221> NAME/KEY: MISC_FEATURE
<222> LOCATION: (2)..(2)
<223> OTHER INFORMATION: N or Y
<220> FEATURE:
<221> NAME/KEY: MISC_FEATURE
<222> LOCATION: (3)..(3)
<223> OTHER INFORMATION: S or A or Y

<400> SEQUENCE: 35

Xaa Xaa Xaa Val Gly
1               5

<210> SEQ ID NO 36
<211> LENGTH: 16
<212> TYPE: PRT
<213> ORGANISM: artificial sequence
<220> FEATURE:
<223> OTHER INFORMATION: 367 to 379 VHCDR2 consensus
<220> FEATURE:
<221> NAME/KEY: MISC_FEATURE
<222> LOCATION: (1)..(1)
<223> OTHER INFORMATION: G or S or N
<220> FEATURE:
<221> NAME/KEY: MISC_FEATURE
<222> LOCATION: (2)..(2)
<223> OTHER INFORMATION: I or V
<220> FEATURE:
<221> NAME/KEY: MISC_FEATURE
<222> LOCATION: (3)..(3)
<223> OTHER INFORMATION: D or Y
<220> FEATURE:
<221> NAME/KEY: MISC_FEATURE
<222> LOCATION: (4)..(4)
<223> OTHER INFORMATION: T or S
<220> FEATURE:
<221> NAME/KEY: MISC_FEATURE
<222> LOCATION: (5)..(5)
<223> OTHER INFORMATION: D or T
<220> FEATURE:
<221> NAME/KEY: MISC_FEATURE
<222> LOCATION: (7)..(7)
<223> OTHER INFORMATION: E or Y or D or R
<220> FEATURE:
<221> NAME/KEY: MISC_FEATURE
<222> LOCATION: (8)..(8)
<223> OTHER INFORMATION: E or T or A
<220> FEATURE:
<221> NAME/KEY: MISC_FEATURE
<222> LOCATION: (9)..(9)
<223> OTHER INFORMATION: G or Y or F
<220> FEATURE:
<221> NAME/KEY: MISC_FEATURE
<222> LOCATION: (10)..(10)
<223> OTHER INFORMATION: Y or F
<220> FEATURE:
<221> NAME/KEY: MISC_FEATURE
<222> LOCATION: (13)..(13)
<223> OTHER INFORMATION: A or V
<220> FEATURE:
<221> NAME/KEY: MISC_FEATURE
<222> LOCATION: (15)..(15)
<223> OTHER INFORMATION: N or K

<400> SEQUENCE: 36

Xaa Xaa Xaa Xaa Xaa Gly Xaa Xaa Xaa Xaa Asn Pro Xaa Leu Xaa Ser
1               5                   10                  15
```

-continued

```
<210> SEQ ID NO 37
<211> LENGTH: 17
<212> TYPE: PRT
<213> ORGANISM: artificial sequence
<220> FEATURE:
<223> OTHER INFORMATION: 367 to 379 VHCDR3 consensus
<220> FEATURE:
<221> NAME/KEY: MISC_FEATURE
<222> LOCATION: (1)..(1)
<223> OTHER INFORMATION: S or T
<220> FEATURE:
<221> NAME/KEY: MISC_FEATURE
<222> LOCATION: (2)..(2)
<223> OTHER INFORMATION: Y or V or A
<220> FEATURE:
<221> NAME/KEY: MISC_FEATURE
<222> LOCATION: (3)..(3)
<223> OTHER INFORMATION: R or N
<220> FEATURE:
<221> NAME/KEY: MISC_FEATURE
<222> LOCATION: (4)..(4)
<223> OTHER INFORMATION: A or T or G or S
<220> FEATURE:
<221> NAME/KEY: MISC_FEATURE
<222> LOCATION: (5)..(5)
<223> OTHER INFORMATION: D or nothing
<220> FEATURE:
<221> NAME/KEY: MISC_FEATURE
<222> LOCATION: (6)..(6)
<223> OTHER INFORMATION: G or nothing
<220> FEATURE:
<221> NAME/KEY: MISC_FEATURE
<222> LOCATION: (7)..(7)
<223> OTHER INFORMATION: L or Y or F or nothing
<220> FEATURE:
<221> NAME/KEY: MISC_FEATURE
<222> LOCATION: (8)..(8)
<223> OTHER INFORMATION: A or nothing
<220> FEATURE:
<221> NAME/KEY: MISC_FEATURE
<222> LOCATION: (9)..(9)
<223> OTHER INFORMATION: Y or H
<220> FEATURE:
<221> NAME/KEY: MISC_FEATURE
<222> LOCATION: (10)..(10)
<223> OTHER INFORMATION: G or P
<220> FEATURE:
<221> NAME/KEY: MISC_FEATURE
<222> LOCATION: (11)..(11)
<223> OTHER INFORMATION: Y or D
<220> FEATURE:
<221> NAME/KEY: MISC_FEATURE
<222> LOCATION: (13)..(13)
<223> OTHER INFORMATION: Q or Y
<220> FEATURE:
<221> NAME/KEY: MISC_FEATURE
<222> LOCATION: (14)..(14)
<223> OTHER INFORMATION: A or Y
<220> FEATURE:
<221> NAME/KEY: MISC_FEATURE
<222> LOCATION: (16)..(16)
<223> OTHER INFORMATION: D or E
<220> FEATURE:
<221> NAME/KEY: MISC_FEATURE
<222> LOCATION: (17)..(17)
<223> OTHER INFORMATION: Y or R or K

<400> SEQUENCE: 37

Xaa Xaa Xaa Xaa Xaa Xaa Xaa Xaa Xaa Xaa Xaa Val Xaa Xaa Ile Xaa
1               5                   10                  15

Xaa

<210> SEQ ID NO 38
<211> LENGTH: 11
<212> TYPE: PRT
<213> ORGANISM: artificial sequence
```

```
<220> FEATURE:
<223> OTHER INFORMATION: 367 to 379 VLCDR1 consensus
<220> FEATURE:
<221> NAME/KEY: MISC_FEATURE
<222> LOCATION: (3)..(3)
<223> OTHER INFORMATION: S or R
<220> FEATURE:
<221> NAME/KEY: MISC_FEATURE
<222> LOCATION: (4)..(4)
<223> OTHER INFORMATION: F or Y or D
<220> FEATURE:
<221> NAME/KEY: MISC_FEATURE
<222> LOCATION: (5)..(5)
<223> OTHER INFORMATION: I or L or V
<220> FEATURE:
<221> NAME/KEY: MISC_FEATURE
<222> LOCATION: (6)..(6)
<223> OTHER INFORMATION: G or S
<220> FEATURE:
<221> NAME/KEY: MISC_FEATURE
<222> LOCATION: (7)..(7)
<223> OTHER INFORMATION: I or S or R
<220> FEATURE:
<221> NAME/KEY: MISC_FEATURE
<222> LOCATION: (9)..(9)
<223> OTHER INFORMATION: S or R or A or G

<400> SEQUENCE: 38

Ser Gly Xaa Xaa Xaa Xaa Xaa Ser Xaa Val Gly
1               5                   10

<210> SEQ ID NO 39
<211> LENGTH: 14
<212> TYPE: PRT
<213> ORGANISM: artificial sequence
<220> FEATURE:
<223> OTHER INFORMATION: CC5, CA12, CA7, 412E10 and 412G11 VLCDR1

<400> SEQUENCE: 39

Ser Gly Ser Ser Ser Asn Val Gly Tyr Gly Asn Tyr Val Gly
1               5                   10

<210> SEQ ID NO 40
<211> LENGTH: 7
<212> TYPE: PRT
<213> ORGANISM: artificial sequence
<220> FEATURE:
<223> OTHER INFORMATION: 367 to 379 VLCDR2 consensus
<220> FEATURE:
<221> NAME/KEY: MISC_FEATURE
<222> LOCATION: (1)..(1)
<223> OTHER INFORMATION: A or D
<220> FEATURE:
<221> NAME/KEY: MISC_FEATURE
<222> LOCATION: (2)..(2)
<223> OTHER INFORMATION: S or A
<220> FEATURE:
<221> NAME/KEY: MISC_FEATURE
<222> LOCATION: (3)..(3)
<223> OTHER INFORMATION: D or S or T
<220> FEATURE:
<221> NAME/KEY: MISC_FEATURE
<222> LOCATION: (4)..(4)
<223> OTHER INFORMATION: G or S
<220> FEATURE:
<221> NAME/KEY: MISC_FEATURE
<222> LOCATION: (6)..(6)
<223> OTHER INFORMATION: P or A

<400> SEQUENCE: 40

Xaa Xaa Xaa Xaa Arg Xaa Ser
1               5
```

-continued

```
<210> SEQ ID NO 41
<211> LENGTH: 11
<212> TYPE: PRT
<213> ORGANISM: artificial sequence
<220> FEATURE:
<223> OTHER INFORMATION: 367 to 379 VLCDR3 consensus
<220> FEATURE:
<221> NAME/KEY: MISC_FEATURE
<222> LOCATION: (1)..(1)
<223> OTHER INFORMATION: G or S
<220> FEATURE:
<221> NAME/KEY: MISC_FEATURE
<222> LOCATION: (2)..(2)
<223> OTHER INFORMATION: S or I or V
<220> FEATURE:
<221> NAME/KEY: MISC_FEATURE
<222> LOCATION: (3)..(3)
<223> OTHER INFORMATION: S or F or Y or T
<220> FEATURE:
<221> NAME/KEY: MISC_FEATURE
<222> LOCATION: (4)..(4)
<223> OTHER INFORMATION: D or G or A or Q
<220> FEATURE:
<221> NAME/KEY: MISC_FEATURE
<222> LOCATION: (5)..(5)
<223> OTHER INFORMATION: R or P or nothing
<220> FEATURE:
<221> NAME/KEY: MISC_FEATURE
<222> LOCATION: (6)..(6)
<223> OTHER INFORMATION: T or nothing
<220> FEATURE:
<221> NAME/KEY: MISC_FEATURE
<222> LOCATION: (7)..(7)
<223> OTHER INFORMATION: P or Q or D or G
<220> FEATURE:
<221> NAME/KEY: MISC_FEATURE
<222> LOCATION: (8)..(8)
<223> OTHER INFORMATION: Y or R or H or N
<220> FEATURE:
<221> NAME/KEY: MISC_FEATURE
<222> LOCATION: (9)..(9)
<223> OTHER INFORMATION: T or N
<220> FEATURE:
<221> NAME/KEY: MISC_FEATURE
<222> LOCATION: (10)..(10)
<223> OTHER INFORMATION: G or Y
<220> FEATURE:
<221> NAME/KEY: MISC_FEATURE
<222> LOCATION: (11)..(11)
<223> OTHER INFORMATION: V or I or L

<400> SEQUENCE: 41

Xaa Xaa Xaa Xaa Xaa Xaa Xaa Xaa Xaa Xaa Xaa
1               5                   10

<210> SEQ ID NO 42
<211> LENGTH: 5
<212> TYPE: PRT
<213> ORGANISM: artificial sequence
<220> FEATURE:
<223> OTHER INFORMATION: VHCDR1 S1G2, S1B1, S1D9, S1F4, S1G10, S1H9,
      S2C6, S2D1, S2D4, CA9, CC12, S1A12, S1A5, S1E12, CB9

<400> SEQUENCE: 42

Ser Asn Ser Val Gly
1               5

<210> SEQ ID NO 43
<211> LENGTH: 729
<212> TYPE: PRT
<213> ORGANISM: artificial sequence
<220> FEATURE:
<223> OTHER INFORMATION: E2B7 nucleotide sequence

<400> SEQUENCE: 43
```

-continued

```
Cys Ala Gly Gly Thr Gly Cys Ala Gly Cys Thr Gly Cys Ala Gly Gly
1               5                   10                  15

Ala Gly Thr Cys Gly Gly Gly Ala Cys Cys Ala Gly Cys Cys Thr
            20                  25                  30

Gly Gly Thr Gly Ala Ala Gly Cys Cys Cys Thr Cys Ala Cys Ala Gly
        35                  40                  45

Ala Cys Cys Cys Thr Cys Thr Cys Cys Cys Thr Cys Ala Cys Cys Thr
    50                  55                  60

Gly Cys Ala Cys Gly Gly Thr Cys Thr Cys Thr Gly Gly Ala Thr Thr
65              70                  75                  80

Cys Thr Cys Ala Thr Thr Ala Ala Cys Cys Ala Gly Cys Thr Gly Gly
                85                  90                  95

Gly Gly Thr Gly Thr Ala Gly Cys Thr Thr Gly Gly Gly Thr Cys Cys
        100                 105                 110

Gly Cys Cys Ala Gly Gly Cys Thr Cys Cys Ala Gly Gly Ala Ala Ala
    115                 120                 125

Gly Gly Cys Ala Cys Thr Gly Gly Ala Gly Thr Gly Gly Cys Thr Thr
    130                 135                 140

Gly Gly Thr Ala Cys Cys Ala Thr Gly Cys Gly Thr Ala Gly Thr Gly
145             150                 155                 160

Gly Thr Gly Gly Thr Gly Gly Thr Ala Cys Ala Gly Ala Ala Thr Ala
            165                 170                 175

Thr Ala Ala Thr Cys Cys Gly Gly Cys Cys Cys Thr Gly Ala Ala Ala
            180                 185                 190

Thr Cys Cys Cys Gly Cys Cys Thr Cys Ala Gly Cys Ala Thr Cys Ala
            195                 200                 205

Cys Cys Ala Gly Gly Gly Ala Cys Ala Cys Cys Thr Cys Cys Ala Ala
    210                 215                 220

Gly Ala Gly Cys Cys Ala Ala Gly Thr Cys Thr Cys Cys Cys Thr Gly
225             230                 235                 240

Thr Cys Ala Cys Thr Gly Ala Gly Cys Ala Gly Cys Gly Thr Gly Ala
            245                 250                 255

Cys Ala Ala Cys Thr Gly Ala Gly Gly Ala Cys Ala Thr Gly Gly Cys
        260                 265                 270

Cys Ala Thr Gly Thr Ala Cys Thr Ala Cys Thr Gly Thr Gly Cys Cys
    275                 280                 285

Ala Gly Ala Gly Gly Thr Thr Ala Thr Thr Thr Gly Ala Gly Thr Gly
    290                 295                 300

Gly Thr Ala Thr Thr Cys Ala Thr Thr Ala Thr Gly Cys Cys Thr Gly
305             310                 315                 320

Gly Gly Gly Cys Cys Gly Ala Gly Gly Ala Cys Thr Cys Cys Thr Ala
            325                 330                 335

Gly Thr Cys Thr Cys Cys Gly Thr Cys Thr Cys Cys Thr Cys Ala Gly
        340                 345                 350

Ala Ala Gly Gly Thr Ala Ala Ala Thr Cys Thr Thr Cys Thr Gly Gly
        355                 360                 365

Cys Gly Cys Gly Thr Cys Thr Gly Gly Cys Gly Ala Gly Thr Cys Thr
    370                 375                 380

Ala Ala Ala Gly Thr Gly Gly Ala Thr Gly Ala Cys Cys Ala Gly Gly
385             390                 395                 400

Cys Thr Gly Thr Gly Cys Thr Gly Ala Cys Thr Cys Ala Gly Cys Thr
        405                 410                 415
```

-continued

```
Gly Thr Cys Cys Thr Cys Cys Gly Thr Gly Thr Cys Thr Gly Gly Gly
            420                 425                 430

Thr Cys Cys Cys Thr Gly Gly Gly Cys Cys Ala Gly Ala Gly Gly Gly
            435                 440                 445

Thr Cys Thr Cys Cys Ala Thr Cys Ala Cys Cys Thr Gly Cys Thr Cys
            450                 455                 460

Thr Gly Gly Ala Ala Gly Cys Ala Gly Cys Ala Gly Cys Ala Ala Cys
465                 470                 475                 480

Gly Thr Thr Gly Gly Ala Gly Ala Thr Gly Gly Thr Gly Ala Thr Thr
                485                 490                 495

Ala Thr Gly Thr Gly Gly Gly Cys Thr Gly Gly Thr Thr Cys Cys Ala
                500                 505                 510

Ala Cys Ala Gly Cys Thr Cys Cys Cys Ala Gly Gly Ala Thr Cys Ala
            515                 520                 525

Gly Cys Cys Cys Cys Cys Ala Ala Ala Cys Thr Cys Cys Thr Cys Ala
            530                 535                 540

Thr Cys Thr Ala Thr Ala Gly Thr Gly Cys Gly Cys Gly Cys Ala Ala
545                 550                 555                 560

Thr Cys Gly Ala Gly Cys Cys Thr Cys Gly Gly Gly Gly Thr Cys
            565                 570                 575

Cys Cys Cys Gly Ala Cys Cys Gly Ala Thr Thr Cys Thr Cys Cys Gly
            580                 585                 590

Gly Cys Thr Cys Cys Ala Gly Gly Thr Cys Thr Gly Gly Cys Ala Ala
            595                 600                 605

Cys Ala Cys Ala Gly Cys Gly Ala Cys Thr Cys Thr Ala Ala Cys Cys
            610                 615                 620

Ala Thr Cys Ala Cys Cys Thr Cys Gly Cys Thr Cys Cys Ala Gly Gly
625                 630                 635                 640

Cys Thr Gly Ala Gly Gly Ala Cys Gly Ala Gly Gly Cys Cys Gly Ala
            645                 650                 655

Thr Thr Ala Thr Thr Ala Cys Thr Gly Thr Gly Cys Ala Thr Cys Thr
            660                 665                 670

Ala Thr Thr Gly Ala Cys Ala Cys Cys Ala Gly Thr Cys Gly Cys Thr
            675                 680                 685

Cys Thr Cys Ala Cys Ala Thr Thr Thr Thr Cys Gly Gly Cys Ala Gly
            690                 695                 700

Cys Gly Gly Gly Ala Cys Cys Ala Gly Ala Cys Thr Gly Ala Cys Cys
705                 710                 715                 720

Gly Thr Cys Cys Thr Gly Gly Gly Thr
                725
```

<210> SEQ ID NO 44
<211> LENGTH: 5
<212> TYPE: PRT
<213> ORGANISM: artificial sequence
<220> FEATURE:
<223> OTHER INFORMATION: VHCDR1 CA12, VHCDR1 CA7

<400> SEQUENCE: 44

```
Ser Tyr Tyr Val Gly
1               5
```

<210> SEQ ID NO 45
<211> LENGTH: 5
<212> TYPE: PRT
<213> ORGANISM: artificial sequence
<220> FEATURE:

<223> OTHER INFORMATION: VHCDR1 CB2, NS2A1

<400> SEQUENCE: 45

Thr Asn Ser Val Gly
1               5

<210> SEQ ID NO 46
<211> LENGTH: 16
<212> TYPE: PRT
<213> ORGANISM: artificial sequence
<220> FEATURE:
<223> OTHER INFORMATION: VHCDR2 S1G2, S1B1, S1F4, S1G10, S2D1, S2D4,
      CA9, S1A12, S1A5, S1E12

<400> SEQUENCE: 46

Gly Ile Asp Thr Asp Gly Glu Glu Gly Tyr Asn Pro Ala Leu Asn Ser
1               5                   10                  15

<210> SEQ ID NO 47
<211> LENGTH: 16
<212> TYPE: PRT
<213> ORGANISM: artificial sequence
<220> FEATURE:
<223> OTHER INFORMATION: VHCDR2 S1D2, S1H6, MD12

<400> SEQUENCE: 47

Ser Val Asp Ser Asp Gly Tyr Thr Tyr Tyr Asn Pro Ala Leu Lys Ser
1               5                   10                  15

<210> SEQ ID NO 48
<211> LENGTH: 16
<212> TYPE: PRT
<213> ORGANISM: artificial sequence
<220> FEATURE:
<223> OTHER INFORMATION: VHCDR2 S1D9, CC12, S1D5, CB9

<400> SEQUENCE: 48

Gly Ile Asp Ser Asp Gly Glu Glu Gly Tyr Asn Pro Ala Leu Asn Ser
1               5                   10                  15

<210> SEQ ID NO 49
<211> LENGTH: 16
<212> TYPE: PRT
<213> ORGANISM: artificial sequence
<220> FEATURE:
<223> OTHER INFORMATION: VHCDR2 S1H9

<400> SEQUENCE: 49

Gly Ile Asp Ser Asp Gly Glu Glu Gly Tyr Asn Pro Ala Leu Lys Ser
1               5                   10                  15

<210> SEQ ID NO 50
<211> LENGTH: 16
<212> TYPE: PRT
<213> ORGANISM: artificial sequence
<220> FEATURE:
<223> OTHER INFORMATION: VHCDR2 S2C3, MC5

<400> SEQUENCE: 50

Ser Val Asp Ser Asp Gly Asp Thr Tyr Tyr Asn Pro Ala Leu Lys Ser
1               5                   10                  15

<210> SEQ ID NO 51
<211> LENGTH: 16
<212> TYPE: PRT
<213> ORGANISM: artificial sequence
<220> FEATURE:

-continued

```
<223> OTHER INFORMATION: VHCDR2 S2C6

<400> SEQUENCE: 51

Gly Ile Asp Thr Asp Gly Glu Glu Gly Tyr Asn Pro Ala Leu Lys Ser
1               5                   10                  15

<210> SEQ ID NO 52
<211> LENGTH: 16
<212> TYPE: PRT
<213> ORGANISM: artificial sequence
<220> FEATURE:
<223> OTHER INFORMATION: VHCDR2 CA12, VHCDR2 CA7

<400> SEQUENCE: 52

Asn Ile Tyr Ser Thr Gly Arg Ala Phe Tyr Asn Pro Ala Leu Lys Ser
1               5                   10                  15

<210> SEQ ID NO 53
<211> LENGTH: 16
<212> TYPE: PRT
<213> ORGANISM: artificial sequence
<220> FEATURE:
<223> OTHER INFORMATION: VHCDR2 CB2, NS2A1

<400> SEQUENCE: 53

Gly Ile Asp Thr Asp Gly Glu Glu Gly Phe Asn Pro Val Leu Lys Ser
1               5                   10                  15

<210> SEQ ID NO 54
<211> LENGTH: 17
<212> TYPE: PRT
<213> ORGANISM: artificial sequence
<220> FEATURE:
<223> OTHER INFORMATION: VHCDR3 S1F4, S1G2, S1G10, CC12, S1E12, S1D5,
     CB9

<400> SEQUENCE: 54

Ser Tyr Arg Ala Asp Gly Leu Ala Tyr Gly Tyr Val Gln Ala Ile Asp
1               5                   10                  15

Tyr

<210> SEQ ID NO 55
<211> LENGTH: 17
<212> TYPE: PRT
<213> ORGANISM: artificial sequence
<220> FEATURE:
<223> OTHER INFORMATION: VHCDR3 S1B1, S2D1, CB2, NS2A1

<400> SEQUENCE: 55

Ser Tyr Arg Thr Asp Gly Leu Ala Tyr Gly Tyr Val Gln Ala Ile Asp
1               5                   10                  15

Tyr

<210> SEQ ID NO 56
<211> LENGTH: 13
<212> TYPE: PRT
<213> ORGANISM: artificial sequence
<220> FEATURE:
<223> OTHER INFORMATION: VHCDR3 S1D2, S1H6, MC5, MD12

<400> SEQUENCE: 56

Ser Val Asn Gly His Pro Asp Val Tyr Tyr Ile Asp Arg
1               5                   10

<210> SEQ ID NO 57
```

-continued

```
<211> LENGTH: 17
<212> TYPE: PRT
<213> ORGANISM: artificial sequence
<220> FEATURE:
<223> OTHER INFORMATION: VHCDR3 S1D9

<400> SEQUENCE: 57

Thr Tyr Arg Thr Asp Gly Tyr Ala Tyr Gly Tyr Val Gln Ala Ile Asp
1               5                   10                  15

Tyr

<210> SEQ ID NO 58
<211> LENGTH: 17
<212> TYPE: PRT
<213> ORGANISM: artificial sequence
<220> FEATURE:
<223> OTHER INFORMATION: VHCDR3 S1H9, CA9

<400> SEQUENCE: 58

Ser Tyr Arg Ser Asp Gly Leu Ala Tyr Gly Tyr Val Gln Ala Ile Asp
1               5                   10                  15

Tyr

<210> SEQ ID NO 59
<211> LENGTH: 13
<212> TYPE: PRT
<213> ORGANISM: artificial sequence
<220> FEATURE:
<223> OTHER INFORMATION: VHCDR3 S2C3

<400> SEQUENCE: 59

Ser Ala Asn Gly His Pro Asp Val Tyr Tyr Ile Asp Lys
1               5                   10

<210> SEQ ID NO 60
<211> LENGTH: 17
<212> TYPE: PRT
<213> ORGANISM: artificial sequence
<220> FEATURE:
<223> OTHER INFORMATION: VHCDR3 S2C6

<400> SEQUENCE: 60

Thr Tyr Arg Thr Asp Gly Phe Ala Tyr Gly Tyr Val Gln Ala Ile Asp
1               5                   10                  15

Tyr

<210> SEQ ID NO 61
<211> LENGTH: 17
<212> TYPE: PRT
<213> ORGANISM: artificial sequence
<220> FEATURE:
<223> OTHER INFORMATION: VHCDR3 S2D4

<400> SEQUENCE: 61

Ser Tyr Arg Thr Asp Gly Leu Ala Tyr Gly Tyr Val Gln Ala Ile Glu
1               5                   10                  15

Tyr

<210> SEQ ID NO 62
<211> LENGTH: 124
<212> TYPE: PRT
<213> ORGANISM: artificial sequence
<220> FEATURE:
<223> OTHER INFORMATION: S1D12 antibody variable heavy chain
```

```
<400> SEQUENCE: 62

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Asn Asn Asn
            20                  25                  30

Ala Val Gly Trp Val Arg Gln Ala Pro Gly Lys Val Pro Glu Ser Leu
        35                  40                  45

Val Gly Cys Ser Ser Asp Gly Thr Cys Tyr Tyr Asn Ser Ala Leu Lys
    50                  55                  60

Ser Arg Leu Asp Ile Thr Arg Asp Thr Ser Lys Asn Gln Ile Ser Leu
65                  70                  75                  80

Ser Leu Ser Ser Val Thr Thr Asp Asp Ala Ala Val Tyr Tyr Cys Thr
                85                  90                  95

Arg Gly His Tyr Ser Ile Tyr Gly Tyr Asp Tyr Leu Gly Thr Ile Asp
            100                 105                 110

Tyr Trp Gly Pro Gly Leu Leu Val Thr Val Ser Ser
        115                 120

<210> SEQ ID NO 63
<211> LENGTH: 11
<212> TYPE: PRT
<213> ORGANISM: artificial sequence
<220> FEATURE:
<223> OTHER INFORMATION: VLCDR1 S1G2, S1B1, S1D9, S1F4, S1G10, S1H9,
      CA9, S1A12, S1D5, S1E12, S2C6

<400> SEQUENCE: 63

Ser Gly Ser Phe Ile Gly Ile Ser Ser Val Gly
1               5                   10

<210> SEQ ID NO 64
<211> LENGTH: 11
<212> TYPE: PRT
<213> ORGANISM: artificial sequence
<220> FEATURE:
<223> OTHER INFORMATION: VLCDR1 S1D2, S2C3, MD12

<400> SEQUENCE: 64

Ser Gly Ser Tyr Ile Ser Ser Ser Arg Val Gly
1               5                   10

<210> SEQ ID NO 65
<211> LENGTH: 11
<212> TYPE: PRT
<213> ORGANISM: artificial sequence
<220> FEATURE:
<223> OTHER INFORMATION: VLCDR1 S1H6

<400> SEQUENCE: 65

Ser Gly Ser Asp Leu Gly Ser Ser Arg Val Gly
1               5                   10

<210> SEQ ID NO 66
<211> LENGTH: 11
<212> TYPE: PRT
<213> ORGANISM: artificial sequence
<220> FEATURE:
<223> OTHER INFORMATION: VLCDR1 S2D1

<400> SEQUENCE: 66

Ser Gly Ser Tyr Ile Gly Ser Ser Ala Val Gly
1               5                   10
```

-continued

```
<210> SEQ ID NO 67
<211> LENGTH: 11
<212> TYPE: PRT
<213> ORGANISM: artificial sequence
<220> FEATURE:
<223> OTHER INFORMATION: VLCDR1 S2D4, CC12, CB9

<400> SEQUENCE: 67

Ser Gly Arg Phe Ile Gly Ile Ser Ser Val Gly
1               5                   10

<210> SEQ ID NO 68
<211> LENGTH: 11
<212> TYPE: PRT
<213> ORGANISM: artificial sequence
<220> FEATURE:
<223> OTHER INFORMATION: VLCDR1 CB2, NS2A1

<400> SEQUENCE: 68

Ser Gly Ser Tyr Ile Gly Ser Ser Gly Val Gly
1               5                   10

<210> SEQ ID NO 69
<211> LENGTH: 11
<212> TYPE: PRT
<213> ORGANISM: artificial sequence
<220> FEATURE:
<223> OTHER INFORMATION: VLCDR1 MC5

<400> SEQUENCE: 69

Ser Gly Ser Tyr Val Ser Arg Ser Arg Val Gly
1               5                   10

<210> SEQ ID NO 70
<211> LENGTH: 7
<212> TYPE: PRT
<213> ORGANISM: artificial sequence
<220> FEATURE:
<223> OTHER INFORMATION: 297-390 VLCDR2 alternative consensus sequence,
      VLCDR2 S1G2, S1B1, S1D9, S1F4, S1G10, S1H9, S2D1, S2D4, CA9, CB2,
      CC12, NS2A1, S1A12, S1D5, S1E12, CB9, S2C6

<400> SEQUENCE: 70

Ala Ser Asp Gly Arg Pro Ser
1               5

<210> SEQ ID NO 71
<211> LENGTH: 7
<212> TYPE: PRT
<213> ORGANISM: artificial sequence
<220> FEATURE:
<223> OTHER INFORMATION: VLCDR2 S1D2, S1H6, S2C3, MC5, MD12

<400> SEQUENCE: 71

Asp Ser Ser Ser Arg Pro Ser
1               5

<210> SEQ ID NO 72
<211> LENGTH: 7
<212> TYPE: PRT
<213> ORGANISM: artificial sequence
<220> FEATURE:
<223> OTHER INFORMATION: VLCDR2 CA12 and CA7

<400> SEQUENCE: 72

Ala Ala Thr Ser Arg Ala Ser
1               5
```

-continued

```
<210> SEQ ID NO 73
<211> LENGTH: 11
<212> TYPE: PRT
<213> ORGANISM: artificial sequence
<220> FEATURE:
<223> OTHER INFORMATION: VLCDR3 S1G2

<400> SEQUENCE: 73

Gly Ser Ser Asp Arg Thr Pro Tyr Thr Gly Val
1               5                   10

<210> SEQ ID NO 74
<211> LENGTH: 11
<212> TYPE: PRT
<213> ORGANISM: artificial sequence
<220> FEATURE:
<223> OTHER INFORMATION: VLCDR3 S1B1, S1D9, S1F4, S1G10, S1H9, CA9,
      CC12, S1A12, S1D5, S1E12, CB9, S2C6

<400> SEQUENCE: 74

Gly Ser Ser Asp Arg Thr Gln Tyr Thr Gly Val
1               5                   10

<210> SEQ ID NO 75
<211> LENGTH: 9
<212> TYPE: PRT
<213> ORGANISM: artificial sequence
<220> FEATURE:
<223> OTHER INFORMATION: VLCDR3 S1D2, MD12

<400> SEQUENCE: 75

Gly Val Phe Gly Asp Arg Asn Tyr Ile
1               5

<210> SEQ ID NO 76
<211> LENGTH: 9
<212> TYPE: PRT
<213> ORGANISM: artificial sequence
<220> FEATURE:
<223> OTHER INFORMATION: VLCDR3 S1H6, S2C3

<400> SEQUENCE: 76

Gly Ile Phe Gly Asp Arg Asn Tyr Ile
1               5

<210> SEQ ID NO 77
<211> LENGTH: 11
<212> TYPE: PRT
<213> ORGANISM: artificial sequence
<220> FEATURE:
<223> OTHER INFORMATION: VLCDR3 S2D4

<400> SEQUENCE: 77

Gly Ser Thr Ala Pro Thr Pro His Thr Gly Val
1               5                   10

<210> SEQ ID NO 78
<211> LENGTH: 10
<212> TYPE: PRT
<213> ORGANISM: artificial sequence
<220> FEATURE:
<223> OTHER INFORMATION: VLCDR3 CA12 and CA7

<400> SEQUENCE: 78

Ser Ser Tyr Gln Arg Gly Asn Thr Gly Val
1               5                   10
```

```
<210> SEQ ID NO 79
<211> LENGTH: 11
<212> TYPE: PRT
<213> ORGANISM: artificial sequence
<220> FEATURE:
<223> OTHER INFORMATION: VLCDR3 CB2 and NS2A1

<400> SEQUENCE: 79

Gly Ser Ser Asp Arg Thr Gln Tyr Thr Gly Leu
1               5                   10

<210> SEQ ID NO 80
<211> LENGTH: 9
<212> TYPE: PRT
<213> ORGANISM: artificial sequence
<220> FEATURE:
<223> OTHER INFORMATION: VLCDR3 MC5

<400> SEQUENCE: 80

Gly Ile Tyr Gly Asp Arg Asn Tyr Ile
1               5

<210> SEQ ID NO 81
<211> LENGTH: 249
<212> TYPE: PRT
<213> ORGANISM: artificial sequence
<220> FEATURE:
<223> OTHER INFORMATION: S1G2 amino acid sequence

<400> SEQUENCE: 81

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Asn
            20                  25                  30

Ser Val Gly Trp Val Arg Gln Ala Pro Gly Lys Ala Pro Glu Trp Val
        35                  40                  45

Ala Gly Ile Asp Thr Asp Gly Glu Glu Gly Tyr Asn Pro Ala Leu Asn
    50                  55                  60

Ser Arg Leu Ser Ile Thr Arg Asp Thr Ser Lys Ser Gln Val Ser Leu
65                  70                  75                  80

Ser Leu Ser Ser Val Thr Ser Glu Asp Thr Ala Val Tyr Tyr Cys Gly
            85                  90                  95

Arg Ser Tyr Arg Ala Asp Gly Leu Ala Tyr Gly Tyr Val Gln Ala Ile
            100                 105                 110

Asp Tyr Trp Gly Pro Gly Leu Leu Val Thr Val Ser Ser Glu Gly Lys
        115                 120                 125

Ser Ser Gly Ala Ser Gly Glu Ser Lys Val Asp Asp Gln Ala Val Val
    130                 135                 140

Thr Gln Pro Ser Ser Val Ser Gly Ser Leu Gly Gln Arg Val Ser Ile
145                 150                 155                 160

Thr Cys Ser Gly Ser Phe Ile Gly Ile Ser Ser Val Gly Trp Phe Gln
            165                 170                 175

Gln Leu Pro Gly Ser Gly Leu Arg Thr Ile Ile Val Ala Ser Asp Gly
            180                 185                 190

Arg Pro Ser Gly Val Pro Asp Arg Phe Ser Met Ser Lys Ser Gly Asn
        195                 200                 205

Thr Ala Thr Leu Thr Ile Ser Ser Leu Gln Ala Glu Asp Glu Ala Asp
    210                 215                 220
```

-continued

```
Tyr Phe Cys Gly Ser Ser Asp Arg Thr Pro Tyr Thr Gly Val Phe Gly
225                 230                 235                 240

Ser Gly Thr Arg Leu Thr Val Leu Gly
                245

<210> SEQ ID NO 82
<211> LENGTH: 32
<212> TYPE: PRT
<213> ORGANISM: Homo sapiens

<400> SEQUENCE: 82

Val Glu Val Lys Ser Glu Lys Leu Asp Phe Lys Asp Arg Val Gln Ser
1               5                   10                  15

Lys Ile Gly Ser Leu Asp Asn Ile Thr His Val Pro Gly Gly Gly Asn
            20                  25                  30

<210> SEQ ID NO 83
<211> LENGTH: 5
<212> TYPE: PRT
<213> ORGANISM: artificial sequence
<220> FEATURE:
<223> OTHER INFORMATION: 337 to 363 VHCDR1 consensus, VHCDR1 NS2A3,
      NS2A8, NS2C5, NS2C8, NS2D3, CA4

<400> SEQUENCE: 83

Ser Tyr Ser Val Tyr
1               5

<210> SEQ ID NO 84
<211> LENGTH: 16
<212> TYPE: PRT
<213> ORGANISM: artificial sequence
<220> FEATURE:
<223> OTHER INFORMATION: 337 to 363 VHCDR2 consensus, VHCDR2 NS2A3,
      NS2A8, NS2C5, NS2C8, NS2D3, CA4

<400> SEQUENCE: 84

Ile Met Tyr Ala Ser Gly Arg Val Asp Tyr Asn Pro Ala Leu Lys Ser
1               5                   10                  15

<210> SEQ ID NO 85
<211> LENGTH: 4
<212> TYPE: PRT
<213> ORGANISM: artificial sequence
<220> FEATURE:
<223> OTHER INFORMATION: 337 to 363 VHCDR3 consensus
<220> FEATURE:
<221> NAME/KEY: MISC_FEATURE
<222> LOCATION: (4)..(4)
<223> OTHER INFORMATION: N or D

<400> SEQUENCE: 85

Gly Ile Glu Xaa
1

<210> SEQ ID NO 86
<211> LENGTH: 11
<212> TYPE: PRT
<213> ORGANISM: artificial sequence
<220> FEATURE:
<223> OTHER INFORMATION: 337 to 363 VLCDR1 consensus
<220> FEATURE:
<221> NAME/KEY: MISC_FEATURE
<222> LOCATION: (3)..(3)
<223> OTHER INFORMATION: S or N
<220> FEATURE:
<221> NAME/KEY: MISC_FEATURE
<222> LOCATION: (4)..(4)
```

```
<223> OTHER INFORMATION: Q or E
<220> FEATURE:
<221> NAME/KEY: MISC_FEATURE
<222> LOCATION: (5)..(5)
<223> OTHER INFORMATION: S or N
<220> FEATURE:
<221> NAME/KEY: MISC_FEATURE
<222> LOCATION: (6)..(6)
<223> OTHER INFORMATION: V or I
<220> FEATURE:
<221> NAME/KEY: MISC_FEATURE
<222> LOCATION: (7)..(7)
<223> OTHER INFORMATION: N or G or D
<220> FEATURE:
<221> NAME/KEY: MISC_FEATURE
<222> LOCATION: (8)..(8)
<223> OTHER INFORMATION: N or S
<220> FEATURE:
<221> NAME/KEY: MISC_FEATURE
<222> LOCATION: (9)..(9)
<223> OTHER INFORMATION: Y or G
<220> FEATURE:
<221> NAME/KEY: MISC_FEATURE
<222> LOCATION: (11)..(11)
<223> OTHER INFORMATION: S or A

<400> SEQUENCE: 86

Arg Thr Xaa Xaa Xaa Xaa Xaa Xaa Xaa Leu Xaa
1               5                   10

<210> SEQ ID NO 87
<211> LENGTH: 7
<212> TYPE: PRT
<213> ORGANISM: artificial sequence
<220> FEATURE:
<223> OTHER INFORMATION: 337 to 363 VLCDR2 consensus
<220> FEATURE:
<221> NAME/KEY: MISC_FEATURE
<222> LOCATION: (6)..(6)
<223> OTHER INFORMATION: Y or H

<400> SEQUENCE: 87

Tyr Ala Thr Tyr Leu Xaa Thr
1               5

<210> SEQ ID NO 88
<211> LENGTH: 9
<212> TYPE: PRT
<213> ORGANISM: artificial sequence
<220> FEATURE:
<223> OTHER INFORMATION: 337 to 363 VLCDR3 consensus
<220> FEATURE:
<221> NAME/KEY: MISC_FEATURE
<222> LOCATION: (4)..(4)
<223> OTHER INFORMATION: D or G or E
<220> FEATURE:
<221> NAME/KEY: MISC_FEATURE
<222> LOCATION: (5)..(5)
<223> OTHER INFORMATION: S or T
<220> FEATURE:
<221> NAME/KEY: MISC_FEATURE
<222> LOCATION: (9)..(9)
<223> OTHER INFORMATION: A or T

<400> SEQUENCE: 88

Leu Gln Tyr Xaa Xaa Thr Pro Leu Xaa
1               5

<210> SEQ ID NO 89
<211> LENGTH: 4
<212> TYPE: PRT
<213> ORGANISM: artificial sequence
<220> FEATURE:
```

<223> OTHER INFORMATION: VHCDR3 NS2A3, NS2A8, NS2C8, CA4

<400> SEQUENCE: 89

Gly Ile Glu Asn
1

<210> SEQ ID NO 90
<211> LENGTH: 4
<212> TYPE: PRT
<213> ORGANISM: artificial sequence
<220> FEATURE:
<223> OTHER INFORMATION: VHCDR3 NS2C5, NS2D3

<400> SEQUENCE: 90

Gly Ile Glu Asp
1

<210> SEQ ID NO 91
<211> LENGTH: 11
<212> TYPE: PRT
<213> ORGANISM: artificial sequence
<220> FEATURE:
<223> OTHER INFORMATION: VLCDR1 NS2A3, NS2C8, CA4

<400> SEQUENCE: 91

Arg Thr Ser Gln Ser Val Asn Asn Tyr Leu Ser
1               5                   10

<210> SEQ ID NO 92
<211> LENGTH: 11
<212> TYPE: PRT
<213> ORGANISM: artificial sequence
<220> FEATURE:
<223> OTHER INFORMATION: VLCDR1 NS2A8

<400> SEQUENCE: 92

Arg Thr Asn Glu Ser Val Gly Asn Tyr Leu Ser
1               5                   10

<210> SEQ ID NO 93
<211> LENGTH: 11
<212> TYPE: PRT
<213> ORGANISM: artificial sequence
<220> FEATURE:
<223> OTHER INFORMATION: VLCDR1 NS2C5

<400> SEQUENCE: 93

Arg Thr Ser Gln Asn Ile Asp Asn Gly Leu Ala
1               5                   10

<210> SEQ ID NO 94
<211> LENGTH: 11
<212> TYPE: PRT
<213> ORGANISM: artificial sequence
<220> FEATURE:
<223> OTHER INFORMATION: VLCDR1 NS2D3

<400> SEQUENCE: 94

Arg Thr Ser Gln Ser Val Gly Ser Tyr Leu Ser
1               5                   10

<210> SEQ ID NO 95
<211> LENGTH: 7
<212> TYPE: PRT
<213> ORGANISM: artificial sequence
<220> FEATURE:
<223> OTHER INFORMATION: VLCDR2 NS2A3, NS2C8, CA4

-continued

```
<400> SEQUENCE: 95

Tyr Ala Thr Arg Leu Tyr Thr
1               5

<210> SEQ ID NO 96
<211> LENGTH: 7
<212> TYPE: PRT
<213> ORGANISM: artificial sequence
<220> FEATURE:
<223> OTHER INFORMATION: VLCDR2 NS2A8, NS2C5, NS2D3

<400> SEQUENCE: 96

Tyr Ala Thr Arg Leu His Thr
1               5

<210> SEQ ID NO 97
<211> LENGTH: 9
<212> TYPE: PRT
<213> ORGANISM: artificial sequence
<220> FEATURE:
<223> OTHER INFORMATION: VLCDR3 NS2A3, NS2C8, CA4

<400> SEQUENCE: 97

Leu Gln Tyr Asp Ser Thr Pro Leu Ala
1               5

<210> SEQ ID NO 98
<211> LENGTH: 9
<212> TYPE: PRT
<213> ORGANISM: artificial sequence
<220> FEATURE:
<223> OTHER INFORMATION: VLDDR3 NS2D3

<400> SEQUENCE: 98

Leu Gln Tyr Asp Ser Thr Pro Leu Thr
1               5

<210> SEQ ID NO 99
<211> LENGTH: 9
<212> TYPE: PRT
<213> ORGANISM: artificial sequence
<220> FEATURE:
<223> OTHER INFORMATION: VLCDR3 NS2C5

<400> SEQUENCE: 99

Leu Gln Tyr Glu Ser Thr Pro Leu Ala
1               5

<210> SEQ ID NO 100
<211> LENGTH: 9
<212> TYPE: PRT
<213> ORGANISM: artificial sequence
<220> FEATURE:
<223> OTHER INFORMATION: VLCDR3 NS2A8

<400> SEQUENCE: 100

Leu Gln Tyr Gly Thr Thr Pro Leu Ala
1               5

<210> SEQ ID NO 101
<211> LENGTH: 22
<212> TYPE: PRT
<213> ORGANISM: Homo sapiens

<400> SEQUENCE: 101
```

-continued

```
Lys Lys Ile Glu Thr His Lys Leu Thr Phe Arg Glu Asn Ala Lys Ala
1               5                   10                  15

Lys Thr Asp His Gly Ala
            20

<210> SEQ ID NO 102
<211> LENGTH: 5
<212> TYPE: PRT
<213> ORGANISM: artificial sequence
<220> FEATURE:
<223> OTHER INFORMATION: 369 to 390 VHCDR1 consensus, NS4E3, NS3E5,
      NS3H4, NS4F2, NS2B6, MD9

<400> SEQUENCE: 102

Arg Glu Ser Ile Ala
1               5

<210> SEQ ID NO 103
<211> LENGTH: 16
<212> TYPE: PRT
<213> ORGANISM: artificial sequence
<220> FEATURE:
<223> OTHER INFORMATION: 369 to 390 VHCDR2 consensus, NS4E3, NS3E5,
      NS3H4, NS4F2, NS2B6, MD9

<400> SEQUENCE: 103

Gly Val Gly Ile Asp Gly Thr Ser Tyr Tyr Ser Pro Ala Leu Lys Ser
1               5                   10                  15

<210> SEQ ID NO 104
<211> LENGTH: 7
<212> TYPE: PRT
<213> ORGANISM: artificial sequence
<220> FEATURE:
<223> OTHER INFORMATION: 369 to 390 VHCDR3 consensus, VHCDR3 NS4E3,
      NS3E5, NS3H4, NS4F2, NS2B6, MD9

<400> SEQUENCE: 104

Asn Tyr Ile Asp Phe Glu Tyr
1               5

<210> SEQ ID NO 105
<211> LENGTH: 14
<212> TYPE: PRT
<213> ORGANISM: artificial sequence
<220> FEATURE:
<223> OTHER INFORMATION: 369 to 390 VLCDR1 consensus
<220> FEATURE:
<221> NAME/KEY: MISC_FEATURE
<222> LOCATION: (4)..(4)
<223> OTHER INFORMATION: S or N or Y
<220> FEATURE:
<221> NAME/KEY: MISC_FEATURE
<222> LOCATION: (5)..(5)
<223> OTHER INFORMATION: S or N or nothing
<220> FEATURE:
<221> NAME/KEY: MISC_FEATURE
<222> LOCATION: (6)..(6)
<223> OTHER INFORMATION: N or nothing
<220> FEATURE:
<221> NAME/KEY: MISC_FEATURE
<222> LOCATION: (7)..(7)
<223> OTHER INFORMATION: V or nothing
<220> FEATURE:
<221> NAME/KEY: MISC_FEATURE
<222> LOCATION: (8)..(8)
<223> OTHER INFORMATION: G or I
<220> FEATURE:
<221> NAME/KEY: MISC_FEATURE
<222> LOCATION: (9)..(9)
<223> OTHER INFORMATION: Y or S or A or G
```

```
<220> FEATURE:
<221> NAME/KEY: MISC_FEATURE
<222> LOCATION: (10)..(10)
<223> OTHER INFORMATION: E or G or S
<220> FEATURE:
<221> NAME/KEY: MISC_FEATURE
<222> LOCATION: (11)..(11)
<223> OTHER INFORMATION: D or N or T
<220> FEATURE:
<221> NAME/KEY: MISC_FEATURE
<222> LOCATION: (12)..(12)
<223> OTHER INFORMATION: Y or G or D
<220> FEATURE:
<221> NAME/KEY: MISC_FEATURE
<222> LOCATION: (14)..(14)
<223> OTHER INFORMATION: N or S or G

<400> SEQUENCE: 105

Ser Gly Ser Xaa Xaa Xaa Xaa Xaa Xaa Xaa Xaa Xaa Val Xaa
1               5                   10

<210> SEQ ID NO 106
<211> LENGTH: 7
<212> TYPE: PRT
<213> ORGANISM: artificial sequence
<220> FEATURE:
<223> OTHER INFORMATION: 369 to 390 VLCDR2 consensus
<220> FEATURE:
<221> NAME/KEY: MISC_FEATURE
<222> LOCATION: (1)..(1)
<223> OTHER INFORMATION: G or R
<220> FEATURE:
<221> NAME/KEY: MISC_FEATURE
<222> LOCATION: (2)..(2)
<223> OTHER INFORMATION: T or N or S
<220> FEATURE:
<221> NAME/KEY: MISC_FEATURE
<222> LOCATION: (3)..(3)
<223> OTHER INFORMATION: T or S
<220> FEATURE:
<221> NAME/KEY: MISC_FEATURE
<222> LOCATION: (4)..(4)
<223> OTHER INFORMATION: N or T or R
<220> FEATURE:
<221> NAME/KEY: MISC_FEATURE
<222> LOCATION: (6)..(6)
<223> OTHER INFORMATION: P or A

<400> SEQUENCE: 106

Xaa Xaa Xaa Xaa Arg Xaa Ser
1               5

<210> SEQ ID NO 107
<211> LENGTH: 10
<212> TYPE: PRT
<213> ORGANISM: artificial sequence
<220> FEATURE:
<223> OTHER INFORMATION: 369 To 390 VLCDR3 consensus
<220> FEATURE:
<221> NAME/KEY: MISC_FEATURE
<222> LOCATION: (1)..(1)
<223> OTHER INFORMATION: L or A or G
<220> FEATURE:
<221> NAME/KEY: MISC_FEATURE
<222> LOCATION: (5)..(5)
<223> OTHER INFORMATION: R or T or G or S
<220> FEATURE:
<221> NAME/KEY: MISC_FEATURE
<222> LOCATION: (6)..(6)
<223> OTHER INFORMATION: S or T
<220> FEATURE:
<221> NAME/KEY: MISC_FEATURE
<222> LOCATION: (7)..(7)
<223> OTHER INFORMATION: G or N
<220> FEATURE:
```

-continued

```
<221> NAME/KEY: MISC_FEATURE
<222> LOCATION: (8)..(8)
<223> OTHER INFORMATION: S or R or nothing
<220> FEATURE:
<221> NAME/KEY: MISC_FEATURE
<222> LOCATION: (9)..(9)
<223> OTHER INFORMATION: N or G or S or I
<220> FEATURE:
<221> NAME/KEY: MISC_FEATURE
<222> LOCATION: (10)..(10)
<223> OTHER INFORMATION: F or I or V

<400> SEQUENCE: 107

Xaa Ser Tyr Asp Xaa Xaa Xaa Xaa Xaa Xaa
1               5                   10

<210> SEQ ID NO 108
<211> LENGTH: 14
<212> TYPE: PRT
<213> ORGANISM: artificial sequence
<220> FEATURE:
<223> OTHER INFORMATION: VLCDR1 NS4E3

<400> SEQUENCE: 108

Ser Gly Ser Ser Ser Asn Val Gly Tyr Glu Asp Tyr Val Asn
1               5                   10

<210> SEQ ID NO 109
<211> LENGTH: 11
<212> TYPE: PRT
<213> ORGANISM: artificial sequence
<220> FEATURE:
<223> OTHER INFORMATION: VLCDR1 NS3H4

<400> SEQUENCE: 109

Ser Gly Ser Asn Ile Ala Gly Asn Gly Val Gly
1               5                   10

<210> SEQ ID NO 110
<211> LENGTH: 14
<212> TYPE: PRT
<213> ORGANISM: artificial sequence
<220> FEATURE:
<223> OTHER INFORMATION: VLCDR1 NS4F2

<400> SEQUENCE: 110

Ser Gly Ser Ser Asn Asn Val Gly Ser Gly Asp Tyr Val Ser
1               5                   10

<210> SEQ ID NO 111
<211> LENGTH: 11
<212> TYPE: PRT
<213> ORGANISM: artificial sequence
<220> FEATURE:
<223> OTHER INFORMATION: VLCDR1 NS3E5

<400> SEQUENCE: 111

Ser Gly Ser Tyr Ile Gly Ser Thr Asp Val Gly
1               5                   10

<210> SEQ ID NO 112
<211> LENGTH: 7
<212> TYPE: PRT
<213> ORGANISM: artificial sequence
<220> FEATURE:
<223> OTHER INFORMATION: VLCDR2 NS4E3

<400> SEQUENCE: 112
```

-continued

Gly Thr Thr Asn Arg Pro Ser
1               5

<210> SEQ ID NO 113
<211> LENGTH: 7
<212> TYPE: PRT
<213> ORGANISM: artificial sequence
<220> FEATURE:
<223> OTHER INFORMATION: VLCDR2 NS3E5

<400> SEQUENCE: 113

Gly Ser Thr Arg Arg Pro Ser
1               5

<210> SEQ ID NO 114
<211> LENGTH: 7
<212> TYPE: PRT
<213> ORGANISM: artificial sequence
<220> FEATURE:
<223> OTHER INFORMATION: VLCDR2 NS3H4

<400> SEQUENCE: 114

Arg Asn Ser Asn Arg Pro Ser
1               5

<210> SEQ ID NO 115
<211> LENGTH: 7
<212> TYPE: PRT
<213> ORGANISM: artificial sequence
<220> FEATURE:
<223> OTHER INFORMATION: VLCDR2 NS4F2

<400> SEQUENCE: 115

Arg Thr Thr Thr Arg Ala Ser
1               5

<210> SEQ ID NO 116
<211> LENGTH: 10
<212> TYPE: PRT
<213> ORGANISM: artificial sequence
<220> FEATURE:
<223> OTHER INFORMATION: VLCDR3 NS4E3

<400> SEQUENCE: 116

Leu Ser Tyr Asp Arg Ser Gly Ser Asn Phe
1               5                   10

<210> SEQ ID NO 117
<211> LENGTH: 10
<212> TYPE: PRT
<213> ORGANISM: artificial sequence
<220> FEATURE:
<223> OTHER INFORMATION: VLCDR3 NS4F2

<400> SEQUENCE: 117

Ala Ser Tyr Asp Thr Ser Asn Arg Gly Ile
1               5                   10

<210> SEQ ID NO 118
<211> LENGTH: 9
<212> TYPE: PRT
<213> ORGANISM: artificial sequence
<220> FEATURE:
<223> OTHER INFORMATION: VLCDR3 NS3H4

<400> SEQUENCE: 118

Gly Ser Tyr Asp Gly Thr Asn Ser Phe

-continued

```
1               5

<210> SEQ ID NO 119
<211> LENGTH: 10
<212> TYPE: PRT
<213> ORGANISM: artificial sequence
<220> FEATURE:
<223> OTHER INFORMATION: VLCDR3 NS3E5

<400> SEQUENCE: 119

Ala Ser Tyr Asp Ser Asn Asn Ser Ile Val
1               5                   10

<210> SEQ ID NO 120
<211> LENGTH: 30
<212> TYPE: PRT
<213> ORGANISM: Homo sapiens

<400> SEQUENCE: 120

Ser Ser Thr Gly Ser Ile Asp Met Val Asp Ser Pro Gln Leu Ala Thr
1               5                   10                  15

Leu Ala Asp Glu Val Ser Ala Ser Leu Ala Lys Gln Gly Leu
                20                  25                  30

<210> SEQ ID NO 121
<211> LENGTH: 5
<212> TYPE: PRT
<213> ORGANISM: artificial sequence
<220> FEATURE:
<223> OTHER INFORMATION: 412 to 441 VHCDR1 consensus
<220> FEATURE:
<221> NAME/KEY: MISC_FEATURE
<222> LOCATION: (1)..(1)
<223> OTHER INFORMATION: S or N
<220> FEATURE:
<221> NAME/KEY: MISC_FEATURE
<222> LOCATION: (2)..(2)
<223> OTHER INFORMATION: D or Y
<220> FEATURE:
<221> NAME/KEY: MISC_FEATURE
<222> LOCATION: (3)..(3)
<223> OTHER INFORMATION: S or G or A
<220> FEATURE:
<221> NAME/KEY: MISC_FEATURE
<222> LOCATION: (4)..(4)
<223> OTHER INFORMATION: V or L
<220> FEATURE:
<221> NAME/KEY: MISC_FEATURE
<222> LOCATION: (5)..(5)
<223> OTHER INFORMATION: A or G

<400> SEQUENCE: 121

Xaa Xaa Xaa Xaa Xaa
1               5

<210> SEQ ID NO 122
<211> LENGTH: 16
<212> TYPE: PRT
<213> ORGANISM: artificial sequence
<220> FEATURE:
<223> OTHER INFORMATION: 412 to 441 VHCDR2 consensus
<220> FEATURE:
<221> NAME/KEY: MISC_FEATURE
<222> LOCATION: (1)..(1)
<223> OTHER INFORMATION: A or N
<220> FEATURE:
<221> NAME/KEY: MISC_FEATURE
<222> LOCATION: (2)..(2)
<223> OTHER INFORMATION: S or I
<220> FEATURE:
<221> NAME/KEY: MISC_FEATURE
```

-continued

```
<222> LOCATION: (3)..(3)
<223> OTHER INFORMATION: G or Y or W
<220> FEATURE:
<221> NAME/KEY: MISC_FEATURE
<222> LOCATION: (4)..(4)
<223> OTHER INFORMATION: S or R
<220> FEATURE:
<221> NAME/KEY: MISC_FEATURE
<222> LOCATION: (5)..(5)
<223> OTHER INFORMATION: S or G
<220> FEATURE:
<221> NAME/KEY: MISC_FEATURE
<222> LOCATION: (7)..(7)
<223> OTHER INFORMATION: N or S or R
<220> FEATURE:
<221> NAME/KEY: MISC_FEATURE
<222> LOCATION: (8)..(8)
<223> OTHER INFORMATION: K or T or I
<220> FEATURE:
<221> NAME/KEY: MISC_FEATURE
<222> LOCATION: (9)..(9)
<223> OTHER INFORMATION: Y or E

<400> SEQUENCE: 122

Xaa Xaa Xaa Xaa Xaa Gly Xaa Xaa Xaa Tyr Asn Pro Ala Leu Lys Ser
1               5                   10                  15

<210> SEQ ID NO 123
<211> LENGTH: 8
<212> TYPE: PRT
<213> ORGANISM: artificial sequence
<220> FEATURE:
<223> OTHER INFORMATION: 412 to 441 VHCDR3 consensus
<220> FEATURE:
<221> NAME/KEY: MISC_FEATURE
<222> LOCATION: (2)..(2)
<223> OTHER INFORMATION: I or G
<220> FEATURE:
<221> NAME/KEY: MISC_FEATURE
<222> LOCATION: (3)..(3)
<223> OTHER INFORMATION: I or V
<220> FEATURE:
<221> NAME/KEY: MISC_FEATURE
<222> LOCATION: (4)..(4)
<223> OTHER INFORMATION: A or G
<220> FEATURE:
<221> NAME/KEY: MISC_FEATURE
<222> LOCATION: (5)..(5)
<223> OTHER INFORMATION: G or S

<400> SEQUENCE: 123

Gly Xaa Xaa Xaa Xaa Val Asp Val
1               5

<210> SEQ ID NO 124
<211> LENGTH: 4
<212> TYPE: PRT
<213> ORGANISM: artificial sequence
<220> FEATURE:
<223> OTHER INFORMATION: VHDR3 412G11

<400> SEQUENCE: 124

Ser Gly Gly Asp
1

<210> SEQ ID NO 125
<211> LENGTH: 13
<212> TYPE: PRT
<213> ORGANISM: artificial sequence
<220> FEATURE:
<223> OTHER INFORMATION: 412 to 441 VLCDR1 consensus
<220> FEATURE:
<221> NAME/KEY: MISC_FEATURE
```

```
<222> LOCATION: (3)..(3)
<223> OTHER INFORMATION: S or G
<220> FEATURE:
<221> NAME/KEY: MISC_FEATURE
<222> LOCATION: (4)..(4)
<223> OTHER INFORMATION: S or N
<220> FEATURE:
<221> NAME/KEY: MISC_FEATURE
<222> LOCATION: (6)..(6)
<223> OTHER INFORMATION: V or I
<220> FEATURE:
<221> NAME/KEY: MISC_FEATURE
<222> LOCATION: (8)..(8)
<223> OTHER INFORMATION: Y or R
<220> FEATURE:
<221> NAME/KEY: MISC_FEATURE
<222> LOCATION: (10)..(10)
<223> OTHER INFORMATION: N or D or T
<220> FEATURE:
<221> NAME/KEY: MISC_FEATURE
<222> LOCATION: (11)..(11)
<223> OTHER INFORMATION: Y or F
<220> FEATURE:
<221> NAME/KEY: MISC_FEATURE
<222> LOCATION: (13)..(13)
<223> OTHER INFORMATION: G or D

<400> SEQUENCE: 125

Ser Gly Xaa Xaa Asn Xaa Gly Xaa Gly Xaa Xaa Val Xaa
1               5                   10

<210> SEQ ID NO 126
<211> LENGTH: 7
<212> TYPE: PRT
<213> ORGANISM: artificial sequence
<220> FEATURE:
<223> OTHER INFORMATION: 412 To 441 VLCDR2 consensus
<220> FEATURE:
<221> NAME/KEY: MISC_FEATURE
<222> LOCATION: (2)..(2)
<223> OTHER INFORMATION: T or A
<220> FEATURE:
<221> NAME/KEY: MISC_FEATURE
<222> LOCATION: (3)..(3)
<223> OTHER INFORMATION: A or D or T
<220> FEATURE:
<221> NAME/KEY: MISC_FEATURE
<222> LOCATION: (4)..(4)
<223> OTHER INFORMATION: I or S or R
<220> FEATURE:
<221> NAME/KEY: MISC_FEATURE
<222> LOCATION: (6)..(6)
<223> OTHER INFORMATION: A or P
<220> FEATURE:
<221> NAME/KEY: MISC_FEATURE
<222> LOCATION: (7)..(7)
<223> OTHER INFORMATION: S or P

<400> SEQUENCE: 126

Gly Xaa Xaa Xaa Arg Xaa Xaa
1               5

<210> SEQ ID NO 127
<211> LENGTH: 11
<212> TYPE: PRT
<213> ORGANISM: artificial sequence
<220> FEATURE:
<223> OTHER INFORMATION: 412 to 441 VLCDR3 consensus
<220> FEATURE:
<221> NAME/KEY: MISC_FEATURE
<222> LOCATION: (2)..(2)
<223> OTHER INFORMATION: S or T
<220> FEATURE:
<221> NAME/KEY: MISC_FEATURE
<222> LOCATION: (4)..(4)
```

-continued

```
<223> OTHER INFORMATION: Q or D
<220> FEATURE:
<221> NAME/KEY: MISC_FEATURE
<222> LOCATION: (5)..(5)
<223> OTHER INFORMATION: S or Y or R
<220> FEATURE:
<221> NAME/KEY: MISC_FEATURE
<222> LOCATION: (6)..(6)
<223> OTHER INFORMATION: N or S
<220> FEATURE:
<221> NAME/KEY: MISC_FEATURE
<222> LOCATION: (7)..(7)
<223> OTHER INFORMATION: Y or D or N or E
<220> FEATURE:
<221> NAME/KEY: MISC_FEATURE
<222> LOCATION: (8)..(8)
<223> OTHER INFORMATION: A or G or D or S
<220> FEATURE:
<221> NAME/KEY: MISC_FEATURE
<222> LOCATION: (9)..(9)
<223> OTHER INFORMATION: Nothing or G or M or V
<220> FEATURE:
<221> NAME/KEY: MISC_FEATURE
<222> LOCATION: (10)..(10)
<223> OTHER INFORMATION: Nothing or I
<220> FEATURE:
<221> NAME/KEY: MISC_FEATURE
<222> LOCATION: (11)..(11)
<223> OTHER INFORMATION: F or V or I

<400> SEQUENCE: 127

Ala Xaa Tyr Xaa Xaa Xaa Xaa Xaa Xaa Xaa Xaa
1               5                   10

<210> SEQ ID NO 128
<211> LENGTH: 5
<212> TYPE: PRT
<213> ORGANISM: artificial sequence
<220> FEATURE:
<223> OTHER INFORMATION: VHCDR1 412E10 and 412B9

<400> SEQUENCE: 128

Ser Asp Ser Val Ala
1               5

<210> SEQ ID NO 129
<211> LENGTH: 5
<212> TYPE: PRT
<213> ORGANISM: artificial sequence
<220> FEATURE:
<223> OTHER INFORMATION: VHCDR1 412E6

<400> SEQUENCE: 129

Asn Tyr Gly Val Gly
1               5

<210> SEQ ID NO 130
<211> LENGTH: 5
<212> TYPE: PRT
<213> ORGANISM: artificial sequence
<220> FEATURE:
<223> OTHER INFORMATION: VHCDR1 412G11

<400> SEQUENCE: 130

Ser Tyr Ala Leu Gly
1               5

<210> SEQ ID NO 131
<211> LENGTH: 16
<212> TYPE: PRT
<213> ORGANISM: artificial sequence
```

-continued

```
<220> FEATURE:
<223> OTHER INFORMATION: VHCDR2 412E10 and 412B9

<400> SEQUENCE: 131

Ala Ser Gly Ser Ser Gly Asn Lys Tyr Tyr Asn Pro Ala Leu Lys Ser
1               5                   10                  15

<210> SEQ ID NO 132
<211> LENGTH: 16
<212> TYPE: PRT
<213> ORGANISM: artificial sequence
<220> FEATURE:
<223> OTHER INFORMATION: VHCDR2 412G11

<400> SEQUENCE: 132

Asn Ile Trp Arg Gly Gly Arg Ile Glu Tyr Asn Pro Ala Leu Lys Ser
1               5                   10                  15

<210> SEQ ID NO 133
<211> LENGTH: 16
<212> TYPE: PRT
<213> ORGANISM: artificial sequence
<220> FEATURE:
<223> OTHER INFORMATION: VHCDR2 412E6

<400> SEQUENCE: 133

Asn Ile Tyr Ser Gly Gly Ser Thr Tyr Tyr Asn Pro Ala Leu Lys Ser
1               5                   10                  15

<210> SEQ ID NO 134
<211> LENGTH: 8
<212> TYPE: PRT
<213> ORGANISM: artificial sequence
<220> FEATURE:
<223> OTHER INFORMATION: VHCDR3 412E10 and 412B9

<400> SEQUENCE: 134

Gly Ile Ile Ala Gly Val Asp Val
1               5

<210> SEQ ID NO 135
<211> LENGTH: 8
<212> TYPE: PRT
<213> ORGANISM: artificial sequence
<220> FEATURE:
<223> OTHER INFORMATION: VHCDR3 412E6

<400> SEQUENCE: 135

Gly Gly Val Gly Ser Val Asp Val
1               5

<210> SEQ ID NO 136
<211> LENGTH: 5
<212> TYPE: PRT
<213> ORGANISM: artificial sequence
<220> FEATURE:
<223> OTHER INFORMATION: 297 to 390 VHCDR1 consensus
<220> FEATURE:
<221> NAME/KEY: MISC_FEATURE
<222> LOCATION: (1)..(1)
<223> OTHER INFORMATION: S or R or D or T
<220> FEATURE:
<221> NAME/KEY: MISC_FEATURE
<222> LOCATION: (2)..(2)
<223> OTHER INFORMATION: N or E or Y or H
<220> FEATURE:
<221> NAME/KEY: MISC_FEATURE
<222> LOCATION: (3)..(3)
<223> OTHER INFORMATION: S or G
```

-continued

```
<220> FEATURE:
<221> NAME/KEY: MISC_FEATURE
<222> LOCATION: (4)..(4)
<223> OTHER INFORMATION: V or I
<220> FEATURE:
<221> NAME/KEY: MISC_FEATURE
<222> LOCATION: (5)..(5)
<223> OTHER INFORMATION: G or A

<400> SEQUENCE: 136

Xaa Xaa Xaa Xaa Xaa
1               5

<210> SEQ ID NO 137
<211> LENGTH: 14
<212> TYPE: PRT
<213> ORGANISM: artificial sequence
<220> FEATURE:
<223> OTHER INFORMATION: VLCDR1 412E6

<400> SEQUENCE: 137

Ser Gly Gly Arg Asn Asn Ile Gly Arg Gly Thr Phe Val Asp
1               5                   10

<210> SEQ ID NO 138
<211> LENGTH: 14
<212> TYPE: PRT
<213> ORGANISM: artificial sequence
<220> FEATURE:
<223> OTHER INFORMATION: VLCDR1 412B9, 3aD3, 3aA6

<400> SEQUENCE: 138

Ser Gly Ser Ser Ser Asn Val Gly Tyr Gly Asp Tyr Val Gly
1               5                   10

<210> SEQ ID NO 139
<211> LENGTH: 7
<212> TYPE: PRT
<213> ORGANISM: artificial sequence
<220> FEATURE:
<223> OTHER INFORMATION: VLCDR2 412E10

<400> SEQUENCE: 139

Gly Thr Ala Ile Arg Ala Ser
1               5

<210> SEQ ID NO 140
<211> LENGTH: 6
<212> TYPE: PRT
<213> ORGANISM: artificial sequence
<220> FEATURE:
<223> OTHER INFORMATION: VLCDR2 412B9

<400> SEQUENCE: 140

Ala Ala Ser Arg Ala Ser
1               5

<210> SEQ ID NO 141
<211> LENGTH: 7
<212> TYPE: PRT
<213> ORGANISM: artificial sequence
<220> FEATURE:
<223> OTHER INFORMATION: VLCDR2 412G11, VLCDR2 3aG3, VLCDR2 3bF4, VLCDR2
      CB7, CG11, CE2/E1B8, CC5

<400> SEQUENCE: 141

Gly Ala Thr Ser Arg Ala Ser
1               5
```

```
<210> SEQ ID NO 142
<211> LENGTH: 7
<212> TYPE: PRT
<213> ORGANISM: artificial sequence
<220> FEATURE:
<223> OTHER INFORMATION: VLCDR2 412E6

<400> SEQUENCE: 142

Gly Thr Asp Arg Arg Pro Pro
1               5

<210> SEQ ID NO 143
<211> LENGTH: 9
<212> TYPE: PRT
<213> ORGANISM: artificial sequence
<220> FEATURE:
<223> OTHER INFORMATION: VLCDR3 412E10

<400> SEQUENCE: 143

Ala Ser Tyr Gln Ser Asn Tyr Ala Phe
1               5

<210> SEQ ID NO 144
<211> LENGTH: 10
<212> TYPE: PRT
<213> ORGANISM: artificial sequence
<220> FEATURE:
<223> OTHER INFORMATION: VLCDR3 412G11

<400> SEQUENCE: 144

Ala Ser Tyr Asp Arg Ser Glu Ser Val Val
1               5                   10

<210> SEQ ID NO 145
<211> LENGTH: 10
<212> TYPE: PRT
<213> ORGANISM: artificial sequence
<220> FEATURE:
<223> OTHER INFORMATION: VLCDR3 412B9

<400> SEQUENCE: 145

Ala Ser Tyr Asp Ser Ser Asp Gly Gly Val
1               5                   10

<210> SEQ ID NO 146
<211> LENGTH: 11
<212> TYPE: PRT
<213> ORGANISM: artificial sequence
<220> FEATURE:
<223> OTHER INFORMATION: VLCDR3 412E6

<400> SEQUENCE: 146

Ala Thr Tyr Asp Tyr Ser Asn Asp Met Ile Ile
1               5                   10

<210> SEQ ID NO 147
<211> LENGTH: 241
<212> TYPE: PRT
<213> ORGANISM: artificial sequence
<220> FEATURE:
<223> OTHER INFORMATION: 412E10 amino acid sequence

<400> SEQUENCE: 147

Gln Val Gln Leu Gln Glu Ser Gly Pro Ser Leu Val Lys Pro Ser Gln
1               5                   10                  15
```

-continued

```
Thr Leu Ser Leu Thr Cys Thr Val Ser Gly Phe Ser Val Ile Ser Asp
            20              25                  30

Ser Val Ala Trp Val Arg Gln Ala Pro Gly Lys Val Pro Glu Trp Leu
        35              40                  45

Gly Ala Ser Gly Ser Ser Gly Asn Lys Tyr Tyr Asn Pro Ala Leu Lys
    50              55                  60

Ser Arg Leu Ser Ile Thr Arg Asp Thr Ser Lys Ser Gln Val Ser Leu
65                  70                  75                  80

Ser Leu Ser Ser Val Thr Thr Glu Asp Thr Ala Val Tyr Tyr Cys Ala
                85                  90                  95

Arg Gly Ile Ile Ala Gly Val Asp Val Trp Gly Arg Gly Leu Leu Val
            100             105             110

Thr Val Ser Ser Glu Gly Lys Ser Ser Gly Ala Ser Gly Glu Ser Lys
            115             120             125

Val Asp Asp Gln Ala Val Leu Thr Gln Pro Ser Ser Val Ser Gly Ser
    130             135             140

Leu Gly Gln Arg Val Ser Ile Thr Cys Ser Gly Ser Ser Ser Asn Val
145             150             155             160

Gly Tyr Gly Asn Tyr Val Gly Trp Tyr Gln Gln Val Pro Gly Ser Ala
            165             170             175

Pro Lys Leu Leu Ile Tyr Gly Thr Ala Ile Arg Ala Ser Gly Val Pro
            180             185             190

Asp Arg Phe Ser Gly Ser Arg Ser Gly Asp Thr Ala Thr Leu Thr Ile
            195             200             205

Thr Ser Leu Gln Ala Glu Asp Glu Ala Asp Tyr Tyr Cys Ala Ser Tyr
    210             215             220

Gln Ser Asn Tyr Ala Phe Phe Gly Ser Gly Thr Arg Leu Thr Val Leu
225             230             235             240

Gly
```

```
<210> SEQ ID NO 148
<211> LENGTH: 49
<212> TYPE: PRT
<213> ORGANISM: Homo sapiens

<400> SEQUENCE: 148
```

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20              25                  30

Gln Asp Gln Glu Gly Asp Thr Asp Ala Gly Leu Lys Glu Ser Pro Leu
        35              40                  45

Gln
```

```
<210> SEQ ID NO 149
<211> LENGTH: 5
<212> TYPE: PRT
<213> ORGANISM: artificial sequence
<220> FEATURE:
<223> OTHER INFORMATION: 1 to 49 VHCDR1 consensus, VHCDR1 3aG3, VHCDR1
      3aD3, VHCDR1 3aH6, VHCDR1 3bG4; 49 to 111 VHCDR1 consensus, VHCDR1
      3aB7, VHCDR1 3bF4

<400> SEQUENCE: 149
```

```
Ser Asn Gly Val Gly
1               5
```

```
<210> SEQ ID NO 150
<211> LENGTH: 16
<212> TYPE: PRT
<213> ORGANISM: artificial sequence
<220> FEATURE:
<223> OTHER INFORMATION: 1 to 49 VHDR2 consensus
<220> FEATURE:
<221> NAME/KEY: MISC_FEATURE
<222> LOCATION: (3)..(3)
<223> OTHER INFORMATION: S or A
<220> FEATURE:
<221> NAME/KEY: MISC_FEATURE
<222> LOCATION: (5)..(5)
<223> OTHER INFORMATION: S or V or G
<220> FEATURE:
<221> NAME/KEY: MISC_FEATURE
<222> LOCATION: (8)..(8)
<223> OTHER INFORMATION: A or K or V
<220> FEATURE:
<221> NAME/KEY: MISC_FEATURE
<222> LOCATION: (10)..(10)
<223> OTHER INFORMATION: A or S or G
<220> FEATURE:
<221> NAME/KEY: MISC_FEATURE
<222> LOCATION: (11)..(11)
<223> OTHER INFORMATION: N or H

<400> SEQUENCE: 150

Asp Ile Xaa Ser Xaa Gly Lys Xaa Tyr Xaa Xaa Pro Ala Leu Lys Ser
1               5                   10                  15

<210> SEQ ID NO 151
<211> LENGTH: 14
<212> TYPE: PRT
<213> ORGANISM: artificial sequence
<220> FEATURE:
<223> OTHER INFORMATION: 1 to 49 VHDR3 consensus
<220> FEATURE:
<221> NAME/KEY: MISC_FEATURE
<222> LOCATION: (7)..(7)
<223> OTHER INFORMATION: S or T
<220> FEATURE:
<221> NAME/KEY: MISC_FEATURE
<222> LOCATION: (12)..(12)
<223> OTHER INFORMATION: I or S

<400> SEQUENCE: 151

Cys Arg Asp Gly Gly Val Xaa Tyr Gly Tyr Asp Xaa Asp Tyr
1               5                   10

<210> SEQ ID NO 152
<211> LENGTH: 14
<212> TYPE: PRT
<213> ORGANISM: artificial sequence
<220> FEATURE:
<223> OTHER INFORMATION: 1 to 49 VLDR1 consensus
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (5)..(5)
<223> OTHER INFORMATION: S or G
<220> FEATURE:
<221> NAME/KEY: MISC_FEATURE
<222> LOCATION: (7)..(7)
<223> OTHER INFORMATION: I or V
<220> FEATURE:
<221> NAME/KEY: MISC_FEATURE
<222> LOCATION: (9)..(9)
<223> OTHER INFORMATION: G or S or Y
<220> FEATURE:
<221> NAME/KEY: MISC_FEATURE
<222> LOCATION: (11)..(11)
```

```
<223> OTHER INFORMATION: N or D
<220> FEATURE:
<221> NAME/KEY: MISC_FEATURE
<222> LOCATION: (12)..(12)
<223> OTHER INFORMATION: Y or D
<220> FEATURE:
<221> NAME/KEY: MISC_FEATURE
<222> LOCATION: (13)..(13)
<223> OTHER INFORMATION: L or V
<220> FEATURE:
<221> NAME/KEY: MISC_FEATURE
<222> LOCATION: (14)..(14)
<223> OTHER INFORMATION: S or G

<400> SEQUENCE: 152

Ser Gly Ser Xaa Xaa Asn Xaa Gly Xaa Gly Xaa Xaa Xaa Xaa
1               5                   10

<210> SEQ ID NO 153
<211> LENGTH: 7
<212> TYPE: PRT
<213> ORGANISM: artificial sequence
<220> FEATURE:
<223> OTHER INFORMATION: 1 to 49 VLDR2 consensus
<220> FEATURE:
<221> NAME/KEY: MISC_FEATURE
<222> LOCATION: (2)..(2)
<223> OTHER INFORMATION: A or V
<220> FEATURE:
<221> NAME/KEY: MISC_FEATURE
<222> LOCATION: (4)..(4)
<223> OTHER INFORMATION: S or N or E
<220> FEATURE:
<221> NAME/KEY: MISC_FEATURE
<222> LOCATION: (5)..(5)
<223> OTHER INFORMATION: R or L

<400> SEQUENCE: 153

Gly Xaa Thr Xaa Xaa Ala Ser
1               5

<210> SEQ ID NO 154
<211> LENGTH: 10
<212> TYPE: PRT
<213> ORGANISM: artificial sequence
<220> FEATURE:
<223> OTHER INFORMATION: 1 to 49 VLDR3 consensus
<220> FEATURE:
<221> NAME/KEY: MISC_FEATURE
<222> LOCATION: (1)..(1)
<223> OTHER INFORMATION: A or G
<220> FEATURE:
<221> NAME/KEY: MISC_FEATURE
<222> LOCATION: (3)..(3)
<223> OTHER INFORMATION: F or Y
<220> FEATURE:
<221> NAME/KEY: MISC_FEATURE
<222> LOCATION: (5)..(5)
<223> OTHER INFORMATION: T or S or D
<220> FEATURE:
<221> NAME/KEY: MISC_FEATURE
<222> LOCATION: (6)..(6)
<223> OTHER INFORMATION: S or N
<220> FEATURE:
<221> NAME/KEY: MISC_FEATURE
<222> LOCATION: (10)..(10)
<223> OTHER INFORMATION: I or V

<400> SEQUENCE: 154

Xaa Ser Xaa Asp Xaa Xaa Ser Gly Gly Xaa
1               5                   10

<210> SEQ ID NO 155
```

-continued

```
<211> LENGTH: 16
<212> TYPE: PRT
<213> ORGANISM: artificial sequence
<220> FEATURE:
<223> OTHER INFORMATION: VHCDR2 3aG3

<400> SEQUENCE: 155

Asp Ile Ser Ser Ser Gly Lys Ala Tyr Ala Asn Pro Ala Leu Lys Ser
1               5                   10                  15

<210> SEQ ID NO 156
<211> LENGTH: 16
<212> TYPE: PRT
<213> ORGANISM: artificial sequence
<220> FEATURE:
<223> OTHER INFORMATION: VHCDR2 3aD3

<400> SEQUENCE: 156

Asp Ile Ser Ser Gly Gly Lys Val Tyr Gly His Pro Ala Leu Lys Ser
1               5                   10                  15

<210> SEQ ID NO 157
<211> LENGTH: 16
<212> TYPE: PRT
<213> ORGANISM: artificial sequence
<220> FEATURE:
<223> OTHER INFORMATION: VHCDR2 3aH6, VHCDR2 3bF4, VHCDR2 CA2, VHCDR2
      CB6, VHCDR2 CA10

<400> SEQUENCE: 157

Asp Ile Ser Ser Val Gly Lys Lys Tyr Ala Asn Pro Ala Leu Lys Ser
1               5                   10                  15

<210> SEQ ID NO 158
<211> LENGTH: 16
<212> TYPE: PRT
<213> ORGANISM: artificial sequence
<220> FEATURE:
<223> OTHER INFORMATION: VHCDR2 3bG4, CC4

<400> SEQUENCE: 158

Asp Ile Ala Ser Ser Gly Lys Ala Tyr Ser Asn Pro Ala Leu Lys Ser
1               5                   10                  15

<210> SEQ ID NO 159
<211> LENGTH: 14
<212> TYPE: PRT
<213> ORGANISM: artificial sequence
<220> FEATURE:
<223> OTHER INFORMATION: VHCDR3 3aG3

<400> SEQUENCE: 159

Cys Arg Asp Gly Gly Val Ser Tyr Gly Tyr Asp Ile Asp Tyr
1               5                   10

<210> SEQ ID NO 160
<211> LENGTH: 14
<212> TYPE: PRT
<213> ORGANISM: artificial sequence
<220> FEATURE:
<223> OTHER INFORMATION: VHCDR3 3aD3, CB5

<400> SEQUENCE: 160

Cys Arg Asp Gly Gly Val Ser Tyr Gly Tyr Asp Ser Asp Tyr
1               5                   10

<210> SEQ ID NO 161
```

-continued

```
<211> LENGTH: 14
<212> TYPE: PRT
<213> ORGANISM: artificial sequence
<220> FEATURE:
<223> OTHER INFORMATION: VHCDR3 3aH6, VHCDR3 3bG4 VHCDR3 3bF4, VHCDR3
      CA2, VHCDR3 CB6, VHCDR3 CA10, VHCDR3 CA6, VHCDR3 CC4, VHCDR3 CC5,
      VHCDR3 CA2

<400> SEQUENCE: 161

Cys Arg Asp Gly Gly Val Thr Tyr Gly Tyr Asp Ile Asp Tyr
1               5                   10

<210> SEQ ID NO 162
<211> LENGTH: 16
<212> TYPE: PRT
<213> ORGANISM: artificial sequence
<220> FEATURE:
<223> OTHER INFORMATION: 297 to 390 VHCDR2 consensus
<220> FEATURE:
<221> NAME/KEY: MISC_FEATURE
<222> LOCATION: (2)..(2)
<223> OTHER INFORMATION: I or V
<220> FEATURE:
<221> NAME/KEY: MISC_FEATURE
<222> LOCATION: (3)..(3)
<223> OTHER INFORMATION: D or G or N
<220> FEATURE:
<221> NAME/KEY: MISC_FEATURE
<222> LOCATION: (4)..(4)
<223> OTHER INFORMATION: T or I or Y or S
<220> FEATURE:
<221> NAME/KEY: MISC_FEATURE
<222> LOCATION: (7)..(7)
<223> OTHER INFORMATION: E or T or R
<220> FEATURE:
<221> NAME/KEY: MISC_FEATURE
<222> LOCATION: (8)..(8)
<223> OTHER INFORMATION: E or S or T
<220> FEATURE:
<221> NAME/KEY: MISC_FEATURE
<222> LOCATION: (9)..(9)
<223> OTHER INFORMATION: G or Y or E
<220> FEATURE:
<221> NAME/KEY: MISC_FEATURE
<222> LOCATION: (10)..(10)
<223> OTHER INFORMATION: Y or F
<220> FEATURE:
<221> NAME/KEY: MISC_FEATURE
<222> LOCATION: (11)..(11)
<223> OTHER INFORMATION: N or S
<220> FEATURE:
<221> NAME/KEY: MISC_FEATURE
<222> LOCATION: (12)..(12)
<223> OTHER INFORMATION: P or S
<220> FEATURE:
<221> NAME/KEY: MISC_FEATURE
<222> LOCATION: (13)..(13)
<223> OTHER INFORMATION: A or V
<220> FEATURE:
<221> NAME/KEY: MISC_FEATURE
<222> LOCATION: (15)..(15)
<223> OTHER INFORMATION: N or K

<400> SEQUENCE: 162

Gly Xaa Xaa Xaa Asp Gly Xaa Xaa Xaa Xaa Xaa Xaa Xaa Leu Xaa Ser
1               5                   10                  15

<210> SEQ ID NO 163
<211> LENGTH: 14
<212> TYPE: PRT
<213> ORGANISM: artificial sequence
<220> FEATURE:
<223> OTHER INFORMATION: VLCDR1 3aG3

<400> SEQUENCE: 163
```

-continued

```
Ser Gly Ser Ser Ser Asn Ile Gly Gly Gly Asn Tyr Leu Ser
1               5                   10
```

<210> SEQ ID NO 164
<211> LENGTH: 17
<212> TYPE: PRT
<213> ORGANISM: artificial sequence
<220> FEATURE:
<223> OTHER INFORMATION: 297 to 390 VHCDR3 consensus
<220> FEATURE:
<221> NAME/KEY: MISC_FEATURE
<222> LOCATION: (1)..(1)
<223> OTHER INFORMATION: S or N or D or T
<220> FEATURE:
<221> NAME/KEY: MISC_FEATURE
<222> LOCATION: (2)..(2)
<223> OTHER INFORMATION: Y or nothing or S
<220> FEATURE:
<221> NAME/KEY: MISC_FEATURE
<222> LOCATION: (3)..(3)
<223> OTHER INFORMATION: R or nothing or K
<220> FEATURE:
<221> NAME/KEY: MISC_FEATURE
<222> LOCATION: (4)..(4)
<223> OTHER INFORMATION: A or nothing or G or S or T
<220> FEATURE:
<221> NAME/KEY: MISC_FEATURE
<222> LOCATION: (5)..(5)
<223> OTHER INFORMATION: D or nothing
<220> FEATURE:
<221> NAME/KEY: MISC_FEATURE
<222> LOCATION: (6)..(6)
<223> OTHER INFORMATION: G or nothing
<220> FEATURE:
<221> NAME/KEY: MISC_FEATURE
<222> LOCATION: (7)..(7)
<223> OTHER INFORMATION: L or nothing or Y
<220> FEATURE:
<221> NAME/KEY: MISC_FEATURE
<222> LOCATION: (8)..(8)
<223> OTHER INFORMATION: A or nothing or G
<220> FEATURE:
<221> NAME/KEY: MISC_FEATURE
<222> LOCATION: (9)..(9)
<223> OTHER INFORMATION: Y or nothing or W
<220> FEATURE:
<221> NAME/KEY: MISC_FEATURE
<222> LOCATION: (10)..(10)
<223> OTHER INFORMATION: G or nothing
<220> FEATURE:
<221> NAME/KEY: MISC_FEATURE
<222> LOCATION: (11)..(11)
<223> OTHER INFORMATION: Y or nothing or H
<220> FEATURE:
<221> NAME/KEY: MISC_FEATURE
<222> LOCATION: (12)..(12)
<223> OTHER INFORMATION: V or Y
<220> FEATURE:
<221> NAME/KEY: MISC_FEATURE
<222> LOCATION: (13)..(13)
<223> OTHER INFORMATION: Q or I or Y
<220> FEATURE:
<221> NAME/KEY: MISC_FEATURE
<222> LOCATION: (14)..(14)
<223> OTHER INFORMATION: A or D or Q
<220> FEATURE:
<221> NAME/KEY: MISC_FEATURE
<222> LOCATION: (15)..(15)
<223> OTHER INFORMATION: I or F
<220> FEATURE:
<221> NAME/KEY: MISC_FEATURE
<222> LOCATION: (16)..(16)
<223> OTHER INFORMATION: D or E

<400> SEQUENCE: 164

Xaa Xaa Xaa Xaa Xaa Xaa Xaa Xaa Xaa Xaa Xaa Xaa Xaa Xaa Xaa Xaa

-continued

```
1               5               10              15

Tyr

<210> SEQ ID NO 165
<211> LENGTH: 14
<212> TYPE: PRT
<213> ORGANISM: artificial sequence
<220> FEATURE:
<223> OTHER INFORMATION: VLCDR1 3aH6, VLCDR1 CA2

<400> SEQUENCE: 165

Ser Gly Ser Ser Gly Asn Val Gly Tyr Gly Asp Tyr Val Ser
1               5               10

<210> SEQ ID NO 166
<211> LENGTH: 14
<212> TYPE: PRT
<213> ORGANISM: artificial sequence
<220> FEATURE:
<223> OTHER INFORMATION: VLCDR1 3bG4

<400> SEQUENCE: 166

Ser Gly Ser Thr Ser Asn Val Gly Ser Gly Asn Asp Val Ser
1               5               10

<210> SEQ ID NO 167
<211> LENGTH: 14
<212> TYPE: PRT
<213> ORGANISM: artificial sequence
<220> FEATURE:
<223> OTHER INFORMATION: 297 to 390 VLCDR1 consensus
<220> FEATURE:
<221> NAME/KEY: MISC_FEATURE
<222> LOCATION: (4)..(4)
<223> OTHER INFORMATION: F or N or S or Y
<220> FEATURE:
<221> NAME/KEY: MISC_FEATURE
<222> LOCATION: (5)..(5)
<223> OTHER INFORMATION: I or S
<220> FEATURE:
<221> NAME/KEY: MISC_FEATURE
<222> LOCATION: (6)..(6)
<223> OTHER INFORMATION: G or N
<220> FEATURE:
<221> NAME/KEY: MISC_FEATURE
<222> LOCATION: (7)..(7)
<223> OTHER INFORMATION: I or S or V
<220> FEATURE:
<221> NAME/KEY: MISC_FEATURE
<222> LOCATION: (8)..(8)
<223> OTHER INFORMATION: S or A or G
<220> FEATURE:
<221> NAME/KEY: MISC_FEATURE
<222> LOCATION: (9)..(9)
<223> OTHER INFORMATION: S or Y or G
<220> FEATURE:
<221> NAME/KEY: MISC_FEATURE
<222> LOCATION: (10)..(10)
<223> OTHER INFORMATION: Nothing or G
<220> FEATURE:
<221> NAME/KEY: MISC_FEATURE
<222> LOCATION: (11)..(11)
<223> OTHER INFORMATION: Nothing or D
<220> FEATURE:
<221> NAME/KEY: MISC_FEATURE
<222> LOCATION: (12)..(12)
<223> OTHER INFORMATION: Nothing or Y
<220> FEATURE:
<221> NAME/KEY: MISC_FEATURE
<222> LOCATION: (14)..(14)
<223> OTHER INFORMATION: G or T or S

<400> SEQUENCE: 167
```

Ser Gly Ser Xaa Xaa Xaa Xaa Xaa Xaa Xaa Xaa Xaa Val Xaa
1               5                   10

<210> SEQ ID NO 168
<211> LENGTH: 7
<212> TYPE: PRT
<213> ORGANISM: artificial sequence
<220> FEATURE:
<223> OTHER INFORMATION: VLCDR2 3aD3

<400> SEQUENCE: 168

Gly Val Thr Glu Arg Ala Ser
1               5

<210> SEQ ID NO 169
<211> LENGTH: 7
<212> TYPE: PRT
<213> ORGANISM: artificial sequence
<220> FEATURE:
<223> OTHER INFORMATION: VLCDR2 3aH6, VLCDR2 CA2

<400> SEQUENCE: 169

Gly Ala Thr Asn Leu Ala Ser
1               5

<210> SEQ ID NO 170
<211> LENGTH: 7
<212> TYPE: PRT
<213> ORGANISM: artificial sequence
<220> FEATURE:
<223> OTHER INFORMATION: VLCDR2 E2A6, 3bG4, CC4

<400> SEQUENCE: 170

Gly Ala Thr Asn Arg Ala Ser
1               5

<210> SEQ ID NO 171
<211> LENGTH: 10
<212> TYPE: PRT
<213> ORGANISM: artificial sequence
<220> FEATURE:
<223> OTHER INFORMATION: VLCDR3 3aG3

<400> SEQUENCE: 171

Ala Ser Phe Asp Thr Ser Ser Gly Gly Ile
1               5                   10

<210> SEQ ID NO 172
<211> LENGTH: 10
<212> TYPE: PRT
<213> ORGANISM: artificial sequence
<220> FEATURE:
<223> OTHER INFORMATION: VLCDR3 3aD3

<400> SEQUENCE: 172

Ala Ser Tyr Asp Asp Ser Ser Gly Gly Ile
1               5                   10

<210> SEQ ID NO 173
<211> LENGTH: 10
<212> TYPE: PRT
<213> ORGANISM: artificial sequence
<220> FEATURE:
<223> OTHER INFORMATION: VLCDR3 3aH6, VLCDR3 CA2

<400> SEQUENCE: 173

```
Ala Ser Tyr Asp Ser Ser Ser Gly Gly Val
1               5                   10
```

<210> SEQ ID NO 174
<211> LENGTH: 10
<212> TYPE: PRT
<213> ORGANISM: artificial sequence
<220> FEATURE:
<223> OTHER INFORMATION: VLCDR3 3bG4

<400> SEQUENCE: 174

```
Gly Ser Tyr Asp Ser Asn Ser Gly Gly Ile
1               5                   10
```

<210> SEQ ID NO 175
<211> LENGTH: 63
<212> TYPE: PRT
<213> ORGANISM: Homo sapiens

<400> SEQUENCE: 175

```
Gln Thr Pro Thr Glu Asp Gly Ser Glu Glu Pro Gly Ser Glu Thr Ser
1               5                   10                  15

Asp Ala Lys Ser Thr Pro Thr Ala Glu Asp Val Thr Ala Pro Leu Val
            20                  25                  30

Asp Glu Gly Ala Pro Gly Lys Gln Ala Ala Ala Gln Pro His Thr Glu
        35                  40                  45

Ile Pro Glu Gly Thr Thr Ala Glu Glu Ala Gly Ile Gly Asp Thr
        50                  55                  60
```

<210> SEQ ID NO 176
<211> LENGTH: 16
<212> TYPE: PRT
<213> ORGANISM: artificial sequence
<220> FEATURE:
<223> OTHER INFORMATION: 49 to 111 VHCDR2 consensus
<220> FEATURE:
<221> NAME/KEY: MISC_FEATURE
<222> LOCATION: (2)..(2)
<223> OTHER INFORMATION: I or K
<220> FEATURE:
<221> NAME/KEY: MISC_FEATURE
<222> LOCATION: (5)..(5)
<223> OTHER INFORMATION: V or A
<220> FEATURE:
<221> NAME/KEY: MISC_FEATURE
<222> LOCATION: (8)..(8)
<223> OTHER INFORMATION: K orT
<220> FEATURE:
<221> NAME/KEY: MISC_FEATURE
<222> LOCATION: (10)..(10)
<223> OTHER INFORMATION: A or G

<400> SEQUENCE: 176

```
Asp Xaa Ser Ser Xaa Ser Lys Xaa Tyr Xaa Asn Pro Ala Leu Lys Ser
1               5                   10                  15
```

<210> SEQ ID NO 177
<211> LENGTH: 14
<212> TYPE: PRT
<213> ORGANISM: artificial sequence
<220> FEATURE:
<223> OTHER INFORMATION: 49 to 111 VHCDR3 consensus
<220> FEATURE:
<221> NAME/KEY: MISC_FEATURE
<222> LOCATION: (12)..(12)
<223> OTHER INFORMATION: I or V

<400> SEQUENCE: 177

-continued

```
Cys Arg Asp Gly Gly Val Thr Tyr Gly Tyr Asp Xaa Asp Tyr
1               5                   10

<210> SEQ ID NO 178
<211> LENGTH: 14
<212> TYPE: PRT
<213> ORGANISM: artificial sequence
<220> FEATURE:
<223> OTHER INFORMATION: 49 to 111 VLCDR1 consensus
<220> FEATURE:
<221> NAME/KEY: MISC_FEATURE
<222> LOCATION: (9)..(9)
<223> OTHER INFORMATION: L or Y
<220> FEATURE:
<221> NAME/KEY: MISC_FEATURE
<222> LOCATION: (10)..(10)
<223> OTHER INFORMATION: R or G
<220> FEATURE:
<221> NAME/KEY: MISC_FEATURE
<222> LOCATION: (11)..(11)
<223> OTHER INFORMATION: N or D
<220> FEATURE:
<221> NAME/KEY: MISC_FEATURE
<222> LOCATION: (12)..(12)
<223> OTHER INFORMATION: Y or V
<220> FEATURE:
<221> NAME/KEY: MISC_FEATURE
<222> LOCATION: (14)..(14)
<223> OTHER INFORMATION: T or S

<400> SEQUENCE: 178

Ser Gly Ser Ser Ser Asn Val Gly Xaa Xaa Xaa Xaa Val Xaa
1               5                   10

<210> SEQ ID NO 179
<211> LENGTH: 7
<212> TYPE: PRT
<213> ORGANISM: artificial sequence
<220> FEATURE:
<223> OTHER INFORMATION: 49 to 111 VLCDR2 consensus
<220> FEATURE:
<221> NAME/KEY: MISC_FEATURE
<222> LOCATION: (2)..(2)
<223> OTHER INFORMATION: A or T
<220> FEATURE:
<221> NAME/KEY: MISC_FEATURE
<222> LOCATION: (4)..(4)
<223> OTHER INFORMATION: S or T

<400> SEQUENCE: 179

Gly Xaa Thr Xaa Arg Ala Ser
1               5

<210> SEQ ID NO 180
<211> LENGTH: 10
<212> TYPE: PRT
<213> ORGANISM: artificial sequence
<220> FEATURE:
<223> OTHER INFORMATION: 49 to 111 VLCDR3 consensus
<220> FEATURE:
<221> NAME/KEY: MISC_FEATURE
<222> LOCATION: (3)..(3)
<223> OTHER INFORMATION: A or F
<220> FEATURE:
<221> NAME/KEY: MISC_FEATURE
<222> LOCATION: (5)..(5)
<223> OTHER INFORMATION: T or S
<220> FEATURE:
<221> NAME/KEY: MISC_FEATURE
<222> LOCATION: (6)..(6)
<223> OTHER INFORMATION: N or D
<220> FEATURE:
<221> NAME/KEY: MISC_FEATURE
<222> LOCATION: (7)..(7)
```

<223> OTHER INFORMATION: D or S
<220> FEATURE:
<221> NAME/KEY: MISC_FEATURE
<222> LOCATION: (10)..(10)
<223> OTHER INFORMATION: V or I

<400> SEQUENCE: 180

Ala Ser Xaa Asp Xaa Xaa Xaa Gly Gly Xaa
1               5                   10

<210> SEQ ID NO 181
<211> LENGTH: 7
<212> TYPE: PRT
<213> ORGANISM: artificial sequence
<220> FEATURE:
<223> OTHER INFORMATION: 297 to 390 VLCDR2 consensus
<220> FEATURE:
<221> NAME/KEY: MISC_FEATURE
<222> LOCATION: (1)..(1)
<223> OTHER INFORMATION: A or R or D
<220> FEATURE:
<221> NAME/KEY: MISC_FEATURE
<222> LOCATION: (2)..(2)
<223> OTHER INFORMATION: S or N or A
<220> FEATURE:
<221> NAME/KEY: MISC_FEATURE
<222> LOCATION: (3)..(3)
<223> OTHER INFORMATION: D or R or T
<220> FEATURE:
<221> NAME/KEY: MISC_FEATURE
<222> LOCATION: (4)..(4)
<223> OTHER INFORMATION: G or N
<220> FEATURE:
<221> NAME/KEY: MISC_FEATURE
<222> LOCATION: (6)..(6)
<223> OTHER INFORMATION: P or A

<400> SEQUENCE: 181

Xaa Xaa Xaa Xaa Arg Xaa Ser
1               5

<210> SEQ ID NO 182
<211> LENGTH: 16
<212> TYPE: PRT
<213> ORGANISM: artificial sequence
<220> FEATURE:
<223> OTHER INFORMATION: VHCDR2 3aB7, CB12, CC3, CA3, CD1

<400> SEQUENCE: 182

Asp Lys Ser Ser Ala Gly Lys Thr Tyr Gly Asn Pro Ala Leu Lys Ser
1               5                   10                  15

<210> SEQ ID NO 183
<211> LENGTH: 11
<212> TYPE: PRT
<213> ORGANISM: artificial sequence
<220> FEATURE:
<223> OTHER INFORMATION: 297 to 390 VLCDR3 consensus
<220> FEATURE:
<221> NAME/KEY: MISC_FEATURE
<222> LOCATION: (1)..(1)
<223> OTHER INFORMATION: G or A
<220> FEATURE:
<221> NAME/KEY: MISC_FEATURE
<222> LOCATION: (3)..(3)
<223> OTHER INFORMATION: S or Y or H
<220> FEATURE:
<221> NAME/KEY: MISC_FEATURE
<222> LOCATION: (4)..(4)
<223> OTHER INFORMATION: D or nothing
<220> FEATURE:
<221> NAME/KEY: MISC_FEATURE
<222> LOCATION: (5)..(5)

-continued

```
<223> OTHER INFORMATION: R or Q or D
<220> FEATURE:
<221> NAME/KEY: MISC_FEATURE
<222> LOCATION: (6)..(6)
<223> OTHER INFORMATION: T or S or N
<220> FEATURE:
<221> NAME/KEY: MISC_FEATURE
<222> LOCATION: (7)..(7)
<223> OTHER INFORMATION: Q or W or R
<220> FEATURE:
<221> NAME/KEY: MISC_FEATURE
<222> LOCATION: (8)..(8)
<223> OTHER INFORMATION: Y or G or I
<220> FEATURE:
<221> NAME/KEY: MISC_FEATURE
<222> LOCATION: (9)..(9)
<223> OTHER INFORMATION: T or S
<220> FEATURE:
<221> NAME/KEY: MISC_FEATURE
<222> LOCATION: (10)..(10)
<223> OTHER INFORMATION: G or A
<220> FEATURE:
<221> NAME/KEY: MISC_FEATURE
<222> LOCATION: (11)..(11)
<223> OTHER INFORMATION: V or L

<400> SEQUENCE: 183

Xaa Ser Xaa Xaa Xaa Xaa Xaa Xaa Xaa Xaa Xaa
1               5                   10

<210> SEQ ID NO 184
<211> LENGTH: 14
<212> TYPE: PRT
<213> ORGANISM: artificial sequence
<220> FEATURE:
<223> OTHER INFORMATION: VHCDR3 3aB7, CA3

<400> SEQUENCE: 184

Cys Arg Asp Gly Gly Val Thr Tyr Gly Tyr Asp Val Asp Tyr
1               5                   10

<210> SEQ ID NO 185
<211> LENGTH: 14
<212> TYPE: PRT
<213> ORGANISM: artificial sequence
<220> FEATURE:
<223> OTHER INFORMATION: VLCDR1 3bF4

<400> SEQUENCE: 185

Ser Gly Ser Ser Ser Asn Val Gly Leu Arg Asn Tyr Val Thr
1               5                   10

<210> SEQ ID NO 186
<211> LENGTH: 14
<212> TYPE: PRT
<213> ORGANISM: artificial sequence
<220> FEATURE:
<223> OTHER INFORMATION: VLCDR1 3aB7

<400> SEQUENCE: 186

Ser Gly Ser Ser Ser Asn Val Gly Tyr Gly Asp Val Val Ser
1               5                   10

<210> SEQ ID NO 187
<211> LENGTH: 5
<212> TYPE: PRT
<213> ORGANISM: artificial sequence
<220> FEATURE:
<223> OTHER INFORMATION: VHCDR1 S1D5

<400> SEQUENCE: 187
```

```
Ser His Ser Val Gly
1               5

<210> SEQ ID NO 188
<211> LENGTH: 7
<212> TYPE: PRT
<213> ORGANISM: artificial sequence
<220> FEATURE:
<223> OTHER INFORMATION: VLCDR2 3aB7, CC3, CD1

<400> SEQUENCE: 188

Gly Thr Thr Thr Arg Ala Ser
1               5

<210> SEQ ID NO 189
<211> LENGTH: 10
<212> TYPE: PRT
<213> ORGANISM: artificial sequence
<220> FEATURE:
<223> OTHER INFORMATION: VLCDR3 3bF4

<400> SEQUENCE: 189

Ala Ser Ala Asp Thr Asn Asp Gly Gly Val
1               5                   10

<210> SEQ ID NO 190
<211> LENGTH: 10
<212> TYPE: PRT
<213> ORGANISM: artificial sequence
<220> FEATURE:
<223> OTHER INFORMATION: VLCDR3 3aB7

<400> SEQUENCE: 190

Ala Ser Phe Asp Ser Asp Ser Gly Gly Ile
1               5                   10

<210> SEQ ID NO 191
<211> LENGTH: 11
<212> TYPE: PRT
<213> ORGANISM: Homo sapiens

<400> SEQUENCE: 191

Gly Lys Thr Lys Ile Ala Thr Pro Arg Gly Ala
1               5                   10

<210> SEQ ID NO 192
<211> LENGTH: 5
<212> TYPE: PRT
<213> ORGANISM: artificial sequence
<220> FEATURE:
<223> OTHER INFORMATION: 147 to 157 VHCDR1 consensus
<220> FEATURE:
<221> NAME/KEY: MISC_FEATURE
<222> LOCATION: (5)..(5)
<223> OTHER INFORMATION: I or G

<400> SEQUENCE: 192

Ser Asn Ala Val Xaa
1               5

<210> SEQ ID NO 193
<211> LENGTH: 16
<212> TYPE: PRT
<213> ORGANISM: artificial sequence
<220> FEATURE:
<223> OTHER INFORMATION: 147 to 157 VHCDR2 consensus
<220> FEATURE:
```

-continued

```
<221> NAME/KEY: MISC_FEATURE
<222> LOCATION: (4)..(4)
<223> OTHER INFORMATION: V or I
<220> FEATURE:
<221> NAME/KEY: MISC_FEATURE
<222> LOCATION: (8)..(8)
<223> OTHER INFORMATION: A or T
<220> FEATURE:
<221> NAME/KEY: MISC_FEATURE
<222> LOCATION: (11)..(11)
<223> OTHER INFORMATION: D or N
<220> FEATURE:
<221> NAME/KEY: MISC_FEATURE
<222> LOCATION: (15)..(15)
<223> OTHER INFORMATION: K or E

<400> SEQUENCE: 193

Leu Ile Asp Xaa Asp Gly Asp Xaa Ala Tyr Xaa Pro Ala Leu Xaa Ser
1               5                   10                  15

<210> SEQ ID NO 194
<211> LENGTH: 13
<212> TYPE: PRT
<213> ORGANISM: artificial sequence
<220> FEATURE:
<223> OTHER INFORMATION: 147 to 157 VHCDR3 consensus
<220> FEATURE:
<221> NAME/KEY: MISC_FEATURE
<222> LOCATION: (1)..(1)
<223> OTHER INFORMATION: D or H
<220> FEATURE:
<221> NAME/KEY: MISC_FEATURE
<222> LOCATION: (3)..(3)
<223> OTHER INFORMATION: G or D
<220> FEATURE:
<221> NAME/KEY: MISC_FEATURE
<222> LOCATION: (4)..(4)
<223> OTHER INFORMATION: S or K
<220> FEATURE:
<221> NAME/KEY: MISC_FEATURE
<222> LOCATION: (8)..(8)
<223> OTHER INFORMATION: V or A
<220> FEATURE:
<221> NAME/KEY: MISC_FEATURE
<222> LOCATION: (9)..(9)
<223> OTHER INFORMATION: S or D
<220> FEATURE:
<221> NAME/KEY: MISC_FEATURE
<222> LOCATION: (10)..(10)
<223> OTHER INFORMATION: D or S

<400> SEQUENCE: 194

Xaa Tyr Xaa Xaa Trp Gly Tyr Xaa Xaa Xaa Ile Asp Tyr
1               5                   10

<210> SEQ ID NO 195
<211> LENGTH: 14
<212> TYPE: PRT
<213> ORGANISM: artificial sequence
<220> FEATURE:
<223> OTHER INFORMATION: 147 to 157 VLCDR1 consensus
<220> FEATURE:
<221> NAME/KEY: MISC_FEATURE
<222> LOCATION: (4)..(4)
<223> OTHER INFORMATION: D or S
<220> FEATURE:
<221> NAME/KEY: MISC_FEATURE
<222> LOCATION: (5)..(5)
<223> OTHER INFORMATION: Nothing or S
<220> FEATURE:
<221> NAME/KEY: MISC_FEATURE
<222> LOCATION: (6)..(6)
<223> OTHER INFORMATION: Nothing or N
<220> FEATURE:
<221> NAME/KEY: MISC_FEATURE
```

```
<222> LOCATION: (7)..(7)
<223> OTHER INFORMATION: Nothing or V
<220> FEATURE:
<221> NAME/KEY: MISC_FEATURE
<222> LOCATION: (8)..(8)
<223> OTHER INFORMATION: I or G
<220> FEATURE:
<221> NAME/KEY: MISC_FEATURE
<222> LOCATION: (9)..(9)
<223> OTHER INFORMATION: G or Y
<220> FEATURE:
<221> NAME/KEY: MISC_FEATURE
<222> LOCATION: (11)..(11)
<223> OTHER INFORMATION: A or D
<220> FEATURE:
<221> NAME/KEY: MISC_FEATURE
<222> LOCATION: (12)..(12)
<223> OTHER INFORMATION: D or Y

<400> SEQUENCE: 195

Ser Gly Ser Xaa Xaa Xaa Xaa Xaa Xaa Gly Xaa Xaa Val Gly
1               5                   10

<210> SEQ ID NO 196
<211> LENGTH: 7
<212> TYPE: PRT
<213> ORGANISM: artificial sequence
<220> FEATURE:
<223> OTHER INFORMATION: 147 to 157 VLCDR2 consensus
<220> FEATURE:
<221> NAME/KEY: MISC_FEATURE
<222> LOCATION: (2)..(2)
<223> OTHER INFORMATION: N or A
<220> FEATURE:
<221> NAME/KEY: MISC_FEATURE
<222> LOCATION: (3)..(3)
<223> OTHER INFORMATION: D or T
<220> FEATURE:
<221> NAME/KEY: MISC_FEATURE
<222> LOCATION: (4)..(4)
<223> OTHER INFORMATION: N or T
<220> FEATURE:
<221> NAME/KEY: MISC_FEATURE
<222> LOCATION: (6)..(6)
<223> OTHER INFORMATION: P or A

<400> SEQUENCE: 196

Asp Xaa Xaa Xaa Arg Xaa Ser
1               5

<210> SEQ ID NO 197
<211> LENGTH: 10
<212> TYPE: PRT
<213> ORGANISM: artificial sequence
<220> FEATURE:
<223> OTHER INFORMATION: 147 to 157 VLCDR3 consensus
<220> FEATURE:
<221> NAME/KEY: MISC_FEATURE
<222> LOCATION: (1)..(1)
<223> OTHER INFORMATION: G or A
<220> FEATURE:
<221> NAME/KEY: MISC_FEATURE
<222> LOCATION: (2)..(2)
<223> OTHER INFORMATION: T or S
<220> FEATURE:
<221> NAME/KEY: MISC_FEATURE
<222> LOCATION: (4)..(4)
<223> OTHER INFORMATION: S or Q
<220> FEATURE:
<221> NAME/KEY: MISC_FEATURE
<222> LOCATION: (5)..(5)
<223> OTHER INFORMATION: G or N
<220> FEATURE:
<221> NAME/KEY: MISC_FEATURE
<222> LOCATION: (6)..(6)
```

```
<223> OTHER INFORMATION: A or E
<220> FEATURE:
<221> NAME/KEY: MISC_FEATURE
<222> LOCATION: (7)..(7)
<223> OTHER INFORMATION: N or R
<220> FEATURE:
<221> NAME/KEY: MISC_FEATURE
<222> LOCATION: (8)..(8)
<223> OTHER INFORMATION: Y or S
<220> FEATURE:
<221> NAME/KEY: MISC_FEATURE
<222> LOCATION: (10)..(10)
<223> OTHER INFORMATION: I or V

<400> SEQUENCE: 197

Xaa Xaa Tyr Xaa Xaa Xaa Xaa Xaa Gly Xaa
1               5                   10

<210> SEQ ID NO 198
<211> LENGTH: 5
<212> TYPE: PRT
<213> ORGANISM: artificial sequence
<220> FEATURE:
<223> OTHER INFORMATION: VHCDR1 3aD6, CB11, CC7, CA1, CD2

<400> SEQUENCE: 198

Ser Asn Ala Val Ile
1               5

<210> SEQ ID NO 199
<211> LENGTH: 5
<212> TYPE: PRT
<213> ORGANISM: artificial sequence
<220> FEATURE:
<223> OTHER INFORMATION: VHCDR1 NS1B2

<400> SEQUENCE: 199

Asp Tyr Gly Ile Gly
1               5

<210> SEQ ID NO 200
<211> LENGTH: 16
<212> TYPE: PRT
<213> ORGANISM: artificial sequence
<220> FEATURE:
<223> OTHER INFORMATION: VHCDR2 3aD6, CB11, CC7, CD2

<400> SEQUENCE: 200

Leu Ile Asp Val Asp Gly Asp Ala Ala Tyr Asp Pro Ala Leu Lys Ser
1               5                   10                  15

<210> SEQ ID NO 201
<211> LENGTH: 16
<212> TYPE: PRT
<213> ORGANISM: artificial sequence
<220> FEATURE:
<223> OTHER INFORMATION: VHCDR2 3aA6

<400> SEQUENCE: 201

Leu Ile Asp Ile Asp Gly Asp Thr Ala Tyr Asn Pro Ala Leu Glu Ser
1               5                   10                  15

<210> SEQ ID NO 202
<211> LENGTH: 13
<212> TYPE: PRT
<213> ORGANISM: artificial sequence
<220> FEATURE:
<223> OTHER INFORMATION: VHCDR3 3aD6, CB11, CC7, CD2
```

-continued

```
<400> SEQUENCE: 202

Asp Tyr Gly Ser Trp Gly Tyr Val Ser Asp Ile Asp Tyr
1               5                   10

<210> SEQ ID NO 203
<211> LENGTH: 13
<212> TYPE: PRT
<213> ORGANISM: artificial sequence
<220> FEATURE:
<223> OTHER INFORMATION: VHCDR3 3aA6

<400> SEQUENCE: 203

His Tyr Asp Lys Trp Gly Tyr Ala Asp Ser Ile Asp Tyr
1               5                   10

<210> SEQ ID NO 204
<211> LENGTH: 11
<212> TYPE: PRT
<213> ORGANISM: artificial sequence
<220> FEATURE:
<223> OTHER INFORMATION: VLCDR1 3aD6

<400> SEQUENCE: 204

Ser Gly Ser Asp Ile Gly Gly Ala Asp Val Gly
1               5                   10

<210> SEQ ID NO 205
<211> LENGTH: 16
<212> TYPE: PRT
<213> ORGANISM: artificial sequence
<220> FEATURE:
<223> OTHER INFORMATION: VHDR2 NS1B2

<400> SEQUENCE: 205

Gly Ile Asn Tyr Asp Gly Arg Thr Glu Tyr Asn Ser Ala Leu Lys Ser
1               5                   10                  15

<210> SEQ ID NO 206
<211> LENGTH: 7
<212> TYPE: PRT
<213> ORGANISM: artificial sequence
<220> FEATURE:
<223> OTHER INFORMATION: VLCDR2 3aD6

<400> SEQUENCE: 206

Asp Asn Asp Asn Arg Pro Ser
1               5

<210> SEQ ID NO 207
<211> LENGTH: 7
<212> TYPE: PRT
<213> ORGANISM: artificial sequence
<220> FEATURE:
<223> OTHER INFORMATION: VLCDR2 3aA6, CA6

<400> SEQUENCE: 207

Asp Ala Thr Thr Arg Ala Ser
1               5

<210> SEQ ID NO 208
<211> LENGTH: 10
<212> TYPE: PRT
<213> ORGANISM: artificial sequence
<220> FEATURE:
<223> OTHER INFORMATION: VLCDR3 3aD6

<400> SEQUENCE: 208
```

```
Gly Thr Tyr Ser Gly Ala Asn Tyr Gly Ile
1               5                   10

<210> SEQ ID NO 209
<211> LENGTH: 10
<212> TYPE: PRT
<213> ORGANISM: artificial sequence
<220> FEATURE:
<223> OTHER INFORMATION: VLCDR3 3aA6

<400> SEQUENCE: 209

Ala Ser Tyr Gln Asn Glu Arg Ser Gly Val
1               5                   10

<210> SEQ ID NO 210
<211> LENGTH: 17
<212> TYPE: PRT
<213> ORGANISM: artificial sequence
<220> FEATURE:
<223> OTHER INFORMATION: VHCDR3 S1A12, S1A5

<400> SEQUENCE: 210

Thr Tyr Arg Ser Asp Gly Tyr Ala Tyr Gly Tyr Val Gln Ala Ile Asp
1               5                   10                  15

Tyr

<210> SEQ ID NO 211
<211> LENGTH: 14
<212> TYPE: PRT
<213> ORGANISM: artificial sequence
<220> FEATURE:
<223> OTHER INFORMATION: VHCDR3 NS1B2

<400> SEQUENCE: 211

Asp Ser Lys Gly Gly Trp Gly His Val Tyr Gln Phe Asp Tyr
1               5                   10

<210> SEQ ID NO 212
<211> LENGTH: 11
<212> TYPE: PRT
<213> ORGANISM: artificial sequence
<220> FEATURE:
<223> OTHER INFORMATION: VLCDR1 NS2B6

<400> SEQUENCE: 212

Ser Gly Ser Asn Ile Gly Ser Ala Ser Val Thr
1               5                   10

<210> SEQ ID NO 213
<211> LENGTH: 14
<212> TYPE: PRT
<213> ORGANISM: artificial sequence
<220> FEATURE:
<223> OTHER INFORMATION: VLCDR1 NS1B2

<400> SEQUENCE: 213

Ser Gly Ser Ser Ser Asn Val Gly Tyr Gly Asp Tyr Val Ser
1               5                   10

<210> SEQ ID NO 214
<211> LENGTH: 7
<212> TYPE: PRT
<213> ORGANISM: artificial sequence
<220> FEATURE:
<223> OTHER INFORMATION: VLCDR2 NS2B6
```

-continued

```
<400> SEQUENCE: 214

Arg Asn Arg Asn Arg Pro Ser
1               5

<210> SEQ ID NO 215
<211> LENGTH: 7
<212> TYPE: PRT
<213> ORGANISM: artificial sequence
<220> FEATURE:
<223> OTHER INFORMATION: VLCDR2 NS1B2

<400> SEQUENCE: 215

Asp Ala Thr Asn Arg Ala Ser
1               5

<210> SEQ ID NO 216
<211> LENGTH: 10
<212> TYPE: PRT
<213> ORGANISM: artificial sequence
<220> FEATURE:
<223> OTHER INFORMATION: VLCDR3 NS1B2

<400> SEQUENCE: 216

Ala Ser His Asp Asn Arg Ile Ser Ala Val
1               5                   10

<210> SEQ ID NO 217
<211> LENGTH: 10
<212> TYPE: PRT
<213> ORGANISM: artificial sequence
<220> FEATURE:
<223> OTHER INFORMATION: VLCDR3 NS2B6

<400> SEQUENCE: 217

Gly Ser Tyr Gln Ser Trp Gly Ser Gly Val
1               5                   10

<210> SEQ ID NO 218
<211> LENGTH: 249
<212> TYPE: PRT
<213> ORGANISM: artificial sequence
<220> FEATURE:
<223> OTHER INFORMATION: S1E12 amino acid sequence

<400> SEQUENCE: 218

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Gly Ser Asn
            20                  25                  30

Ser Val Gly Trp Val Arg Gln Ala Pro Gly Lys Ala Pro Glu Trp Val
        35                  40                  45

Ala Gly Ile Asp Thr Asp Gly Glu Gly Tyr Asn Pro Ala Leu Asn
    50                  55                  60

Ser Arg Leu Ser Ile Thr Arg Asp Thr Ser Lys Ser Gln Val Ser Leu
65                  70                  75                  80

Ser Leu Ser Ser Val Thr Ser Glu Asp Thr Ala Val Tyr Tyr Cys Gly
                85                  90                  95

Arg Ser Tyr Arg Ala Asp Gly Leu Ala Tyr Gly Tyr Val Gln Ala Ile
            100                 105                 110

Asp Tyr Trp Gly Pro Gly Leu Leu Val Thr Val Ser Ser Glu Gly Lys
        115                 120                 125

Ser Ser Gly Ala Ser Gly Glu Ser Lys Val Asp Asp Arg Val Val Arg
```

-continued

```
        130              135              140
Thr Gln Pro Ser Ser Val Ser Gly Ser Leu Gly Gln Arg Val Ser Ile
145                 150              155                 160

Thr Cys Ser Gly Ser Phe Ile Gly Ile Ser Ser Val Gly Trp Phe Gln
                165              170              175

Gln Leu Pro Gly Ser Gly Leu Arg Thr Ile Ile Val Ala Ser Asp Gly
            180              185              190

Arg Pro Ser Gly Val Pro Asp Arg Phe Ser Met Ser Lys Ser Gly Asn
        195              200              205

Thr Ala Thr Leu Thr Ile Ser Ser Leu Gln Ala Glu Asp Glu Ala Asp
        210              215              220

Tyr Phe Cys Gly Ser Ser Asp Arg Thr Gln Tyr Thr Gly Val Phe Gly
225                 230              235                 240

Ser Gly Thr Arg Leu Thr Val Leu Gly
            245
```

<210> SEQ ID NO 219
<211> LENGTH: 747
<212> TYPE: DNA
<213> ORGANISM: artificial sequence
<220> FEATURE:
<223> OTHER INFORMATION: S1E12 nucleotide sequence

<400> SEQUENCE: 219

```
caggtgcagt tgcaggagtc gggacccagc ctggtgaagc cctcacagac cctctccctc     60
acctgcacgg tctccggatt ctcattaggc agcaattctg taggctgggt ccgccaggct    120
ccaggaaagg cgccggagtg ggttgctggt atagatactg atggagaaga aggctataat    180
ccagccctta actcccggct cagcatcacc agggacacct ccaagagtca ggtctctttg    240
tcattgagca gcgtgacaag tgaggacacg gccgtgtact actgtggaag aagttatagg    300
gctgatggtc ttgcttacgg ttatgtccaa gccatcgact actggggccc aggactcctg    360
gtcaccgtct cctcagaagg taaatcttct ggcgcgtctg gcgagtctaa agtggatgac    420
agggtcgtgc ggactcaacc gtcctccgtg tctgggtccc tgggccagag ggtctccatc    480
acctgctctg gaagcttcat cggtattagt agtgtaggct ggttccaaca gctcccagga    540
tcgggcctca gaaccatcat cgtggcgagt gacggtcgac cctcaggggt ccccgaccga    600
ttctctatgt ccaaatcggg caacacagcc accctgacca tcagctcgct ccaggctgag    660
gacgaggccg attatttctg tggaagtagt gataggactc aatatactgg agttttcggc    720
agcgggacca ggctgaccgt cctgggt                                        747
```

<210> SEQ ID NO 220
<211> LENGTH: 249
<212> TYPE: PRT
<213> ORGANISM: artificial sequence
<220> FEATURE:
<223> OTHER INFORMATION: NS2A1 amino acid sequence

<400> SEQUENCE: 220

```
Gln Val Gln Leu Gln Glu Ser Gly Pro Ser Leu Val Lys Pro Ser Gln
1               5               10                  15

Thr Leu Ser Leu Thr Cys Thr Val Ser Gly Phe Ser Leu Ser Thr Asn
                20              25              30

Ser Val Gly Trp Val Arg Gln Ala Pro Gly Lys Ala Pro Glu Trp Val
        35              40              45

Ala Gly Ile Asp Thr Asp Gly Glu Glu Gly Phe Asn Pro Val Leu Lys
```

-continued

```
        50              55              60

Ser Arg Leu Ser Ile Thr Arg Asp Thr Ser Lys Ser Gln Val Ser Leu
65              70              75              80

Ser Leu Ser Asn Val Thr Ser Glu Asp Thr Ala Val Tyr Tyr Cys Gly
                85              90              95

Arg Ser Tyr Arg Thr Asp Gly Leu Ala Tyr Gly Tyr Val Gln Ala Ile
            100             105             110

Asp Tyr Trp Gly Pro Gly Leu Leu Val Thr Ile Ser Ser Glu Gly Lys
        115             120             125

Ser Ser Gly Ala Ser Gly Glu Ser Lys Val Asp Asp Gln Ser Val Leu
        130             135             140

Thr Gln Pro Ser Ser Val Ser Gly Ser Pro Gly Gln Thr Val Ser Ile
145             150             155             160

Thr Cys Ser Gly Ser Tyr Ile Gly Ser Ser Gly Val Gly Trp Phe Gln
            165             170             175

Gln Leu Pro Gly Ser Gly Leu Arg Thr Ile Ile Val Ala Ser Asp Gly
        180             185             190

Arg Pro Ser Gly Val Pro Asp Gly Phe Ser Met Ser Lys Ser Gly Asn
        195             200             205

Thr Ala Thr Leu Thr Ile Ser Ser Leu Gln Ala Glu Asp Glu Ala Asp
    210             215             220

Tyr Phe Cys Gly Ser Ser Asp Arg Thr Gln Tyr Thr Gly Leu Phe Gly
225             230             235             240

Ser Gly Thr Arg Leu Thr Val Leu Gly
            245
```

```
<210> SEQ ID NO 221
<211> LENGTH: 13
<212> TYPE: PRT
<213> ORGANISM: artificial sequence
<220> FEATURE:
<223> OTHER INFORMATION: E2E8, E1E8 epitope, residues 379-391

<400> SEQUENCE: 221

Arg Glu Asn Ala Lys Ala Lys Thr Asp His Gly Ala Glu
1               5               10
```

```
<210> SEQ ID NO 222
<211> LENGTH: 13
<212> TYPE: PRT
<213> ORGANISM: artificial sequence
<220> FEATURE:
<223> OTHER INFORMATION: E2E8, E1E8 general epitope
<220> FEATURE:
<221> NAME/KEY: MISC_FEATURE
<222> LOCATION: (1)..(12)
<223> OTHER INFORMATION: Where X is any amino acid

<400> SEQUENCE: 222

Xaa Xaa Xaa Xaa Xaa Xaa Xaa Xaa Xaa Xaa Xaa Xaa Glu
1               5                       10
```

```
<210> SEQ ID NO 223
<211> LENGTH: 5
<212> TYPE: PRT
<213> ORGANISM: artificial sequence
<220> FEATURE:
<223> OTHER INFORMATION: 379-391 VHDR1 consensus
<220> FEATURE:
<221> NAME/KEY: MISC_FEATURE
<222> LOCATION: (1)..(1)
<223> OTHER INFORMATION: D or S
```

-continued

```
<220> FEATURE:
<221> NAME/KEY: MISC_FEATURE
<222> LOCATION: (2)..(2)
<223> OTHER INFORMATION: R or W

<400> SEQUENCE: 223

Xaa Xaa Gly Val Ala
1               5

<210> SEQ ID NO 224
<211> LENGTH: 16
<212> TYPE: PRT
<213> ORGANISM: artificial sequence
<220> FEATURE:
<223> OTHER INFORMATION: 379-391 VHDR2 consensus
<220> FEATURE:
<221> NAME/KEY: MISC_FEATURE
<222> LOCATION: (7)..(7)
<223> OTHER INFORMATION: T or G
<220> FEATURE:
<221> NAME/KEY: MISC_FEATURE
<222> LOCATION: (8)..(8)
<223> OTHER INFORMATION: I or T
<220> FEATURE:
<221> NAME/KEY: MISC_FEATURE
<222> LOCATION: (9)..(9)
<223> OTHER INFORMATION: D or E
<220> FEATURE:
<221> NAME/KEY: MISC_FEATURE
<222> LOCATION: (10)..(10)
<223> OTHER INFORMATION: Y or D

<400> SEQUENCE: 224

Thr Met Arg Ser Gly Gly Xaa Xaa Xaa Xaa Asn Pro Ala Leu Lys Ser
1               5                   10                  15

<210> SEQ ID NO 225
<211> LENGTH: 9
<212> TYPE: PRT
<213> ORGANISM: artificial sequence
<220> FEATURE:
<223> OTHER INFORMATION: 379-391 VHDR3 consensus
<220> FEATURE:
<221> NAME/KEY: MISC_FEATURE
<222> LOCATION: (6)..(6)
<223> OTHER INFORMATION: D or I or V
<220> FEATURE:
<221> NAME/KEY: MISC_FEATURE
<222> LOCATION: (7)..(7)
<223> OTHER INFORMATION: R or H

<400> SEQUENCE: 225

Gly Tyr Leu Ser Gly Xaa Xaa Tyr Ala
1               5

<210> SEQ ID NO 226
<211> LENGTH: 14
<212> TYPE: PRT
<213> ORGANISM: artificial sequence
<220> FEATURE:
<223> OTHER INFORMATION: 379-391 VLDR1 consensus
<220> FEATURE:
<221> NAME/KEY: MISC_FEATURE
<222> LOCATION: (4)..(4)
<223> OTHER INFORMATION: R or S
<220> FEATURE:
<221> NAME/KEY: MISC_FEATURE
<222> LOCATION: (6)..(6)
<223> OTHER INFORMATION: D or N
<220> FEATURE:
<221> NAME/KEY: MISC_FEATURE
<222> LOCATION: (7)..(7)
<223> OTHER INFORMATION: I or V
```

-continued

```
<220> FEATURE:
<221> NAME/KEY: MISC_FEATURE
<222> LOCATION: (9)..(9)
<223> OTHER INFORMATION: Y or D or A
<220> FEATURE:
<221> NAME/KEY: MISC_FEATURE
<222> LOCATION: (11)..(11)
<223> OTHER INFORMATION: N or D or R
<220> FEATURE:
<221> NAME/KEY: MISC_FEATURE
<222> LOCATION: (14)..(14)
<223> OTHER INFORMATION: S or G

<400> SEQUENCE: 226

Ser Gly Ser Xaa Ser Xaa Xaa Gly Xaa Gly Xaa Tyr Val Xaa
1               5                   10

<210> SEQ ID NO 227
<211> LENGTH: 7
<212> TYPE: PRT
<213> ORGANISM: artificial sequence
<220> FEATURE:
<223> OTHER INFORMATION: 379-391 VLDR2 consensus
<220> FEATURE:
<221> NAME/KEY: MISC_FEATURE
<222> LOCATION: (1)..(1)
<223> OTHER INFORMATION: D or S or G
<220> FEATURE:
<221> NAME/KEY: MISC_FEATURE
<222> LOCATION: (2)..(2)
<223> OTHER INFORMATION: T or A
<220> FEATURE:
<221> NAME/KEY: MISC_FEATURE
<222> LOCATION: (3)..(3)
<223> OTHER INFORMATION: N or R or T
<220> FEATURE:
<221> NAME/KEY: MISC_FEATURE
<222> LOCATION: (4)..(4)
<223> OTHER INFORMATION: T or N or S

<400> SEQUENCE: 227

Xaa Xaa Xaa Xaa Arg Ala Ser
1               5

<210> SEQ ID NO 228
<211> LENGTH: 10
<212> TYPE: PRT
<213> ORGANISM: artificial sequence
<220> FEATURE:
<223> OTHER INFORMATION: 379-391 VLDR3 consensus
<220> FEATURE:
<221> NAME/KEY: MISC_FEATURE
<222> LOCATION: (2)..(2)
<223> OTHER INFORMATION: N or S
<220> FEATURE:
<221> NAME/KEY: MISC_FEATURE
<222> LOCATION: (5)..(5)
<223> OTHER INFORMATION: S or T
<220> FEATURE:
<221> NAME/KEY: MISC_FEATURE
<222> LOCATION: (6)..(6)
<223> OTHER INFORMATION: S or G
<220> FEATURE:
<221> NAME/KEY: MISC_FEATURE
<222> LOCATION: (7)..(7)
<223> OTHER INFORMATION: R or N
<220> FEATURE:
<221> NAME/KEY: MISC_FEATURE
<222> LOCATION: (8)..(8)
<223> OTHER INFORMATION: S or N
<220> FEATURE:
<221> NAME/KEY: MISC_FEATURE
<222> LOCATION: (9)..(9)
<223> OTHER INFORMATION: H or L
<220> FEATURE:
```

-continued

```
<221> NAME/KEY: MISC_FEATURE
<222> LOCATION: (10)..(10)
<223> OTHER INFORMATION: L or I

<400> SEQUENCE: 228

Ala Xaa Ile Asp Xaa Xaa Xaa Xaa Xaa Xaa
1               5                   10

<210> SEQ ID NO 229
<211> LENGTH: 5
<212> TYPE: PRT
<213> ORGANISM: artificial sequence
<220> FEATURE:
<223> OTHER INFORMATION: VHCDR1 E2E8

<400> SEQUENCE: 229

Asp Arg Gly Val Ala
1               5

<210> SEQ ID NO 230
<211> LENGTH: 5
<212> TYPE: PRT
<213> ORGANISM: artificial sequence
<220> FEATURE:
<223> OTHER INFORMATION: VHCDR1 E1E8, E2A6

<400> SEQUENCE: 230

Asp Trp Gly Val Ala
1               5

<210> SEQ ID NO 231
<211> LENGTH: 5
<212> TYPE: PRT
<213> ORGANISM: artificial sequence
<220> FEATURE:
<223> OTHER INFORMATION: VHCDR1 E2B7

<400> SEQUENCE: 231

Ser Trp Gly Val Ala
1               5

<210> SEQ ID NO 232
<211> LENGTH: 16
<212> TYPE: PRT
<213> ORGANISM: artificial sequence
<220> FEATURE:
<223> OTHER INFORMATION: VHCDR2 E2E8

<400> SEQUENCE: 232

Thr Met Arg Ser Gly Gly Thr Ile Asp Tyr Asn Pro Ala Leu Lys Ser
1               5                   10                  15

<210> SEQ ID NO 233
<211> LENGTH: 16
<212> TYPE: PRT
<213> ORGANISM: artificial sequence
<220> FEATURE:
<223> OTHER INFORMATION: VHCDR2 E2B7

<400> SEQUENCE: 233

Thr Met Arg Ser Gly Gly Gly Thr Glu Tyr Asn Pro Ala Leu Lys Ser
1               5                   10                  15

<210> SEQ ID NO 234
<211> LENGTH: 16
<212> TYPE: PRT
<213> ORGANISM: artificial sequence
```

-continued

```
<220> FEATURE:
<223> OTHER INFORMATION: VHCDR2 E1E8, E2A6

<400> SEQUENCE: 234

Thr Met Arg Ser Gly Gly Thr Thr Asp Asp Asn Pro Ala Leu Lys Ser
1               5                   10                  15

<210> SEQ ID NO 235
<211> LENGTH: 9
<212> TYPE: PRT
<213> ORGANISM: artificial sequence
<220> FEATURE:
<223> OTHER INFORMATION: VHCDR3 E2E8

<400> SEQUENCE: 235

Gly Tyr Leu Ser Gly Asp Arg Tyr Ala
1               5

<210> SEQ ID NO 236
<211> LENGTH: 9
<212> TYPE: PRT
<213> ORGANISM: artificial sequence
<220> FEATURE:
<223> OTHER INFORMATION: VHCDR3 E2B7

<400> SEQUENCE: 236

Gly Tyr Leu Ser Gly Ile His Tyr Ala
1               5

<210> SEQ ID NO 237
<211> LENGTH: 9
<212> TYPE: PRT
<213> ORGANISM: artificial sequence
<220> FEATURE:
<223> OTHER INFORMATION: VHCDR3 E1E8, E2A6

<400> SEQUENCE: 237

Gly Tyr Leu Ser Gly Val His Tyr Ala
1               5

<210> SEQ ID NO 238
<211> LENGTH: 14
<212> TYPE: PRT
<213> ORGANISM: artificial sequence
<220> FEATURE:
<223> OTHER INFORMATION: VLCDR1 E2E8

<400> SEQUENCE: 238

Ser Gly Ser Arg Ser Asp Ile Gly Tyr Gly Asn Tyr Val Ser
1               5                   10

<210> SEQ ID NO 239
<211> LENGTH: 14
<212> TYPE: PRT
<213> ORGANISM: artificial sequence
<220> FEATURE:
<223> OTHER INFORMATION: VLCDR1 E2A6

<400> SEQUENCE: 239

Ser Gly Ser Ser Ser Asn Val Gly Ala Gly Asn Tyr Val Gly
1               5                   10

<210> SEQ ID NO 240
<211> LENGTH: 14
<212> TYPE: PRT
<213> ORGANISM: artificial sequence
<220> FEATURE:
```

```
<223> OTHER INFORMATION: VLCDR1 E2B7

<400> SEQUENCE: 240

Ser Gly Ser Ser Ser Asn Val Gly Asp Gly Asp Tyr Val Gly
1               5                   10

<210> SEQ ID NO 241
<211> LENGTH: 14
<212> TYPE: PRT
<213> ORGANISM: artificial sequence
<220> FEATURE:
<223> OTHER INFORMATION: VLCDR1 E1E8

<400> SEQUENCE: 241

Ser Gly Ser Ser Ser Asn Val Gly Asp Gly Arg Tyr Val Ser
1               5                   10

<210> SEQ ID NO 242
<211> LENGTH: 7
<212> TYPE: PRT
<213> ORGANISM: artificial sequence
<220> FEATURE:
<223> OTHER INFORMATION: VLCDR2 E2E8

<400> SEQUENCE: 242

Asp Thr Asn Thr Arg Ala Ser
1               5

<210> SEQ ID NO 243
<211> LENGTH: 7
<212> TYPE: PRT
<213> ORGANISM: artificial sequence
<220> FEATURE:
<223> OTHER INFORMATION: VLCDR2 E1E8

<400> SEQUENCE: 243

Asp Thr Thr Ser Arg Ala Ser
1               5

<210> SEQ ID NO 244
<211> LENGTH: 7
<212> TYPE: PRT
<213> ORGANISM: artificial sequence
<220> FEATURE:
<223> OTHER INFORMATION: VLCDR2 E2B7

<400> SEQUENCE: 244

Ser Ala Arg Asn Arg Ala Ser
1               5

<210> SEQ ID NO 245
<211> LENGTH: 10
<212> TYPE: PRT
<213> ORGANISM: artificial sequence
<220> FEATURE:
<223> OTHER INFORMATION: VLCDR3 E2E8

<400> SEQUENCE: 245

Ala Asn Ile Asp Ser Ser Arg Ser His Leu
1               5                   10

<210> SEQ ID NO 246
<211> LENGTH: 10
<212> TYPE: PRT
<213> ORGANISM: artificial sequence
<220> FEATURE:
<223> OTHER INFORMATION: VLCDR3 E1E8
```

-continued

<400> SEQUENCE: 246

Ala Ser Ile Asp Ser Gly Asn Asn Leu Leu
1               5                   10

<210> SEQ ID NO 247
<211> LENGTH: 10
<212> TYPE: PRT
<213> ORGANISM: artificial sequence
<220> FEATURE:
<223> OTHER INFORMATION: VLCDR3 E2A6, E2B7

<400> SEQUENCE: 247

Ala Ser Ile Asp Thr Ser Arg Ser His Ile
1               5                   10

<210> SEQ ID NO 248
<211> LENGTH: 243
<212> TYPE: PRT
<213> ORGANISM: artificial sequence
<220> FEATURE:
<223> OTHER INFORMATION: E2E8 amino acid sequence

<400> SEQUENCE: 248

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Asp Arg
            20                  25                  30

Gly Val Ala Trp Val Arg Gln Ala Pro Gly Lys Ala Leu Glu Trp Val
            35                  40                  45

Gly Thr Met Arg Ser Gly Gly Thr Ile Asp Tyr Asn Pro Ala Leu Lys
        50                  55                  60

Ser Arg Leu Ser Ile Thr Arg Asp Thr Ser Lys Ser Gln Val Phe Leu
65                  70                  75                  80

Ser Leu Ser Ser Val Thr Thr Glu Asp Met Ala Met Tyr Tyr Cys Ala
            85                  90                  95

Arg Gly Tyr Leu Ser Gly Asp Arg Tyr Ala Trp Gly Arg Gly Leu Leu
            100                 105                 110

Val Thr Val Ser Ser Glu Gly Lys Ser Ser Gly Ala Ser Gly Glu Ser
        115                 120                 125

Lys Val Asp Asp Gln Ala Val Leu Thr Gln Pro Ser Ser Val Ser Lys
        130                 135                 140

Ser Leu Gly Gln Ser Val Ser Ile Ala Cys Ser Gly Ser Arg Ser Asp
145                 150                 155                 160

Ile Gly Tyr Gly Asn Tyr Val Ser Trp Phe Gln Gln Ile Pro Gly Ser
                165                 170                 175

Ala Pro Lys Leu Leu Ile Tyr Asp Thr Asn Thr Arg Ala Ser Gly Val
            180                 185                 190

Pro Asp Arg Phe Ser Gly Ala Arg Ser Gly Asn Thr Ala Thr Leu Thr
            195                 200                 205

Ile Asn Ser Leu Gln Ala Glu Asp Glu Ala Asp Tyr Tyr Cys Ala Asn
        210                 215                 220

Ile Asp Ser Ser Arg Ser His Leu Phe Gly Ser Gly Thr Arg Leu Thr
225                 230                 235                 240

Val Leu Gly

<210> SEQ ID NO 249
<211> LENGTH: 729

-continued

<212> TYPE: DNA
<213> ORGANISM: artificial sequence
<220> FEATURE:
<223> OTHER INFORMATION: E2E8 nucleotide sequence

<400> SEQUENCE: 249

```
caggtgcagc tgcaggagtc gggacccagc ctggtgaagc cctcacagac cctctccctc      60
acctgcacgg tctctggatt ctcattaacc gaccgtggtg tagcctgggt ccgccaggct     120
ccaggaaagg cactggagtg ggttggtact atgcgtagtg gtggaacgat agactataac     180
ccggccctga atcccggct cagcatcacc aggacacct ccaagagcca agtttcctg       240 tcactgagca gcgtcacaac tgaggacatg gccatgtact actgtgccag aggttatttg     300
agcggtgatc gttatgcctg gggccgagga ctcctggtca ccgtctcctc agaaggtaaa     360
tcttctggcg cgtctggcga gtctaaagtg gatgaccagg ctgtgctgac tcagccgtcc     420
tccgtgtcca gtccctgggc cagagtgtc tccatcgcct gctctggaag caggagcgac     480
attggatatg gtaattatgt gagctggttc aacagatcc caggatcagc ccccaaactc     540
cttatttatg atacaaacac tcgggcctcg gggtcccccg accgattctc cggcgccagg     600
tctggcaaca cagcaacact gaccatcaac tcgctccagg ctgaggacga ggccgattat     660
tactgtgcaa atattgacag tagtcgcagt catctttcg gcagtggcac cagactgacc     720
gtcctgggt                                                            729
```

<210> SEQ ID NO 250
<211> LENGTH: 243
<212> TYPE: PRT
<213> ORGANISM: artificial sequence
<220> FEATURE:
<223> OTHER INFORMATION: E1E8 amino acid sequence

<400> SEQUENCE: 250

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Asp Trp
            20                  25                  30

Gly Val Ala Trp Val Arg Gln Ala Pro Gly Lys Ala Leu Glu Trp Leu
        35                  40                  45

Gly Thr Met Arg Ser Gly Gly Thr Thr Asp Asp Asn Pro Ala Leu Lys
    50                  55                  60

Ser Arg Leu Ser Ile Thr Arg Asp Thr Ser Lys Ser Gln Val Ser Leu
65                  70                  75                  80

Ser Leu Ser Ser Val Thr Thr Glu Asp Met Ala Met Tyr Tyr Cys Ala
                85                  90                  95

Arg Gly Tyr Leu Ser Gly Val His Tyr Ala Trp Gly Arg Gly Leu Leu
            100                 105                 110

Val Thr Val Ser Ser Glu Gly Lys Ser Ser Gly Ala Ser Gly Glu Ser
            115                 120                 125

Lys Val Asp Asp Gln Ala Val Leu Thr Gln Pro Ser Ser Val Ser Gly
        130                 135                 140

Ser Leu Gly Gln Ser Val Ser Ile Thr Cys Ser Gly Ser Ser Ser Asn
145                 150                 155                 160

Val Gly Asp Gly Arg Tyr Val Ser Trp Phe Gln Gln Val Pro Gly Ser
                165                 170                 175

Ala Pro Lys Leu Leu Ile Tyr Asp Thr Thr Ser Arg Ala Ser Gly Val
            180                 185                 190
```

-continued

```
Pro Asp Arg Phe Ser Gly Ser Arg Ser Gly Asn Thr Ala Thr Leu Ile
    195                 200             205

Ile Thr Ser Leu Gln Ala Glu Asp Glu Ala Asp Tyr Tyr Cys Ala Ser
    210                 215             220

Ile Asp Ser Gly Asn Asn Leu Leu Phe Gly Ser Gly Thr Arg Leu Thr
225                 230             235             240

Val Leu Gly
```

```
<210> SEQ ID NO 251
<211> LENGTH: 729
<212> TYPE: DNA
<213> ORGANISM: artificial sequence
<220> FEATURE:
<223> OTHER INFORMATION: E1E8 nucleotide sequence

<400> SEQUENCE: 251
caggtgcagc tgcaggagtc gggacccagc ctggtgaagc cctcacagac cctctccctc      60
acctgcacgg tctctggatt ctcattaact gactggggtg tagcttgggt ccgccaggct     120
ccaggaaagg cactggagtg gcttggtacg atgcgtagtg gtgggactac agacgataac     180
ccggccctga atcccgcct cagcatcacc agggacacct ctaagagcca gtctccctg      240 tcactgagca gcgtgacaac tgaggacatg gccatgtact actgtgccag aggttatttg     300
agtggtgtgc attatgcctg gggccgagga ctcctggtca ccgtctcctc agaaggtaaa     360
tcttctggcg cgtctggcga gtctaaagtg gatgaccagg ctgtgctgac tcagccgtcc     420
tccgtatctg ggtccctggg ccagagtgtc tccatcacct gctctggaag cagcagcaac     480
gtgggagatg gtagatatgt gagctggttc aacaggtcc caggatcagc ccccaaactc      540
ctcatctatg atacaaccag tcgagcctcg ggggttcccg accgattctc cggctccagg     600
tctggcaaca cagcgactct catcatcacc tcgctccagg ctgaggacga ggccgattat     660
tactgtgcat ctattgacag cggtaacaat cttctttcg cagcggcac caggctgacc      720 gtcctgggt                                                             729
```

```
<210> SEQ ID NO 252
<211> LENGTH: 243
<212> TYPE: PRT
<213> ORGANISM: artificial sequence
<220> FEATURE:
<223> OTHER INFORMATION: E2A6 amino acid sequence

<400> SEQUENCE: 252
```

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Asp Trp
            20                  25                  30

Gly Val Ala Trp Val Arg Gln Ala Pro Gly Lys Ala Leu Glu Trp Leu
        35                  40                  45

Gly Thr Met Arg Ser Gly Gly Thr Thr Asp Asp Asn Pro Ala Leu Lys
    50                  55                  60

Ser Arg Leu Ser Ile Thr Arg Asp Thr Ser Lys Ser Gln Val Ser Leu
65                  70                  75                  80

Ser Leu Ser Ser Val Thr Thr Glu Asp Met Ala Met Tyr Tyr Cys Ala
                85                  90                  95

Arg Gly Tyr Leu Ser Gly Val His Tyr Ala Trp Gly Arg Gly Leu Leu
            100                 105                 110

Val Thr Val Ser Ser Glu Gly Lys Ser Ser Gly Ala Ser Gly Glu Ser
```

-continued

```
           115                   120                   125
Lys Val Asp Asp Arg Val Val Arg Thr Gln Pro Ser Ser Val Ser Lys
    130                   135                   140

Ser Leu Gly Gln Ser Val Ser Ile Thr Cys Ser Gly Ser Ser Ser Asn
145                   150                   155                   160

Val Gly Ala Gly Asn Tyr Val Gly Trp Phe Gln Gln Val Pro Gly Ser
                165                   170                   175

Ala Pro Lys Leu Leu Ile Tyr Gly Ala Thr Asn Arg Ala Ser Gly Val
                180                   185                   190

Pro Ala Arg Phe Ser Gly Ser Lys Ser Gly Val Thr Ala Thr Leu Thr
                195                   200                   205

Ile Thr Ser Leu Gln Ala Glu Asp Glu Ala Asp Tyr Tyr Cys Ala Ser
    210                   215                   220

Ile Asp Thr Ser Arg Ser His Ile Phe Gly Ser Gly Thr Arg Leu Thr
225                   230                   235                   240

Val Leu Gly
```

```
<210> SEQ ID NO 253
<211> LENGTH: 729
<212> TYPE: DNA
<213> ORGANISM: artificial sequence
<220> FEATURE:
<223> OTHER INFORMATION: E2A6 nucleotide sequence

<400> SEQUENCE: 253
caggtgcagc tgcaggagtc gggacccagc ctggtgaagc cctcacagac cctctccctc      60
acctgcacgg tctctggatt ctcattaact gactggggtg tagcttgggt ccgccaggct     120
ccaggaaagg cactggagtg gcttggtacg atgcgtagtg gtgggactac agacgataac     180
ccggccctga atcccgcct cagcatcacc agggacacct ctaagagcca agtctccctg      240
tcactgagca gcgtgacaac tgaggacatg gccatgtact actgtgccag aggttatttg      300
agtggtgtgc attatgcctg gggccgagga ctcctggtca ccgtctcctc agaaggtaaa      360
tcttctggcg cgtctggcga gtctaaagtg gatgaccggg tcgtgcggac tcagccgtcc     420
tccgtgtcca agtccctggg ccagagtgtc tccatcacct gctctggaag cagcagcaac     480
gttggagctg gtaattatgt gggctggttc aacaggtcc caggatcagc ccccaaactc      540
ctcatctatg gtgcaaccaa tcgagcctcg ggggtccccg cccgattctc aggctccaag      600
tctggcgtca cagcgactct aaccatcacc tcgctccagg ctgaggacga ggccgattat     660
tactgtgcat ctattgacac cagtcgctct cacattttcg gcagcgggac caggctgacc     720
gtcctgggt                                                              729
```

```
<210> SEQ ID NO 254
<211> LENGTH: 243
<212> TYPE: PRT
<213> ORGANISM: artificial sequence
<220> FEATURE:
<223> OTHER INFORMATION: E2B7 amino acid sequence

<400> SEQUENCE: 254

Gln Val Gln Leu Gln Glu Ser Gly Pro Ser Leu Val Lys Pro Ser Gln
1                   5                   10                  15

Thr Leu Ser Leu Thr Cys Thr Val Ser Gly Phe Ser Leu Thr Ser Trp
            20                  25                  30

Gly Val Ala Trp Val Arg Gln Ala Pro Gly Lys Ala Leu Glu Trp Leu
        35                  40                  45
```

-continued

```
Gly Thr Met Arg Ser Gly Gly Gly Thr Glu Tyr Asn Pro Ala Leu Lys
    50              55                  60

Ser Arg Leu Ser Ile Thr Arg Asp Thr Ser Lys Ser Gln Val Ser Leu
65              70                  75                  80

Ser Leu Ser Ser Val Thr Thr Glu Asp Met Ala Met Tyr Tyr Cys Ala
                85                  90                  95

Arg Gly Tyr Leu Ser Gly Ile His Tyr Ala Trp Gly Arg Gly Leu Leu
            100             105                 110

Val Ser Val Ser Ser Glu Gly Lys Ser Ser Gly Ala Ser Gly Glu Ser
            115             120                 125

Lys Val Asp Asp Gln Ala Val Leu Thr Gln Leu Ser Ser Val Ser Gly
    130             135                 140

Ser Leu Gly Gln Arg Val Ser Ile Thr Cys Ser Gly Ser Ser Ser Asn
145             150                 155                 160

Val Gly Asp Gly Asp Tyr Val Gly Trp Phe Gln Gln Leu Pro Gly Ser
            165             170                 175

Ala Pro Lys Leu Leu Ile Tyr Ser Ala Arg Asn Arg Ala Ser Gly Val
            180             185                 190

Pro Asp Arg Phe Ser Gly Ser Arg Ser Gly Asn Thr Ala Thr Leu Thr
            195             200                 205

Ile Thr Ser Leu Gln Ala Glu Asp Glu Ala Asp Tyr Tyr Cys Ala Ser
    210             215                 220

Ile Asp Thr Ser Arg Ser His Ile Phe Gly Ser Gly Thr Arg Leu Thr
225             230                 235                 240

Val Leu Gly
```

```
<210> SEQ ID NO 255
<211> LENGTH: 126
<212> TYPE: PRT
<213> ORGANISM: Homo sapiens

<400> SEQUENCE: 255

Ser Leu Glu Asp Glu Ala Ala Gly His Val Thr Gln Ala Arg Met Val
1               5                   10                  15

Ser Lys Ser Lys Asp Gly Thr Gly Ser Asp Asp Lys Lys Ala Lys Gly
            20                  25                  30

Ala Asp Gly Lys Thr Lys Ile Ala Thr Pro Arg Gly Ala Ala Pro Pro
        35                  40                  45

Gly Gln Lys Gly Gln Ala Asn Ala Thr Arg Ile Pro Ala Lys Thr Pro
    50                  55                  60

Pro Ala Pro Lys Thr Pro Pro Ser Ser Gly Glu Pro Pro Lys Ser Gly
65                  70                  75                  80

Asp Arg Ser Gly Tyr Ser Ser Pro Gly Ser Pro Gly Thr Pro Gly Ser
                85                  90                  95

Arg Ser Arg Thr Pro Ser Leu Pro Thr Pro Pro Thr Arg Glu Pro Lys
            100                 105                 110

Lys Val Ala Val Val Arg Thr Pro Pro Lys Ser Pro Ser Ser
            115                 120                 125
```

```
<210> SEQ ID NO 256
<211> LENGTH: 11
<212> TYPE: PRT
<213> ORGANISM: artificial sequence
<220> FEATURE:
<223> OTHER INFORMATION: VLCDR1 CB11
```

-continued

```
<400> SEQUENCE: 256

Ser Gly Ser Asn Ile Gly Ser Asn Asp Val Gly
1               5                   10

<210> SEQ ID NO 257
<211> LENGTH: 7
<212> TYPE: PRT
<213> ORGANISM: artificial sequence
<220> FEATURE:
<223> OTHER INFORMATION: VLCDR2 CB11

<400> SEQUENCE: 257

Asp Asn Asn Asn Arg Pro Ser
1               5

<210> SEQ ID NO 258
<211> LENGTH: 11
<212> TYPE: PRT
<213> ORGANISM: artificial sequence
<220> FEATURE:
<223> OTHER INFORMATION: VLCDR3 CB11

<400> SEQUENCE: 258

Gly Gly Tyr Ala Gly Ser Ser Ser Asn Phe Leu
1               5                   10

<210> SEQ ID NO 259
<211> LENGTH: 5
<212> TYPE: PRT
<213> ORGANISM: artificial sequence
<220> FEATURE:
<223> OTHER INFORMATION: VHCDR1 CA2, CB6, CB12, CC3, CA3, CA10, CA6,
      CB5, CC4, CD1, CC5

<400> SEQUENCE: 259

Ser Asn Gly Val Gly
1               5

<210> SEQ ID NO 260
<211> LENGTH: 238
<212> TYPE: PRT
<213> ORGANISM: Homo sapiens

<400> SEQUENCE: 260

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140
```

-continued

```
Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser
225                 230                 235
```

```
<210> SEQ ID NO 261
<211> LENGTH: 14
<212> TYPE: PRT
<213> ORGANISM: artificial sequence
<220> FEATURE:
<223> OTHER INFORMATION: VLCDR1 CB6

<400> SEQUENCE: 261

Ser Gly Ser Ser Ser Asn Ile Gly Thr Gly Asn Tyr Val Gly
1               5                   10
```

```
<210> SEQ ID NO 262
<211> LENGTH: 7
<212> TYPE: PRT
<213> ORGANISM: artificial sequence
<220> FEATURE:
<223> OTHER INFORMATION: VLCDR2 CB6

<400> SEQUENCE: 262

Gly Ala Val Thr Arg Ala Ser
1               5
```

```
<210> SEQ ID NO 263
<211> LENGTH: 10
<212> TYPE: PRT
<213> ORGANISM: artificial sequence
<220> FEATURE:
<223> OTHER INFORMATION: VLCDR3 CB6, CB7

<400> SEQUENCE: 263

Ala Ser Tyr Asp Ser Thr Ser Gly Gly Val
1               5                   10
```

```
<210> SEQ ID NO 264
<211> LENGTH: 319
<212> TYPE: PRT
<213> ORGANISM: Homo sapiens

<400> SEQUENCE: 264

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
```

-continued

```
65                70                75                80

Asp Glu Gly Ala Pro Gly Lys Gln Ala Ala Gln Pro His Thr Glu
              85                90                95

Ile Pro Glu Gly Thr Thr Ala Glu Glu Ala Gly Ile Gly Asp Thr Pro
              100               105               110

Ser Leu Glu Asp Glu Ala Ala Gly His Val Thr Gln Ala Arg Met Val
              115               120               125

Ser Lys Ser Lys Asp Gly Thr Gly Ser Asp Asp Lys Lys Ala Lys Gly
          130               135               140

Ala Asp Gly Lys Thr Lys Ile Ala Thr Pro Arg Gly Ala Ala Pro Pro
      145               150               155               160

Gly Gln Lys Gly Gln Ala Asn Ala Thr Arg Ile Pro Ala Lys Thr Pro
              165               170               175

Pro Ala Pro Lys Thr Pro Pro Ser Ser Gly Glu Pro Pro Lys Ser Gly
              180               185               190

Asp Arg Ser Gly Tyr Ser Ser Pro Gly Ser Pro Gly Thr Pro Gly Ser
              195               200               205

Arg Ser Arg Thr Pro Ser Leu Pro Thr Pro Pro Thr Arg Glu Pro Lys
      210               215               220

Lys Val Ala Val Val Arg Thr Pro Pro Lys Ser Pro Ser Ser Ala Lys
225               230               235               240

Ser Arg Leu Gln Thr Ala Pro Val Pro Met Pro Asp Leu Lys Asn Val
              245               250               255

Lys Ser Lys Ile Gly Ser Thr Glu Asn Leu Lys His Gln Pro Gly Gly
              260               265               270

Gly Lys Val Gln Ile Ile Asn Lys Lys Leu Asp Leu Ser Asn Val Gln
          275               280               285

Ser Lys Cys Gly Ser Lys Asp Asn Ile Lys His Val Pro Gly Gly Gly
      290               295               300

Ser Val Gln Ile Val Tyr Lys Pro Val Asp Leu Ser Lys Val Thr
305               310               315
```

```
<210> SEQ ID NO 265
<211> LENGTH: 17
<212> TYPE: PRT
<213> ORGANISM: artificial sequence
<220> FEATURE:
<223> OTHER INFORMATION: VHCDR3 CA7, CA12

<400> SEQUENCE: 265

Gly Ser Tyr Tyr His Gly Gly Gly Asn Gly Met Val Asp Phe Phe Asp
1               5                10                15

Tyr

<210> SEQ ID NO 266
<211> LENGTH: 5
<212> TYPE: PRT
<213> ORGANISM: artificial sequence
<220> FEATURE:
<223> OTHER INFORMATION: VHCDR1 CA8

<400> SEQUENCE: 266

Ser Asn Ala Val Val
1               5

<210> SEQ ID NO 267
<211> LENGTH: 16
<212> TYPE: PRT
```

<213> ORGANISM: artificial sequence
<220> FEATURE:
<223> OTHER INFORMATION: VHCDR2 CA8

<400> SEQUENCE: 267

Ala Ile Asp Lys Asp Gly Asp Thr Ile Tyr Asn Pro Ala Leu Lys Ser
1               5                   10                  15

<210> SEQ ID NO 268
<211> LENGTH: 12
<212> TYPE: PRT
<213> ORGANISM: artificial sequence
<220> FEATURE:
<223> OTHER INFORMATION: VHCDR3 CA8

<400> SEQUENCE: 268

Asp Pro Ser Gly Trp Gly Tyr Pro Asp Val Asp Tyr
1               5                   10

<210> SEQ ID NO 269
<211> LENGTH: 11
<212> TYPE: PRT
<213> ORGANISM: artificial sequence
<220> FEATURE:
<223> OTHER INFORMATION: VLCDR1 CA8

<400> SEQUENCE: 269

Ser Gly Thr Tyr Ile Gly Ser Ser Asp Val Gly
1               5                   10

<210> SEQ ID NO 270
<211> LENGTH: 7
<212> TYPE: PRT
<213> ORGANISM: artificial sequence
<220> FEATURE:
<223> OTHER INFORMATION: VLCDR2 CA8

<400> SEQUENCE: 270

Gly Thr Ser Ser Arg Pro Ser
1               5

<210> SEQ ID NO 271
<211> LENGTH: 11
<212> TYPE: PRT
<213> ORGANISM: artificial sequence
<220> FEATURE:
<223> OTHER INFORMATION: VLCDR3 CA8

<400> SEQUENCE: 271

Ala Thr Tyr Glu Ser Ser Tyr His Asn Ser Val
1               5                   10

<210> SEQ ID NO 272
<211> LENGTH: 5
<212> TYPE: PRT
<213> ORGANISM: artificial sequence
<220> FEATURE:
<223> OTHER INFORMATION: VHCDR1 CB10, CA11

<400> SEQUENCE: 272

Ser Asn Thr Val Ala
1               5

<210> SEQ ID NO 273
<211> LENGTH: 16
<212> TYPE: PRT
<213> ORGANISM: artificial sequence -continued

```
<220> FEATURE:
<223> OTHER INFORMATION: VHCDR2 CB10, CA11

<400> SEQUENCE: 273

Glu Ile Asn Ser Gly Gly Ser Thr Tyr Tyr Asn Pro Ala Leu Lys Ser
1               5                   10                  15

<210> SEQ ID NO 274
<211> LENGTH: 9
<212> TYPE: PRT
<213> ORGANISM: artificial sequence
<220> FEATURE:
<223> OTHER INFORMATION: VHCDR3 CB10, CA11

<400> SEQUENCE: 274

Gly Ala Arg Ser Thr Tyr Ala Ala Tyr
1               5

<210> SEQ ID NO 275
<211> LENGTH: 14
<212> TYPE: PRT
<213> ORGANISM: artificial sequence
<220> FEATURE:
<223> OTHER INFORMATION: VLCDR1 CB10

<400> SEQUENCE: 275

Ser Gly Ser Ser Ser Asp Val Gly Tyr Ser Thr Trp Val Tyr
1               5                   10

<210> SEQ ID NO 276
<211> LENGTH: 7
<212> TYPE: PRT
<213> ORGANISM: artificial sequence
<220> FEATURE:
<223> OTHER INFORMATION: VLCDR2 CB10

<400> SEQUENCE: 276

His Ile Ser Asn Arg Ala Ser
1               5

<210> SEQ ID NO 277
<211> LENGTH: 11
<212> TYPE: PRT
<213> ORGANISM: artificial sequence
<220> FEATURE:
<223> OTHER INFORMATION: VLCDR3 CB10

<400> SEQUENCE: 277

Ala Ala Tyr Asp Ser Ser Asn Asn Val Trp Ile
1               5                   10

<210> SEQ ID NO 278
<211> LENGTH: 13
<212> TYPE: PRT
<213> ORGANISM: Homo sapiens

<400> SEQUENCE: 278

Asp His Ala Gly Thr Tyr Gly Leu Gly Asp Arg Lys Asp
1               5                   10

<210> SEQ ID NO 279
<211> LENGTH: 5
<212> TYPE: PRT
<213> ORGANISM: artificial sequence
<220> FEATURE:
<223> OTHER INFORMATION: VHCDR1 CB7
```

-continued

```
<400> SEQUENCE: 279

Asn Tyr Arg Val Gly
1               5

<210> SEQ ID NO 280
<211> LENGTH: 16
<212> TYPE: PRT
<213> ORGANISM: artificial sequence
<220> FEATURE:
<223> OTHER INFORMATION: VHCDR2 CB7

<400> SEQUENCE: 280

Asn Ile Arg Ser Gly Gly Thr Thr Trp Tyr Asn Pro Ala Leu Lys Ser
1               5               10                  15

<210> SEQ ID NO 281
<211> LENGTH: 11
<212> TYPE: PRT
<213> ORGANISM: artificial sequence
<220> FEATURE:
<223> OTHER INFORMATION: VHCDR3 CB7

<400> SEQUENCE: 281

Asp Ser Ser Gly Asp Leu Tyr Ala Tyr Asp Tyr
1               5                   10

<210> SEQ ID NO 282
<211> LENGTH: 14
<212> TYPE: PRT
<213> ORGANISM: artificial sequence
<220> FEATURE:
<223> OTHER INFORMATION: VLCDR1 CB7

<400> SEQUENCE: 282

Ser Gly Ser Ser Ser Asn Val Gly Tyr Gly Asn Tyr Met Ala
1               5                   10

<210> SEQ ID NO 283
<211> LENGTH: 13
<212> TYPE: PRT
<213> ORGANISM: Homo sapiens

<400> SEQUENCE: 283

Ala Asp Gly Lys Thr Lys Ile Ala Thr Pro Arg Gly Ala
1               5                   10

<210> SEQ ID NO 284
<211> LENGTH: 7
<212> TYPE: PRT
<213> ORGANISM: artificial sequence
<220> FEATURE:
<223> OTHER INFORMATION: VLCDR2 CC7

<400> SEQUENCE: 284

Asp Asn Asn Asp Arg Pro Ser
1               5

<210> SEQ ID NO 285
<211> LENGTH: 10
<212> TYPE: PRT
<213> ORGANISM: artificial sequence
<220> FEATURE:
<223> OTHER INFORMATION: VLCDR3 CC7

<400> SEQUENCE: 285

Ala Ser Tyr Asp Thr Ser Asn Ile Gly Leu
```

-continued

```
1               5                    10

<210> SEQ ID NO 286
<211> LENGTH: 14
<212> TYPE: PRT
<213> ORGANISM: artificial sequence
<220> FEATURE:
<223> OTHER INFORMATION: VHCDR3 CB12, CC3, CD1

<400> SEQUENCE: 286

Cys Arg Asp Gly Gly Val Ser Tyr Gly Tyr Asp Val Asp Tyr
1               5                    10

<210> SEQ ID NO 287
<211> LENGTH: 13
<212> TYPE: PRT
<213> ORGANISM: artificial sequence
<220> FEATURE:
<223> OTHER INFORMATION: VLCDR1 CB12

<400> SEQUENCE: 287

Ser Gly Ser Ser Ser Asn Val Gly Gly Asp Tyr Val Gly
1               5                    10

<210> SEQ ID NO 288
<211> LENGTH: 7
<212> TYPE: PRT
<213> ORGANISM: artificial sequence
<220> FEATURE:
<223> OTHER INFORMATION: VLCDR2 CB12, CA1

<400> SEQUENCE: 288

Asp Thr Thr Ser Arg Pro Ser
1               5

<210> SEQ ID NO 289
<211> LENGTH: 10
<212> TYPE: PRT
<213> ORGANISM: artificial sequence
<220> FEATURE:
<223> OTHER INFORMATION: VLCDR3 CB12

<400> SEQUENCE: 289

Ala Ser Val Asp Lys Thr Thr Gly Gly Val
1               5                    10

<210> SEQ ID NO 290
<211> LENGTH: 14
<212> TYPE: PRT
<213> ORGANISM: artificial sequence
<220> FEATURE:
<223> OTHER INFORMATION: VLCDR1 CC3, CD1

<400> SEQUENCE: 290

Ser Gly Ser Ser Ser Asn Val Gly Tyr Gly Thr Tyr Val Ser
1               5                    10

<210> SEQ ID NO 291
<211> LENGTH: 10
<212> TYPE: PRT
<213> ORGANISM: artificial sequence
<220> FEATURE:
<223> OTHER INFORMATION: VLCDR3 CC3, CD1

<400> SEQUENCE: 291

Ala Ser Tyr Asp Thr Gly Ser Gly Gly Val
1               5                    10
```

-continued

```
<210> SEQ ID NO 292
<211> LENGTH: 11
<212> TYPE: PRT
<213> ORGANISM: artificial sequence
<220> FEATURE:
<223> OTHER INFORMATION: VLCDR1 CC7

<400> SEQUENCE: 292

Ser Gly Ser Tyr Ile Thr Gly Ser Ser Val Gly
1               5                   10

<210> SEQ ID NO 293
<211> LENGTH: 155
<212> TYPE: PRT
<213> ORGANISM: Homo sapiens

<400> SEQUENCE: 293

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg
145                 150                 155

<210> SEQ ID NO 294
<211> LENGTH: 73
<212> TYPE: PRT
<213> ORGANISM: Homo sapiens

<400> SEQUENCE: 294

Arg Gly Ala Ala Pro Pro Gly Gln Lys Gly Gln Ala Asn Ala Thr Arg
1               5                   10                  15

Ile Pro Ala Lys Thr Pro Pro Ala Pro Lys Thr Pro Pro Ser Ser Gly
                20                  25                  30

Glu Pro Pro Lys Ser Gly Asp Arg Ser Gly Tyr Ser Ser Pro Gly Ser
        35                  40                  45

Pro Gly Thr Pro Gly Ser Arg Ser Arg Thr Pro Ser Leu Pro Thr Pro
    50                  55                  60

Pro Thr Arg Glu Pro Lys Lys Val Ala
65                  70

<210> SEQ ID NO 295
<211> LENGTH: 84
<212> TYPE: PRT
```

-continued

```
<213> ORGANISM: Homo sapiens

<400> SEQUENCE: 295

Arg Gly Ala Ala Pro Pro Gly Gln Lys Gly Gln Ala Asn Ala Thr Arg
1               5                   10                  15

Ile Pro Ala Lys Thr Pro Pro Ala Pro Lys Thr Pro Pro Ser Ser Gly
            20                  25                  30

Glu Pro Pro Lys Ser Gly Asp Arg Ser Gly Tyr Ser Ser Pro Gly Ser
        35                  40                  45

Pro Gly Thr Pro Gly Ser Arg Ser Arg Thr Pro Ser Leu Pro Thr Pro
    50                  55                  60

Pro Thr Arg Glu Pro Lys Lys Val Ala Val Val Arg Thr Pro Pro Lys
65                  70                  75                  80

Ser Pro Ser Ser

<210> SEQ ID NO 296
<211> LENGTH: 16
<212> TYPE: PRT
<213> ORGANISM: artificial sequence
<220> FEATURE:
<223> OTHER INFORMATION: VHCDR2 CA1

<400> SEQUENCE: 296

Asp Ile Arg Ala Asp Gly Ala Thr Asn Tyr Asn Ala Ala Leu Lys Ser
1               5                   10                  15

<210> SEQ ID NO 297
<211> LENGTH: 17
<212> TYPE: PRT
<213> ORGANISM: artificial sequence
<220> FEATURE:
<223> OTHER INFORMATION: VHCDR3 CA1

<400> SEQUENCE: 297

Pro Gly Asn Tyr Tyr Tyr Gly Ala Gly Arg Asp Val Ala Arg Leu Ala
1               5                   10                  15

Asp

<210> SEQ ID NO 298
<211> LENGTH: 14
<212> TYPE: PRT
<213> ORGANISM: artificial sequence
<220> FEATURE:
<223> OTHER INFORMATION: VLCDR1 CA1

<400> SEQUENCE: 298

Ser Gly Ser Ser Ser Asn Ile Gly Gly Gly Asn Ala Val Gly
1               5                   10

<210> SEQ ID NO 299
<211> LENGTH: 11
<212> TYPE: PRT
<213> ORGANISM: artificial sequence
<220> FEATURE:
<223> OTHER INFORMATION: VLCDR3 CA1

<400> SEQUENCE: 299

Ala Ala Met Asp Ser Ser Ser Leu Ile Gly Val
1               5                   10

<210> SEQ ID NO 300
<211> LENGTH: 78
<212> TYPE: PRT
```

```
<213> ORGANISM: Homo sapiens

<400> SEQUENCE: 300

Gly Glu Pro Pro Lys Ser Gly Asp Arg Ser Gly Tyr Ser Ser Pro Gly
1               5                   10                  15

Ser Pro Gly Thr Pro Gly Ser Arg Ser Arg Thr Pro Ser Leu Pro Thr
            20                  25                  30

Pro Pro Thr Arg Glu Pro Lys Lys Val Ala Val Val Arg Thr Pro Pro
        35                  40                  45

Lys Ser Pro Ser Ser Ala Lys Ser Arg Leu Gln Thr Ala Pro Val Pro
    50                  55                  60

Met Pro Asp Leu Lys Asn Val Lys Ser Lys Ile Gly Ser Thr
65                  70                  75

<210> SEQ ID NO 301
<211> LENGTH: 14
<212> TYPE: PRT
<213> ORGANISM: artificial sequence
<220> FEATURE:
<223> OTHER INFORMATION: VLCDR1 CA3

<400> SEQUENCE: 301

Ser Gly Ser Ser Gly Asn Ile Gly Tyr Asp Asp Tyr Val Ser
1               5                   10

<210> SEQ ID NO 302
<211> LENGTH: 7
<212> TYPE: PRT
<213> ORGANISM: artificial sequence
<220> FEATURE:
<223> OTHER INFORMATION: VLCDR2 CA3

<400> SEQUENCE: 302

Gly Ala Thr Arg Arg Ser Ser
1               5

<210> SEQ ID NO 303
<211> LENGTH: 10
<212> TYPE: PRT
<213> ORGANISM: artificial sequence
<220> FEATURE:
<223> OTHER INFORMATION: VLCDR3 CA3

<400> SEQUENCE: 303

Ala Ser Tyr Asp Ser Ser Gly Gly Gly Val
1               5                   10

<210> SEQ ID NO 304
<211> LENGTH: 165
<212> TYPE: PRT
<213> ORGANISM: Homo sapiens

<400> SEQUENCE: 304

Gly Glu Pro Pro Lys Ser Gly Asp Arg Ser Gly Tyr Ser Ser Pro Gly
1               5                   10                  15

Ser Pro Gly Thr Pro Gly Ser Arg Ser Arg Thr Pro Ser Leu Pro Thr
            20                  25                  30

Pro Pro Thr Arg Glu Pro Lys Lys Val Ala Val Val Arg Thr Pro Pro
        35                  40                  45

Lys Ser Pro Ser Ser Ala Lys Ser Arg Leu Gln Thr Ala Pro Val Pro
    50                  55                  60

Met Pro Asp Leu Lys Asn Val Lys Ser Lys Ile Gly Ser Thr Glu Asn
```

-continued

```
65                  70                  75                  80

Leu Lys His Gln Pro Gly Gly Gly Lys Val Gln Ile Ile Asn Lys Lys
                    85                  90                  95

Leu Asp Leu Ser Asn Val Gln Ser Lys Cys Gly Ser Lys Asp Asn Ile
                    100                 105                 110

Lys His Val Pro Gly Gly Gly Ser Val Gln Ile Val Tyr Lys Pro Val
                    115                 120                 125

Asp Leu Ser Lys Val Thr Ser Lys Cys Gly Ser Leu Gly Asn Ile His
        130                 135                 140

His Lys Pro Gly Gly Gly Gln Val Glu Val Lys Ser Glu Lys Leu Asp
145                 150                 155                 160

Phe Lys Asp Arg Val
                    165
```

```
<210> SEQ ID NO 305
<211> LENGTH: 11
<212> TYPE: PRT
<213> ORGANISM: artificial sequence
<220> FEATURE:
<223> OTHER INFORMATION: VLCDR1 CD2

<400> SEQUENCE: 305

Ser Gly Ser Asn Ile Gly Asp Ala Asp Val Gly
1               5                   10
```

```
<210> SEQ ID NO 306
<211> LENGTH: 7
<212> TYPE: PRT
<213> ORGANISM: artificial sequence
<220> FEATURE:
<223> OTHER INFORMATION: VLCDR2 CD2

<400> SEQUENCE: 306

Tyr Asn Glu Asn Arg Pro Ser
1               5
```

```
<210> SEQ ID NO 307
<211> LENGTH: 12
<212> TYPE: PRT
<213> ORGANISM: artificial sequence
<220> FEATURE:
<223> OTHER INFORMATION: VLCDR3 CD2

<400> SEQUENCE: 307

Gly Ser Tyr Ala Gly Asp Thr Tyr Asn His Gly Val
1               5                   10
```

```
<210> SEQ ID NO 308
<211> LENGTH: 110
<212> TYPE: PRT
<213> ORGANISM: Homo sapiens

<400> SEQUENCE: 308

Ala Lys Ser Arg Leu Gln Thr Ala Pro Val Pro Met Pro Asp Leu Lys
1               5                   10                  15

Asn Val Lys Ser Lys Ile Gly Ser Thr Glu Asn Leu Lys His Gln Pro
                20                  25                  30

Gly Gly Gly Lys Val Gln Ile Ile Asn Lys Lys Leu Asp Leu Ser Asn
            35                  40                  45

Val Gln Ser Lys Cys Gly Ser Lys Asp Asn Ile Lys His Val Pro Gly
        50                  55                  60
```

-continued

```
Gly Gly Ser Val Gln Ile Val Tyr Lys Pro Val Asp Leu Ser Lys Val
65                  70                  75                  80

Thr Ser Lys Cys Gly Ser Leu Gly Asn Ile His His Lys Pro Gly Gly
                85                  90                  95

Gly Gln Val Glu Val Lys Ser Glu Lys Leu Asp Phe Lys Asp
            100                 105                 110

<210> SEQ ID NO 309
<211> LENGTH: 94
<212> TYPE: PRT
<213> ORGANISM: Homo sapiens

<400> SEQUENCE: 309

Leu Lys His Gln Pro Gly Gly Gly Lys Val Gln Ile Ile Asn Lys Lys
1               5                   10                  15

Leu Asp Leu Ser Asn Val Gln Ser Lys Cys Gly Ser Lys Asp Asn Ile
            20                  25                  30

Lys His Val Pro Gly Gly Gly Ser Val Gln Ile Val Tyr Lys Pro Val
        35                  40                  45

Asp Leu Ser Lys Val Thr Ser Lys Cys Gly Ser Leu Gly Asn Ile His
    50                  55                  60

His Lys Pro Gly Gly Gly Gln Val Glu Val Lys Ser Glu Lys Leu Asp
65                  70                  75                  80

Phe Lys Asp Arg Val Gln Ser Lys Ile Gly Ser Leu Asp Asn
                85                  90

<210> SEQ ID NO 310
<211> LENGTH: 5
<212> TYPE: PRT
<213> ORGANISM: artificial sequence
<220> FEATURE:
<223> OTHER INFORMATION: VHCDR1 CG11, CE2/E1B8

<400> SEQUENCE: 310

Asn Tyr Pro Val Gly
1               5

<210> SEQ ID NO 311
<211> LENGTH: 16
<212> TYPE: PRT
<213> ORGANISM: artificial sequence
<220> FEATURE:
<223> OTHER INFORMATION: VHCDR2 CG11, CE2/E1B8

<400> SEQUENCE: 311

Asn Ile Glu Asn Asp Gly Ser Ala Asn Tyr Ala Ser Ala Leu Lys Ser
1               5                   10                  15

<210> SEQ ID NO 312
<211> LENGTH: 16
<212> TYPE: PRT
<213> ORGANISM: artificial sequence
<220> FEATURE:
<223> OTHER INFORMATION: VHCDR3 CG11, CE2/E1B8

<400> SEQUENCE: 312

Glu Phe Gly Gly Ser Asp Gly Tyr Thr Tyr Phe Val Asp Ile Asp Tyr
1               5                   10                  15

<210> SEQ ID NO 313
<211> LENGTH: 14
<212> TYPE: PRT
<213> ORGANISM: artificial sequence
```

```
<220> FEATURE:
<223> OTHER INFORMATION: VLCDR1 CG11, CE2/E1B8

<400> SEQUENCE: 313

Ser Gly Ser Ser Ser Asn Val Gly Tyr Gly Asn Tyr Val Ser
1               5                   10

<210> SEQ ID NO 314
<211> LENGTH: 10
<212> TYPE: PRT
<213> ORGANISM: artificial sequence
<220> FEATURE:
<223> OTHER INFORMATION: VLCDR3 CG11, CE2/E1B8

<400> SEQUENCE: 314

Ala Ser Tyr Asp Gly Ser Ser Ser Gly Val
1               5                   10

<210> SEQ ID NO 315
<211> LENGTH: 43
<212> TYPE: PRT
<213> ORGANISM: Homo sapiens

<400> SEQUENCE: 315

Ile Ile Asn Lys Lys Leu Asp Leu Ser Asn Val Gln Ser Lys Cys Gly
1               5                   10                  15

Ser Lys Asp Asn Ile Lys His Val Pro Gly Gly Gly Ser Val Gln Ile
            20                  25                  30

Val Tyr Lys Pro Val Asp Leu Ser Lys Val Thr
        35                  40

<210> SEQ ID NO 316
<211> LENGTH: 14
<212> TYPE: PRT
<213> ORGANISM: artificial sequence
<220> FEATURE:
<223> OTHER INFORMATION: VLCDR1 CA10

<400> SEQUENCE: 316

Ser Gly Ser Ser Ser Asn Val Gly Tyr Gly Asn Tyr Val Thr
1               5                   10

<210> SEQ ID NO 317
<211> LENGTH: 7
<212> TYPE: PRT
<213> ORGANISM: artificial sequence
<220> FEATURE:
<223> OTHER INFORMATION: VLCDR2 CA10

<400> SEQUENCE: 317

Asp Ala Thr Thr Arg Val Ser
1               5

<210> SEQ ID NO 318
<211> LENGTH: 10
<212> TYPE: PRT
<213> ORGANISM: artificial sequence
<220> FEATURE:
<223> OTHER INFORMATION: VLCDR3 CA10

<400> SEQUENCE: 318

Ala Ala His Asp Ser Ser Ser Gly Gly Val
1               5                   10

<210> SEQ ID NO 319
```

-continued

```
<211> LENGTH: 13
<212> TYPE: PRT
<213> ORGANISM: Homo sapiens

<400> SEQUENCE: 319

Thr Ser Lys Cys Gly Ser Leu Gly Asn Ile His His Lys
1               5                   10

<210> SEQ ID NO 320
<211> LENGTH: 13
<212> TYPE: PRT
<213> ORGANISM: artificial sequence
<220> FEATURE:
<223> OTHER INFORMATION: CE2/E1B8 general epitope
<220> FEATURE:
<221> NAME/KEY: MISC_FEATURE
<222> LOCATION: (1)..(13)
<223> OTHER INFORMATION: Where X is any amino acid

<400> SEQUENCE: 320

Xaa Xaa Xaa Xaa Gly Ser Leu Gly Asn Ile Xaa Xaa Xaa
1               5                   10

<210> SEQ ID NO 321
<211> LENGTH: 30
<212> TYPE: PRT
<213> ORGANISM: Homo sapiens

<400> SEQUENCE: 321

Lys Pro Gly Gly Gly Gln Val Glu Val Lys Ser Glu Lys Leu Asp Phe
1               5                   10                  15

Lys Asp Arg Val Gln Ser Lys Ile Gly Ser Leu Asp Asn Ile
            20                  25                  30

<210> SEQ ID NO 322
<211> LENGTH: 43
<212> TYPE: PRT
<213> ORGANISM: Homo sapiens

<400> SEQUENCE: 322

Asp Arg Val Gln Ser Lys Ile Gly Ser Leu Asp Asn Ile Thr His Val
1               5                   10                  15

Pro Gly Gly Gly Asn Lys Lys Ile Glu Thr His Lys Leu Thr Phe Arg
            20                  25                  30

Glu Asn Ala Lys Ala Lys Thr Asp His Gly Ala
        35                  40

<210> SEQ ID NO 323
<211> LENGTH: 16
<212> TYPE: PRT
<213> ORGANISM: artificial sequence
<220> FEATURE:
<223> OTHER INFORMATION: VHCDR2 CA6

<400> SEQUENCE: 323

Asp Lys Ser Ser Gly Gly Lys Thr Tyr Gly Asn Pro Ala Leu Lys Ser
1               5                   10                  15

<210> SEQ ID NO 324
<211> LENGTH: 14
<212> TYPE: PRT
<213> ORGANISM: artificial sequence
<220> FEATURE:
<223> OTHER INFORMATION: VLCDR1 CA6

<400> SEQUENCE: 324
```

```
Ser Gly Ser Arg Asn Asn Ile Gly Tyr Gly Asn His Val Gly
1               5               10

<210> SEQ ID NO 325
<211> LENGTH: 10
<212> TYPE: PRT
<213> ORGANISM: artificial sequence
<220> FEATURE:
<223> OTHER INFORMATION: VLCDR3 CA6

<400> SEQUENCE: 325

Ala Ser Phe Asp Arg Gly Ser Gly Gly Ile
1               5               10

<210> SEQ ID NO 326
<211> LENGTH: 94
<212> TYPE: PRT
<213> ORGANISM: Homo sapiens

<400> SEQUENCE: 326

Asp Arg Val Gln Ser Lys Ile Gly Ser Leu Asp Asn Ile Thr His Val
1               5               10              15

Pro Gly Gly Gly Asn Lys Lys Ile Glu Thr His Lys Leu Thr Phe Arg
            20              25              30

Glu Asn Ala Lys Ala Lys Thr Asp His Gly Ala Glu Ile Val Tyr Lys
        35              40              45

Ser Pro Val Val Ser Gly Asp Thr Ser Pro Arg His Leu Ser Asn Val
    50              55              60

Ser Ser Thr Gly Ser Ile Asp Met Val Asp Ser Pro Gln Leu Ala Thr
65              70              75              80

Leu Ala Asp Glu Val Ser Ala Ser Leu Ala Lys Gln Gly Leu
            85              90

<210> SEQ ID NO 327
<211> LENGTH: 14
<212> TYPE: PRT
<213> ORGANISM: artificial sequence
<220> FEATURE:
<223> OTHER INFORMATION: VLCDR1 CA11

<400> SEQUENCE: 327

Ser Gly Ser Gly Ser Asn Ile Gly Ala Gly Asn Trp Val Ser
1               5               10

<210> SEQ ID NO 328
<211> LENGTH: 7
<212> TYPE: PRT
<213> ORGANISM: artificial sequence
<220> FEATURE:
<223> OTHER INFORMATION: VLCDR2 CA11

<400> SEQUENCE: 328

Gly Ala Thr Ser Arg Pro Ser
1               5

<210> SEQ ID NO 329
<211> LENGTH: 10
<212> TYPE: PRT
<213> ORGANISM: artificial sequence
<220> FEATURE:
<223> OTHER INFORMATION: VLCDR3 CA11

<400> SEQUENCE: 329
```

-continued

```
Ala Ala Tyr Asp Ser Gly Ser Ser Ile Val
1               5                   10

<210> SEQ ID NO 330
<211> LENGTH: 13
<212> TYPE: PRT
<213> ORGANISM: Homo sapiens

<400> SEQUENCE: 330

Gly Ser Leu Asp Asn Ile Thr His Val Pro Gly Gly Gly
1               5                   10

<210> SEQ ID NO 331
<211> LENGTH: 13
<212> TYPE: PRT
<213> ORGANISM: artificial sequence
<220> FEATURE:
<223> OTHER INFORMATION: CA4 general epitope
<220> FEATURE:
<221> NAME/KEY: MISC_FEATURE
<222> LOCATION: (1)..(13)
<223> OTHER INFORMATION: Where X is any amino acid

<400> SEQUENCE: 331

Xaa Xaa Xaa Asp Xaa Ile Thr His Xaa Pro Xaa Xaa Xaa
1               5                   10

<210> SEQ ID NO 332
<211> LENGTH: 33
<212> TYPE: PRT
<213> ORGANISM: Homo sapiens

<400> SEQUENCE: 332

Asn Ile Thr His Val Pro Gly Gly Gly Asn Lys Lys Ile Glu Thr His
1               5                   10                  15

Lys Leu Thr Phe Arg Glu Asn Ala Lys Ala Lys Thr Asp His Gly Ala
            20                  25                  30

Glu

<210> SEQ ID NO 333
<211> LENGTH: 31
<212> TYPE: PRT
<213> ORGANISM: Homo sapiens

<400> SEQUENCE: 333

Ile Thr His Val Pro Gly Gly Gly Asn Lys Lys Ile Glu Thr His Lys
1               5                   10                  15

Leu Thr Phe Arg Glu Asn Ala Lys Ala Lys Thr Asp His Gly Ala
            20                  25                  30

<210> SEQ ID NO 334
<211> LENGTH: 5
<212> TYPE: PRT
<213> ORGANISM: artificial sequence
<220> FEATURE:
<223> OTHER INFORMATION: VHCDR1 CB3

<400> SEQUENCE: 334

Ser Val Ala Val Asn
1               5

<210> SEQ ID NO 335
<211> LENGTH: 16
<212> TYPE: PRT
<213> ORGANISM: artificial sequence
```

-continued

```
<220> FEATURE:
<223> OTHER INFORMATION: VHCDR2 CB3

<400> SEQUENCE: 335

Gly Ile Ile Ser Asn Gly Gly Thr Gly Tyr Asn Pro Ala Leu Lys Ser
1               5                   10                  15

<210> SEQ ID NO 336
<211> LENGTH: 10
<212> TYPE: PRT
<213> ORGANISM: artificial sequence
<220> FEATURE:
<223> OTHER INFORMATION: VHCDR3 CB3

<400> SEQUENCE: 336

Gly Val Glu Trp Glu Gly Ser Met Asp Tyr
1               5                   10

<210> SEQ ID NO 337
<211> LENGTH: 14
<212> TYPE: PRT
<213> ORGANISM: artificial sequence
<220> FEATURE:
<223> OTHER INFORMATION: VLCDR1 CB3

<400> SEQUENCE: 337

Ser Gly Ser Ser Ser Asn Val Gly Ala Gly Ser Tyr Val Gly
1               5                   10

<210> SEQ ID NO 338
<211> LENGTH: 7
<212> TYPE: PRT
<213> ORGANISM: artificial sequence
<220> FEATURE:
<223> OTHER INFORMATION: VLCDR2 CB3

<400> SEQUENCE: 338

Gly Ala Thr Lys Arg Ala Ser
1               5

<210> SEQ ID NO 339
<211> LENGTH: 10
<212> TYPE: PRT
<213> ORGANISM: artificial sequence
<220> FEATURE:
<223> OTHER INFORMATION: VLCDR3 CB3

<400> SEQUENCE: 339

Val Ser Tyr Gln Thr Asp Phe Thr Leu Val
1               5                   10

<210> SEQ ID NO 340
<211> LENGTH: 65
<212> TYPE: PRT
<213> ORGANISM: Homo sapiens

<400> SEQUENCE: 340

Gln Thr Pro Thr Glu Asp Gly Ser Glu Glu Pro Gly Ser Glu Thr Ser
1               5                   10                  15

Asp Ala Lys Ser Thr Pro Thr Ala Glu Asp Val Thr Ala Pro Leu Val
                20                  25                  30

Asp Glu Gly Ala Pro Gly Lys Gln Ala Ala Gln Pro His Thr Glu
            35                  40                  45

Ile Pro Glu Gly Thr Thr Ala Glu Glu Ala Gly Ile Gly Asp Thr Pro
        50                  55                  60
```

Ser
65

<210> SEQ ID NO 341
<211> LENGTH: 16
<212> TYPE: PRT
<213> ORGANISM: artificial sequence
<220> FEATURE:
<223> OTHER INFORMATION: VHCDR2 CB5

<400> SEQUENCE: 341

Asp Ile Thr Ser Gly Gly Arg Thr Tyr Gly Asn Leu Ala Leu Lys Ser
1               5                   10                  15

<210> SEQ ID NO 342
<211> LENGTH: 14
<212> TYPE: PRT
<213> ORGANISM: artificial sequence
<220> FEATURE:
<223> OTHER INFORMATION: VLCDR1 CB5

<400> SEQUENCE: 342

Ser Gly Ser Ser Ser Asn Val Gly Ser Gly Asp His Val Asn
1               5                   10

<210> SEQ ID NO 343
<211> LENGTH: 7
<212> TYPE: PRT
<213> ORGANISM: artificial sequence
<220> FEATURE:
<223> OTHER INFORMATION: VLCDR2 CB5

<400> SEQUENCE: 343

Arg Thr Thr Asn Arg Ala Ser
1               5

<210> SEQ ID NO 344
<211> LENGTH: 10
<212> TYPE: PRT
<213> ORGANISM: artificial sequence
<220> FEATURE:
<223> OTHER INFORMATION: VLCDR3 CB5

<400> SEQUENCE: 344

Ala Ser His Asp Asn Asn Ser Gly Gly Val
1               5                   10

<210> SEQ ID NO 345
<211> LENGTH: 107
<212> TYPE: PRT
<213> ORGANISM: Homo sapiens

<400> SEQUENCE: 345

Gln Thr Pro Thr Glu Asp Gly Ser Glu Glu Pro Gly Ser Glu Thr Ser
1               5                   10                  15

Asp Ala Lys Ser Thr Pro Thr Ala Glu Asp Val Thr Ala Pro Leu Val
            20                  25                  30

Asp Glu Gly Ala Pro Gly Lys Gln Ala Ala Ala Gln Pro His Thr Glu
        35                  40                  45

Ile Pro Glu Gly Thr Thr Ala Glu Glu Ala Gly Ile Gly Asp Thr Pro
    50                  55                  60

Ser Leu Glu Asp Glu Ala Ala Gly His Val Thr Gln Ala Arg Met Val
65                  70                  75                  80

-continued

```
Ser Lys Ser Lys Asp Gly Thr Gly Ser Asp Asp Lys Lys Ala Lys Gly
                85                  90                  95

Ala Asp Gly Lys Thr Lys Ile Ala Thr Pro Arg
            100                 105

<210> SEQ ID NO 346
<211> LENGTH: 19
<212> TYPE: PRT
<213> ORGANISM: artificial sequence
<220> FEATURE:
<223> OTHER INFORMATION: VLCDR1 CC4

<400> SEQUENCE: 346

Ser Gly Ser Ser Ser Asn Val Gly Tyr Thr Asn Leu Gly Tyr Ser Asn
1               5                   10                  15

Leu Val Thr

<210> SEQ ID NO 347
<211> LENGTH: 10
<212> TYPE: PRT
<213> ORGANISM: artificial sequence
<220> FEATURE:
<223> OTHER INFORMATION: VLCDR3 CC4

<400> SEQUENCE: 347

Ala Ser Tyr Asp Ser Ser Asn Gly Gly Ile
1               5                   10

<210> SEQ ID NO 348
<211> LENGTH: 190
<212> TYPE: PRT
<213> ORGANISM: Homo sapiens

<400> SEQUENCE: 348

Gln Thr Pro Thr Glu Asp Gly Ser Glu Glu Pro Gly Ser Glu Thr Ser
1               5                   10                  15

Asp Ala Lys Ser Thr Pro Thr Ala Glu Asp Val Thr Ala Pro Leu Val
                20                  25                  30

Asp Glu Gly Ala Pro Gly Lys Gln Ala Ala Ala Gln Pro His Thr Glu
            35                  40                  45

Ile Pro Glu Gly Thr Thr Ala Glu Glu Ala Gly Ile Gly Asp Thr Pro
        50                  55                  60

Ser Leu Glu Asp Glu Ala Ala Gly His Val Thr Gln Ala Arg Met Val
65                  70                  75                  80

Ser Lys Ser Lys Asp Gly Thr Gly Ser Asp Asp Lys Lys Ala Lys Gly
                85                  90                  95

Ala Asp Gly Lys Thr Lys Ile Ala Thr Pro Arg Gly Ala Ala Pro Pro
            100                 105                 110

Gly Gln Lys Gly Gln Ala Asn Ala Thr Arg Ile Pro Ala Lys Thr Pro
        115                 120                 125

Pro Ala Pro Lys Thr Pro Pro Ser Ser Gly Glu Pro Pro Lys Ser Gly
        130                 135                 140

Asp Arg Ser Gly Tyr Ser Ser Pro Gly Ser Pro Gly Thr Pro Gly Ser
145                 150                 155                 160

Arg Ser Arg Thr Pro Ser Leu Pro Thr Pro Pro Thr Arg Glu Pro Lys
                165                 170                 175

Lys Val Ala Val Val Arg Thr Pro Pro Lys Ser Pro Ser Ser
            180                 185                 190
```

-continued

```
<210> SEQ ID NO 349
<211> LENGTH: 16
<212> TYPE: PRT
<213> ORGANISM: artificial sequence
<220> FEATURE:
<223> OTHER INFORMATION: VHCDR2 CC5

<400> SEQUENCE: 349

Asp Ile Ser Ser Val Gly Lys Lys Tyr Ala Ser Pro Ala Leu Lys Ser
1               5                   10                  15

<210> SEQ ID NO 350
<211> LENGTH: 10
<212> TYPE: PRT
<213> ORGANISM: artificial sequence
<220> FEATURE:
<223> OTHER INFORMATION: VLCDR3 CC5

<400> SEQUENCE: 350

Ala Ser Tyr Asp Ser Ser Asn Gly Gly Val
1               5                   10

<210> SEQ ID NO 351
<211> LENGTH: 13
<212> TYPE: PRT
<213> ORGANISM: Homo sapiens

<400> SEQUENCE: 351

Thr His Lys Leu Thr Phe Arg Glu Asn Ala Lys Ala Lys
1               5                   10

<210> SEQ ID NO 352
<211> LENGTH: 13
<212> TYPE: PRT
<213> ORGANISM: artificial sequence
<220> FEATURE:
<223> OTHER INFORMATION: VLCDR1 MD9

<400> SEQUENCE: 352

Ser Gly Ser Ser Ser Asn Val Gly Ile Tyr Asp Val Ser
1               5                   10

<210> SEQ ID NO 353
<211> LENGTH: 7
<212> TYPE: PRT
<213> ORGANISM: artificial sequence
<220> FEATURE:
<223> OTHER INFORMATION: VLCDR2 MD9

<400> SEQUENCE: 353

Gly Thr Asn Asn Arg Pro Ser
1               5

<210> SEQ ID NO 354
<211> LENGTH: 10
<212> TYPE: PRT
<213> ORGANISM: artificial sequence
<220> FEATURE:
<223> OTHER INFORMATION: VLCDR3 MD9

<400> SEQUENCE: 354

Ala Ala Gly Asp Ser Ser Thr Ile Ala Val
1               5                   10

<210> SEQ ID NO 355
<211> LENGTH: 31
<212> TYPE: PRT
```

```
<213> ORGANISM: Homo sapiens

<400> SEQUENCE: 355

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly Ser
            20                  25                  30

<210> SEQ ID NO 356
<211> LENGTH: 32
<212> TYPE: PRT
<213> ORGANISM: Homo sapiens

<400> SEQUENCE: 356

Val Glu Val Lys Ser Glu Lys Leu Asp Phe Lys Asp Arg Val Gln Ser
1               5                   10                  15

Lys Ile Gly Ser Leu Asp Asn Ile Thr His Val Pro Gly Gly Gly Asn
            20                  25                  30

<210> SEQ ID NO 357
<211> LENGTH: 5
<212> TYPE: PRT
<213> ORGANISM: artificial sequence
<220> FEATURE:
<223> OTHER INFORMATION: VHCDR1 NS1G7

<400> SEQUENCE: 357

Ser Tyr Gly Val Gly
1               5

<210> SEQ ID NO 358
<211> LENGTH: 16
<212> TYPE: PRT
<213> ORGANISM: artificial sequence
<220> FEATURE:
<223> OTHER INFORMATION: VHCDR2 NS1G7

<400> SEQUENCE: 358

Ser Ile Ser Ser Gly Gly Thr Thr Phe Tyr Asn Pro Ala Leu Lys Ser
1               5                   10                  15

<210> SEQ ID NO 359
<211> LENGTH: 18
<212> TYPE: PRT
<213> ORGANISM: artificial sequence
<220> FEATURE:
<223> OTHER INFORMATION: VHCDR3 NS1G7

<400> SEQUENCE: 359

Asp Val His Ile Tyr Tyr Asn Asp Tyr Gly Ala Ala Tyr Gly Asp Arg
1               5                   10                  15

Asp Tyr

<210> SEQ ID NO 360
<211> LENGTH: 14
<212> TYPE: PRT
<213> ORGANISM: artificial sequence
<220> FEATURE:
<223> OTHER INFORMATION: VLCDR1 NS1G7

<400> SEQUENCE: 360

Ser Gly Ser Ser Ser Asn Ile Gly Gly Gly Asn Tyr Val Ser
1               5                   10
```

```
<210> SEQ ID NO 361
<211> LENGTH: 7
<212> TYPE: PRT
<213> ORGANISM: artificial sequence
<220> FEATURE:
<223> OTHER INFORMATION: VLCDR2 NS1G7

<400> SEQUENCE: 361

Gly Thr Thr Ser Arg Ala Ser
1               5

<210> SEQ ID NO 362
<211> LENGTH: 10
<212> TYPE: PRT
<213> ORGANISM: artificial sequence
<220> FEATURE:
<223> OTHER INFORMATION: VLCDR3 NS1G7

<400> SEQUENCE: 362

Ala Ser Tyr Asp Thr Asn Ser Gly Ser Val
1               5               10

<210> SEQ ID NO 363
<211> LENGTH: 244
<212> TYPE: PRT
<213> ORGANISM: artificial sequence
<220> FEATURE:
<223> OTHER INFORMATION: CA2 amino acid sequence

<400> SEQUENCE: 363

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Ser Ser Val
            20                  25                  30

Ala Val Asn Trp Val Arg Gln Ala Pro Gly Lys Val Pro Glu Trp Leu
        35                  40                  45

Gly Gly Ile Ile Ser Asn Gly Gly Thr Gly Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ala Leu Thr His Val Thr Thr Glu Asp Thr Ala Val Tyr Tyr Cys Gly
                85                  90                  95

Arg Gly Val Glu Trp Glu Gly Ser Met Asp Tyr Leu Gly Pro Gly Leu
            100                 105                 110

Leu Val Thr Val Ser Ser Glu Gly Lys Ser Ser Gly Ser Gly Ser Glu
        115                 120                 125

Thr Lys Val Asp Asp Gln Ser Val Leu Thr Gln Pro Ser Ser Val Ser
    130                 135                 140

Gly Phe Leu Gly Gln Arg Val Thr Ile Thr Cys Ser Gly Ser Ser Ser
145                 150                 155                 160

Asn Val Gly Ala Gly Ser Tyr Val Gly Trp Tyr Gln Gln Val Pro Gly
                165                 170                 175

Ser Gly Leu Arg Ile Leu Ile Tyr Gly Ala Thr Lys Arg Ala Ser Gly
            180                 185                 190

Leu Pro Asp Arg Phe Ser Gly Ser Arg Ser Gly Asn Thr Ala Thr Leu
            195                 200                 205

Thr Ile Ser Ser Leu Gln Ala Glu Asp Glu Ala Asp Tyr Tyr Cys Val
    210                 215                 220

Ser Tyr Gln Thr Asp Phe Thr Leu Val Phe Gly Ser Gly Thr Arg Leu
225                 230                 235                 240
```

Thr Val Leu Gly

<210> SEQ ID NO 364
<211> LENGTH: 245
<212> TYPE: PRT
<213> ORGANISM: artificial sequence
<220> FEATURE:
<223> OTHER INFORMATION: CB7 amino acid sequence

<400> SEQUENCE: 364

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Asn Tyr
            20                  25                  30

Arg Val Gly Trp Val Arg Gln Ala Pro Gly Lys Ala Leu Glu Trp Val
            35                  40                  45

Ser Asn Ile Arg Ser Gly Gly Thr Thr Trp Tyr Asn Pro Ala Leu Lys
        50                  55                  60

Ser Arg Leu Ser Ile Thr Ala Asp Thr Ser Lys Ser Gln Val Ser Leu
65                  70                  75                  80

Ser Leu Ser Ser Val Thr Thr Glu Asp Thr Ala Val Tyr Tyr Cys Ala
                85                  90                  95

Arg Asp Ser Ser Gly Asp Leu Tyr Ala Tyr Asp Tyr Trp Gly Pro Gly
            100                 105                 110

Leu Leu Val Thr Val Ser Ser Glu Gly Lys Ser Ser Gly Ala Ser Gly
            115                 120                 125

Glu Ser Lys Val Asp Asp Gln Ala Val Leu Thr Gln Pro Ser Ser Val
            130                 135                 140

Ser Arg Ser Leu Gly Gln Ser Val Ser Met Thr Cys Ser Gly Ser Ser
145                 150                 155                 160

Ser Asn Val Gly Tyr Gly Asn Tyr Met Ala Trp Phe Gln Gln Val Pro
                165                 170                 175

Gly Ser Ala Pro Lys Leu Leu Ile Tyr Gly Ala Thr Ser Arg Ala Ser
            180                 185                 190

Gly Val Pro Asp Arg Phe Ser Gly Ser Arg Ser Gly Asn Thr Ala Thr
            195                 200                 205

Leu Thr Ile Ser Ser Leu Gln Ala Glu Asp Glu Ala Asp Tyr Tyr Cys
        210                 215                 220

Ala Ser Tyr Asp Ser Thr Ser Gly Gly Val Phe Gly Ser Gly Thr Arg
225                 230                 235                 240

Leu Thr Val Leu Gly
            245

<210> SEQ ID NO 365
<211> LENGTH: 244
<212> TYPE: PRT
<213> ORGANISM: artificial sequence
<220> FEATURE:
<223> OTHER INFORMATION: CC7 amino acid sequence

<400> SEQUENCE: 365

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Asn
            20                  25                  30

Ala Val Ile Trp Val Arg Gln Ala Pro Gly Lys Ala Pro Glu Trp Val
            35                  40                  45

```
Ala Leu Ile Asp Val Asp Gly Asp Ala Ala Tyr Asp Pro Ala Leu Lys
    50              55              60

Ser Arg Leu Ser Ile Thr Arg Asp Thr Ser Lys Ser Gln Val Ser Leu
65              70              75              80

Ser Leu Arg Ser Val Thr Thr Glu Asp Thr Ala Val Tyr Tyr Cys Ala
                85              90              95

Arg Asp Tyr Gly Ser Trp Gly Tyr Val Ser Asp Ile Asp Tyr Trp Gly
            100             105             110

Pro Gly Leu Leu Val Thr Val Ser Ser Glu Gly Lys Ser Ser Gly Ala
            115             120             125

Ser Gly Glu Ser Lys Val Asp Asp Arg Val Val Arg Thr Gln Pro Ser
    130             135             140

Ser Val Ser Gly Ser Leu Gly Gln Arg Val Ser Ile Thr Cys Ser Gly
145             150             155             160

Ser Tyr Ile Thr Gly Ser Ser Val Gly Trp Phe Gln Gln Val Pro Gly
            165             170             175

Ser Gly Leu Lys Thr Val Ile Tyr Asp Asn Asn Asp Arg Pro Ser Gly
            180             185             190

Val Pro Asp Arg Phe Ser Gly Ser Lys Ser Gly Asp Thr Ala Thr Leu
    195             200             205

Thr Ile Ser Ser Leu Gln Ala Glu Asp Glu Ala Asp Tyr Tyr Cys Ala
    210             215             220

Ser Tyr Asp Thr Ser Asn Ile Gly Leu Phe Gly Ser Gly Thr Arg Leu
225             230             235             240

Thr Val Leu Gly
```

<210> SEQ ID NO 366
<211> LENGTH: 250
<212> TYPE: PRT
<213> ORGANISM: artificial sequence
<220> FEATURE:
<223> OTHER INFORMATION: CE2/E1B8 amino acid sequence

<400> SEQUENCE: 366

```
Gln Val Gln Leu Gln Glu Ser Gly Pro Ser Leu Val Lys Pro Ser Gln
1               5               10              15

Thr Leu Ser Leu Thr Cys Thr Val Ser Gly Phe Ser Leu Thr Asn Tyr
            20              25              30

Pro Val Gly Trp Val Arg Gln Ala Pro Gly Lys Ala Leu Glu Trp Ile
            35              40              45

Gly Asn Ile Glu Asn Asp Gly Ser Ala Asn Tyr Ala Ser Ala Leu Lys
    50              55              60

Ser Arg Leu Ser Ile Thr Arg Asp Thr Ser Lys Asn Gln Val Ser Leu
65              70              75              80

Ser Leu Ser Ser Ala Thr Thr Glu Asp Thr Ala Val Tyr Tyr Cys Gly
                85              90              95

Arg Glu Phe Gly Gly Ser Asp Gly Tyr Thr Tyr Phe Val Asp Ile Asp
            100             105             110

Tyr Trp Gly Pro Gly Leu Leu Val Thr Val Ser Ser Glu Gly Lys Ser
            115             120             125

Ser Gly Ala Ser Gly Glu Ser Lys Val Asp Asp Gln Ala Val Leu Thr
    130             135             140

Gln Pro Ser Ser Val Ser Lys Ser Leu Gly Gln Ser Val Ser Ile Thr
145             150             155             160
```

-continued

```
Cys Ser Gly Ser Ser Ser Asn Val Gly Tyr Gly Asn Tyr Val Ser Trp
                165                 170                 175

Phe Gln Gln Val Pro Gly Ser Ala Pro Lys Ile Leu Ile Tyr Gly Ala
            180                 185                 190

Thr Ser Arg Ala Ser Gly Val Pro Asp Arg Phe Ser Gly Ser Arg Ser
        195                 200                 205

Gly Asn Thr Ala Thr Leu Thr Ile Thr Ser Leu Gln Ala Glu Asp Glu
    210                 215                 220

Ala Asp Tyr Tyr Cys Ala Ser Tyr Asp Gly Ser Ser Ser Gly Val Phe
225                 230                 235                 240

Gly Ser Gly Thr Arg Leu Thr Val Leu Gly
                245                 250

<210> SEQ ID NO 367
<211> LENGTH: 250
<212> TYPE: PRT
<213> ORGANISM: artificial sequence
<220> FEATURE:
<223> OTHER INFORMATION: CE3 amino acid sequence

<400> SEQUENCE: 367

Gln Val Arg Leu Gln Glu Ser Gly Pro Ser Leu Val Lys Pro Ser Gln
1               5                   10                  15

Thr Leu Ser Val Thr Cys Thr Val Ser Gly Phe Ser Leu Ile Ser Asn
            20                  25                  30

Ala Val Gly Trp Val Arg Gln Ala Pro Gly Lys Val Pro Glu Ser Leu
        35                  40                  45

Ala Gly Cys Ser Ser Asp Gly Lys Cys Tyr Tyr Asn Ser Ala Leu Lys
    50                  55                  60

Ser Arg Leu Asp Ile Thr Arg Asp Thr Ser Lys Asn Gln Ile Ser Leu
65                  70                  75                  80

Ser Leu Ser Ser Val Thr Thr Asp Asp Ala Ala Val Tyr Tyr Cys Thr
                85                  90                  95

Arg Gly Tyr Tyr Pro Val Tyr Gly Tyr Asp Tyr Leu Gly Thr Ile Asp
            100                 105                 110

Tyr Trp Gly Pro Gly Leu Leu Val Thr Val Ser Ser Glu Gly Lys Ser
        115                 120                 125

Ser Gly Ala Ser Gly Glu Ser Lys Val Asp Asp Gln Ala Val Leu Thr
    130                 135                 140

Gln Pro Ser Ser Val Ser Gly Ser Leu Gly Gln Arg Val Ser Ile Thr
145                 150                 155                 160

Cys Ser Gly Ser Ser Ser Asn Val Gly Arg Asn Asp Val Ala Trp Phe
                165                 170                 175

Gln Gln Leu Pro Gly Ser Gly Leu Arg Thr Ile Ile Tyr Gly Thr Thr
            180                 185                 190

Ser Arg Pro Ser Gly Ile Pro Asp Arg Phe Ser Gly Ser Lys Ser Gly
        195                 200                 205

Val Thr Ala Thr Leu Thr Ile Asp Ser Leu Gln Ala Glu Asp Glu Ala
    210                 215                 220

Asp Tyr Phe Cys Ala Ser Gly Asp Ser Ser Ala Ile Asn Asp Ile Phe
225                 230                 235                 240

Gly Ser Gly Thr Arg Leu Thr Val Leu Gly
                245                 250

<210> SEQ ID NO 368
<211> LENGTH: 234
```

```
<212> TYPE: PRT
<213> ORGANISM: artificial sequence
<220> FEATURE:
<223> OTHER INFORMATION: CA4 amino acid sequence

<400> SEQUENCE: 368

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Tyr
            20                  25                  30

Ser Val Tyr Trp Val Arg Gln Ala Pro Gly Gln Ala Leu Glu Trp Ile
        35                  40                  45

Ser Ile Met Tyr Ala Ser Gly Arg Val Asp Tyr Asn Pro Ala Leu Lys
    50                  55                  60

Ser Arg Leu Ser Ile Thr Arg Asp Thr Ser Lys Ser Gln Phe Ser Leu
65                  70                  75                  80

Ser Leu Ser Ser Val Thr Thr Glu Asp Thr Ala Val Tyr Tyr Cys Thr
                85                  90                  95

Arg Gly Ile Glu Asn Trp Gly Pro Gly Leu Leu Val Thr Val Ser Ser
            100                 105                 110

Glu Gly Lys Ser Ser Gly Ala Ser Gly Glu Ser Lys Val Asp Asp Asp
        115                 120                 125

Ile Gln Val Thr Gln Ser Pro Ser Ser Leu Ser Ala Ser Leu Thr Glu
    130                 135                 140

Arg Val Ser Ile Thr Cys Arg Thr Ser Gln Ser Val Asn Asn Tyr Leu
145                 150                 155                 160

Ser Trp Tyr Gln Gln Lys Pro Gly Gln Ala Pro Lys Leu Leu Ile Tyr
                165                 170                 175

Tyr Ala Thr Arg Leu Tyr Thr Asp Val Pro Ser Arg Phe Ser Gly Ser
            180                 185                 190

Gly Ser Gly Thr Asp Tyr Thr Leu Thr Ile Thr Ser Leu Glu Ala Asp
        195                 200                 205

Asp Thr Ala Thr Tyr Tyr Cys Leu Gln Tyr Asp Ser Thr Pro Leu Ala
    210                 215                 220

Phe Gly Gly Gly Thr Asn Val Glu Ile Lys
225                 230

<210> SEQ ID NO 369
<211> LENGTH: 249
<212> TYPE: PRT
<213> ORGANISM: artificial sequence
<220> FEATURE:
<223> OTHER INFORMATION: CB2 amino acid sequence

<400> SEQUENCE: 369

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Ser Thr Asn
            20                  25                  30

Ser Val Gly Trp Val Arg Gln Ala Pro Gly Lys Ala Pro Glu Trp Val
        35                  40                  45

Ala Gly Ile Asp Thr Asp Gly Glu Glu Gly Phe Asn Pro Val Leu Lys
    50                  55                  60

Ser Arg Leu Ser Ile Thr Arg Asp Thr Ser Lys Ser Gln Val Ser Leu
65                  70                  75                  80

Ser Leu Ser Asn Val Thr Ser Glu Asp Thr Ala Val Tyr Tyr Cys Gly
                85                  90                  95
```

```
Arg Ser Tyr Arg Thr Asp Gly Leu Ala Tyr Gly Tyr Val Gln Ala Ile
            100             105             110

Asp Tyr Trp Gly Pro Gly Leu Leu Val Thr Ile Ser Ser Glu Gly Lys
        115             120             125

Ser Ser Gly Ala Ser Gly Glu Ser Lys Val Asp Asp Gln Ser Val Leu
    130             135             140

Thr Gln Pro Ser Ser Val Ser Gly Ser Pro Gly Gln Thr Val Ser Ile
145             150             155             160

Thr Cys Ser Gly Ser Tyr Ile Gly Ser Ser Gly Val Gly Trp Phe Gln
                165             170             175

Gln Leu Pro Gly Ser Gly Leu Arg Thr Ile Ile Val Ala Ser Asp Gly
            180             185             190

Arg Pro Ser Gly Val Pro Asp Arg Phe Ser Met Ser Lys Ser Gly Asn
        195             200             205

Thr Ala Thr Leu Thr Ile Ser Ser Leu Gln Ala Glu Asp Glu Ala Asp
    210             215             220

Tyr Phe Cys Gly Ser Ser Asp Arg Thr Gln Tyr Thr Gly Leu Phe Gly
225             230             235             240

Ser Gly Thr Arg Leu Thr Val Leu Gly
                245
```

```
<210> SEQ ID NO 370
<211> LENGTH: 244
<212> TYPE: PRT
<213> ORGANISM: artificial sequence
<220> FEATURE:
<223> OTHER INFORMATION: CB3 amino acid sequence

<400> SEQUENCE: 370
```

```
Gln Val Gln Leu Gln Glu Ser Gly Pro Ser Leu Val Lys Pro Ser Gln
1               5               10              15

Thr Leu Ser Leu Thr Cys Thr Val Ser Gly Phe Ser Leu Ser Ser Val
            20              25              30

Ala Val Asn Trp Val Arg Gln Ala Pro Gly Lys Val Pro Glu Trp Leu
        35              40              45

Gly Gly Ile Ile Ser Asn Gly Gly Thr Gly Tyr Asn Pro Ala Leu Lys
    50              55              60

Ser Arg Leu Ser Ile Thr Arg Asp Thr Ser Lys Ser Gln Val Ser Leu
65              70              75              80

Ala Leu Thr His Val Thr Thr Glu Asp Thr Ala Val Tyr Tyr Cys Gly
            85              90              95

Arg Gly Val Glu Trp Glu Gly Ser Met Asp Tyr Leu Gly Pro Gly Leu
            100             105             110

Leu Val Thr Val Ser Ser Glu Gly Lys Ser Ser Gly Ser Gly Ser Glu
            115             120             125

Thr Lys Val Asp Asp Gln Ser Val Leu Thr Gln Pro Ser Ser Val Ser
    130             135             140

Gly Phe Leu Gly Gln Arg Val Thr Ile Thr Cys Ser Gly Ser Ser Ser
145             150             155             160

Asn Val Gly Ala Gly Ser Tyr Val Gly Trp Tyr Gln Gln Val Pro Gly
                165             170             175

Ser Gly Leu Arg Ile Leu Ile Tyr Gly Ala Thr Lys Arg Ala Ser Gly
            180             185             190

Leu Pro Asp Arg Phe Ser Gly Ser Arg Ser Gly Asn Thr Ala Thr Leu
        195             200             205
```

-continued

```
Thr Ile Ser Ser Leu Gln Ala Glu Asp Glu Ala Asp Tyr Tyr Cys Val
    210                 215                 220

Ser Tyr Gln Thr Asp Phe Thr Leu Val Phe Gly Ser Gly Thr Arg Leu
225                 230                 235                 240

Thr Val Leu Gly

<210> SEQ ID NO 371
<211> LENGTH: 249
<212> TYPE: PRT
<213> ORGANISM: artificial sequence
<220> FEATURE:
<223> OTHER INFORMATION: CA9 amino acid sequence

<400> SEQUENCE: 371

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Asn
            20                  25                  30

Ser Val Gly Trp Val Arg Gln Ala Pro Gly Lys Ala Pro Glu Trp Val
        35                  40                  45

Ala Gly Ile Asp Thr Asp Gly Glu Glu Gly Tyr Asn Pro Ala Leu Asn
    50                  55                  60

Ser Arg Leu Ser Ile Thr Arg Asp Thr Ser Lys Ser Gln Val Ser Leu
65                  70                  75                  80

Ser Leu Ser Ser Val Thr Ser Glu Asp Thr Ala Val Tyr Tyr Cys Gly
                85                  90                  95

Arg Ser Tyr Arg Ser Asp Gly Leu Ala Tyr Gly Tyr Val Gln Ala Ile
            100                 105                 110

Asp Tyr Trp Gly Pro Gly Leu Leu Val Thr Val Ser Ser Glu Gly Lys
            115                 120                 125

Ser Ser Gly Ala Ser Gly Glu Ser Lys Val Asp Asp Gln Ala Val Leu
    130                 135                 140

Thr Gln Pro Ala Ser Val Ser Gly Ser Leu Gly Gln Arg Val Ser Ile
145                 150                 155                 160

Thr Cys Ser Gly Ser Phe Ile Gly Ile Ser Ser Val Gly Trp Phe Gln
                165                 170                 175

Gln Leu Pro Gly Ser Gly Leu Arg Thr Ile Ile Val Ala Ser Asp Gly
            180                 185                 190

Arg Pro Ser Gly Val Pro Asp Arg Phe Ser Met Ser Lys Ser Gly Asn
            195                 200                 205

Thr Ala Thr Leu Thr Ile Ser Ser Leu Gln Ala Glu Asp Glu Ala Asp
    210                 215                 220

Tyr Phe Cys Gly Ser Ser Asp Arg Thr Gln Tyr Thr Gly Val Phe Gly
225                 230                 235                 240

Ser Gly Thr Arg Leu Thr Val Leu Gly
                245

<210> SEQ ID NO 372
<211> LENGTH: 251
<212> TYPE: PRT
<213> ORGANISM: artificial sequence
<220> FEATURE:
<223> OTHER INFORMATION: CA12 amino acid sequence

<400> SEQUENCE: 372

Gln Val Gln Leu Gln Gly Ser Gly Pro Ser Leu Val Lys Pro Ser Gln
1               5                   10                  15
```

-continued

```
Thr Leu Ser Leu Thr Cys Thr Val Ser Gly Phe Ser Phe Asp Ser Tyr
            20                  25                  30

Tyr Val Gly Trp Val Arg Gln Ala Pro Gly Lys Ala Leu Glu Trp Leu
            35                  40                  45

Gly Asn Ile Tyr Ser Thr Gly Arg Ala Phe Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ser Val Ser Ser Val Thr Ile Glu Asp Thr Ala Leu Tyr Tyr Cys Val
            85                  90                  95

Arg Gly Ser Tyr Tyr His Gly Gly Gly Asn Gly Met Val Asp Phe Phe
            100                 105                 110

Asp Tyr Trp Ser Pro Gly Leu Leu Val Thr Val Ser Ser Glu Gly Lys
            115                 120                 125

Ser Ser Gly Ala Ser Gly Glu Ser Lys Val Asp Asp Gln Val Val Arg
    130                 135                 140

Thr Gln Pro Ser Ser Val Ser Gly Ser Leu Gly Gln Arg Val Ser Ile
145                 150                 155                 160

Thr Cys Ser Gly Ser Ser Ser Asn Val Gly Tyr Gly Asn Tyr Val Gly
            165                 170                 175

Trp Phe Gln Gln Val Pro Gly Ser Ala Pro Lys Leu Leu Ile Tyr Ala
            180                 185                 190

Ala Thr Ser Arg Ala Ser Gly Val Pro Asp Arg Phe Ser Gly Ser Arg
            195                 200                 205

Ser Gly Asn Thr Ala Thr Leu Thr Ile Asp Ser Leu Gln Ala Glu Asp
    210                 215                 220

Glu Ala Asp Tyr Tyr Cys Ser Ser Tyr Gln Arg Gly Asn Thr Gly Val
225                 230                 235                 240

Phe Gly Ser Gly Thr Arg Leu Thr Val Leu Gly
            245                 250
```

```
<210> SEQ ID NO 373
<211> LENGTH: 240
<212> TYPE: PRT
<213> ORGANISM: artificial sequence
<220> FEATURE:
<223> OTHER INFORMATION: MD9 amino acid sequence

<400> SEQUENCE: 373
```

```
Gln Val Arg Leu Gln Glu Ser Gly Pro Ser Leu Val Lys Ser Ser Gln
1               5                   10                  15

Thr Leu Ser Leu Thr Cys Thr Val Ser Gly Phe Ser Leu Thr Arg Glu
            20                  25                  30

Ser Ile Ala Trp Val Arg Gln Ala Pro Gly Lys Val Pro Glu Trp Leu
            35                  40                  45

Gly Gly Val Gly Ile Asp Gly Thr Ser Tyr Tyr Ser Pro Ala Leu Lys
    50                  55                  60

Ser Arg Leu Ser Ile Thr Arg Asp Thr Ser Lys Ser Gln Ala Ser Leu
65                  70                  75                  80

Ser Leu Ser Ser Val Ala Thr Glu Asp Thr Ala Met Tyr Tyr Cys Ala
            85                  90                  95

Arg Asn Tyr Ile Asp Phe Glu Tyr Trp Gly Pro Gly Leu Leu Val Thr
            100                 105                 110

Val Ser Ser Glu Gly Lys Ser Ser Gly Ala Ser Gly Glu Ser Lys Val
            115                 120                 125
```

```
Asp Asp Gln Ala Val Leu Thr Gln Leu Ser Ser Val Ser Gly Ser Leu
130                 135                 140

Gly Gln Arg Ile Ser Ile Thr Cys Ser Gly Ser Ser Ser Asn Val Gly
145                 150                 155                 160

Ile Tyr Asp Val Ser Trp Phe Gln Gln Leu Pro Gly Ser Gly Leu Arg
                165                 170                 175

Thr Val Ile Tyr Gly Thr Asn Asn Arg Pro Ser Gly Val Pro Asp Arg
                180                 185                 190

Phe Ser Gly Ser Arg Ser Gly Asn Thr Ala Thr Leu Thr Ile Ser Ser
                195                 200                 205

Leu Gln Ser Glu Asp Glu Ala Ile Tyr Tyr Cys Ala Ala Gly Asp Ser
210                 215                 220

Ser Thr Ile Ala Val Phe Gly Ser Gly Thr Arg Leu Thr Val Leu Gly
225                 230                 235                 240

<210> SEQ ID NO 374
<211> LENGTH: 252
<212> TYPE: PRT
<213> ORGANISM: artificial sequence
<220> FEATURE:
<223> OTHER INFORMATION: NS1G7 amino acid sequence

<400> SEQUENCE: 374

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Tyr
                20                  25                  30

Gly Val Gly Trp Val Arg Gln Ala Pro Gly Lys Thr Leu Glu Trp Ile
            35                  40                  45

Ser Ser Ile Ser Ser Gly Gly Thr Thr Phe Tyr Asn Pro Ala Leu Lys
        50                  55                  60

Ser Arg Leu Ser Ile Thr Arg Asp Thr Ser Glu Ser Gln Val Ser Leu
65                  70                  75                  80

Ser Leu Ser Ser Val Thr Thr Glu Asp Thr Ala Val Tyr Tyr Cys Thr
                85                  90                  95

Arg Asp Val His Ile Tyr Tyr Asn Asp Tyr Gly Ala Ala Tyr Gly Asp
                100                 105                 110

Arg Asp Tyr Trp Gly Pro Gly Leu Leu Val Thr Val Ser Ser Glu Gly
            115                 120                 125

Lys Ser Ser Gly Ala Ser Gly Glu Ser Lys Val Asp Asp Gln Ala Val
        130                 135                 140

Val Thr Gln Pro Pro Ser Val Ser Gly Ser Pro Gly Gln Arg Val Ser
145                 150                 155                 160

Ile Thr Cys Ser Gly Ser Ser Ser Asn Ile Gly Gly Gly Asn Tyr Val
                165                 170                 175

Ser Trp Tyr Gln Gln Leu Pro Gly Ser Gly Leu Arg Thr Leu Ile Tyr
                180                 185                 190

Gly Thr Thr Ser Arg Ala Ser Gly Val Pro Asp Arg Phe Ser Gly Ser
            195                 200                 205

Gly Ser Gly Asn Thr Ala Thr Leu Thr Ile Ser Ser Leu Gln Ala Glu
        210                 215                 220

Asp Glu Ala Asp Tyr Tyr Cys Ala Ser Tyr Asp Thr Asn Ser Gly Ser
225                 230                 235                 240

Val Phe Gly Ser Gly Thr Arg Leu Thr Val Leu Gly
                245                 250
```

<210> SEQ ID NO 375
<211> LENGTH: 21
<212> TYPE: PRT
<213> ORGANISM: Homo sapiens

<400> SEQUENCE: 375

Gly Gly Gly Gln Val Glu Val Lys Ser Glu Lys Leu Asp Phe Lys Asp
1               5                   10                  15

Arg Val Gln Ser Lys
            20

<210> SEQ ID NO 376
<211> LENGTH: 12
<212> TYPE: PRT
<213> ORGANISM: Homo sapiens

<400> SEQUENCE: 376

Cys Gly Ser Leu Gly Asn Ile His His Lys Pro Gly
1               5                   10

<210> SEQ ID NO 377
<211> LENGTH: 9
<212> TYPE: PRT
<213> ORGANISM: Homo sapiens

<400> SEQUENCE: 377

Ser Leu Asp Asn Ile Thr His Val Pro
1               5

<210> SEQ ID NO 378
<211> LENGTH: 9
<212> TYPE: PRT
<213> ORGANISM: Homo sapiens

<400> SEQUENCE: 378

Val Gln Ile Val Tyr Lys Pro Val Asp
1               5

<210> SEQ ID NO 379
<211> LENGTH: 10
<212> TYPE: PRT
<213> ORGANISM: Homo sapiens

<400> SEQUENCE: 379

Lys Lys Ile Glu Thr His Lys Leu Thr Phe
1               5                   10

<210> SEQ ID NO 380
<211> LENGTH: 753
<212> TYPE: DNA
<213> ORGANISM: artificial sequence
<220> FEATURE:
<223> OTHER INFORMATION: S1D12 nucleotide sequence

<400> SEQUENCE: 380
caggtgcagc tgcaggagtc gggacccagc ctggtgaagc cctcacagac cctctccctc      60
acctgcacgg tctctggatt ctcattgaac aacaatgctg taggctgggt ccgccaggct     120
ccaggaaagg tgccggagtc gcttgtgggt tgtagcagtg atggaacgtg ttactataat     180
tcggccctga atcccggct cgacatcacc agggacacct ccaagaacca gatctccctg      240
tcactgagca gcgttacaac tgacgacgcg gccgtgtact attgtacaag aggccattat     300

-continued

```
agtatttatg gttatgacta tcttggcact atcgactact ggggcccagg actcctggtc      360
accgtctcct cagaaggtaa atcttctggc gcgtctggcg agtctaaagt ggatgaccag      420
gctgtgctga ctcagccgtc ctccgtgtcc gggtccctgg gccagagggt ctccatcacc      480
tgctctggaa gcagcagcaa cgtcgggggg ggtaatagtg tgggctggta ccaacacctc      540
ccaggctcag gcctcaaaac catcatctat gatactaaca gtcgaccctc gggggtcccg      600
gaccgattct ctggctccag gtctggcaac acggccaccc taaccatcaa ctcgctccag      660
gctgaggacg aggtgatta ttactgtgta acgggtgaca gcactactca tgatgatctt      720
gtcggcagcg ggaccaggct gaccgtcctg ggg                                   753

<210> SEQ ID NO 381
<211> LENGTH: 747
<212> TYPE: DNA
<213> ORGANISM: artificial sequence
<220> FEATURE:
<223> OTHER INFORMATION: S1G2 nucleotide sequence

<400> SEQUENCE: 381
caggtgcagc tgcaggagtc gggacccagc ctggtgaagc cctcacagac cctctccctc       60
acctgcacgg tctctggatt ctcattaacc agcaattctg tgggctgggt ccgacaggct      120
ccaggaaagg cgccggagtg ggttgctggt atagatactg atggagaaga aggctataat      180 ccagcccta actcccggct cagcatcacc agggacacct ccaagagtca gtctctttg        240 tcattgagca gcgtgacaag tgaggacacg gccgtgtact actgtggaag aagttatagg      300
gctgatggtc ttgcttacgg ttatgtccaa gccatcgact actggggccc aggactcctg      360
gtcaccgtct cctcagaagg taaatcttct ggcgcgtctg gcgagtctaa agtggatgac      420
caggccgtgg tgactcagcc gtcctccgtg tctgggtccc tgggccagag ggtctccatc      480
acctgctctg gaagcttcat cggtattagt agtgtaggct ggttccaaca gctcccagga      540
tcgggcctca gaaccatcat cgtggcgagt gacggtcgac cctcaggggt ccccgaccga      600
ttctctatgt ccaaatcggg caacacagcc accctgacca tcagctcgct ccaggctgag      660
gacgaggccg attatttctg tggaagtagt gataggactc cttatactgg ggtcttcggc      720
agcgggacca ggctgaccgt cctgggt                                         747

<210> SEQ ID NO 382
<211> LENGTH: 705
<212> TYPE: DNA
<213> ORGANISM: artificial sequence
<220> FEATURE:
<223> OTHER INFORMATION: CA4 nucleotide sequence

<400> SEQUENCE: 382
caggttcagc tgcaggagtc gggacccagc ctggtgaagc cctcacagac cctctccctc       60
acctgcacgg tctctggatt ctcattaacc agctattccg tatactgggt ccgccaggct      120
ccaggccagg cactggagtg gattagtatt atgtatgcta gtggaagagt agactataac      180
ccggccctga atcccggct cagcatcacc agggacacct ccaagagtca attctccctg        240
tcattgagca gcgtgacaac tgaggacacg gccgtctact actgtacaag aggaatcgaa      300 aactgggggcc ccggactcct ggtcaccgtc tcctcagaag gtaaatcttc tggcgcgtct      360
ggcgagtcta aagtggatga cgacatccag gtgaccagt ctccgtcctc cctgtctgca      420
tctctaacag agagagtctc catcacttgc cggaccagtc agagcgttaa caattactta      480
agctggtatc agcagaaacc agggcaagct cctaagctcc tgatctatta tgcaaccaga      540
```

-continued

```
ttgtacaccg atgtcccatc ccggttcagt ggcagtggat ctgggacaga ttacaccctc      600
accatcacca gcctggaggc ggacgacact gcaacttatt actgtctaca atatgatagt      660
acacctcttg cattcggcgg tgggaccaac gtggaaatca aacgg                      705

<210> SEQ ID NO 383
<211> LENGTH: 750
<212> TYPE: DNA
<213> ORGANISM: artificial sequence
<220> FEATURE:
<223> OTHER INFORMATION: CE2 nucleotide sequence

<400> SEQUENCE: 383
caggtgcagc tgcaggagtc gggacccagc ctggtgaagc cctcacagac cctctccctc       60
acctgcacgg tctctggatt ctcattaacc aactatcctg taggctgggt ccgccaggct      120
ccaggaaagg cactggagtg gattggtaac atagaaaatg atggaagtgc gaactatgcc      180
tcggccctga atcccgact cagcatcacc agggacacct ccaagaacca agtctccctg       240
tcactgagca gcgcgacaac tgaggacacg gccgtttact actgtggaag agaattcggt      300
gggagtgatg gttatactta tttcgttgat atcgactact ggggcccagg actcctggtc      360
accgtctcct cagaaggtaa atcttctggc gcgtctggcg agtctaaagt ggatgaccag      420
gctgtgctga ctcagccgtc ctccgtgtcc aagtccctgg ccagagtgt ctccatcacc       480 tgctctggaa gcagcagcaa cgttggatat ggtaattatg tgagctggtt ccaacaggtc      540
ccaggatcag cccccaaaat cctcatctat ggtgcaacca gtcgagcctc ggggtcccc       600 gaccgattct ccggctccag gtctggcaac acagcgactc tgaccatcac ctcgctccag      660
gctgaggacg aggccgatta ttactgtgca tcttatgacg gcagtagcag tggtgttttc      720
ggcagcggga ccaggctgac cgtcctgggt                                        750

<210> SEQ ID NO 384
<211> LENGTH: 750
<212> TYPE: DNA
<213> ORGANISM: artificial sequence
<220> FEATURE:
<223> OTHER INFORMATION: CE3 nucleotide sequence

<400> SEQUENCE: 384
caggtgcgac tgcaggagtc gggacccagc ctggtgaagc cctcacagac cctctccgtc       60
acctgcacgg tctctggatt ctcattgatc agcaatgctg taggctgggt ccgccaggct      120
ccaggaaagg tgccggagtc gcttgctggt tgtagcagtg atggaaagtg ttactataac      180
tcggccctga atcccggct cgacatcacc agggacacct cgaagaacca gatctccctg       240
tcactgagca gcgtcacaac tgacgacgcg gccgtgtact actgtacaag aggctattat      300
cctgtttatg gttatgacta tcttggcact atcgactact ggggccccgg actcctggtc      360
accgtctcct cagaaggtaa atcttctggc gcgtctggcg agtctaaagt ggatgaccaa      420
gctgtgctga ctcaaccgtc ctccgtgtct gggtccctgg ccagagggt ctccatcacc       480 tgctctggaa gcagcagcaa cgttggtaga aatgatgtag cctggttcca acaactccca      540
ggatcaggcc tcagaaccat catctatggt actaccagtc gaccctcagg tatcccggac      600
cgattctccg gctccaagtc tggcgttacg gccaccctga ccatcgactc gctccaggct      660
gaggacgagg ccgattattt ctgtgcctct ggtgacagta gtgccattaa tgatattttc      720
ggcagcggga ccaggctgac cgtcctgggt                                        750
```

-continued

```
<210> SEQ ID NO 385
<211> LENGTH: 735
<212> TYPE: DNA
<213> ORGANISM: artificial sequence
<220> FEATURE:
<223> OTHER INFORMATION: CB7 nucleotide sequence

<400> SEQUENCE: 385
caggtgcagc tgcaggagtc gggacccagc ctggtgaagc cctcacagac cctctccctc      60
acctgcacgg tctctggatt ctcattaacc aactatcgtg taggttgggt ccgccaggct     120
ccaggaaagg cactggagtg ggttagtaac atacggagtg gtggaactac atggtataac     180
ccggccctga aatcccggct cagcatcacc gcggacacct ccaagagcca agtctccctg     240
tcactgagca gcgtgacaac tgaggacacg gccgtatatt attgtgcaag agattcctct     300
ggtgatcttt atgcgtatga ttactggggc ccaggactcc tggtcaccgt ctcctcagaa     360
ggtaaatctt ctggcgcgtc tggcgagtct aaagtggatg accaggccgt gctgactcag     420
ccgtcctccg tgtccaggtc cctgggccag agtgtctcca tgacctgctc tggaagcagc     480
agcaacgttg gatatggtaa ttatatggcc tggttccaac aggttccagg atcagccccc     540
aaactcctca tctatggtgc aaccagtcga gcctcggggg tccccgaccg attctccggc     600
tccaggtctg gcaacacagc gactctgacc atcagctcgc tccaggctga ggacgaggcc     660
gattactact gtgcatctta tgacagcact agcggggggtg tcttcggcag cgggaccagg     720
ctgaccgtcc tgggt                                                      735

<210> SEQ ID NO 386
<211> LENGTH: 732
<212> TYPE: DNA
<213> ORGANISM: artificial sequence
<220> FEATURE:
<223> OTHER INFORMATION: CC7 nucleotide sequence

<400> SEQUENCE: 386
caggtgcagc tgcaggagtc gggacccagc ctggtgaagc cctcacagac cctctccctc      60
acctgcacgg tctctggatt ctcactaacc agcaatgctg tgatctgggt ccggcaggct     120
ccaggaaagg cgccggagtg ggttgctttg atagatgttg atggagatgc agcctatgac     180 ccagcccta agtcccgcct cagcatcacc agggacacct ccaagagtca agtctccctt     240
tcactgcgca gcgtgacaac tgaggacacg gccgtgtact actgtgcaag agactatggt     300 agttgggggtt atgtttccga catcgactac tggggcccag gactcctggt caccgtctcc     360
tcagaaggta aatcttctgg cgcgtctggc gagtctaaag tggatgacag ggtcgtgcgg     420
actcaaccgt cctccgtgtc tgggtccctg ggccagaggg tctccatcac ctgctctgga     480
agctacatca ctggtagttc tgtaggctgg ttccaacagg tcccaggatc gggcctcaaa     540
accgtcatct atgacaataa cgatcgaccc tcagggtcc ccgaccgatt ctctggctcc     600
aagtcgggcg acacagccac cctgaccatc agctcgctcc aggctgagga cgaggccgat     660
tattactgtg catcttatga caccagtaac attggtcttt tcggcagcgg gaccaggctg     720
accgtcctgg gt                                                         732

<210> SEQ ID NO 387
<211> LENGTH: 723
<212> TYPE: DNA
<213> ORGANISM: artificial sequence
<220> FEATURE:
<223> OTHER INFORMATION: 412E10 nucleotide sequence
```

-continued

```
<400> SEQUENCE: 387
caggtgcagc tgcaggagtc gggacccagc ctggtgaagc cctcacagac cctctccctc      60
acctgcacgg tctctggctt ctctgtaata agcgattctg tagcctgggt ccgccaggct     120
ccaggaaaag tgccggagtg gcttggtgct agcggcagtt ctggaaacaa atactataac     180
ccggccctaa aatcccggct cagcatcacc aggacacct ccaagagcca agtctccctg       240
tcactgagca gcgtgacaac tgaggatacg gccgtgtact actgtgcgag aggtattatc      300
gccggtgtag atgtctgggg ccgaggactc ctggtcaccg tctcctcaga aggtaaatct      360
tctggcgcgt ctggcgagtc taaagtggat gaccaggctg tgctgactca gccgtcctcc      420
gtgtctgggt ccctgggcca gagggtctcc atcacctgct ctggaagcag cagcaacgtt      480
ggatatggta attatgtggg ctggtaccaa caggtcccag gatcagcccc caaactcctc      540
atctatggta cagccattcg agcctcgggg gtccccgacc gattctccgg ctccaggtct      600
ggggacacag ccacccttac catcacctcg ctccaggctg aggacgaggc cgattactac      660
tgtgcatctt atcagagtaa ttacgctttt ttcggcagcg ggaccaggct gaccgtcctg      720
ggt                                                                   723

<210> SEQ ID NO 388
<211> LENGTH: 747
<212> TYPE: DNA
<213> ORGANISM: artificial sequence
<220> FEATURE:
<223> OTHER INFORMATION: S1B1 nucleotide sequence

<400> SEQUENCE: 388
caggtgcagc tgcaggagtc gggacccagc ctggtgaagc cctcacagac cctctccctc      60
acctgcacgg tctctggatt ctcattgtcc agcaattctg tgggctgggt ccgacaggct     120
ccaggaaagg cgccggagtg ggttgctggt atagatactg atggagaaga aggctataat     180
ccagccctta actcccggct cagcatcacc aggacacct ccaagagtca agtctctttg       240
tcattgagca gcgtgacaag tgaggacacg gccgtgtact actgtgtaag aagttatagg      300
actgatggtc ttgcttacgg ttatgtccaa gccatcgact actggggccc aggactcctg      360
gtcaccgtct cctcagaagg taaatcttct ggcgcgtctg gcgagtctaa agtggatgac      420
caggctgtgc tgactcagcc gtcctccgtg tctgggtccc tgggcagag ggtctccatc       480 acctgctctg gaagcttcat cggtattagt agtgtaggct ggttccaaca gctcccagga      540
tcgggcctca gaaccgtcat cgttgcgagt gacggtcgac cctcagggt ccccgaccga       600 ttctctaact ccaaatcggg caacacagcc accctgacca tcagctcgct ccaggctgag      660
gacgaggccg attatttctg tggaagtagt gataggactc aatatactgg agttttcggc      720
agcgggacca ggctgaccgt ccttggt                                         747

<210> SEQ ID NO 389
<211> LENGTH: 747
<212> TYPE: DNA
<213> ORGANISM: artificial sequence
<220> FEATURE:
<223> OTHER INFORMATION: S1D9 nucleotide sequence

<400> SEQUENCE: 389
caggtgcagc tgcaggagtc gggacccagc ctggtgaagc cctcacagac cctctccctc      60
acctgcacgg tctctggatt ctcattaacc agcaattctg tgggctgggt ccgacaggct     120
```

-continued

```
ccaggaaagg cgccggagtg ggttgctggt atagatagtg atggagaaga aggctataat      180 ccagcccta actcccggct cagcatcacc agggacacct ccaagaatca agtctctttg      240
tcattgagca gagtgacaag tgaggacacg gccgtttact actgtggaag aacttatagg      300
actgatggtt atgcttacgg ttatgtccaa gccatcgact actggggccc aggactcctg      360
gtcaccgtct cctcagaagg taaatcttct ggcgcgtctg gcgagtctaa agtggatgac      420
cgggtcatgc tgactcagcc accctccgtg tccgggtccc cgggccagac ggtatccatc      480
acctgctctg gaagcttcat cggtattagt agtgtaggct ggttccaaca gctcccagga      540
tcgggcctca gaaccgtcat ttttgcgagt gacggtcgac cctcaggggt ccccgatcga      600
ttctctaact ccaaatcggg caacacagcc accctgacca tcagctcgct ccaggctgag      660
gacgaggccg attatttctg tggaagtagt gataggactc aatatactgg agttttcggc      720
agcgggacca ggctgaccgt cctgagt                                         747
```

```
<210> SEQ ID NO 390
<211> LENGTH: 747
<212> TYPE: DNA
<213> ORGANISM: artificial sequence
<220> FEATURE:
<223> OTHER INFORMATION: S1F4 nucleotide sequence

<400> SEQUENCE: 390
caggtgcagt tgcaagagtc gggacccagc ctggtgaagc cctcacagac cctctccctc       60
acctgcacgg tctctggatt ctcattaagt agcaattctg tcggctgggt ccgacaggct      120
ccaggaaagg cgccggagtg ggttgctggt atagatactg atggagaaga aggctataat      180 ccagcccta actcccggct cagcatcacc agggacacct ccaagagtca agtctcattg      240
tcattgagca gcgttacaag tgaggacacg gccgtgtact actgtgtaag aagttataga      300
gctgatggtc ttgcttacgg ttatgtccaa gccatcgact actggggccc aggactcctg      360
ctcaccatct cctcagaagg taaatcttct ggcgcgtctg gcgagtctaa agtggatgac      420
caggccgtgg tgactcagcc gtcctccgtg tctgggtccc tgggccagag ggtctccatc      480
acctgctctg gaagcttcat cggtattagt agtgtaggct ggttccaaca gctcccagga      540
tcgggcctca gaaccgtcat cgtggcgagt gacggtcgac cctcaggggt ccccgaccga      600
ttctctaact ccaaatcggg caacacagcc accctgacca tcagctcgct ccaggctgag      660
gacgaggccg attatttctg tggaagtagt gataggactc aatatactgg agttttcggc      720
agcgggacca ggctgaccgt cctgggt                                         747
```

```
<210> SEQ ID NO 391
<211> LENGTH: 747
<212> TYPE: DNA
<213> ORGANISM: artificial sequence
<220> FEATURE:
<223> OTHER INFORMATION: S1G10 nucleotide sequence

<400> SEQUENCE: 391
caggttcagt tgcaggagtc gggacccagc ctggtgaagc cctcacagac cctctccctc       60
acctgcacgg tctctggatt ctcattaacc agcaattctg tgggctgggt ccgacaggct      120
ccaggaaagg cgccggagtg ggttgctggt atagatactg atggagaaga aggctataat      180 ccagcccta actcccggct cagcatcacc agggacacct ccaagagtca agtctcattg      240
tcattgagca gcgtgacaag tgaggacacg gccgtgtact actgtggaag aagttataga      300
gctgatggtc ttgcttacgg ttatgtccaa gccatcgact actggggccc aggactcctg      360
```

```
gtcaccgtct cctcagaagg taaatcttct ggcgcgtctg gcgagtctaa agtggatgac    420
caggctgtgc tgactcagcc gtcctccatg tccgggtccc tgggccagag ggtctccatc    480
acctgttctg gaagcttcat cggtattagt agtgtaggct ggttccaaca gctcccagga    540
tcgggcctca gaaccatcat cgtggcgagt gacggtcgac cctcagggtgt ccccgaccga    600
```

```
tcgggcctca gaaccatcat cgtggcgagt gacggtcgac cctcaggggt ccccgaccga    600
ttctctatgt ccaaatcggg caacacagcc accctgacca tcagctcgct ccaggctgag    660
gacgaggccg attatttctg tggaagtagt gataggactc aatatactgg agttttcggc    720
agcgggacca ggctgaccgt cctgggt                                         747
```

```
<210> SEQ ID NO 392
<211> LENGTH: 750
<212> TYPE: DNA
<213> ORGANISM: artificial sequence
<220> FEATURE:
<223> OTHER INFORMATION: S2C6 nucleotide sequence

<400> SEQUENCE: 392
caggtgcagc tgcaggagtc gggacccagc ctggtgaagc cctcacagac cctctccctc    60
acctgcacgg tctctggatt ctcattaatc agcaattctg tgggctgggt ccgacaggct    120
ccaggaaagg cgccggagtg ggttgctggt atagatactg atggagaaga aggctataat    180 ccagcccta agtcccaata tgcagctagt gatccggaca cctccaagag tcaagtctcc    240
```

```
ccagcccta agtcccaata tgcagctagt gatccggaca cctccaagag tcaagtctcc    240
ttgtcattga gcagcgtgac aagtgaggac acggccgtgt actactgtgg aagaacttat    300
aggactgatg gttttgctta tggttatgtc caagccatcg actactgggg cccaggactc    360
ctgctcacta tctcctcaga aggtaaatct tctggcgcgt ctggcgagtc taaagtggat    420
gaccaggctg tgctgactca gccgtcctcc gtgtctgggt ccctgggcca gagggtctcc    480
atcacctgct ctggaagctt tattggtatt agtagtgtag ctggttcca acagctccca    540 ggatcgggcc tcagaaccat catcgtggcg agtgacggtc gaccctcagg ggtccccgac    600
cgattctcta tgtccaaatc gggcaacaca gccaccctga ccatcagctc gctccaggct    660
gaggacgagg ccgattattt ctgtggaagt agtgatagga ctcaatatac tggagttttc    720
ggcagcggga ccaggctgac cgtcctgggt                                      750
```

```
<210> SEQ ID NO 393
<211> LENGTH: 720
<212> TYPE: DNA
<213> ORGANISM: artificial sequence
<220> FEATURE:
<223> OTHER INFORMATION: MD9 nucleotide sequence

<400> SEQUENCE: 393
caggtgcggc tgcaggagtc gggacccagc ctggtgaagt cctcacagac cctctccctc    60
acctgcacgg tctctggatt ctcattaacc agggaatcta tagcctgggt ccgccaggct    120
ccaggaaagg tgccggagtg gcttggtggt gtaggcattg atggaacctc atactatagc    180
ccggccctga atcccggct cagtatcacg agggacacct ccaagagcca gcctccctg    240 tcactgagca gcgtggcaac tgaggacacg gccatgtatt actgtgcacg taattatatt    300
gatttcgagt actgggcccc aggactcctg gtcaccgtct cctcagaagg taaatcttct    360
ggcgcgtctg gcgagtctaa agtggatgac caggctgtgc tgactcaact gtcctccgta    420
tctgggtccc tgggccagag gatctccatc acctgctctg gaagcagcag caacgttggt    480
atatatgatg tgtcttggtt ccaacaactc ccaggatcag gcctcagaac cgtcatctat    540
```

-continued

```
ggtactaaca atcgaccctc gggtgtcccg gaccgattct ccggctccag gtctggcaac      600
acggccaccc tgactatcag ctctctccag tctgaggacg aggccattta ttactgtgct      660
gctggtgaca gcagtactat tgctgttttc ggcagcggga ccaggctgac cgtcctgggt      720
```

```
<210> SEQ ID NO 394
<211> LENGTH: 726
<212> TYPE: DNA
<213> ORGANISM: artificial sequence
<220> FEATURE:
<223> OTHER INFORMATION: 412B9 nucleotide sequence

<400> SEQUENCE: 394
caggtgcagc tgcaggagtc gggacccagc ctggtgaagc cctcacagac cctctccctc       60
acctgcacgg tctctggatt ctctgtaata agcgattctg tagcctgggt ccgccaggct      120
ccaggaaaag tgccggagtg gcttggtgct agcggcagtt ctggaaacaa atactataac      180
ccggccctaa atcccggct cagcatcacc agggacacct ccaagagcca agtctccctg        240
tcactgagca gcgtgacaac tgaggatacg gccgtgtact actgtgcgag aggtattatc      300
gccggtgtag atgtctgggg ccgaggactc ctggtctccg tctcctcaga aggtaaatct      360
tctggcgcgt ctggcgagtc taaagtggat gaccaggctg tgctgactca gccgtcctcc      420
gtgtctgggg ccctgggcca gagggtctcc atcacctgct ctggaagcag cagcaacgtt      480
ggatatggtg attatgtggg ctggtaccaa caggtcccag gatcagcccc caaactcctc      540
atctatggtg cagccagtcg agcctcgggg gtccccgacc gattctctgg ctccaggtct      600
ggcaacacag cgactctgac catcagctcg ctccaggctg aggacgaggc cgattattac      660
tgtgcatctt atgacagcag tgacggtggt gttttcggca gcgggaccag gctgaccgtc      720
ctgggt                                                                 726
```

```
<210> SEQ ID NO 395
<211> LENGTH: 729
<212> TYPE: DNA
<213> ORGANISM: artificial sequence
<220> FEATURE:
<223> OTHER INFORMATION: 412E6 nucleotide sequence

<400> SEQUENCE: 395
caggtgcagc tgcaggagtc gggacccagc ctggtgaagc cctcagagac cctctccctc       60
acctgcacgg tctctggatt ctcattaaca aactatggtg tgggctgggt ccgccaggct      120
ccaggaaagg cactggagtg gcttggtaac atatatagtg gtgggtctac atactataac      180
ccggccctga atcccgact cagcatcacc agggacacct ccaagagcca agtctccctg        240
tcactgaaca gcgtgacact tgaggacacg gccgtttatt actgtggaag aggaggtgtt      300
gggagtgtcg acgtctgggg cccaggactc ctggtcaccg tctcctcaga aggtaaatct      360
tctggcgcgt ctggcgagtc taaagtggat gaccaggctg tgctgactca gccgccctcc      420
gtgtccggtt ccccaggcca gagggtctcc atcacctgct ctggaggcag gaataacatc      480
gggcgtggta cctttgtgga ctggtaccag caactcccag gatcaggcct caaaaccgtc      540
atctatggta ctgaccgtcg accaccgggg gtcccggacc gattctccgg ctccaagact      600
ggcaacgcgg ccaccctgac catcacctcc ctccaggctg aggacgaggc cgattattgg      660
tgtgctactt atgattacag taatgatatg attattctcg gcagcgggac caggctgacc      720
gtcctgggt                                                              729
```

-continued

```
<210> SEQ ID NO 396
<211> LENGTH: 714
<212> TYPE: DNA
<213> ORGANISM: artificial sequence
<220> FEATURE:
<223> OTHER INFORMATION: 412G11 nucleotide sequence
<220> FEATURE:
<221> NAME/KEY: misc_feature
<222> LOCATION: (522)..(522)
<223> OTHER INFORMATION: n is a, c, g, or t

<400> SEQUENCE: 396
caggtgcggc tgcaggagtc gggacccagc ctggtgaagc cctcacagac cctctccctc      60
acctgtacgg tctctggatt ctcattaacc agctatgctt taggctgggt ccgccaggct     120
ccaggaaggg ctccggagtg gattggtaac atatggaggg gtggacgaat agaatataac     180
ccggccctga atcccggct cagcatcact agggacacct ccaagagcca gtctcgctg      240 tcactgagca gcgtgacaac tgaggatacg gccgtgtact actgttcaag aagtggcggc     300
gactggggcc caggactcct ggtcaccgtc tcctcagaag gtaaatcttc tggcgcgtct     360
ggcgagtcta aagtggatga ccaggctgtg ctgactcagc cgtcctccgt gtctgggtcc     420
ctgggccaga gggtctccat cacctgctct ggaagcagca gcaacgttgg atatggtaat     480
tatgtgggct ggtaccaaca ggtcccagga tcagccccca anctcctcat ctatggtgca     540
accagtcgag cctcgggggt ccccgaccga ttctccggct ccaggtctga gaacacagcc     600
accctgacca tcagctccct ccaggctgag gacgaggccg attattactg tgcgtcttat     660
gataggagtg agagtgttgt gttcggcagc gggaccagac tgaccgtcct gggt           714

<210> SEQ ID NO 397
<211> LENGTH: 732
<212> TYPE: DNA
<213> ORGANISM: artificial sequence
<220> FEATURE:
<223> OTHER INFORMATION: CA2 nucleotide sequence

<400> SEQUENCE: 397
caggttcagc tgcaggagtc gggacccagc ctggtgaagc cctcacagac cctctccctc      60
acctgcacgg tctctggatt ctcattaagc agcgtcgctg taaactgggt ccgccaggct     120
ccaggaaagg tgccggagtg gcttggtggc attattagta atggaggcac aggctataat     180
ccggccctga atctcggct gagcatcacc agggacacct ccaagagcca gtctccctg      240 gcactgaccc acgtgacaac tgaggacacg gccgtgtact actgtggaag gggagttgaa     300 tgggaggggct ctatggacta cttgggccca ggactcctgg tcaccgtctc ctcagaaggt     360
aaatcttctg gctctggctc tgagactaaa gtggatgacc agtctgtgct gactcagccg     420
tcctccgtgt ccgggttcct gggccagagg gtcaccatca cctgctctgg aagcagcagc     480
aacgttggag ctggtagtta tgtgggctgg taccagcagg tcccaggatc gggcctcaga     540
atcctcatct atggtgcaac caagcgagcc tcgggactcc cgaccgattc tccggctcc      600 aggtctggga acacagccac cctgaccatc agctcgctcc aggctgagga cgaggccgat     660
tattactgcg tatcttatca gactgatttt actttagttt tcggcagcgg gaccaggctg     720
accgtcctag gt                                                        732

<210> SEQ ID NO 398
<211> LENGTH: 747
<212> TYPE: DNA
<213> ORGANISM: artificial sequence
<220> FEATURE:
```

-continued

```
<223> OTHER INFORMATION: CA9 nucleotide sequence

<400> SEQUENCE: 398
caggtgcagc ttcaggagtc gggacccagc ctggtgaagc cctcacagac cctctccctc      60
acctgcacgg tctctggatt ctcattaacc agcaattctg tgggctgggt ccgacaggct     120
ccaggaaagg cgccggagtg ggttgctggt atagatactg atggagaaga aggctataat     180 ccagcccta actcccggct cagcatcacc agggacacct ccaagagtca agtctctttg      240
tcattgagca gcgtgacaag tgaggacacg gccgtgtact actgtggaag aagttatagg     300
agtgatggtc ttgcttacgg ttatgtccaa gccatcgact actggggccc aggactcctg     360
gtcaccgtct cctcagaagg taaatcttct ggcgcgtctg gcgagtctaa agtggatgac     420
caagctgtgc tgactcagcc ggcctccgtg tctgggtccc tgggccagag ggtctccatc     480
acctgttctg gaagcttcat cggtattagt agtgtaggct ggttccaaca gctcccagga     540
tcgggcctca gaaccatcat cgtggcgagt gacggtcgac cctcaggggt ccccgaccga     600
ttctctatgt ccaaatcggg caacacagcc accctgacca tcagctcgct ccaggctgag     660
gacgaggccg attatttctg tggaagtagt gataggactc aatatactgg agttttcggc     720
agcgggacca ggctgaccgt cctgggt                                        747

<210> SEQ ID NO 399
<211> LENGTH: 753
<212> TYPE: DNA
<213> ORGANISM: artificial sequence
<220> FEATURE:
<223> OTHER INFORMATION: CA12 nucleotide sequence

<400> SEQUENCE: 399
caggtgcagc tgcaggggtc gggacccagc ctggtgaagc cctcacagac cctctccctc      60
acctgcacgg tctctggatt ctcttttgac agctattatg taggctgggt ccgccaggct     120
ccaggaaagg cactggagtg gcttggtaat atatatagta ctggaagggc attctataac     180
ccggccctga atcccggct cagcatcacc agggacacct ccaagagcca gtctccctta      240
tcagtgagca gcgtgacaat tgaggacacg gccctgtact actgtgtcag aggctcgtat     300
tatcacggtg gtggcaatgg gatggtcgac tttttcgact actggagccc aggactcctg     360
gtcaccgtct cctcagaagg taaatcttct ggcgcgtctg gcgagtctaa agtggatgac     420
caggtcgtgc ggactcagcc gtcctccgtg tctgggtccc tgggccagag ggtctccatc     480
acctgctctg gaagcagcag caatgttgga tatggtaatt atgtgggctg gttccaacag     540
gtgccagggt cagcccccaa actcctcatc tatgctgcaa ccagtcgagc ctcggggggtc     600 cccgaccgat tctccggctc caggtctggg aatacagcca ccctgaccat cgactcgctc     660
caggctgagg acgaggccga ttattactgt tcatcttatc aacgcggtaa cactggtgtt     720
ttcggcagcg ggaccaggct gaccgtcctg ggt                                 753

<210> SEQ ID NO 400
<211> LENGTH: 747
<212> TYPE: DNA
<213> ORGANISM: artificial sequence
<220> FEATURE:
<223> OTHER INFORMATION: CB2 nucleotide sequence

<400> SEQUENCE: 400
caggttcagc ttcaggagtc gggacccagc ctggtgaagc cctcacagac cctctccctc      60
acctgcacgg tctctggatt ctcattaagc actaattctg tgggctgggt ccgacaggct     120
```

-continued

```
ccaggaaagg cgccggagtg ggttgctggt atagatactg atggagaaga aggctttaat      180
ccagtcctta agtcccggct cagcatcacc agggacacct ccaagagtca agtctctttg      240
tcattgagca acgtgacaag tgaagacacg gccgtgtact actgtggaag aagttatagg      300
actgatggtc ttgcttacgg ttatgtccaa gccatcgact actggggccc aggactcctg      360
gtcactatct cctcagaagg taaatcttct ggcgcgtctg gcgagtctaa agtggatgac      420
cagtctgtgc tgactcagcc gtcctccgtg tccgggtccc cgggccagac agtctccatc      480
acctgctctg gaagctatat cggtagtagt ggtgtaggct ggttccaaca gctcccagga      540
tcgggcctca gaaccatcat cgtggcgagt gacggtcgac cctcagggct ccccgaccga      600
ttctctatgt ccaaatcggg caacacagcc accctgacca tcagctcgct ccaggctgag      660
gacgaggccg attatttctg tggaagtagt gataggactc aatatactgg acttttcggc      720
agcgggacca ggctgaccgt cctgggt                                         747
```

```
<210> SEQ ID NO 401
<211> LENGTH: 732
<212> TYPE: DNA
<213> ORGANISM: artificial sequence
<220> FEATURE:
<223> OTHER INFORMATION: CB3 nucleotide sequence

<400> SEQUENCE: 401
caggttcagc tgcaggagtc gggacccagc ctggtgaagc cctcacagac cctctccctc       60
acctgcacgg tctctggatt ctcattaagc agcgtcgctg taaactgggt ccgccaggct      120
ccaggaaagg tgccggagtg gcttggtggc attattagta atggaggcac aggctataat      180
ccggccctga aatctcggct gagcatcacc agggacacct ccaagagcca agtctccctg      240
gcactgaccc acgtgacaac tgaggacacg gccgtgtact actgtggaag gggagttgaa      300
tgggagggct ctatggacta cttgggccca ggactcctgg tcaccgtctc ctcagaaggt      360
aaatcttctg gctctggctc tgagactaaa gtggatgacc agtctgtgct gactcagccg      420
tcctccgtgt ccgggttcct gggccagagg gtcaccatca cctgctctgg aagcagcagc      480
aacgttggag ctggtagtta tgtgggctgg taccagcagg tcccaggatc gggcctcaga      540
atcctcatct atggtgcaac caagcgagcc tcgggactcc ccgaccgatt ctccggctcc      600
aggtctggga cacagccacc ctgaccatc agctcgctcc aggctgagga cgaggccgat      660
tattactgcg tatcttatca gactgatttt actttagttt tcggcagcgg gaccaggctg      720
accgtcctag gt                                                         732
```

```
<210> SEQ ID NO 402
<211> LENGTH: 735
<212> TYPE: DNA
<213> ORGANISM: artificial sequence
<220> FEATURE:
<223> OTHER INFORMATION: CB7 nucleotide sequence

<400> SEQUENCE: 402
caggtgcagc tgcaggagtc gggacccagc ctggtgaagc cctcacagac cctctccctc       60
acctgcacgg tctctggatt ctcattaacc aactatcgtg taggttgggt ccgccaggct      120
ccaggaaagg cactggagtg ggttagtaac atacggagtg gtggaactac atggtataac      180
ccggccctga aatcccggct cagcatcacc gcggacacct ccaagagcca agtctccctg      240
tcactgagca gcgtgacaac tgaggacacg gccgtatatt attgtgcaag agattcctct      300
```

-continued

```
ggtgatcttt atgcgtatga ttactggggc ccaggactcc tggtcaccgt ctcctcagaa      360
ggtaaatctt ctggcgcgtc tggcgagtct aaagtggatg accaggccgt gctgactcag      420
ccgtcctccg tgtccaggtc cctgggccag agtgtctcca tgacctgctc tggaagcagc      480
agcaacgttg gatatggtaa ttatatggcc tggttccaac aggttccagg atcagccccc      540
aaactcctca tctatggtgc aaccagtcga gcctcggggg tccccgaccg attctccggc      600
tccaggtctg gcaacacagc gactctgacc atcagctcgc tccaggctga ggacgaggcc      660
gattactact gtgcatctta tgacagcact agcggggggtg tcttcggcag cgggaccagg      720
ctgaccgtcc tgggt                                                       735
```

```
<210> SEQ ID NO 403
<211> LENGTH: 732
<212> TYPE: DNA
<213> ORGANISM: artificial sequence
<220> FEATURE:
<223> OTHER INFORMATION: CC7 nucleotide sequence

<400> SEQUENCE: 403
caggtgcagc tgcaggagtc gggacccagc ctggtgaagc cctcacagac cctctccctc       60
acctgcacgg tctctggatt ctcactaacc agcaatgctg tgatctgggt ccggcaggct      120
ccaggaaagg cgccggagtg ggttgctttg atagatgttg atggagatgc agcctatgac      180
ccagccctta agtcccgcct cagcatcacc agggacacct ccaagagtca agtctccctt      240
tcactgcgca gcgtgacaac tgaggacacg ccgtgtact actgtgcaag agactatggt      300 agttgggggtt atgtttccga catcgactac tggggcccag actcctggt caccgtctcc      360 tcagaaggta aatcttctgg cgcgtctggc gagtctaaag tggatgacag ggtcgtgcgg      420
actcaaccgt cctccgtgtc tgggtccctg ggccagaggg tctccatcac ctgctctgga      480
agctacatca ctggtagttc tgtaggctgg ttccaacagg tcccaggatc gggcctcaaa      540
accgtcatct atgacaataa cgatcgaccc tcaggggtcc ccgaccgatt ctctggctcc      600
aagtcgggcg acacagccac cctgaccatc agctcgctcc aggctgagga cgaggccgat      660
tattactgtg catcttatga caccagtaac attggtcttt tcggcagcgg gaccaggctg      720
accgtcctgg gt                                                         732
```

```
<210> SEQ ID NO 404
<211> LENGTH: 741
<212> TYPE: DNA
<213> ORGANISM: artificial sequence
<220> FEATURE:
<223> OTHER INFORMATION: 3aA6 nucleotide sequence

<400> SEQUENCE: 404
caggtgcggc tgcaggagtc gggatccagt ctggtgaagc cctcacagac cctctccctc       60
gtctgcacgg tctctggatt cccattaacc agcaatgctg taggctgggt ccgccaggct      120
ccaggaaagg cgccggagtg gctaggtctc atagatattg atggagacac agcctataac      180
ccagcccttg agtcccggct cagcatcacc agggacacct ccaagagtca agtctccctg      240
tcactgagca gcgtggcaat tgaggacacg ccgtgtact attgtgctcg tcattatgat      300
aaatggggtt atgctgattc gatcgactac tggggcccag actcctggt caccgtctcc      360 tcagaaggta aatcttctgg cgcgtctggc gagtctaaag tggatgacca ggccctgctg      420
actcagccgt cctccgtgtt tggttccctg ggccagaggg tctccatcac ctgctctgga      480
agcagcagca acgttggata tggtgattat gtaggctggt accaacaggt cccaggatca      540
```

-continued

```
gcccccaaac tcctcatcta tgatgcaacc actcgagcct cgggggtccc cgaccgattc    600
tccggctcca ggtctgggaa cacagccacc ctgaccatca gctcgctcca ggctgaggac    660
gaggccgatt attactgtgc atcttatcag aatgaaagaa gtggtgtttt cggcagcggg    720
accaggctga ccgtcctggg t    741

<210> SEQ ID NO 405
<211> LENGTH: 732
<212> TYPE: DNA
<213> ORGANISM: artificial sequence
<220> FEATURE:
<223> OTHER INFORMATION: 3aD6 nucleotide sequence

<400> SEQUENCE: 405
caggtgcagc tgcaggagtc gggacccagc ctggtgaagc cctcacagac cctctccctc     60
acctgcacgg tctctggatt ctcactaacc agcaatgctg tgatctgggt ccggcaggct    120
ccaggaaagg cgccggagtg ggttgctttg atagatgttg atggagatgc agcctatgac    180
ccagccctta gtcccgcct cagcatcacc agggacacct ccaagagtca agtctccctt    240
tcactgcgca gcgtgacaac tgaggacacg gccgtgtact actgtgcaag agactatggt    300 agttgggggtt atgtttccga catcgactac tggggcccag gactcctggt caccgtctcc    360
tcagaaggta aatcttctgg cgcgtctggc gagtctaaag tggatgacca ggctgtgctg    420
actcagccgt cctccgtgtc tgggtccctg gccagaggg tctccatcac ctgctctgga    480
agcgacatcg gtggtgctga tgtaggctgg ttccaacagg tcccaggatc gggcctcaga    540
accctcatct atgataatga caatcgaccc tcaggggtcc ccgaccgatt ctctggctcc    600
aagtcgggca acacagccac cctgaccatc agctcgctcc agcctgagga tgaggccgat    660
tatttctgtg cacttattc tggtgctaac tatggtattt ttggcagcgg gaccaggctg    720
accgtcctgg gt    732

<210> SEQ ID NO 406
<211> LENGTH: 744
<212> TYPE: DNA
<213> ORGANISM: artificial sequence
<220> FEATURE:
<223> OTHER INFORMATION: 3aB7 nucleotide sequence

<400> SEQUENCE: 406
caggttcagc tgcaggagtc gggacccagc ctggtgaagc cctcacagac cctctccctc     60
acctgcacgg tctctggatt ctcattaact agcaatggtg taggctgggt ccgccaggct    120
ccaggaaagg tgccggagtg ggttggtgat aaaagcagtg ctggaaagac atacggtaac    180
ccggccctga atcccggct cagcatcacc agggacacct ccaagagcca gtctccctg    240 tcactgagca gcgtgacaac tgaggacacg gccgtgtact actgtgtaag atgcagggat    300
ggtggtgtga cttatggtta tgacgtcgac tactggggcc aggactcct ggtcaccgtc    360 tcctcagaag gtaaatcttc tggcgcgtct ggcgagtcta aagtggatga ccaggctgtg    420
ctgactcagc cgtcctccgt gtccaagtcc ctgggccaga gtgtctccat cacctgctct    480
ggaagcagca gcaacgttgg atatggtgat gttgtgagct ggttccaaca gttcccagga    540
tcagccccca aactcctcat tttcggtaca cgactcgag cctcgggggt ccccgaccga    600
ttctccggct ccaggtctgg caacgcagcg actctaacca tcaactctct ccaggctgag    660
gacgaggccg actattactg tgcgtctttt gatagtgata gcggtggaat tgccggcagc    720
```

-continued

```
gggaccaggc tgaccgtcct gggt                                        744

<210> SEQ ID NO 407
<211> LENGTH: 744
<212> TYPE: DNA
<213> ORGANISM: artificial sequence
<220> FEATURE:
<223> OTHER INFORMATION: 3bF4 nucleotide sequence

<400> SEQUENCE: 407
caggtgcagc tgcaggagtc gggacccagc ctggtgaagc cctcacagac cctctccctc      60
acctgcacgg tctctggatt ctccttgagt agcaatggtg taggctgggt ccgccaggct     120
ccaggaaagg tgccggagtg gcttggtgat ataagcagtg ttggaaaaaa atacgctaac     180
ccggccctga atctcggct cagcttcact agggacacct ccaagagcca agtgtccctg      240
tcactgagca gcgtgacaac tgaggacacg gccgtgtact attgtgtaaa atgcagggat     300
ggtggtgtga cttatggtta tgatatcgac tactggggc caggactcct ggtcaccgtc      360
tcctcagaag gtaaatcttc tggcgcgtct ggcgagtcta aagtggatga ccaggctgtg     420
ctgactcagc cgtcctccgt gtctaagtcc acgggccaga ctgtctccat cacctgctct     480
ggaagcagca gcaacgttgg gttacgtaat tatgtgacct ggttccaaca ggtcccagga     540
tcagccccca aactcctcat ctatggtgca accagtcgag cctcggggat ccccgaccga     600
ttctccggct ccaggtctgg caacacagcg actctgatca tcagctcgct ccaggctgag     660
gacgaggccg attattactg tgcatctgct gacaccaatg acggtggtgt tttcggcagc     720
gggaccaggc tgaccgtcct gggt                                        744

<210> SEQ ID NO 408
<211> LENGTH: 744
<212> TYPE: DNA
<213> ORGANISM: artificial sequence
<220> FEATURE:
<223> OTHER INFORMATION: 3aD3 nucleotide sequence

<400> SEQUENCE: 408
caggtgcagc tgcaggagtc gggacccagc ctggtgaagc cctcacagac cctctccctc      60
acctgcacgg tctctggatt ctcattaact agcaatggtg taggctgggt ccgccgggct     120
ccaggaaagg tgccggagtg ggttggtgat ataagcagtg gtggaaaagt atacgggcac     180
ccggccctga atcccggct cagcatcacc agggacacct ccaagagcca agtctccctg      240
tcagtgagca gcgtgacaag tgaggacacg gccgtgtact actgtgtaag atgcagggat     300
ggtggtgtga gttatggtta tgatagcgac tactggggc caggactcct ggtcaccgtc      360
tcctcagaag gtaaatcttc tggcgcgtct ggcgagtcta aagtggatga ccaggctgtg     420
gtgactcagc cgtcctccgt gtccaagtcc ctgggccaga gtgtctccat cacctgctct     480
ggaagcagca gcaacgttgg atatggtgat tatgtgggct ggttccaaca ggtcccagga     540
tcagccccca aactcctcat ctatggtgta accgagcgag cctcgggggt ccccgaccga     600
ttctccggct ccaggtctgg caacacagcg actctgacca tcagctcgat ccaggctgag     660
gacgaggccg attattactg tgcatcttat gacgacagta gcggtggtat tttcggcagc     720
gggaccaggc tgaccgtcct gggt                                        744

<210> SEQ ID NO 409
<211> LENGTH: 744
<212> TYPE: DNA
<213> ORGANISM: artificial sequence
```

```
<220> FEATURE:
<223> OTHER INFORMATION: 3aH6 nucleotide sequence

<400> SEQUENCE: 409
caggtgcagc tgcaggagtc gggacccagc ctggtgaagc cctcacagac cctctccctc      60
acctgcacgg tctctggatt ctccttgagt agcaatggtg taggctgggt ccgccaggct     120
ccaggaaagg tgccggagtg gcttggtgat ataagcagtg ttggaaaaaa atacgctaac     180
ccggccctga aatctcggct cagcttcact agggacacct ccaagagcca agtgtccctg     240
tcactgagca gcgtgacaac tgaggacacg gccgtgtact attgtgtaaa atgcagggat     300
ggtggtgtga cttatggtta tgatatcgac tactggggcc aggactact ggtcaccgcc      360 tcctcagaag gtaaatcttc tggcgcgtct ggcgagtcta aagtggatga ccaggccgtg     420
gtgactcagc cgtcctccgt gtctgggtcc ctgggccaga gtgtctccat cacctgctcc     480
ggaagctccg gcaacgttgg ctatggcgat tatgtgagtt ggttccaaca attccacgga     540
tcggccccca aactcctcat ctatggtgca accaatcttg cctcgggagt tcccgcccga     600
ttctccggct ccaggtctgg caacacggcc acccttacta tcagctcgct ccacgctgag     660
gacgaggccg attactattg tgcatcttat gacagcagta gcggcggtgt gttcggcagc     720
gggaccaggc tgaccgtcct gggt                                            744

<210> SEQ ID NO 410
<211> LENGTH: 744
<212> TYPE: DNA
<213> ORGANISM: artificial sequence
<220> FEATURE:
<223> OTHER INFORMATION: 3aG3 nucleotide sequence

<400> SEQUENCE: 410
caggtgcagc tgcaggagtc gggacccagc ctggtgaagc cctcacagac cctctccctc      60
acctgcacgg tctctggatt ctcattaagt agtaatggtg taggctgggt ccgccaggct     120
ccaggaaagg tgccggagtg ggttggtgat ataagtagta gtggaaaagc atacgctaat     180
ccggccctga aatcccggct cagcatcacc agggacaccg ccaagaccca agtcttcctg     240
tcactgagca gcgtgacaac tgaggacacg gccgtgtact actgtgtaag atgcagggat     300
ggtggtgtaa gttatggtta tgatatcgac tactggggcc aggactcct ggtcaccgtc      360 tcctcagaag gtaaatcttc tggcgcgtct ggcgagtcta aagtggatga ccaggctgtg     420
ctgactcagc caccctccgt gtccgggtcc ccgggccaga gggtatccat tacctgctct     480
ggaagcagca gcaacatcgg gggtggtaat tatctgagct ggttccaaca ggtcccagga     540 tcagcccca aactcctcat ctatggtgca accagtcgag cctcgggggt ccccgaccga      600
ttctccggct ccagatctgg caacacagcg actctgacaa tcagctcgct ccaggctgag     660
gacgaggccg attattactg tgcatctttt gacaccagta gcggtggtat tttcggcgcc     720
gggaccaggc tgaccgtcct gggt                                            744

<210> SEQ ID NO 411
<211> LENGTH: 744
<212> TYPE: DNA
<213> ORGANISM: artificial sequence
<220> FEATURE:
<223> OTHER INFORMATION: 3bG4 nucleotide sequence

<400> SEQUENCE: 411
caggtgcagc ttcaggagtc gggacccagc ctggtgaagc cctcacagac cctctccctc      60
```

-continued

```
acctgcacaa tctctggatt ctcattaatc agcaatggtg taggctgggt ccgccaggct      120
ccaggaaagg tgccggagtg ggttggtgat attgctagta gtggaaaggc atacagtaac      180
ccggccctga atcccggct cagcatcacc agggacacct ccaagagcca agtctccctg       240
tcactgagga gcgtgacaac tgaggacacg gccgtgtact actgtgtaag atgcagggat      300
ggtggtgtga cttatggtta tgatatcgac tactggggcc aggactcct ggtcaccgtc       360 tcctcagaag gtaaatcttc tggcgcgtct ggcgagtcta aagtggatga ccaggctgtg      420
ctgactcagc cgtcatccgt gtccaagtcc ctgggccaga gtgtctccat cacctgctcc      480
ggaagcacta gcaacgttgg aagtggtaat gatgtgagct ggttccaaca ggtcccagga      540
tcagccccca aactcctctt ctacggtgca accaaccgag cctcgggggt ccccgaccga      600
ttctccggct ccaggtctgg caacacagcg actctgacca tcacctcgct tcaggctgag      660
gacgaggccg attattactg tggatcttat gacagcaata cggtggtat tttcggcagt       720 gggaccaggc tgaccgtcct gggt                                            744
```

<210> SEQ ID NO 412
<211> LENGTH: 249
<212> TYPE: PRT
<213> ORGANISM: artificial sequence
<220> FEATURE:
<223> OTHER INFORMATION: S1B1 amino acid sequence

<400> SEQUENCE: 412

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Ser Ser Asn
            20                  25                  30

Ser Val Gly Trp Val Arg Gln Ala Pro Gly Lys Ala Pro Glu Trp Val
        35                  40                  45

Ala Gly Ile Asp Thr Asp Gly Glu Glu Gly Tyr Asn Pro Ala Leu Asn
    50                  55                  60

Ser Arg Leu Ser Ile Thr Arg Asp Thr Ser Lys Ser Gln Val Ser Leu
65                  70                  75                  80

Ser Leu Ser Ser Val Thr Ser Glu Asp Thr Ala Val Tyr Tyr Cys Val
                85                  90                  95

Arg Ser Tyr Arg Thr Asp Gly Leu Ala Tyr Gly Tyr Val Gln Ala Ile
            100                 105                 110

Asp Tyr Trp Gly Pro Gly Leu Leu Val Thr Val Ser Ser Glu Gly Lys
        115                 120                 125

Ser Ser Gly Ala Ser Gly Glu Ser Lys Val Asp Asp Gln Ala Val Leu
    130                 135                 140

Thr Gln Pro Ser Ser Val Ser Gly Ser Leu Gly Gln Arg Val Ser Ile
145                 150                 155                 160

Thr Cys Ser Gly Ser Phe Ile Gly Ile Ser Ser Val Gly Trp Phe Gln
                165                 170                 175

Gln Leu Pro Gly Ser Gly Leu Arg Thr Val Ile Val Ala Ser Asp Gly
            180                 185                 190

Arg Pro Ser Gly Val Pro Asp Arg Phe Ser Asn Ser Lys Ser Gly Asn
        195                 200                 205

Thr Ala Thr Leu Thr Ile Ser Ser Leu Gln Ala Glu Asp Glu Ala Asp
    210                 215                 220

Tyr Phe Cys Gly Ser Ser Asp Arg Thr Gln Tyr Thr Gly Val Phe Gly
225                 230                 235                 240
```

-continued

Ser Gly Thr Arg Leu Thr Val Leu Gly
            245

<210> SEQ ID NO 413
<211> LENGTH: 249
<212> TYPE: PRT
<213> ORGANISM: artificial sequence
<220> FEATURE:
<223> OTHER INFORMATION: S1D9 amino acid sequence

<400> SEQUENCE: 413

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Asn
            20                  25                  30

Ser Val Gly Trp Val Arg Gln Ala Pro Gly Lys Ala Pro Glu Trp Val
        35                  40                  45

Ala Gly Ile Asp Ser Asp Gly Glu Glu Gly Tyr Asn Pro Ala Leu Asn
    50                  55                  60

Ser Arg Leu Ser Ile Thr Arg Asp Thr Ser Lys Asn Gln Val Ser Leu
65                  70                  75                  80

Ser Leu Ser Arg Val Thr Ser Glu Asp Thr Ala Val Tyr Tyr Cys Gly
                85                  90                  95

Arg Thr Tyr Arg Thr Asp Gly Tyr Ala Tyr Gly Tyr Val Gln Ala Ile
            100                 105                 110

Asp Tyr Trp Gly Pro Gly Leu Leu Val Thr Val Ser Ser Glu Gly Lys
        115                 120                 125

Ser Ser Gly Ala Ser Gly Glu Ser Lys Val Asp Asp Arg Val Met Leu
    130                 135                 140

Thr Gln Pro Pro Ser Val Ser Gly Ser Pro Gly Gln Thr Val Ser Ile
145                 150                 155                 160

Thr Cys Ser Gly Ser Phe Ile Gly Ile Ser Ser Val Gly Trp Phe Gln
                165                 170                 175

Gln Leu Pro Gly Ser Gly Leu Arg Thr Val Ile Phe Ala Ser Asp Gly
            180                 185                 190

Arg Pro Ser Gly Val Pro Asp Arg Phe Ser Asn Ser Lys Ser Gly Asn
        195                 200                 205

Thr Ala Thr Leu Thr Ile Ser Ser Leu Gln Ala Glu Asp Glu Ala Asp
    210                 215                 220

Tyr Phe Cys Gly Ser Ser Asp Arg Thr Gln Tyr Thr Gly Val Phe Gly
225                 230                 235                 240

Ser Gly Thr Arg Leu Thr Val Leu Ser
            245

<210> SEQ ID NO 414
<211> LENGTH: 249
<212> TYPE: PRT
<213> ORGANISM: artificial sequence
<220> FEATURE:
<223> OTHER INFORMATION: S1F4 amino acid sequence

<400> SEQUENCE: 414

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Ser Ser Asn
            20                  25                  30

Ser Val Gly Trp Val Arg Gln Ala Pro Gly Lys Ala Pro Glu Trp Val
        35                  40                  45

-continued

```
Ala Gly Ile Asp Thr Asp Gly Glu Glu Gly Tyr Asn Pro Ala Leu Asn
    50              55              60

Ser Arg Leu Ser Ile Thr Arg Asp Thr Ser Lys Ser Gln Val Ser Leu
65              70              75              80

Ser Leu Ser Ser Val Thr Ser Glu Asp Thr Ala Val Tyr Tyr Cys Val
                85              90              95

Arg Ser Tyr Arg Ala Asp Gly Leu Ala Tyr Gly Tyr Val Gln Ala Ile
            100             105             110

Asp Tyr Trp Gly Pro Gly Leu Leu Leu Thr Ile Ser Ser Glu Gly Lys
        115             120             125

Ser Ser Gly Ala Ser Gly Glu Ser Lys Val Asp Asp Gln Ala Val Val
    130             135             140

Thr Gln Pro Ser Ser Val Ser Gly Ser Leu Gly Gln Arg Val Ser Ile
145             150             155             160

Thr Cys Ser Gly Ser Phe Ile Gly Ile Ser Ser Val Gly Trp Phe Gln
            165             170             175

Gln Leu Pro Gly Ser Gly Leu Arg Thr Val Ile Val Ala Ser Asp Gly
        180             185             190

Arg Pro Ser Gly Val Pro Asp Arg Phe Ser Asn Ser Lys Ser Gly Asn
    195             200             205

Thr Ala Thr Leu Thr Ile Ser Ser Leu Gln Ala Glu Asp Glu Ala Asp
    210             215             220

Tyr Phe Cys Gly Ser Ser Asp Arg Thr Gln Tyr Thr Gly Val Phe Gly
225             230             235             240

Ser Gly Thr Arg Leu Thr Val Leu Gly
            245

<210> SEQ ID NO 415
<211> LENGTH: 249
<212> TYPE: PRT
<213> ORGANISM: artificial sequence
<220> FEATURE:
<223> OTHER INFORMATION: S1G10 amino acid sequence

<400> SEQUENCE: 415

Gln Val Gln Leu Gln Glu Ser Gly Pro Ser Leu Val Lys Pro Ser Gln
1               5               10              15

Thr Leu Ser Leu Thr Cys Thr Val Ser Gly Phe Ser Leu Thr Ser Asn
            20              25              30

Ser Val Gly Trp Val Arg Gln Ala Pro Gly Lys Ala Pro Glu Trp Val
        35              40              45

Ala Gly Ile Asp Thr Asp Gly Glu Glu Gly Tyr Asn Pro Ala Leu Asn
    50              55              60

Ser Arg Leu Ser Ile Thr Arg Asp Thr Ser Lys Ser Gln Val Ser Leu
65              70              75              80

Ser Leu Ser Ser Val Thr Ser Glu Asp Thr Ala Val Tyr Tyr Cys Gly
                85              90              95

Arg Ser Tyr Arg Ala Asp Gly Leu Ala Tyr Gly Tyr Val Gln Ala Ile
            100             105             110

Asp Tyr Trp Gly Pro Gly Leu Leu Val Thr Val Ser Ser Glu Gly Lys
        115             120             125

Ser Ser Gly Ala Ser Gly Glu Ser Lys Val Asp Asp Gln Ala Val Leu
    130             135             140

Thr Gln Pro Ser Ser Met Ser Gly Ser Leu Gly Gln Arg Val Ser Ile
145             150             155             160
```

-continued

```
Thr Cys Ser Gly Ser Phe Ile Gly Ile Ser Ser Val Gly Trp Phe Gln
            165             170             175

Gln Leu Pro Gly Ser Gly Leu Arg Thr Ile Ile Val Ala Ser Asp Gly
            180             185             190

Arg Pro Ser Gly Val Pro Asp Arg Phe Ser Met Ser Lys Ser Gly Asn
            195             200             205

Thr Ala Thr Leu Thr Ile Ser Ser Leu Gln Ala Glu Asp Glu Ala Asp
            210             215             220

Tyr Phe Cys Gly Ser Ser Asp Arg Thr Gln Tyr Thr Gly Val Phe Gly
225             230             235             240

Ser Gly Thr Arg Leu Thr Val Leu Gly
            245

<210> SEQ ID NO 416
<211> LENGTH: 250
<212> TYPE: PRT
<213> ORGANISM: artificial sequence
<220> FEATURE:
<223> OTHER INFORMATION: S2C6 amino acid sequence

<400> SEQUENCE: 416

Gln Val Gln Leu Gln Glu Ser Gly Pro Ser Leu Val Lys Pro Ser Gln
1               5               10              15

Thr Leu Ser Leu Thr Cys Thr Val Ser Gly Phe Ser Leu Ile Ser Asn
            20              25              30

Ser Val Gly Trp Val Arg Gln Ala Pro Gly Lys Ala Pro Glu Trp Val
            35              40              45

Ala Gly Ile Asp Thr Asp Gly Glu Glu Gly Tyr Asn Pro Ala Leu Lys
            50              55              60

Ser Gln Tyr Ala Ala Ser Asp Pro Asp Thr Ser Lys Ser Gln Val Ser
65              70              75              80

Leu Ser Leu Ser Ser Val Thr Ser Glu Asp Thr Ala Val Tyr Tyr Cys
            85              90              95

Gly Arg Thr Tyr Arg Thr Asp Gly Phe Ala Tyr Gly Tyr Val Gln Ala
            100             105             110

Ile Asp Tyr Trp Gly Pro Gly Leu Leu Leu Thr Ile Ser Ser Glu Gly
            115             120             125

Lys Ser Ser Gly Ala Ser Gly Glu Ser Lys Val Asp Asp Gln Ala Val
            130             135             140

Leu Thr Gln Pro Ser Ser Val Ser Gly Ser Leu Gly Gln Arg Val Ser
145             150             155             160

Ile Thr Cys Ser Gly Ser Phe Ile Gly Ile Ser Ser Val Gly Trp Phe
            165             170             175

Gln Gln Leu Pro Gly Ser Gly Leu Arg Thr Ile Ile Val Ala Ser Asp
            180             185             190

Gly Arg Pro Ser Gly Val Pro Asp Arg Phe Ser Met Ser Lys Ser Gly
            195             200             205

Asn Thr Ala Thr Leu Thr Ile Ser Ser Leu Gln Ala Glu Asp Glu Ala
            210             215             220

Asp Tyr Phe Cys Gly Ser Ser Asp Arg Thr Gln Tyr Thr Gly Val Phe
225             230             235             240

Gly Ser Gly Thr Arg Leu Thr Val Leu Gly
            245             250

<210> SEQ ID NO 417
```

<211> LENGTH: 242
<212> TYPE: PRT
<213> ORGANISM: artificial sequence
<220> FEATURE:
<223> OTHER INFORMATION: 412B9 amino acid sequence

<400> SEQUENCE: 417

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Val Ile Ser Asp
            20                  25                  30

Ser Val Ala Trp Val Arg Gln Ala Pro Gly Lys Val Pro Glu Trp Leu
        35                  40                  45

Gly Ala Ser Gly Ser Ser Gly Asn Lys Tyr Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ser Leu Ser Ser Val Thr Thr Glu Asp Thr Ala Val Tyr Tyr Cys Ala
                85                  90                  95

Arg Gly Ile Ile Ala Gly Val Asp Val Trp Gly Arg Gly Leu Leu Val
            100                 105                 110

Ser Val Ser Ser Glu Gly Lys Ser Ser Gly Ala Ser Gly Glu Ser Lys
        115                 120                 125

Val Asp Asp Gln Ala Val Leu Thr Gln Pro Ser Ser Val Ser Gly Ala
    130                 135                 140

Leu Gly Gln Arg Val Ser Ile Thr Cys Ser Gly Ser Ser Ser Asn Val
145                 150                 155                 160

Gly Tyr Gly Asp Tyr Val Gly Trp Tyr Gln Gln Val Pro Gly Ser Ala
                165                 170                 175

Pro Lys Leu Leu Ile Tyr Gly Ala Ala Ser Arg Ala Ser Gly Val Pro
            180                 185                 190

Asp Arg Phe Ser Gly Ser Arg Ser Gly Asn Thr Ala Thr Leu Thr Ile
            195                 200                 205

Ser Ser Leu Gln Ala Glu Asp Glu Ala Asp Tyr Tyr Cys Ala Ser Tyr
    210                 215                 220

Asp Ser Ser Asp Gly Gly Val Phe Gly Ser Gly Thr Arg Leu Thr Val
225                 230                 235                 240

Leu Gly
```

<210> SEQ ID NO 418
<211> LENGTH: 247
<212> TYPE: PRT
<213> ORGANISM: artificial sequence
<220> FEATURE:
<223> OTHER INFORMATION: 3aA6 amino acid sequence

<400> SEQUENCE: 418

```
Gln Val Arg Leu Gln Glu Ser Gly Ser Ser Leu Val Lys Pro Ser Gln
1               5                   10                  15

Thr Leu Ser Leu Val Cys Thr Val Ser Gly Phe Pro Leu Thr Ser Asn
            20                  25                  30

Ala Val Gly Trp Val Arg Gln Ala Pro Gly Lys Ala Pro Glu Trp Leu
        35                  40                  45

Gly Leu Ile Asp Ile Asp Gly Asp Thr Ala Tyr Asn Pro Ala Leu Glu
    50                  55                  60

Ser Arg Leu Ser Ile Thr Arg Asp Thr Ser Lys Ser Gln Val Ser Leu
65                  70                  75                  80
```

-continued

```
Ser Leu Ser Ser Val Ala Ile Glu Asp Thr Ala Val Tyr Tyr Cys Ala
                85                  90                  95

Arg His Tyr Asp Lys Trp Gly Tyr Ala Asp Ser Ile Asp Tyr Trp Gly
               100                 105                 110

Pro Gly Leu Leu Val Thr Val Ser Ser Glu Gly Lys Ser Ser Gly Ala
           115                 120                 125

Ser Gly Glu Ser Lys Val Asp Asp Gln Ala Leu Leu Thr Gln Pro Ser
    130                 135                 140

Ser Val Phe Gly Ser Leu Gly Gln Arg Val Ser Ile Thr Cys Ser Gly
145                 150                 155                 160

Ser Ser Ser Asn Val Gly Tyr Gly Asp Tyr Val Gly Trp Tyr Gln Gln
               165                 170                 175

Val Pro Gly Ser Ala Pro Lys Leu Leu Ile Tyr Asp Ala Thr Thr Arg
           180                 185                 190

Ala Ser Gly Val Pro Asp Arg Phe Ser Gly Ser Arg Ser Gly Asn Thr
           195                 200                 205

Ala Thr Leu Thr Ile Ser Ser Leu Gln Ala Glu Asp Glu Ala Asp Tyr
    210                 215                 220

Tyr Cys Ala Ser Tyr Gln Asn Glu Arg Ser Gly Val Phe Gly Ser Gly
225                 230                 235                 240

Thr Arg Leu Thr Val Leu Gly
               245
```

```
<210> SEQ ID NO 419
<211> LENGTH: 244
<212> TYPE: PRT
<213> ORGANISM: artificial sequence
<220> FEATURE:
<223> OTHER INFORMATION: 3aD6 amino acid sequence

<400> SEQUENCE: 419

Gln Val Gln Leu Gln Glu Ser Gly Pro Ser Leu Val Lys Pro Ser Gln
1               5                  10                  15

Thr Leu Ser Leu Thr Cys Thr Val Ser Gly Phe Ser Leu Thr Ser Asn
            20                  25                  30

Ala Val Ile Trp Val Arg Gln Ala Pro Gly Lys Ala Pro Glu Trp Val
           35                  40                  45

Ala Leu Ile Asp Val Asp Gly Asp Ala Ala Tyr Asp Pro Ala Leu Lys
    50                  55                  60

Ser Arg Leu Ser Ile Thr Arg Asp Thr Ser Lys Ser Gln Val Ser Leu
65                  70                  75                  80

Ser Leu Arg Ser Val Thr Thr Glu Asp Thr Ala Val Tyr Tyr Cys Ala
                85                  90                  95

Arg Asp Tyr Gly Ser Trp Gly Tyr Val Ser Asp Ile Asp Tyr Trp Gly
               100                 105                 110

Pro Gly Leu Leu Val Thr Val Ser Ser Glu Gly Lys Ser Ser Gly Ala
           115                 120                 125

Ser Gly Glu Ser Lys Val Asp Asp Gln Ala Val Leu Thr Gln Pro Ser
    130                 135                 140

Ser Val Ser Gly Ser Leu Gly Gln Arg Val Ser Ile Thr Cys Ser Gly
145                 150                 155                 160

Ser Asp Ile Gly Gly Ala Asp Val Gly Trp Phe Gln Gln Val Pro Gly
               165                 170                 175

Ser Gly Leu Arg Thr Leu Ile Tyr Asp Asn Asp Asn Arg Pro Ser Gly
           180                 185                 190
```

```
Val Pro Asp Arg Phe Ser Gly Ser Lys Ser Gly Asn Thr Ala Thr Leu
        195             200             205

Thr Ile Ser Ser Leu Gln Pro Glu Asp Glu Ala Asp Tyr Phe Cys Gly
        210             215             220

Thr Tyr Ser Gly Ala Asn Tyr Gly Ile Phe Gly Ser Gly Thr Arg Leu
225             230             235             240

Thr Val Leu Gly

<210> SEQ ID NO 420
<211> LENGTH: 248
<212> TYPE: PRT
<213> ORGANISM: artificial sequence
<220> FEATURE:
<223> OTHER INFORMATION: 3aB7 amino acid sequence

<400> SEQUENCE: 420

Gln Val Gln Leu Gln Glu Ser Gly Pro Ser Leu Val Lys Pro Ser Gln
1               5               10              15

Thr Leu Ser Leu Thr Cys Thr Val Ser Gly Phe Ser Leu Thr Ser Asn
        20              25              30

Gly Val Gly Trp Val Arg Gln Ala Pro Gly Lys Val Pro Glu Trp Val
        35              40              45

Gly Asp Lys Ser Ser Ala Gly Lys Thr Tyr Gly Asn Pro Ala Leu Lys
        50              55              60

Ser Arg Leu Ser Ile Thr Arg Asp Thr Ser Lys Ser Gln Val Ser Leu
65              70              75              80

Ser Leu Ser Ser Val Thr Thr Glu Asp Thr Ala Val Tyr Tyr Cys Val
                85              90              95

Arg Cys Arg Asp Gly Gly Val Thr Tyr Gly Tyr Asp Val Asp Tyr Trp
            100             105             110

Gly Pro Gly Leu Leu Val Thr Val Ser Ser Glu Gly Lys Ser Ser Gly
        115             120             125

Ala Ser Gly Glu Ser Lys Val Asp Asp Gln Ala Val Leu Thr Gln Pro
        130             135             140

Ser Ser Val Ser Lys Ser Leu Gly Gln Ser Val Ser Ile Thr Cys Ser
145             150             155             160

Gly Ser Ser Ser Asn Val Gly Tyr Gly Asp Val Val Ser Trp Phe Gln
            165             170             175

Gln Phe Pro Gly Ser Ala Pro Lys Leu Leu Ile Phe Gly Thr Thr Thr
            180             185             190

Arg Ala Ser Gly Val Pro Asp Arg Phe Ser Gly Ser Arg Ser Gly Asn
        195             200             205

Ala Ala Thr Leu Thr Ile Asn Ser Leu Gln Ala Glu Asp Glu Ala Asp
        210             215             220

Tyr Tyr Cys Ala Ser Phe Asp Ser Asp Ser Gly Gly Ile Ala Gly Ser
225             230             235             240

Gly Thr Arg Leu Thr Val Leu Gly
                245

<210> SEQ ID NO 421
<211> LENGTH: 248
<212> TYPE: PRT
<213> ORGANISM: artificial sequence
<220> FEATURE:
<223> OTHER INFORMATION: 3bF4 amino acid sequence

<400> SEQUENCE: 421
```

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Ser Ser Asn
            20                  25                  30

Gly Val Gly Trp Val Arg Gln Ala Pro Gly Lys Val Pro Glu Trp Leu
        35                  40                  45

Gly Asp Ile Ser Ser Val Gly Lys Lys Tyr Ala Asn Pro Ala Leu Lys
    50                  55                  60

Ser Arg Leu Ser Phe Thr Arg Asp Thr Ser Lys Ser Gln Val Ser Leu
65                  70                  75                  80

Ser Leu Ser Ser Val Thr Thr Glu Asp Thr Ala Val Tyr Tyr Cys Val
                85                  90                  95

Lys Cys Arg Asp Gly Gly Val Thr Tyr Gly Tyr Asp Ile Asp Tyr Trp
            100                 105                 110

Gly Pro Gly Leu Leu Val Thr Val Ser Ser Glu Gly Lys Ser Ser Gly
        115                 120                 125

Ala Ser Gly Glu Ser Lys Val Asp Asp Gln Ala Val Leu Thr Gln Pro
    130                 135                 140

Ser Ser Val Ser Lys Ser Thr Gly Gln Thr Val Ser Ile Thr Cys Ser
145                 150                 155                 160

Gly Ser Ser Ser Asn Val Gly Leu Arg Asn Tyr Val Thr Trp Phe Gln
                165                 170                 175

Gln Val Pro Gly Ser Ala Pro Lys Leu Leu Ile Tyr Gly Ala Thr Ser
            180                 185                 190

Arg Ala Ser Gly Ile Pro Asp Arg Phe Ser Gly Ser Arg Ser Gly Asn
            195                 200                 205

Thr Ala Thr Leu Ile Ile Ser Ser Leu Gln Ala Glu Asp Glu Ala Asp
    210                 215                 220

Tyr Tyr Cys Ala Ser Ala Asp Thr Asn Asp Gly Gly Val Phe Gly Ser
225                 230                 235                 240

Gly Thr Arg Leu Thr Val Leu Gly
                245
```

<210> SEQ ID NO 422
<211> LENGTH: 248
<212> TYPE: PRT
<213> ORGANISM: artificial sequence
<220> FEATURE:
<223> OTHER INFORMATION: 3aD3 amino acid sequence

<400> SEQUENCE: 422

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Asn
            20                  25                  30

Gly Val Gly Trp Val Arg Arg Ala Pro Gly Lys Val Pro Glu Trp Val
        35                  40                  45

Gly Asp Ile Ser Ser Gly Gly Lys Val Tyr Gly His Pro Ala Leu Lys
    50                  55                  60

Ser Arg Leu Ser Ile Thr Arg Asp Thr Ser Lys Ser Gln Val Ser Leu
65                  70                  75                  80

Ser Val Ser Ser Val Thr Ser Glu Asp Thr Ala Val Tyr Tyr Cys Val
                85                  90                  95

Arg Cys Arg Asp Gly Gly Val Ser Tyr Gly Tyr Asp Ser Asp Tyr Trp
            100                 105                 110
```

-continued

```
Gly Pro Gly Leu Leu Val Thr Val Ser Ser Glu Gly Lys Ser Ser Gly
        115                 120                 125

Ala Ser Gly Glu Ser Lys Val Asp Asp Gln Ala Val Val Thr Gln Pro
        130                 135                 140

Ser Ser Val Ser Lys Ser Leu Gly Gln Ser Val Ser Ile Thr Cys Ser
145                 150                 155                 160

Gly Ser Ser Ser Asn Val Gly Tyr Gly Asp Tyr Val Gly Trp Phe Gln
                165                 170                 175

Gln Val Pro Gly Ser Ala Pro Lys Leu Leu Ile Tyr Gly Val Thr Glu
                180                 185                 190

Arg Ala Ser Gly Val Pro Asp Arg Phe Ser Gly Ser Arg Ser Gly Asn
        195                 200                 205

Thr Ala Thr Leu Thr Ile Ser Ser Ile Gln Ala Glu Asp Glu Ala Asp
        210                 215                 220

Tyr Tyr Cys Ala Ser Tyr Asp Asp Ser Ser Gly Gly Ile Phe Gly Ser
225                 230                 235                 240

Gly Thr Arg Leu Thr Val Leu Gly
                245
```

<210> SEQ ID NO 423
<211> LENGTH: 248
<212> TYPE: PRT
<213> ORGANISM: artificial sequence
<220> FEATURE:
<223> OTHER INFORMATION: 3aH6 amino acid sequence

<400> SEQUENCE: 423

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Ser Ser Asn
                20                  25                  30

Gly Val Gly Trp Val Arg Gln Ala Pro Gly Lys Val Pro Glu Trp Leu
        35                  40                  45

Gly Asp Ile Ser Ser Val Gly Lys Lys Tyr Ala Asn Pro Ala Leu Lys
        50                  55                  60

Ser Arg Leu Ser Phe Thr Arg Asp Thr Ser Lys Ser Gln Val Ser Leu
65                  70                  75                  80

Ser Leu Ser Ser Val Thr Thr Glu Asp Thr Ala Val Tyr Tyr Cys Val
                85                  90                  95

Lys Cys Arg Asp Gly Gly Val Thr Tyr Gly Tyr Asp Ile Asp Tyr Trp
                100                 105                 110

Gly Pro Gly Leu Leu Val Thr Ala Ser Ser Glu Gly Lys Ser Ser Gly
        115                 120                 125

Ala Ser Gly Glu Ser Lys Val Asp Asp Gln Ala Val Val Thr Gln Pro
        130                 135                 140

Ser Ser Val Ser Gly Ser Leu Gly Gln Ser Val Ser Ile Thr Cys Ser
145                 150                 155                 160

Gly Ser Ser Gly Asn Val Gly Tyr Gly Asp Tyr Val Ser Trp Phe Gln
                165                 170                 175

Gln Phe His Gly Ser Ala Pro Lys Leu Leu Ile Tyr Gly Ala Thr Asn
                180                 185                 190

Leu Ala Ser Gly Val Pro Ala Arg Phe Ser Gly Ser Arg Ser Gly Asn
        195                 200                 205

Thr Ala Thr Leu Thr Ile Ser Ser Leu His Ala Glu Asp Glu Ala Asp
        210                 215                 220
```

-continued

```
Tyr Tyr Cys Ala Ser Tyr Asp Ser Ser Gly Gly Val Phe Gly Ser
225                 230                 235                 240

Gly Thr Arg Leu Thr Val Leu Gly
                245

<210> SEQ ID NO 424
<211> LENGTH: 248
<212> TYPE: PRT
<213> ORGANISM: artificial sequence
<220> FEATURE:
<223> OTHER INFORMATION: 3aG3 amino acid sequence

<400> SEQUENCE: 424

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Ser Ser Asn
            20                  25                  30

Gly Val Gly Trp Val Arg Gln Ala Pro Gly Lys Val Pro Glu Trp Val
        35                  40                  45

Gly Asp Ile Ser Ser Ser Gly Lys Ala Tyr Ala Asn Pro Ala Leu Lys
    50                  55                  60

Ser Arg Leu Ser Ile Thr Arg Asp Thr Ala Lys Thr Gln Val Phe Leu
65                  70                  75                  80

Ser Leu Ser Ser Val Thr Thr Glu Asp Thr Ala Val Tyr Tyr Cys Val
                85                  90                  95

Arg Cys Arg Asp Gly Gly Val Ser Tyr Gly Tyr Asp Ile Asp Tyr Trp
            100                 105                 110

Gly Pro Gly Leu Leu Val Thr Val Ser Ser Glu Gly Lys Ser Ser Gly
        115                 120                 125

Ala Ser Gly Glu Ser Lys Val Asp Asp Gln Ala Val Leu Thr Gln Pro
    130                 135                 140

Pro Ser Val Ser Gly Ser Pro Gly Gln Arg Val Ser Ile Thr Cys Ser
145                 150                 155                 160

Gly Ser Ser Ser Asn Ile Gly Gly Gly Asn Tyr Leu Ser Trp Phe Gln
                165                 170                 175

Gln Val Pro Gly Ser Ala Pro Lys Leu Leu Ile Tyr Gly Ala Thr Ser
            180                 185                 190

Arg Ala Ser Gly Val Pro Asp Arg Phe Ser Gly Ser Arg Ser Gly Asn
        195                 200                 205

Thr Ala Thr Leu Thr Ile Ser Ser Leu Gln Ala Glu Asp Glu Ala Asp
    210                 215                 220

Tyr Tyr Cys Ala Ser Phe Asp Thr Ser Ser Gly Gly Ile Phe Gly Ala
225                 230                 235                 240

Gly Thr Arg Leu Thr Val Leu Gly
                245

<210> SEQ ID NO 425
<211> LENGTH: 248
<212> TYPE: PRT
<213> ORGANISM: artificial sequence
<220> FEATURE:
<223> OTHER INFORMATION: 3bG4 amino acid sequence

<400> SEQUENCE: 425

Gln Val Gln Leu Gln Glu Ser Gly Pro Ser Leu Val Lys Pro Ser Gln
1               5                   10                  15

Thr Leu Ser Leu Thr Cys Thr Ile Ser Gly Phe Ser Leu Ile Ser Asn
```

-continued

```
            20              25              30

Gly Val Gly Trp Val Arg Gln Ala Pro Gly Lys Val Pro Glu Trp Val
        35                  40                  45

Gly Asp Ile Ala Ser Ser Gly Lys Ala Tyr Ser Asn Pro Ala Leu Lys
    50                  55                  60

Ser Arg Leu Ser Ile Thr Arg Asp Thr Ser Lys Ser Gln Val Ser Leu
65                  70                  75                  80

Ser Leu Arg Ser Val Thr Thr Glu Asp Thr Ala Val Tyr Tyr Cys Val
                85                  90                  95

Arg Cys Arg Asp Gly Gly Val Thr Tyr Gly Tyr Asp Ile Asp Tyr Trp
            100                 105                 110

Gly Pro Gly Leu Leu Val Thr Val Ser Ser Glu Gly Lys Ser Ser Gly
        115                 120                 125

Ala Ser Gly Glu Ser Lys Val Asp Asp Gln Ala Val Leu Thr Gln Pro
    130                 135                 140

Ser Ser Val Ser Lys Ser Leu Gly Gln Ser Val Ser Ile Thr Cys Ser
145                 150                 155                 160

Gly Ser Thr Ser Asn Val Gly Ser Gly Asn Asp Val Ser Trp Phe Gln
                165                 170                 175

Gln Val Pro Gly Ser Ala Pro Lys Leu Leu Phe Tyr Gly Ala Thr Asn
            180                 185                 190

Arg Ala Ser Gly Val Pro Asp Arg Phe Ser Gly Ser Arg Ser Gly Asn
        195                 200                 205

Thr Ala Thr Leu Thr Ile Thr Ser Leu Gln Ala Glu Asp Glu Ala Asp
    210                 215                 220

Tyr Tyr Cys Gly Ser Tyr Asp Ser Asn Ser Gly Gly Ile Phe Gly Ser
225                 230                 235                 240

Gly Thr Arg Leu Thr Val Leu Gly
                245
```

```
<210> SEQ ID NO 426
<211> LENGTH: 5
<212> TYPE: PRT
<213> ORGANISM: artificial sequence
<220> FEATURE:
<223> OTHER INFORMATION: 297-390 VHCDR1 alternative consensus sequence
<220> FEATURE:
<221> NAME/KEY: MISC_FEATURE
<222> LOCATION: (1)..(1)
<223> OTHER INFORMATION: S or T
<220> FEATURE:
<221> NAME/KEY: MISC_FEATURE
<222> LOCATION: (2)..(2)
<223> OTHER INFORMATION: N or H

<400> SEQUENCE: 426

Xaa Xaa Ser Val Gly
1               5

<210> SEQ ID NO 427
<211> LENGTH: 16
<212> TYPE: PRT
<213> ORGANISM: artificial sequence
<220> FEATURE:
<223> OTHER INFORMATION: 297-390 VHCDR2 alternative consensus sequence
<220> FEATURE:
<221> NAME/KEY: MISC_FEATURE
<222> LOCATION: (4)..(4)
<223> OTHER INFORMATION: T or S
<220> FEATURE:
<221> NAME/KEY: MISC_FEATURE
<222> LOCATION: (10)..(10)
```

```
<223> OTHER INFORMATION: Y or F
<220> FEATURE:
<221> NAME/KEY: MISC_FEATURE
<222> LOCATION: (13)..(13)
<223> OTHER INFORMATION: A or V
<220> FEATURE:
<221> NAME/KEY: MISC_FEATURE
<222> LOCATION: (15)..(15)
<223> OTHER INFORMATION: N or K

<400> SEQUENCE: 427

Gly Ile Asp Xaa Asp Gly Glu Glu Gly Xaa Asn Pro Xaa Leu Xaa Ser
1               5                   10                  15

<210> SEQ ID NO 428
<211> LENGTH: 15
<212> TYPE: PRT
<213> ORGANISM: artificial sequence
<220> FEATURE:
<223> OTHER INFORMATION: 297-390 VHCDR3 alternative consensus sequence
<220> FEATURE:
<221> NAME/KEY: MISC_FEATURE
<222> LOCATION: (1)..(1)
<223> OTHER INFORMATION: S or T
<220> FEATURE:
<221> NAME/KEY: MISC_FEATURE
<222> LOCATION: (4)..(4)
<223> OTHER INFORMATION: A or T or S
<220> FEATURE:
<221> NAME/KEY: MISC_FEATURE
<222> LOCATION: (7)..(7)
<223> OTHER INFORMATION: L or Y

<400> SEQUENCE: 428

Xaa Tyr Arg Xaa Asp Gly Xaa Gly Tyr Val Gln Ala Ile Asp Tyr
1               5                   10                  15

<210> SEQ ID NO 429
<211> LENGTH: 11
<212> TYPE: PRT
<213> ORGANISM: artificial sequence
<220> FEATURE:
<223> OTHER INFORMATION: 297-390 VLCDR1 alternative consensus sequence
<220> FEATURE:
<221> NAME/KEY: MISC_FEATURE
<222> LOCATION: (4)..(4)
<223> OTHER INFORMATION: F or Y
<220> FEATURE:
<221> NAME/KEY: MISC_FEATURE
<222> LOCATION: (7)..(7)
<223> OTHER INFORMATION: I or S
<220> FEATURE:
<221> NAME/KEY: MISC_FEATURE
<222> LOCATION: (9)..(9)
<223> OTHER INFORMATION: S or G

<400> SEQUENCE: 429

Ser Gly Ser Xaa Ile Gly Xaa Ser Xaa Val Gly
1               5                   10

<210> SEQ ID NO 430
<211> LENGTH: 6
<212> TYPE: PRT
<213> ORGANISM: artificial sequence
<220> FEATURE:
<223> OTHER INFORMATION: 430 hexapeptide

<400> SEQUENCE: 430

Val Gln Ile Val Tyr Lys
1               5
```

<210> SEQ ID NO 431
<211> LENGTH: 747
<212> TYPE: DNA
<213> ORGANISM: artificial sequence
<220> FEATURE:
<223> OTHER INFORMATION: NS2A1 nucleotide sequence

<400> SEQUENCE: 431
caggtgcagt tgcaggagtc gggacccagc ctcgtgaagc cctcacagac cctctccctc       60
acctgcacgg tctctggatt ctcattaagc actaattctg tgggctgggt ccgacaggct      120
ccaggaaagg cgccggagtg ggttgctggt atagatactg atggagaaga aggctttaat      180
ccagtcctta agtcccggct cagcatcacc agggacacct ccaagagtca agtctctttg      240
tcattgagca acgtgacaag tgaagacacg gccgtgtact actgtggaag aagttatagg      300
actgatggtc ttgcttacgg ttatgtccaa gccatcgact actggggccc aggactcctg      360
gtcactatct cctcagaagg taaatcttct ggcgcgtctg gcgagtctaa agtggatgac      420
cagtctgtgc tgactcagcc gtcctccgtg tccgggtccc cgggccagac agtctccatc      480
acctgctctg aagctatat cggtagtagt ggtgtaggct ggttccaaca gctcccagga      540
tcgggcctca gaaccatcat cgtggcgagt gacggtcgac cctcagggt ccccgacgga      600 ttctctatgt ccaaatcggg caacacagcc accctgacca tcagctcgct ccaggctgag      660
gacgaggccg attatttctg tggaagtagt gataggactc aatatactgg acttttcggc      720
agcgggacca ggctgaccgt cctgggt                                          747

<210> SEQ ID NO 432
<211> LENGTH: 11
<212> TYPE: PRT
<213> ORGANISM: artificial sequence
<220> FEATURE:
<223> OTHER INFORMATION: 297-390 VLCDR3 alternative consensus sequence
<220> FEATURE:
<221> NAME/KEY: MISC_FEATURE
<222> LOCATION: (11)..(11)
<223> OTHER INFORMATION: V or L

<400> SEQUENCE: 432

Gly Ser Ser Asp Arg Thr Gln Tyr Thr Gly Xaa
1               5                   10

<210> SEQ ID NO 433
<211> LENGTH: 112
<212> TYPE: PRT
<213> ORGANISM: artificial sequence
<220> FEATURE:
<223> OTHER INFORMATION: S1D12 antibody variable light chain

<400> SEQUENCE: 433

Gln Ala Val Leu Thr Gln Pro Ser Ser Val Ser Gly Ser Leu Gly Gln
1               5                   10                  15

Arg Val Ser Ile Thr Cys Ser Gly Ser Ser Ser Asn Val Gly Gly Gly
            20                  25                  30

Asn Ser Val Gly Trp Tyr Gln His Leu Pro Gly Ser Gly Leu Lys Thr
        35                  40                  45

Ile Ile Tyr Asp Thr Asn Ser Arg Pro Ser Gly Val Pro Asp Arg Phe
    50                  55                  60

Ser Gly Ser Arg Ser Gly Asn Thr Ala Thr Leu Thr Ile Asn Ser Leu
65                  70                  75                  80

Gln Ala Glu Asp Glu Gly Asp Tyr Tyr Cys Val Thr Gly Asp Ser Thr
                85                  90                  95

-continued

```
Thr His Asp Asp Leu Val Gly Ser Gly Thr Arg Leu Thr Val Leu Gly
            100                 105                 110

<210> SEQ ID NO 434
<211> LENGTH: 238
<212> TYPE: PRT
<213> ORGANISM: artificial sequence
<220> FEATURE:
<223> OTHER INFORMATION: 412G11 amino acid sequence

<400> SEQUENCE: 434

Gln Val Arg Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Tyr
            20                  25                  30

Ala Leu Gly Trp Val Arg Gln Ala Pro Gly Arg Ala Pro Glu Trp Ile
            35                  40                  45

Gly Asn Ile Trp Arg Gly Gly Arg Ile Glu Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ser Leu Ser Ser Val Thr Thr Glu Asp Thr Ala Val Tyr Tyr Cys Ser
                85                  90                  95

Arg Ser Gly Gly Asp Trp Gly Pro Gly Leu Leu Val Thr Val Ser Ser
            100                 105                 110

Glu Gly Lys Ser Ser Gly Ala Ser Gly Glu Ser Lys Val Asp Asp Gln
            115                 120                 125

Ala Val Leu Thr Gln Pro Ser Ser Val Ser Gly Ser Leu Gly Gln Arg
    130                 135                 140

Val Ser Ile Thr Cys Ser Gly Ser Ser Asn Val Gly Tyr Gly Asn
145                 150                 155                 160

Tyr Val Gly Trp Tyr Gln Gln Val Pro Gly Ser Ala Pro Lys Leu Leu
            165                 170                 175

Ile Tyr Gly Ala Thr Ser Arg Ala Ser Gly Val Pro Asp Arg Phe Ser
            180                 185                 190

Gly Ser Arg Ser Glu Asn Thr Ala Thr Leu Thr Ile Ser Ser Leu Gln
            195                 200                 205

Ala Glu Asp Glu Ala Asp Tyr Tyr Cys Ala Ser Tyr Asp Arg Ser Glu
    210                 215                 220

Ser Val Val Phe Gly Ser Gly Thr Arg Leu Thr Val Leu Gly
225                 230                 235

<210> SEQ ID NO 435
<211> LENGTH: 30
<212> TYPE: PRT
<213> ORGANISM: artificial sequence
<220> FEATURE:
<223> OTHER INFORMATION: S1D12 VHFR1

<400> SEQUENCE: 435

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Asn
            20                  25                  30

<210> SEQ ID NO 436
<211> LENGTH: 14
<212> TYPE: PRT
```

-continued

<213> ORGANISM: artificial sequence
<220> FEATURE:
<223> OTHER INFORMATION: S1D12 VHFR2

<400> SEQUENCE: 436

Trp Val Arg Gln Ala Pro Gly Lys Val Pro Glu Ser Leu Val
1               5                   10

<210> SEQ ID NO 437
<211> LENGTH: 32
<212> TYPE: PRT
<213> ORGANISM: artificial sequence
<220> FEATURE:
<223> OTHER INFORMATION: S1D12 VHFR3

<400> SEQUENCE: 437

Arg Leu Asp Ile Thr Arg Asp Thr Ser Lys Asn Gln Ile Ser Leu Ser
1               5                   10                  15

Leu Ser Ser Val Thr Thr Asp Asp Ala Ala Val Tyr Tyr Cys Thr Arg
            20                  25                  30

<210> SEQ ID NO 438
<211> LENGTH: 11
<212> TYPE: PRT
<213> ORGANISM: artificial sequence
<220> FEATURE:
<223> OTHER INFORMATION: S1D12 VHFR4

<400> SEQUENCE: 438

Trp Gly Pro Gly Leu Leu Val Thr Val Ser Ser
1               5                   10

<210> SEQ ID NO 439
<211> LENGTH: 22
<212> TYPE: PRT
<213> ORGANISM: artificial sequence
<220> FEATURE:
<223> OTHER INFORMATION: S1D12 VLFR1

<400> SEQUENCE: 439

Gln Ala Val Leu Thr Gln Pro Ser Ser Val Ser Gly Ser Leu Gly Gln
1               5                   10                  15

Arg Val Ser Ile Thr Cys
            20

<210> SEQ ID NO 440
<211> LENGTH: 15
<212> TYPE: PRT
<213> ORGANISM: artificial sequence
<220> FEATURE:
<223> OTHER INFORMATION: S1D12 VLFR2

<400> SEQUENCE: 440

Trp Tyr Gln His Leu Pro Gly Ser Gly Leu Lys Thr Ile Ile Tyr
1               5                   10                  15

<210> SEQ ID NO 441
<211> LENGTH: 32
<212> TYPE: PRT
<213> ORGANISM: artificial sequence
<220> FEATURE:
<223> OTHER INFORMATION: S1D12 VLFR3

<400> SEQUENCE: 441

Gly Val Pro Asp Arg Phe Ser Gly Ser Arg Ser Gly Asn Thr Ala Thr
1               5                   10                  15

-continued

```
Leu Thr Ile Asn Ser Leu Gln Ala Glu Asp Glu Gly Asp Tyr Tyr Cys
            20                  25                  30

<210> SEQ ID NO 442
<211> LENGTH: 11
<212> TYPE: PRT
<213> ORGANISM: artificial sequence
<220> FEATURE:
<223> OTHER INFORMATION: S1D12 VLFR4

<400> SEQUENCE: 442

Val Gly Ser Gly Thr Arg Leu Thr Val Leu Gly
1               5                   10

<210> SEQ ID NO 443
<211> LENGTH: 124
<212> TYPE: PRT
<213> ORGANISM: artificial sequence
<220> FEATURE:
<223> OTHER INFORMATION: S1D12 VH Domain

<400> SEQUENCE: 443

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Asn Asn Asn
            20                  25                  30

Ala Val Gly Trp Val Arg Gln Ala Pro Gly Lys Val Pro Glu Ser Leu
        35                  40                  45

Val Gly Cys Ser Ser Asp Gly Thr Cys Tyr Tyr Asn Ser Ala Leu Lys
    50                  55                  60

Ser Arg Leu Asp Ile Thr Arg Asp Thr Ser Lys Asn Gln Ile Ser Leu
65                  70                  75                  80

Ser Leu Ser Ser Val Thr Thr Asp Asp Ala Ala Val Tyr Tyr Cys Thr
                85                  90                  95

Arg Gly His Tyr Ser Ile Tyr Gly Tyr Asp Tyr Leu Gly Thr Ile Asp
            100                 105                 110

Tyr Trp Gly Pro Gly Leu Leu Val Thr Val Ser Ser
        115                 120

<210> SEQ ID NO 444
<211> LENGTH: 112
<212> TYPE: PRT
<213> ORGANISM: artificial sequence
<220> FEATURE:
<223> OTHER INFORMATION: S1D12 VL Domain

<400> SEQUENCE: 444

Gln Ala Val Leu Thr Gln Pro Ser Ser Val Ser Gly Ser Leu Gly Gln
1               5                   10                  15

Arg Val Ser Ile Thr Cys Ser Gly Ser Ser Ser Asn Val Gly Gly Gly
            20                  25                  30

Asn Ser Val Gly Trp Tyr Gln His Leu Pro Gly Ser Gly Leu Lys Thr
            35                  40                  45

Ile Ile Tyr Asp Thr Asn Ser Arg Pro Ser Gly Val Pro Asp Arg Phe
    50                  55                  60

Ser Gly Ser Arg Ser Gly Asn Thr Ala Thr Leu Thr Ile Asn Ser Leu
65                  70                  75                  80

Gln Ala Glu Asp Glu Gly Asp Tyr Tyr Cys Val Thr Gly Asp Ser Thr
                85                  90                  95
```

```
Thr His Asp Asp Leu Val Gly Ser Gly Thr Arg Leu Thr Val Leu Gly
        100                 105                 110

<210> SEQ ID NO 445
<211> LENGTH: 454
<212> TYPE: PRT
<213> ORGANISM: artificial sequence
<220> FEATURE:
<223> OTHER INFORMATION: S1D12 mAB Heavy Chain

<400> SEQUENCE: 445

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Asn Asn Asn
        20                  25                  30

Ala Val Gly Trp Val Arg Gln Ala Pro Gly Lys Val Pro Glu Ser Leu
        35                  40                  45

Val Gly Cys Ser Ser Asp Gly Thr Cys Tyr Tyr Asn Ser Ala Leu Lys
    50                  55                  60

Ser Arg Leu Asp Ile Thr Arg Asp Thr Ser Lys Asn Gln Ile Ser Leu
65                  70                  75                  80

Ser Leu Ser Ser Val Thr Thr Asp Asp Ala Ala Val Tyr Tyr Cys Thr
                85                  90                  95

Arg Gly His Tyr Ser Ile Tyr Gly Tyr Asp Tyr Leu Gly Thr Ile Asp
            100                 105                 110

Tyr Trp Gly Pro Gly Leu Leu Val Thr Val Ser Ser Ala Lys Thr Thr
        115                 120                 125

Ala Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg
    210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Ile Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ala Pro Ile Glu Arg Thr Ile Ser Lys Pro Lys Gly Ser Val Arg Ala
            340                 345                 350
```

-continued

```
Pro Gln Val Tyr Val Leu Pro Pro Pro Glu Glu Glu Met Thr Lys Lys
        355             360             365

Gln Val Thr Leu Thr Cys Met Val Thr Asp Phe Met Pro Glu Asp Ile
    370             375             380

Tyr Val Glu Trp Thr Asn Asn Gly Lys Thr Glu Leu Asn Tyr Lys Asn
385             390             395             400

Thr Glu Pro Val Leu Asp Ser Asp Gly Ser Tyr Phe Met Tyr Ser Lys
            405             410             415

Leu Arg Val Glu Lys Lys Asn Trp Val Glu Arg Asn Ser Tyr Ser Cys
            420             425             430

Ser Val Val His Glu Gly Leu His Asn His His Thr Thr Lys Ser Phe
            435             440             445

Ser Arg Thr Pro Gly Lys
    450
```

```
<210> SEQ ID NO 446
<211> LENGTH: 218
<212> TYPE: PRT
<213> ORGANISM: artificial sequence
<220> FEATURE:
<223> OTHER INFORMATION: S1D12 mAB Light Chain

<400> SEQUENCE: 446
```

```
Gln Ala Val Leu Thr Gln Pro Ser Ser Val Ser Gly Ser Leu Gly Gln
1               5               10              15

Arg Val Ser Ile Thr Cys Ser Gly Ser Ser Ser Asn Val Gly Gly Gly
            20              25              30

Asn Ser Val Gly Trp Tyr Gln His Leu Pro Gly Ser Gly Leu Lys Thr
        35              40              45

Ile Ile Tyr Asp Thr Asn Ser Arg Pro Ser Gly Val Pro Asp Arg Phe
    50              55              60

Ser Gly Ser Arg Ser Gly Asn Thr Ala Thr Leu Thr Ile Asn Ser Leu
65              70              75              80

Gln Ala Glu Asp Glu Gly Asp Tyr Tyr Cys Val Thr Gly Asp Ser Thr
            85              90              95

Thr His Asp Asp Leu Val Gly Ser Gly Thr Arg Leu Thr Val Leu Gly
            100             105             110

Gly Gln Pro Lys Ser Ser Pro Ser Val Thr Leu Phe Pro Pro Ser Ser
            115             120             125

Glu Glu Leu Glu Thr Asn Lys Ala Thr Leu Val Cys Thr Ile Thr Asp
    130             135             140

Phe Tyr Pro Gly Val Val Thr Val Asp Trp Lys Val Asp Gly Thr Pro
145             150             155             160

Val Thr Gln Gly Met Glu Thr Thr Gln Pro Ser Lys Gln Ser Asn Asn
            165             170             175

Lys Tyr Met Ala Ser Ser Tyr Leu Thr Leu Thr Ala Arg Ala Trp Glu
            180             185             190

Arg His Ser Ser Tyr Ser Cys Gln Val Thr His Glu Gly His Thr Val
            195             200             205

Glu Lys Ser Leu Ser Arg Ala Asp Cys Ser
    210             215
```

```
<210> SEQ ID NO 447
<211> LENGTH: 30
<212> TYPE: PRT
<213> ORGANISM: artificial sequence
<220> FEATURE:
```

-continued

<223> OTHER INFORMATION: S1G2 VHFR1

<400> SEQUENCE: 447

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr
            20                  25                  30
```

<210> SEQ ID NO 448
<211> LENGTH: 14
<212> TYPE: PRT
<213> ORGANISM: artificial sequence
<220> FEATURE:
<223> OTHER INFORMATION: S1G2 VHFR2

<400> SEQUENCE: 448

```
Trp Val Arg Gln Ala Pro Gly Lys Ala Pro Glu Trp Val Ala
1               5                   10
```

<210> SEQ ID NO 449
<211> LENGTH: 32
<212> TYPE: PRT
<213> ORGANISM: artificial sequence
<220> FEATURE:
<223> OTHER INFORMATION: S1G2 VHFR3

<400> SEQUENCE: 449

```
Arg Leu Ser Ile Thr Arg Asp Thr Ser Lys Ser Gln Val Ser Leu Ser
1               5                   10                  15

Leu Ser Ser Val Thr Ser Glu Asp Thr Ala Val Tyr Tyr Cys Gly Arg
            20                  25                  30
```

<210> SEQ ID NO 450
<211> LENGTH: 11
<212> TYPE: PRT
<213> ORGANISM: artificial sequence
<220> FEATURE:
<223> OTHER INFORMATION: S1G2 VHFR4

<400> SEQUENCE: 450

```
Trp Gly Pro Gly Leu Leu Val Thr Val Ser Ser
1               5                   10
```

<210> SEQ ID NO 451
<211> LENGTH: 22
<212> TYPE: PRT
<213> ORGANISM: artificial sequence
<220> FEATURE:
<223> OTHER INFORMATION: S1G2 VLFR1

<400> SEQUENCE: 451

```
Gln Ala Val Val Thr Gln Pro Ser Ser Val Ser Gly Ser Leu Gly Gln
1               5                   10                  15

Arg Val Ser Ile Thr Cys
            20
```

<210> SEQ ID NO 452
<211> LENGTH: 15
<212> TYPE: PRT
<213> ORGANISM: artificial sequence
<220> FEATURE:
<223> OTHER INFORMATION: S1G2 VLFR2

<400> SEQUENCE: 452

```
Trp Phe Gln Gln Leu Pro Gly Ser Gly Leu Arg Thr Ile Ile Val
```

-continued

```
1              5              10             15
```

<210> SEQ ID NO 453
<211> LENGTH: 32
<212> TYPE: PRT
<213> ORGANISM: artificial sequence
<220> FEATURE:
<223> OTHER INFORMATION: S1G2 VLFR3

<400> SEQUENCE: 453

```
Gly Val Pro Asp Arg Phe Ser Met Ser Lys Ser Gly Asn Thr Ala Thr
1              5              10             15

Leu Thr Ile Ser Ser Leu Gln Ala Glu Asp Glu Ala Asp Tyr Phe Cys
            20             25             30
```

<210> SEQ ID NO 454
<211> LENGTH: 11
<212> TYPE: PRT
<213> ORGANISM: artificial sequence
<220> FEATURE:
<223> OTHER INFORMATION: S1G2 VLFR4

<400> SEQUENCE: 454

```
Phe Gly Ser Gly Thr Arg Leu Thr Val Leu Gly
1              5              10
```

<210> SEQ ID NO 455
<211> LENGTH: 125
<212> TYPE: PRT
<213> ORGANISM: artificial sequence
<220> FEATURE:
<223> OTHER INFORMATION: S1G2 VH Domain

<400> SEQUENCE: 455

```
Gln Val Gln Leu Gln Glu Ser Gly Pro Ser Leu Val Lys Pro Ser Gln
1              5              10             15

Thr Leu Ser Leu Thr Cys Thr Val Ser Gly Phe Ser Leu Thr Ser Asn
            20             25             30

Ser Val Gly Trp Val Arg Gln Ala Pro Gly Lys Ala Pro Glu Trp Val
        35             40             45

Ala Gly Ile Asp Thr Asp Gly Glu Glu Gly Tyr Asn Pro Ala Leu Asn
    50             55             60

Ser Arg Leu Ser Ile Thr Arg Asp Thr Ser Lys Ser Gln Val Ser Leu
65             70             75             80

Ser Leu Ser Ser Val Thr Ser Glu Asp Thr Ala Val Tyr Tyr Cys Gly
            85             90             95

Arg Ser Tyr Arg Ala Asp Gly Leu Ala Tyr Gly Tyr Val Gln Ala Ile
            100            105            110

Asp Tyr Trp Gly Pro Gly Leu Leu Val Thr Val Ser Ser
        115            120            125
```

<210> SEQ ID NO 456
<211> LENGTH: 109
<212> TYPE: PRT
<213> ORGANISM: artificial sequence
<220> FEATURE:
<223> OTHER INFORMATION: S1G2 VL Domain

<400> SEQUENCE: 456

```
Gln Ala Val Val Thr Gln Pro Ser Ser Val Ser Gly Ser Leu Gly Gln
1              5              10             15

Arg Val Ser Ile Thr Cys Ser Gly Ser Phe Ile Gly Ile Ser Ser Val
```

-continued

```
              20              25              30

Gly Trp Phe Gln Gln Leu Pro Gly Ser Gly Leu Arg Thr Ile Ile Val
        35              40              45

Ala Ser Asp Gly Arg Pro Ser Gly Val Pro Asp Arg Phe Ser Met Ser
    50              55              60

Lys Ser Gly Asn Thr Ala Thr Leu Thr Ile Ser Ser Leu Gln Ala Glu
65              70              75              80

Asp Glu Ala Asp Tyr Phe Cys Gly Ser Ser Asp Arg Thr Pro Tyr Thr
                85              90              95

Gly Val Phe Gly Ser Gly Thr Arg Leu Thr Val Leu Gly
            100             105

<210> SEQ ID NO 457
<211> LENGTH: 455
<212> TYPE: PRT
<213> ORGANISM: artificial sequence
<220> FEATURE:
<223> OTHER INFORMATION: S1G2 mAB Heavy Chain

<400> SEQUENCE: 457

Gln Val Gln Leu Gln Glu Ser Gly Pro Ser Leu Val Lys Pro Ser Gln
1               5               10              15

Thr Leu Ser Leu Thr Cys Thr Val Ser Gly Phe Ser Leu Thr Ser Asn
            20              25              30

Ser Val Gly Trp Val Arg Gln Ala Pro Gly Lys Ala Pro Glu Trp Val
        35              40              45

Ala Gly Ile Asp Thr Asp Gly Glu Glu Gly Tyr Asn Pro Ala Leu Asn
    50              55              60

Ser Arg Leu Ser Ile Thr Arg Asp Thr Ser Lys Ser Gln Val Ser Leu
65              70              75              80

Ser Leu Ser Ser Val Thr Ser Glu Asp Thr Ala Val Tyr Tyr Cys Gly
                85              90              95

Arg Ser Tyr Arg Ala Asp Gly Leu Ala Tyr Gly Tyr Val Gln Ala Ile
            100             105             110

Asp Tyr Trp Gly Pro Gly Leu Leu Val Thr Val Ser Ser Ala Lys Thr
            115             120             125

Thr Ala Pro Ser Val Tyr Pro Leu Ala Pro Val Cys Gly Asp Thr Thr
    130             135             140

Gly Ser Ser Val Thr Leu Gly Cys Leu Val Lys Gly Tyr Phe Pro Glu
145             150             155             160

Pro Val Thr Leu Thr Trp Asn Ser Gly Ser Leu Ser Ser Gly Val His
            165             170             175

Thr Phe Pro Ala Val Leu Gln Ser Asp Leu Tyr Thr Leu Ser Ser Ser
            180             185             190

Val Thr Val Thr Ser Ser Thr Trp Pro Ser Gln Ser Ile Thr Cys Asn
            195             200             205

Val Ala His Pro Ala Ser Ser Thr Lys Val Asp Lys Lys Ile Glu Pro
    210             215             220

Arg Gly Pro Thr Ile Lys Pro Cys Pro Pro Cys Lys Cys Pro Ala Pro
225             230             235             240

Asn Leu Leu Gly Gly Pro Ser Val Phe Ile Phe Pro Pro Lys Ile Lys
                245             250             255

Asp Val Leu Met Ile Ser Leu Ser Pro Ile Val Thr Cys Val Val Val
            260             265             270

Asp Val Ser Glu Asp Asp Pro Asp Val Gln Ile Ser Trp Phe Val Asn
```

-continued

```
            275                 280                 285

Asn Val Glu Val His Thr Ala Gln Thr Gln Thr His Arg Glu Asp Tyr
    290                 295                 300

Asn Ser Thr Leu Arg Val Val Ser Ala Leu Pro Ile Gln His Gln Asp
305                 310                 315                 320

Trp Met Ser Gly Lys Glu Phe Lys Cys Lys Val Asn Asn Lys Asp Leu
                325                 330                 335

Pro Ala Pro Ile Glu Arg Thr Ile Ser Lys Pro Lys Gly Ser Val Arg
                340                 345                 350

Ala Pro Gln Val Tyr Val Leu Pro Pro Glu Glu Glu Met Thr Lys
                355                 360                 365

Lys Gln Val Thr Leu Thr Cys Met Val Thr Asp Phe Met Pro Glu Asp
    370                 375                 380

Ile Tyr Val Glu Trp Thr Asn Asn Gly Lys Thr Glu Leu Asn Tyr Lys
385                 390                 395                 400

Asn Thr Glu Pro Val Leu Asp Ser Asp Gly Ser Tyr Phe Met Tyr Ser
                405                 410                 415

Lys Leu Arg Val Glu Lys Lys Asn Trp Val Glu Arg Asn Ser Tyr Ser
                420                 425                 430

Cys Ser Val Val His Glu Gly Leu His Asn His His Thr Thr Lys Ser
                435                 440                 445

Phe Ser Arg Thr Pro Gly Lys
    450                 455
```

```
<210> SEQ ID NO 458
<211> LENGTH: 215
<212> TYPE: PRT
<213> ORGANISM: artificial sequence
<220> FEATURE:
<223> OTHER INFORMATION: S1G2 mAB Light Chain

<400> SEQUENCE: 458

Gln Ala Val Val Thr Gln Pro Ser Ser Val Ser Gly Ser Leu Gly Gln
1               5                   10                  15

Arg Val Ser Ile Thr Cys Ser Gly Ser Phe Ile Gly Ile Ser Ser Val
                20                  25                  30

Gly Trp Phe Gln Gln Leu Pro Gly Ser Gly Leu Arg Thr Ile Ile Val
                35                  40                  45

Ala Ser Asp Gly Arg Pro Ser Gly Val Pro Asp Arg Phe Ser Met Ser
    50                  55                  60

Lys Ser Gly Asn Thr Ala Thr Leu Thr Ile Ser Ser Leu Gln Ala Glu
65                  70                  75                  80

Asp Glu Ala Asp Tyr Phe Cys Gly Ser Ser Asp Arg Thr Pro Tyr Thr
                85                  90                  95

Gly Val Phe Gly Ser Gly Thr Arg Leu Thr Val Leu Gly Gly Gln Pro
                100                 105                 110

Lys Ser Ser Pro Ser Val Thr Leu Phe Pro Pro Ser Ser Glu Glu Leu
                115                 120                 125

Glu Thr Asn Lys Ala Thr Leu Val Cys Thr Ile Thr Asp Phe Tyr Pro
    130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
                165                 170                 175

Ala Ser Ser Tyr Leu Thr Leu Thr Ala Arg Ala Trp Glu Arg His Ser
```

-continued

```
            180                185                190
Ser Tyr Ser Cys Gln Val Thr His Glu Gly His Thr Val Glu Lys Ser
        195                200                205

Leu Ser Arg Ala Asp Cys Ser
    210                215

<210> SEQ ID NO 459
<211> LENGTH: 30
<212> TYPE: PRT
<213> ORGANISM: artificial sequence
<220> FEATURE:
<223> OTHER INFORMATION: 412E10 VHFR1

<400> SEQUENCE: 459

Gln Val Gln Leu Gln Glu Ser Gly Pro Ser Leu Val Lys Pro Ser Gln
1               5                  10                 15

Thr Leu Ser Leu Thr Cys Thr Val Ser Gly Phe Ser Val Ile
            20                 25                 30

<210> SEQ ID NO 460
<211> LENGTH: 14
<212> TYPE: PRT
<213> ORGANISM: artificial sequence
<220> FEATURE:
<223> OTHER INFORMATION: 412E10 VHFR2

<400> SEQUENCE: 460

Trp Val Arg Gln Ala Pro Gly Lys Val Pro Glu Trp Leu Gly
1               5                  10

<210> SEQ ID NO 461
<211> LENGTH: 32
<212> TYPE: PRT
<213> ORGANISM: artificial sequence
<220> FEATURE:
<223> OTHER INFORMATION: 412E10 VHFR3

<400> SEQUENCE: 461

Arg Leu Ser Ile Thr Arg Asp Thr Ser Lys Ser Gln Val Ser Leu Ser
1               5                  10                 15

Leu Ser Ser Val Thr Thr Glu Asp Thr Ala Val Tyr Tyr Cys Ala Arg
            20                 25                 30

<210> SEQ ID NO 462
<211> LENGTH: 11
<212> TYPE: PRT
<213> ORGANISM: artificial sequence
<220> FEATURE:
<223> OTHER INFORMATION: 412E10 VHFR4

<400> SEQUENCE: 462

Trp Gly Arg Gly Leu Leu Val Thr Val Ser Ser
1               5                  10

<210> SEQ ID NO 463
<211> LENGTH: 22
<212> TYPE: PRT
<213> ORGANISM: artificial sequence
<220> FEATURE:
<223> OTHER INFORMATION: 412E10 VLFR1

<400> SEQUENCE: 463

Gln Ala Val Leu Thr Gln Pro Ser Ser Val Ser Gly Ser Leu Gly Gln
1               5                  10                 15
```

-continued

```
Arg Val Ser Ile Thr Cys
        20

<210> SEQ ID NO 464
<211> LENGTH: 15
<212> TYPE: PRT
<213> ORGANISM: artificial sequence
<220> FEATURE:
<223> OTHER INFORMATION: 412E10 VLFR2

<400> SEQUENCE: 464

Trp Tyr Gln Gln Val Pro Gly Ser Ala Pro Lys Leu Leu Ile Tyr
1               5                   10                  15

<210> SEQ ID NO 465
<211> LENGTH: 32
<212> TYPE: PRT
<213> ORGANISM: artificial sequence
<220> FEATURE:
<223> OTHER INFORMATION: 412E10 VLFR3

<400> SEQUENCE: 465

Gly Val Pro Asp Arg Phe Ser Gly Ser Arg Ser Gly Asp Thr Ala Thr
1               5                   10                  15

Leu Thr Ile Thr Ser Leu Gln Ala Glu Asp Glu Ala Asp Tyr Tyr Cys
            20                  25                  30

<210> SEQ ID NO 466
<211> LENGTH: 11
<212> TYPE: PRT
<213> ORGANISM: artificial sequence
<220> FEATURE:
<223> OTHER INFORMATION: 412E10 VLFR4

<400> SEQUENCE: 466

Phe Gly Ser Gly Thr Arg Leu Thr Val Leu Gly
1               5                   10

<210> SEQ ID NO 467
<211> LENGTH: 116
<212> TYPE: PRT
<213> ORGANISM: artificial sequence
<220> FEATURE:
<223> OTHER INFORMATION: 412E10 VH Domain

<400> SEQUENCE: 467

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Val Ile Ser Asp
            20                  25                  30

Ser Val Ala Trp Val Arg Gln Ala Pro Gly Lys Val Pro Glu Trp Leu
        35                  40                  45

Gly Ala Ser Gly Ser Ser Gly Asn Lys Tyr Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ser Leu Ser Ser Val Thr Thr Glu Asp Thr Ala Val Tyr Tyr Cys Ala
                85                  90                  95

Arg Gly Ile Ile Ala Gly Val Asp Val Trp Gly Arg Gly Leu Leu Val
            100                 105                 110

Thr Val Ser Ser
        115
```

<210> SEQ ID NO 468
<211> LENGTH: 110
<212> TYPE: PRT
<213> ORGANISM: artificial sequence
<220> FEATURE:
<223> OTHER INFORMATION: 412E10 VL Domain

<400> SEQUENCE: 468

Gln Ala Val Leu Thr Gln Pro Ser Ser Val Ser Gly Ser Leu Gly Gln
1               5                   10                  15

Arg Val Ser Ile Thr Cys Ser Gly Ser Ser Asn Val Gly Tyr Gly
            20                  25                  30

Asn Tyr Val Gly Trp Tyr Gln Gln Val Pro Gly Ser Ala Pro Lys Leu
        35                  40                  45

Leu Ile Tyr Gly Thr Ala Ile Arg Ala Ser Gly Val Pro Asp Arg Phe
    50                  55                  60

Ser Gly Ser Arg Ser Gly Asp Thr Ala Thr Leu Thr Ile Thr Ser Leu
65                  70                  75                  80

Gln Ala Glu Asp Glu Ala Asp Tyr Tyr Cys Ala Ser Tyr Gln Ser Asn
                85                  90                  95

Tyr Ala Phe Phe Gly Ser Gly Thr Arg Leu Thr Val Leu Gly
            100                 105                 110

<210> SEQ ID NO 469
<211> LENGTH: 446
<212> TYPE: PRT
<213> ORGANISM: artificial sequence
<220> FEATURE:
<223> OTHER INFORMATION: 412E10 mAB Heavy Chain

<400> SEQUENCE: 469

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Val Ile Ser Asp
            20                  25                  30

Ser Val Ala Trp Val Arg Gln Ala Pro Gly Lys Val Pro Glu Trp Leu
        35                  40                  45

Gly Ala Ser Gly Ser Ser Gly Asn Lys Tyr Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ser Leu Ser Ser Val Thr Thr Glu Asp Thr Ala Val Tyr Tyr Cys Ala
                85                  90                  95

Arg Gly Ile Ile Ala Gly Val Asp Val Trp Gly Arg Gly Leu Leu Val
            100                 105                 110

Thr Val Ser Ser Ala Lys Thr Thr Ala Pro Ser Val Tyr Pro Leu Ala
            115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
            165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
            195                 200                 205

```
Val Asp Lys Lys Ile Glu Pro Arg Gly Pro Thr Ile Lys Pro Cys Pro
    210             215             220

Pro Cys Lys Cys Pro Ala Pro Asn Leu Leu Gly Gly Pro Ser Val Phe
225             230             235             240

Ile Phe Pro Pro Lys Ile Lys Asp Val Leu Met Ile Ser Leu Ser Pro
            245             250             255

Ile Val Thr Cys Val Val Val Asp Val Ser Glu Asp Asp Pro Asp Val
            260             265             270

Gln Ile Ser Trp Phe Val Asn Asn Val Glu Val His Thr Ala Gln Thr
    275             280             285

Gln Thr His Arg Glu Asp Tyr Asn Ser Thr Leu Arg Val Val Ser Ala
    290             295             300

Leu Pro Ile Gln His Gln Asp Trp Met Ser Gly Lys Glu Phe Lys Cys
305             310             315             320

Lys Val Asn Asn Lys Asp Leu Pro Ala Pro Ile Glu Arg Thr Ile Ser
            325             330             335

Lys Pro Lys Gly Ser Val Arg Ala Pro Gln Val Tyr Val Leu Pro Pro
            340             345             350

Pro Glu Glu Glu Met Thr Lys Lys Gln Val Thr Leu Thr Cys Met Val
    355             360             365

Thr Asp Phe Met Pro Glu Asp Ile Tyr Val Glu Trp Thr Asn Asn Gly
    370             375             380

Lys Thr Glu Leu Asn Tyr Lys Asn Thr Glu Pro Val Leu Asp Ser Asp
385             390             395             400

Gly Ser Tyr Phe Met Tyr Ser Lys Leu Arg Val Glu Lys Lys Asn Trp
            405             410             415

Val Glu Arg Asn Ser Tyr Ser Cys Ser Val Val His Glu Gly Leu His
            420             425             430

Asn His His Thr Thr Lys Ser Phe Ser Arg Thr Pro Gly Lys
        435             440             445
```

```
<210> SEQ ID NO 470
<211> LENGTH: 216
<212> TYPE: PRT
<213> ORGANISM: artificial sequence
<220> FEATURE:
<223> OTHER INFORMATION: 412E10 mAB Light Chain

<400> SEQUENCE: 470
```

```
Gln Ala Val Leu Thr Gln Pro Ser Ser Val Ser Gly Ser Leu Gly Gln
1               5               10              15

Arg Val Ser Ile Thr Cys Ser Gly Ser Ser Ser Asn Val Gly Tyr Gly
            20              25              30

Asn Tyr Val Gly Trp Tyr Gln Gln Val Pro Gly Ser Ala Pro Lys Leu
        35              40              45

Leu Ile Tyr Gly Thr Ala Ile Arg Ala Ser Gly Val Pro Asp Arg Phe
    50              55              60

Ser Gly Ser Arg Ser Gly Asp Thr Ala Thr Leu Thr Ile Thr Ser Leu
65              70              75              80

Gln Ala Glu Asp Glu Ala Asp Tyr Tyr Cys Ala Ser Tyr Gln Ser Asn
                85              90              95

Tyr Ala Phe Phe Gly Ser Gly Thr Arg Leu Thr Val Leu Gly Gly Gln
            100             105             110

Pro Lys Ser Ser Pro Ser Val Thr Leu Phe Pro Pro Ser Ser Glu Glu
        115             120             125
```

-continued

```
Leu Glu Thr Asn Lys Ala Thr Leu Val Cys Thr Ile Thr Asp Phe Tyr
    130                 135                 140

Pro Gly Val Val Thr Val Asp Trp Lys Val Asp Gly Thr Pro Val Thr
145                 150                 155                 160

Gln Gly Met Glu Thr Thr Gln Pro Ser Lys Gln Ser Asn Asn Lys Tyr
                165                 170                 175

Met Ala Ser Ser Tyr Leu Thr Leu Thr Ala Arg Ala Trp Glu Arg His
            180                 185                 190

Ser Ser Tyr Ser Cys Gln Val Thr His Glu Gly His Thr Val Glu Lys
        195                 200                 205

Ser Leu Ser Arg Ala Asp Cys Ser
    210                 215
```

```
<210> SEQ ID NO 471
<211> LENGTH: 30
<212> TYPE: PRT
<213> ORGANISM: artificial sequence
<220> FEATURE:
<223> OTHER INFORMATION: 3bG4 VHFR1

<400> SEQUENCE: 471

Gln Val Gln Leu Gln Glu Ser Gly Pro Ser Leu Val Lys Pro Ser Gln
1               5                   10                  15

Thr Leu Ser Leu Thr Cys Thr Ile Ser Gly Phe Ser Leu Ile
            20                  25                  30
```

```
<210> SEQ ID NO 472
<211> LENGTH: 14
<212> TYPE: PRT
<213> ORGANISM: artificial sequence
<220> FEATURE:
<223> OTHER INFORMATION: 3bG4 VHFR2

<400> SEQUENCE: 472

Trp Val Arg Gln Ala Pro Gly Lys Val Pro Glu Trp Val Gly
1               5                   10
```

```
<210> SEQ ID NO 473
<211> LENGTH: 32
<212> TYPE: PRT
<213> ORGANISM: artificial sequence
<220> FEATURE:
<223> OTHER INFORMATION: 3bG4 VHFR3

<400> SEQUENCE: 473

Arg Leu Ser Ile Thr Arg Asp Thr Ser Lys Ser Gln Val Ser Leu Ser
1               5                   10                  15

Leu Arg Ser Val Thr Thr Glu Asp Thr Ala Val Tyr Tyr Cys Val Arg
            20                  25                  30
```

```
<210> SEQ ID NO 474
<211> LENGTH: 11
<212> TYPE: PRT
<213> ORGANISM: artificial sequence
<220> FEATURE:
<223> OTHER INFORMATION: 3bG4 VHFR4

<400> SEQUENCE: 474

Trp Gly Pro Gly Leu Leu Val Thr Val Ser Ser
1               5                   10
```

```
<210> SEQ ID NO 475
```

-continued

```
<211> LENGTH: 22
<212> TYPE: PRT
<213> ORGANISM: artificial sequence
<220> FEATURE:
<223> OTHER INFORMATION: 3bG4 VLFR1

<400> SEQUENCE: 475

Gln Ala Val Leu Thr Gln Pro Ser Ser Val Ser Lys Ser Leu Gly Gln
1               5                   10                  15

Ser Val Ser Ile Thr Cys
            20

<210> SEQ ID NO 476
<211> LENGTH: 15
<212> TYPE: PRT
<213> ORGANISM: artificial sequence
<220> FEATURE:
<223> OTHER INFORMATION: 3bG4 VLFR2

<400> SEQUENCE: 476

Trp Phe Gln Gln Val Pro Gly Ser Ala Pro Lys Leu Leu Phe Tyr
1               5                   10                  15

<210> SEQ ID NO 477
<211> LENGTH: 32
<212> TYPE: PRT
<213> ORGANISM: artificial sequence
<220> FEATURE:
<223> OTHER INFORMATION: 3bG4 VLFR3

<400> SEQUENCE: 477

Gly Val Pro Asp Arg Phe Ser Gly Ser Arg Ser Gly Asn Thr Ala Thr
1               5                   10                  15

Leu Thr Ile Thr Ser Leu Gln Ala Glu Asp Glu Ala Asp Tyr Tyr Cys
            20                  25                  30

<210> SEQ ID NO 478
<211> LENGTH: 11
<212> TYPE: PRT
<213> ORGANISM: artificial sequence
<220> FEATURE:
<223> OTHER INFORMATION: 3bG4 VLFR4

<400> SEQUENCE: 478

Phe Gly Ser Gly Thr Arg Leu Thr Val Leu Gly
1               5                   10

<210> SEQ ID NO 479
<211> LENGTH: 122
<212> TYPE: PRT
<213> ORGANISM: artificial sequence
<220> FEATURE:
<223> OTHER INFORMATION: 3bG4 VH Domain

<400> SEQUENCE: 479

Gln Val Gln Leu Gln Glu Ser Gly Pro Ser Leu Val Lys Pro Ser Gln
1               5                   10                  15

Thr Leu Ser Leu Thr Cys Thr Ile Ser Gly Phe Ser Leu Ile Ser Asn
            20                  25                  30

Gly Val Gly Trp Val Arg Gln Ala Pro Gly Lys Val Pro Glu Trp Val
            35                  40                  45

Gly Asp Ile Ala Ser Ser Gly Lys Ala Tyr Ser Asn Pro Ala Leu Lys
        50                  55                  60

Ser Arg Leu Ser Ile Thr Arg Asp Thr Ser Lys Ser Gln Val Ser Leu
```

-continued

```
65                  70                  75                  80

Ser Leu Arg Ser Val Thr Thr Glu Asp Thr Ala Val Tyr Tyr Cys Val
                85                  90                  95

Arg Cys Arg Asp Gly Gly Val Thr Tyr Gly Tyr Asp Ile Asp Tyr Trp
            100                 105                 110

Gly Pro Gly Leu Leu Val Thr Val Ser Ser
        115                 120

<210> SEQ ID NO 480
<211> LENGTH: 111
<212> TYPE: PRT
<213> ORGANISM: artificial sequence
<220> FEATURE:
<223> OTHER INFORMATION: 3bG4 VL Domain

<400> SEQUENCE: 480

Gln Ala Val Leu Thr Gln Pro Ser Ser Val Ser Lys Ser Leu Gly Gln
1               5                   10                  15

Ser Val Ser Ile Thr Cys Ser Gly Ser Thr Ser Asn Val Gly Ser Gly
                20                  25                  30

Asn Asp Val Ser Trp Phe Gln Gln Val Pro Gly Ser Ala Pro Lys Leu
            35                  40                  45

Leu Phe Tyr Gly Ala Thr Asn Arg Ala Ser Gly Val Pro Asp Arg Phe
        50                  55                  60

Ser Gly Ser Arg Ser Gly Asn Thr Ala Thr Leu Thr Ile Thr Ser Leu
65                  70                  75                  80

Gln Ala Glu Asp Glu Ala Asp Tyr Tyr Cys Gly Ser Tyr Asp Ser Asn
                85                  90                  95

Ser Gly Gly Ile Phe Gly Ser Gly Thr Arg Leu Thr Val Leu Gly
            100                 105                 110

<210> SEQ ID NO 481
<211> LENGTH: 452
<212> TYPE: PRT
<213> ORGANISM: artificial sequence
<220> FEATURE:
<223> OTHER INFORMATION: 3bG4 mAB Heavy Chain

<400> SEQUENCE: 481

Gln Val Gln Leu Gln Glu Ser Gly Pro Ser Leu Val Lys Pro Ser Gln
1               5                   10                  15

Thr Leu Ser Leu Thr Cys Thr Ile Ser Gly Phe Ser Leu Ile Ser Asn
                20                  25                  30

Gly Val Gly Trp Val Arg Gln Ala Pro Gly Lys Val Pro Glu Trp Val
            35                  40                  45

Gly Asp Ile Ala Ser Ser Gly Lys Ala Tyr Ser Asn Pro Ala Leu Lys
        50                  55                  60

Ser Arg Leu Ser Ile Thr Arg Asp Thr Ser Lys Ser Gln Val Ser Leu
65                  70                  75                  80

Ser Leu Arg Ser Val Thr Thr Glu Asp Thr Ala Val Tyr Tyr Cys Val
                85                  90                  95

Arg Cys Arg Asp Gly Gly Val Thr Tyr Gly Tyr Asp Ile Asp Tyr Trp
            100                 105                 110

Gly Pro Gly Leu Leu Val Thr Val Ser Ser Ala Lys Thr Thr Ala Pro
        115                 120                 125

Ser Val Tyr Pro Leu Ala Pro Val Cys Gly Asp Thr Thr Gly Ser Ser
    130                 135                 140
```

-continued

```
Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
                180                 185                 190

Thr Ser Ser Thr Trp Pro Ser Gln Ser Ile Thr Cys Asn Val Ala His
        195                 200                 205

Pro Ala Ser Ser Thr Lys Val Asp Lys Lys Ile Glu Pro Arg Gly Pro
    210                 215                 220

Thr Ile Lys Pro Cys Pro Pro Cys Lys Cys Pro Ala Pro Asn Leu Leu
225                 230                 235                 240

Gly Gly Pro Ser Val Phe Ile Phe Pro Pro Lys Ile Lys Asp Val Leu
                245                 250                 255

Met Ile Ser Leu Ser Pro Ile Val Thr Cys Val Val Val Asp Val Ser
                260                 265                 270

Glu Asp Asp Pro Asp Val Gln Ile Ser Trp Phe Val Asn Asn Val Glu
        275                 280                 285

Val His Thr Ala Gln Thr Gln Thr His Arg Glu Asp Tyr Asn Ser Thr
    290                 295                 300

Leu Arg Val Val Ser Ala Leu Pro Ile Gln His Gln Asp Trp Met Ser
305                 310                 315                 320

Gly Lys Glu Phe Lys Cys Lys Val Asn Asn Lys Asp Leu Pro Ala Pro
                325                 330                 335

Ile Glu Arg Thr Ile Ser Lys Pro Lys Gly Ser Val Arg Ala Pro Gln
                340                 345                 350

Val Tyr Val Leu Pro Pro Pro Glu Glu Glu Met Thr Lys Lys Gln Val
        355                 360                 365

Thr Leu Thr Cys Met Val Thr Asp Phe Met Pro Glu Asp Ile Tyr Val
    370                 375                 380

Glu Trp Thr Asn Asn Gly Lys Thr Glu Leu Asn Tyr Lys Asn Thr Glu
385                 390                 395                 400

Pro Val Leu Asp Ser Asp Gly Ser Tyr Phe Met Tyr Ser Lys Leu Arg
                405                 410                 415

Val Glu Lys Lys Asn Trp Val Glu Arg Asn Ser Tyr Ser Cys Ser Val
        420                 425                 430

Val His Glu Gly Leu His Asn His His Thr Thr Lys Ser Phe Ser Arg
    435                 440                 445

Thr Pro Gly Lys
    450
```

```
<210> SEQ ID NO 482
<211> LENGTH: 217
<212> TYPE: PRT
<213> ORGANISM: artificial sequence
<220> FEATURE:
<223> OTHER INFORMATION: 3bG4 mAB Light Chain

<400> SEQUENCE: 482

Gln Ala Val Leu Thr Gln Pro Ser Ser Val Ser Lys Ser Leu Gly Gln
1                   5                   10                  15

Ser Val Ser Ile Thr Cys Ser Gly Ser Thr Ser Asn Val Gly Ser Gly
                20                  25                  30

Asn Asp Val Ser Trp Phe Gln Gln Val Pro Gly Ser Ala Pro Lys Leu
            35                  40                  45
```

-continued

---

```
Leu Phe Tyr Gly Ala Thr Asn Arg Ala Ser Gly Val Pro Asp Arg Phe
    50                  55                  60

Ser Gly Ser Arg Ser Gly Asn Thr Ala Thr Leu Thr Ile Thr Ser Leu
65                  70                  75                  80

Gln Ala Glu Asp Glu Ala Asp Tyr Tyr Cys Gly Ser Tyr Asp Ser Asn
                85                  90                  95

Ser Gly Gly Ile Phe Gly Ser Gly Thr Arg Leu Thr Val Leu Gly Gly
                100                 105                 110

Gln Pro Lys Ser Ser Pro Ser Val Thr Leu Phe Pro Pro Ser Ser Glu
                115                 120                 125

Glu Leu Glu Thr Asn Lys Ala Thr Leu Val Cys Thr Ile Thr Asp Phe
    130                 135                 140

Tyr Pro Gly Val Val Thr Val Asp Trp Lys Val Asp Gly Thr Pro Val
145                 150                 155                 160

Thr Gln Gly Met Glu Thr Thr Gln Pro Ser Lys Gln Ser Asn Asn Lys
                165                 170                 175

Tyr Met Ala Ser Ser Tyr Leu Thr Leu Thr Ala Arg Ala Trp Glu Arg
                180                 185                 190

His Ser Ser Tyr Ser Cys Gln Val Thr His Glu Gly His Thr Val Glu
                195                 200                 205

Lys Ser Leu Ser Arg Ala Asp Cys Ser
    210                 215
```

```
<210> SEQ ID NO 483
<211> LENGTH: 30
<212> TYPE: PRT
<213> ORGANISM: artificial sequence
<220> FEATURE:
<223> OTHER INFORMATION: E2E8 VHFR1

<400> SEQUENCE: 483

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr
                20                  25                  30
```

```
<210> SEQ ID NO 484
<211> LENGTH: 14
<212> TYPE: PRT
<213> ORGANISM: artificial sequence
<220> FEATURE:
<223> OTHER INFORMATION: E2E8 VHFR2

<400> SEQUENCE: 484

Trp Val Arg Gln Ala Pro Gly Lys Ala Leu Glu Trp Val Gly
1               5                   10
```

```
<210> SEQ ID NO 485
<211> LENGTH: 32
<212> TYPE: PRT
<213> ORGANISM: artificial sequence
<220> FEATURE:
<223> OTHER INFORMATION: E2E8 VHFR3

<400> SEQUENCE: 485

Arg Leu Ser Ile Thr Arg Asp Thr Ser Lys Ser Gln Val Phe Leu Ser
1               5                   10                  15

Leu Ser Ser Val Thr Thr Glu Asp Met Ala Met Tyr Tyr Cys Ala Arg
                20                  25                  30
```

```
<210> SEQ ID NO 486
<211> LENGTH: 11
<212> TYPE: PRT
<213> ORGANISM: artificial sequence
<220> FEATURE:
<223> OTHER INFORMATION: E2E8 VHFR4

<400> SEQUENCE: 486

Trp Gly Arg Gly Leu Leu Val Thr Val Ser Ser
1               5                   10

<210> SEQ ID NO 487
<211> LENGTH: 22
<212> TYPE: PRT
<213> ORGANISM: artificial sequence
<220> FEATURE:
<223> OTHER INFORMATION: E2E8 VLFR1

<400> SEQUENCE: 487

Gln Ala Val Leu Thr Gln Pro Ser Ser Val Ser Lys Ser Leu Gly Gln
1               5                   10                  15

Ser Val Ser Ile Ala Cys
            20

<210> SEQ ID NO 488
<211> LENGTH: 15
<212> TYPE: PRT
<213> ORGANISM: artificial sequence
<220> FEATURE:
<223> OTHER INFORMATION: E2E8 VLFR2

<400> SEQUENCE: 488

Trp Phe Gln Gln Ile Pro Gly Ser Ala Pro Lys Leu Leu Ile Tyr
1               5                   10                  15

<210> SEQ ID NO 489
<211> LENGTH: 32
<212> TYPE: PRT
<213> ORGANISM: artificial sequence
<220> FEATURE:
<223> OTHER INFORMATION: E2E8 VLFR3

<400> SEQUENCE: 489

Gly Val Pro Asp Arg Phe Ser Gly Ala Arg Ser Gly Asn Thr Ala Thr
1               5                   10                  15

Leu Thr Ile Asn Ser Leu Gln Ala Glu Asp Glu Ala Asp Tyr Tyr Cys
            20                  25                  30

<210> SEQ ID NO 490
<211> LENGTH: 11
<212> TYPE: PRT
<213> ORGANISM: artificial sequence
<220> FEATURE:
<223> OTHER INFORMATION: E2E8 VLFR4

<400> SEQUENCE: 490

Phe Gly Ser Gly Thr Arg Leu Thr Val Leu Gly
1               5                   10

<210> SEQ ID NO 491
<211> LENGTH: 117
<212> TYPE: PRT
<213> ORGANISM: artificial sequence
<220> FEATURE:
<223> OTHER INFORMATION: E2E8 VH Domain

<400> SEQUENCE: 491
```

-continued

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Asp Arg
            20                  25                  30

Gly Val Ala Trp Val Arg Gln Ala Pro Gly Lys Ala Leu Glu Trp Val
            35                  40                  45

Gly Thr Met Arg Ser Gly Gly Thr Ile Asp Tyr Asn Pro Ala Leu Lys
    50                  55                  60

Ser Arg Leu Ser Ile Thr Arg Asp Thr Ser Lys Ser Gln Val Phe Leu
65              70                  75                  80

Ser Leu Ser Ser Val Thr Thr Glu Asp Met Ala Met Tyr Tyr Cys Ala
            85                  90                  95

Arg Gly Tyr Leu Ser Gly Asp Arg Tyr Ala Trp Gly Arg Gly Leu Leu
            100                 105                 110

Val Thr Val Ser Ser
        115
```

<210> SEQ ID NO 492
<211> LENGTH: 111
<212> TYPE: PRT
<213> ORGANISM: artificial sequence
<220> FEATURE:
<223> OTHER INFORMATION: E2E8 VL Domain

<400> SEQUENCE: 492

```
Gln Ala Val Leu Thr Gln Pro Ser Ser Val Ser Lys Ser Leu Gly Gln
1               5                   10                  15

Ser Val Ser Ile Ala Cys Ser Gly Ser Arg Ser Asp Ile Gly Tyr Gly
            20                  25                  30

Asn Tyr Val Ser Trp Phe Gln Gln Ile Pro Gly Ser Ala Pro Lys Leu
            35                  40                  45

Leu Ile Tyr Asp Thr Asn Thr Arg Ala Ser Gly Val Pro Asp Arg Phe
    50                  55                  60

Ser Gly Ala Arg Ser Gly Asn Thr Ala Thr Leu Thr Ile Asn Ser Leu
65              70                  75                  80

Gln Ala Glu Asp Glu Ala Asp Tyr Tyr Cys Ala Asn Ile Asp Ser Ser
            85                  90                  95

Arg Ser His Leu Phe Gly Ser Gly Thr Arg Leu Thr Val Leu Gly
            100                 105                 110
```

<210> SEQ ID NO 493
<211> LENGTH: 447
<212> TYPE: PRT
<213> ORGANISM: artificial sequence
<220> FEATURE:
<223> OTHER INFORMATION: E2E8 mAB Heavy Chain

<400> SEQUENCE: 493

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Asp Arg
            20                  25                  30

Gly Val Ala Trp Val Arg Gln Ala Pro Gly Lys Ala Leu Glu Trp Val
            35                  40                  45

Gly Thr Met Arg Ser Gly Gly Thr Ile Asp Tyr Asn Pro Ala Leu Lys
    50                  55                  60

Ser Arg Leu Ser Ile Thr Arg Asp Thr Ser Lys Ser Gln Val Phe Leu
```

-continued

```
65                  70                  75                  80

Ser Leu Ser Ser Val Thr Thr Glu Asp Met Ala Met Tyr Tyr Cys Ala
                85                  90                  95

Arg Gly Tyr Leu Ser Gly Asp Arg Tyr Ala Trp Gly Arg Gly Leu Leu
            100                 105                 110

Val Thr Val Ser Ser Ala Lys Thr Thr Ala Pro Ser Val Tyr Pro Leu
            115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
            275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
            435                 440                 445

<210> SEQ ID NO 494
<211> LENGTH: 217
<212> TYPE: PRT
<213> ORGANISM: artificial sequence
<220> FEATURE:
<223> OTHER INFORMATION: E2E8 mAB Light Chain
```

<400> SEQUENCE: 494

```
Gln Ala Val Leu Thr Gln Pro Ser Ser Val Ser Lys Ser Leu Gly Gln
1               5                   10                  15

Ser Val Ser Ile Ala Cys Ser Gly Ser Arg Ser Asp Ile Gly Tyr Gly
                20                  25                  30

Asn Tyr Val Ser Trp Phe Gln Gln Ile Pro Gly Ser Ala Pro Lys Leu
        35                  40                  45

Leu Ile Tyr Asp Thr Asn Thr Arg Ala Ser Gly Val Pro Asp Arg Phe
    50                  55                  60

Ser Gly Ala Arg Ser Gly Asn Thr Ala Thr Leu Thr Ile Asn Ser Leu
65                  70                  75                  80

Gln Ala Glu Asp Glu Ala Asp Tyr Tyr Cys Ala Asn Ile Asp Ser Ser
                85                  90                  95

Arg Ser His Leu Phe Gly Ser Gly Thr Arg Leu Thr Val Leu Gly Gly
                100                 105                 110

Gln Pro Lys Ser Ser Pro Ser Val Thr Leu Phe Pro Pro Ser Ser Glu
        115                 120                 125

Glu Leu Glu Thr Asn Lys Ala Thr Leu Val Cys Thr Ile Thr Asp Phe
    130                 135                 140

Tyr Pro Gly Val Val Thr Val Asp Trp Lys Val Asp Gly Thr Pro Val
145                 150                 155                 160

Thr Gln Gly Met Glu Thr Thr Gln Pro Ser Lys Gln Ser Asn Asn Lys
                165                 170                 175

Tyr Met Ala Ser Ser Tyr Leu Thr Leu Thr Ala Arg Ala Trp Glu Arg
                180                 185                 190

His Ser Ser Tyr Ser Cys Gln Val Thr His Glu Gly His Thr Val Glu
        195                 200                 205

Lys Ser Leu Ser Arg Ala Asp Cys Ser
    210                 215
```

<210> SEQ ID NO 495
<211> LENGTH: 30
<212> TYPE: PRT
<213> ORGANISM: artificial sequence
<220> FEATURE:
<223> OTHER INFORMATION: CA7 VHFR1

<400> SEQUENCE: 495

```
Arg Val Arg Leu Gln Gly Ser Gly Pro Ser Leu Val Lys Pro Ser Gln
1               5                   10                  15

Thr Leu Ser Leu Thr Cys Thr Val Ser Gly Phe Ser Phe Asp
        20                  25                  30
```

<210> SEQ ID NO 496
<211> LENGTH: 14
<212> TYPE: PRT
<213> ORGANISM: artificial sequence
<220> FEATURE:
<223> OTHER INFORMATION: CA7 VHFR2

<400> SEQUENCE: 496

```
Trp Val Arg Gln Ala Pro Gly Lys Ala Leu Glu Trp Leu Gly
1               5                   10
```

<210> SEQ ID NO 497
<211> LENGTH: 32
<212> TYPE: PRT
<213> ORGANISM: artificial sequence
<220> FEATURE:

<223> OTHER INFORMATION: CA7 VHFR3

<400> SEQUENCE: 497

Arg Leu Ser Ile Thr Arg Asp Thr Ser Lys Ser Gln Val Ser Leu Ser
1               5                   10                  15

Val Ser Ser Val Thr Ile Glu Asp Thr Ala Leu Tyr Tyr Cys Val Arg
            20                  25                  30

<210> SEQ ID NO 498
<211> LENGTH: 11
<212> TYPE: PRT
<213> ORGANISM: artificial sequence
<220> FEATURE:
<223> OTHER INFORMATION: CA7 VHFR4

<400> SEQUENCE: 498

Trp Ser Pro Gly Leu Leu Val Thr Val Ser Ser
1               5                   10

<210> SEQ ID NO 499
<211> LENGTH: 22
<212> TYPE: PRT
<213> ORGANISM: artificial sequence
<220> FEATURE:
<223> OTHER INFORMATION: CA7 VLFR1

<400> SEQUENCE: 499

Gln Val Val Arg Thr Gln Pro Ser Ser Val Ser Gly Ser Leu Gly Gln
1               5                   10                  15

Arg Val Ser Ile Thr Cys
            20

<210> SEQ ID NO 500
<211> LENGTH: 15
<212> TYPE: PRT
<213> ORGANISM: artificial sequence
<220> FEATURE:
<223> OTHER INFORMATION: CA7 VLFR2

<400> SEQUENCE: 500

Trp Phe Gln Gln Val Pro Gly Ser Ala Pro Lys Leu Leu Ile Tyr
1               5                   10                  15

<210> SEQ ID NO 501
<211> LENGTH: 32
<212> TYPE: PRT
<213> ORGANISM: artificial sequence
<220> FEATURE:
<223> OTHER INFORMATION: CA7 VLFR3

<400> SEQUENCE: 501

Gly Val Pro Asp Arg Phe Ser Gly Ser Arg Ser Gly Asn Thr Ala Thr
1               5                   10                  15

Leu Thr Ile Asp Ser Leu Gln Ala Glu Asp Glu Ala Asp Tyr Tyr Cys
            20                  25                  30

<210> SEQ ID NO 502
<211> LENGTH: 11
<212> TYPE: PRT
<213> ORGANISM: artificial sequence
<220> FEATURE:
<223> OTHER INFORMATION: CA7 VLFR4

<400> SEQUENCE: 502

Phe Gly Ser Gly Thr Arg Leu Thr Val Leu Gly

-continued

```
1             5              10

<210> SEQ ID NO 503
<211> LENGTH: 125
<212> TYPE: PRT
<213> ORGANISM: artificial sequence
<220> FEATURE:
<223> OTHER INFORMATION: CA7 VH Domain

<400> SEQUENCE: 503

Arg Val Arg Leu Gln Gly Ser Gly Pro Ser Leu Val Lys Pro Ser Gln
1               5                   10                  15

Thr Leu Ser Leu Thr Cys Thr Val Ser Gly Phe Ser Phe Asp Ser Tyr
            20                  25                  30

Tyr Val Gly Trp Val Arg Gln Ala Pro Gly Lys Ala Leu Glu Trp Leu
        35                  40                  45

Gly Asn Ile Tyr Ser Thr Gly Arg Ala Phe Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ser Val Ser Ser Val Thr Ile Glu Asp Thr Ala Leu Tyr Tyr Cys Val
                85                  90                  95

Arg Gly Ser Tyr Tyr His Gly Gly Gly Asn Gly Met Val Asp Phe Phe
            100                 105                 110

Asp Tyr Trp Ser Pro Gly Leu Leu Val Thr Val Ser Ser
            115                 120                 125

<210> SEQ ID NO 504
<211> LENGTH: 111
<212> TYPE: PRT
<213> ORGANISM: artificial sequence
<220> FEATURE:
<223> OTHER INFORMATION: CA7 VL Domain

<400> SEQUENCE: 504

Gln Val Val Arg Thr Gln Pro Ser Ser Val Ser Gly Ser Leu Gly Gln
1               5                   10                  15

Arg Val Ser Ile Thr Cys Ser Gly Ser Ser Ser Asn Val Gly Tyr Gly
            20                  25                  30

Asn Tyr Val Gly Trp Phe Gln Gln Val Pro Gly Ser Ala Pro Lys Leu
        35                  40                  45

Leu Ile Tyr Ala Ala Thr Ser Arg Ala Ser Gly Val Pro Asp Arg Phe
    50                  55                  60

Ser Gly Ser Arg Ser Gly Asn Thr Ala Thr Leu Thr Ile Asp Ser Leu
65                  70                  75                  80

Gln Ala Glu Asp Glu Ala Asp Tyr Tyr Cys Ser Ser Tyr Gln Arg Gly
                85                  90                  95

Asn Thr Gly Val Phe Gly Ser Gly Thr Arg Leu Thr Val Leu Gly
            100                 105                 110

<210> SEQ ID NO 505
<211> LENGTH: 455
<212> TYPE: PRT
<213> ORGANISM: artificial sequence
<220> FEATURE:
<223> OTHER INFORMATION: CA7 mAB Heavy Chain

<400> SEQUENCE: 505

Arg Val Arg Leu Gln Gly Ser Gly Pro Ser Leu Val Lys Pro Ser Gln
1               5                   10                  15
```

-continued

```
Thr Leu Ser Leu Thr Cys Thr Val Ser Gly Phe Ser Phe Asp Ser Tyr
            20                  25                  30

Tyr Val Gly Trp Val Arg Gln Ala Pro Gly Lys Ala Leu Glu Trp Leu
            35                  40                  45

Gly Asn Ile Tyr Ser Thr Gly Arg Ala Phe Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ser Val Ser Ser Val Thr Ile Glu Asp Thr Ala Leu Tyr Tyr Cys Val
            85                  90                  95

Arg Gly Ser Tyr Tyr His Gly Gly Gly Asn Gly Met Val Asp Phe Phe
            100                 105                 110

Asp Tyr Trp Ser Pro Gly Leu Leu Val Thr Val Ser Ser Ala Lys Thr
            115                 120                 125

Thr Ala Pro Ser Val Tyr Pro Leu Ala Pro Val Cys Gly Asp Thr Thr
    130                 135                 140

Gly Ser Ser Val Thr Leu Gly Cys Leu Val Lys Gly Tyr Phe Pro Glu
145                 150                 155                 160

Pro Val Thr Leu Thr Trp Asn Ser Gly Ser Leu Ser Ser Gly Val His
            165                 170                 175

Thr Phe Pro Ala Val Leu Gln Ser Asp Leu Tyr Thr Leu Ser Ser Ser
            180                 185                 190

Val Thr Val Thr Ser Ser Thr Trp Pro Ser Gln Ser Ile Thr Cys Asn
            195                 200                 205

Val Ala His Pro Ala Ser Ser Thr Lys Val Asp Lys Lys Ile Glu Pro
    210                 215                 220

Arg Gly Pro Thr Ile Lys Pro Cys Pro Pro Cys Lys Cys Pro Ala Pro
225                 230                 235                 240

Asn Leu Leu Gly Gly Pro Ser Val Phe Ile Phe Pro Pro Lys Ile Lys
            245                 250                 255

Asp Val Leu Met Ile Ser Leu Ser Pro Ile Val Thr Cys Val Val Val
            260                 265                 270

Asp Val Ser Glu Asp Asp Pro Asp Val Gln Ile Ser Trp Phe Val Asn
            275                 280                 285

Asn Val Glu Val His Thr Ala Gln Thr Gln Thr His Arg Glu Asp Tyr
    290                 295                 300

Asn Ser Thr Leu Arg Val Val Ser Ala Leu Pro Ile Gln His Gln Asp
305                 310                 315                 320

Trp Met Ser Gly Lys Glu Phe Lys Cys Lys Val Asn Asn Lys Asp Leu
            325                 330                 335

Pro Ala Pro Ile Glu Arg Thr Ile Ser Lys Pro Lys Gly Ser Val Arg
            340                 345                 350

Ala Pro Gln Val Tyr Val Leu Pro Pro Pro Glu Glu Glu Met Thr Lys
            355                 360                 365

Lys Gln Val Thr Leu Thr Cys Met Val Thr Asp Phe Met Pro Glu Asp
    370                 375                 380

Ile Tyr Val Glu Trp Thr Asn Asn Gly Lys Thr Glu Leu Asn Tyr Lys
385                 390                 395                 400

Asn Thr Glu Pro Val Leu Asp Ser Asp Gly Ser Tyr Phe Met Tyr Ser
            405                 410                 415

Lys Leu Arg Val Glu Lys Lys Asn Trp Val Glu Arg Asn Ser Tyr Ser
            420                 425                 430
```

-continued

```
Cys Ser Val Val His Glu Gly Leu His Asn His His Thr Thr Lys Ser
        435                 440                 445

Phe Ser Arg Thr Pro Gly Lys
    450                 455

<210> SEQ ID NO 506
<211> LENGTH: 217
<212> TYPE: PRT
<213> ORGANISM: artificial sequence
<220> FEATURE:
<223> OTHER INFORMATION: CA7 mAB Light Chain

<400> SEQUENCE: 506

Gln Val Val Arg Thr Gln Pro Ser Ser Val Ser Gly Ser Leu Gly Gln
1               5                   10                  15

Arg Val Ser Ile Thr Cys Ser Gly Ser Ser Ser Asn Val Gly Tyr Gly
            20                  25                  30

Asn Tyr Val Gly Trp Phe Gln Gln Val Pro Gly Ser Ala Pro Lys Leu
        35                  40                  45

Leu Ile Tyr Ala Ala Thr Ser Arg Ala Ser Gly Val Pro Asp Arg Phe
    50                  55                  60

Ser Gly Ser Arg Ser Gly Asn Thr Ala Thr Leu Thr Ile Asp Ser Leu
65                  70                  75                  80

Gln Ala Glu Asp Glu Ala Asp Tyr Tyr Cys Ser Ser Tyr Gln Arg Gly
                85                  90                  95

Asn Thr Gly Val Phe Gly Ser Gly Thr Arg Leu Thr Val Leu Gly Gly
                100                 105                 110

Gln Pro Lys Ser Ser Pro Ser Val Thr Leu Phe Pro Pro Ser Ser Glu
            115                 120                 125

Glu Leu Glu Thr Asn Lys Ala Thr Leu Val Cys Thr Ile Thr Asp Phe
    130                 135                 140

Tyr Pro Gly Val Val Thr Val Asp Trp Lys Val Asp Gly Thr Pro Val
145                 150                 155                 160

Thr Gln Gly Met Glu Thr Thr Gln Pro Ser Lys Gln Ser Asn Asn Lys
                165                 170                 175

Tyr Met Ala Ser Ser Tyr Leu Thr Leu Thr Ala Arg Ala Trp Glu Arg
            180                 185                 190

His Ser Ser Tyr Ser Cys Gln Val Thr His Glu Gly His Thr Val Glu
        195                 200                 205

Lys Ser Leu Ser Arg Ala Asp Cys Ser
    210                 215

<210> SEQ ID NO 507
<211> LENGTH: 30
<212> TYPE: PRT
<213> ORGANISM: artificial sequence
<220> FEATURE:
<223> OTHER INFORMATION: CB7 VHFR1

<400> SEQUENCE: 507

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr
            20                  25                  30

<210> SEQ ID NO 508
<211> LENGTH: 14
<212> TYPE: PRT
<213> ORGANISM: artificial sequence
```

-continued

```
<220> FEATURE:
<223> OTHER INFORMATION: CB7 VHFR2

<400> SEQUENCE: 508

Trp Val Arg Gln Ala Pro Gly Lys Ala Leu Glu Trp Val Ser
1               5                   10

<210> SEQ ID NO 509
<211> LENGTH: 32
<212> TYPE: PRT
<213> ORGANISM: artificial sequence
<220> FEATURE:
<223> OTHER INFORMATION: CB7 VHFR3

<400> SEQUENCE: 509

Arg Leu Ser Ile Thr Ala Asp Thr Ser Lys Ser Gln Val Ser Leu Ser
1               5                   10                  15

Leu Ser Ser Val Thr Thr Glu Asp Thr Ala Val Tyr Tyr Cys Ala Arg
            20                  25                  30

<210> SEQ ID NO 510
<211> LENGTH: 11
<212> TYPE: PRT
<213> ORGANISM: artificial sequence
<220> FEATURE:
<223> OTHER INFORMATION: CB7 VHFR4

<400> SEQUENCE: 510

Trp Gly Pro Gly Leu Leu Val Thr Val Ser Ser
1               5                   10

<210> SEQ ID NO 511
<211> LENGTH: 22
<212> TYPE: PRT
<213> ORGANISM: artificial sequence
<220> FEATURE:
<223> OTHER INFORMATION: CB7 VLFR1

<400> SEQUENCE: 511

Gln Ala Val Leu Thr Gln Pro Ser Ser Val Ser Arg Ser Leu Gly Gln
1               5                   10                  15

Ser Val Ser Met Thr Cys
            20

<210> SEQ ID NO 512
<211> LENGTH: 15
<212> TYPE: PRT
<213> ORGANISM: artificial sequence
<220> FEATURE:
<223> OTHER INFORMATION: CB7 VLFR2

<400> SEQUENCE: 512

Trp Phe Gln Gln Val Pro Gly Ser Ala Pro Lys Leu Leu Ile Tyr
1               5                   10                  15

<210> SEQ ID NO 513
<211> LENGTH: 32
<212> TYPE: PRT
<213> ORGANISM: artificial sequence
<220> FEATURE:
<223> OTHER INFORMATION: CB7 VLFR3

<400> SEQUENCE: 513

Gly Val Pro Asp Arg Phe Ser Gly Ser Arg Ser Gly Asn Thr Ala Thr
1               5                   10                  15
```

-continued

```
Leu Thr Ile Ser Ser Leu Gln Ala Glu Asp Glu Ala Asp Tyr Tyr Cys
            20                  25                  30

<210> SEQ ID NO 514
<211> LENGTH: 11
<212> TYPE: PRT
<213> ORGANISM: artificial sequence
<220> FEATURE:
<223> OTHER INFORMATION: CB7 VLFR4

<400> SEQUENCE: 514

Phe Gly Ser Gly Thr Arg Leu Thr Val Leu Gly
1               5                   10

<210> SEQ ID NO 515
<211> LENGTH: 119
<212> TYPE: PRT
<213> ORGANISM: artificial sequence
<220> FEATURE:
<223> OTHER INFORMATION: CB7 VH Domain

<400> SEQUENCE: 515

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Asn Tyr
            20                  25                  30

Arg Val Gly Trp Val Arg Gln Ala Pro Gly Lys Ala Leu Glu Trp Val
        35                  40                  45

Ser Asn Ile Arg Ser Gly Gly Thr Thr Trp Tyr Asn Pro Ala Leu Lys
    50                  55                  60

Ser Arg Leu Ser Ile Thr Ala Asp Thr Ser Lys Ser Gln Val Ser Leu
65                  70                  75                  80

Ser Leu Ser Ser Val Thr Thr Glu Asp Thr Ala Val Tyr Tyr Cys Ala
                85                  90                  95

Arg Asp Ser Ser Gly Asp Leu Tyr Ala Tyr Asp Tyr Trp Gly Pro Gly
            100                 105                 110

Leu Leu Val Thr Val Ser Ser
        115

<210> SEQ ID NO 516
<211> LENGTH: 111
<212> TYPE: PRT
<213> ORGANISM: artificial sequence
<220> FEATURE:
<223> OTHER INFORMATION: CB7 VL Domain

<400> SEQUENCE: 516

Gln Ala Val Leu Thr Gln Pro Ser Ser Val Ser Arg Ser Leu Gly Gln
1               5                   10                  15

Ser Val Ser Met Thr Cys Ser Gly Ser Ser Ser Asn Val Gly Tyr Gly
            20                  25                  30

Asn Tyr Met Ala Trp Phe Gln Gln Val Pro Gly Ser Ala Pro Lys Leu
        35                  40                  45

Leu Ile Tyr Gly Ala Thr Ser Arg Ala Ser Gly Val Pro Asp Arg Phe
    50                  55                  60

Ser Gly Ser Arg Ser Gly Asn Thr Ala Thr Leu Thr Ile Ser Ser Leu
65                  70                  75                  80

Gln Ala Glu Asp Glu Ala Asp Tyr Tyr Cys Ala Ser Tyr Asp Ser Thr
                85                  90                  95

Ser Gly Gly Val Phe Gly Ser Gly Thr Arg Leu Thr Val Leu Gly
```

-continued

```
            100              105              110
```

<210> SEQ ID NO 517
<211> LENGTH: 449
<212> TYPE: PRT
<213> ORGANISM: artificial sequence
<220> FEATURE:
<223> OTHER INFORMATION: CB7 mAB Heavy Chain

<400> SEQUENCE: 517

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Asn Tyr
            20                  25                  30

Arg Val Gly Trp Val Arg Gln Ala Pro Gly Lys Ala Leu Glu Trp Val
        35                  40                  45

Ser Asn Ile Arg Ser Gly Gly Thr Thr Trp Tyr Asn Pro Ala Leu Lys
    50                  55                  60

Ser Arg Leu Ser Ile Thr Ala Asp Thr Ser Lys Ser Gln Val Ser Leu
65                  70                  75                  80

Ser Leu Ser Ser Val Thr Thr Glu Asp Thr Ala Val Tyr Tyr Cys Ala
            85                  90                  95

Arg Asp Ser Ser Gly Asp Leu Tyr Ala Tyr Asp Tyr Trp Gly Pro Gly
            100                 105                 110

Leu Leu Val Thr Val Ser Ser Ala Lys Thr Thr Ala Pro Ser Val Tyr
            115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
            245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
            275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
            325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
```

-continued

```
            355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
                420                 425                 430

Gly Leu His Asn His His Thr Thr Lys Ser Phe Ser Arg Thr Pro Gly
            435                 440                 445

Lys
```

```
<210> SEQ ID NO 518
<211> LENGTH: 217
<212> TYPE: PRT
<213> ORGANISM: artificial sequence
<220> FEATURE:
<223> OTHER INFORMATION: CB7 mAB Light Chain

<400> SEQUENCE: 518

Gln Ala Val Leu Thr Gln Pro Ser Ser Val Ser Arg Ser Leu Gly Gln
1               5                   10                  15

Ser Val Ser Met Thr Cys Ser Gly Ser Ser Ser Asn Val Gly Tyr Gly
            20                  25                  30

Asn Tyr Met Ala Trp Phe Gln Gln Val Pro Gly Ser Ala Pro Lys Leu
        35                  40                  45

Leu Ile Tyr Gly Ala Thr Ser Arg Ala Ser Gly Val Pro Asp Arg Phe
    50                  55                  60

Ser Gly Ser Arg Ser Gly Asn Thr Ala Thr Leu Thr Ile Ser Ser Leu
65                  70                  75                  80

Gln Ala Glu Asp Glu Ala Asp Tyr Tyr Cys Ala Ser Tyr Asp Ser Thr
                85                  90                  95

Ser Gly Gly Val Phe Gly Ser Gly Thr Arg Leu Thr Val Leu Gly Gly
                100                 105                 110

Gln Pro Lys Ser Ser Pro Ser Val Thr Leu Phe Pro Pro Ser Ser Glu
            115                 120                 125

Glu Leu Glu Thr Asn Lys Ala Thr Leu Val Cys Thr Ile Thr Asp Phe
        130                 135                 140

Tyr Pro Gly Val Val Thr Val Asp Trp Lys Val Asp Gly Thr Pro Val
145                 150                 155                 160

Thr Gln Gly Met Glu Thr Thr Gln Pro Ser Lys Gln Ser Asn Asn Lys
                165                 170                 175

Tyr Met Ala Ser Ser Tyr Leu Thr Leu Thr Ala Arg Ala Trp Glu Arg
            180                 185                 190

His Ser Ser Tyr Ser Cys Gln Val Thr His Glu Gly His Thr Val Glu
            195                 200                 205

Lys Ser Leu Ser Arg Ala Asp Cys Ser
    210                 215
```

```
<210> SEQ ID NO 519
<211> LENGTH: 30
<212> TYPE: PRT
<213> ORGANISM: artificial sequence
<220> FEATURE:
<223> OTHER INFORMATION: CC7 VHFR1
```

<400> SEQUENCE: 519

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr
            20                  25                  30

<210> SEQ ID NO 520
<211> LENGTH: 14
<212> TYPE: PRT
<213> ORGANISM: artificial sequence
<220> FEATURE:
<223> OTHER INFORMATION: CC7 VHFR2

<400> SEQUENCE: 520

Trp Val Arg Gln Ala Pro Gly Lys Ala Pro Glu Trp Val Ala
1               5                   10

<210> SEQ ID NO 521
<211> LENGTH: 32
<212> TYPE: PRT
<213> ORGANISM: artificial sequence
<220> FEATURE:
<223> OTHER INFORMATION: CC7 VHFR3

<400> SEQUENCE: 521

Arg Leu Ser Ile Thr Arg Asp Thr Ser Lys Ser Gln Val Ser Leu Ser
1               5                   10                  15

Leu Arg Ser Val Thr Thr Glu Asp Thr Ala Val Tyr Tyr Cys Ala Arg
            20                  25                  30

<210> SEQ ID NO 522
<211> LENGTH: 11
<212> TYPE: PRT
<213> ORGANISM: artificial sequence
<220> FEATURE:
<223> OTHER INFORMATION: CC7 VHFR4

<400> SEQUENCE: 522

Trp Gly Pro Gly Leu Leu Val Thr Val Ser Ser
1               5                   10

<210> SEQ ID NO 523
<211> LENGTH: 22
<212> TYPE: PRT
<213> ORGANISM: artificial sequence
<220> FEATURE:
<223> OTHER INFORMATION: CC7 VLFR1

<400> SEQUENCE: 523

Arg Val Val Arg Thr Gln Pro Ser Ser Val Ser Gly Ser Leu Gly Gln
1               5                   10                  15

Arg Val Ser Ile Thr Cys
            20

<210> SEQ ID NO 524
<211> LENGTH: 15
<212> TYPE: PRT
<213> ORGANISM: artificial sequence
<220> FEATURE:
<223> OTHER INFORMATION: CC7 VLFR2

<400> SEQUENCE: 524

Trp Phe Gln Gln Val Pro Gly Ser Gly Leu Lys Thr Val Ile Tyr
1               5                   10                  15

-continued

<210> SEQ ID NO 525
<211> LENGTH: 32
<212> TYPE: PRT
<213> ORGANISM: artificial sequence
<220> FEATURE:
<223> OTHER INFORMATION: CC7 VLFR3

<400> SEQUENCE: 525

Gly Val Pro Asp Arg Phe Ser Gly Ser Lys Ser Gly Asp Thr Ala Thr
1               5                   10                  15

Leu Thr Ile Ser Ser Leu Gln Ala Glu Asp Glu Ala Asp Tyr Tyr Cys
            20                  25                  30

<210> SEQ ID NO 526
<211> LENGTH: 11
<212> TYPE: PRT
<213> ORGANISM: artificial sequence
<220> FEATURE:
<223> OTHER INFORMATION: CC7 VLFR4

<400> SEQUENCE: 526

Phe Gly Ser Gly Thr Arg Leu Thr Val Leu Gly
1               5                   10

<210> SEQ ID NO 527
<211> LENGTH: 121
<212> TYPE: PRT
<213> ORGANISM: artificial sequence
<220> FEATURE:
<223> OTHER INFORMATION: CC7 VH Domain

<400> SEQUENCE: 527

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Asn
            20                  25                  30

Ala Val Ile Trp Val Arg Gln Ala Pro Gly Lys Ala Pro Glu Trp Val
        35                  40                  45

Ala Leu Ile Asp Val Asp Gly Asp Ala Ala Tyr Asp Pro Ala Leu Lys
    50                  55                  60

Ser Arg Leu Ser Ile Thr Arg Asp Thr Ser Lys Ser Gln Val Ser Leu
65                  70                  75                  80

Ser Leu Arg Ser Val Thr Thr Glu Asp Thr Ala Val Tyr Tyr Cys Ala
                85                  90                  95

Arg Asp Tyr Gly Ser Trp Gly Tyr Val Ser Asp Ile Asp Tyr Trp Gly
            100                 105                 110

Pro Gly Leu Leu Val Thr Val Ser Ser
        115                 120

<210> SEQ ID NO 528
<211> LENGTH: 108
<212> TYPE: PRT
<213> ORGANISM: artificial sequence
<220> FEATURE:
<223> OTHER INFORMATION: CC7 VL Domain

<400> SEQUENCE: 528

Arg Val Val Arg Thr Gln Pro Ser Ser Val Ser Gly Ser Leu Gly Gln
1               5                   10                  15

Arg Val Ser Ile Thr Cys Ser Gly Ser Tyr Ile Thr Gly Ser Ser Val
            20                  25                  30

```
Gly Trp Phe Gln Gln Val Pro Gly Ser Gly Leu Lys Thr Val Ile Tyr
        35                  40                  45

Asp Asn Asn Asp Arg Pro Ser Gly Val Pro Asp Arg Phe Ser Gly Ser
    50                  55                  60

Lys Ser Gly Asp Thr Ala Thr Leu Thr Ile Ser Ser Leu Gln Ala Glu
65                  70                  75                  80

Asp Glu Ala Asp Tyr Tyr Cys Ala Ser Tyr Asp Thr Ser Asn Ile Gly
                85                  90                  95

Leu Phe Gly Ser Gly Thr Arg Leu Thr Val Leu Gly
            100                 105

<210> SEQ ID NO 529
<211> LENGTH: 451
<212> TYPE: PRT
<213> ORGANISM: artificial sequence
<220> FEATURE:
<223> OTHER INFORMATION: CC7 mAB Heavy Chain

<400> SEQUENCE: 529

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Asn
            20                  25                  30

Ala Val Ile Trp Val Arg Gln Ala Pro Gly Lys Ala Pro Glu Trp Val
            35                  40                  45

Ala Leu Ile Asp Val Asp Gly Asp Ala Ala Tyr Asp Pro Ala Leu Lys
    50                  55                  60

Ser Arg Leu Ser Ile Thr Arg Asp Thr Ser Lys Ser Gln Val Ser Leu
65                  70                  75                  80

Ser Leu Arg Ser Val Thr Thr Glu Asp Thr Ala Val Tyr Tyr Cys Ala
                85                  90                  95

Arg Asp Tyr Gly Ser Trp Gly Tyr Val Ser Asp Ile Asp Tyr Trp Gly
            100                 105                 110

Pro Gly Leu Leu Val Thr Val Ser Ser Ala Lys Thr Thr Ala Pro Ser
            115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
            165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
            195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
            245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
    275                 280                 285
```

-continued

```
His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
                340                 345                 350

Tyr Val Leu Pro Pro Pro Glu Glu Glu Met Thr Lys Lys Gln Val Thr
                355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
                420                 425                 430

His Glu Gly Leu His Asn His His Thr Thr Lys Ser Phe Ser Arg Thr
                435                 440                 445

Pro Gly Lys
    450

<210> SEQ ID NO 530
<211> LENGTH: 214
<212> TYPE: PRT
<213> ORGANISM: artificial sequence
<220> FEATURE:
<223> OTHER INFORMATION: CC7 mAB Light Chain

<400> SEQUENCE: 530

Arg Val Val Arg Thr Gln Pro Ser Ser Val Ser Gly Ser Leu Gly Gln
1               5                   10                  15

Arg Val Ser Ile Thr Cys Ser Gly Ser Tyr Ile Thr Gly Ser Ser Val
                20                  25                  30

Gly Trp Phe Gln Gln Val Pro Gly Ser Gly Leu Lys Thr Val Ile Tyr
        35                  40                  45

Asp Asn Asn Asp Arg Pro Ser Gly Val Pro Asp Arg Phe Ser Gly Ser
    50                  55                  60

Lys Ser Gly Asp Thr Ala Thr Leu Thr Ile Ser Ser Leu Gln Ala Glu
65                  70                  75                  80

Asp Glu Ala Asp Tyr Tyr Cys Ala Ser Tyr Asp Thr Ser Asn Ile Gly
                85                  90                  95

Leu Phe Gly Ser Gly Thr Arg Leu Thr Val Leu Gly Gly Gln Pro Lys
                100                 105                 110

Ser Ser Pro Ser Val Thr Leu Phe Pro Pro Ser Ser Glu Glu Leu Glu
        115                 120                 125

Thr Asn Lys Ala Thr Leu Val Cys Thr Ile Thr Asp Phe Tyr Pro Gly
    130                 135                 140

Val Val Thr Val Asp Trp Lys Val Asp Gly Thr Pro Val Thr Gln Gly
145                 150                 155                 160

Met Glu Thr Thr Gln Pro Ser Lys Gln Ser Asn Asn Lys Tyr Met Ala
                165                 170                 175

Ser Ser Tyr Leu Thr Leu Thr Ala Arg Ala Trp Glu Arg His Ser Ser
            180                 185                 190
```

-continued

```
Tyr Ser Cys Gln Val Thr His Glu Gly His Thr Val Glu Lys Ser Leu
        195                 200                 205

Ser Arg Ala Asp Cys Ser
    210

<210> SEQ ID NO 531
<211> LENGTH: 30
<212> TYPE: PRT
<213> ORGANISM: artificial sequence
<220> FEATURE:
<223> OTHER INFORMATION: CE2 VHFR1

<400> SEQUENCE: 531

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr
            20                  25                  30

<210> SEQ ID NO 532
<211> LENGTH: 14
<212> TYPE: PRT
<213> ORGANISM: artificial sequence
<220> FEATURE:
<223> OTHER INFORMATION: CE2 VHFR2

<400> SEQUENCE: 532

Trp Val Arg Gln Ala Pro Gly Lys Ala Leu Glu Trp Ile Gly
1               5                   10

<210> SEQ ID NO 533
<211> LENGTH: 32
<212> TYPE: PRT
<213> ORGANISM: artificial sequence
<220> FEATURE:
<223> OTHER INFORMATION: CE2 VHFR3

<400> SEQUENCE: 533

Arg Leu Ser Ile Thr Arg Asp Thr Ser Lys Asn Gln Val Ser Leu Ser
1               5                   10                  15

Leu Ser Ser Ala Thr Thr Glu Asp Thr Ala Val Tyr Tyr Cys Gly Arg
            20                  25                  30

<210> SEQ ID NO 534
<211> LENGTH: 11
<212> TYPE: PRT
<213> ORGANISM: artificial sequence
<220> FEATURE:
<223> OTHER INFORMATION: CE2 VHFR4

<400> SEQUENCE: 534

Trp Gly Pro Gly Leu Leu Val Thr Val Ser Ser
1               5                   10

<210> SEQ ID NO 535
<211> LENGTH: 22
<212> TYPE: PRT
<213> ORGANISM: artificial sequence
<220> FEATURE:
<223> OTHER INFORMATION: CE2 VLFR1

<400> SEQUENCE: 535

Gln Ala Val Leu Thr Gln Pro Ser Ser Val Ser Lys Ser Leu Gly Gln
1               5                   10                  15

Ser Val Ser Ile Thr Cys
            20
```

```
<210> SEQ ID NO 536
<211> LENGTH: 15
<212> TYPE: PRT
<213> ORGANISM: artificial sequence
<220> FEATURE:
<223> OTHER INFORMATION: CE2 VLFR2

<400> SEQUENCE: 536

Trp Phe Gln Gln Val Pro Gly Ser Ala Pro Lys Ile Leu Ile Tyr
1               5                   10                  15

<210> SEQ ID NO 537
<211> LENGTH: 32
<212> TYPE: PRT
<213> ORGANISM: artificial sequence
<220> FEATURE:
<223> OTHER INFORMATION: CE2 VLFR3

<400> SEQUENCE: 537

Gly Val Pro Asp Arg Phe Ser Gly Ser Arg Ser Gly Asn Thr Ala Thr
1               5                   10                  15

Leu Thr Ile Thr Ser Leu Gln Ala Glu Asp Glu Ala Asp Tyr Tyr Cys
            20                  25                  30

<210> SEQ ID NO 538
<211> LENGTH: 11
<212> TYPE: PRT
<213> ORGANISM: artificial sequence
<220> FEATURE:
<223> OTHER INFORMATION: CE2 VLFR4

<400> SEQUENCE: 538

Phe Gly Ser Gly Thr Arg Leu Thr Val Leu Gly
1               5                   10

<210> SEQ ID NO 539
<211> LENGTH: 124
<212> TYPE: PRT
<213> ORGANISM: artificial sequence
<220> FEATURE:
<223> OTHER INFORMATION: CE2 VH Domain

<400> SEQUENCE: 539

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Asn Tyr
            20                  25                  30

Pro Val Gly Trp Val Arg Gln Ala Pro Gly Lys Ala Leu Glu Trp Ile
        35                  40                  45

Gly Asn Ile Glu Asn Asp Gly Ser Ala Asn Tyr Ala Ser Ala Leu Lys
    50                  55                  60

Ser Arg Leu Ser Ile Thr Arg Asp Thr Ser Lys Asn Gln Val Ser Leu
65                  70                  75                  80

Ser Leu Ser Ser Ala Thr Thr Glu Asp Thr Ala Val Tyr Tyr Cys Gly
                85                  90                  95

Arg Glu Phe Gly Gly Ser Asp Gly Tyr Thr Tyr Phe Val Asp Ile Asp
            100                 105                 110

Tyr Trp Gly Pro Gly Leu Leu Val Thr Val Ser Ser
        115                 120

<210> SEQ ID NO 540
```

<211> LENGTH: 111
<212> TYPE: PRT
<213> ORGANISM: artificial sequence
<220> FEATURE:
<223> OTHER INFORMATION: CE2 VL Domain

<400> SEQUENCE: 540

```
Gln Ala Val Leu Thr Gln Pro Ser Ser Val Ser Lys Ser Leu Gly Gln
1               5                   10                  15

Ser Val Ser Ile Thr Cys Ser Gly Ser Ser Ser Asn Val Gly Tyr Gly
            20                  25                  30

Asn Tyr Val Ser Trp Phe Gln Gln Val Pro Gly Ser Ala Pro Lys Ile
        35                  40                  45

Leu Ile Tyr Gly Ala Thr Ser Arg Ala Ser Gly Val Pro Asp Arg Phe
    50                  55                  60

Ser Gly Ser Arg Ser Gly Asn Thr Ala Thr Leu Thr Ile Thr Ser Leu
65                  70                  75                  80

Gln Ala Glu Asp Glu Ala Asp Tyr Tyr Cys Ala Ser Tyr Asp Gly Ser
                85                  90                  95

Ser Ser Gly Val Phe Gly Ser Gly Thr Arg Leu Thr Val Leu Gly
            100                 105                 110
```

<210> SEQ ID NO 541
<211> LENGTH: 454
<212> TYPE: PRT
<213> ORGANISM: artificial sequence
<220> FEATURE:
<223> OTHER INFORMATION: CE2 mAB Heavy Chain

<400> SEQUENCE: 541

```
Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Asn Tyr
            20                  25                  30

Pro Val Gly Trp Val Arg Gln Ala Pro Gly Lys Ala Leu Glu Trp Ile
        35                  40                  45

Gly Asn Ile Glu Asn Asp Gly Ser Ala Asn Tyr Ala Ser Ala Leu Lys
    50                  55                  60

Ser Arg Leu Ser Ile Thr Arg Asp Thr Ser Lys Asn Gln Val Ser Leu
65                  70                  75                  80

Ser Leu Ser Ser Ala Thr Thr Glu Asp Thr Ala Val Tyr Tyr Cys Gly
                85                  90                  95

Arg Glu Phe Gly Gly Ser Asp Gly Tyr Thr Tyr Phe Val Asp Ile Asp
            100                 105                 110

Tyr Trp Gly Pro Gly Leu Leu Val Thr Val Ser Ser Ala Lys Thr Thr
        115                 120                 125

Ala Pro Ser Val Tyr Pro Leu Ala Pro Val Cys Gly Asp Thr Thr Gly
    130                 135                 140

Ser Ser Val Thr Leu Gly Cys Leu Val Lys Gly Tyr Phe Pro Glu Pro
145                 150                 155                 160

Val Thr Leu Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Thr Ser Ser Thr Trp Pro Ser Gln Ser Ile Thr Cys Asn Val
        195                 200                 205

Ala His Pro Ala Ser Ser Thr Lys Val Asp Lys Lys Ile Glu Pro Arg
```

-continued

```
       210              215              220

Gly Pro Thr Ile Lys Pro Cys Pro Pro Cys Lys Cys Pro Ala Pro Asn
225              230              235              240

Leu Leu Gly Gly Pro Ser Val Phe Ile Phe Pro Pro Lys Ile Lys Asp
                 245              250              255

Val Leu Met Ile Ser Leu Ser Pro Ile Val Thr Cys Val Val Val Asp
                 260              265              270

Val Ser Glu Asp Asp Pro Asp Val Gln Ile Ser Trp Phe Val Asn Asn
             275              280              285

Val Glu Val His Thr Ala Gln Thr Gln Thr His Arg Glu Asp Tyr Asn
         290              295              300

Ser Thr Leu Arg Val Val Ser Ala Leu Pro Ile Gln His Gln Asp Trp
305              310              315              320

Met Ser Gly Lys Glu Phe Lys Cys Lys Val Asn Asn Lys Asp Leu Pro
                 325              330              335

Ala Pro Ile Glu Arg Thr Ile Ser Lys Pro Lys Gly Ser Val Arg Ala
                 340              345              350

Pro Gln Val Tyr Val Leu Pro Pro Pro Glu Glu Glu Met Thr Lys Lys
             355              360              365

Gln Val Thr Leu Thr Cys Met Val Thr Asp Phe Met Pro Glu Asp Ile
         370              375              380

Tyr Val Glu Trp Thr Asn Asn Gly Lys Thr Glu Leu Asn Tyr Lys Asn
385              390              395              400

Thr Glu Pro Val Leu Asp Ser Asp Gly Ser Tyr Phe Met Tyr Ser Lys
                 405              410              415

Leu Arg Val Glu Lys Lys Asn Trp Val Glu Arg Asn Ser Tyr Ser Cys
                 420              425              430

Ser Val Val His Glu Gly Leu His Asn His His Thr Thr Lys Ser Phe
             435              440              445

Ser Arg Thr Pro Gly Lys
    450

<210> SEQ ID NO 542
<211> LENGTH: 217
<212> TYPE: PRT
<213> ORGANISM: artificial sequence
<220> FEATURE:
<223> OTHER INFORMATION: CE2 mAB Light Chain

<400> SEQUENCE: 542

Gln Ala Val Leu Thr Gln Pro Ser Ser Val Ser Lys Ser Leu Gly Gln
1               5               10               15

Ser Val Ser Ile Thr Cys Ser Gly Ser Ser Ser Asn Val Gly Tyr Gly
                 20               25               30

Asn Tyr Val Ser Trp Phe Gln Gln Val Pro Gly Ser Ala Pro Lys Ile
                 35               40               45

Leu Ile Tyr Gly Ala Thr Ser Arg Ala Ser Gly Val Pro Asp Arg Phe
    50               55               60

Ser Gly Ser Arg Ser Gly Asn Thr Ala Thr Leu Thr Ile Thr Ser Leu
65               70               75               80

Gln Ala Glu Asp Glu Ala Asp Tyr Tyr Cys Ala Ser Tyr Asp Gly Ser
                 85               90               95

Ser Ser Gly Val Phe Gly Ser Gly Thr Arg Leu Thr Val Leu Gly Gly
             100              105              110

Gln Pro Lys Ser Ser Pro Ser Val Thr Leu Phe Pro Pro Ser Ser Glu
```

-continued

```
          115                 120                 125

Glu Leu Glu Thr Asn Lys Ala Thr Leu Val Cys Thr Ile Thr Asp Phe
    130                 135                 140

Tyr Pro Gly Val Val Thr Val Asp Trp Lys Val Asp Gly Thr Pro Val
145                 150                 155                 160

Thr Gln Gly Met Glu Thr Thr Gln Pro Ser Lys Gln Ser Asn Asn Lys
                165                 170                 175

Tyr Met Ala Ser Ser Tyr Leu Thr Leu Thr Ala Arg Ala Trp Glu Arg
                180                 185                 190

His Ser Ser Tyr Ser Cys Gln Val Thr His Glu Gly His Thr Val Glu
                195                 200                 205

Lys Ser Leu Ser Arg Ala Asp Cys Ser
    210                 215

<210> SEQ ID NO 543
<211> LENGTH: 30
<212> TYPE: PRT
<213> ORGANISM: artificial sequence
<220> FEATURE:
<223> OTHER INFORMATION: CE3 VHFR1

<400> SEQUENCE: 543

Gln Val Arg Leu Gln Glu Ser Gly Pro Ser Leu Val Lys Pro Ser Gln
1               5                   10                  15

Thr Leu Ser Val Thr Cys Thr Val Ser Gly Phe Ser Leu Ile
            20                  25                  30

<210> SEQ ID NO 544
<211> LENGTH: 14
<212> TYPE: PRT
<213> ORGANISM: artificial sequence
<220> FEATURE:
<223> OTHER INFORMATION: CE3 VHFR2

<400> SEQUENCE: 544

Trp Val Arg Gln Ala Pro Gly Lys Val Pro Glu Ser Leu Ala
1               5                   10

<210> SEQ ID NO 545
<211> LENGTH: 32
<212> TYPE: PRT
<213> ORGANISM: artificial sequence
<220> FEATURE:
<223> OTHER INFORMATION: CE3 VHFR3

<400> SEQUENCE: 545

Arg Leu Asp Ile Thr Arg Asp Thr Ser Lys Asn Gln Ile Ser Leu Ser
1               5                   10                  15

Leu Ser Ser Val Thr Thr Asp Asp Ala Ala Val Tyr Tyr Cys Thr Arg
            20                  25                  30

<210> SEQ ID NO 546
<211> LENGTH: 11
<212> TYPE: PRT
<213> ORGANISM: artificial sequence
<220> FEATURE:
<223> OTHER INFORMATION: CE3 VHFR4

<400> SEQUENCE: 546

Trp Gly Pro Gly Leu Leu Val Thr Val Ser Ser
1               5                   10
```

```
<210> SEQ ID NO 547
<211> LENGTH: 22
<212> TYPE: PRT
<213> ORGANISM: artificial sequence
<220> FEATURE:
<223> OTHER INFORMATION: CE3 VLFR1

<400> SEQUENCE: 547

Gln Ala Val Leu Thr Gln Pro Ser Ser Val Ser Gly Ser Leu Gly Gln
1               5                   10                  15

Arg Val Ser Ile Thr Cys
            20

<210> SEQ ID NO 548
<211> LENGTH: 15
<212> TYPE: PRT
<213> ORGANISM: artificial sequence
<220> FEATURE:
<223> OTHER INFORMATION: CE3 VLFR2

<400> SEQUENCE: 548

Trp Phe Gln Gln Leu Pro Gly Ser Gly Leu Arg Thr Ile Ile Tyr
1               5                   10                  15

<210> SEQ ID NO 549
<211> LENGTH: 32
<212> TYPE: PRT
<213> ORGANISM: artificial sequence
<220> FEATURE:
<223> OTHER INFORMATION: CE3 VLFR3

<400> SEQUENCE: 549

Gly Ile Pro Asp Arg Phe Ser Gly Ser Lys Ser Gly Val Thr Ala Thr
1               5                   10                  15

Leu Thr Ile Asp Ser Leu Gln Ala Glu Asp Glu Ala Asp Tyr Phe Cys
            20                  25                  30

<210> SEQ ID NO 550
<211> LENGTH: 11
<212> TYPE: PRT
<213> ORGANISM: artificial sequence
<220> FEATURE:
<223> OTHER INFORMATION: CE3 VLFR4

<400> SEQUENCE: 550

Phe Gly Ser Gly Thr Arg Leu Thr Val Leu Gly
1               5                   10

<210> SEQ ID NO 551
<211> LENGTH: 124
<212> TYPE: PRT
<213> ORGANISM: artificial sequence
<220> FEATURE:
<223> OTHER INFORMATION: CE3 VH Domain

<400> SEQUENCE: 551

Gln Val Arg Leu Gln Glu Ser Gly Pro Ser Leu Val Lys Pro Ser Gln
1               5                   10                  15

Thr Leu Ser Val Thr Cys Thr Val Ser Gly Phe Ser Leu Ile Ser Asn
            20                  25                  30

Ala Val Gly Trp Val Arg Gln Ala Pro Gly Lys Val Pro Glu Ser Leu
        35                  40                  45

Ala Gly Cys Ser Ser Asp Gly Lys Cys Tyr Tyr Asn Ser Ala Leu Lys
    50                  55                  60
```

-continued

```
Ser Arg Leu Asp Ile Thr Arg Asp Thr Ser Lys Asn Gln Ile Ser Leu
65                  70                  75                  80

Ser Leu Ser Ser Val Thr Thr Asp Asp Ala Ala Val Tyr Tyr Cys Thr
                85                  90                  95

Arg Gly Tyr Tyr Pro Val Tyr Gly Tyr Asp Tyr Leu Gly Thr Ile Asp
            100                 105                 110

Tyr Trp Gly Pro Gly Leu Leu Val Thr Val Ser Ser
        115                 120

<210> SEQ ID NO 552
<211> LENGTH: 111
<212> TYPE: PRT
<213> ORGANISM: artificial sequence
<220> FEATURE:
<223> OTHER INFORMATION: CE3 VL Domain

<400> SEQUENCE: 552

Gln Ala Val Leu Thr Gln Pro Ser Ser Val Ser Gly Ser Leu Gly Gln
1               5                   10                  15

Arg Val Ser Ile Thr Cys Ser Gly Ser Ser Ser Asn Val Gly Arg Asn
                20                  25                  30

Asp Val Ala Trp Phe Gln Gln Leu Pro Gly Ser Gly Leu Arg Thr Ile
            35                  40                  45

Ile Tyr Gly Thr Thr Ser Arg Pro Ser Gly Ile Pro Asp Arg Phe Ser
        50                  55                  60

Gly Ser Lys Ser Gly Val Thr Ala Thr Leu Thr Ile Asp Ser Leu Gln
65                  70                  75                  80

Ala Glu Asp Glu Ala Asp Tyr Phe Cys Ala Ser Gly Asp Ser Ser Ala
                85                  90                  95

Ile Asn Asp Ile Phe Gly Ser Gly Thr Arg Leu Thr Val Leu Gly
            100                 105                 110

<210> SEQ ID NO 553
<211> LENGTH: 454
<212> TYPE: PRT
<213> ORGANISM: artificial sequence
<220> FEATURE:
<223> OTHER INFORMATION: CE3 mAB Heavy Chain

<400> SEQUENCE: 553

Gln Val Arg Leu Gln Glu Ser Gly Pro Ser Leu Val Lys Pro Ser Gln
1               5                   10                  15

Thr Leu Ser Val Thr Cys Thr Val Ser Gly Phe Ser Leu Ile Ser Asn
                20                  25                  30

Ala Val Gly Trp Val Arg Gln Ala Pro Gly Lys Val Pro Glu Ser Leu
            35                  40                  45

Ala Gly Cys Ser Ser Asp Gly Lys Cys Tyr Tyr Asn Ser Ala Leu Lys
        50                  55                  60

Ser Arg Leu Asp Ile Thr Arg Asp Thr Ser Lys Asn Gln Ile Ser Leu
65                  70                  75                  80

Ser Leu Ser Ser Val Thr Thr Asp Asp Ala Ala Val Tyr Tyr Cys Thr
                85                  90                  95

Arg Gly Tyr Tyr Pro Val Tyr Gly Tyr Asp Tyr Leu Gly Thr Ile Asp
            100                 105                 110

Tyr Trp Gly Pro Gly Leu Leu Val Thr Val Ser Ser Ala Lys Thr Thr
        115                 120                 125

Ala Pro Ser Val Tyr Pro Leu Ala Pro Val Cys Gly Asp Thr Thr Gly
        130                 135                 140
```

-continued

Ser Ser Val Thr Leu Gly Cys Leu Val Lys Gly Tyr Phe Pro Glu Pro
145                150                155                160

Val Thr Leu Thr Trp Asn Ser Gly Ser Leu Ser Ser Gly Val His Thr
                165                170                175

Phe Pro Ala Val Leu Gln Ser Asp Leu Tyr Thr Leu Ser Ser Ser Val
            180                185                190

Thr Val Thr Ser Ser Thr Trp Pro Ser Gln Ser Ile Thr Cys Asn Val
            195                200                205

Ala His Pro Ala Ser Ser Thr Lys Val Asp Lys Lys Ile Glu Pro Arg
        210                215                220

Gly Pro Thr Ile Lys Pro Cys Pro Pro Cys Lys Cys Pro Ala Pro Asn
225                230                235                240

Leu Leu Gly Gly Pro Ser Val Phe Ile Phe Pro Pro Lys Ile Lys Asp
                245                250                255

Val Leu Met Ile Ser Leu Ser Pro Ile Val Thr Cys Val Val Val Asp
            260                265                270

Val Ser Glu Asp Asp Pro Asp Val Gln Ile Ser Trp Phe Val Asn Asn
        275                280                285

Val Glu Val His Thr Ala Gln Thr Gln Thr His Arg Glu Asp Tyr Asn
        290                295                300

Ser Thr Leu Arg Val Val Ser Ala Leu Pro Ile Gln His Gln Asp Trp
305                310                315                320

Met Ser Gly Lys Glu Phe Lys Cys Lys Val Asn Asn Lys Asp Leu Pro
                325                330                335

Ala Pro Ile Glu Arg Thr Ile Ser Lys Pro Lys Gly Ser Val Arg Ala
            340                345                350

Pro Gln Val Tyr Val Leu Pro Pro Pro Glu Glu Glu Met Thr Lys Lys
            355                360                365

Gln Val Thr Leu Thr Cys Met Val Thr Asp Phe Met Pro Glu Asp Ile
        370                375                380

Tyr Val Glu Trp Thr Asn Asn Gly Lys Thr Glu Leu Asn Tyr Lys Asn
385                390                395                400

Thr Glu Pro Val Leu Asp Ser Asp Gly Ser Tyr Phe Met Tyr Ser Lys
                405                410                415

Leu Arg Val Glu Lys Lys Asn Trp Val Glu Arg Asn Ser Tyr Ser Cys
            420                425                430

Ser Val Val His Glu Gly Leu His Asn His His Thr Thr Lys Ser Phe
            435                440                445

Ser Arg Thr Pro Gly Lys
        450

<210> SEQ ID NO 554
<211> LENGTH: 217
<212> TYPE: PRT
<213> ORGANISM: artificial sequence
<220> FEATURE:
<223> OTHER INFORMATION: CE3 mAB Light Chain

<400> SEQUENCE: 554

Gln Ala Val Leu Thr Gln Pro Ser Ser Val Ser Gly Ser Leu Gly Gln
1                5                10                15

Arg Val Ser Ile Thr Cys Ser Gly Ser Ser Ser Asn Val Gly Arg Asn
                20                25                30

Asp Val Ala Trp Phe Gln Gln Leu Pro Gly Ser Gly Leu Arg Thr Ile
            35                40                45

```
Ile Tyr Gly Thr Thr Ser Arg Pro Ser Gly Ile Pro Asp Arg Phe Ser
    50                  55                  60

Gly Ser Lys Ser Gly Val Thr Ala Thr Leu Thr Ile Asp Ser Leu Gln
65                  70                  75                  80

Ala Glu Asp Glu Ala Asp Tyr Phe Cys Ala Ser Gly Asp Ser Ser Ala
                85                  90                  95

Ile Asn Asp Ile Phe Gly Ser Gly Thr Arg Leu Thr Val Leu Gly Gly
            100                 105                 110

Gln Pro Lys Ser Ser Pro Ser Val Thr Leu Phe Pro Pro Ser Ser Glu
            115                 120                 125

Glu Leu Glu Thr Asn Lys Ala Thr Leu Val Cys Thr Ile Thr Asp Phe
    130                 135                 140

Tyr Pro Gly Val Val Thr Val Asp Trp Lys Val Asp Gly Thr Pro Val
145                 150                 155                 160

Thr Gln Gly Met Glu Thr Thr Gln Pro Ser Lys Gln Ser Asn Asn Lys
                165                 170                 175

Tyr Met Ala Ser Ser Tyr Leu Thr Leu Thr Ala Arg Ala Trp Glu Arg
            180                 185                 190

His Ser Ser Tyr Ser Cys Gln Val Thr His Glu Gly His Thr Val Glu
            195                 200                 205

Lys Ser Leu Ser Arg Ala Asp Cys Ser
    210                 215

<210> SEQ ID NO 555
<211> LENGTH: 30
<212> TYPE: PRT
<213> ORGANISM: artificial sequence
<220> FEATURE:
<223> OTHER INFORMATION: CA4 VHFR1

<400> SEQUENCE: 555

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr
                20                  25                  30

<210> SEQ ID NO 556
<211> LENGTH: 14
<212> TYPE: PRT
<213> ORGANISM: artificial sequence
<220> FEATURE:
<223> OTHER INFORMATION: CA4 VHFR2

<400> SEQUENCE: 556

Trp Val Arg Gln Ala Pro Gly Gln Ala Leu Glu Trp Ile Ser
1               5                   10

<210> SEQ ID NO 557
<211> LENGTH: 32
<212> TYPE: PRT
<213> ORGANISM: artificial sequence
<220> FEATURE:
<223> OTHER INFORMATION: CA4 VHFR3

<400> SEQUENCE: 557

Arg Leu Ser Ile Thr Arg Asp Thr Ser Lys Ser Gln Phe Ser Leu Ser
1               5                   10                  15

Leu Ser Ser Val Thr Thr Glu Asp Thr Ala Val Tyr Tyr Cys Thr Arg
                20                  25                  30
```

-continued

```
<210> SEQ ID NO 558
<211> LENGTH: 11
<212> TYPE: PRT
<213> ORGANISM: artificial sequence
<220> FEATURE:
<223> OTHER INFORMATION: CA4 VHFR4

<400> SEQUENCE: 558

Trp Gly Pro Gly Leu Leu Val Thr Val Ser Ser
1               5                   10

<210> SEQ ID NO 559
<211> LENGTH: 23
<212> TYPE: PRT
<213> ORGANISM: artificial sequence
<220> FEATURE:
<223> OTHER INFORMATION: CA4 VLFR1

<400> SEQUENCE: 559

Asp Ile Gln Val Thr Gln Ser Pro Ser Ser Leu Ser Ala Ser Leu Thr
1               5                   10                  15

Glu Arg Val Ser Ile Thr Cys
            20

<210> SEQ ID NO 560
<211> LENGTH: 15
<212> TYPE: PRT
<213> ORGANISM: artificial sequence
<220> FEATURE:
<223> OTHER INFORMATION: CA4 VLFR2

<400> SEQUENCE: 560

Trp Tyr Gln Gln Lys Pro Gly Gln Ala Pro Lys Leu Leu Ile Tyr
1               5                   10                  15

<210> SEQ ID NO 561
<211> LENGTH: 32
<212> TYPE: PRT
<213> ORGANISM: artificial sequence
<220> FEATURE:
<223> OTHER INFORMATION: CA4 VLFR3

<400> SEQUENCE: 561

Asp Val Pro Ser Arg Phe Ser Gly Ser Gly Ser Gly Thr Asp Tyr Thr
1               5                   10                  15

Leu Thr Ile Thr Ser Leu Glu Ala Asp Asp Thr Ala Thr Tyr Tyr Cys
                20                  25                  30

<210> SEQ ID NO 562
<211> LENGTH: 10
<212> TYPE: PRT
<213> ORGANISM: artificial sequence
<220> FEATURE:
<223> OTHER INFORMATION: CA4 VLFR4

<400> SEQUENCE: 562

Phe Gly Gly Gly Thr Asn Val Glu Ile Lys
1               5                   10

<210> SEQ ID NO 563
<211> LENGTH: 112
<212> TYPE: PRT
<213> ORGANISM: artificial sequence
<220> FEATURE:
<223> OTHER INFORMATION: CA4 VH Domain
```

```
<400> SEQUENCE: 563

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Tyr
            20                  25                  30

Ser Val Tyr Trp Val Arg Gln Ala Pro Gly Gln Ala Leu Glu Trp Ile
        35                  40                  45

Ser Ile Met Tyr Ala Ser Gly Arg Val Asp Tyr Asn Pro Ala Leu Lys
    50                  55                  60

Ser Arg Leu Ser Ile Thr Arg Asp Thr Ser Lys Ser Gln Phe Ser Leu
65                  70                  75                  80

Ser Leu Ser Ser Val Thr Thr Glu Asp Thr Ala Val Tyr Tyr Cys Thr
                85                  90                  95

Arg Gly Ile Glu Asn Trp Gly Pro Gly Leu Leu Val Thr Val Ser Ser
            100                 105                 110

<210> SEQ ID NO 564
<211> LENGTH: 107
<212> TYPE: PRT
<213> ORGANISM: artificial sequence
<220> FEATURE:
<223> OTHER INFORMATION: CA4 VL Domain

<400> SEQUENCE: 564

Asp Ile Gln Val Thr Gln Ser Pro Ser Ser Leu Ser Ala Ser Leu Thr
1               5                   10                  15

Glu Arg Val Ser Ile Thr Cys Arg Thr Ser Gln Ser Val Asn Asn Tyr
            20                  25                  30

Leu Ser Trp Tyr Gln Gln Lys Pro Gly Gln Ala Pro Lys Leu Leu Ile
        35                  40                  45

Tyr Tyr Ala Thr Arg Leu Tyr Thr Asp Val Pro Ser Arg Phe Ser Gly
    50                  55                  60

Ser Gly Ser Gly Thr Asp Tyr Thr Leu Thr Ile Thr Ser Leu Glu Ala
65                  70                  75                  80

Asp Asp Thr Ala Thr Tyr Tyr Cys Leu Gln Tyr Asp Ser Thr Pro Leu
                85                  90                  95

Ala Phe Gly Gly Gly Thr Asn Val Glu Ile Lys
            100                 105

<210> SEQ ID NO 565
<211> LENGTH: 442
<212> TYPE: PRT
<213> ORGANISM: artificial sequence
<220> FEATURE:
<223> OTHER INFORMATION: CA4 mAB Heavy Chain

<400> SEQUENCE: 565

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Ser Tyr
            20                  25                  30

Ser Val Tyr Trp Val Arg Gln Ala Pro Gly Gln Ala Leu Glu Trp Ile
        35                  40                  45

Ser Ile Met Tyr Ala Ser Gly Arg Val Asp Tyr Asn Pro Ala Leu Lys
    50                  55                  60

Ser Arg Leu Ser Ile Thr Arg Asp Thr Ser Lys Ser Gln Phe Ser Leu
65                  70                  75                  80
```

```
Ser Leu Ser Ser Val Thr Thr Glu Asp Thr Ala Val Tyr Tyr Cys Thr
            85              90              95

Arg Gly Ile Glu Asn Trp Gly Pro Gly Leu Leu Val Thr Val Ser Ser
        100             105             110

Ala Lys Thr Thr Ala Pro Ser Val Tyr Pro Leu Ala Pro Val Cys Gly
        115             120             125

Asp Thr Thr Gly Ser Ser Val Thr Leu Gly Cys Leu Val Lys Gly Tyr
    130             135             140

Phe Pro Glu Pro Val Thr Leu Thr Trp Asn Ser Gly Ser Leu Ser Ser
145             150             155             160

Gly Val His Thr Phe Pro Ala Val Leu Gln Ser Asp Leu Tyr Thr Leu
                165             170             175

Ser Ser Ser Val Thr Val Thr Ser Ser Thr Trp Pro Ser Gln Ser Ile
                180             185             190

Thr Cys Asn Val Ala His Pro Ala Ser Ser Thr Lys Val Asp Lys Lys
        195             200             205

Ile Glu Pro Arg Gly Pro Thr Ile Lys Pro Cys Pro Pro Cys Lys Cys
    210             215             220

Pro Ala Pro Asn Leu Leu Gly Gly Pro Ser Val Phe Ile Phe Pro Pro
225             230             235             240

Lys Ile Lys Asp Val Leu Met Ile Ser Leu Ser Pro Ile Val Thr Cys
            245             250             255

Val Val Val Asp Val Ser Glu Asp Asp Pro Asp Val Gln Ile Ser Trp
            260             265             270

Phe Val Asn Asn Val Glu Val His Thr Ala Gln Thr Gln Thr His Arg
            275             280             285

Glu Asp Tyr Asn Ser Thr Leu Arg Val Val Ser Ala Leu Pro Ile Gln
    290             295             300

His Gln Asp Trp Met Ser Gly Lys Glu Phe Lys Cys Lys Val Asn Asn
305             310             315             320

Lys Asp Leu Pro Ala Pro Ile Glu Arg Thr Ile Ser Lys Pro Lys Gly
            325             330             335

Ser Val Arg Ala Pro Gln Val Tyr Val Leu Pro Pro Pro Glu Glu Glu
            340             345             350

Met Thr Lys Lys Gln Val Thr Leu Thr Cys Met Val Thr Asp Phe Met
            355             360             365

Pro Glu Asp Ile Tyr Val Glu Trp Thr Asn Asn Gly Lys Thr Glu Leu
    370             375             380

Asn Tyr Lys Asn Thr Glu Pro Val Leu Asp Ser Asp Gly Ser Tyr Phe
385             390             395             400

Met Tyr Ser Lys Leu Arg Val Glu Lys Lys Asn Trp Val Glu Arg Asn
            405             410             415

Ser Tyr Ser Cys Ser Val Val His Glu Gly Leu His Asn His His Thr
            420             425             430

Thr Lys Ser Phe Ser Arg Thr Pro Gly Lys
            435             440
```

<210> SEQ ID NO 566
<211> LENGTH: 213
<212> TYPE: PRT
<213> ORGANISM: artificial sequence
<220> FEATURE:
<223> OTHER INFORMATION: CA4 mAB Light Chain

<400> SEQUENCE: 566

-continued

```
Asp Ile Gln Val Thr Gln Ser Pro Ser Ser Leu Ser Ala Ser Leu Thr
1               5                   10                  15

Glu Arg Val Ser Ile Thr Cys Arg Thr Ser Gln Ser Val Asn Asn Tyr
            20                  25                  30

Leu Ser Trp Tyr Gln Gln Lys Pro Gly Gln Ala Pro Lys Leu Leu Ile
        35                  40                  45

Tyr Tyr Ala Thr Arg Leu Tyr Thr Asp Val Pro Ser Arg Phe Ser Gly
    50                  55                  60

Ser Gly Ser Gly Thr Asp Tyr Thr Leu Thr Ile Thr Ser Leu Glu Ala
65                  70                  75                  80

Asp Asp Thr Ala Thr Tyr Tyr Cys Leu Gln Tyr Asp Ser Thr Pro Leu
                85                  90                  95

Ala Phe Gly Gly Gly Thr Asn Val Glu Ile Lys Gly Gln Pro Lys Ser
            100                 105                 110

Ser Pro Ser Val Thr Leu Phe Pro Pro Ser Ser Glu Glu Leu Glu Thr
        115                 120                 125

Asn Lys Ala Thr Leu Val Cys Thr Ile Thr Asp Phe Tyr Pro Gly Val
    130                 135                 140

Val Thr Val Asp Trp Lys Val Asp Gly Thr Pro Val Thr Gln Gly Met
145                 150                 155                 160

Glu Thr Thr Gln Pro Ser Lys Gln Ser Asn Asn Lys Tyr Met Ala Ser
            165                 170                 175

Ser Tyr Leu Thr Leu Thr Ala Arg Ala Trp Glu Arg His Ser Ser Tyr
        180                 185                 190

Ser Cys Gln Val Thr His Glu Gly His Thr Val Glu Lys Ser Leu Ser
        195                 200                 205

Arg Ala Asp Cys Ser
    210

<210> SEQ ID NO 567
<211> LENGTH: 372
<212> TYPE: DNA
<213> ORGANISM: artificial sequence
<220> FEATURE:
<223> OTHER INFORMATION: S1D12 VH Nucleotide Sequence

<400> SEQUENCE: 567
caggtgcagc tgcaggagtc gggacccagc ctggtgaagc cctcacagac cctctccctc      60
acctgcacgg tctctggatt ctcattgaac aacaatgctg taggctgggt ccgccaggct     120
ccaggaaagg tgccggagtc gcttgtgggt gtagcagtg atggaacgtg ttactataat      180
tcggccctga atcccggct cgacatcacc agggacacct ccaagaacca gatctccctg       240
tcactgagca gcgttacaac tgacgacgcg gccgtgtact attgtacaag aggccattat      300
agtatttatg gttatgacta tcttggcact atcgactact ggggcccagg actcctggtc      360
accgtctcct ca                                                          372

<210> SEQ ID NO 568
<211> LENGTH: 336
<212> TYPE: DNA
<213> ORGANISM: artificial sequence
<220> FEATURE:
<223> OTHER INFORMATION: S1D12 VL Nucleotide Sequence

<400> SEQUENCE: 568
caggctgtgc tgactcagcc gtcctccgtg tccgggtccc tgggccagag ggtctccatc      60
acctgctctg gaagcagcag caacgtcggg ggtggtaata gtgtgggctg gtaccaacac     120
```

-continued

```
ctcccaggct caggcctcaa aaccatcatc tatgatacta acagtcgacc ctcgggggtc       180
ccggaccgat tctctggctc caggtctggc aacacggcca ccctaaccat caactcgctc       240
caggctgagg acgagggtga ttattactgt gtaacgggtg acagcactac tcatgatgat       300
cttgtcggca gcgggaccag gctgaccgtc ctgggg                                 336

<210> SEQ ID NO 569
<211> LENGTH: 375
<212> TYPE: DNA
<213> ORGANISM: artificial sequence
<220> FEATURE:
<223> OTHER INFORMATION: S1G2 VH Nucleotide Sequence

<400> SEQUENCE: 569
caggtgcagc tgcaggagtc gggacccagc ctggtgaagc cctcacagac cctctccctc        60
acctgcacgg tctctggatt ctcattaacc agcaattctg tgggctgggt ccgacaggct       120
ccaggaaagg cgccggagtg ggttgctggt atagatacta tggagaaga aggctataat        180 ccagcccrta actcccggct cagcatcacc agggacacct ccaagagtca agtctctttg       240
tcattgagca gcgtgacaag tgaggacacg gccgtgtact actgtggaag aagttatagg       300
gctgatggtc ttgcttacgg ttatgtccaa gccatcgact actgggccc aggactcctg        360 gtcaccgtct cctca                                                        375

<210> SEQ ID NO 570
<211> LENGTH: 327
<212> TYPE: DNA
<213> ORGANISM: artificial sequence
<220> FEATURE:
<223> OTHER INFORMATION: S1G2 VL Nucleotide Sequence

<400> SEQUENCE: 570
caggccgtgg tgactcagcc gtcctccgtg tctgggtccc tgggccagag ggtctccatc        60
acctgctctg gaagcttcat cggtattagt agtgtaggct ggttccaaca gctcccagga       120
tcgggcctca gaaccatcat cgtggcgagt gacggtcgac cctcagggt ccccgaccga       180 ttctctatgt ccaaatcggg caacacagcc accctgacca tcagctcgct ccaggctgag       240
gacgaggccg attatttctg tggaagtagt gataggactc cttatactgg ggtcttcggc      300
agcgggacca ggctgaccgt cctgggt                                           327

<210> SEQ ID NO 571
<211> LENGTH: 357
<212> TYPE: DNA
<213> ORGANISM: artificial sequence
<220> FEATURE:
<223> OTHER INFORMATION: CB7 VH Nucleotide Sequence

<400> SEQUENCE: 571
caggtgcagc tgcaggagtc gggacccagc ctggtgaagc cctcacagac cctctccctc        60
acctgcacgg tctctggatt ctcattaacc aactatcgtg taggttgggt ccgccaggct       120
ccaggaaagg cactggagtg ggttagtaac atacggagtg gtggaactac atggtataac       180
ccggccctga atcccggct cagcatcacc gcggacacct ccaagagcca agtcccctg        240 tcactgagca gcgtgacaac tgaggacacg gccgtatatt attgtgcaag agattcctct       300
ggtgatcttt atgcgtatga ttactggggc caggactcc tggtcaccgt ctcctca          357

<210> SEQ ID NO 572
```

-continued

```
<211> LENGTH: 333
<212> TYPE: DNA
<213> ORGANISM: artificial sequence
<220> FEATURE:
<223> OTHER INFORMATION: CB7 VL Nucleotide Sequence

<400> SEQUENCE: 572
caggccgtgc tgactcagcc gtcctccgtg tccaggtccc tgggccagag tgtctccatg      60
acctgctctg gaagcagcag caacgttgga tatggtaatt atatggcctg gttccaacag     120
gttccaggat cagcccccaa actcctcatc tatggtgcaa ccagtcgagc ctcggggggtc     180 cccgaccgat tctccggctc caggtctggc aacacagcga ctctgaccat cagctcgctc     240
caggctgagg acgaggccga ttactactgt gcatcttatg acagcactag cggggggtgtc     300 ttcggcagcg ggaccaggct gaccgtcctg ggt                                   333

<210> SEQ ID NO 573
<211> LENGTH: 363
<212> TYPE: DNA
<213> ORGANISM: artificial sequence
<220> FEATURE:
<223> OTHER INFORMATION: CC7 VH Nucleotide Sequence

<400> SEQUENCE: 573
caggtgcagc tgcaggagtc gggacccagc ctggtgaagc cctcacagac cctctccctc      60
acctgcacgg tctctggatt ctcactaacc agcaatgctg tgatctgggt ccggcaggct     120
ccaggaaagg cgccggagtg ggttgctttg atagatgttg atggagatgc agcctatgac     180
ccagccctta gtcccgcct cagcatcacc agggacacct ccaagagtca agtctccctt      240
tcactgcgca gcgtgacaac tgaggacacg gccgtgtact actgtgcaag agactatggt     300 agttgggggtt atgtttccga catcgactac tggggcccag gactcctggt caccgtctcc     360
tca                                                                    363

<210> SEQ ID NO 574
<211> LENGTH: 324
<212> TYPE: DNA
<213> ORGANISM: artificial sequence
<220> FEATURE:
<223> OTHER INFORMATION: CC7 VL Nucleotide Sequence

<400> SEQUENCE: 574
agggtcgtgc ggactcaacc gtcctccgtg tctgggtccc tgggccagag ggtctccatc      60
acctgctctg gaagctacat cactggtagt tctgtaggct ggttccaaca ggtcccagga     120
tcgggcctca aaaccgtcat ctatgacaat aacgatcgac cctcaggggt ccccgaccga     180
ttctctggct ccaagtcggg cgacacagcc accctgacca tcagctcgct ccaggctgag     240
gacgaggccg attattactg tgcatcttat gacaccagta acattggtct tttcggcagc     300
gggaccaggc tgaccgtcct gggt                                             324

<210> SEQ ID NO 575
<211> LENGTH: 336
<212> TYPE: DNA
<213> ORGANISM: artificial sequence
<220> FEATURE:
<223> OTHER INFORMATION: CA4 VH Nucleotide Sequence

<400> SEQUENCE: 575
caggttcagc tgcaggagtc gggacccagc ctggtgaagc cctcacagac cctctccctc      60
acctgcacgg tctctggatt ctcattaacc agctattccg tatactgggt ccgccaggct     120
```

-continued

```
ccaggccagg cactggagtg gattagtatt atgtatgcta gtggaagagt agactataac      180
ccggccctga aatcccggct cagcatcacc agggacacct ccaagagtca attctccctg      240
tcattgagca gcgtgacaac tgaggacacg gccgtctact actgtacaag aggaatcgaa      300
aactggggcc ccggactcct ggtcaccgtc tcctca                                336

<210> SEQ ID NO 576
<211> LENGTH: 324
<212> TYPE: DNA
<213> ORGANISM: artificial sequence
<220> FEATURE:
<223> OTHER INFORMATION: CA4 VL Nucleotide Sequence

<400> SEQUENCE: 576
gacatccagg tgacccagtc tccgtcctcc ctgtctgcat ctctaacaga gagagtctcc       60
atcacttgcc ggaccagtca gagcgttaac aattacttaa gctggtatca gcagaaacca      120
gggcaagctc ctaagctcct gatctattat gcaaccagat tgtacaccga gtcccatcc       180 cggttcagtg gcagtggatc tgggacagat tacaccctca ccatcaccag cctggaggcg      240
gacgacactg caacttatta ctgtctacaa tatgatagta cacctcttgc attcggcggt      300
gggaccaacg tggaaatcaa acgg                                             324

<210> SEQ ID NO 577
<211> LENGTH: 366
<212> TYPE: DNA
<213> ORGANISM: artificial sequence
<220> FEATURE:
<223> OTHER INFORMATION: 3bG4 VH Nucleotide Sequence

<400> SEQUENCE: 577
caggtgcagc ttcaggagtc gggacccagc ctggtgaagc cctcacagac cctctccctc       60
acctgcacaa tctctggatt ctcattaatc agcaatggtg taggctgggt ccgccaggct      120
ccaggaaagg tgccggagtg ggttggtgat attgctagta gtggaaaggc atacagtaac      180
ccggccctga aatcccggct cagcatcacc agggacacct ccaagagcca agtctccctg      240
tcactgagga gcgtgacaac tgaggacacg gccgtgtact actgtgtaag atgcagggat      300
ggtggtgtga cttatggtta tgatatcgac tactggggcc caggactcct ggtcaccgtc      360
tcctca                                                                 366

<210> SEQ ID NO 578
<211> LENGTH: 333
<212> TYPE: DNA
<213> ORGANISM: artificial sequence
<220> FEATURE:
<223> OTHER INFORMATION: 3bG4 VL Nucleotide Sequence

<400> SEQUENCE: 578
caggctgtgc tgactcagcc gtcatccgtg tccaagtccc tgggccagag tgtctccatc       60
acctgctccg gaagcactag caacgttgga agtggtaatg atgtgagctg gttccaacag      120
gtcccaggat cagcccccaa actcctcttc tacggtgcaa ccaaccgagc tcgggggtc       180 cccgaccgat tctccggctc caggtctggc aacacagcgc tctgaccat cacctcgctt       240 caggctgagg acgaggccga ttattactgt ggatcttatg acagcaatag cggtggtatt      300
ttcggcagtg ggaccaggct gaccgtcctg ggt                                   333

<210> SEQ ID NO 579
```

```
<211> LENGTH: 375
<212> TYPE: DNA
<213> ORGANISM: artificial sequence
<220> FEATURE:
<223> OTHER INFORMATION: CA7 VH Nucleotide Sequence

<400> SEQUENCE: 579
cgggtgcggc tgcaggggtc gggacccagc ctggtgaaac cttcacagac cctctccctc      60
acctgcacgg tctctggatt ctcttttgac agctattatg taggctgggt ccgccaggct     120
ccaggaaagg cactggagtg gcttggtaat atatatagta ctggaagggc attctataac     180
ccggccctga atcccggct cagcatcacc agggacacct ccaagagcca agtctcccta     240
tcagtgagca gcgtgacaat tgaggacacg gccctgtact actgtgtcag aggctcgtat     300
tatcacggtg gtggcaatgg gatggtcgac ttttttcgact actggagccc aggactcctg     360
gtcaccgtct cctca                                                        375

<210> SEQ ID NO 580
<211> LENGTH: 333
<212> TYPE: DNA
<213> ORGANISM: artificial sequence
<220> FEATURE:
<223> OTHER INFORMATION: CA7 VL Nucleotide Sequence

<400> SEQUENCE: 580
caggtcgtgc ggactcagcc gtcctccgtg tctgggtccc tgggccagag ggtctccatc      60
acctgctctg gaagcagcag caatgttgga tatggtaatt atgtgggctg gttccaacag     120
gtgccagggt cagcccccaa actcctcatc tatgctgcaa ccagtcgagc ctcggggggtc     180 cccgaccgat tctccggctc caggtctggg aatacagcca ccctgaccat cgactcgctc     240
caggctgagg acgaggccga ttattactgt tcatcttatc aacgcggtaa cactggtgtt     300
ttcggcagcg ggaccaggct gaccgtcctg ggt                                    333

<210> SEQ ID NO 581
<211> LENGTH: 351
<212> TYPE: DNA
<213> ORGANISM: artificial sequence
<220> FEATURE:
<223> OTHER INFORMATION: E2E8 VH Nucleotide Sequence

<400> SEQUENCE: 581
caggtgcagc tgcaggagtc gggacccagc ctggtgaagc cctcacagac cctctccctc      60
acctgcacgg tctctggatt ctcattaacc gaccgtggtg tagcctgggt ccgccaggct     120
ccaggaaagg cactggagtg ggttggtact atgcgtagtg gtggaacgat agactataac     180
ccggccctga atcccggct cagcatcacc agggacacct ccaagagcca agttttcctg     240
tcactgagca gcgtcacaac tgaggacatg gccatgtact actgtgccag aggttatttg     300
agcggtgatc gttatgcctg gggccgagga ctcctggtca ccgtctcctc a               351

<210> SEQ ID NO 582
<211> LENGTH: 333
<212> TYPE: DNA
<213> ORGANISM: artificial sequence
<220> FEATURE:
<223> OTHER INFORMATION: E2E8 VL Nucleotide Sequence

<400> SEQUENCE: 582
caggctgtgc tgactcagcc gtcctccgtg tccaagtccc tgggccagag tgtctccatc      60
gcctgctctg gaagcaggag cgacattgga tatggtaatt atgtgagctg gttccaacag     120
```

-continued

```
atcccaggat cagcccccaa actccttatt tatgatacaa acactcgggc ctcgggggtc     180
cccgaccgat tctccggcgc caggtctggc aacacagcaa cactgaccat caactcgctc     240
caggctgagg acgaggccga ttattactgt gcaaatattg acagtagtcg cagtcatctt     300
ttcggcagtg gcaccagact gaccgtcctg ggt                                  333

<210> SEQ ID NO 583
<211> LENGTH: 348
<212> TYPE: DNA
<213> ORGANISM: artificial sequence
<220> FEATURE:
<223> OTHER INFORMATION: 412E10 VH Nucleotide Sequence

<400> SEQUENCE: 583
caggtgcagc tgcaggagtc gggacccagc ctggtgaagc cctcacagac cctctccctc      60
acctgcacgg tctctggctt ctctgtaata agcgattctg tagcctgggt ccgccaggct     120
ccaggaaaag tgccggagtg gcttggtgct agcggcagtt ctggaaacaa atactataac     180
ccggccctaa atcccggct cagcatcacc agggacacct ccaagagcca agtctccctg      240
tcactgagca gcgtgacaac tgaggatacg gccgtgtact actgtgcgag aggtattatc     300
gccggtgtag atgtctgggg ccgaggactc ctggtcaccg tctcctca                  348

<210> SEQ ID NO 584
<211> LENGTH: 330
<212> TYPE: DNA
<213> ORGANISM: artificial sequence
<220> FEATURE:
<223> OTHER INFORMATION: 412E10 VL Nucleotide Sequence

<400> SEQUENCE: 584
caggctgtgc tgactcagcc gtcctccgtg tctgggtccc tgggccagag ggtctccatc      60
acctgctctg gaagcagcag caacgttgga tatggtaatt atgtgggctg gtaccaacag     120
gtcccaggat cagcccccaa actcctcatc tatggtacag ccattcgagc ctcgggggtc     180
cccgaccgat tctccggctc caggtctggg acacagcca cccttaccat cacctcgctc      240
caggctgagg acgaggccga ttactactgt gcatcttatc agagtaatta cgcttttttc     300
ggcagcggga ccaggctgac cgtcctgggt                                       330

<210> SEQ ID NO 585
<211> LENGTH: 372
<212> TYPE: DNA
<213> ORGANISM: artificial sequence
<220> FEATURE:
<223> OTHER INFORMATION: CE2 VH Nucleotide Sequence

<400> SEQUENCE: 585
caggtgcagc tgcaggagtc gggacccagc ctggtgaagc cctcacagac cctctccctc      60
acctgcacgg tctctggatt ctcattaacc aactatcctg taggctgggt ccgccaggct     120
ccaggaaagg cactggagtg gattggtaac atagaaaatg atggaagtgc gaactatgcc     180
tcggccctga atcccgact cagcatcacc agggacacct ccaagaacca agtctccctg      240
tcactgagca gcgcgacaac tgaggacacg gccgtttact actgtggaag agaattcggt     300
gggagtgatg gttatactta tttcgttgat atcgactact ggggcccagg actcctggtc     360
accgtctcct ca                                                         372

<210> SEQ ID NO 586
```

<211> LENGTH: 333
<212> TYPE: DNA
<213> ORGANISM: artificial sequence
<220> FEATURE:
<223> OTHER INFORMATION: CE2 VL Nucleotide Sequence

<400> SEQUENCE: 586
caggctgtgc tgactcagcc gtcctccgtg tccaagtccc tgggccagag tgtctccatc        60
acctgctctg gaagcagcag caacgttgga tatggtaatt atgtgagctg gttccaacag       120
gtcccaggat cagcccccaa aatcctcatc tatggtgcaa ccagtcgagc ctcggggggtc      180 cccgaccgat tctccggctc caggtctggc aacacagcga ctctgaccat cacctcgctc       240
caggctgagg acgaggccga ttattactgt gcatcttatg acggcagtag cagtggtgtt       300
ttcggcagcg ggaccaggct gaccgtcctg ggt                                     333

<210> SEQ ID NO 587
<211> LENGTH: 372
<212> TYPE: DNA
<213> ORGANISM: artificial sequence
<220> FEATURE:
<223> OTHER INFORMATION: CE3 VH Nucleotide Sequence

<400> SEQUENCE: 587
caggtgcgac tgcaggagtc gggacccagc ctggtgaagc cctcacagac cctctccgtc        60
acctgcacgg tctctggatt ctcattgatc agcaatgctg taggctgggt ccgccaggct       120
ccaggaaagg tgccggagtc gcttgctggt tgtagcagtg atggaaagtg ttactataac        180
tcggccctga atcccggct cgacatcacc agggacacct cgaagaacca gatctccctg         240
tcactgagca gcgtcacaac tgacgacgcg gccgtgtact actgtacaag aggctattat       300 cctgttttatg gttatgacta tcttggcact atcgactact ggggcccgg actcctggtc       360 accgtctcct ca                                                             372

<210> SEQ ID NO 588
<211> LENGTH: 333
<212> TYPE: DNA
<213> ORGANISM: artificial sequence
<220> FEATURE:
<223> OTHER INFORMATION: CE3 VL Nucleotide Sequence

<400> SEQUENCE: 588
caagctgtgc tgactcaacc gtcctccgtg tctgggtccc tgggccagag ggtctccatc        60
acctgctctg gaagcagcag caacgttggt agaaatgatg tagcctggtt ccaacaactc       120
ccaggatcag gcctcagaac catcatctat ggtactacca gtcgaccctc aggtatcccg       180
gaccgattct ccggctccaa gtctggcgtt acggccaccc tgaccatcga ctcgctccag       240
gctgaggacg aggccgatta tttctgtgcc tctggtgaca gtagtgccat taatgatatt       300
ttcggcagcg ggaccaggct gaccgtcctg ggt                                     333

<210> SEQ ID NO 589
<211> LENGTH: 430
<212> TYPE: PRT
<213> ORGANISM: Mus musculus

<400> SEQUENCE: 589

Met Ala Asp Pro Arg Gln Glu Phe Asp Thr Met Glu Asp His Ala Gly
1                   5                   10                  15

Asp Tyr Thr Leu Leu Gln Asp Gln Glu Gly Asp Met Asp His Gly Leu
                20                  25                  30

-continued

```
Lys Glu Ser Pro Pro Gln Pro Pro Ala Asp Asp Gly Ala Glu Glu Pro
        35                  40                  45

Gly Ser Glu Thr Ser Asp Ala Lys Ser Thr Pro Thr Ala Glu Asp Val
        50                  55                  60

Thr Ala Pro Leu Val Asp Glu Arg Ala Pro Asp Lys Gln Ala Ala Ala
65                  70                  75                  80

Gln Pro His Thr Glu Ile Pro Glu Gly Ile Thr Ala Glu Glu Ala Gly
                85                  90                  95

Ile Gly Asp Thr Pro Asn Gln Glu Asp Gln Ala Ala Gly His Val Thr
                100                 105                 110

Gln Ala Arg Val Ala Ser Lys Asp Arg Thr Gly Asn Asp Glu Lys Lys
                115                 120                 125

Ala Lys Gly Ala Asp Gly Lys Thr Gly Ala Lys Ile Ala Thr Pro Arg
        130                 135                 140

Gly Ala Ala Ser Pro Ala Gln Lys Gly Thr Ser Asn Ala Thr Arg Ile
145                 150                 155                 160

Pro Ala Lys Thr Thr Pro Ser Pro Lys Thr Pro Pro Gly Ser Gly Glu
                165                 170                 175

Pro Pro Lys Ser Gly Glu Arg Ser Gly Tyr Ser Ser Pro Gly Ser Pro
                180                 185                 190

Gly Thr Pro Gly Ser Arg Ser Arg Thr Pro Ser Leu Pro Thr Pro Pro
                195                 200                 205

Thr Arg Glu Pro Lys Lys Val Ala Val Val Arg Thr Pro Pro Lys Ser
        210                 215                 220

Pro Ser Ala Ser Lys Ser Arg Leu Gln Thr Ala Pro Val Pro Met Pro
225                 230                 235                 240

Asp Leu Lys Asn Val Arg Ser Lys Ile Gly Ser Thr Glu Asn Leu Lys
                245                 250                 255

His Gln Pro Gly Gly Gly Lys Val Gln Ile Ile Asn Lys Lys Leu Asp
                260                 265                 270

Leu Ser Asn Val Gln Ser Lys Cys Gly Ser Lys Asp Asn Ile Lys His
        275                 280                 285

Val Pro Gly Gly Gly Ser Val Gln Ile Val Tyr Lys Pro Val Asp Leu
        290                 295                 300

Ser Lys Val Thr Ser Lys Cys Gly Ser Leu Gly Asn Ile His His Lys
305                 310                 315                 320

Pro Gly Gly Gly Gln Val Glu Val Lys Ser Glu Lys Leu Asp Phe Lys
                325                 330                 335

Asp Arg Val Gln Ser Lys Ile Gly Ser Leu Asp Asn Ile Thr His Val
                340                 345                 350

Pro Gly Gly Gly Asn Lys Lys Ile Glu Thr His Lys Leu Thr Phe Arg
                355                 360                 365

Glu Asn Ala Lys Ala Lys Thr Asp His Gly Ala Glu Ile Val Tyr Lys
        370                 375                 380

Ser Pro Val Val Ser Gly Asp Thr Ser Pro Arg His Leu Ser Asn Val
385                 390                 395                 400

Ser Ser Thr Gly Ser Ile Asp Met Val Asp Ser Pro Gln Leu Ala Thr
                405                 410                 415

Leu Ala Asp Glu Val Ser Ala Ser Leu Ala Lys Gln Gly Leu
                420                 425                 430
```